(12) United States Patent
Mickanin et al.

(10) Patent No.: US 11,466,271 B2
(45) Date of Patent: Oct. 11, 2022

(54) COMPOSITIONS AND METHODS FOR THE TREATMENT OF HEMOGLOBINOPATHIES

(71) Applicants: Novartis AG, Basel (CH); Intellia Therapeutics, Inc., Cambridge, MA (US)

(72) Inventors: Craig Stephen Mickanin, Hopkinton, MA (US); Christian Schmedt, El Cerrito, CA (US); Jennifer Snead, San Diego, CA (US); Susan Stevenson, Ashland, MA (US); Yi Yang, Belmont, MA (US)

(73) Assignees: Novartis AG, Basel (CH); Intellia Therapeutics, Inc.

( * ) Notice: Subject to any disclaimer, the term of this patent is extended or adjusted under 35 U.S.C. 154(b) by 89 days.

(21) Appl. No.: 16/484,046

(22) PCT Filed: Feb. 5, 2018

(86) PCT No.: PCT/IB2018/050712
§ 371 (c)(1),
(2) Date: Aug. 6, 2019

(87) PCT Pub. No.: WO2018/142364
PCT Pub. Date: Aug. 9, 2018

(65) Prior Publication Data
US 2020/0102561 A1     Apr. 2, 2020

Related U.S. Application Data

(60) Provisional application No. 62/455,464, filed on Feb. 6, 2017.

(51) Int. Cl.
| | | |
|---|---|---|
| *C12N 15/113* | (2010.01) | |
| *A61K 31/713* | (2006.01) | |
| *C12N 9/22* | (2006.01) | |
| *C12N 15/10* | (2006.01) | |

(52) U.S. Cl.
CPC .......... *C12N 15/113* (2013.01); *A61K 31/713* (2013.01); *C12N 9/22* (2013.01); *C12N 15/102* (2013.01); *C12N 2310/20* (2017.05); *C12N 2320/11* (2013.01)

(58) Field of Classification Search
CPC ...... C12N 15/113; C12N 9/22; C12N 15/102; C12N 2310/20; C12N 2320/11; A61K 31/713
See application file for complete search history.

(56) References Cited

U.S. PATENT DOCUMENTS

| | | |
|---|---|---|
| 5,800,815 A | 9/1998 | Chestnut et al. |
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,667,036 B2 | 12/2003 | Cummings et al. |
| 6,777,185 B2 | 8/2004 | Case et al. |
| 6,780,590 B2 | 8/2004 | Case et al. |
| 6,785,613 B2 | 8/2004 | Eisenberg et al. |
| 6,824,978 B1 | 11/2004 | Cox, III et al. |
| 6,869,765 B2 | 3/2005 | Edwards et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,070,934 B2 | 7/2006 | Cox, III et al. |
| 7,163,824 B2 | 1/2007 | Cox, III et al. |
| 7,177,766 B2 | 2/2007 | Eisenberg et al. |
| 7,220,719 B2 | 5/2007 | Case et al. |
| 7,235,354 B2 | 6/2007 | Case et al. |
| 7,491,531 B2 | 2/2009 | Case et al. |
| 7,788,044 B2 | 8/2010 | Eisenberg et al. |
| 7,888,121 B2 | 2/2011 | Urnov et al. |
| 7,901,671 B2 | 3/2011 | Leboulch et al. |
| 7,910,624 B1 | 3/2011 | Perrine et al. |
| 7,943,553 B2 | 5/2011 | Case et al. |
| 7,972,854 B2 | 7/2011 | Miller et al. |
| 7,985,887 B2 | 7/2011 | Cox, III et al. |
| 8,268,618 B2 | 9/2012 | Cox, III et al. |
| 8,349,810 B2 | 1/2013 | Miller et al. |
| 8,377,440 B2 | 2/2013 | McEver et al. |
| 8,383,604 B2 | 2/2013 | Orkin et al. |
| 8,409,861 B2 | 4/2013 | Guschin et al. |
| 8,524,500 B2 | 9/2013 | Urnov et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |

(Continued)

FOREIGN PATENT DOCUMENTS

| | | |
|---|---|---|
| EP | 1075540 B1 | 9/2003 |
| EP | 1061805 B1 | 9/2005 |

(Continued)

OTHER PUBLICATIONS

Traxler et al., "Genome Editing Recreates Hereditary Persistence of Fetal Hemoglobin in Primary Human Erythroblasts", Blood, 2015, 126(23):640.
Canver, et al., "BCL11A enhancer dissection by Cas9-mediated in situ saturating mutagenesis", Nature, 527(7577):192-197. 2015.
Wang, et al., "Genetic Screens in Human Cells Using the CRISPR-Cas9 System", Science, 343(6166):80-84. 2014.
Traxler et al., "A genome-editing strategy to treat beta-hemoglobinopathies that recpaitulates a mutation associated with a benign genetic condition", Nature Medicine, 22(9):987-990. 2016.

(Continued)

*Primary Examiner* — J. E. Angell
(74) *Attorney, Agent, or Firm* — Wei Zhang

(57) ABSTRACT

The present invention is directed to genome editing systems, reagents and methods for the treatment of hemoglobinopathies.

17 Claims, 51 Drawing Sheets
Specification includes a Sequence Listing.

(56) References Cited

U.S. PATENT DOCUMENTS

| | | |
|---|---|---|
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,565 B2 | 2/2015 | Rollins et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,068,001 B2 | 6/2015 | Rollins et al. |
| 9,234,213 B2 | 1/2016 | Wu |
| 9,267,135 B2 | 2/2016 | Church et al. |
| 9,322,037 B2 | 4/2016 | Liu et al. |
| 9,388,430 B2 | 7/2016 | Liu et al. |
| 9,491,934 B2 | 11/2016 | Cox, III et al. |
| 9,650,648 B2 | 5/2017 | Cost et al. |
| 9,822,355 B2 | 11/2017 | Orkin et al. |
| 9,850,497 B2 | 12/2017 | Perlingeiro et al. |
| 9,873,894 B2 | 1/2018 | Conway et al. |
| 9,885,041 B2 | 2/2018 | Orkin et al. |
| 9,902,974 B2 | 2/2018 | Conway et al. |
| 9,957,501 B2 | 5/2018 | Reik et al. |
| 2002/0081614 A1 | 6/2002 | Case et al. |
| 2002/0094529 A1 | 7/2002 | Case et al. |
| 2002/0146691 A1 | 10/2002 | Case et al. |
| 2002/0160940 A1 | 10/2002 | Case et al. |
| 2002/0164575 A1 | 11/2002 | Case et al. |
| 2003/0087817 A1 | 5/2003 | Cox et al. |
| 2003/0092000 A1 | 5/2003 | Eisenberg et al. |
| 2003/0105593 A1 | 6/2003 | Eisenberg et al. |
| 2003/0134318 A1 | 7/2003 | Case et al. |
| 2003/0166141 A1 | 9/2003 | Case et al. |
| 2004/0203064 A1 | 10/2004 | Case et al. |
| 2004/0204345 A1 | 10/2004 | Case et al. |
| 2005/0025753 A1 | 2/2005 | Han et al. |
| 2005/0032108 A1 | 2/2005 | Case et al. |
| 2005/0064474 A1 | 3/2005 | Urnov et al. |
| 2005/0130304 A1 | 6/2005 | Cox et al. |
| 2005/0215502 A1 | 9/2005 | Cox et al. |
| 2005/0239203 A1 | 10/2005 | Case et al. |
| 2005/0244851 A1 | 11/2005 | Blume et al. |
| 2006/0014286 A1 | 1/2006 | Cox et al. |
| 2006/0057725 A1 | 3/2006 | Leboulch et al. |
| 2006/0078878 A1 | 4/2006 | Cox et al. |
| 2006/0166263 A1 | 7/2006 | Case et al. |
| 2006/0188987 A1 | 8/2006 | Guschin et al. |
| 2006/0276427 A1 | 12/2006 | Cox et al. |
| 2006/0281704 A1 | 12/2006 | Cox et al. |
| 2006/0292621 A1 | 12/2006 | Case et al. |
| 2007/0218528 A1 | 9/2007 | Miller |
| 2007/0287189 A1 | 12/2007 | Eisenberg et al. |
| 2009/0082444 A1 | 3/2009 | Perrine et al. |
| 2010/0216664 A1 | 8/2010 | Lathrop et al. |
| 2010/0261271 A1 | 10/2010 | Cox, III et al. |
| 2010/0279406 A1 | 11/2010 | Cox, III et al. |
| 2011/0030076 A1 | 2/2011 | Urnov et al. |
| 2011/0182867 A1 | 7/2011 | Orkin et al. |
| 2011/0247087 A1 | 10/2011 | Cox, III et al. |
| 2011/0274669 A1 | 11/2011 | Leboulch et al. |
| 2011/0293617 A1 | 12/2011 | Rollins et al. |
| 2012/0009161 A1 | 1/2012 | Leboulch et al. |
| 2012/0014928 A1 | 1/2012 | Miller et al. |
| 2012/0294838 A1 | 11/2012 | Cox, III et al. |
| 2013/0129629 A1 | 5/2013 | Orkin et al. |
| 2013/0280222 A1 | 10/2013 | Kay et al. |
| 2013/0315884 A1 | 11/2013 | Galetto et al. |
| 2014/0017214 A1 | 1/2014 | Cost |
| 2014/0018410 A1 | 1/2014 | Novobrantseva et al. |
| 2014/0068797 A1 | 3/2014 | Doudna et al. |
| 2014/0080216 A1 | 3/2014 | Cost et al. |
| 2014/0093913 A1 | 4/2014 | Cost et al. |
| 2014/0127814 A1 | 5/2014 | Chandrasegaran et al. |
| 2014/0134142 A1 | 5/2014 | Smith et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0256798 A1 | 9/2014 | Osborn et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0287938 A1 | 9/2014 | Zhang et al. |
| 2014/0295556 A1 | 10/2014 | Joung et al. |
| 2014/0295557 A1 | 10/2014 | Joung et al. |
| 2014/0295558 A1 | 10/2014 | Chen et al. |
| 2014/0310830 A1 | 10/2014 | Zhang et al. |
| 2014/0315985 A1 | 10/2014 | May et al. |
| 2014/0325691 A1 | 10/2014 | Cox, III et al. |
| 2014/0335620 A1 | 11/2014 | Zhang et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356958 A1 | 12/2014 | Mali et al. |
| 2014/0356959 A1 | 12/2014 | Church et al. |
| 2014/0357530 A1 | 12/2014 | Zhang et al. |
| 2014/0364588 A1 | 12/2014 | Haugwitz et al. |
| 2014/0377868 A1 | 12/2014 | Joung et al. |
| 2015/0017136 A1 | 1/2015 | Galetto et al. |
| 2015/0020223 A1 | 1/2015 | Zhang et al. |
| 2015/0031134 A1 | 1/2015 | Zhang et al. |
| 2015/0044772 A1 | 2/2015 | Zhao |
| 2015/0056629 A1 | 2/2015 | Guthrie-Honea |
| 2015/0056705 A1 | 2/2015 | Conway et al. |
| 2015/0059010 A1 | 2/2015 | Cigan et al. |
| 2015/0064138 A1 | 3/2015 | Lu et al. |
| 2015/0071898 A1 | 3/2015 | Liu et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0082478 A1 | 3/2015 | Cigan et al. |
| 2015/0118216 A1 | 4/2015 | Liu et al. |
| 2015/0125429 A1 | 5/2015 | Perlingeiro et al. |
| 2015/0128300 A1 | 5/2015 | Warming et al. |
| 2015/0132269 A1 | 5/2015 | Orkin et al. |
| 2015/0152436 A1 | 6/2015 | Musunuru et al. |
| 2015/0166969 A1 | 6/2015 | Takeuchi et al. |
| 2015/0184139 A1 | 7/2015 | Zhang et al. |
| 2015/0184199 A1 | 7/2015 | Horwitz et al. |
| 2015/0191744 A1 | 7/2015 | Wolfe et al. |
| 2015/0203817 A1 | 7/2015 | Galetto et al. |
| 2015/0203872 A1 | 7/2015 | Zhang |
| 2015/0218253 A1 | 8/2015 | Liu et al. |
| 2015/0225730 A1 | 8/2015 | Minshull et al. |
| 2015/0225773 A1 | 8/2015 | Farmer et al. |
| 2015/0232833 A1 | 8/2015 | Mali et al. |
| 2015/0232881 A1 | 8/2015 | Glucksmann et al. |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291965 A1 | 10/2015 | Zhang et al. |
| 2015/0291966 A1 | 10/2015 | Zhang et al. |
| 2015/0307867 A1 | 10/2015 | Orkin et al. |
| 2015/0315252 A1 | 11/2015 | Haugwitz et al. |
| 2015/0322457 A1 | 11/2015 | Kim et al. |

(56) References Cited

U.S. PATENT DOCUMENTS

| | | |
|---|---|---|
| 2015/0344912 A1 | 12/2015 | Kim et al. |
| 2015/0353917 A1 | 12/2015 | Miller |
| 2015/0356239 A1 | 12/2015 | Zhang et al. |
| 2015/0376586 A1 | 12/2015 | May et al. |
| 2015/0376587 A1 | 12/2015 | May et al. |
| 2015/0376628 A1 | 12/2015 | Schoenherr et al. |
| 2015/0376650 A1 | 12/2015 | Auerbach et al. |
| 2015/0376651 A1 | 12/2015 | Frendewey et al. |
| 2016/0002644 A1 | 1/2016 | Tuskan et al. |
| 2016/0002670 A1 | 1/2016 | Church et al. |
| 2016/0010076 A1 | 1/2016 | Joung et al. |
| 2016/0017366 A1 | 1/2016 | Chen et al. |
| 2016/0017393 A1 | 1/2016 | Jacobson et al. |
| 2016/0024523 A1 | 1/2016 | Joung et al. |
| 2016/0024524 A1 | 1/2016 | Joung et al. |
| 2016/0024529 A1 | 1/2016 | Carstens |
| 2016/0024568 A1 | 1/2016 | May et al. |
| 2016/0090607 A1 | 3/2016 | Conway et al. |
| 2016/0153003 A1 | 6/2016 | Joung et al. |
| 2016/0281111 A1 | 9/2016 | Cotta-Ramusino et al. |
| 2016/0298096 A1 | 10/2016 | Charpentier et al. |
| 2016/0340660 A1 | 11/2016 | Zhang et al. |
| 2016/0355795 A1 | 12/2016 | Ran et al. |
| 2016/0355797 A1 | 12/2016 | Konermann et al. |
| 2016/0369262 A1 | 12/2016 | Reik et al. |
| 2017/0152507 A1 | 6/2017 | Yin et al. |
| 2017/0173185 A1 | 6/2017 | Sadelain et al. |
| 2017/0251645 A1 | 9/2017 | Cox, III et al. |
| 2017/0298329 A1 | 10/2017 | Takeuchi et al. |
| 2017/0314015 A1 | 11/2017 | Friedland et al. |
| 2017/0369855 A1 | 12/2017 | Novina et al. |
| 2018/0002379 A1 | 1/2018 | Miller et al. |
| 2018/0008725 A1 | 1/2018 | Rivella et al. |
| 2018/0021413 A1 | 1/2018 | Porteus |
| 2018/0030438 A1 | 2/2018 | Porteus et al. |
| 2018/0087072 A1 | 3/2018 | Miller et al. |
| 2018/0111975 A1 | 4/2018 | Reik |
| 2018/0112213 A1 | 4/2018 | Welstead et al. |

FOREIGN PATENT DOCUMENTS

| | | |
|---|---|---|
| EP | 1236045 B1 | 11/2005 |
| EP | 1238067 B1 | 12/2005 |
| EP | 1352975 B1 | 9/2006 |
| EP | 2266396 A2 | 12/2010 |
| EP | 2771468 B1 | 2/2015 |
| EP | 2784162 B1 | 4/2015 |
| EP | 1720995 B1 | 5/2015 |
| EP | 2764103 B1 | 8/2015 |
| EP | 2896697 B1 | 9/2015 |
| EP | 2898075 B1 | 3/2016 |
| EP | 2931898 B1 | 3/2016 |
| EP | 2921557 B1 | 7/2016 |
| EP | 2334794 B1 | 11/2016 |
| EP | 2840140 B1 | 11/2016 |
| EP | 2825654 B1 | 4/2017 |
| EP | 2800811 B1 | 5/2017 |
| EP | 2872154 B1 | 5/2017 |
| EP | 2836226 B1 | 6/2017 |
| EP | 3004352 B1 | 9/2017 |
| EP | 2931897 B1 | 11/2017 |
| EP | 1651660 B1 | 1/2018 |
| EP | 3272356 A1 | 1/2018 |
| EP | 2877571 B1 | 5/2018 |
| EP | 2912175 B1 | 8/2018 |
| EP | 2931892 B1 | 9/2018 |
| EP | 2893004 B1 | 10/2018 |
| EP | 2925864 B1 | 10/2018 |
| EP | 2971041 B1 | 11/2018 |
| EP | 2766041 B1 | 12/2018 |
| EP | 3068881 B1 | 2/2019 |
| EP | 2940140 B1 | 3/2019 |
| EP | 2931891 B1 | 5/2019 |
| EP | 2848690 B1 | 8/2020 |
| WO | 9219774 A1 | 1/1992 |
| WO | 1993021956 | 11/1993 |
| WO | 9414980 A1 | 7/1994 |
| WO | 1995034324 | 12/1995 |
| WO | 0042219 A1 | 7/2000 |
| WO | 2000041566 A1 | 7/2000 |
| WO | 0119981 A2 | 3/2001 |
| WO | 0140798 A2 | 6/2001 |
| WO | 0168147 A2 | 9/2001 |
| WO | 2001085765 A2 | 11/2001 |
| WO | 0238738 A2 | 5/2002 |
| WO | 2002044386 A2 | 6/2002 |
| WO | 2002086443 A2 | 10/2002 |
| WO | 03020887 A2 | 3/2003 |
| WO | 2003027247 A2 | 4/2003 |
| WO | 2004037977 A2 | 5/2004 |
| WO | 2004054512 A2 | 7/2004 |
| WO | 04098508 A2 | 11/2004 |
| WO | 2005014791 A2 | 2/2005 |
| WO | 2005060697 A3 | 7/2005 |
| WO | 2005084190 A2 | 9/2005 |
| WO | 2005100402 A1 | 10/2005 |
| WO | 2007014181 A2 | 2/2007 |
| WO | 2008069999 A2 | 6/2008 |
| WO | 2009007685 A2 | 1/2009 |
| WO | 10030963 A2 | 3/2010 |
| WO | 2010059401 A2 | 5/2010 |
| WO | 2011076807 A3 | 6/2011 |
| WO | 11103215 A1 | 8/2011 |
| WO | 2012006378 A1 | 1/2012 |
| WO | 12021632 A2 | 2/2012 |
| WO | 2012031046 A3 | 3/2012 |
| WO | 2012075027 A1 | 6/2012 |
| WO | 2012079046 A2 | 6/2012 |
| WO | 2012112232 A1 | 8/2012 |
| WO | 2013/04419 A1 | 1/2013 |
| WO | 2013006825 A1 | 1/2013 |
| WO | 13019745 A1 | 2/2013 |
| WO | 2013055985 A1 | 4/2013 |
| WO | 2013059343 A1 | 4/2013 |
| WO | 2013103467 A1 | 7/2013 |
| WO | 13126794 A1 | 8/2013 |
| WO | 2013110198 A1 | 8/2013 |
| WO | 2013158309 A2 | 10/2013 |
| WO | 13176772 A1 | 11/2013 |
| WO | 13176915 A1 | 11/2013 |
| WO | 13176916 A1 | 11/2013 |
| WO | 14011901 A2 | 1/2014 |
| WO | 14018423 A1 | 1/2014 |
| WO | 14039523 A1 | 3/2014 |
| WO | 2014036219 A2 | 3/2014 |
| WO | 14065596 A1 | 5/2014 |
| WO | 14089290 A1 | 6/2014 |
| WO | 14093595 A1 | 6/2014 |
| WO | 14093622 A2 | 6/2014 |
| WO | 14093635 A1 | 6/2014 |
| WO | 14093655 A2 | 6/2014 |
| WO | 14093661 A2 | 6/2014 |
| WO | 14093694 A1 | 6/2014 |
| WO | 14093701 A1 | 6/2014 |
| WO | 14093709 A1 | 6/2014 |
| WO | 14093712 A1 | 6/2014 |
| WO | 14093718 A1 | 6/2014 |
| WO | 14099744 A1 | 6/2014 |
| WO | 14099750 A2 | 6/2014 |
| WO | 2014085593 A1 | 6/2014 |
| WO | 2014130955 A1 | 8/2014 |
| WO | 14143381 A1 | 9/2014 |
| WO | 14144288 A1 | 9/2014 |
| WO | 14144592 A2 | 9/2014 |
| WO | 14144761 A2 | 9/2014 |
| WO | 14145599 A2 | 9/2014 |
| WO | 14150624 A1 | 9/2014 |
| WO | 14152432 A2 | 9/2014 |
| WO | 2014134412 A1 | 9/2014 |
| WO | 2014136086 A1 | 9/2014 |
| WO | 2014140211 A1 | 9/2014 |
| WO | 2014150256 A1 | 9/2014 |
| WO | 14165349 A1 | 10/2014 |
| WO | 14172470 A2 | 10/2014 |

(56) References Cited

FOREIGN PATENT DOCUMENTS

| | | |
|---|---|---|
| WO | 14184143 A1 | 11/2014 |
| WO | 14184741 A1 | 11/2014 |
| WO | 14184744 A1 | 11/2014 |
| WO | 14188001 A1 | 11/2014 |
| WO | 2014186585 A2 | 11/2014 |
| WO | 2014/205133 A2 | 12/2014 |
| WO | 14191128 A1 | 12/2014 |
| WO | 14191521 A2 | 12/2014 |
| WO | 14197568 A2 | 12/2014 |
| WO | 14197748 A2 | 12/2014 |
| WO | 14200659 A1 | 12/2014 |
| WO | 14204578 A1 | 12/2014 |
| WO | 14204723 A1 | 12/2014 |
| WO | 14204724 A1 | 12/2014 |
| WO | 14204725 A1 | 12/2014 |
| WO | 14204726 A1 | 12/2014 |
| WO | 14204727 A1 | 12/2014 |
| WO | 14204728 A1 | 12/2014 |
| WO | 14204729 A1 | 12/2014 |
| WO | 15006294 A2 | 1/2015 |
| WO | 15006747 A2 | 1/2015 |
| WO | 2015006498 A2 | 1/2015 |
| WO | 15021426 A1 | 2/2015 |
| WO | 15026883 A1 | 2/2015 |
| WO | 15026885 A1 | 2/2015 |
| WO | 15026886 A1 | 2/2015 |
| WO | 15026887 A1 | 2/2015 |
| WO | 2015023982 A1 | 2/2015 |
| WO | 15028969 A2 | 3/2015 |
| WO | 15034872 A2 | 3/2015 |
| WO | 15035136 A2 | 3/2015 |
| WO | 15035162 A2 | 3/2015 |
| WO | 15040402 A1 | 3/2015 |
| WO | 15048577 A2 | 4/2015 |
| WO | 15048690 A1 | 4/2015 |
| WO | 15049897 A1 | 4/2015 |
| WO | 15052231 A2 | 4/2015 |
| WO | 15054507 A1 | 4/2015 |
| WO | 15065964 A1 | 5/2015 |
| WO | 15070083 A1 | 5/2015 |
| WO | 15071474 A2 | 5/2015 |
| WO | 15073683 A2 | 5/2015 |
| WO | 15075195 A1 | 5/2015 |
| WO | 15079056 A1 | 6/2015 |
| WO | 15079057 A2 | 6/2015 |
| WO | 15089277 A1 | 6/2015 |
| WO | 15089351 A1 | 6/2015 |
| WO | 15089354 A1 | 6/2015 |
| WO | 15089364 A1 | 6/2015 |
| WO | 15089419 A2 | 6/2015 |
| WO | 15089427 A1 | 6/2015 |
| WO | 15089462 A1 | 6/2015 |
| WO | 15089465 A1 | 6/2015 |
| WO | 15089473 A1 | 6/2015 |
| WO | 15089486 A2 | 6/2015 |
| WO | 15095804 A1 | 6/2015 |
| WO | 2015089406 A1 | 6/2015 |
| WO | 2015095340 A1 | 6/2015 |
| WO | 2015095346 A1 | 6/2015 |
| WO | 15099850 A1 | 7/2015 |
| WO | 15103153 A1 | 7/2015 |
| WO | 15105928 A1 | 7/2015 |
| WO | 15112896 A2 | 7/2015 |
| WO | 15117081 A2 | 8/2015 |
| WO | 15122967 A1 | 8/2015 |
| WO | 15126927 A2 | 8/2015 |
| WO | 15131101 A1 | 9/2015 |
| WO | 15134812 A1 | 9/2015 |
| WO | 15138510 A1 | 9/2015 |
| WO | 15139139 A1 | 9/2015 |
| WO | 2015/152305 A1 | 10/2015 |
| WO | 15148431 A1 | 10/2015 |
| WO | 15148670 A1 | 10/2015 |
| WO | 15148860 A1 | 10/2015 |
| WO | 15148863 A2 | 10/2015 |
| WO | 15153780 A1 | 10/2015 |
| WO | 15153789 A1 | 10/2015 |
| WO | 15153791 A1 | 10/2015 |
| WO | 15153940 A1 | 10/2015 |
| WO | 15157070 A2 | 10/2015 |
| WO | 15159068 A1 | 10/2015 |
| WO | 15161276 A2 | 10/2015 |
| WO | 2015164750 A2 | 10/2015 |
| WO | 15166272 A2 | 11/2015 |
| WO | 15168800 A1 | 11/2015 |
| WO | 15173436 A1 | 11/2015 |
| WO | 15179540 A1 | 11/2015 |
| WO | 15188056 A1 | 12/2015 |
| WO | 15188065 A1 | 12/2015 |
| WO | 15188109 A1 | 12/2015 |
| WO | 15191693 A2 | 12/2015 |
| WO | 15191911 A2 | 12/2015 |
| WO | 15200334 A1 | 12/2015 |
| WO | 15200555 A2 | 12/2015 |
| WO | 15200805 A2 | 12/2015 |
| WO | 16007948 A1 | 1/2016 |
| WO | 16011080 A2 | 1/2016 |
| WO | 2016022363 A9 | 2/2016 |
| WO | 16037138 A1 | 3/2016 |
| WO | 16044416 A1 | 3/2016 |
| WO | 16049258 A2 | 3/2016 |
| WO | 16057835 A2 | 4/2016 |
| WO | 2016057961 A1 | 4/2016 |
| WO | 16073990 A2 | 5/2016 |
| WO | 16094872 A1 | 6/2016 |
| WO | 16094880 A1 | 6/2016 |
| WO | 16103233 A2 | 6/2016 |
| WO | 2016106244 A1 | 6/2016 |
| WO | 16115326 A1 | 7/2016 |
| WO | 16118715 A1 | 7/2016 |
| WO | 16118726 A2 | 7/2016 |
| WO | 16118780 A1 | 7/2016 |
| WO | 16130600 A2 | 8/2016 |
| WO | 2016131009 A1 | 8/2016 |
| WO | 16135557 A2 | 9/2016 |
| WO | 16135558 A2 | 9/2016 |
| WO | 16145150 A2 | 9/2016 |
| WO | 16154579 A2 | 9/2016 |
| WO | 16154596 A1 | 9/2016 |
| WO | 16156404 A1 | 10/2016 |
| WO | 16164356 A1 | 10/2016 |
| WO | 16182893 A1 | 11/2016 |
| WO | 16182917 A1 | 11/2016 |
| WO | 16183298 A2 | 11/2016 |
| WO | 2016182959 A1 | 11/2016 |
| WO | 16205703 A1 | 12/2016 |
| WO | 2016201272 A1 | 12/2016 |
| WO | 17053729 A1 | 3/2017 |
| WO | 17059241 A1 | 4/2017 |
| WO | 17077394 A2 | 5/2017 |
| WO | 17115268 A1 | 7/2017 |
| WO | 17160890 A1 | 9/2017 |
| WO | 17182881 A2 | 10/2017 |
| WO | 17191503 A1 | 11/2017 |
| WO | 17218948 A2 | 12/2017 |
| WO | 18009506 A1 | 1/2018 |
| WO | 18022619 A1 | 2/2018 |
| WO | 18035423 A1 | 2/2018 |
| WO | 18039440 A1 | 3/2018 |
| WO | 18039448 A1 | 3/2018 |
| WO | 2018064387 A1 | 4/2018 |

OTHER PUBLICATIONS

Lederer et al., "Beta testing: preclinical genome editing in [beta]-globin disoprders", Cell and Gene Therapy Insghts, 1(2): 2015.

Lettre et al., "Fetal haemoglobin in sickle-cell disease: from genetic epidemiology to new therapeutic strategies", The Lancet (Letters to the Editor), The Lancet Publishing Group, GB, 387(10037):2554-2564. 2016.

Canver et al., "Customizing the genome as therapy for the b-hemoglobinopathies", Blood, 127(21):2536-2545. 2016.

(56) References Cited

OTHER PUBLICATIONS

Perumbeti et al., "A novel human gamma-globin gene vector for genetic correction of sickle cell anemia in a humanized sickle mouse model: critical determinants for successful correction", Blood, 2009, 114(6):1174-1185.
Eridani, et al., "Fetal hemoglobin reactivation nad cell engineering in the treatment of sickle cell anemia", Journal of Blood Medicine, 2011, 2:23-30.
Papanikolaou et al., "The New Self-Inactivating Lentiviral Vector for Thalassemia Gene Therapy Combining Two HPFH Activating Eements Corrects Human Thalassemi Hematopoetic Stem Cells", Human Gene Therapy, 2012, 23:15-31.
Breda et al., "Gene Therapy in Thalassemia and Hemoglobinopathies", Mediterr J Hematol Infect Dis, 2009, 1(1) e2009008.
Smith et al., "Hemoglobin genetics: recent contributions of GWAS and gene editing", Human Molecular Genetics, 2016, 25(R2):R99-R105.
Cottle et al., "Treating Hemoglobinopathies Using Gene Correction Approaches: Promises and Challenges", Human Genetics, 2016, 135(9):993-1010.
Cebrian et al, "Combination of a triple alpha-globin gene with beta-thalassemia in a gypsy family: importance of the genetic testing in the diagnosis and search for a donor for bone marrow transplantation for one of their children", BMC Res Notes, 2016, 9(1):220.
Glaser et al., "The therapeuic potential of genome editing for Beta-thalassemia", F1000Res, 2015, 4:F1000 Faculty Rev-1431.
Mettananda et al., "Understanding alpha-globin gene regulation and implications for the treatment of Beta-thalassemia", Ann N Y Acad Sci., 2016, 68(1):16-24.
Yang et al., "Naive Induced Pluripotent Stem Cells Generated From Beta-Thalassemia Fibroblasts AllowEfficient Gene Correction with CRISPR/Cas9", Stem Cells Transl Med., 2016, 5(1):8-19.
Reardon, S., "Leukaemia success heralds wave of gene-editing therapies", Nature, 2015, 527(7577):146-147.
Bauer and Orkin, "Hemoglobin switching's surprise: the versatile transcription factor BCL11A is a master repressor of fetal hemoglobin", Curr Opin Genet Dev., 2015, 33:62-70.
Ngo and Steinberg, "Genomic aproaches to identifying targets for treating Beta hemoglobinopathies", BMC Medical Genomics, 2015, 8:44-56.
Weinert et al., "Editing the genome to introduce a beneficial naturally occurring mutation associated with increased fetal globin", Nat Commun., 2015, 14(6):7085-7092.
Ma et al., "Factor-induced Reprogramming and Zinc Finger Nuclease-aided Gene Targeting Cause Different Genome Instability in beta-Thalassemia Induced Pluripotent Stem Cels (iPSCs)", J Biol Chem, 2015, 290(19):12079-89.
Sankaran, et al., "Anemia: progress in molecular mechanisms and therapies", Nat Med, 2015, 21(3):221-230.
Finotti et al., "Recent trends in the gene therapy of Beta-thalassemia", J Blood Med., 2015, 6:69-85.
Donato et al., "Hereditary spherocytosis: Review. Part I. History, demographics, pathogenesis, and diagnosis", Arch Argent Pediatr, 2015, 113(1):69-80.
Song et al., "Improved hematopoietic differentiation efficiency of gene-corrected beta-thalassemia induced pluripotent stem cells by CRISPR/Cas9 system", Stem Cells Dev, 2015, 24(9):1053-65.
Xie et al., "Seamless gene correction of beta-thalassemia mutations in patient-specificiPSCs using CRISPR/Cas9 and piggyBac", Genome Res, 2014, 24(9):1526-33.
Chandrakasan and Malik, "Gene Therapy for Hemoglobinopathies: the State of the Field and the Future", 2014, Hematol Oncol Clin North Am, 28(2):199-216.
Voit et al., "Nuclease-mediated gene editing by homologou recombination of the human globin locus", Nucleic Acids Res, 2014,42(2):1365-78.
Chin et al., "Triplex-forming peptide nucleic acids induce heritable elevations in gamma-globin expression in hematopoietic progenitor cells", Mol Ther, 2013, 21(3):580-7.

McNeer et al., "Polymer delivery systems for site-specific genome editing", J Control Release, 2011, 155(2):312-6.
Moorjani and Isaac, "Neurotic manifestations in adolescents with thalassemia major", Indian J. pediatr., 2006, 73(7):603-7.
Gruenert et al., "Sequence-specific modification of genomic DNA by small DNA fragments", J Clin Invest, 2003, 121(5):637-41.
Yuan et al., "Defective assembly of membrane proteins in erythroid precursors of beta-thalassemic mice", Blood, 1994, 84(2):632-7.
Sanjana, Neville E. et al., "Improved vectors and genome-wide libraries for CRISPR screening" Nat Methods. Aug. 2014; 11(8): 783-784.
Sankaran, Vijay G. et al., "A functional element necessary for fetal hemoglobin silencing" NEJM, Sep. 1, 2011 365:807-814.
Shalem, Ophir et al., "Genome-Scale CRISPR-Cas9 Knockout Screening in Human Cells" Science. Jan. 3, 2014;343(6166):84-87.
Shalem, Ophir et al., "High-throughput functional genomics using CRISPR-Cas9" Nature Reviews: Genetics (May 2015) 16, 299-311.
Slaymaker, Ian M. et al., "Rationally engineered Cas9 nucleases with improved specificity" Science. Jan. 1, 2016;351(6268):84-8.
Stern, Adi et al., "Self-targeting by CRISPR: gene regulation or autoimmunity?" Trends. Genet (2010) 28: 335-340.
Sternberg, Samuel H. et al., "DNA interrogation by the CRISPR RNA-guided endonuclease Cas9" Nature. Mar. 6, 2014;507(7490):62-7.
Swiech, Lukasz, et al., "In vivo interrogation of gene function in the mammalian brain using CRISPR-Cas9" Nat Biotechnol. Jan. 2015;33(1):102-6.
Taylor, C.F. et al. "Genomic deletions in MSH2 or MLH1 are a frequent cause of hereditary non-polyposis colorectal Dancer: Identification of novel and recurrent deletions by MLPA" Hum Mutat. 2003;22(6):428-33.
Tsai, Shengdar Q. et al., "Dimeric CRISPR RNA-guided FokI nucleases for highly specific genome editing" Nat Biotechnol. Jun. 2014;32(6):569-76.
Tsai, Shengdar Q. et al., "GUIDE-seq enables genome-wide profiling of off-target cleavage by CRISPR-Cas nucleases" Nat Biotechnol. Feb. 2015;33(2): 187-197.
Wang, Haoyi et al., "One-step generation of mice carrying mutations in multiple genes by CRISPR/Cas-mediated genome engineering" Cell, 2013, 153(4):910-918.
Wiedenheft, Blake et al., "RNA-guided genetic silencing systems in bacteria and archaea" Nature (2012) 482:331-8.
Wu, Xuebing et al.," Genome-wide binding of the CRISPR endonuclease Cas9 in mammalian cells" Nat Biotechnol. Jul. 2014;32(7):670-6.
Xiao, An et al., "CasOT: a genome-wide Cas9/gRNA off-target searching tool" Bioinformatics. Apr. 15, 2014;30(8):1180-1182.
Xu, Jian et al., "Correction of sickle cell disease in adult mice by interference with fetal hemoglobin silencing" Science. Nov. 18, 2011;334(6058):993-6.
Xu, Han et al., "Sequence determinants of improved CRISPR sgRNA design" Genome Research (Aug. 2015) 25, 1147-1157.
Yu, Bing et al., "DNA mutation detection using denaturing high-performance liquid chromatography (DHPLC)" Current Protocols in Human Genetics (2006) 7.10.1-7.10.14.
Zetsche, Bernd et al., "Cpf1 is a single RNA-guided endonuclease of a class 2 CRISPR-Cas system" Cell, Oct. 22, 2015, 163:759-771.
Zetsche, Bernd et al., "A split-Cas9 architecture for inducible genome editing and transcription modulation" Nat Biotechnol. Feb. 2015;33(2): 139-42.
https://www.addgene.org/52963/.
Bauer, D. E. et al. "An erythroid enhancer of BCL11A subject to genetic variation determines fetal hemoglobin level." Science, 2013, vol. 342, 6155, p. 253-257 and Supplementary Material. doi:10.1126/science.1242088.
Lopatina, V., Treating sickle-cell anaemia with a combination of gene therapy methods and RNA interference, Cell Transplantology and Tissue Engineering, 2006, No. 2(4), p. 11-12.
Bae, Sangsu et al., "Cas-OFFinder: a fast and versatile algorithm that searches for potential off-target sites of Cas9 RNA-guided endonucleases" Bioinformatics. May 15, 2014;30(10):1473-5.
Barrangou, Rodolphe et al., "CRISPR Provides Acquired Resistance Against Viruses in Prokaryotes" (2007) Science 315: 1709-1712.

(56) References Cited

OTHER PUBLICATIONS

Bolotin, Alexander et al., "Clustered regularly interspaced short palindrome repeats (CRISPRs) have spacers of extrachromosomal origin" (2005) Microbiol. 151: 2551-2561.
Boulad, Farid et al., "Safe mobilization of CD34+ cells in adults with p-thalassemia and validation of effective globin gene transfer for clinical investigation" Blood, Mar. 6, 2014;123(10):1483-6.
Brouns, Stan JJ et al., "Small CRISPR RNAs guide antiviral defense in prokaryotes" (2008) Science 321: 960-964.
Chen, Sidi et al., "Genome-wide CRISPR Screen in a Mouse Model of Tumor Growth and Metastasis," Cell. Mar. 12, 2015;160(6):1246-60.
Chiappini, C. et al., "Biodegradable silicon nanoneedles delivering nucleic acids intracellularly induce localized in Vivo neovascularization" Nat Mater. May 2015;14(5):532-9.
Chylinski, Krzysztof et al., "The tracrRNA and Cas9 families of type II CRISPR-Cas immunity systems" RNA Biol. May 1, 2013; 10(5): 726-737.
Cong, Le et al., "Multiplex Genome Engineering Using CRISPR/Cas Systems" SCIENCE 2013, 399(6121):819-823.
Deveau, Hélène et al., "Phage response to CRISPR-encoded resistance in Streptococcus thermophilus" J Bacteriol 2008; 190(4): 1390-1400.
Do, Hongdo et al., "High resolution melting analysis for rapid and sensitive EGFR and KRAS mutation detection in formalin fixed paraffin embedded biopsies" BMC Cancer May 21, 2008;8:142.
Doench, John G. et al., "Rational design of highly active sgRNAs for CRISPR-Cas9-mediated gene inactivation" Nat Biotechnol. Dec. 2014;32(12):1262-7.
Fackenthal, Donna Lee, et al., "Denaturing high-performance liquid chromatography for mutation detection and genotyping" Methods Mol Biol. (2005) 311:73-96.
Flomenberg, Neal et al., "The use of AMD3100 plus G-CSF for autologous hematopoietic progenitor cell mobilization is superior to G-CSF alone" Blood. Sep. 1, 2005;106(5):1867-74.
Fodde, R, et al., "Mutation detection by denaturing gradient gel electrophoresis(DGGE)" Hum Mutat. 1994;3(2):83-94.
Fu, Yanfang et al., "High-frequency off-target mutagenesis induced by CRISPR-Cas nucleases in human cells" Nat Biotechnol. Sep. 2013;31(9):822-6.
Glavac, Damjan et al.,"Applications of heteroduplex analysis for mutation detection in disease genes" Hum Mutat. 1995;6(4):281-7.
Grissa, Ibtissem et al.,"The CRISPRdb database and tools to display CRISPRs and to generate dictionaries of spacers and repeats" BMC Bioinformatics (2007) 8:172.
Haft, Daniel H. et al., "A guild of 45 CRISPR-associated (Cas) protein families and multiple CRISPR/Cas subtypes exist in prokaryotic genomes" PLoS Comput Biol. Nov. 2005;1(6):e60.
Heigwer, Florian et al., "E-CRISP: fast CRISPR target site identification" Nat Methods, Feb. 2014, 11(2): 122-123.
Hendel, Ayal et al., "Chemically modified guide RNAs enhance CRISPR-Cas genome editing in human primary cells" Nat Biotechnol. Sep. 2015;33(9):985-989.
Horvath, Philippe et al., "CRISPR/Cas, the immune system of bacteria and archaea" Science 2010; 327(5962) 167-170.
Hou, Zhonggang et al., "Efficient genome engineering in human pluripotent stem cells using Cas9 from Neisseria meningitidis" Proc Natl Acad Sci USA. Sep. 24, 2013;110(39):15644-9.
Hsu, Patrick D. et al., "DNA targeting specificity of RNA-guided Cas9 nucleases" Nat Biotechnol, 2013, 31 (9): 827-32.
Hsu, Patrick D. et al., "Development and Applications of CRISPR-Cas9 for Genome Engineering" Cell (Jun. 5, 2014) 157, 1262-1278.
Jiang, Wenyan et al.,"RNA-guided editing of bacterial genomes using CRISPR-Cas systems" Nat Biotechnol, Mar. 2013; 31(3):233-9.

Jinek, Martin et al., "A programmable dual-RNA-guided DNA endonuclease in adaptive bacterial immunity" Science. Aug. 17, 2012;337(6096):816-21.
Jurinke, Christian et al., "MALDI-TOF mass spectrometry: a versatile tool for high-performance DNA analysis" Mol. Biotechnol. (2004) 26, 147-163.
Kakavas, V. Konstantinos, et al., "PCR-SSCP: A method for the molecular analysis of genetic diseases" Mol Biotechnol. 2008;38(2): 155-63.
Kleinstiver, Benjamin P. et al., "High-fidelity CRISPR-Cas9 nucleases with No. detectable genome-wide off-target affects" Nature. Jan. 28, 2016;529(7587):490-5.
Konermann, Silvana et al., "Optical control of mammalian endogenous transcription and epigenetic states" Nature. Aug. 22, 2013;500(7463):472-6.
Konermann, Silvana et al., "Genome-scale transcriptional activation by an engineered CRISPR-Cas9 complex" Nature, Jan. 29, 2015;517(7536):583-8.
Kothiyal, Prachi et al., "An Overview of Custom Array Sequencing" Curr Protoc Hum Genet. Apr. 2009; 0 7: Unit-7.17.
Kunin, Victor et al., "Evolutionary conservation of sequence and secondary structures in CRISPR repeats" Genome Biol, (2007) 8: R61.
Lin, Steven et al., "Enhanced homology-directed human genome engineering by controlled timing of CRISPR/Cas9 delivery" Elife. Dec. 15, 2014;3:e04766.
Makarova, Kira S. et al., "Evolution and classification of the CRISPR-Cas systems" Nat Rev Microbiol. Jun. 2011;9(6):467-77.
Mali, Prashant et al., "RNA-Guided Human Genome Engineering via Cas9" Science, 2013, 339(6121): 823-826.
Marraffini, Luciano et al., "CRISPR interference limits horizontal gene transfer in staphylococci by targeting DNA" (2008) Science 322: 1843-1845.
Mojica, Francisco J. M. et al., "Intervening sequences of regularly spaced prokaryotic repeats derive from foreign genetic elements" J. Mol. Evol. (2005) 60: 174-182.
Newton, C.R. et al. "Analysis of any point mutation in DNA. The amplification refractory mutation system(ARMS)" Nucleic Acids Res. 1989;17(7):2503-16.
Nishimasu, Hiroshi et al., "Crystal structure of Cas9 in complex with guide RNA and target DNA" Cell. Feb. 27, 2014;156(5):935-49.
Nishimasu, Hiroshi et al., "Crystal Structure of Staphylococcus aureus Cas9" Cell (Aug. 27, 2015)162, 1113-1126.
Parnas, Oren et al.,"A Genome-wide CRISPR Screen in Primary Immune Cells to Dissect Regulatory Networks" Cell (Jul. 30, 2015) 162, 675-686.
Platt, Randall J. et al.," CRISPR-Cas9 Knockin Mice for Genome Editing and Cancer Modeling" Cell (2014) 159(2): 440-155.
Pourcel, C. et al., "CRISPR elements in Yersinia pestis acquire new repeats by preferential uptake of bacteriophage DNA, and provide additional tools for evolutionary studies" Microbiol. (2005) 151: 653-663.
Ramanan, Vyas et al., "CRISPR/Cas9 cleavage of viral DNA efficiently suppresses hepatitis B virus" Scientific Reports 5:10833. doi: 10.1038/srep10833 (Jun. 2, 2015).
Ran, F. Ann et al., ""Double nicking by RNA-guided CRISPR Cas9 for enhanced genome editing specificity" Cell. Sep. 12, 2013;154(6):1380-9.
Ran, F. Ann et al., "Genome engineering using the CRISPR-Cas9 system" Nature Protocols, Oct. 24, 2013;8(11):2281-308.
Ran, F. Ann et al., "In vivo genome editing using *Staphylococcus aureus* Cas9" Nature, vol. 520, 2015, pp. 186-191.
Sakuma, Tetsushi et al., "MMEJ-assisted gene knock-in using TALENs and CRISPR-Cas9 with the PITCh systems" Nat Protoc. Jan. 2016; 11(1):118-33.

Cont. From
FIG.4B

GAAGCACCCTTCAGCAGTCCAGTTCCACACACTGGCTTCTGGAACCTGTGAGTTATCAATAAGCTCCTAGTCCAGACGCCATGGTCATTTCACAGAGGAGGACAAGGCTA 3'
CTTCGTGGGAAGTCGTCAAGGTGTGTGACCGAAGACCTTGGACGAATCAGGTCTGCCGGTACCCAGTAAAGTGTCTCCTCCTGTTCCGAT 5' 492

MetGlyHisPheThrGluGluAspLysAla
                                                                    ENSG00000213934.6 chr11: 5,249,833–5,249,927; hg38

HBG1

☐ EKLF     ☐ +1 Inr     ☐ +27 MTE     ☐ +32 DPE

Cont.
From
FIG.4C

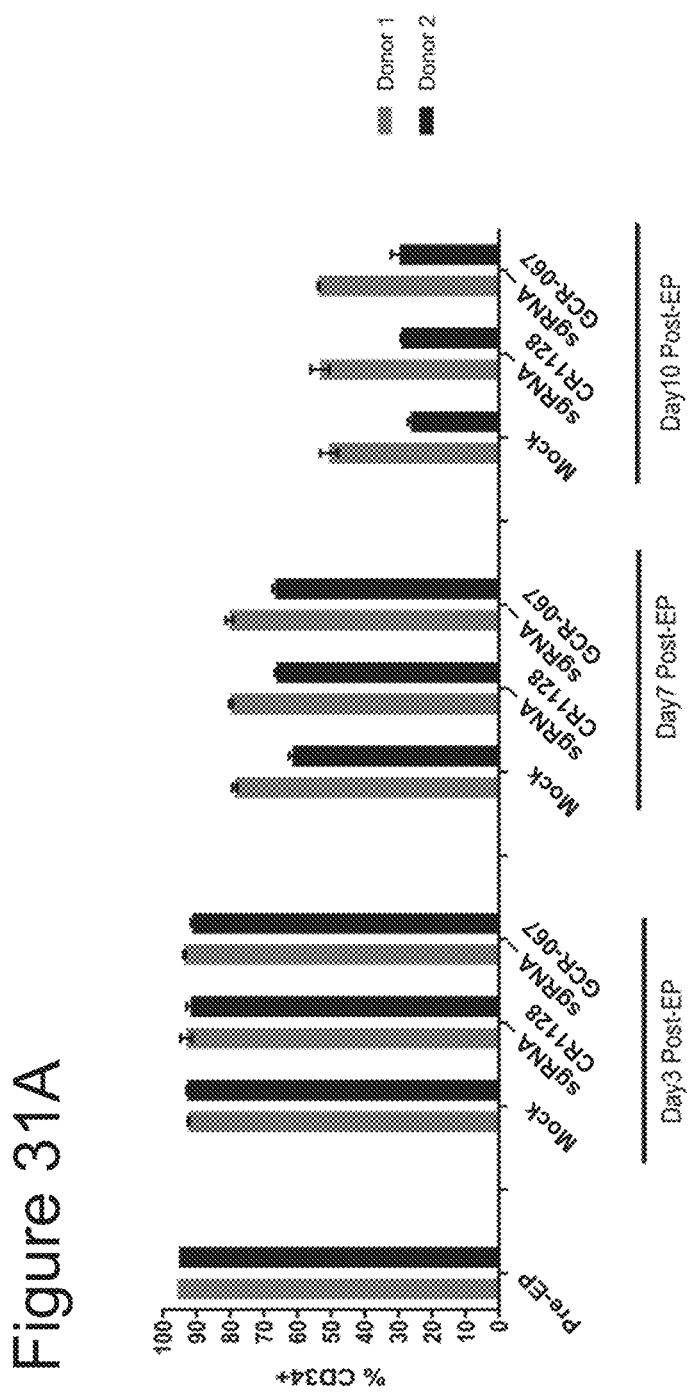

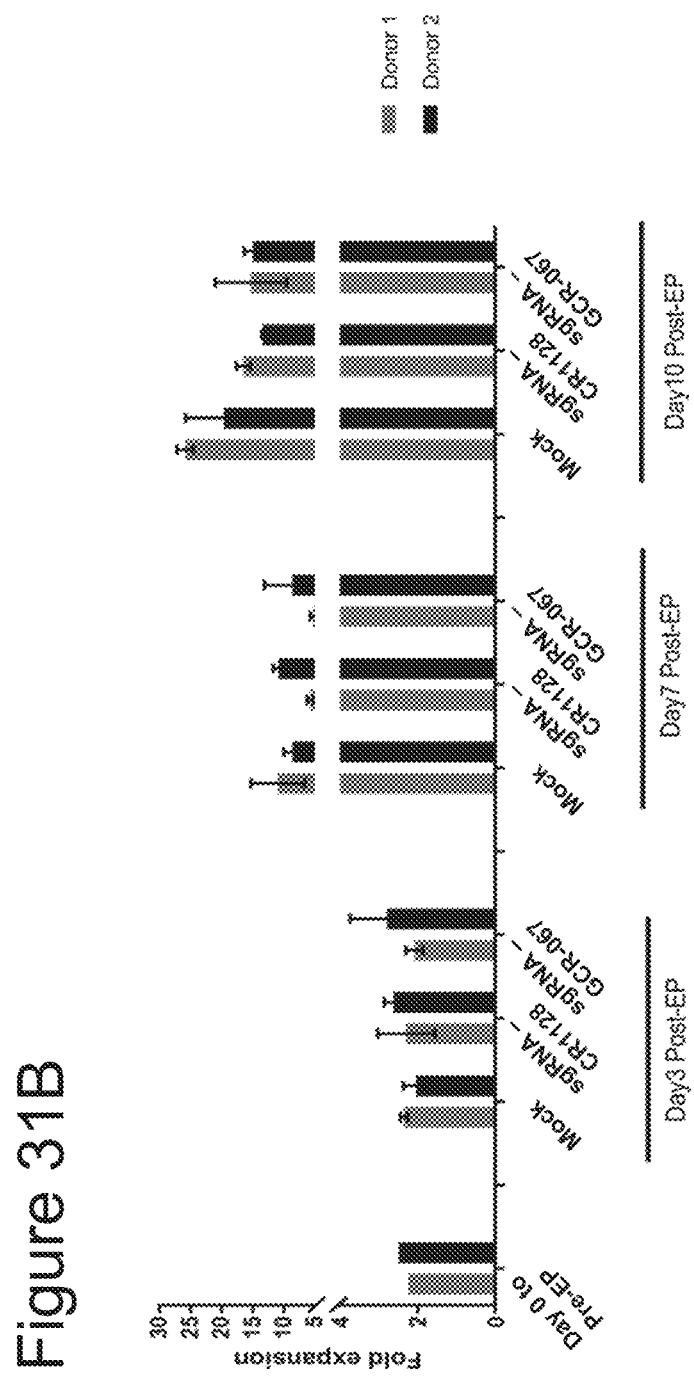

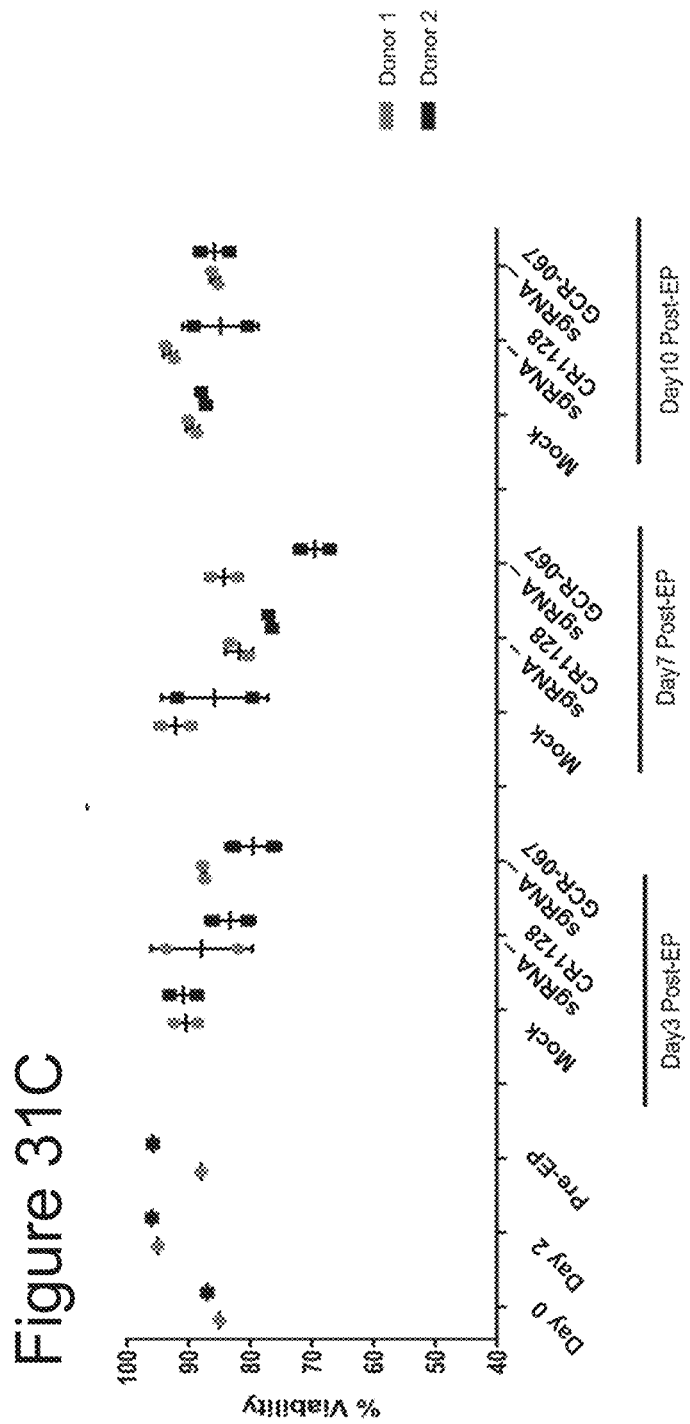

COMPOSITIONS AND METHODS FOR THE TREATMENT OF HEMOGLOBINOPATHIES

CROSS REFERENCE TO RELATED APPLICATIONS

This application is a 371 U.S. national phase application of the International Application No. PCT/IB2018/050712, filed on Feb. 5, 2018, which claims priority to, and the benefit of, U.S. Provisional patent application No. 62/455,464, filed on Feb. 6, 2017, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 30, 2018, is named PAT057603-WO-PCT_SL.txt and is 258,837 bytes in size.

BACKGROUND

CRISPRs (Clustered Regularly Interspaced Short Palindromic Repeats) evolved in bacteria as an adaptive immune system to defend against viral attack. Upon exposure to a virus, short segments of viral DNA are integrated into the CRISPR locus of the bacterial genome. RNA is transcribed from a portion of the CRISPR locus that includes the viral sequence. That RNA, which contains sequence complimentary to the viral genome, mediates targeting of a Cas9 protein to the sequence in the viral genome. The Cas9 protein cleaves and thereby silences the viral target.

Recently, the CRISPR/Cas system has been adapted for genome editing in eukaryotic cells. The introduction of site-specific single (SSBs) or double strand breaks (DSBs) allows for target sequence alteration through, for example, non-homologous end joining (NHEJ) or homology-directed repair (HDR).

SUMMARY OF THE INVENTION

Without being bound by theory, the invention is based in part on the discovery that CRISPR systems, e.g., Cas9 CRISPR systems, e.g., as described herein, can be used to modify cells (e.g., hematopoietic stem and progenitor cells (HSPCs)), for example, at a nondeltional HPFH region, as described herein, to increase fetal hemoglobin (HbF) expression and/or decrease expression of beta globin (e.g., a beta globin gene having a disease-causing mutation), for example in progeny, for example red blood cell progeny, of the modified cells, and that the modified cells (e.g., modified HSPCs) may be used to treat hemoglobinopathies, e.g., sickle cell disease and beta thalassemia. In one aspect, it has surprisingly been shown herein that introduction of gene editing systems, e.g., CRISPR systems, e.g., as described herein, to cells (e.g., HSPCs), that target regions of the genome to which no known HPFH mutation or deletion maps creates modified HSPCs (e.g., HSPCs that comprise one or more indels, for example, as described herein) that are able to efficiently engraft into an organism, persist long-term in the engrafted organism, and differentiate, including into erythrocytes with increased fetal hemoblobin expression. In addition, these modified HSPCs are capable of being cultured ex vivo, for example, in the presence of a stem cell expander (for example as described herein) under conditions that cause them to expand and proliferate while maintaining stemness. When the gene editing systems, e.g., CRISPR systems, e.g, as described herein, are introduced into HPSCs derived from sickle cell disease patients, the modified cells and their progeny (e.g., erythroid progeny) surprisingly show not only upregulation of fetal hemoglobin, but also show a significant decrease in sickle beta-globin, and a significant decrease in the number of sickle cells and increase the number of normal red blood cells, relative to unmodified cell populations.

Thus, in an aspect, the invention provides CRISPR systems (e.g., Cas CRISPR systems, e.g., Cas9 CRISPR systems, e.g., S. pyogenes Cas9 CRISPR systems) comprising one or more, e.g., one, gRNA molecule as described herein. Any of the gRNA molecules described herein may be used in such systems, and in the methods and cells described herein.

In an aspect, the invention provides a gRNA molecule including a tracer and crRNA, wherein the crRNA includes a targeting domain that:

a) is complementary with a target sequence of a nondeletional HFPH region (e.g., a human nondeletional HPFH region);

b) is complementary with a target sequence within the genomic nucleic acid sequence at Chr11:5,249,833 to Chr11:5,250,237, – strand, hg38;

c) is complementary with a target sequence within the genomic nucleic acid sequence at Chr11:5,254,738 to Chr11:5,255,164, – strand, hg38;

d) is complementary with a target sequence within the genomic nucleic acid sequence at Chr11:5,250,094-5,250,237, – strand, hg38;

e) is complementary with a target sequence within the genomic nucleic acid sequence at Chr11:5,255,022-5,255,164, – strand, hg38;

f) is complementary with a target sequence within the genomic nucleic acid sequence at Chr11:5,249,833-5,249,927, – strand, hg38;

g) is complementary with a target sequence within the genomic nucleic acid sequence at Chr11:5,254,738-5,254,851, – strand, hg38;

h) is complementary with a target sequence within the genomic nucleic acid sequence at Chr11:5,250,139-5,250,237, – strand, hg38; or i) combinations thereof.

In embodiments, the targeting domain includes, e.g., consists of, any one of SEQ ID NO: 1 to SEQ ID NO: 72. In embodiments, the targeting domain includes, e.g., consists of, any one of SEQ ID NO: 1, SEQ ID NO: 6, SEQ ID NO: 8, SEQ ID NO: 9, SEQ ID NO: 10, SEQ ID NO: 11, SEQ ID NO: 12, SEQ ID NO: 28, SEQ ID NO: 34, SEQ ID NO: 45, SEQ ID NO: 46, SEQ ID NO: 47, SEQ ID NO: 48, SEQ ID NO: 50, SEQ ID NO: 51, SEQ ID NO: 53, SEQ ID NO: 54, SEQ ID NO: 58, SEQ ID NO: 62, SEQ ID NO: 63, or SEQ ID NO: 67. In embodiments, the targeting domain includes, e.g., consists of, any one of a) SEQ ID NO: 6, SEQ ID NO: 8, SEQ ID NO: 28, SEQ ID NO: 34, SEQ ID NO: 48, SEQ ID NO: 51, or SEQ ID NO: 67; orb) SEQ ID NO: 1, SEQ ID NO: 8, SEQ ID NO: 9, SEQ ID NO: 10, SEQ ID NO: 12, or SEQ ID NO: 54. In embodiments, the gRNA molecule includes a targeting domain which includes, e.g., consists of, SEQ ID NO: 8. In embodiments, the gRNA molecule includes a targeting domain which includes, e.g., consists of, SEQ ID NO: 67. In embodiments, the gRNA molecule includes a targeting domain which includes (e.g., consists of) a fragment of any of the sequences above.

In any of the aforementioned aspects and embodiments, the gRNA molecule may further have regions and/or properties described herein. In embodiments, the gRNA molecule includes a fragment of any of the aforementioned targeting domains. In embodiments, the targeting domain includes, e.g., consists of, 17, 18, 19, or 20 consecutive nucleic acids of any one of the recited targeting domain sequences. In embodiments, the 17, 18, 19, or 20 consecutive nucleic acids of any one of the recited targeting domain sequences are the 17, 18, 19, or 20 consecutive nucleic acids disposed at the 3' end of the recited targeting domain sequence. In other embodiments, the 17, 18, 19, or 20 consecutive nucleic acids of any one of the recited targeting domain sequences are the 17, 18, 19, or 20 consecutive nucleic acids disposed at the 5' end of the recited targeting domain sequence. In other embodiments, the 17, 18, 19, or 20 consecutive nucleic acids of any one of the recited targeting domain sequences do not include either the 5' or 3' nucleic acid of the recited targeting domain sequence. In embodiments, the targeting domain consists of the recited targeting domain sequence.

In an aspect, including in any of the aforementioned aspects and embodiments, a portion of the crRNA and a portion of the tracr hybridize to form a flagpole including SEQ ID NO: 182 or 183. In an aspect, including in any of the aforementioned aspects and embodiments, the flagpole further includes a first flagpole extension, located 3' to the crRNA portion of the flagpole, wherein said first flagpole extension includes SEQ ID NO: 184. In an aspect, including in any of the aforementioned aspects and embodiments, the flagpole further includes a second flagpole extension located 3' to the crRNA portion of the flagpole and, if present, the first flagpole extension, wherein said second flagpole extension includes SEQ ID NO: 185.

In an aspect, including in any of the aforementioned aspects and embodiments, the tracr includes SEQ ID NO: 224 or SEQ ID NO: 225. In an aspect, including in any of the aforementioned aspects and embodiments, the tracr includes SEQ ID NO: 232, optionally further including, at the 3' end, an additional 1, 2, 3, 4, 5, 6, or 7 uracil (U) nucleotides. In an aspect, including in any of the aforementioned aspects and embodiments, the crRNA includes, from 5' to 3', [targeting domain]–: a) SEQ ID NO:182; b) SEQ ID NO: 183; c) SEQ ID NO: 199; d) SEQ ID NO: 200; e) SEQ ID NO: 201; f) SEQ ID NO: 202; or g) SEQ ID NO: 226.

In an aspect, including in any of the aforementioned aspects and embodiments, the tracr includes, from 5' to 3': a) SEQ ID NO: 187; b) SEQ ID NO: 188; c) SEQ ID NO: 203; d) SEQ ID NO: 204; e) SEQ ID NO: 224; f) SEQ ID NO: 225; g) SEQ ID NO: 232; h) SEQ ID NO: 227; i) (SEQ ID NO: 228; j) SEQ ID NO: 229; k) any of a) to j), above, further including, at the 3' end, at least 1, 2, 3, 4, 5, 6 or 7 uracil (U) nucleotides, e.g., 1, 2, 3, 4, 5, 6, or 7 uracil (U) nucleotides; l) any of a) to k), above, further including, at the 3' end, at least 1, 2, 3, 4, 5, 6 or 7 adenine (A) nucleotides, e.g., 1, 2, 3, 4, 5, 6, or 7 adenine (A) nucleotides; or m) any of a) to l), above, further including, at the 5' end (e.g., at the 5' terminus), at least 1, 2, 3, 4, 5, 6 or 7 adenine (A) nucleotides, e.g., 1, 2, 3, 4, 5, 6, or 7 adenine (A) nucleotides.

In an aspect, including in any of the aforementioned aspects and embodiments, the targeting domain and the tracr are disposed on separate nucleic acid molecules. In an aspect, including in any of the aforementioned aspects and embodiments, the targeting domain and the tracr are disposed on separate nucleic acid molecules, and the nucleic acid molecule including the targeting domain includes SEQ ID NO: 201, optionally disposed immediately 3' to the targeting domain, and the nucleic acid molecule including the tracr includes, e.g., consists of, SEQ ID NO: 224. In an aspect, including in any of the aforementioned aspects and embodiments, the crRNA portion of the flagpole includes SEQ ID NO: 201 or SEQ ID NO: 202. In an aspect, including in any of the aforementioned aspects and embodiments, the tracr includes SEQ ID NO: 187 or 188, and optionally, if a first flagpole extension is present, a first tracr extension, disposed 5' to SEQ ID NO: 187 or 188, said first tracr extension including SEQ ID NO: 189.

In an aspect, including in any of the aforementioned aspects and embodiments, the targeting domain and the tracr are disposed on a single nucleic acid molecule, for example, wherein the tracr is disposed 3' to the targeting domain. In an aspect, the gRNA molecule includes a loop, disposed 3' to the targeting domain and 5' to the tracr. In embodiments, the loop includes SEQ ID NO: 186. In an aspect, including in any of the aforementioned aspects and embodiments, the gRNA molecule includes, from 5' to 3', [targeting domain]–: (a) SEQ ID NO: 195; (b) SEQ ID NO: 196; (c) SEQ ID NO: 197; (d) SEQ ID NO: 198; (e) SEQ ID NO: 231; or (f) any of (a) to (e), above, further including, at the 3' end, 1, 2, 3, 4, 5, 6 or 7 uracil (U) nucleotides.

In an aspect, including in any of the aforementioned aspects and embodiments, the targeting domain and the tracr are disposed on a single nucleic acid molecule, and wherein said nucleic acid molecule includes, e.g., consists of, said targeting domain and SEQ ID NO: 231, optionally disposed immediately 3' to said targeting domain.

In an aspect, including in any of the aforementioned aspects and embodiments, one, or optionally more than one, of the nucleic acid molecules including the gRNA molecule includes:

a) one or more, e.g., three, phosphorothioate modifications at the 3' end of said nucleic acid molecule or molecules;

b) one or more, e.g., three, phosphorothioate modifications at the 5' end of said nucleic acid molecule or molecules;

c) one or more, e.g., three, 2'-O-methyl modifications at the 3' end of said nucleic acid molecule or molecules;

d) one or more, e.g., three, 2'-O-methyl modifications at the 5' end of said nucleic acid molecule or molecules;

e) a 2' O-methyl modification at each of the $4^{th}$-to-terminal, $3^{rd}$-to-terminal, and $2^{nd}$-to-terminal 3' residues of said nucleic acid molecule or molecules;

f) a 2' O-methyl modification at each of the $4^{th}$-to-terminal, $3^{rd}$-to-terminal, and $2^{nd}$-to-terminal 5' residues of said nucleic acid molecule or molecules; or f) any combination thereof.

In an aspect, the invention provides a gRNA molecule, including, e.g., consisting of, the sequence:
(a) SEQ ID NO: 74;
(b) SEQ ID NO: 75; or
(c) SEQ ID NO: 76.

In an aspect, the invention provides a gRNA molecule, including, e.g., consisting of, the sequence:
(a) a crRNA including, e.g., consisting of, SEQ ID NO: 77, and a tracr including, e.g., consisting of, SEQ ID NO: 224;
(b) a crRNA including, e.g., consisting of, SEQ ID NO: 77, and a tracr including, e.g., consisting of, SEQ ID NO: 73;
(c) a crRNA including, e.g., consisting of, SEQ ID NO: 78, and a tracr including, e.g., consisting of, SEQ ID NO: 224; or
(d) a crRNA including, e.g., consisting of, SEQ ID NO: 78, and a tracr including, e.g., consisting of, SEQ ID NO: 73.

In an aspect, the invention provides a gRNA molecule, including, e.g., consisting of, the sequence:
(a) SEQ ID NO: 79;
(b) SEQ ID NO: 80; or
(c) SEQ ID NO: 81.

In an aspect, the invention provides a gRNA molecule, including, e.g., consisting of, the sequence:
(a) a crRNA including, e.g., consisting of, SEQ ID NO: 82, and a tracr including, e.g., consisting of, SEQ ID NO: 224;
(b) a crRNA including, e.g., consisting of, SEQ ID NO: 82, and a tracr including, e.g., consisting of, SEQ ID NO: 73;
(c) a crRNA including, e.g., consisting of, SEQ ID NO: 83, and a tracr including, e.g., consisting of, SEQ ID NO: 224; or
(d) a crRNA including, e.g., consisting of, SEQ ID NO: 83, and a tracr including, e.g., consisting of, SEQ ID NO: 73.

In an aspect, the invention provides a gRNA molecule, including, e.g., consisting of, the sequence:
(a) SEQ ID NO: 84;
(b) SEQ ID NO: 85; or
(c) SEQ ID NO: 86.

In an aspect, the invention provides a gRNA molecule, including, e.g., consisting of, the sequence:
(a) a crRNA including, e.g., consisting of, SEQ ID NO: 87, and a tracr including, e.g., consisting of, SEQ ID NO: 224;
(b) a crRNA including, e.g., consisting of, SEQ ID NO: 87, and a tracr including, e.g., consisting of, SEQ ID NO: 73;
(c) a crRNA including, e.g., consisting of, SEQ ID NO: 88, and a tracr including, e.g., consisting of, SEQ ID NO: 224; or
(d) a crRNA including, e.g., consisting of, SEQ ID NO: 88, and a tracr including, e.g., consisting of, SEQ ID NO: 73.

In an aspect, the invention provides a gRNA molecule, including, e.g., consisting of, the sequence:
(a) SEQ ID NO: 89;
(b) SEQ ID NO: 90; or
(c) SEQ ID NO: 91.

In an aspect, the invention provides a gRNA molecule, including, e.g., consisting of, the sequence:
(a) a crRNA including, e.g., consisting of, SEQ ID NO: 92, and a tracr including, e.g., consisting of, SEQ ID NO: 224;
(b) a crRNA including, e.g., consisting of, SEQ ID NO: 92, and a tracr including, e.g., consisting of, SEQ ID NO: 73;
(c) a crRNA including, e.g., consisting of, SEQ ID NO: 93, and a tracr including, e.g., consisting of, SEQ ID NO: 224; or
(d) a crRNA including, e.g., consisting of, SEQ ID NO: 93, and a tracr including, e.g., consisting of, SEQ ID NO: 73.

In an aspect, the invention provides a gRNA molecule, including, e.g., consisting of, the sequence:
(a) SEQ ID NO: 94;
(b) SEQ ID NO: 95; or
(c) SEQ ID NO: 96.

In an aspect, the invention provides a gRNA molecule, including, e.g., consisting of, the sequence:
(a) a crRNA including, e.g., consisting of, SEQ ID NO: 97, and a tracr including, e.g., consisting of, SEQ ID NO: 224;
(b) a crRNA including, e.g., consisting of, SEQ ID NO: 97, and a tracr including, e.g., consisting of, SEQ ID NO: 73;
(c) a crRNA including, e.g., consisting of, SEQ ID NO: 98, and a tracr including, e.g., consisting of, SEQ ID NO: 224; or
(d) a crRNA including, e.g., consisting of, SEQ ID NO: 98, and a tracr including, e.g., consisting of, SEQ ID NO: 73.

In an aspect, the invention provides a gRNA molecule, including, e.g., consisting of, the sequence:
(a) SEQ ID NO: 99;
(b) SEQ ID NO: 100; or
(c) SEQ ID NO: 101.

In an aspect, the invention provides a gRNA molecule, including, e.g., consisting of, the sequence:
(a) a crRNA including, e.g., consisting of, SEQ ID NO: 102, and a tracr including, e.g., consisting of, SEQ ID NO: 224;
(b) a crRNA including, e.g., consisting of, SEQ ID NO: 102, and a tracr including, e.g., consisting of, SEQ ID NO: 73;
(c) a crRNA including, e.g., consisting of, SEQ ID NO: 103, and a tracr including, e.g., consisting of, SEQ ID NO: 224; or
(d) a crRNA including, e.g., consisting of, SEQ ID NO: 103, and a tracr including, e.g., consisting of, SEQ ID NO: 73.

In an aspect, the invention provides a gRNA molecule, including, e.g., consisting of, the sequence:
(a) SEQ ID NO: 104;
(b) SEQ ID NO: 105; or
(c) SEQ ID NO: 106.

In an aspect, the invention provides a gRNA molecule, including, e.g., consisting of, the sequence:
(a) a crRNA including, e.g., consisting of, SEQ ID NO: 107, and a tracr including, e.g., consisting of, SEQ ID NO: 224;
(b) a crRNA including, e.g., consisting of, SEQ ID NO: 107, and a tracr including, e.g., consisting of, SEQ ID NO: 73;
(c) a crRNA including, e.g., consisting of, SEQ ID NO: 108, and a tracr including, e.g., consisting of, SEQ ID NO: 224; or
(d) a crRNA including, e.g., consisting of, SEQ ID NO: 108, and a tracr including, e.g., consisting of, SEQ ID NO: 73.

In an aspect, the invention provides a gRNA molecule, including, e.g., consisting of, the sequence:
(a) SEQ ID NO: 109;
(b) SEQ ID NO: 110; or
(c) SEQ ID NO: 111.

In an aspect, the invention provides a gRNA molecule, including, e.g., consisting of, the sequence:
(a) a crRNA including, e.g., consisting of, SEQ ID NO: 112, and a tracr including, e.g., consisting of, SEQ ID NO: 224;
(b) a crRNA including, e.g., consisting of, SEQ ID NO: 112, and a tracr including, e.g., consisting of, SEQ ID NO: 73;
(c) a crRNA including, e.g., consisting of, SEQ ID NO: 113, and a tracr including, e.g., consisting of, SEQ ID NO: 224; or
(d) a crRNA including, e.g., consisting of, SEQ ID NO: 113, and a tracr including, e.g., consisting of, SEQ ID NO: 73.

In an aspect, the invention provides a gRNA molecule, including, e.g., consisting of, the sequence:
(a) SEQ ID NO: 114;
(b) SEQ ID NO: 115; or
(c) SEQ ID NO: 116.

In an aspect, the invention provides a gRNA molecule, including, e.g., consisting of, the sequence:

(a) a crRNA including, e.g., consisting of, SEQ ID NO: 117, and a tracr including, e.g., consisting of, SEQ ID NO: 224;

(b) a crRNA including, e.g., consisting of, SEQ ID NO: 117, and a tracr including, e.g., consisting of, SEQ ID NO: 73;

(c) a crRNA including, e.g., consisting of, SEQ ID NO: 118, and a tracr including, e.g., consisting of, SEQ ID NO: 224; or (d) a crRNA including, e.g., consisting of, SEQ ID NO: 118, and a tracr including, e.g., consisting of, SEQ ID NO: 73.

In an aspect, the invention provides a gRNA molecule, including, e.g., consisting of, the sequence:
(a) SEQ ID NO: 119;
(b) SEQ ID NO: 120; or
(c) SEQ ID NO: 121.

In an aspect, the invention provides a gRNA molecule, including, e.g., consisting of, the sequence:
(a) a crRNA including, e.g., consisting of, SEQ ID NO: 122, and a tracr including, e.g., consisting of, SEQ ID NO: 224;

(b) a crRNA including, e.g., consisting of, SEQ ID NO: 122, and a tracr including, e.g., consisting of, SEQ ID NO: 73;

(c) a crRNA including, e.g., consisting of, SEQ ID NO: 123, and a tracr including, e.g., consisting of, SEQ ID NO: 224; or (d) a crRNA including, e.g., consisting of, SEQ ID NO: 123, and a tracr including, e.g., consisting of, SEQ ID NO: 73.

In an aspect, the invention provides a gRNA molecule, including, e.g., consisting of, the sequence:
(a) SEQ ID NO: 124;
(b) SEQ ID NO: 125; or
(c) SEQ ID NO:126.

In an aspect, the invention provides a gRNA molecule, including, e.g., consisting of, the sequence:
(a) a crRNA including, e.g., consisting of, SEQ ID NO: 127, and a tracr including, e.g., consisting of, SEQ ID NO: 224;

(b) a crRNA including, e.g., consisting of, SEQ ID NO: 127, and a tracr including, e.g., consisting of, SEQ ID NO: 73;

(c) a crRNA including, e.g., consisting of, SEQ ID NO: 128, and a tracr including, e.g., consisting of, SEQ ID NO: 224; or (d) a crRNA including, e.g., consisting of, SEQ ID NO: 128, and a tracr including, e.g., consisting of, SEQ ID NO: 73.

In an aspect, the invention provides a gRNA molecule, including, e.g., consisting of, the sequence:
(a) SEQ ID NO: 129;
(b) SEQ ID NO: 130; or
(c) SEQ ID NO: 131.

In an aspect, the invention provides a gRNA molecule, including, e.g., consisting of, the sequence:
(a) a crRNA including, e.g., consisting of, SEQ ID NO: 132, and a tracr including, e.g., consisting of, SEQ ID NO: 224;

(b) a crRNA including, e.g., consisting of, SEQ ID NO: 132, and a tracr including, e.g., consisting of, SEQ ID NO: 73;

(c) a crRNA including, e.g., consisting of, SEQ ID NO: 133, and a tracr including, e.g., consisting of, SEQ ID NO: 224; or (d) a crRNA including, e.g., consisting of, SEQ ID NO: 133, and a tracr including, e.g., consisting of, SEQ ID NO: 73.

In an aspect, the invention provides a gRNA molecule, including, e.g., consisting of, the sequence:
(a) SEQ ID NO: 134;
(b) SEQ ID NO: 135; or
(c) SEQ ID NO:136.

In an aspect, the invention provides a gRNA molecule, including, e.g., consisting of, the sequence:
(a) a crRNA including, e.g., consisting of, SEQ ID NO: 137, and a tracr including, e.g., consisting of, SEQ ID NO: 224;

(b) a crRNA including, e.g., consisting of, SEQ ID NO: 137, and a tracr including, e.g., consisting of, SEQ ID NO: 73;

(c) a crRNA including, e.g., consisting of, SEQ ID NO: 138, and a tracr including, e.g., consisting of, SEQ ID NO: 224; or (d) a crRNA including, e.g., consisting of, SEQ ID NO: 138, and a tracr including, e.g., consisting of, SEQ ID NO: 73.

In an aspect, the invention provides a gRNA molecule, including, e.g., consisting of, the sequence:
(a) SEQ ID NO: 139;
(b) SEQ ID NO: 140; or
(c) SEQ ID NO: 141.

In an aspect, the invention provides a gRNA molecule, including, e.g., consisting of, the sequence:
(a) a crRNA including, e.g., consisting of, SEQ ID NO: 142, and a tracr including, e.g., consisting of, SEQ ID NO: 224;

(b) a crRNA including, e.g., consisting of, SEQ ID NO: 142, and a tracr including, e.g., consisting of, SEQ ID NO: 73;

(c) a crRNA including, e.g., consisting of, SEQ ID NO: 143, and a tracr including, e.g., consisting of, SEQ ID NO: 224; or (d) a crRNA including, e.g., consisting of, SEQ ID NO: 143, and a tracr including, e.g., consisting of, SEQ ID NO: 73.

In an aspect, the invention provides a gRNA molecule, including, e.g., consisting of, the sequence:
(a) SEQ ID NO: 144;
(b) SEQ ID NO: 145; or
(c) SEQ ID NO:146.

In an aspect, the invention provides a gRNA molecule, including, e.g., consisting of, the sequence:
(a) a crRNA including, e.g., consisting of, SEQ ID NO: 147, and a tracr including, e.g., consisting of, SEQ ID NO: 224;

(b) a crRNA including, e.g., consisting of, SEQ ID NO: 147, and a tracr including, e.g., consisting of, SEQ ID NO: 73;

(c) a crRNA including, e.g., consisting of, SEQ ID NO: 148, and a tracr including, e.g., consisting of, SEQ ID NO: 224; or (d) a crRNA including, e.g., consisting of, SEQ ID NO: 148, and a tracr including, e.g., consisting of, SEQ ID NO: 73.

In an aspect, the invention provides a gRNA molecule, including, e.g., consisting of, the sequence:
(a) SEQ ID NO: 149;
(b) SEQ ID NO: 150; or
(c) SEQ ID NO: 151.

In an aspect, the invention provides a gRNA molecule, including, e.g., consisting of, the sequence:

(a) a crRNA including, e.g., consisting of, SEQ ID NO: 152, and a tracr including, e.g., consisting of, SEQ ID NO: 224;

(b) a crRNA including, e.g., consisting of, SEQ ID NO: 152, and a tracr including, e.g., consisting of, SEQ ID NO: 73;

(c) a crRNA including, e.g., consisting of, SEQ ID NO: 153, and a tracr including, e.g., consisting of, SEQ ID NO: 224; or (d) a crRNA including, e.g., consisting of, SEQ ID NO: 153, and a tracr including, e.g., consisting of, SEQ ID NO: 73.

In an aspect, the invention provides a gRNA molecule, including, e.g., consisting of, the sequence:

(a) SEQ ID NO: 154;
(b) SEQ ID NO: 155; or
(c) SEQ ID NO:156.

In an aspect, the invention provides a gRNA molecule, including, e.g., consisting of, the sequence:

(a) a crRNA including, e.g., consisting of, SEQ ID NO: 157, and a tracr including, e.g., consisting of, SEQ ID NO: 224;

(b) a crRNA including, e.g., consisting of, SEQ ID NO: 157, and a tracr including, e.g., consisting of, SEQ ID NO: 73;

(c) a crRNA including, e.g., consisting of, SEQ ID NO: 158, and a tracr including, e.g., consisting of, SEQ ID NO: 224; or (d) a crRNA including, e.g., consisting of, SEQ ID NO: 158, and a tracr including, e.g., consisting of, SEQ ID NO: 73.

In an aspect, the invention provides a gRNA molecule, including, e.g., consisting of, the sequence:

(a) SEQ ID NO: 159;
(b) SEQ ID NO: 160; or
(c) SEQ ID NO: 161.

In an aspect, the invention provides a gRNA molecule, including, e.g., consisting of, the sequence:

(a) a crRNA including, e.g., consisting of, SEQ ID NO: 162, and a tracr including, e.g., consisting of, SEQ ID NO: 224;

(b) a crRNA including, e.g., consisting of, SEQ ID NO: 162, and a tracr including, e.g., consisting of, SEQ ID NO: 73;

(c) a crRNA including, e.g., consisting of, SEQ ID NO: 163, and a tracr including, e.g., consisting of, SEQ ID NO: 224; or (d) a crRNA including, e.g., consisting of, SEQ ID NO: 163, and a tracr including, e.g., consisting of, SEQ ID NO: 73.

In an aspect, the invention provides a gRNA molecule, including, e.g., consisting of, the sequence:

(a) SEQ ID NO: 164;
(b) SEQ ID NO: 165; or
(c) SEQ ID NO:166.

In an aspect, the invention provides a gRNA molecule, including, e.g., consisting of, the sequence:

(a) a crRNA including, e.g., consisting of, SEQ ID NO: 167, and a tracr including, e.g., consisting of, SEQ ID NO: 224;

(b) a crRNA including, e.g., consisting of, SEQ ID NO: 167, and a tracr including, e.g., consisting of, SEQ ID NO: 73;

(c) a crRNA including, e.g., consisting of, SEQ ID NO: 168, and a tracr including, e.g., consisting of, SEQ ID NO: 224; or (d) a crRNA including, e.g., consisting of, SEQ ID NO: 168, and a tracr including, e.g., consisting of, SEQ ID NO: 73.

In an aspect, the invention provides a gRNA molecule, including, e.g., consisting of, the sequence:

(a) SEQ ID NO: 169;
(b) SEQ ID NO: 170; or
(c) SEQ ID NO: 171.

In an aspect, the invention provides a gRNA molecule, including, e.g., consisting of, the sequence:

(a) a crRNA including, e.g., consisting of, SEQ ID NO: 172, and a tracr including, e.g., consisting of, SEQ ID NO: 224;

(b) a crRNA including, e.g., consisting of, SEQ ID NO: 172, and a tracr including, e.g., consisting of, SEQ ID NO: 73;

(c) a crRNA including, e.g., consisting of, SEQ ID NO: 173, and a tracr including, e.g., consisting of, SEQ ID NO: 224; or (d) a crRNA including, e.g., consisting of, SEQ ID NO: 173, and a tracr including, e.g., consisting of, SEQ ID NO: 73.

In an aspect, the invention provides a gRNA molecule, including, e.g., consisting of, the sequence:

(a) SEQ ID NO: 174;
(b) SEQ ID NO: 175; or
(c) SEQ ID NO:176.

In an aspect, the invention provides a gRNA molecule, including, e.g., consisting of, the sequence:

(a) a crRNA including, e.g., consisting of, SEQ ID NO: 177, and a tracr including, e.g., consisting of, SEQ ID NO: 224;

(b) a crRNA including, e.g., consisting of, SEQ ID NO: 177, and a tracr including, e.g., consisting of, SEQ ID NO: 73;

(c) a crRNA including, e.g., consisting of, SEQ ID NO: 178, and a tracr including, e.g., consisting of, SEQ ID NO: 224; or (d) a crRNA including, e.g., consisting of, SEQ ID NO: 178, and a tracr including, e.g., consisting of, SEQ ID NO: 73.

In an aspect, including in any of the aforementioned aspects and embodiments the invention provides a gRNA molecule, wherein:

a) when a CRISPR system (e.g., an RNP as described herein) including the gRNA molecule is introduced into a cell, an indel is formed at or near the target sequence complementary to the targeting domain of the gRNA molecule; and/or b) when a CRISPR system (e.g., an RNP as described herein) including the gRNA molecule is introduced into a cell, a deletion is created including sequence, e.g., including substantially all the sequence, between a sequence complementary to the gRNA targeting domain (e.g., at least 90% complementary to the gRNA targeting domain, e.g., fully complementary to the gRNA targeting domain) in the HBG1 promoter region and a sequence complementary to the gRNA targeting domain (e.g., at least 90% complementary to the gRNA targeting domain, e.g., fully complementary to the gRNA targeting domain) in the HBG2 promoter region. In embodiments, the indel does not include a nucleotide of a nondeletional HPFH or transcription factor binding site.

In an aspect, including in any of the aforementioned aspects and embodiments, the invention provides a gRNA molecule, wherein when a CRISPR system (e.g., an RNP as described herein) including the gRNA molecule is introduced into a population of cells, an indel is formed at or near the target sequence complementary to the targeting domain of the gRNA molecule in at least about 15%, e.g., at least about 17%, e.g., at least about 20%, e.g., at least about 30%, e.g., at least about 40%, e.g., at least about 50%, e.g., at least about 55%, e.g., at least about 60%, e.g., at least about 70%, e.g., at least about 75%, of the cells of the population. In an aspect, including in any of the aforementioned aspects and embodiments, the indel includes at least one nucleotide of an HBG1 promoter region or at least one nucleotide of an HBG2 promoter region. In embodiments, at least about 15% of the cells of the population include an indel which includes at least one nucleotide of an HBG1 promoter region and an indel which includes at least one nucleotide of an HBG2 promoter region. In an aspect, including in any of the aforementioned aspects and embodiments, the percentage of the cells of the population which include an indel which includes at least one nucleotide of an HBG1 promoter region differs from percentage of the cells of the population which include an indel which includes at least one nucleotide of an HBG2 promoter region by at least about 5%, e.g., at least about 10%, e.g., at least about 20%, e.g., at least about 30%. In embodiments, the indel is as measured by next generation sequencing (NGS).

In an aspect, including in any of the aforementioned aspects and embodiments, the invention provides a gRNA molecule, wherein when a CRISPR system (e.g., an RNP as described herein) including the gRNA molecule is introduced into a cell, expression of fetal hemoglobin is increased in said cell or its progeny, e.g., its erythroid progeny, e.g., its red blood cell progeny. In embodiments, when a CRISPR system (e.g., an RNP as described herein) including the gRNA molecule is introduced into a population of cells, the percentage of F cells in said population or population of its progeny, e.g., its erythroid progeny, e.g., its red blood cell progeny, is increased by at least about 15%, e.g., at least about 17%, e.g., at least about 20%, e.g., at least about 25%, e.g., at least about 30%, e.g., at least about 35%, e.g., at least about 40%, relative to the percentage of F cells in a population of cells to which the gRNA molecule was not introduced or a population of its progeny, e.g., its erythroid progeny, e.g., its red blood cell progeny. In embodiments, said cell or its progeny, e.g., its erythroid progeny, e.g., its red blood cell progeny, produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell.

In an aspect, including in any of the aforementioned aspects and embodiments, the invention provides a gRNA molecule, wherein when a CRISPR system (e.g., an RNP as described herein) including the gRNA molecule is introduced into a cell, no off-target indels are formed in said cell, e.g., no off-target indels are formed outside of the HBG1 and/or HBG2 promoter regions (e.g., within a gene, e.g., a coding region of a gene), e.g., as detectible by next generation sequencing and/or a nucleotide insertional assay.

In an aspect, including in any of the aforementioned aspects and embodiments, the invention provides a gRNA molecule, wherein when a CRISPR system (e.g., an RNP as described herein) including the gRNA molecule is introduced into a population of cells, no off-target indel, e.g., no off-target indel outside of the HBG1 and/or HBG2 promoter regions (e.g., within a gene, e.g., a coding region of a gene), is detected in more than about 5%, e.g., more than about 1%, e.g., more than about 0.1%, e.g., more than about 0.01%, of the cells of the population of cells, e.g., as detectible by next generation sequencing and/or a nucleotide insertional assay.

In an aspect, including of any of the aforementioned aspects and embodiments, the cell is (or population of cells includes) a mammalian, primate, or human cell, e.g., is a human cell, e.g., the cell is (or population of cells includes) an HSPC, e.g., the HSPC is CD34+, e.g., the HSPC is CD34+CD90+. In embodiments, the cell is autologous with respect to a patient to be administered said cell. In other embodiments, the cell is allogeneic with respect to a patient to be administered said cell.

In an aspect, the gRNA molecules, genome editing systems (e.g., CRISPR systems), and/or methods described herein relate to cells, e.g., as described herein, that include or result in one or more of the following properties:

(a) at least about 40%, at least about 50%, at least about 60%, at least about 70%, at least about 80%, at least about 90%, at least about 95%, at least about 96%, at least about 97%, at least about 98% or at least about 99% of the cells of a population of cells described herein comprise an indel at or near a genomic DNA sequence complementary to the targeting domain of a gRNA molecule described herein, optionally wherein the indel is selected from an indel listed in Table 2-7, optionally wherein no cell of the population comprises a deletion of a nucleotide disposed between 5,250,092 and 5,249,833, – strand (hg38);

(b) a cell (e.g., population of cells) described herein is capable of differentiating into a differentiated cell of an erythroid lineage (e.g., a red blood cell), and wherein said differentiated cell exhibits an increased level of fetal hemoglobin, e.g., relative to an unaltered cell (e.g., population of cells);

(c) a population of cells described herein is capable of differentiating into a population of differentiated cells, e.g., a population of cells of an erythroid lineage (e.g., a population of red blood cells), and wherein said population of differentiated cells has an increased percentage of F cells (e.g., at least about 15%, at least about 20%, at least about 25%, at least about 30%, or at least about 40% higher percentage of F cells) e.g., relative to a population of unaltered cells;

(d) a cell (e.g., population of cells) described herein is capable of differentiating into a differentiated cell, e.g., a cell of an erythroid lineage (e.g., a red blood cell), and wherein said differentiated cell (e.g., population of differentiated cells) produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell;

(e) no off-target indels are formed in a cell described herein, e.g., no off-target indels are formed outside of the HBG1 and/or HBG2 promoter regions (e.g., within a gene, e.g., a coding region of a gene), e.g., as detectible by next generation sequencing and/or a nucleotide insertional assay;

(f) no off-target indel, e.g., no off-target indel outside of the HBG1 and/or HBG2 promoter regions (e.g., within a gene, e.g., a coding region of a gene), is detected in more than about 5%, e.g., more than about 1%, e.g., more than about 0.1%, e.g., more than about 0.01%, of the cells of a population of cells described herein, e.g., as detectible by next generation sequencing and/or a nucleotide insertional assay;

(g) a cell described herein or its progeny is detectible, e.g., detectible in the bone marrow or detectible in the peripheral blood, in a patient to which it is transplanted at more than 16 weeks, more than 20 weeks or more than 24 weeks after transplantation, optionally as detected by detecting an indel at or near a genomic DNA sequence complementary to the targeting domain of a gRNA molecule of any of claims 1-22, optionally wherein the indel is selected from an indel listed in Table 2-7, optionally wherein the indel is a large deletion indel;

(h) a population of cells described herein is capable of differentiating into a population of differentiated cells, e.g., a population of cells of an erythroid lineage (e.g., a population of red blood cells), and wherein said population of differentiated cells includes a reduced percentage of sickle cells (e.g., at least about 15%, at least about 20%, at least about 25%, at least about 30%, at least about 40%, at least about 50%, at least about 60%, at least about 70%, at least about 80%, or at least about 90% lower percentage of sickle cells) e.g., relative to a population of unaltered cells; and/or (i) a cell or population of cells described herein is capable of differentiating into a population of differentiated cells, e.g., a population of cells of an erythroid lineage (e.g., a population of red blood cells), and wherein said population of differentiated cells includes cells which produce a reduced level (e.g., at least about 15%, at least about 20%, at least about 25%, at least about 30%, at least about 40%, at least about 50%, at least about 60%, at least about 70%, at least about 80%, or at least about 90% lower level) of sickle hemoglobin (HbS), e.g., relative to a population of unaltered cells.

In an aspect, the invention provides a composition including:

1) one or more gRNA molecules (including a first gRNA molecule) described herein, e.g., of any of the aforementioned gRNA aspects and embodiments, and a Cas9 molecule, e.g., described herein;

2) one or more gRNA molecules (including a first gRNA molecule) described herein, e.g., of any of the aforementioned gRNA aspects and embodiments, and nucleic acid encoding a Cas9 molecule, e.g., described herein;

3) nucleic acid encoding one or more gRNA molecules (including a first gRNA molecule) described herein, e.g., of any of the aforementioned gRNA aspects and embodiments, and a Cas9 molecule, e.g., described herein;

4) nucleic acid encoding one or more gRNA molecules (including a first gRNA molecule) described herein, e.g., of any of the aforementioned gRNA aspects and embodiments, and nucleic acid encoding a Cas9 molecule, e.g., described herein; or 5) any of 1) to 4), above, and a template nucleic acid; or 6) any of 1) to 4) above, and nucleic acid including sequence encoding a template nucleic acid.

In an aspect, the invention provides a composition including a first gRNA molecule described herein, e.g., of any of the aforementioned gRNA aspects and embodiments, further including a Cas9 molecule, e.g., described herein, e.g., wherein the Cas9 molecule is an active or inactive s. *pyogenes* Cas9, for example, wherein the Cas9 molecule includes SEQ ID NO: 205. In aspects, the Cas9 molecule includes, e.g., consists of: (a) SEQ ID NO: 233; (b) SEQ ID NO: 234; (c) SEQ ID NO: 235; (d) SEQ ID NO: 236; (e) SEQ ID NO: 237; (f) SEQ ID NO: 238; (g) SEQ ID NO: 239; (h) SEQ ID NO: 240; (i) SEQ ID NO: 241; (j) SEQ ID NO: 242; (k) SEQ ID NO: 243 or (l) SEQ ID NO: 244.

In an aspect, including in any of the aforementioned composition aspects and embodiments, the first gRNA molecule and Cas9 molecule are present in a ribonuclear protein complex (RNP).

In an aspect, including in any of the aforementioned composition aspects and embodiments, the invention provides a composition further including a second gRNA molecule; a second gRNA molecule and a third gRNA molecule; or a second gRNA molecule, optionally, a third gRNA molecule, and, optionally, a fourth gRNA molecule, wherein the second gRNA molecule, the optional third gRNA molecule, and the optional fourth gRNA molecule are a gRNA molecule described herein, e.g., are a gRNA molecule of any of the aforementioned gRNA molecule aspects and embodiments, and wherein each gRNA molecule of the composition is complementary to a different target sequence. In embodiments, two or more of the first gRNA molecule, the second gRNA molecule, the optional third gRNA molecule, and the optional fourth gRNA molecule are complementary to target sequences within the same gene or region. In embodiments, the first gRNA molecule, the second gRNA molecule, the optional third gRNA molecule, and the optional fourth gRNA molecule are complementary to target sequences not more than 6000 nucleotides, not more than 5000 nucleotides, not more than 500, not more than 400 nucleotides, not more than 300, not more than 200 nucleotides, not more than 100 nucleotides, not more than 90 nucleotides, not more than 80 nucleotides, not more than 70 nucleotides, not more than 60 nucleotides, not more than 50 nucleotides, not more than 40 nucleotides, not more than 30 nucleotides, not more than 20 nucleotides or not more than 10 nucleotides apart. In embodiments, two or more of the first gRNA molecule, the second gRNA molecule, the optional third gRNA molecule, and the optional fourth gRNA molecule include at least one gRNA molecule which includes a targeting domain complementary to a target sequence of an HBG1 promoter region and at least one gRNA molecule which includes a targeting domain complementary to a target sequence of an HBG2 promoter region. In an aspect, including in any of the aforementioned composition aspects and embodiments, the composition includes (e.g., consists of) a first gRNA molecule and a second gRNA molecule, wherein the first gRNA molecule and second gRNA molecule are: (a) independently selected and target a nondeletional HPFH region, e.g., described herein, and are complementary to different target sequences; (b) independently selected from the gRNA molecules of Table 1, and are complementary to different target sequences; c) independently selected from the gRNA molecules of Table 2, and are complementary to different target sequences; or (d) independently selected from the gRNA molecules of Table 3a and are complementary to different target sequences, (e) independently selected from the gRNA molecules of Table 3b and are complementary to different target sequences; or (f) independently selected from the gRNA molecules of any of the aforementioned aspects and embodiments, and are complementary to different target sequences.

In an aspect, including in any of the aforementioned composition aspects and embodiments, the composition includes a first gRNA molecule and a second gRNA molecule, wherein:

a) the first gRNA molecule is complementary to a target sequence including at least 1 nucleotide (e.g., including 20 consecutive nucleotides) within:

i) Chr11:5,249,833 to Chr11:5,250,237 (hg38);
ii) Chr11:5,250,094-5,250,237 (hg38);
iii) Chr11:5,249,833-5,249,927 (hg38); or
iv) Chr11:5,250,139-5,250,237 (hg38);

b) the second gRNA molecule is complementary to a target sequence including at least 1 nucleotide (e.g., comprising 20 consecutive nucleotides) within:

i) Chr11:5,254,738 to Chr11:5,255,164 (hg38);
ii) Chr11:5,255,022-5,255,164 (hg38); or
iii) Chr11:5,254,738-5,254,851 (hg38).

In an aspect, with respect to the gRNA molecule components of the composition, the composition consists of a first gRNA molecule and a second gRNA molecule.

In an aspect, including in any of the aforementioned composition aspects and embodiments, each of said gRNA molecules is in a ribonuclear protein complex (RNP) with a Cas9 molecule, e.g., described herein.

In an aspect, including in any of the aforementioned composition aspects and embodiments, the composition includes a template nucleic acid, wherein the template nucleic acid includes a nucleotide that corresponds to a nucleotide at or near the target sequence of the first gRNA molecule. In embodiments, the template nucleic acid includes nucleic acid encoding: (a) human beta globin, e.g., human beta globin including one or more of the mutations G16D, E22A and T87Q, or fragment thereof; or (b) human gamma globin, or fragment thereof.

In an aspect, including in any of the aforementioned composition aspects and embodiments, the composition is formulated in a medium suitable for electroporation.

In an aspect, including in any of the aforementioned composition aspects and embodiments, each of said gRNA molecules of said composition is in a RNP with a Cas9 molecule described herein, and wherein each of said RNP is at a concentration of less than about 10 uM, e.g., less than about 3 uM, e.g., less than about 1 uM, e.g., less than about 0.5 uM, e.g., less than about 0.3 uM, e.g., less than about 0.1 uM. In embodiments, the RNP is at a concentration of about 1 uM. In embodiments, the RNP is at a concentration of about 2 uM. In embodiments, said concentration is the concentration of RNP in a composition comprising the cells, e.g., as described herein, optionally wherein the composition comprising the cells and the RNP is suitable for electroporation.

In an aspect, the invention provides a nucleic acid sequence that encodes one or more gRNA molecules described herein, e.g., of any of the aforementioned gRNA molecule aspects and embodiments. In embodiments, the nucleic acid includes a promoter operably linked to the sequence that encodes the one or more gRNA molecules, for example, the promoter is a promoter recognized by an RNA polymerase II or RNA polymerase III, or, for example, the promoter is a U6 promoter or an HI promoter.

In an aspect, including in any of the aforementioned nucleic acid aspects and embodiments, the nucleic acid further encodes a Cas9 molecule, for example, a Cas9 molecule that includes, e.g., consists of, any of SEQ ID NO: 205, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243 or SEQ ID NO: 244. In embodiments, said nucleic acid includes a promoter operably linked to the sequence that encodes a Cas9 molecule, for example, an EF-1 promoter, a CMV IE gene promoter, an EF-1α promoter, an ubiquitin C promoter, or a phosphoglycerate kinase (PGK) promoter.

In an aspect, the invention provides a vector including the nucleic acid of any of the aforementioned nucleic acid aspects and embodiments. In embodiments, the vector is selected from the group consisting of a lentiviral vector, an adenoviral vector, an adeno-associated viral (AAV) vector, a herpes simplex virus (HSV) vector, a plasmid, a minicircle, a nanoplasmid, and an RNA vector.

In an aspect, the invention provides a method of altering a cell (e.g., a population of cells), (e.g., altering the structure (e.g., sequence) of nucleic acid) at or near a target sequence within said cell, including contacting (e.g., introducing into) said cell (e.g., population of cells) with:

1) one or more gRNA molecules described herein (e.g., of any of the aforementioned gRNA molecule aspects and embodiments) and a Cas9 molecule, e.g., described herein;

2) one or more gRNA molecules described herein (e.g., of any of the aforementioned gRNA molecule aspects and embodiments) and nucleic acid encoding a Cas9 molecule, e.g., described herein;

3) nucleic acid encoding one or more gRNA molecules described herein (e.g., of any of the aforementioned gRNA molecule aspects and embodiments) and a Cas9 molecule, e.g., described herein;

4) nucleic acid encoding one or more gRNA molecules described herein (e.g., of any of the aforementioned gRNA molecule aspects and embodiments) and nucleic acid encoding a Cas9 molecule, e.g., described herein;

5) any of 1) to 4), above, and a template nucleic acid;

6) any of 1) to 4) above, and nucleic acid including sequence encoding a template nucleic acid;

7) a composition described herein, e.g., a composition of any of the aforementioned composition aspects and embodiments; or 8) a vector described herein, e.g., a vector of any of the aforementioned vector aspects and embodiments.

In an aspect, including in any of the aforementioned method aspects and embodiments, the gRNA molecule or nucleic acid encoding the gRNA molecule, and the Cas9 molecule or nucleic acid encoding the Cas9 molecule, are formulated in a single composition. In another aspect, the gRNA molecule or nucleic acid encoding the gRNA molecule, and the Cas9 molecule or nucleic acid encoding the Cas9 molecule, are formulated in more than one composition. In an aspect, the more than one composition are delivered simultaneously or sequentially.

In an aspect of the methods described herein, including in any of the aforementioned method aspects and embodiments, the cell is an animal cell, for example, the cell is a mammalian, primate, or human cell, for example, the cell is a hematopoietic stem or progenitor cell (HSPC) (e.g., a population of HSPCs), for example, the cell is a CD34+ cell, for example, the cell is a CD34+CD90+ cell. In embodiments of the methods described herein, the cell is disposed in a composition including a population of cells that has been enriched for CD34+ cells. In embodiments of the methods described herein, the cell (e.g. population of cells) has been isolated from bone marrow, mobilized peripheral blood, or umbilical cord blood. In embodiments of the methods described herein, the cell is autologous or allogeneic, e.g., autologous, with respect to a patient to be administered said cell.

In an aspect of the methods described herein, including in any of the aforementioned method aspects and embodiments, a) the altering results in an indel at or near a genomic DNA sequence complementary to the targeting domain of the one or more gRNA molecules; or b) the altering results in a deletion including sequence, e.g., substantially all the sequence, between a sequence complementary to the targeting domain of the one or more gRNA molecules (e.g., at least 90% complementary to the gRNA targeting domain, e.g., fully complementary to the gRNA targeting domain) in the HBG1 promoter region and a sequence complementary to the targeting domain of the one or more gRNA molecules (e.g., at least 90% complementary to the gRNA targeting domain, e.g., fully complementary to the gRNA targeting domain) in the HBG2 promoter region. In aspects of the method, the indel is an insertion or deletion of less than about 40 nucleotides, e.g., less than 30 nucleotides, e.g., less than 20 nucleotides, e.g., less than 10 nucleotides, for example, is a single nucleotide deletion.

In an aspect of the methods described herein, including in any of the aforementioned method aspects and embodiments, the method results in a population of cells wherein at least about 15%, e.g., at least about 17%, e.g., at least about 20%, e.g., at least about 30%, e.g., at least about 40%, e.g., at least about 50%, e.g., at least about 55%, e.g., at least about 60%, e.g., at least about 70%, e.g., at least about 75% of the population have been altered, e.g., include an indel.

In an aspect of the methods described herein, including in any of the aforementioned method aspects and embodiments, the altering results in a cell (e.g., population of cells) that is capable of differentiating into a differentiated cell of an erythroid lineage (e.g., a red blood cell), and wherein said differentiated cell exhibits an increased level of fetal hemoglobin, e.g., relative to an unaltered cell (e.g., population of cells).

In an aspect of the methods described herein, including in any of the aforementioned method aspects and embodiments, the altering results in a population of cells that is capable of differentiating into a population of differentiated cells, e.g., a population of cells of an erythroid lineage (e.g., a population of red blood cells), and wherein said population of differentiated cells has an increased percentage of F cells (e.g., at least about 15%, at least about 20%, at least about 25%, at least about 30%, or at least about 40% higher percentage of F cells) e.g., relative to a population of unaltered cells.

In an aspect of the methods described herein, including in any of the aforementioned method aspects and embodiments, the altering results in a cell that is capable of differentiating into a differentiated cell, e.g., a cell of an erythroid lineage (e.g., a red blood cell), and wherein said differentiated cell produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell.

In an aspect, the invention provides a cell, altered by a method described herein, for example, a method of any of the aforementioned method aspects and embodiments.

In an aspect, the invention provides a cell, obtainable by a method described herein, for example, a method of any of the aforementioned method aspects and embodiments.

In an aspect, the invention provides a cell, including a first gRNA molecule described herein, e.g., of any of the aforementioned gRNA molecule aspects or embodiments, or a composition described herein, e.g., of any of the aforementioned composition aspects or embodiments, a nucleic acid described herein, e.g., of any of the aforementioned nucleic acid aspects or embodiments, or a vector described herein, e.g., of any of the aforementioned vector aspects or embodiments.

In an aspect of the cell described herein, including in any of the aforementioned cell aspects and embodiments, the cell further includes a Cas9 molecule, e.g., described herein, e.g., a Cas9 molecule that includes any one of SEQ ID NO: 205, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243 or SEQ ID NO: 244.

In an aspect of the cell described herein, including in any of the aforementioned cell aspects and embodiments, the cell includes, has included, or will include a second gRNA molecule described herein, e.g., of any of the aforementioned gRNA molecule aspects or embodiments, or nucleic acid encoding said gRNA molecule, wherein the first gRNA molecule and second gRNA molecule include nonidentical targeting domains.

In an aspect of the cell described herein, including in any of the aforementioned cell aspects and embodiments, expression of fetal hemoglobin is increased in said cell or its progeny (e.g., its erythroid progeny, e.g., its red blood cell progeny) relative to a cell or its progeny of the same cell type that has not been modified to include a gRNA molecule.

In an aspect of the cell described herein, including in any of the aforementioned cell aspects and embodiments, the cell is capable of differentiating into a differentiated cell, e.g., a cell of an erythroid lineage (e.g., a red blood cell), and wherein said differentiated cell exhibits an increased level of fetal hemoglobin, e.g., relative to a cell of the same type that has not been modified to include a gRNA molecule.

In an aspect of the cell described herein, including in any of the aforementioned cell aspects and embodiments, the differentiated cell (e.g., cell of an erythroid lineage, e.g., red blood cell) produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin, e.g., relative to a differentiated cell of the same type that has not been modified to include a gRNA molecule.

In an aspect of the cell described herein, including in any of the aforementioned cell aspects and embodiments, the cell has been contacted, e.g., contacted ex vivo, with a stem cell expander, for example, a stem cell expander selected from: a) (1r,4r)—$N^1$-(2-benzyl-7-(2-methyl-2H-tetrazol-5-yl)-9H-pyrimido[4,5-b]indol-4-yl)cyclohexane-1,4-diamine; b) methyl 4-(3-piperidin-1-ylpropylamino)-9H-pyrimido[4,5-b]indole-7-carboxy late; c) 4-(2-(2-(benzo[b]thiophen-3-yl)-9-isopropyl-9H-purin-6-ylamino)ethyl) phenol; d) (S)-2-(6-(2-(1H-indol-3-yl)ethylamino)-2-(5-fluoropyridin-3-yl)-9H-purin-9-yl)propan-1-ol; ore) combinations thereof (e.g., a combination of (1r,4r)—$N^1$-(2-benzyl-7-(2-methyl-2H-tetrazol-5-yl)-9H-pyrimido[4,5-b]indol-4-yl)cyclohexane-1,4-diamine and (S)-2-(6-(2-(1H-indol-3-yl)ethylamino)-2-(5-fluoropyridin-3-yl)-9H-purin-9-yl)propan-1-ol). In embodiments, the stem cell expander is (S)-2-(6-(2-(1H-indol-3-yl)ethylamino)-2-(5-fluoropyridin-3-yl)-9H-purin-9-yl)propan-1-ol.

In an aspect of the cell described herein, including in any of the aforementioned cell aspects and embodiments, the cell includes: a) an indel at or near a genomic DNA sequence complementary to the targeting domain of a gRNA molecule described herein, e.g., of any of the aforementioned gRNA molecule aspects or embodiments; orb) a deletion including sequence, e.g., substantially all the sequence, between a sequence complementary to the targeting domain of a gRNA molecule described herein, e.g., of any of the aforementioned gRNA molecule aspects or embodiments (e.g., at least 90% complementary to the gRNA targeting domain, e.g., fully complementary to the gRNA targeting domain) in the HBG1 promoter region and a sequence complementary to the targeting domain of a gRNA molecule described herein, e.g., of any of the aforementioned gRNA molecule aspects or embodiments (e.g., at least 90% complementary to the gRNA targeting domain, e.g., fully complementary to the gRNA targeting domain) in the HBG2 promoter region. In an aspect, the indel is an insertion or deletion of less than about 40 nucleotides, e.g., less than 30 nucleotides, e.g., less than 20 nucleotides, e.g., less than 10 nucleotides, for example, the indel is a single nucleotide deletion.

In an aspect of the cell described herein, including in any of the aforementioned cell aspects and embodiments, the cell is an animal cell, for example, the cell is a mammalian, a primate, or a human cell. In an aspect, the cell is a hematopoietic stem or progenitor cell (HSPC) (e.g., a population of HSPCs), e.g., the cell is a CD34+ cell, e.g., the cell is a CD34+CD90+ cell. In embodiments, the cell (e.g. population of cells) has been isolated from bone marrow, mobilized peripheral blood, or umbilical cord blood. In embodiments, the cell is autologous with respect to a patient to be administered said cell. In embodiments, the cell the cell is allogeneic with respect to a patient to be administered said cell.

In an aspect, the invention provides a population of cells described herein, e.g., a population of cells that include a cell described herein, e.g., a cell of any of the aforementioned cell aspects and embodiments. In aspects, the invention provides a population of cells, wherein at least about 50%, e.g., at least about 60%, e.g., at least about 70%, e.g., at least about 80%, e.g., at least about 90% (e.g., at least about 95%, at least about 96%, at least about 97%, at least about 98%, or at least about 99%) of the cells of the population are a cell described herein, e.g., a cell of any of the aforementioned cell aspects and embodiments. In aspects, the population of cells (e.g., a cell of the population of cells) is capable of differentiating into a population of differentiated cells, e.g., a population of cells of an erythroid lineage (e.g., a population of red blood cells), and wherein said population of differentiated cells has an increased percentage of F cells (e.g., at least about 15%, at least about 17%, at least about 20%, at least about 25%, at least about 30%, or at least about 40% higher percentage of F cells) e.g., relative to a population of unmodified cells of the same type. In aspects, the F cells of the population of differentiated cells produce an average of at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell.

In an aspect, including in any of the aforementioned population of cell aspects and embodiments, the invention provides population of cells, including: 1) at least 1e6 CD34+ cells/kg body weight of the patient to whom the cells are to be administered; 2) at least 2e6 CD34+ cells/kg body weight of the patient to whom the cells are to be administered; 3) at least 3e6 CD34+ cells/kg body weight of the patient to whom the cells are to be administered; 4) at least 4e6 CD34+ cells/kg body weight of the patient to whom the cells are to be administered; or 5) from 2e6 to 10e6 CD34+ cells/kg body weight of the patient to whom the cells are to be administered. In embodiments, at least about 40%, e.g., at least about 50%, (e.g., at least about 60%, at least about 70%, at least about 80%, or at least about 90%) of the cells of the population are CD34+ cells. In embodiments, at least about 5%, e.g., at least about 10%, e.g., at least about 15%, e.g., at least about 20%, e.g., at least about 30% of the cells of the population are CD34+CD90+ cells. In embodiments, the population of cells is derived from umbilical cord blood, peripheral blood (e.g., mobilized peripheral blood), or bone marrow, e.g., is derived from bone marrow. In embodiments, the population of cells includes, e.g., consists of, mammalian cells, e.g., human cells. In embodiments, the population of cells is autologous relative to a patient to which it is to be administered. In other embodiments, the population of cells is allogeneic relative to a patient to which it is to be administered.

In an aspect, the invention provides a composition including a cell described herein, e.g., a cell of any of the aforementioned cell aspects and embodiments, or a population of cells described herein, e.g., a population of cells of any of the aforementioned population of cell aspects and embodiments. In an aspect, the composition includes a pharmaceutically acceptable medium, e.g., a pharmaceutically acceptable medium suitable for cryopreservation.

In an aspect, the invention provides a method of treating a hemoglobinopathy, including administering to a patient a cell described herein, e.g., a cell of any of the aforementioned cell aspects and embodiments, a population of cells described herein, e.g., a population of cells of any of the aforementioned population of cell aspects and embodiments, or a composition described herein, e.g., a composition of any of the aforementioned composition aspects and embodiments.

In an aspect, the invention provides a method of increasing fetal hemoglobin expression in a mammal, including administering to a patient a cell described herein, e.g., a cell of any of the aforementioned cell aspects and embodiments, a population of cells described herein, e.g., a population of cells of any of the aforementioned population of cell aspects and embodiments, or a composition described herein, e.g., a composition of any of the aforementioned composition aspects and embodiments. In aspects, the hemoglobinopathy is beta-thalassemia. In aspects, the hemoglobinopathy is sickle cell disease.

In an aspect, the invention provides a method of preparing a cell (e.g., a population of cells) including:

(a) providing a cell (e.g., a population of cells) (e.g., a HSPC (e.g., a population of HSPCs));

(b) culturing said cell (e.g., said population of cells) ex vivo in a cell culture medium including a stem cell expander; and (c) introducing into said cell a first gRNA molecule, e.g., described herein, e.g., a first gRNA molecule of any of the aforementioned gRNA molecule aspects and embodiments; a nucleic acid molecule encoding a first gRNA molecule; a composition described herein, e.g., a composition of any of the aforementioned composition aspects and embodiments; or a vector described herein, e.g., a vector of any of the aforementioned aspects and embodiments. In aspects of the method, after said introducing of step (c), said cell (e.g., population of cells) is capable of differentiating into a differentiated cell (e.g., population of differentiated cells), e.g., a cell of an erythroid lineage (e.g., population of cells of an erythroid lineage), e.g., a red blood cell (e.g., a population of red blood cells), and wherein said differentiated cell (e.g., population of differentiated cells) produces increased fetal hemoglobin, e.g., relative to the same cell which has not been subjected to step (c). In aspects of the method, the stem cell expander is: a) (1r,4r)—N1-(2-benzyl-7-(2-methyl-2H-tetrazol-5-yl)-9H-pyrimido[4,5-b]indol-4-yl)cyclohexane-1,4-diamine; b) methyl 4-(3-piperidin-1-yl-propylamino)-9H-pyrimido[4,5-b]indole-7-carboxylate; c) 4-(2-(2-(benzo[b]thiophen-3-yl)-9-isopropyl-9H-purin-6-ylamino)ethyl)phenol; d) (S)-2-(6-(2-(1H-indol-3-yl)ethyl-amino)-2-(5-fluoropyridin-3-yl)-9H-purin-9-yl)propan-1-ol; ore) combinations thereof (e.g., a combination of (1r,4r)—N1-(2-benzyl-7-(2-methyl-2H-tetrazol-5-yl)-9H-pyrimido[4,5-b]indol-4-yl)cyclohexane-1,4-diamine and (S)-2-(6-(2-(1H-indol-3-yl)ethylamino)-2-(5-fluoropyridin-3-yl)-9H-purin-9-yl)propan-1-ol). In embodiments, the stem cell expander is (S)-2-(6-(2-(1H-indol-3-yl)ethylamino)-2-(5-fluoropyridin-3-yl)-9H-purin-9-yl)propan-1-ol. In aspects, the cell culture medium includes thrombopoietin (Tpo), Flt3 ligand (Flt-3L), and human stem cell factor (SCF). In aspects, the cell culture medium further includes human interleukin-6 (IL-6). In aspects, the cell culture medium includes thrombopoietin (Tpo), Flt3 ligand (Flt-3L), and human stem cell factor (SCF) each at a concentration ranging from about 10 ng/mL to about 1000 ng/mL, for example, each at a concentration of about 50 ng/mL, for example, each at a concentration of 50 ng/mL. In aspects, the cell culture medium includes human interleukin-6 (IL-6) at a concentration ranging from about 10 ng/mL to about 1000 ng/mL, for example, at a concentration of about 50 ng/mL, for example, at a concentration of 50 ng/mL. In aspects, the cell culture medium includes a stem cell expander at a concentration ranging from about 1 nM to about 1 mM, for example, at a concentration ranging from about 1 uM to about 100 nM, for example, at a concentration ranging from about 500 nM to about 750 nM. In aspects, the cell culture medium includes a stem cell expander at a concentration of about 500 nM, e.g., at a concentration of 500 nM. In aspects, the cell culture medium includes a stem cell expander at a concentration of about 750 nM, e.g., at a concentration of 750 nM.

In aspects of the method of preparing a cell (e.g., a population of cells), the culturing of step (b) includes a period of culturing before the introducing of step (c), for example, the period of culturing before the introducing of step (c) is at least 12 hours, e.g., is for a period of about 1 day to about 12 days, e.g., is for a period of about 1 day to about 6 days, e.g., is for a period of about 1 day to about 3 days, e.g., is for a period of about 1 day to about 2 days, e.g., is for a period of about 2 days. In aspects of the method of preparing a cell (e.g., a population of cells), including in any of the aforementioned aspects and embodiments of the method, the culturing of step (b) includes a period of culturing after the introducing of step (c), for example, the period of culturing after the introducing of step (c) is at least 12 hours, e.g., is for a period of about 1 day to about 12 days, e.g., is for a period of about 1 day to about 6 days, e.g., is for a period of about 2 days to about 4 days, e.g., is for a period of about 2 days or is for a period of about 3 days or is for a period of about 4 days. In aspects of the method of preparing a cell (e.g., a population of cells), including in any of the aforementioned aspects and embodiments of the method, the population of cells is expanded at least 4-fold, e.g., at least 5-fold, e.g, at least 10-fold, e.g., relative to cells which are not cultured according to step (b).

In aspects of the method of preparing a cell (e.g., a population of cells), including in any of the aforementioned aspects and embodiments of the method, the introducing of step (c) includes an electroporation. In aspects, the electroporation includes 1 to 5 pulses, e.g., 1 pulse, and wherein each pulse is at a pulse voltage ranging from 700 volts to 2000 volts and has a pulse duration ranging from 10 ms to 100 ms. In aspects, the electroporation includes, e.g., consists of, 1 pulse. In aspects, the pulse (or more than one pulse) voltage ranges from 1500 to 1900 volts, e.g., is 1700 volts. In aspects, the pulse duration of the one pulse or more than one pulse ranges from 10 ms to 40 ms, e.g., is 20 ms.

In aspects of the method of preparing a cell (e.g., a population of cells), including in any of the aforementioned aspects and embodiments of the method, the cell (e.g., population of cells) provided in step (a) is a human cell (e.g., a population of human cells). In aspects of the method of preparing a cell (e.g., a population of cells), including in any of the aforementioned aspects and embodiments of the method, the cell (e.g., population of cells) provided in step (a) is isolated from bone marrow, peripheral blood (e.g., mobilized peripheral blood) or umbilical cord blood. In aspects of the method of preparing a cell (e.g., a population of cells), including in any of the aforementioned aspects and embodiments of the method, the cell (e.g., population of cells) provided in step (a) is isolated from bone marrow, e.g., is isolated from bone marrow of a patient suffering from a hemoglobinopathy.

In aspects of the method of preparing a cell (e.g., a population of cells), including in any of the aforementioned aspects and embodiments of the method, the population of cells provided in step (a) is enriched for CD34+ cells.

In aspects of the method of preparing a cell (e.g., a population of cells), including in any of the aforementioned aspects and embodiments of the method, subsequent to the introducing of step (c), the cell (e.g., population of cells) is cryopreserved.

In aspects of the method of preparing a cell (e.g., a population of cells), including in any of the aforementioned aspects and embodiments of the method, subsequent to the introducing of step (c), the cell (e.g., population of cells) includes: a) an indel at or near a genomic DNA sequence complementary to the targeting domain of the first gRNA molecule; orb) a deletion including sequence, e.g., substantially all the sequence, between a sequence complementary to the targeting domain of the first gRNA molecule (e.g., at least 90% complementary to the gRNA targeting domain, e.g., fully complementary to the gRNA targeting domain) in the HBG1 promoter region and a sequence complementary to the targeting domain of the first gRNA molecule (e.g., at least 90% complementary to the gRNA targeting domain, e.g., fully complementary to the gRNA targeting domain) in the HBG2 promoter region.

In aspects of the method of preparing a cell (e.g., a population of cells), including in any of the aforementioned aspects and embodiments of the method, after the introducing of step (c), at least about 40%, at least about 50%, at least about 60%, at least about 70%, at least about 80%, at least about 90%, at least about 95%, at least about 96%, at least about 97%, at least about 98% or at least about 99% of the cells of the population of cells include an indel at or near a genomic DNA sequence complementary to the targeting domain of the first gRNA molecule.

In an aspect, the invention provides a cell (e.g., population of cells), obtainable by a method of preparing a cell (e.g., a population of cells) described herein, e.g., described in any of the aforementioned method of preparing a cell aspects and embodiments.

In an aspect, the invention provides a method of treating a hemoglobinopathy in a human patient, including administering to a human patient a composition including a cell described herein, e.g., a cell of any of the aforementioned cell aspects and embodiments; or a population of cells described herein, e.g., a population of cells of any of the aforementioned population of cell aspects and embodiments.

In aspects, the hemoglobinopathy is beta-thalassemia. In aspects, the hemoglobinopathy is sickle cell disease.

In an aspect, the invention provides a method of increasing fetal hemoglobin expression in a human patient, including administering to said human patient a composition including a cell described herein, e.g., a cell of any of the aforementioned cell aspects and embodiments; or a population of cells described herein, e.g., a population of cells of any of the aforementioned population of cell aspects and embodiments. In aspects, the human patients has beta-thalassemia. In aspects, the human patient has sickle cell disease.

In aspects of the method of treating a hemoglobinopathy or the method of increasing fetal hemoglobin expression, the human patient is administered a composition including at least about 1e6 cells (e.g., cells as described herein) per kg body weight of the human patient, e.g., at least about 1e6 CD34+ cells (e.g., cells as described herein) per kg body weight of the human patient. In aspects of the method of treating a hemoglobinopathy or the method of increasing fetal hemoglobin expression, the human patient is administered a composition including at least about 2e6 cells (e.g., cells as described herein) per kg body weight of the human patient, e.g., at least about 2e6 CD34+ cells (e.g., cells as described herein) per kg body weight of the human patient. In aspects of the method of treating a hemoglobinopathy or the method of increasing fetal hemoglobin expression, the human patient is administered a composition including about 2e6 cells (e.g., cells as described herein) per kg body weight of the human patient, e.g., about 2e6 CD34+ cells (e.g., cells as described herein) per kg body weight of the human patient. In aspects of the method of treating a hemoglobinopathy or the method of increasing fetal hemoglobin expression, the human patient is administered a composition including at least about 3e6 cells (e.g., cells as described herein) per kg body weight of the human patient, e.g., at least about 3e6 CD34+ cells (e.g., cells as described herein) per kg body weight of the human patient. In aspects of the method of treating a hemoglobinopathy or the method of increasing fetal hemoglobin expression, the human patient is administered a composition including about 3e6 cells (e.g., cells as described herein) per kg body weight of the human patient, e.g., about 3e6 CD34+ cells (e.g., cells as described herein) per kg body weight of the human patient. In aspects of the method of treating a hemoglobinopathy or the method of increasing fetal hemoglobin expression, the human patient is administered a composition including from about 2e6 to about 10e6 cells (e.g., cells as described herein) per kg body weight of the human patient, e.g., from about 2e6 to about 10e6 CD34+ cells (e.g., cells as described herein) per kg body weight of the human patient.

In an aspect, the invention provides: a gRNA molecule described herein, e.g., a gRNA molecule of any of the aforementioned gRNA molecule aspects and embodiments; a composition described herein, e.g., a composition of any of the aforementioned composition aspects and embodiments, a nucleic acid described herein, e.g., a nucleic acid of any of the aforementioned nucleic acid aspects and embodiments; a vector described herein, e.g., a vector of any of the aforementioned vector aspects and embodiments; a cell described herein, e.g., a cell of any of the aforementioned cell aspects and embodiments; or a population of cells described herein, e.g., a population of cells of any of the aforementioned population of cells aspects and embodiments, for use as a medicament.

In an aspect, the invention provides: a gRNA molecule described herein, e.g., a gRNA molecule of any of the aforementioned gRNA molecule aspects and embodiments; a composition described herein, e.g., a composition of any of the aforementioned composition aspects and embodiments, a nucleic acid described herein, e.g., a nucleic acid of any of the aforementioned nucleic acid aspects and embodiments; a vector described herein, e.g., a vector of any of the aforementioned vector aspects and embodiments; a cell described herein, e.g., a cell of any of the aforementioned cell aspects and embodiments; or a population of cells described herein, e.g., a population of cells of any of the aforementioned population of cells aspects and embodiments, for use in the manufacture of a medicament.

In an aspect, the invention provides: a gRNA molecule described herein, e.g., a gRNA molecule of any of the aforementioned gRNA molecule aspects and embodiments; a composition described herein, e.g., a composition of any of the aforementioned composition aspects and embodiments, a nucleic acid described herein, e.g., a nucleic acid of any of the aforementioned nucleic acid aspects and embodiments; a vector described herein, e.g., a vector of any of the aforementioned vector aspects and embodiments; a cell described herein, e.g., a cell of any of the aforementioned cell aspects and embodiments; or a population of cells described herein, e.g., a population of cells of any of the aforementioned population of cells aspects and embodiments, for use in the treatment of a disease.

In an aspect, the invention provides: a gRNA molecule described herein, e.g., a gRNA molecule of any of the aforementioned gRNA molecule aspects and embodiments; a composition described herein, e.g., a composition of any of the aforementioned composition aspects and embodiments, a nucleic acid described herein, e.g., a nucleic acid of any of the aforementioned nucleic acid aspects and embodiments; a vector described herein, e.g., a vector of any of the aforementioned vector aspects and embodiments; a cell described herein, e.g., a cell of any of the aforementioned cell aspects and embodiments; or a population of cells described herein, e.g., a population of cells of any of the aforementioned population of cells aspects and embodiments, for use in the treatment of a disease, wherein the disease is a hemoglobinopathy, for example, beta-thalassemia or sickle cell disease.

BRIEF DESCRIPTION OF THE DRAWINGS

FIG. 4: Overview of the location of high performing gRNA target sequences (e.g., >17% HbF upregulation at Day 7), known non-deletional HPFH polymorphisms and transcription factor binding sites in the HBG1 promoter area. FIGS. 4A-4D disclose SEQ ID NOS 293-312, respectively, in order of appearance.

FIG. 5: Overview of the location of high-performing gRNA target sequences (e.g., >17% HbF upregulation at Day 7), known non-deletional HPFH polymorphisms and transcription factor binding sites in the HBG2 promoter area. FIGS. 5A-5D disclose SEQ ID NOS 313-332, respectively, in order of appearance.

FIG. 13.

FIG. 23A) Peripheral blood chimerism over 18 weeks; FIG. 23B) Lineage distribution in the peripheral blood at 18 weeks. Bone marrow analysis: FIG. 23C) Bone marrow analysis of human cells at week 9; FIG. 23D) human CD45+ engraftment and lineage distribution of human cells in bone marrow at week 9; FIG. 23E) human CD45+ engraftment in bone marrow at week 20 post engraftment; FIG. 23F) Lineage distribution of engrafted cells in the bone marrow at 20 weeks.

FIG. 27A: NGS analysis of CD34+ cells at day 2 post-electroporation of RNPs. FIG. 27B: NGS analysis of whole bone marrow from NSG mice transplanted with edited bone marrow CD34+ cells at (27B) week 9 post-transplantation FIG. 27C: NGS analysis of whole bone marrow from NSG mice transplanted with edited bone marrow CD34+ cells at week 20 post-transplantation. Insertion indels are indicated in black, deletion indels (excluding large deletions comprising an excision of the region between binding HBG1 and HBG2 target sequences for each of gRNA sg-G51, sg-G48 and sg-G67) are indicated in grey. Total % editing is represented by the height of the bars. N=10, data are presented as mean±SEM from one independent experiment.

FIG. 31A. CD34+ cell count of cells derived from mobilized peripheral blood of healthy individuals upon gene-editing. Cells were thawed on day 0, cultured for 3 days prior to electroporation on day 3. Enumeration of CD34+ cell number by ISHAGE over 10 days following electroporation. Two independent experiments were performed in duplicates. Total N=5. Graphs show data from 1 experiment with mean±SEM.

FIG. 31B. CD34+ cell expansion of cells derived from mobilized peripheral blood of healthy individuals upon gene-editing. Cells were thawed on day 0, cultured for 3 days prior to electroporation on day 3. Expansion of total mononuclear cells at day 3, 7, and 10 upon editing. Two independent experiments were performed in duplicates. Total N=5. Graphs show data from 1 experiment with mean±SEM.

FIG. 31C. CD34+ cell viability of cells derived from mobilized peripheral blood of healthy individuals upon gene-editing. Cells were thawed on day 0, cultured for 3 days prior to electroporation on day 3. Viability of mononuclear cells at the same time points post-editing. Two independent experiments were performed in duplicates. Total N=5. Graphs show data from 1 experiment with mean±SEM.

FIG. 41A (left panel) shows change in the number of sickle cells in gene-edited patient samples as enumerated by single cell imaging. FIG. 41B (right panel) shows change in the number of normal cells after gene editing in patient samples as enumerated by single cell imaging. Three independent experiments were performed, with each experiment in duplicate. Forty thousand single cell images were enumerated from each patient. Graph show mean±SEM from pooled data.

DEFINITIONS

Figure 1:
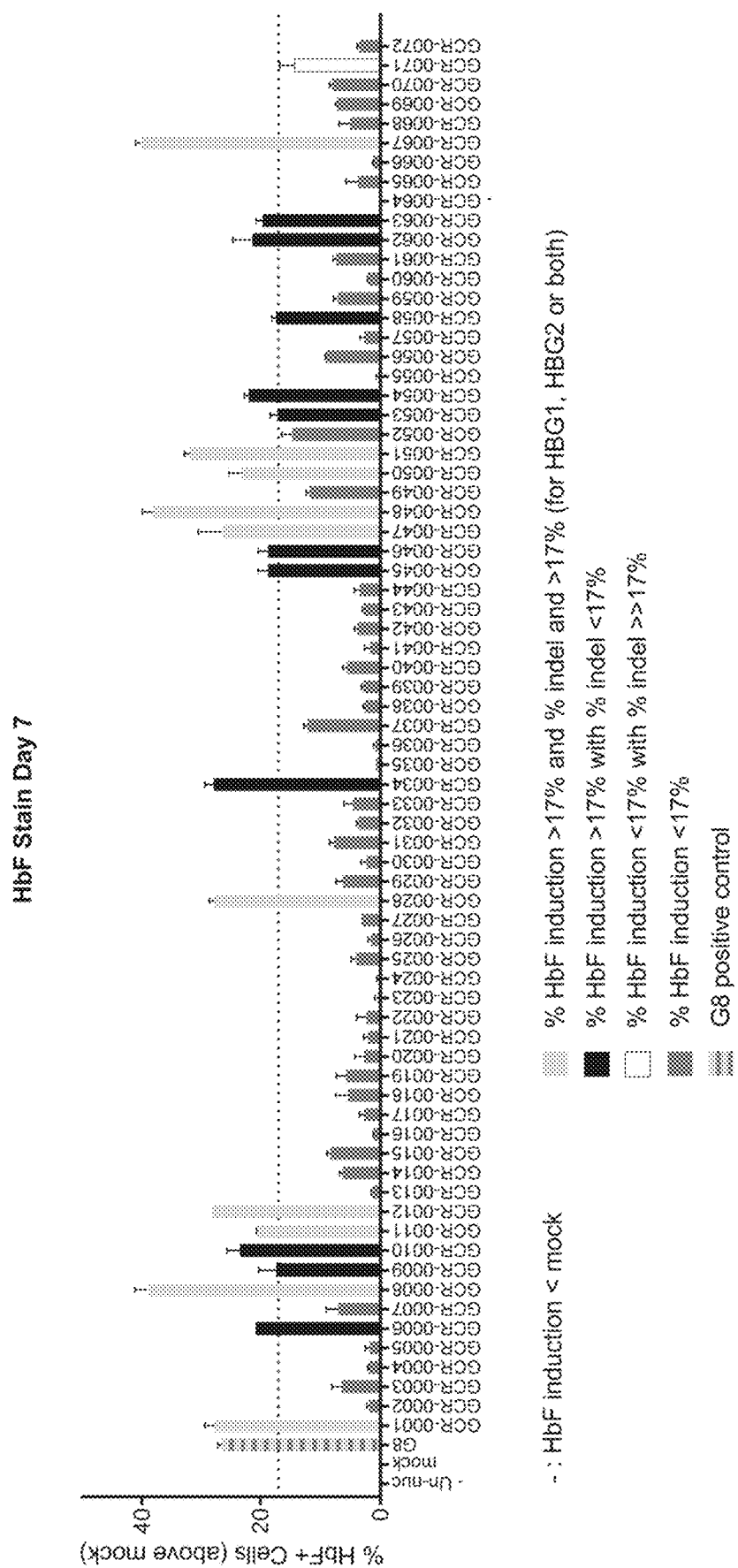
FIG. 1: HbF induction 7 days after editing. For each gRNA target sequence tested the percentage of cells with induced HbF expression corrected for background levels based on mock transfection, is shown as mean with error bar indicating standard deviation. The gRNA G8 against exon 2 of BCL11A serves as a positive control. A dotted line at 17% indicates the threshold level chosen for the analysis. Various grey shading, as indicated in the legend relate the degree of HbF induction to the degree of editing in the HBG1 or HBG2 target loci.

The terms "CRISPR system," "Cas system" or "CRISPR/Cas system" refer to a set of molecules comprising an RNA-guided nuclease or other effector molecule and a gRNA molecule that together are necessary and sufficient to direct and effect modification of nucleic acid at a target sequence by the RNA-guided nuclease or other effector molecule. In one embodiment, a CRISPR system comprises a gRNA and a Cas protein, e.g., a Cas9 protein. Such systems comprising a Cas9 or modified Cas9 molecule are referred to herein as "Cas9 systems" or "CRISPR/Cas9 systems." In one example, the gRNA molecule and Cas molecule may be complexed, to form a ribonuclear protein (RNP) complex.

The terms "guide RNA," "guide RNA molecule," "gRNA molecule" or "gRNA" are used interchangeably, and refer to a set of nucleic acid molecules that promote the specific directing of a RNA-guided nuclease or other effector molecule (typically in complex with the gRNA molecule) to a target sequence. In some embodiments, said directing is accomplished through hybridization of a portion of the gRNA to DNA (e.g., through the gRNA targeting domain), and by binding of a portion of the gRNA molecule to the RNA-guided nuclease or other effector molecule (e.g., through at least the gRNA tracr). In embodiments, a gRNA molecule consists of a single contiguous polynucleotide molecule, referred to herein as a "single guide RNA" or "sgRNA" and the like. In other embodiments, a gRNA molecule consists of a plurality, usually two, polynucleotide molecules, which are themselves capable of association, usually through hybridization, referred to herein as a "dual guide RNA" or "dgRNA," and the like. gRNA molecules are described in more detail below, but generally include a targeting domain and a tracr. In embodiments the targeting domain and tracr are disposed on a single polynucleotide. In other embodiments, the targeting domain and tracr are disposed on separate polynucleotides.

The term "targeting domain" as the term is used in connection with a gRNA, is the portion of the gRNA molecule that recognizes, e.g., is complementary to, a target sequence, e.g., a target sequence within the nucleic acid of a cell, e.g., within a gene.

The term "crRNA" as the term is used in connection with a gRNA molecule, is a portion of the gRNA molecule that comprises a targeting domain and a region that interacts with a tracr to form a flagpole region.

The term "target sequence" refers to a sequence of nucleic acids complimentary, for example fully complementary, to a gRNA targeting domain. In embodiments, the target sequence is disposed on genomic DNA. In an embodiment the target sequence is adjacent to (either on the same strand or on the complementary strand of DNA) a protospacer adjacent motif (PAM) sequence recognized by a protein having nuclease or other effector activity, e.g., a PAM sequence recognized by Cas9. In embodiments, the target sequence is a target sequence within a gene or locus that affects expression of a globin gene, e.g., that affects expression of beta globin or fetal hemoglobin (HbF). In embodiments, the target sequence is a target sequence within a nondeletional HPFH region, for example, is within a HBG1 and/or HBG2 promoter region.

The term "flagpole" as used herein in connection with a gRNA molecule, refers to the portion of the gRNA where the crRNA and the tracr bind to, or hybridize to, one another.

The term "tracr" as used herein in connection with a gRNA molecule, refers to the portion of the gRNA that binds to a nuclease or other effector molecule. In embodiments, the tracr comprises nucleic acid sequence that binds specifically to Cas9. In embodiments, the tracr comprises nucleic acid sequence that forms part of the flagpole.

The terms "Cas9" or "Cas9 molecule" refer to an enzyme from bacterial Type II CRISPR/Cas system responsible for DNA cleavage. Cas9 also includes wild-type protein as well as functional and non-functional mutants thereof. In embodiments, the Cas9 is a Cas9 of *S. pyogenes*.

The term "complementary" as used in connection with nucleic acid, refers to the pairing of bases, A with T or U, and G with C. The term complementary refers to nucleic acid molecules that are completely complementary, that is, form A to T or U pairs and G to C pairs across the entire reference sequence, as well as molecules that are at least 80%, 85%, 90%, 95%, 99% complementary.

"Template Nucleic Acid" as used in connection with homology-directed repair or homologous recombination, refers to nucleic acid to be inserted at the site of modification by the CRISPR system donor sequence for gene repair (insertion) at site of cutting.

An "indel," as the term is used herein, refers to a nucleic acid comprising one or more insertions of nucleotides, one or more deletions of nucleotides, or a combination of insertions and deletions of nucleotides, relative to a reference nucleic acid, that results after being exposed to a composition comprising a gRNA molecule, for example a CRISPR system. Indels can be determined by sequencing nucleic acid after being exposed to a composition comprising a gRNA molecule, for example, by NGS. With respect to the site of an indel, an indel is said to be "at or near" a reference site (e.g., a site complementary to a targeting domain of a gRNA molecule) if it comprises at least one insertion or deletion within about 10, 9, 8, 7, 6, 5, 4, 3, 2, or 1 nucleotide(s) of the reference site, or is overlapping with part or all of said reference site (e.g., comprises at least one insertion or deletion overlapping with, or within 10, 9, 8, 7, 6, 5, 4, 3, 2, or 1 nucleotides of a site complementary to the targeting domain of a gRNA molecule, e.g., a gRNA molecule described herein). In embodiments, the indel is a large deletion, for example, comprising more than about 1 kb, more than about 2 kb, more than about 3 kb, more than about 4 kb, more than about 5 kb, more than about 6 kb, or more than about 10 kb of nucleic acid. In embodiments, the 5' end, the 3' end, or both the 5' and 3' ends of the large deletion are disposed at or near a target sequence of a gRNA molecule described herein. In embodiments, the large deletion comprises about 4.9 kb of DNA disposed between a target sequence of a gRNA molecule, e.g., described herein, disposed within the HBG1 promoter region and a target sequence of a gRNA molecule, e.g., described herein, disposed within the HBG2 promoter region.

An "indel pattern," as the term is used herein, refers to a set of indels that results after exposure to a composition comprising a gRNA molecule. In an embodiment, the indel pattern consists of the top three indels, by frequency of appearance. In an embodiment, the indel pattern consists of the top five indels, by frequency of appearance. In an embodiment, the indel pattern consists of the indels which are present at greater than about 1% frequency relative to all sequencing reads. In an embodiment, the indel pattern consists of the indels which are present at greater than about 5% frequency relative to all sequencing reads. In an embodiment, the indel pattern consists of the indels which are present at greater than about 10% frequency relative to total number of indel sequencing reads (i.e., those reads that do not consist of the unmodified reference nucleic acid sequence). In an embodiment, the indel pattern includes of any 3 of the top five most frequently observed indels. The indel pattern may be determined, for example, by methods described herein, e.g., by sequencing cells of a population of cells which were exposed to the gRNA molecule.

An "off-target indel," as the term is used herein, refers to an indel at or near a site other than the target sequence of the targeting domain of the gRNA molecule. Such sites may comprise, for example, 1, 2, 3, 4, 5 or more mismatch nucleotides relative to the sequence of the targeting domain of the gRNA. In exemplary embodiments, such sites are detected using targeted sequencing of in silico predicted off-target sites, or by an insertional method known in the art. With respect to the gRNAs described herein, examples of off-target indels are indels formed at sequences outside of the HBG1 and/or HBG2 promoter regions. In exemplary embodiments the off-target indel is formed in a sequence of a gene, e.g., within a coding sequence of a gene.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or might be macromolecule besides a polypeptide. Such a biological sample can include, but is not limited to a tissue sample, a cell or a fluid with other biological components.

The term "autologous" refers to any material derived from the same individual into whom it is later to be re-introduced.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

"Derived from" as that term is used herein, indicates a relationship between a first and a second molecule. It generally refers to structural similarity between the first molecule and a second molecule and does not connotate or include a process or source limitation on a first molecule that is derived from a second molecule.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

As used herein in connection with a messenger RNA (mRNA), a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 190), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a disorder, e.g., a hemoglobinopathy, or the amelioration of one or more symptoms (preferably, one or more discernible symptoms) of a disorder, e.g., a hemoglobinopathy, resulting from the administration of one or more therapies (e.g., one or more therapeutic agents such as a gRNA molecule, CRISPR system, or modified cell of the invention). In specific embodiments, the terms "treat", "treatment" and "treating" refer to the amelioration of at least one measurable physical parameter of a hemoglobinopathy disorder, not discernible by the patient. In other embodiments the terms "treat", "treatment" and "treating" refer to the inhibition of the progression of a disorder, either physically by, e.g., stabilization of a discernible symptom, physiologically by, e.g., stabilization of a physical parameter, or both. In other embodiments the terms "treat", "treatment" and "treating" refer to the reduction or stabilization of a symptom of a hemoglobinopathy, e.g., sickle cell disease or beta-thalassemia.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The term "transfected" or "transformed" or "transduced" refers to a process by which exogenous nucleic acid and/or protein is transferred or introduced into the host cell. A "transfected" or "transformed" or "transduced" cell is one which has been transfected, transformed or transduced with exogenous nucleic acid and/or protein. The cell includes the primary subject cell and its progeny.

The term "specifically binds," refers to a molecule recognizing and binding with a binding partner (e.g., a protein or nucleic acid) present in a sample, but which molecule does not substantially recognize or bind other molecules in the sample.

The term "bioequivalent" refers to an amount of an agent other than the reference compound, required to produce an effect equivalent to the effect produced by the reference dose or reference amount of the reference compound.

"Refractory" as used herein refers to a disease, e.g., a hemoglobinopathy, that does not respond to a treatment. In embodiments, a refractory hemoglobinopathy can be resistant to a treatment before or at the beginning of the treatment. In other embodiments, the refractory hemoglobinopathy can become resistant during a treatment. A refractory hemoglobinopathy is also called a resistant hemoglobinopathy.

"Relapsed" as used herein refers to the return of a disease (e.g., hemoglobinopathy) or the signs and symptoms of a disease such as a hemoglobinopathy after a period of improvement, e.g., after prior treatment of a therapy, e.g., hemoglobinopathy therapy.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

The term "BCL11a" refers to B-cell lymphoma/leukemia 11A, a RNA polymerase II core promoter proximal region sequence-specific DNA binding protein, and the gene encoding said protein, together with all introns and exons. This gene encodes a C2H2 type zinc-finger protein. BCL11A has been found to play a role in the suppression of fetal hemoglobin production. BCL11a is also known as B-Cell CLL/Lymphoma 11A (Zinc Finger Protein), CTIP1, EVI9, Ecotropic Viral Integration Site 9 Protein Homolog, COUP-TF-Interacting Protein 1, Zinc Finger Protein 856, KIAA1809, BCL-11A, ZNF856, EVI-9, and B-Cell CLL/Lymphoma 11A. The term encompasses all isoforms and splice variants of BLC11a. The human gene encoding BCL11a is mapped to chromosomal location 2p16.1 (by Ensembl). The human and murine amino acid and nucleic acid sequences can be found in a public database, such as GenBank, UniProt and Swiss-Prot., and the genomic sequence of human BCL11a can be found in GenBank at NC_000002.12. The BCL11a gene refers to this genomic location, including all introns and exons. There are multiple known isotypes of BCL11a.

The sequence of mRNA encoding isoform 1 of human BCL11a can be found at NM_022893.

The peptide sequence of isoform 1 of human BCL11a is:

```
         10         20         30         40
 MSRRKQGKPQ HLSKREFSPE PLEAILTDDE PDHGPLGAPE 50         60         70         80
 GDHDLLTCGQ CQMNFPLGDI LIFIEHKRKQ CNGSLCLEKA 90        100        110        120
 VDKPPSPSPI EMKKASNPVE VGIQVTPEDD DCLSTSSRGI 130        140        150        160
 CPKQEHIADK LLHWRGLSSP RSAHGALIPT PGMSAEYAPQ 170        180        190        200
 GICKDEPSSY TCTTCKQPFT SAWFLLQHAQ NTHGLRIYLE 210        220        230        240
 SEHGSPLTPR VGIPSGLGAE CPSQPPLHGI HIADNNPFNL 250        260        270        280
 LRIPGSVSRE ASGLAEGRFP PTPPLFSPPP RHHLDPHRIE 290        300        310        320
 RLGAEEMALA THHPSAFDRV LRLNPMAMEP PAMDFSRRLR 330        340        350        360
 ELAGNTSSPP LSPGRPSPMQ RLLQPFQPGS KPPFLATPPL 370        380        390        400
 PPLQSAPPPS QPPVKSKSCE FCGKTFKFQS NLVVHRRSHT 410        420        430        440
 GEKPYKCNLC DHACTQASKL KRHMKTHMHK SSPMTVKSDD 450        460        470        480
 GLSTASSPEP GTSDLVGSAS SALKSVVAKF KSENDPNLIP 490        500        510        520
 ENGDEEEEED DEEEEEEEEE EEEELTESER VDYGFGLSLE 530        540        550        560
 AARHHENSSR GAVVGVGDES RALPDVMQGM VLSSMQHFSE 570        580        590        600
 AFHQVLGEKH KRGHLAEAEG HRDTCDEDSV AGESDRIDDG 610        620        630        640
 TVNGRGCSPG ESASGGLSKK LLLGSPSSLS PFSKRIKLEK 650        660        670        680
 EFDLPPAAMP NTENVYSQWL AGYAASRQLK DPFLSFGDSR 690        700        710        720
 QSPFASSSEH SSENGSLRFS TPPGELDGGI SGRSGTGSGG 730        740        750        760
 STPHISGPGP GRPSSKEGRR SDTCEYCGKV FKNCSNLTVH 770        780        790        800
 RRSHTGERPY KCELCNYACA QSSKLTRHMK THGQVGKDVY 810        820        830
 KCEICKMPFS VYSTLEKHMK KWHSDRVLNN DIKTE
```

SEQ ID NO: 245 (Identifier Q9H165-1; and NM_022893.3; and accession ADL14508.1).

The sequences of other BCL11a protein isoforms are provided at:
Isoform 2: Q9H165-2
Isoform 3: Q9H165-3
Isoform 4: Q9H165-4
Isoform 5: Q9H165-5
Isoform 6: Q9H165-6

As used herein, a human BCL11a protein also encompasses proteins that have over its full length at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with BCL11a isoform 1-6, wherein such proteins still have at least one of the functions of BCL11a.

The term "globin locus" as used herein refers to the region of human chromosome 11 comprising genes for embryonic (ε), fetal (G(γ) and A(γ)), adult globin genes (γ and β), locus control regions and DNase I hypersensitivity sites.

The term "complementary" as used in connection with nucleic acid, refers to the pairing of bases, A with T or U, and G with C. The term complementary refers to nucleic acid molecules that are completely complementary, that is, form A to T or U pairs and G to C pairs across the entire reference sequence, as well as molecules that are at least 80%, 85%, 90%, 95%, 99% complementary.

The term "Nondeletional HPFH" refers to a mutation that does not comprise an insertion or deletion of one or more nucleotides, which results in hereditary persistence of fetal hemoglobin, and is characterized in increased fetal hemoglobin in adult red blood cells. In exemplary embodiments, the nondeletional HPFH is a mutation described in Nathan and Oski's Hematology and Oncology of Infancy and Childhood, 8$^{th}$ Ed., 2015, Orkin S H, Fisher D E, Look T, Lux S E, Ginsburg D, Nathan D G, Eds., Elsevier Saunders, the entire contents of which is incorporated herein by reference, for example the nondeltional HPFH mutations described at Table 21-5. The term "Nondeletional HPFH region" refers to a genomic site which comprises or is near a nondeletional HPFH. In exemplary embodiments, the nondeletional HPFH region is the nucleic acid sequence of the HBG1 promoter region (Chr11:5,249,833 to Chr11:5,250,237, hg38; − strand), the nucleic acid sequence of the HBG2 promoter region (Chr11:5,254,738 to Chr11:5,255,164, hg38; − strand), or combinations thereof. In exemplary embodiments, the nondeletional HPFH region includes one or more of the nondeletional HPFH described in Nathan and Oski's Hematology and Oncology of Infancy and Childhood, 8$^{th}$ Ed., 2015, Orkin S H, Fisher D E, Look T, Lux S E, Ginsburg D, Nathan D G, Eds., Elsevier Saunders (e.g., described in Table 21-5 therein). In exemplary embodiments, the nondeletional HPFH region is the nucleic acid sequence at chr11:5,250,094-5,250,237, − strand, hg38; or the nucleic acid sequence at chr11:5,255,022-5,255,164, − strand, hg38; or the nucleic acid sequence at chr11:5,249, 833-5,249,927, − strand, hg38; or the nucleic acid sequence at chr11:5,254,738-5,254,851, − strand, hg38; or the nucleic acid sequence at chr11:5,250,139-5,250,237, − strand, hg38; or combinations thereof.

"BCL11a enhancer" as the term is used herein, refers to nucleic acid sequence which affects, e.g., enhances, expression or function of BCL11a. See e.g., Bauer et al., Science, vol. 342, 2013, pp. 253-257. The BCL11a enhancer may be, for example, operative only in certain cell types, for example, cells of the erythroid lineage. One example of a BCL11a enhancer is the nucleic acid sequence between exon 2 and exon 3 of the BCL11a gene gene (e.g., the nucleic acid at or corresponding to positions +55: Chr2:60497676-60498941; +58: Chr2:60494251-60495546; +62: Chr2:60490409-60491734 as recorded in hg38). In an embodiment, the BCL11a Enhancer is the +62 region of the nucleic acid sequence between exon 2 and exon 3 of the BCL11a gene. In an embodiment, the BCL11a Enhancer is the +58 region of the nucleic acid sequence between exon 2 and exon 3 of the BCL11a gene. In an embodiment, the BCL11a Enhancer is the +55 region of the nucleic acid sequence between exon 2 and exon 3 of the BCL11a gene.

The terms "hematopoietic stem and progenitor cell" or "HSPC" are used interchangeably, and refer to a population of cells comprising both hematopoietic stem cells ("HSCs") and hematopoietic progenitor cells ("HPCs"). Such cells are characterized, for example, as CD34+. In exemplary embodiments, HSPCs are isolated from bone marrow. In other exemplary embodiments, HSPCs are isolated from peripheral blood. In other exemplary embodiments, HSPCs are isolated from umbilical cord blood. In an embodiment, HSPCs are characterized as CD34+/CD38−/CD90+/ CD45RA−. In embodiments, the HSPCs are characterized as CD34+/CD90+/CD49f+ cells. In embodiments, the HSPCs are characterized as CD34+ cells. In embodiments, the HSPC s are characterized as CD34+/CD90+ cells. In embodiments, the HSPCs are characterized as CD34+/ CD90+/CD45RA− cells.

"Stem cell expander" as used herein refers to a compound which causes cells, e.g., HSPCs, HSCs and/or HPCs to proliferate, e.g., increase in number, at a faster rate relative to the same cell types absent said agent. In one exemplary aspect, the stem cell expander is an inhibitor of the aryl hydrocarbon receptor pathway. Additional examples of stem cell expanders are provided below. In embodiments, the proliferation, e.g., increase in number, is accomplished ex vivo.

"Engraftment" or "engraft" refers to the incorporation of a cell or tissue, e.g., a population of HSPCs, into the body of a recipient, e.g., a mammal or human subject. In one example, engraftment includes the growth, expansion and/or differention of the engrafted cells in the recipient. In an example, engraftment of HSPCs includes the differentiation and growth of said HSPCs into erythroid cells within the body of the recipient.

The term "Hematopoietic progenitor cells" (HPCs) as used herein refers to primitive hematopoietic cells that have a limited capacity for self-renewal and the potential for multilineage differentiation (e.g., myeloid, lymphoid), mono-lineage differentiation (e.g., myeloid or lymphoid) or cell-type restricted differentiation (e.g., erythroid progenitor) depending on placement within the hematopoietic hierarchy (Doulatov et al., Cell Stem Cell 2012).

"Hematopoietic stem cells" (HSCs) as used herein refer to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). HSCs are interchangeably described as stem cells throughout the specification. It is known in the art that such cells may or may not include CD34+ cells. CD34+ cells are immature cells that express the CD34 cell surface marker. CD34+ cells are believed to include a subpopulation of cells with the stem cell properties defined above. It is well known in the art that HSCs are multipotent cells that can give rise to primitive progenitor cells (e.g., multipotent progenitor cells) and/or progenitor cells committed to specific hematopoietic lineages (e.g., lymphoid progenitor cells). The stem cells committed to specific hematopoietic lineages may be of T cell lineage, B cell lineage, dendritic cell lineage, Langerhans cell lineage and/or lymphoid tissue-specific macrophage cell lineage. In addition, HSCs also refer to long term HSC (LT-HSC) and short term HSC (ST-HSC). ST-HSCs are more active and more proliferative than LT-HSCs. However, LT-HSC have unlimited self renewal (i.e., they survive throughout adulthood), whereas ST-HSC have limited self renewal (i.e., they survive for only a limited period of time). Any of these HSCs can be used in any of the methods described herein. Optionally, ST-HSCs are useful because they are highly proliferative and thus, quickly increase the number of HSCs and their progeny. Hematopoietic stem cells are optionally obtained from blood products. A blood product includes a product obtained from the body or an organ of the body containing cells of hematopoietic origin. Such sources include un-fractionated bone marrow, umbilical cord, peripheral blood (e.g., mobilized peripheral blood, e.g., mobilized with a mobilization agent such as G-CSF or Plerixafor® (AMD3100), or a combination of G-CSF and Plerixafor® (AMD3100)), liver, thymus, lymph and spleen. All of the aforementioned crude or un-fractionated blood products can be enriched for cells having hematopoietic stem cell characteristics in ways known to those of skill in the art. In an embodiment, HSCs are characterized as CD34+/CD38−/CD90+/CD45RA−. In embodiments, the HSCs are characterized as CD34+/ CD90+/CD49f+ cells. In embodiments, the HSCs are characterized as CD34+ cells. In embodiments, the HSCs are characterized as CD34+/CD90+ cells. In embodiments, the HSCs are characterized as CD34+/CD90+/CD45RA− cells.

"Expansion" or "Expand" in the context of cells refers to an increase in the number of a characteristic cell type, or cell types, from an initial cell population of cells, which may or may not be identical. The initial cells used for expansion may not be the same as the cells generated from expansion.

"Cell population" refers to eukaryotic mammalian, preferably human, cells isolated from biological sources, for example, blood product or tissues and derived from more than one cell.

"Enriched" when used in the context of cell population refers to a cell population selected based on the presence of one or more markers, for example, CD34+.

The term "CD34+ cells" refers to cells that express at their surface CD34 marker. CD34+ cells can be detected and counted using for example flow cytometry and fluorescently labeled anti-CD34 antibodies.

"Enriched in CD34+ cells" means that a cell population has been selected based on the presence of CD34 marker. Accordingly, the percentage of CD34+ cells in the cell population after selection method is higher than the percentage of CD34+ cells in the initial cell population before selecting step based on CD34 markers. For example, CD34+ cells may represent at least 50%, 60%, 70%, 80% or at least 90% of the cells in a cell population enriched in CD34+ cells.

The terms "F cell" and "F-cell" refer to cells, usually erythrocytes (e.g., red blood cells) which contain and/or produce (e.g., express) fetal hemoglobin. For example, an F-cell is a cell that contains or produces detectible levels of fetal hemoglobin. For example, an F-cell is a cell that contains or produces at least 5 picograms of fetal hemoglobin. In another example, an F-cell is a cell that contains or produces at least 6 picograms of fetal hemoglobin. In another example, an F-cell is a cell that contains or produces at least 7 picograms of fetal hemoglobin. In another example, an F-cell is a cell that contains or produces at least 8 picograms of fetal hemoglobin. In another example, an F-cell is a cell that contains or produces at least 9 picograms of fetal hemoglobin. In another example, an F-cell is a cell that contains or produces at least 10 picograms of fetal hemoglobin. Levels of fetal hemoglobin may be measured using an assay described herein or by other method known in the art, for example, flow cytometry using an anti-fetal hemoglobin detection reagent, high performance liquid chromatography, mass spectrometry, or enzyme-linked immunoabsorbent assay.

Unless otherwise stated, all genome or chromosome coordinates are according to hg38.

DETAILED DESCRIPTION

The gRNA molecules, compositions and methods described herein relate to genome editing in eukaryotic cells using the CRISPR/Cas9 system. In particular, the gRNA molecules, compositions and methods described herein relate to regulation of globin levels and are useful, for example, in regulating expression and production of globin genes and protein. The gRNA molecules, compositions and methods can be useful in the treatment of hemoglobinopathies.

I. gRNA Molecules

A gRNA molecule may have a number of domains, as described more fully below, however, a gRNA molecule typically comprises at least a crRNA domain (comprising a targeting domain) and a tracr. The gRNA molecules of the invention, used as a component of a CRISPR system, are useful for modifying (e.g., modifying the sequence) DNA at or near a target site. Such modifications include deletions and or insertions that result in, for example, reduced or eliminated expression of a functional product of the gene comprising the target site. These uses, and additional uses, are described more fully below.

In an embodiment, a unimolecular, or sgRNA comprises, preferably from 5' to 3': a crRNA (which contains a targeting domain complementary to a target sequence and a region that forms part of a flagpole (i.e., a crRNA flagpole region)); a loop; and a tracr (which contains a domain complementary to the crRNA flagpole region, and a domain which additionally binds a nuclease or other effector molecule, e.g., a Cas molecule, e.g., a Cas9 molecule), and may take the following format (from 5' to 3'):

[targeting domain]—[crRNA flagpole region]—[optional first flagpole extension]—[loop]—[optional first tracr extension]—[tracr flagpole region]—[tracr nuclease binding domain].

In embodiments, the tracr nuclease binding domain binds to a Cas protein, e.g., a Cas9 protein.

In an embodiment, a bimolecular, or dgRNA comprises two polynucleotides; the first, preferably from 5' to 3': a crRNA (which contains a targeting domain complementary to a target sequence and a region that forms part of a flagpole; and the second, preferrably from 5' to 3': a tracr (which contains a domain complementary to the crRNA flagpole region, and a domain which additionally binds a nuclease or other effector molecule, e.g., a Cas molecule, e.g., Cas9 molecule), and may take the following format (from 5' to 3'):

Polynucleotide 1 (crRNA): [targeting domain]—[crRNA flagpole region]—[optional first flagpole extension]—[optional second flagpole extension]

Polynucleotide 2 (tracr): [optional first tracr extension]—[tracr flagpole region]—[tracr nuclease binding domain]

In embodiments, the tracr nuclease binding domain binds to a Cas protein, e.g., a Cas9 protein.

In some aspects, the targeting domain comprises or consists of a targeting domain sequence described herein, e.g., a targeting domain described in Table 1, or a targeting domain comprising or consisting of 17, 18, 19, or 20 (preferably 20) consecutive nucleotides of a targeting domain sequence described in Table 1.

In some aspects, the flagpole, e.g., the crRNA flagpole region, comprises, from 5' to 3':

GUUUUAGAGCUA. (SEQ ID NO: 182)

In some aspects, the flagpole, e.g., the crRNA flagpole region, comprises, from 5' to 3':

GUUUAAGAGCUA. (SEQ ID NO: 183)

In some aspects the loop comprises, from 5' to 3': GAAA (SEQ ID NO: 186).

In some aspects the tracr comprises, from 5' to 3': UAGCAAGUUAAAAUAAGGCUAGUCCGUUAUCAACUUGAAAAAGUGGCACCGAGUCGG UGC (SEQ ID NO: 187) and is preferably used in a gRNA molecule comprising SEQ ID NO 182.

In some aspects the tracr comprises, from 5' to 3': UAGCAAGUUUAAAUAAGGCUAGUCCGUUAU- CAACUUGAAAAAGUGGCACCGAGUCGG UGC (SEQ ID NO: 188) and is preferably used in a gRNA molecule comprising SEQ ID NO 183.

In some aspects, the gRNA may also comprise, at the 3' end, additional U nucleic acids. For example the gRNA may comprise an additional 1, 2, 3, 4, 5, 6, 7, 8, 9, or 10 U nucleic acids (SEQ ID NO: 249) at the 3' end. In an embodiment, the gRNA comprises an additional 4 U nucleic acids at the 3' end. In the case of dgRNA, one or more of the polynucleotides of the dgRNA (e.g., the polynucleotide comprising the targeting domain and the polynucleotide comprising the tracr) may comprise, at the 3' end, additional U nucleic acids. For example, the case of dgRNA, one or more of the polynucleotides of the dgRNA (e.g., the polynucleotide comprising the targeting domain and the polynucleotide comprising the tracr) may comprise an additional 1, 2, 3, 4, 5, 6, 7, 8, 9, or 10 U nucleic acids (SEQ ID NO: 249) at the 3' end. In an embodiment, in the case of dgRNA, one or more of the polynucleotides of the dgRNA (e.g., the polynucleotide comprising the targeting domain and the polynucleotide comprising the tracr) comprises an additional 4 U nucleic acids at the 3' end. In an embodiment of a dgRNA, only the polynucleotide comprising the tracr comprises the additional U nucleic acid(s), e.g., 4 U nucleic acids. In an embodiment of a dgRNA, only the polynucleotide comprising the targeting domain comprises the additional U nucleic acid(s). In an embodiment of a dgRNA, both the polynucleotide comprising the targeting domain and the polynucleotide comprising the tracr comprise the additional U nucleic acids, e.g., 4 U nucleic acids.

In some aspects, the gRNA may also comprise, at the 3' end, additional A nucleic acids. For example the gRNA may comprise an additional 1, 2, 3, 4, 5, 6, 7, 8, 9, or 10 A nucleic acids (SEQ ID NO: 250) at the 3' end. In an embodiment, the gRNA comprises an additional 4 A nucleic acids at the 3' end. In the case of dgRNA, one or more of the polynucleotides of the dgRNA (e.g., the polynucleotide comprising the targeting domain and the polynucleotide comprising the tracr) may comprise, at the 3' end, additional A nucleic acids. For example, the case of dgRNA, one or more of the polynucleotides of the dgRNA (e.g., the polynucleotide comprising the targeting domain and the polynucleotide comprising the tracr) may comprise an additional 1, 2, 3, 4, 5, 6, 7, 8, 9, or 10 A nucleic acids (SEQ ID NO: 250) at the 3' end. In an embodiment, in the case of dgRNA, one or more of the polynucleotides of the dgRNA (e.g., the polynucleotide comprising the targeting domain and the polynucleotide comprising the tracr) comprises an additional 4 A nucleic acids at the 3' end. In an embodiment of a dgRNA, only the polynucleotide comprising the tracr comprises the additional A nucleic acid(s), e.g., 4 A nucleic acids. In an embodiment of a dgRNA, only the polynucleotide comprising the targeting domain comprises the additional A nucleic acid(s). In an embodiment of a dgRNA, both the polynucleotide comprising the targeting domain and the polynucleotide comprising the tracr comprise the additional U nucleic acids, e.g., 4 A nucleic acids.

In embodiments, one or more of the polynucleotides of the gRNA molecule may comprise a cap at the 5' end.

In an embodiment, a unimolecular, or sgRNA comprises, preferably from 5' to 3': a crRNA (which contains a targeting domain complementary to a target sequence; a crRNA flagpole region; first flagpole extension; a loop; a first tracr extension (which contains a domain complementary to at least a portion of the first flagpole extension); and a tracr (which contains a domain complementary to the crRNA flagpole region, and a domain which additionally binds a Cas9 molecule). In some aspects, the targeting domain comprises a targeting domain sequence described herein, e.g., a targeting domain described in Table 1, or a targeting domain comprising or consisting of 17, 18, 19, or 20 (preferably 20) consecutive nucleotides of a targeting domain sequence described in Table 1, for example the 3' 17, 18, 19, or 20 (preferably 20) consecutive nucleotides of a targeting domain sequence described in Table 1.

In aspects comprising a first flagpole extension and/or a first tracr extension, the flagpole, loop and tracr sequences may be as described above. In general any first flagpole extension and first tracr extension may be employed, provided that they are complementary. In embodiments, the first flagpole extension and first tracr extension consist of 3, 4, 5, 6, 7, 8, 9, 10 or more complementary nucleotides.

In some aspects, the first flagpole extension comprises, from 5' to 3': UGCUG (SEQ ID NO: 184). In some aspects, the first flagpole extension consists of SEQ ID NO: 184.

In some aspects, the first tracr extension comprises, from 5' to 3': CAGCA (SEQ ID NO: 189). In some aspects, the first tracr extension consists of SEQ ID NO: 189.

In an embodiment, a dgRNA comprises two nucleic acid molecules. In some aspects, the dgRNA comprises a first nucleic acid which contains, preferably from 5' to 3': a targeting domain complementary to a target sequence; a crRNA flagpole region; optionally a first flagpole extension; and, optionally, a second flagpole extension; and a second nucleic acid (which may be referred to herein as a tracr), and comprises at least a domain which binds a Cas molecule, e.g., a Cas9 molecule) comprising preferably from 5' to 3': optionally a first tracr extension; and a tracr (which contains a domain complementary to the crRNA flagpole region, and a domain which additionally binds a Cas, e.g., Cas9, molecule). The second nucleic acid may additionally comprise, at the 3' end (e.g., 3' to the tracr) additional U nucleic acids. For example the tracr may comprise an additional 1, 2, 3, 4, 5, 6, 7, 8, 9, or 10 U nucleic acids (SEQ ID NO: 249) at the 3' end (e.g., 3' to the tracr). The second nucleic acid may additionally or alternately comprise, at the 3' end (e.g., 3' to the tracr) additional A nucleic acids. For example the tracr may comprise an additional 1, 2, 3, 4, 5, 6, 7, 8, 9, or 10 A nucleic acids (SEQ ID NO: 250) at the 3' end (e.g., 3' to the tracr). In some aspects, the targeting domain comprises a targeting domain sequence described herein, e.g., a targeting domain described in Table 1, or a targeting domain comprising or consisting of 17, 18, 19, or 20 (preferably 20) consecutive nucleotides of a targeting domain sequence described in Table 1.

In aspects involving a dgRNA, the crRNA flagpole region, optional first flagpole extension, optional first tracr extension and tracr sequences may be as described above.

In some aspects, the optional second flagpole extension comprises, from 5' to 3': UUUUG (SEQ ID NO: 185).

In embodiments, the 3' 1, 2, 3, 4, or 5 nucleotides, the 5' 1, 2, 3, 4, or 5 nucleotides, or both the 3' and 5' 1, 2, 3, 4, or 5 nucleotides of the gRNA molecule (and in the case of a dgRNA molecule, the polynucleotide comprising the targeting domain and/or the polynucleotide comprising the tracr) are modified nucleic acids, as described more fully in section XIII, below.

The Domains are Discussed Briefly Below:

1) The Targeting Domain:

Guidance on the selection of targeting domains can be found, e.g., in Fu Y el al. NAT BIOTECHNOL 2014 (doi: 10.1038/nbt.2808) and Sternberg S H el al. NATURE 2014 (doi: 10.1038/nature13011).

The targeting domain comprises a nucleotide sequence that is complementary, e.g., at least 80, 85, 90, 95, or 99% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). While not wishing to be bound by theory, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence.

In an embodiment, the targeting domain is 5 to 50, e.g., 10 to 40, e.g., 10 to 30, e.g., 15 to 30, e.g., 15 to 25 nucleotides in length. In an embodiment, the targeting domain is 15, 16, 17, 18, 19, 20, 21, 22, 23, 24 or 25 nucleotides in length. In an embodiment, the targeting domain is 16 nucleotides in length. In an embodiment, the targeting domain is 17 nucleotides in length. In an embodiment, the targeting domain is 18 nucleotides in length. In an embodiment, the targeting domain is 19 nucleotides in length. In an embodiment, the targeting domain is 20 nucleotides in length. In embodiments, the aforementioned 16, 17, 18, 19, or 20 nucleotides comprise the 5'-16, 17, 18, 19, or 20 nucleotides from a targeting domain described in Table 1. In embodiments, the aforementioned 16, 17, 18, 19, or 20 nucleotides comprise the 3'-16, 17, 18, 19, or 20 nucleotides from a targeting domain described in Table 1.

Without being bound by theory, it is believed that the 8, 9, 10, 11 or 12 nucleic acids of the targeting domain disposed at the 3' end of the targeting domain is important for targeting the target sequence, and may thus be referred to as the "core" region of the targeting domain. In an embodiment, the core domain is fully complementary with the target sequence.

The strand of the target nucleic acid with which the targeting domain is complementary is referred to herein as the target sequence. In some aspects, the target sequence is disposed on a chromosome, e.g., is a target within a gene. In some aspects the target sequence is disposed within an exon of a gene. In some aspects the target sequence is disposed within an intron of a gene. In some aspects, the target sequence comprises, or is proximal (e.g., within 10, 20, 30, 40, 50, 100, 200, 300, 400, 500, or 1000 nucleic acids) to a binding site of a regulatory element, e.g., a promoter or transcription factor binding site, of a gene of interest. Some or all of the nucleotides of the domain can have a modification, e.g., modification found in Section XIII herein.

2) crRNA Flagpole Region:

The flagpole contains portions from both the crRNA and the tracr. The crRNA flagpole region is complementary with a portion of the tracr, and in an embodiment, has sufficient complementarity to a portion of the tracr to form a duplexed region under at least some physiological conditions, for example, normal physiological conditions. In an embodiment, the crRNA flagpole region is 5 to 30 nucleotides in length. In an embodiment, the crRNA flagpole region is 5 to 25 nucleotides in length. The crRNA flagpole region can share homology with, or be derived from, a naturally occurring portion of the repeat sequence from a bacterial CRISPR array. In an embodiment, it has at least 50% homology with a crRNA flagpole region disclosed herein, e.g., an *S. pyogenes*, or *S. thermophilus*, crRNA flagpole region.

In an embodiment, the flagpole, e.g., the crRNA flagpole region, comprises SEQ ID NO: 182. In an embodiment, the flagpole, e.g., the crRNA flagpole region, comprises sequence having at least 50%, 60%, 70%, 80%, 85%, 90%, 95% or 99% homology with SEQ ID NO: 182. In an embodiment, the flagpole, e.g., the crRNA flagpole region, comprises at least 5, 6, 7, 8, 9, 10, or 11 nucleotides of SEQ ID NO: 182. In an embodiment, the flagpole, e.g., the crRNA flagpole region, comprises SEQ ID NO: 183. In an embodiment, the flagpole comprises sequence having at least 50%, 60%, 70%, 80%, 85%, 90%, 95% or 99% homology with SEQ ID NO: 183. In an embodiment, the flagpole, e.g., the crRNA flagpole region, comprises at least 5, 6, 7, 8, 9, 10, or 11 nucleotides of SEQ ID NO: 183.

Some or all of the nucleotides of the domain can have a modification, e.g., modification described in Section XIII herein.

3) First Flagpole Extension

When a tracr comprising a first tracr extension is used, the crRNA may comprise a first flagpole extension. In general any first flagpole extension and first tracr extension may be employed, provided that they are complementary. In embodiments, the first flagpole extension and first tracr extension consist of 3, 4, 5, 6, 7, 8, 9, 10 or more complementary nucleotides.

The first flagpole extension may comprise nucleotides that are complementary, e.g., 80%, 85%, 90%, 95% or 99%, e.g., fully complementary, with nucleotides of the first tracr extension. In some aspects, the first flagpole extension nucleotides that hybridize with complementary nucleotides of the first tracr extension are contiguous. In some aspects, the first flagpole extension nucleotides that hybridize with complementary nucleotides of the first tracr extension are discontinuous, e.g., comprises two or more regions of hybridization separated by nucleotides that do not base pair with nucleotides of the first tracr extension. In some aspects, the first flagpole extension comprises at least 2, 3, 4, 5, 6, 7, 8, 9, 10, 11, 12, 13, 14, 15, 16, 17, 18, 19, 20 or more nucleotides. In some aspects, the first flagpole extension comprises, from 5' to 3': UGCUG (SEQ ID NO: 184). In some aspects, the first flagpole extension consists of SEQ ID NO: 184. In some aspects the first flagpole extension comprises nucleic acid that is at least 80%, 85%, 90%, 95% or 99% homology to SEQ ID NO: 184.

Some or all of the nucleotides of the first tracr extension can have a modification, e.g., modification found in Section XIII herein.

3) The Loop

A loop serves to link the crRNA flagpole region (or optionally the first flagpole extension, when present) with the tracr (or optionally the first tracr extension, when present) of a sgRNA. The loop can link the crRNA flagpole region and tracr covalently or non-covalently. In an embodiment, the linkage is covalent. In an embodiment, the loop covalently couples the crRNA flagpole region and tracr. In an embodiment, the loop covalently couples the first flagpole extension and the first tracr extension. In an embodiment, the loop is, or comprises, a covalent bond interposed between the crRNA flagpole region and the domain of the tracr which hybridizes to the crRNA flagpole region. Typically, the loop comprises one or more, e.g., 2, 3, 4, 5, 6, 7, 8, 9, or 10 nucleotides.

In dgRNA molecules the two molecules can be associated by virtue of the hybridization between at least a portion of the crRNA (e.g., the crRNA flagpole region) and at least a portion of the tracr (e.g., the domain of the tracr which is complementary to the crRNA flagpole region).

A wide variety of loops are suitable for use in sgRNAs. Loops can consist of a covalent bond, or be as short as one or a few nucleotides, e.g., 1, 2, 3, 4, or 5 nucleotides in length. In an embodiment, a loop is 2, 3, 4, 5, 6, 7, 8, 9, 10, 15, 20, or 25 or more nucleotides in length. In an embodiment, a loop is 2 to 50, 2 to 40, 2 to 30, 2 to 20, 2 to 10, or 2 to 5 nucleotides in length. In an embodiment, a loop shares homology with, or is derived from, a naturally occurring sequence. In an embodiment, the loop has at least 50% homology with a loop disclosed herein. In an embodiment, the loop comprises SEQ ID NO: 186.

Some or all of the nucleotides of the domain can have a modification, e.g., modification described in Section XIII herein.

4) The Second Flagpole Extension

In an embodiment, a dgRNA can comprise additional sequence, 3' to the crRNA flagpole region or, when present, the first flagpole extension, referred to herein as the second flagpole extension. In an embodiment, the second flagpole extension is, 2-10, 2-9, 2-8, 2-7, 2-6, 2-5, or 2-4 nucleotides in length. In an embodiment, the second flagpole extension is 2, 3, 4, 5, 6, 7, 8, 9, or 10 or more nucleotides in length. In an embodiment, the second flagpole extension comprises SEQ ID NO: 185.

5) The Tracr:

The tracr is the nucleic acid sequence required for nuclease, e.g., Cas9, binding Without being bound by theory, it is believed that each Cas9 species is associated with a particular tracr sequence. Tracr sequences are utilized in both sgRNA and in dgRNA systems. In an embodiment, the tracr comprises sequence from, or derived from, an *S. pyogenes* tracr. In some aspects, the tracr has a portion that hybridizes to the flagpole portion of the crRNA, e.g., has sufficient complementarity to the crRNA flagpole region to form a duplexed region under at least some physiological conditions (sometimes referred to herein as the tracr flagpole region or a tracr domain complementary to the crRNA flagpole region). In embodiments, the domain of the tracr that hybridizes with the crRNA flagpole region comprises at least 5, 6, 7, 8, 9, 10, 11, 12, 13, 14, 15, 16, 17, 18, 19, or 20 nucleotides that hybridize with complementary nucleotides of the crRNA flagpole region. In some aspects, the tracr nucleotides that hybridize with complementary nucleotides of the crRNA flagpole region are contiguous. In some aspects, the tracr nucleotides that hybridize with complementary nucleotides of the crRNA flagpole region are discontinuous, e.g., comprises two or more regions of hybridization separated by nucleotides that do not base pair with nucleotides of the crRNA flagpole region. In some aspects, the portion of the tracr that hybridizes to the crRNA flagpole region comprises, from 5' to 3': UAGCAAGUUAAAA (SEQ ID NO: 191). In some aspects, the portion of the tracr that hybridizes to the crRNA flagpole region comprises, from 5' to 3': UAGCAAGUUAAA (SEQ ID NO: 192). In embodiments, the sequence that hybridizes with the crRNA flagpole region is disposed on the tracr 5'- to the sequence of the tracr that additionally binds a nuclease, e.g., a Cas molecule, e.g., a Cas9 molecule.

The tracr further comprises a domain that additionally binds to a nuclease, e.g., a Cas molecule, e.g., a Cas9 molecule. Without being bound by theory, it is believed that Cas9 from different species bind to different tracr sequences. In some aspects, the tracr comprises sequence that binds to a *S. pyogenes* Cas9 molecule. In some aspects, the tracr comprises sequence that binds to a Cas9 molecule disclosed herein. In some aspects, the domain that additionally binds a Cas9 molecule comprises, from 5' to 3': UAAGGCUA-GUCCGUUAUCAACUUGAAAAAGUGGCACCGAGU-CGGUGC (SEQ ID NO: 193). In some aspects the domain that additionally binds a Cas9 molecule comprises, from 5' to 3':

(SEQ ID NO: 194)
UAAGGCUAGUCCGUUAUCAACUUGAAAAAGUGGCACCGAGUCGGUGCU

UUU.

In some embodiments, the tracr comprises SEQ ID NO: 187. In some embodiments, the tracr comprises SEQ ID NO: 188.

Some or all of the nucleotides of the tracr can have a modification, e.g., modification found in Section XIII herein. In embodiments, the gRNA (e.g., the sgRNA or the tracr and/or crRNA of a dgRNA), e.g., any of the gRNA or gRNA components described above, comprises an inverted abasic residue at the 5' end, the 3' end or both the 5' and 3' end of the gRNA. In embodiments, the gRNA (e.g., the sgRNA or the tracr and/or crRNA of a dgRNA), e.g., any of the gRNA or gRNA components described above, comprises one or more phosphorothioate bonds between residues at the 5' end of the polynucleotide, for example, a phosphorthioate bond between the first two 5' residues, between each of the first three 5' residues, between each of the first four 5' residues, or between each of the first five 5' residues. In embodiments, the gRNA or gRNA component may alternatively or additionally comprise one or more phosphorothioate bonds between residues at the 3' end of the polynucleotide, for example, a phosphorthioate bond between the first two 3' residues, between each of the first three 3' residues, between each of the first four 3' residues, or between each of the first five 3' residues. In an embodiment, the gRNA (e.g., the sgRNA or the tracr and/or crRNA of a dgRNA), e.g., any of the gRNA or gRNA components described above, comprises a phosphorothioate bond between each of the first four 5' residues (e.g., comprises, e.g., consists of, three phosphorothioate bonds at the 5' end(s)), and a phosphorothioate bond between each of the first four 3' residues (e.g., comprises, e.g., consists of, three phosphorothioate bonds at the 3' end(s)). In an embodiment, any of the phosphorothioate modifications described above are combined with an inverted abasic residue at the 5' end, the 3' end, or both the 5' and 3' ends of the polynucleotide. In such embodiments, the inverted abasic nucleotide may be linked to the 5' and/or 3' nucleotide by a phosphate bond or a phosphorothioate bond. In embodiments, the gRNA (e.g., the sgRNA or the tracr and/or crRNA of a dgRNA), e.g., any of the gRNA or gRNA components described above, comprises one or more nucleotides that include a 2' O-methyl modification. In embodiments, each of the first 1, 2, 3, or more of the 5' residues comprise a 2' O-methyl modification. In embodiments, each of the first 1, 2, 3, or more of the 3' residues comprise a 2' O-methyl modification. In embodiments, the $4^{th}$-to-terminal, $3^{rd}$-to-terminal, and $2^{nd}$-to-terminal 3' residues comprise a 2' O-methyl modification. In embodiments, each of the first 1, 2, 3 or more of the 5' residues comprise a 2' O-methyl modification, and each of the first 1, 2, 3 or more of the 3' residues comprise a 2' O-methyl modification. In an embodiment, each of the first 3 of the 5' residues comprise a 2' O-methyl modification, and each of the first 3 of the 3' residues comprise a 2' O-methyl modification. In embodiments, each of the first 3 of the 5' residues comprise a 2' O-methyl modification, and the $4^{th}$-to-terminal, $3^{rd}$-to-terminal, and $2^{nd}$-to-terminal 3' residues comprise a 2' O-methyl modification. In embodiments, any of the 2' O-methyl modifications, e.g., as described above, may be combined with one or more phosphorothioate modifications, e.g., as described above, and/or one or more inverted abasic modifications, e.g., as described above. In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' O-methyl modification at each of the first three 5' residues, and a 2' O-methyl modification at each of the first three 3' residues. In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' O-methyl modification at each of the first three 5' residues, and a 2' O-methyl modification at each of the $4^{th}$-to-terminal, $3^{rd}$-to-terminal, and $2^{nd}$-to-terminal 3' residues.

In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' O-methyl modification at each of the first three 5' residues, a 2' O-methyl modification at each of the first three 3' residues, and an additional inverted abasic residue at each of the 5' and 3' ends.

In an embodiment, the gRNA (e.g., the sgRNA or the tracr and/or crRNA of a dgRNA), e.g., any of the gRNA or gRNA components described above, comprises, e.g., consists of, a phosphorothioate bond between each of the first four 5' residues (e.g., comprises, e.g., consists of three phosphorothioate bonds at the 5' end of the polynucleotide(s)), a phosphorothioate bond between each of the first four 3' residues (e.g., comprises, e.g., consists of three phosphorothioate bonds at the 5' end of the polynucleotide(s)), a 2' O-methyl modification at each of the first three 5' residues, and a 2' O-methyl modification at each of the $4^{th}$-to-terminal, $3^{rd}$-to-terminal, and $2^{nd}$-to-terminal 3' residues, and an additional inverted abasic residue at each of the 5' and 3' ends.

In an embodiment, the gRNA is a dgRNA and comprises, e.g., consists of:
crRNA:
mN*mN*mN*NNNNNNNNNNNNNNNNNG UUUUAGAGCUAU*mG*mC*mU (SEQ ID NO: 251), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and tracr:
AACAGCAUAGCAAGUUAAAAUAAGGCUAGUCCGUUAUCAACUUGAAAAAGUGGCACC GAGUCGGUGCUUUUUUU (SEQ ID NO: 224) (optionally with an inverted abasic residue at the 5' and/or 3' terminus).

In an embodiment, the gRNA is a dgRNA and comprises, e.g., consists of:
crRNA:
mN*mN*mN*NNNNNNNNNNNNNNNNNG UUUUAGAGCUAU*mG*mC*mU (SEQ ID NO: 251), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and tracr:
mA*mA*mC*AGCAUAGCAAGUUAAAAUA AGGCUAGUCCGUUAUCAACUUGAAAAAGUG GCACCGAGUCGGUGCUUUU*mU*mU*mU (SEQ ID NO: 246), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus).

In an embodiment, the gRNA is a dgRNA and comprises, e.g., consists of:
crRNA:
mN*mN*mN*NNNNNNNNNNNNNNNNNG UUUUAGAGCUAUGCUGUU*mU*mU*mG (SEQ ID NO: 252), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and
tracr:
AACAGCAUAGCAAGUUAAAAUAAGGCUAGUCCGUUAUCAACUUGAAAAAGUGGCACC GAGUCGGUGCUUUUUUU (SEQ ID NO: 224) (optionally with an inverted abasic residue at the 5' and/or 3' terminus).

In an embodiment, the gRNA is a dgRNA and comprises, e.g., consists of:
crRNA:
mN*mN*mN*NNNNNNNNNNNNNNNNNG UUUUAGAGCUAUGCUGUU*mU*mU*mG (SEQ ID NO: 252), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus); and tracr:
mA*mA*mC*AGCAUAGCAAGUUAAAAUAA GGCUAGUCCGUUAUCAACUUGAAAAAGUG GCACCGAGUCGGUGCUUUU*mU*mU*mU (SEQ ID NO: 246), where m indicates a base with 2'O-Methyl modification, and * indicates a phosphorothioate bond (optionally with an inverted abasic residue at the 5' and/or 3' terminus).

In an embodiment, the gRNA is a dgRNA and comprises, e.g., consists of:
crRNA:
NNNNNNNNNNNNNNNNNNNNGUUUUAGAGCUAUGCUGUUUG (SEQ ID NO: 253), where N's indicate the residues of the targeting domain, e.g., as described herein, (optionally with an inverted abasic residue at the 5' and/or 3' terminus); and tracr:
mA*mA*mC*AGCAUAGCAAGUUAAAA UAAGGCUAGUCCGUUAUCAACUUGAAAAAGUG GCACCGAGUCGGUGCUUUU*mU*mU*mU (SEQ ID NO: 246), where m indicates a base with 2'O-Methyl modification, and * indicates a phosphorothioate bond (optionally with an inverted abasic residue at the 5' and/or 3' terminus).

In an embodiment, the gRNA is a sgRNA and comprises, e.g., consists of:
NNNNNNNNNNNNNNNNNNNNGUUUUAGAGCUAGAAAUAGCAAGUUAAAAUAAGGCUA GUCCGUUAUCAACUUGAAAAAGUGGCACCGAGU-CGGUGCUUUU (SEQ ID NO: 254), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus).

In an embodiment, the gRNA is a sgRNA and comprises, e.g., consists of:

mN*mN*mN*NNNNNNNNNNNNNNNNNNNGUU UUAGAGCUAGAAAUAGCAAGUUAAAAUA AGGC-UAGUCCGUUAUCAACUUGAAAAAGUG GCACCGAGUCGGUGCU*mU*mU*mU (SEQ ID NO: 255), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus).

In an embodiment, the gRNA is a sgRNA and comprises, e.g., consists of:

mN*mN*mN*NNNNNNNNNNNNNNNNNNNGUU UUAGAGCUAGAAAUAGCAAGUUAAAAUA AGGC-UAGUCCGUUAUCAACUUGAAAAA GUGGCACCGAGUCGGUGCmU*mU*mU*U (SEQ ID NO: 256), where m indicates a base with 2'O-Methyl modification, * indicates a phosphorothioate bond, and N's indicate the residues of the targeting domain, e.g., as described herein, (optionally with an inverted abasic residue at the 5' and/or 3' terminus).

6) First Tracr Extension

Where the gRNA comprises a first flagpole extension, the tracr may comprise a first tracr extension. The first tracr extension may comprise nucleotides that are complementary, e.g., 80%, 85%, 90%, 95% or 99%, e.g., fully complementary, with nucleotides of the first flagpole extension. In some aspects, the first tracr extension nucleotides that hybridize with complementary nucleotides of the first flagpole extension are contiguous. In some aspects, the first tracr extension nucleotides that hybridize with complementary nucleotides of the first flagpole extension are discontinuous, e.g., comprises two or more regions of hybridization separated by nucleotides that do not base pair with nucleotides of the first flagpole extension. In some aspects, the first tracr extension comprises at least 2, 3, 4, 5, 6, 7, 8, 9, 10, 11, 12, 13, 14, 15, 16, 17, 18, 19, 20 or more nucleotides. In some aspects, the first tracr extension comprises SEQ ID NO: 189. In some aspects the first tracr extension comprises nucleic acid that is at least 80%, 85%, 90%, 95% or 99% homology to SEQ ID NO: 189.

Some or all of the nucleotides of the first tracr extension can have a modification, e.g., modification found in Section XIII herein.

In some embodiments, the sgRNA may comprise, from 5' to 3', disposed 3' to the targeting domain.

a)
(SEQ ID NO: 195)
GUUUUAGAGCUAGAAAUAGCAAGUUAAAAUAAGGCUAGUCCGUUAUCAAC

UUGAAAAAGUGGCACCGAGUCGGUGC;

b)
(SEQ ID NO: 196)
GUUUAAGAGCUAGAAAUAGCAAGUUUAAAUAAGGCUAGUCCGUUAUCAAC

UUGAAAAAGUGGCACCGAGUCGGUGC;

c)
(SEQ ID NO: 197)
GUUUUAGAGCUAUGCUGGAAACAGCAUAGCAAGUUAAAAUAAGGCUAGUC

CGUUAUCAACUUGAAAAAGUGGCACCGAGUCGGUGC;

d)
(SEQ ID NO: 198)
GUUUAAGAGCUAUGCUGGAAACAGCAUAGCAAGUUUAAAUAAGGCUAGUC

CGUUAUCAACUUGAAAAAGUGGCACCGAGUCGGUGC;

e) any of a) to d), above, further comprising, at the 3' end, at least 1, 2, 3, 4, 5, 6 or 7 uracil (U) nucleotides, e.g., 1, 2, 3, 4, 5, 6, or 7 uracil (U) nucleotides;

f) any of a) to d), above, further comprising, at the 3' end, at least 1, 2, 3, 4, 5, 6 or 7 adenine (A) nucleotides, e.g., 1, 2, 3, 4, 5, 6, or 7 adenine (A) nucleotides; or g) any of a) to f), above, further comprising, at the 5' end (e.g., at the 5' terminus, e.g., 5' to the targeting domain), at least 1, 2, 3, 4, 5, 6 or 7 adenine (A) nucleotides, e.g., 1, 2, 3, 4, 5, 6, or 7 adenine (A) nucleotides. In embodiments, any of a) to g) above is disposed directly 3' to the targeting domain.

In an embodiment, a sgRNA of the invention comprises, e.g., consists of, from 5' to 3':

[targeting domain]
(SEQ ID NO: 231)
GUUUUAGAGCUAGAAAUAGCAAGUUAAAAUAAGGCUAGUCCGUUAUCAAC

UUGAAAAAGUGGCACCGAGUCGGUGCUUUU.

In an embodiment, a sgRNA of the invention comprises, e.g., consists of, from 5' to 3':

[targeting domain]
(SEQ ID NO: 227)
GUUUAAGAGCUAUGCUGGAAACAGCAUAGCAAGUUUAAAUAAGGCUAGUC

CGUUAUCAACUUGAAAAAGUGGCACCGAGUCGGUGCUUUU.

In some embodiments, the dgRNA may comprise:

A crRNA comprising, from 5' to 3', preferably disposed directly 3' to the targeting domain.

a)
(SEQ ID NO: 182)
GUUUUAGAGCUA;

b)
(SEQ ID NO: 183)
GUUUAAGAGCUA;

c)
(SEQ ID NO: 199)
GUUUUAGAGCUAUGCUG;

d)
(SEQ ID NO: 200)
GUUUAAGAGCUAUGCUG;

e)
(SEQ ID NO: 201)
GUUUUAGAGCUAUGCUGUUUUG;

f)
(SEQ ID NO: 202)
GUUUAAGAGCUAUGCUGUUUUG;

-continued or g)
(SEQ ID NO: 226)
GUUUUAGAGCUAUGCU;

and a tracr comprising, from 5' to 3':

a)
(SEQ ID NO: 187)
UAGCAAGUUAAAAUAAGGCUAGUCCGUUAUCAACUUGAAAAAGUGGCACC

GAGUCGGUGC;

b)
(SEQ ID NO: 188)
UAGCAAGUUUAAAUAAGGCUAGUCCGUUAUCAACUUGAAAAAGUGGCACC

GAGUCGGUGC;

c)
(SEQ ID NO: 203)
CAGCAUAGCAAGUUAAAAUAAGGCUAGUCCGUUAUCAACUUGAAAAAGUG

GCACCGAGUCGGUGC;

d)
(SEQ ID NO: 204)
CAGCAUAGCAAGUUUAAAUAAGGCUAGUCCGUUAUCAACUUGAAAAAGUG

GCACCGAGUCGGUGC;

e)
(SEQ ID NO: 224)
AACAGCAUAGCAAGUUAAAAUAAGGCUAGUCCGUUAUCAACUUGAAAAAG

UGGCACCGAGUCGGUGCUUUUUUU;

f)
(SEQ ID NO: 225)
AACAGCAUAGCAAGUUUAAAUAAGGCUAGUCCGUUAUCAACUUGAAAAAG

UGGCACCGAGUCGGUGCUUUUUUU;

g)
(SEQ ID NO: 232)
AACAGCAUAGCAAGUUAAAAUAAGGCUAGUCCGUUAUCAACUUGAAAAAG

UGGCACCGAGUCGGUGC h)
(SEQ ID NO: 227)
GUUUAAGAGCUAUGCUGGAAACAGCAUAGCAAGUUUAAAUAAGGCUAGUC

CGUUAUCAACUUGAAAAAGUGGCACCGAGUCGGUGCUUUU;

i)
(SEQ ID NO: 228)
AGCAUAGCAAGUUAAAAUAAGGCUAGUCCGUUAUCAACUUGAAAAAGUGG

CACCGAGUCGGUGCUUU;

j)
(SEQ ID NO: 229)
GUUGGAACCAUUCAAAACAGCAUAGCAAGUUAAAAUAAGGCUAGUCCGUU

AUCAACUUGAAAAAGUGGCACCGAGUCGGUGCUUU;

k) any of a) to j), above, further comprising, at the 3' end, at least 1, 2, 3, 4, 5, 6 or 7 uracil (U) nucleotides, e.g., 1, 2, 3, 4, 5, 6, or 7 uracil (U) nucleotides;

l) any of a) to j), above, further comprising, at the 3' end, at least 1, 2, 3, 4, 5, 6 or 7 adenine (A) nucleotides, e.g., 1, 2, 3, 4, 5, 6, or 7 adenine (A) nucleotides; or m) any of a) to l), above, further comprising, at the 5' end (e.g., at the 5' terminus), at least 1, 2, 3, 4, 5, 6 or 7 adenine (A) nucleotides, e.g., 1, 2, 3, 4, 5, 6, or 7 adenine (A) nucleotides.

In an embodiment, the sequence of k), above comprises the 3' sequence UUUUUU, e.g., if a U6 promoter is used for transcription. In an embodiment, the sequence of k), above, comprises the 3' sequence UUUU, e.g., if an H1 promoter is used for transcription. In an embodiment, sequence of k), above, comprises variable numbers of 3' U's depending, e.g., on the termination signal of the pol-III promoter used. In an embodiment, the sequence of k), above, comprises variable 3' sequence derived from the DNA template if a T7 promoter is used. In an embodiment, the sequence of k), above, comprises variable 3' sequence derived from the DNA template, e.g., if in vitro transcription is used to generate the RNA molecule. In an embodiment, the sequence of k), above, comprises variable 3' sequence derived from the DNA template, e.g, if a pol-II promoter is used to drive transcription.

In an embodiment, the crRNA comprises, e.g., consists of, a targeting domain and, disposed 3' to the targeting domain (e.g., disposed directly 3' to the targeting domain), a sequence comprising, e.g., consisting of, SEQ ID NO: 201, and the tracr comprises, e.g., consists of (SEQ ID NO: 224)
AACAGCAUAGCAAGUUAAAAUAAGGCUAGUCCGUUAUCAACUUGAAAAAG

UGGCACCGAGUCGGUGCUUUUUUU.

In an embodiment, the crRNA comprises, e.g., consists of, a targeting domain and, disposed 3' to the targeting domain (e.g., disposed directly 3' to the targeting domain), a sequence comprising, e.g., consisting of, SEQ ID NO: 202, and the tracr comprises, e.g., consists of, (SEQ ID NO: 225)
AACAGCAUAGCAAGUUUAAAUAAGGCUAGUCCGUUAUCAACUUGAAAAAG

UGGCACCGAGUCGGUGCUUUUUUU.

In an embodiment, the crRNA comprises, e.g., consists of, a targeting domain and, disposed 3' to the targeting domain (e.g., disposed directly 3' to the targeting domain), a sequence comprising, e.g., consisting of, GUUUUAGAGC-UAUGCU (SEQ ID NO: 226), and the tracr comprises, e.g., consists of, (SEQ ID NO: 227)
GUUUAAGAGCUAUGCUGGAAACAGCAUAGCAAGUUUAAAUAAGGCUAGUC

CGUUAUCAACUUGAAAAAGUGGCACCGAGUCGGUGCUUUU.

In an embodiment, the crRNA comprises, e.g., consists of, a targeting domain and, disposed 3' to the targeting domain (e.g., disposed directly 3' to the targeting domain), a sequence comprising, e.g., consisting of, GUUUUAGAGC-UAUGCU (SEQ ID NO: 226), and the tracr comprises, e.g., consists of, (SEQ ID NO: 228)
AGCAUAGCAAGUUAAAAUAAGGCUAGUCCGUUAUCAACUUGAAAAAGUGG

CACCGAGUCGGUGCUUU.

In an embodiment, the crRNA comprises, e.g., consists of, a targeting domain and, disposed 3' to the targeting domain (e.g., disposed directly 3' to the targeting domain), a sequence comprising, e.g., consisting of, GUUUUAGAGC-UAUGCUGUUUG (SEQ ID NO: 201), and the tracr comprises, e.g., consists of, (SEQ ID NO: 229)
GUUGGAACCAUUCAAAACAGCAUAGCAAGUUAAAAUAAGGCUAGUCCGUU

AUCAACUUGAAAAAGUGGCACCGAGUCGGUGCUUU.

II. gRNA Targeting Domains Directed to Nondeletional HPFH Regions

Provided in the table below are targeting domains directed to nondeletional HPFH regions, for gRNA molecules of the present invention, and for use in the various aspects of the present invention, for example, in altering expression of globin genes, for example, a fetal hemoglobin gene or a hemoglobin beta gene.

TABLE 1 gRNA targeting domains directed to nondeletional HPFH regions. SEQ ID NO: s refer to the gRNA targeting domain sequence.

| Targeting Domain ID | Target Promoter Region | gRNA targeting domain sequence | genomic location (hg38) 1 | genomic location (hg38) 2 (if present) | strand | SEQ ID NO: |
|---|---|---|---|---|---|---|
| gRNA targeting domains with target sequences only within the HBG1 promoter region ||||||||
| GCR-0001 | HBG1 | AGUCCUGGUAUCCUCUAUGA | chr11: 5250169-5250189 | - | | 1 |
| GCR-0002 | HBG1 | AAUUAGCAGUAUCCUCUUGG | chr11: 5250063-5250083 | - | | 2 |
| GCR-0003 | HBG1 | AGAAUAAAUUAGAGAAAAAC | chr11: 5250123-5250143 | - | | 3 |
| GCR-0004 | HBG1 | AAAAAUUAGCAGUAUCCUCU | chr11: 5250066-5250086 | - | | 4 |
| GCR-0005 | HBG1 | AAAAUUAGCAGUAUCCUCUU | chr11: 5250065-5250085 | - | | 5 |
| GCR-0006 | HBG1 | AAAAACUGGAAUGACUGAAU | chr11: 5250109-5250129 | - | | 6 |
| GCR-0007 | HBG1 | CUCCCAUCAUAGAGGAUACC | chr11: 5250163-5250183 | + | | 7 |
| GCR-0008 | HBG1 | GGAGAAGGAAACUAGCUAAA | chr11: 5250147-5250167 | - | | 8 |
| GCR-0009 | HBG1 | GUUUCCUUCUCCCAUCAUAG | chr11: 5250155-5250175 | + | | 9 |
| GCR-0010 | HBG1 | GGGAGAAGGAAACUAGCUAA | chr11: 5250148-5250168 | - | | 10 |
| GCR-0011 | HBG1 | CACUGGAGCUAGAGACAAGA | chr11: 5250213-5250233 | - | | 11 |
| GCR-0012 | HBG1 | AGAGACAAGAAGGUAAAAAA | chr11: 5250203-5250223 | - | | 12 |
| GCR-0013 | HBG1 | AAAUUAGCAGUAUCCUCUUG | chr11: 5250064-5250084 | - | | 13 |
| GCR-0014 | HBG1 | GUCCUGGUAUCCUCUAUGAU | chr11: 5250168-5250188 | - | | 14 |
| GCR-0015 | HBG1 | GUAUCCUCUAUGAUGGGAGA | chr11: 5250162-5250182 | - | | 15 |
| gRNA targeting domains with target sequences only within the HBG2 promoter region ||||||||
| GCR-0017 | HBG2 | AUUAAGCAGCAGUAUCCUCU | chr11: 5254990-5255010 | - | | 17 |
| GCR-0022 | HBG2 | AGAAUAAAUUAGAGAAAAAU | chr11: 5255051-5255071 | - | | 22 |

TABLE 1-continued gRNA targeting domains directed to nondeletional HPFH regions. SEQ ID NO: s refer to the gRNA targeting domain sequence.

| Targeting Domain ID | Target Promoter Region | gRNA targeting domain sequence | genomic location (hg38) 1 | strand | genomic location (hg38) 2 (if present) | strand | SEQ ID NO: |
|---|---|---|---|---|---|---|---|
| GCR-0029 | HBG2 | AGAAGUCCUGGUAUCUUCUA | chr11: 5255100-5255120 | – | | | 29 |
| GCR-0032 | HBG2 | UUAAGCAGCAGUAUCCUCUU | chr11: 5254989-5255009 | – | | | 32 |
| GCR-0034 | HBG2 | AAAAAUUGGAAUGACUGAAU | chr11: 5255037-5255057 | – | | | 34 |
| GCR-0046 | HBG2 | GGGAGAAGAAAACUAGCUAA | chr11: 5255076-5255096 | – | | | 46 |
| GCR-0051 | HBG2 | GGAGAAGAAAACUAGCUAAA | chr11: 5255075-5255095 | – | | | 51 |
| GCR-0052 | HBG2 | CUCCCACCAUAGAAGAUACC | chr11: 5255091-5255111 | + | | | 52 |
| GCR-0054 | HBG2 | AGUCCUGGUAUCUUCUAUGG | chr11: 5255097-5255117 | – | | | 54 |
| GCR-0058 | HBG2 | GUCCUGGUAUCUUCUAUGGU | chr11: 5255096-5255116 | – | | | 58 |
| GCR-0060 | HBG2 | UAAGCAGCAGUAUCCUCUUG | chr11: 5254988-5255008 | – | | | 60 |
| GCR-0069 | HBG2 | AAGCAGCAGUAUCCUCUUGG | chr11: 5254987-5255007 | – | | | 69 | gRNA with targeting domains within the HBG1 and HBG2 promoter regions

| GCR-0016 | HBG1/HBG2 | CCUAGCCAGCCGCCGGCCCC | chr11: 5249895-5249915 | + | chr11: 5254819-5254839 | + | 16 |
| GCR-0018 | HBG1/HBG2 | UAUCCAGUGAGGCCAGGGGC | chr11: 5249910-5249930 | – | chr11: 5254834-5254854 | – | 18 |
| GCR-0019 | HBG1/HBG2 | CAUUGAGAUAGUGUGGGGAA | chr11: 5250036-5250056 | + | chr11: 5254960-5254980 | + | 19 |
| GCR-0020 | HBG1/HBG2 | CCAGUGAGGCCAGGGGCCGG | chr11: 5249907-5249927 | – | chr11: 5254831-5254851 | – | 20 |
| GCR-0021 | HBG1/HBG2 | GUGGGGAAGGGGCCCCCAAG | chr11: 5250048-5250068 | + | chr11: 5254972-5254992 | + | 21 |
| GCR-0023 | HBG1/HBG2 | CCAGGGGCCGGCGGCUGGCU | chr11: 5249898-5249918 | – | chr11: 5254822-5254842 | – | 23 |
| GCR-0024 | HBG1/HBG2 | UGAGGCCAGGGGCCGGCGGC | chr11: 5249903-5249923 | – | chr11: 5254827-5254847 | – | 24 |
| GCR-0025 | HBG1/HBG2 | CAGUUCCACACACUCGCUUC | chr11: 5249846-5249866 | – | chr11: 5254770-5254790 | – | 25 |
| GCR-0026 | HBG1/HBG2 | CCGCCGGCCCCUGGCCUCAC | chr11: 5249904-5249924 | + | chr11: 5254828-5254848 | + | 26 |
| GCR-0027 | HBG1/HBG2 | GUUUGCCUUGUCAAGGCUAU | chr11: 5249949-5249969 | + | chr11: 5254873-5254893 | + | 27 |
| GCR-0028 | HBG1/HBG2 | GGCUAGGGAUGAAGAAUAAA | chr11: 5249882-5249902 | – | chr11: 5254806-5254826 | – | 28 |
| GCR-0030 | HBG1/HBG2 | CAGGGGCCGGCGGCUGGCUA | chr11: 5249897-5249917 | – | chr11: 5254821-5254841 | – | 30 |
| GCR-0031 | HBG1/HBG2 | ACUGGAUACUCUAAGACUAU | chr11: 5249922-5249942 | + | chr11: 5254846-5254866 | + | 31 |
| GCR-0033 | HBG1/HBG2 | CCCUGGCUAAACUCCACCCA | chr11: 5249995-5250015 | – | chr11: 5254919-5254939 | – | 33 |

TABLE 1-continued gRNA targeting domains directed to nondeletional HPFH regions. SEQ ID NO: s refer to the gRNA targeting domain sequence.

| Targeting Domain ID | Target Promoter Region | gRNA targeting domain sequence | genomic location (hg38) 1 | strand | genomic location (hg38) 2 (if present) | strand | SEQ ID NO: |
|---|---|---|---|---|---|---|---|
| GCR-0035 | HBG1/HBG2 | UUAGAGUAUC CAGUGAGGCC | chr11: 5249916-5249936 | − | chr11: 5254840-5254860 | − | 35 |
| GCR-0036 | HBG1/HBG2 | CCCAUGGGUG GAGUUUAGCC | chr11: 5249991-5250011 | + | chr11: 5254915-5254935 | + | 36 |
| GCR-0037 | HBG1/HBG2 | AGGCAAGGCU GGCCAACCCA | chr11: 5249975-5249995 | + | chr11: 5254899-5254919 | + | 37 |
| GCR-0038 | HBG1/HBG2 | UAGAGUAUCC AGUGAGGCCA | chr11: 5249915-5249935 | − | chr11: 5254839-5254859 | − | 38 |
| GCR-0039 | HBG1/HBG2 | UAUCUGUCUG AAACGGUCCC | chr11: 5250012-5250032 | − | chr11: 5254936-5254956 | − | 39 |
| GCR-0040 | HBG1/HBG2 | AUUGAGAUAG UGUGGGGAAG | chr11: 5250037-5250057 | + | chr11: 5254961-5254981 | + | 40 |
| GCR-0041 | HBG1/HBG2 | CUUCAUCCCU AGCCAGCCGC | chr11: 5249888-5249908 | + | chr11: 5254812-5254832 | + | 41 |
| GCR-0042 | HBG1/HBG2 | GCUAUUGGUC AAGGCAAGGC | chr11: 5249964-5249984 | + | chr11: 5254888-5254908 | + | 42 |
| GCR-0043 | HBG1/HBG2 | AUGCAAAUAU CUGUCUGAAA | chr11: 5250019-5250039 | − | chr11: 5254943-5254963 | − | 43 |
| GCR-0044 | HBG1/HBG2 | GCAUUGAGAU AGUGUGGGGA | chr11: 5250035-5250055 | + | chr11: 5254959-5254979 | + | 44 |
| GCR-0045 | HBG1/HBG2 | UGGUCAAGUU UGCCUUGUCA | chr11: 5249942-5249962 | + | chr11: 5254866-5254886 | + | 45 |
| GCR-0047 | HBG1/HBG2 | GGCAAGGCUG GCCAACCCAU | chr11: 5249976-5249996 | + | chr11: 5254900-5254920 | + | 47 |
| GCR-0048 | HBG1/HBG2 | ACGGCUGACA AAAGAAGUCC | chr11: 5250184-5250204 | − | chr11: 5255112-5255132 | − | 48 |
| GCR-0049 | HBG1/HBG2 | CGAGUGUGUG GAACUGCUGA | chr11: 5249850-5249870 | + | chr11: 5254774-5254794 | + | 49 |
| GCR-0050 | HBG1/HBG2 | CCUGGCUAAA CUCCACCCAU | chr11: 5249994-5250014 | − | chr11: 5254918-5254938 | − | 50 |
| GCR-0053 | HBG1/HBG2 | CUUGUCAAGG CUAUUGGUCA | chr11: 5249955-5249975 | + | chr11: 5254879-5254899 | + | 53 |
| GCR-0055 | HBG1/HBG2 | AUAUUUGCAU UGAGAUAGUG | chr11: 5250029-5250049 | + | chr11: 5254953-5254973 | + | 55 |
| GCR-0056 | HBG1/HBG2 | GCUAAACUCC ACCCAUGGGU | chr11: 5249990-5250010 | − | chr11: 5254914-5254934 | − | 56 |
| GCR-0057 | HBG1/HBG2 | ACGUUCCAGA AGCGAGUGUG | chr11: 5249838-5249858 | + | chr11: 5254762-5254782 | + | 57 |
| GCR-0059 | HBG1/HBG2 | UAUUUGCAUU GAGAUAGUGU | chr11: 5250030-5250050 | + | chr11: 5254954-5254974 | + | 59 |
| GCR-0061 | HBG1/HBG2 | GGAAUGACUG AAUCGGAACA | chr11: 5250102-5250122 | − | chr11: 5255030-5255050 | − | 61 |
| GCR-0062 | HBG1/HBG2 | CUUGACCAAU AGCCUUGACA | chr11: 5249957-5249977 | − | chr11: 5254881-5254901 | − | 62 |
| GCR-0063 | HBG1/HBG2 | CAAGGCUAUU GGUCAAGGCA | chr11: 5249960-5249980 | + | chr11: 5254884-5254904 | + | 63 |
| GCR-0064 | HBG1/HBG2 | AAGGCUGGCC AACCCAUGGG | chr11: 5249979-5249999 | + | chr11: 5254903-5254923 | + | 64 |

TABLE 1-continued gRNA targeting domains directed to nondeletional HPFH regions. SEQ ID NO: s refer to the gRNA targeting domain sequence.

| Targeting Domain ID | Target Promoter Region | gRNA targeting domain sequence | genomic location (hg38) 1 | strand | genomic location (hg38) 2 (if present) | strand | SEQ ID NO: |
|---|---|---|---|---|---|---|---|
| GCR-0065 | HBG1/HBG2 | ACUCGCUUCUGGAACGUCUG | chr11: 5249835-5249855 | - | chr11: 5254759-5254779 | - | 65 |
| GCR-0066 | HBG1/HBG2 | AUUUGCAUUGAGAUAGUGUG | chr11: 5250031-5250051 | + | chr11: 5254955-5254975 | + | 66 |
| GCR-0067 | HBG1/HBG2 | ACUGAAUCGGAACAAGGCAA | chr11: 5250096-5250116 | - | chr11: 5255024-5255044 | - | 67 |
| GCR-0068 | HBG1/HBG2 | CCAUGGGUGGAGUUUAGCCA | chr11: 5249992-5250012 | + | chr11: 5254916-5254936 | + | 68 |
| GCR-0070 | HBG1/HBG2 | AGAGUAUCCAGUGAGGCCAG | chr11: 5249914-5249934 | - | chr11: 5254838-5254858 | - | 70 |
| GCR-0071 | HBG1/HBG2 | GAGUGUGUGGAACUGCUGAA | chr11: 5249851-5249871 | + | chr11: 5254775-5254795 | + | 71 |
| GCR-0072 | HBG1/HBG2 | UAGUCUUAGAGUAUCCAGUG | chr11: 5249921-5249941 | - | chr11: 5254845-5254865 | - | 72 |

Table 2, below, shows those targeting domains which, when included in a gRNA molecule, result in at least a 17% increase in fetal hemoglobin (e.g., in erythroid cells differentiated from modified HSPCs) at 7 days according to the methods described in the Examples. gRNA molecules comprising any of these targeting domains are collectively referred to herein as Tier 2 gRNA molecules.

TABLE 2

Targeting Domains for Tier 2 gRNA Molecules
Targeting Domain ID

GCR-0001
GCR-0006
GCR-0008
GCR-0009
GCR-0010
GCR-0011
GCR-0012
GCR-0028
GCR-0034
GCR-0045
GCR-0046
GCR-0047
GCR-0048
GCR-0050
GCR-0051
GCR-0053
GCR-0054
GCR-0058
GCR-0062
GCR-0063
GCR-0067

Table 3a and Table 3b, below, show those targeting domains which, when included in a gRNA molecule, result in the highest increase in fetal hemoglobin (e.g., in erythroid cells differentiated from modified HSPCs) at 7 days according to the methods described in the Examples. gRNA molecules comprising these targeting domains are collectively referred to as Tier 1 (e.g., Tirr 1a or Tier 1b) gRNA molecules.

TABLE 3a

Targeting Domains for Tier 1a gRNA Molecules
Targeting Domain ID

GCR-0006
GCR-0008
GCR-0028
GCR-0034
GCR-0048
GCR-0067

TABLE 3b

Targeting Domains for Tier 1b gRNA Molecules
Targeting Domain ID

GCR-0001
GCR-0008
GCR-0009
GCR-0010
GCR-0012
GCR-0054

III. Methods for Designing gRNAs

Methods for designing gRNAs are described herein, including methods for selecting, designing and validating target sequences. Exemplary targeting domains are also provided herein. Targeting Domains discussed herein can be incorporated into the gRNAs described herein.

Methods for selection and validation of target sequences as well as off-target analyses are described, e.g., in. Mali el al., 2013 SCIENCE 339(6121): 823-826; Hsu et al, 2013 NAT BIOTECHNOL, 31 (9): 827-32; Fu et al, 2014 NAT BIOTECHNOL, doi: 10.1038/nbt.2808. PubMed PMID: 24463574; Heigwer et al, 2014 NAT METHODS 11(2): 122-3. doi: 10.1038/nmeth.2812. PubMed PMID: 24481216; Bae el al, 2014 BIOINFORMATICS PubMed PMID: 24463181; Xiao A el al, 2014 BIOINFORMATICS PubMed PMID: 24389662.

For example, a software tool can be used to optimize the choice of gRNA within a user's target sequence, e.g., to minimize total off-target activity across the genome. Off target activity may be other than cleavage. For each possible gRNA choice e.g., using *S. pyogenes* Cas9, the tool can identify all off-target sequences (e.g., preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate gRNA molecules can be evaluated by art-known methods or as described herein.

Although software algorithms may be used to generate an initial list of potential gRNA molecules, cutting efficiency and specificity will not necessarily reflect the predicted values, and gRNA molecules typically require screening in specific cell lines, e.g., primary human cell lines, e.g., human HSPCs, e.g., human CD34+ cells, to determine, for example, cutting efficiency, indel formation, cutting specificity and change in desired phenotype. These properties may be assayed by the methods described herein.

In aspects of the invention, a gRNA comprising the targeting domain of GCR-0001 (SEQ ID NO: 1, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0001 #1:
(SEQ ID NO: 74)
AGUCCUGGUAUCCUCUAUGAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0001 #2:
(SEQ ID NO: 75)
mA*mG*mU*CCUGGUAUCCUCUAUGAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0001 #3:
(SEQ ID NO: 76)
mA*mG*mU*CCUGGUAUCCUCUAUGAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0001 #1:
(SEQ ID NO: 77)
crRNA: AGUCCUGGUAUCCUCUAUGAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0001 #2:

crRNA:
(SEQ ID NO: 78)
mA*mG*mU*CCUGGUAUCCUCUAUGAGUUUUAGAGCUAUGCUGUU*mU* mU*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0001 #3:
(SEQ ID NO: 78)
crRNA:
mA*mG*mU*CCUGGUAUCCUCUAUGAGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0006 (SEQ ID NO: 6, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0006 #1:
(SEQ ID NO: 79)
AAAAACUGGAAUGACUGAAUGUUUUAGAGCUAGAAAUAGCAAGUUAAAAU

AAGGCUAGUCCGUUAUCAACUUGAAAAAGUGGCACCGAGUCGGUGCUUUU (SEQ ID NO: 80)
sgRNA GCR-0006 #2:
mA*mA*mA*AACUGGAAUGACUGAAUGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0006 #3:
(SEQ ID NO: 81)
mA*mA*mA*AACUGGAAUGACUGAAUGUUUUAGAGCUAGAAAUAGCAAGU

UAAAAUAAGGCUAGUCCGUUAUCAACUUGAAAAAGUGGCACCGAGUCGGU

GCmU*mU*mU*U

-continued dgRNA GCR-0006 #1:

crRNA: (SEQ ID NO: 82)
AAAAACUGGAAUGACUGAAUGUUUUAGAGCUAUGCUGUUUUG tracr: (SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0006 #2:

crRNA: (SEQ ID NO: 83)
mA*mA*mA*AACUGGAAUGACUGAAUGUUUUAGAGCUAUGCUGUU*mU*m

U*mG tracr: (SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0006 #3:

crRNA: (SEQ ID NO: 83)
mA*mA*mA*AACUGGAAUGACUGAAUGUUUUAGAGCUAUGCUGUU*mU*m

U*mG tracr: (SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0008 (SEQ ID NO: 8, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0008 #1: (SEQ ID NO: 84)
GGAGAAGGAAACUAGCUAAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0008 #2: (SEQ ID NO: 85)
mG*mG*mA*GAAGGAAACUAGCUAAAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0008 #3: (SEQ ID NO: 86)
mG*mG*mA*GAAGGAAACUAGCUAAAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0008 #1:

crRNA: (SEQ ID NO: 87)
GGAGAAGGAAACUAGCUAAAGUUUUAGAGCUAUGCUGUUUUG tracr: (SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0008 #2:

crRNA: (SEQ ID NO: 88)
mG*mG*mA*GAAGGAAACUAGCUAAAGUUUUAGAGCUAUGCUGUU*mU*m

U*mG tracr: (SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0008 #3:

crRNA: (SEQ ID NO: 88)
mG*mG*mA*GAAGGAAACUAGCUAAAGUUUUAGAGCUAUGCUGUU*mU*m

U*mG tracr: (SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-009 (SEQ ID NO: 9, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0009 #1: (SEQ ID NO: 89)
GUUUCCUUCUCCCAUCAUAGGUUUUAGAGCUAGAAAUAGCAAGUUAAAAU

AAGGCUAGUCCGUUAUCAACUUGAAAAAGUGGCACCGAGUCGGUGCUUUU

```
sgRNA GCR-0009 #2:
                                          (SEQ ID NO: 90)
mG*mU*mU*UCCUUCUCCCAUCAUAGGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0009 #3:
                                          (SEQ ID NO: 91)
mG*mU*mU*UCCUUCUCCCAUCAUAGGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0009 #1:
                                          (SEQ ID NO: 92)
crRNA: GUUUCCUUCUCCCAUCAUAGGUUUUAGAGCUAUGCUGUUUUG tracr:
                                         (SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0009 #2:
                                          (SEQ ID NO: 93)
crRNA:
mG*mU*mU*UCCUUCUCCCAUCAUAGGUUUUAGAGCUAUGCUGUU*mU*m

U*mG tracr:
                                          (SEQ ID NO: 73)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA GCR-0009 #3:
                                          (SEQ ID NO: 93)
crRNA:
mG*mU*mU*UCCUUCUCCCAUCAUAGGUUUUAGAGCUAUGCUGUU*mU*m U*mG tracr:
                                         (SEQ ID NO: 224)
AACAGCAUAGCAAGUUAAAAUAAGGCUAGUCCGUUAUCAACUUGAAAAAG

UGGCACCGAGUCGGUGCUUUUUUU.

sgRNA GCR-0010 #1:
                                          (SEQ ID NO: 94)
GGGAGAAGGAAACUAGCUAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0010 #2:
                                          (SEQ ID NO: 95)
mG*mG*mG*AGAAGGAAACUAGCUAAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0010 #3:
                                          (SEQ ID NO: 96)
mG*mG*mG*AGAAGGAAACUAGCUAAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0010 #1:
                                          (SEQ ID NO: 97)
crRNA: GGGAGAAGGAAACUAGCUAAGUUUUAGAGCUAUGCUGUUUUG tracr:
                                         (SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0010 #2:
crRNA:
                                          (SEQ ID NO: 98)
mG*mG*mG*AGAAGGAAACUAGCUAAGUUUUAGAGCUAUGCUGUU*mU*m

U*mG tracr:
                                          (SEQ ID NO: 73)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA GCR-0010 #3:
crRNA:
                                          (SEQ ID NO: 98)
mG*mG*mG*AGAAGGAAACUAGCUAAGUUUUAGAGCUAUGCUGUU*mU*m U*mG tracr:
                                         (SEQ ID NO: 224)
AACAGCAUAGCAAGUUAAAAUAAGGCUAGUCCGUUAUCAACUUGAAAAAG

UGGCACCGAGUCGGUGCUUUUUUU.
```

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0010 (SEQ ID NO: 10, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0011 (SEQ ID NO: 11, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0011 #1:
(SEQ ID NO: 99)
CACUGGAGCUAGAGACAAGAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0011 #2:
(SEQ ID NO: 100)
mC*mA*mC*UGGAGCUAGAGACAAGAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0011 #3:
(SEQ ID NO: 101)
mC*mA*mC*UGGAGCUAGAGACAAGAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0011 #1:
(SEQ ID NO: 102)
crRNA: CACUGGAGCUAGAGACAAGAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0011 #2:
crRNA:
(SEQ ID NO: 103)
mC*mA*mC*UGGAGCUAGAGACAAGAGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0011 #3:
crRNA:
(SEQ ID NO: 103)
mC*mA*mC*UGGAGCUAGAGACAAGAGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

sgRNA GCR-0012 #1:
(SEQ ID NO: 104)
AGAGACAAGAAGGUAAAAAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0012 #2:
(SEQ ID NO: 105)
mA*mG*mA*GACAAGAAGGUAAAAAAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0012 #3:
(SEQ ID NO: 106)
mA*mG*mA*GACAAGAAGGUAAAAAAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0012 #1:
(SEQ ID NO: 107)
crRNA: AGAGACAAGAAGGUAAAAAAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0012 #2:
crRNA:
(SEQ ID NO: 108)
mA*mG*mA*GACAAGAAGGUAAAAAAGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0012 #3:
crRNA:
(SEQ ID NO: 108)
mA*mG*mA*GACAAGAAGGUAAAAAAGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0012 (SEQ ID NO: 12, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0028 (SEQ ID NO: 28, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0028 #1:
(SEQ ID NO: 109)
GGCUAGGGAUGAAGAAUAAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0028 #2:
(SEQ ID NO: 110)
mG*mG*mC*UAGGGAUGAAGAAUAAAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0028 #3:
(SEQ ID NO: 111)
mG*mG*mC*UAGGGAUGAAGAAUAAAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0028 #1:
(SEQ ID NO: 112)
crRNA: GGCUAGGGAUGAAGAAUAAAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0028 #2:
crRNA:
(SEQ ID NO: 113)
mG*mG*mC*UAGGGAUGAAGAAUAAAGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0028 #3:
crRNA:
(SEQ ID NO: 113)
mG*mG*mC*UAGGGAUGAAGAAUAAAGUUUUAGAGCUAUGCUGUU*mU*m

U*mG tracr:
(SEQ ID NO: 224).
AACAGCAUAGCAAGUUAAAAUAAGGCUAGUCCGUUAUCAACUUGAAAAAG

UGGCACCGAGUCGGUGCUUUUUUU sgRNA GCR-0034 #1:
(SEQ ID NO: 114)
AAAAAUUGGAAUGACUGAAUGUUUUAGAGCUAGAAAUAGCAAGUUAAAAU

AAGGCUAGUCCGUUAUCAACUUGAAAAAGUGGCACCGAGUCGGUGCUUUU sgRNA GCR-0034 #2:
(SEQ ID NO: 115)
mA*mA*mA*AAUUGGAAUGACUGAAUGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0034 #3:
(SEQ ID NO: 116)
mA*mA*mA*AAUUGGAAUGACUGAAUGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0034 #1:
(SEQ ID NO: 117)
crRNA: AAAAAUUGGAAUGACUGAAUGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0034 #2:
crRNA:
(SEQ ID NO: 118)
mA*mA*mA*AAUUGGAAUGACUGAAUGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0034 #3:
crRNA:
(SEQ ID NO: 118)
mA*mA*mA*AAUUGGAAUGACUGAAUGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0034 (SEQ ID NO: 34, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0045 (SEQ ID NO: 45, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0045 #1:
(SEQ ID NO: 119)
UGGUCAAGUUUGCCUUGUCAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0045 #2:
(SEQ ID NO: 120)
mU*mG*mG*UCAAGUUUGCCUUGUCAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0045 #3:
(SEQ ID NO: 121)
mU*mG*mG*UCAAGUUUGCCUUGUCAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0045 #1:
(SEQ ID NO: 122)
crRNA: UGGUCAAGUUUGCCUUGUCAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0045 #2:
crRNA:
(SEQ ID NO: 123)
mU*mG*mG*UCAAGUUUGCCUUGUCAGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0045 #3:
crRNA:
(SEQ ID NO: 123)
mU*mG*mG*UCAAGUUUGCCUUGUCAGUUUUAGAGCUAUGCUGUU*mU*m

U*mG tracr:
(SEQ ID NO: 224).
AACAGCAUAGCAAGUUAAAAUAAGGCUAGUCCGUUAUCAACUUGAAAAAG

UGGCACCGAGUCGGUGCUUUUUUU sgRNA GCR-0046 #1:
(SEQ ID NO: 124)
GGGAGAAGAAAACUAGCUAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0046 #2:
(SEQ ID NO: 125)
mG*mG*mG*AGAAGAAAACUAGCUAAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0046 #3:
(SEQ ID NO: 126)
mG*mG*mG*AGAAGAAAACUAGCUAAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0046 #1:
(SEQ ID NO: 127)
crRNA: GGGAGAAGAAAACUAGCUAAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0046 #2:
crRNA:
(SEQ ID NO: 128)
mG*mG*mG*AGAAGAAAACUAGCUAAGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0046 #3:
crRNA:
(SEQ ID NO: 128)
mG*mG*mG*AGAAGAAAACUAGCUAAGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0046 (SEQ ID NO: 46, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0047 (SEQ ID NO: 47, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0047 #1:
(SEQ ID NO: 129)
GGCAAGGCUGGCCAACCCAUGUUUUAGAGCUAGAAAUAGCAAGUUAAAAU

AAGGCUAGUCCGUUAUCAACUUGAAAAAGUGGCACCGAGUCGGUGCUUUU sgRNA GCR-0047 #2:
(SEQ ID NO: 130)
mG*mG*mC*AAGGCUGGCCAACCCAUGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0047 #3:
(SEQ ID NO: 131)
mG*mG*mC*AAGGCUGGCCAACCCAUGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0047 #1:
(SEQ ID NO: 132)
crRNA: GGCAAGGCUGGCCAACCCAUGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0047 #2:
crRNA:
(SEQ ID NO: 133)
mG*mG*mC*AAGGCUGGCCAACCCAUGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0047 #3:
crRNA:
(SEQ ID NO: 133)
mG*mG*mC*AAGGCUGGCCAACCCAUGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

sgRNA GCR-0048 #1:
(SEQ ID NO: 134)
ACGGCUGACAAAAGAAGUCCGUUUUAGAGCUAGAAAUAGCAAGUUAAAAU

AAGGCUAGUCCGUUAUCAACUUGAAAAAGUGGCACCGAGUCGGUGCUUUU sgRNA GCR-0048 #2:
(SEQ ID NO: 135)
mA*mC*mG*GCUGACAAAAGAAGUCCGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0048 #3:
(SEQ ID NO: 136)
mA*mC*mG*GCUGACAAAAGAAGUCCGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0048 #1:
(SEQ ID NO: 137)
crRNA: ACGGCUGACAAAAGAAGUCCGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0048 #2:
crRNA:
(SEQ ID NO: 138)
mA*mC*mG*GCUGACAAAAGAAGUCCGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0048 #3:
(SEQ ID NO: 138)
crRNA: mA*mC*mG*GCUGACAAAAGAAGUCCGUUUUAGAGCUAUGCUG

UU*mU*mU*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0048 (SEQ ID NO: 48, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0050 (SEQ ID NO: 50, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0050 #1:
(SEQ ID NO: 139)
CCUGGCUAAACUCCACCCAUGUUUUAGAGCUAGAAAUAGCAAGUUAAAAU

AAGGCUAGUCCGUUAUCAACUUGAAAAAGUGGCACCGAGUCGGUGCUUUU sgRNA GCR-0050 #2:
(SEQ ID NO: 140)
mC*mC*mU*GGCUAAACUCCACCCAUGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0050 #3:
(SEQ ID NO: 141)
mC*mC*mU*GGCUAAACUCCACCCAUGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0050 #1:
(SEQ ID NO: 142)
crRNA: CCUGGCUAAACUCCACCCAUGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0050 #2:
(SEQ ID NO: 143)
crRNA: mC*mC*mU*GGCUAAACUCCACCCAUGUUUUAGAGCUAUGCUG

UU*mU*mU*mG tracr:
(SEQ ID NO: 73)
mA*mA*mC*AGCAUAGCAAGUUAAAAUAAGGCUAGUCCGUUAUCAACUUG AAAAAGUGGCACCGAGUCGGUGCUUUU*mU*mU*mU dgRNA GCR-0050 #3:
(SEQ ID NO: 143)
crRNA: mC*mC*mU*GGCUAAACUCCACCCAUGUUUUAGAGCUAUGCUG UU*mU*mU*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

sgRNA GCR-0051 #1:
(SEQ ID NO: 144)
GGAGAAGAAAACUAGCUAAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0051 #2:
(SEQ ID NO: 145)
mG*mG*mA*GAAGAAAACUAGCUAAAGUUUUAGAGCUAGAAAUAGCAAGU

UAAAAUAAGGCUAGUCCGUUAUCAACUUGAAAAAGUGGCACCGAGUCGGU

GCU*mU*mU*mU sgRNA GCR-0051 #3:
(SEQ ID NO: 146)
mG*mG*mA*GAAGAAAACUAGCUAAAGUUUUAGAGCUAGAAAUAGCAAGU

UAAAAUAAGGCUAGUCCGUUAUCAACUUGAAAAAGUGGCACCGAGUCGGU

GCmU*mU*mU*U dgRNA GCR-0051 #1:
(SEQ ID NO: 147)
crRNA: GGAGAAGAAAACUAGCUAAAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU dgRNA GCR-0051 #2:
crRNA:
(SEQ ID NO: 148)
mG*mG*mA*GAAGAAAACUAGCUAAAGUUUUAGAGCUAUGCUGUU*mU*m

U*mG tracr:
(SEQ ID NO: 73)
mA*mA*mC*AGCAUAGCAAGUUAAAAUAAGGCUAGUCCGUUAUCAACUUG

AAAAAGUGGCACCGAGUCGGUGCUUUU*mU*mU*mU dgRNA GCR-0051 #3:
crRNA:
(SEQ ID NO: 148)
mG*mG*mA*GAAGAAAACUAGCUAAAGUUUUAGAGCUAUGCUGUU*mU*m

U*mG tracr:
(SEQ ID NO: 224)
AACAGCAUAGCAAGUUAAAAUAAGGCUAGUCCGUUAUCAACUUGAAAAAG

UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0051 (SEQ ID NO: 51, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0053 (SEQ ID NO: 53, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0053 #1:
(SEQ ID NO: 149)
CUUGUCAAGGCUAUUGGUCAGUUUUAGAGCUAGAAAUAGCAAGUUAAAAU
AAGGCUAGUCCGUUAUCAACUUGAAAAAGUGGCACCGAGUCGGUGCUUUU sgRNA GCR-0053 #2:
(SEQ ID NO: 150)
mC*mU*mU*GUCAAGGCUAUUGGUCAGUUUUAGAGCUAGAAAUAGCAAGU
UAAAAUAAGGCUAGUCCGUUAUCAACUUGAAAAAGUGGCACCGAGUCGGU
GCU*mU*mU*mU sgRNA GCR-0053 #3:
(SEQ ID NO: 151)
mC*mU*mU*GUCAAGGCUAUUGGUCAGUUUUAGAGCUAGAAAUAGCAAGU
UAAAAUAAGGCUAGUCCGUUAUCAACUUGAAAAAGUGGCACCGAGUCGGU
GCmU*mU*mU*U dgRNA GCR-0053 #1:
(SEQ ID NO: 152)
crRNA: CUUGUCAAGGCUAUUGGUCAGUUUUAGAGCUAUGCUGUUUUG tracr:
(SEQ ID NO: 224)
AACAGCAUAGCAAGUUAAAAUAAGGCUAGUCCGUUAUCAACUUGAAAAAG
UGGCACCGAGUCGGUGCUUUUUUU dgRNA GCR-0053 #2:
crRNA:
(SEQ ID NO: 153)
mC*mU*mU*GUCAAGGCUAUUGGUCAGUUUUAGAGCUAUGCUGUU*mU*mU*mG tracr:
(SEQ ID NO: 73)
mA*mA*mC*AGCAUAGCAAGUUAAAAUAAGGCUAGUCCGUUAUCAACUUG
AAAAAGUGGCACCGAGUCGGUGCUUUU*mU*mU*mU dgRNA GCR-0053 #3:
crRNA:
(SEQ ID NO: 153)
mC*mU*mU*GUCAAGGCUAUUGGUCAGUUUUAGAGCUAUGCUGUU*mU*mU*mG tracr:
(SEQ ID NO: 224)
AACAGCAUAGCAAGUUAAAAUAAGGCUAGUCCGUUAUCAACUUGAAAAAG
UGGCACCGAGUCGGUGCUUUUUUU.

sgRNA GCR-0054 #1:
(SEQ ID NO: 154)
AGUCCUGGUAUCUUCUAUGGGUUUUAGAGCUAGAAAUAGCAAGUUAAAAU
AAGGCUAGUCCGUUAUCAACUUGAAAAAGUGGCACCGAGUCGGUGCUUUU sgRNA GCR-0054 #2:
(SEQ ID NO: 155)
mA*mG*mU*CCUGGUAUCUUCUAUGGGUUUUAGAGCUAGAAAUAGCAAGU
UAAAAUAAGGCUAGUCCGUUAUCAACUUGAAAAAGUGGCACCGAGUCGGU
GCU*mU*mU*mU sgRNA GCR-0054 #3:
(SEQ ID NO: 156)
mA*mG*mU*CCUGGUAUCUUCUAUGGGUUUUAGAGCUAGAAAUAGCAAGU
UAAAAUAAGGCUAGUCCGUUAUCAACUUGAAAAAGUGGCACCGAGUCGGU
GCmU*mU*mU*U dgRNA GCR-0054 #1:
(SEQ ID NO: 157)
crRNA: AGUCCUGGUAUCUUCUAUGGGUUUUAGAGCUAUGCUGUUUUG tracr:
(SEQ ID NO: 224)
AACAGCAUAGCAAGUUAAAAUAAGGCUAGUCCGUUAUCAACUUGAAAAAG
UGGCACCGAGUCGGUGCUUUUUUU dgRNA GCR-0054 #2:
crRNA:
(SEQ ID NO: 158)
mA*mG*mU*CCUGGUAUCUUCUAUGGGUUUUAGAGCUAUGCUGUU*mU*mU*mG tracr:
(SEQ ID NO: 73)
mA*mA*mC*AGCAUAGCAAGUUAAAAUAAGGCUAGUCCGUUAUCAACUUG
AAAAAGUGGCACCGAGUCGGUGCUUUU*mU*mU*mU dgRNA GCR-0054 #3:
crRNA:
(SEQ ID NO: 158)
mA*mG*mU*CCUGGUAUCUUCUAUGGGUUUUAGAGCUAUGCUGUU*mU*mU*mG tracr:
(SEQ ID NO: 224)
AACAGCAUAGCAAGUUAAAAUAAGGCUAGUCCGUUAUCAACUUGAAAAAG
UGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0054 (SEQ ID NO: 54, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0058 (SEQ ID NO: 58, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0058 #1:
(SEQ ID NO: 159)
GUCCUGGUAUCUUCUAUGGUGUUUUAGAGCUAGAAAAUAGCAAGUUAAAAU

AAGGCUAGUCCGUUAUCAACUUGAAAAAGUGGCACCGAGUCGGUGCUUUU sgRNA GCR-0058 #2:
(SEQ ID NO: 160)
mG*mU*mC*CUGGUAUCUUCUAUGGUGUUUUAGAGCUAGAAAUAGCAA

GUUAAAAUAAGGCUAGUCCGUUAUCAACUUGAAAAAGUGGCACCGAG

UCGGUGCU*mU*mU*mU sgRNA GCR-0058 #3:
(SEQ ID NO: 161)
mG*mU*mC*CUGGUAUCUUCUAUGGUGUUUUAGAGCUAGAAAUAGCAA

GUUAAAAUAAGGCUAGUCCGUUAUCAACUUGAAAAAGUGGCACCGA

GUCGGUGCmU*mU*mU*U dgRNA GCR-0058 #1:
(SEQ ID NO: 162)
crRNA:
GUCCUGGUAUCUUCUAUGGUGUUUUAGAGCUAUGCUGUUUUG tracr:
(SEQ ID NO: 224)
AACAGCAUAGCAAGUUAAAAUAAGGCUAGUCCGUUAUCAACUUGAAA

AAGUGGCACCGAGUCGGUGCUUUUUUU dgRNA GCR-0058 #2:
crRNA:
(SEQ ID NO 163)
mG*mU*mC*CUGGUAUCUUCUAUGGUGUUUUAGAGCUAUGCUGU

U*mU*mU*mG tracr:
(SEQ ID NO: 73)
mA*mA*mC*AGCAUAGCAAGUUAAAAUAAGGCUAGUCCGUUAUCAACU UGAAAAGUGGCACCGAGUCGGUGCUUUU*mU*mU*mU dgRNA GCR-0058 #3:
crRNA:
(SEQ ID NO: 163)
mG*mU*mC*CUGGUAUCUUCUAUGGUGUUUUAGAGCUAUGCUGU U*mU*mU*mG tracr:
(SEQ ID NO: 224)
AACAGCAUAGCAAGUUAAAAUAAGGCUAGUCCGUUAUCAACUUGAAA

AAGUGGCACCGAGUCGGUGCUUUUUUU.

sgRNA GCR-0062 #1:
(SEQ ID NO: 164)
CUUGACCAAUAGCCUUGACAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0062 #2:
mC*mU*mU*GACCAAUAGCCUUGACAGUUUUAGAGCUAGAAAUAGC

AAGUUAAAAUAAGGCUAGUCCGUUAUCAACUUGAAAAAGUGGCAC

CGAGUCGGUGCU*mU*mU*mU sgRNA GCR-0062 #3:
(SEQ ID NO: 166)
mC*mU*mU*GACCAAUAGCCUUGACAGUUUUAGAGCUAGAAAUAGCA

AGUUAAAAUAAGGCUAGUCCGUUAUCAACUUGAAAAAGUGGCACCG

AGUCGGUGCmU*mU*mU*U dgRNA GCR-0062 #1:
(SEQ ID NO: 167)
crRNA:
CUUGACCAAUAGCCUUGACAGUUUUAGAGCUAUGCUGUUUUG tracr:
(SEQ ID NO: 224)
AACAGCAUAGCAAGUUAAAAUAAGGCUAGUCCGUUAUCAACUUGAAA

AAGUGGCACCGAGUCGGUGCUUUUUUU dgRNA GCR-0062 #2:
(SEQ ID NO: 168)
crRNA:
mC*mU*mU*GACCAAUAGCCUUGACAGUUUUAGAGCUAUGCUGU

U*mU*mU*mG tracr:
(SEQ ID NO: 73)
mA*mA*mC*AGCAUAGCAAGUUAAAAUAAGGCUAGUCCGUUAUCAAC UUGAAAAGUGGCACCGAGUCGGUGCUUUU*mU*mU*mU dgRNA GCR-0062 #3:
(SEQ ID NO: 168)
crRNA:
mC*mU*mU*GACCAAUAGCCUUGACAGUUUUAGAGCUAUGCU GUU*mU*mU*mG tracr:
(SEQ ID NO: 224)
AACAGCAUAGCAAGUUAAAAUAAGGCUAGUCCGUUAUCAACUUGAA

AAAGUGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0062 (SEQ ID NO: 62, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0063 (SEQ ID NO: 63, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

sgRNA GCR-0063 #1:
(SEQ ID NO: 169)
CAAGGCUAUUGGUCAAGGCAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0063 #2:
(SEQ ID NO: 170)
mC*mA*mA*GGCUAUUGGUCAAGGCAGUUUUAGAGCUAGAAAUAGC

AAGUUAAAAUAAGGCUAGUCCGUUAUCAACUUGAAAAAGUGGCAC

CGAGUCGGUGCU*mU*mU*mU sgRNA GCR-0063 #3:
(SEQ ID NO: 171)
mC*mA*mA*GGCUAUUGGUCAAGGCAGUUUUAGAGCUAGAAAUAGC

AAGUUAAAAUAAGGCUAGUCCGUUAUCAACUUGAAAAAGUGGCAC

CGAGUCGGUGCmU*mU*mU*U dgRNA GCR-0063 #1:
(SEQ ID NO: 172)
crRNA:
CAAGGCUAUUGGUCAAGGCAGUUUUAGAGCUAUGCUGUUUUG tracr:
(SEQ ID NO: 224)
AACAGCAUAGCAAGUUAAAAUAAGGCUAGUCCGUUAUCAACUUG

AAAAAGUGGCACCGAGUCGGUGCUUUUUUU dgRNA GCR-0063 #2:
crRNA:
(SEQ ID NO: 173)
mC*mA*mA*GGCUAUUGGUCAAGGCAGUUUUAGAGCUAUGCUG

UU*mU*mU*mG tracr:
(SEQ ID NO: 73)
mA*mA*mC*AGCAUAGCAAGUUAAAAUAAGGCUAGUCCGUUAUCA ACUUGAAAAAGUGGCACCGAGUCGGUGCUUUU*mU*mU*mU dgRNA GCR-0063 #3:
crRNA:
(SEQ ID NO: 173)
mC*mA*mA*GGCUAUUGGUCAAGGCAGUUUUAGAGCUAUGCUGU U*mU*mU*mG tracr:
(SEQ ID NO: 224)
AACAGCAUAGCAAGUUAAAAUAAGGCUAGUCCGUUAUCAACUUGA

AAAAGUGGCACCGAGUCGGUGCUUUUUUU.

sgRNA GCR-0067 #1:
(SEQ ID NO: 174)
ACUGAAUCGGAACAAGGCAAGUUUUAGAGCUAGAAAUAGCAAGUUAAAAU

AAGGCUAGUCCGUUAUCAACUUGAAAAAGUGGCACCGAGUCGGUGCUUUU sgRNA GCR-0067 #2:
(SEQ ID NO: 175)
mA*mC*mU*GAAUCGGAACAAGGCAAGUUUUAGAGCUAGAAAUAGC

AAGUUAAAAUAAGGCUAGUCCGUUAUCAACUUGAAAAAGUGGCAC

CGAGUCGGUGCU*mU*mU*mU sgRNA GCR-0067 #3:
(SEQ ID NO: 176)
mA*mC*mU*GAAUCGGAACAAGGCAAGUUUUAGAGCUAGAAAUAGC

AAGUUAAAAUAAGGCUAGUCCGUUAUCAACUUGAAAAAGUGGCAC

CGAGUCGGUGCmU*mU*mU*U dgRNA GCR-0067 #1:
(SEQ ID NO: 177)
crRNA:
ACUGAAUCGGAACAAGGCAAGUUUUAGAGCUAUGCUGUUUUG tracr:
(SEQ ID NO: 224)
AACAGCAUAGCAAGUUAAAAUAAGGCUAGUCCGUUAUCAACUUGAA

AAAGUGGCACCGAGUCGGUGCUUUUUUU dgRNA GCR-0067 #2:
crRNA:
(SEQ ID NO: 178)
mA*mC*mU*GAAUCGGAACAAGGCAAGUUUUAGAGCUAUGCUGU

U*mU*mU*mG tracr:
(SEQ ID NO: 73)
mA*mA*mC*AGCAUAGCAAGUUAAAAUAAGGCUAGUCCGUUAUCAA CUUGAAAAAGUGGCACCGAGUCGGUGCUUUU*mU*mU*mU dgRNA GCR-0067 #3:
crRNA:
(SEQ ID NO: 178)
mA*mC*mU*GAAUCGGAACAAGGCAAGUUUUAGAGCUAUGCUGU U*mU*mU*mG tracr:
(SEQ ID NO: 224)
AACAGCAUAGCAAGUUAAAAUAAGGCUAGUCCGUUAUCAACUUGAA

AAGUGGCACCGAGUCGGUGCUUUUUUU.

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

In aspects of the invention, a gRNA comprising the targeting domain of GCR-0067 (SEQ ID NO: 67, unmodified sequence underlined below), e.g., one of the gRNA molecules described below, is useful in the CRISPR systems, methods, cells and other aspects and embodiments of the invention, including in aspects involving more than one gRNA molecule, e.g., described herein:

In each of the gRNA molecules described above, a "*" denotes a phosphorothioate bond between the adjacent nucleotides, and "mN" (where N=A, G, C or U) denotes a 2'-OMe modified nucleotide. In embodiments, any of the gRNA molecules described herein, e.g., described above, is complexed with a Cas9 molecule, e.g., as described herein, to form a ribonuclear protein complex (RNP). Such RNPs are particularly useful in the methods, cells, and other aspects and embodiments of the invention, e.g., described herein.

IV. Cas Molecules
Cas9 Molecules

In preferred embodiments, the Cas molecule is a Cas9 molecule. Cas9 molecules of a variety of species can be used in the methods and compositions described herein. While the *S. pyogenes* Cas9 molecule are the subject of much of the disclosure herein, Cas9 molecules of, derived from, or based on the Cas9 proteins of other species listed herein can be used as well. In other words, other Cas9 molecules, e.g., *S. thermophilus, Staphylococcus aureus* and/or *Neisseria meningitidis* Cas9 molecules, may be used in the systems, methods and compositions described herein. Additional Cas9 species include: *Acidovorax avenae, Actinobacillus pleuropneumoniae, Actinobacillus succinogenes, Actinobacillus suis, Actinomyces* sp., *Cycliphilus denitrificans, Aminomonas paucivorans, Bacillus cereus, Bacillus smithii, Bacillus thuringiensis, Bacteroides* sp., *Blastopirellula marina, Bradyrhiz obium* sp., *Brevibacillus latemsporus, Campylobacter coli, Campylobacter jejuni, Campylobacter lad, Candidatus Puniceispirillum, Clostridiu cellulolyticum, Clostridium perfringens, Corynebacterium accolens, Corynebacterium diphtheria, Corynebacterium matruchotii, Dinoroseobacter sliibae, Eubacterium dolichum, Gamma proteobacterium, Gluconacetobacler diazotrophicus, Haemophilus parainfluenzae, Haemophilus sputorum, Helicobacter canadensis, Helicobacter cinaedi, Helicobacter mustelae, Ilyobacler polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica. Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tislrella mobilis, Treponema* sp., or *Verminephrobacter eiseniae*.

A Cas9 molecule, as that term is used herein, refers to a molecule that can interact with a gRNA molecule (e.g., sequence of a domain of a tracr) and, in concert with the gRNA molecule, localize (e.g., target or home) to a site which comprises a target sequence and PAM sequence.

In an embodiment, the Cas9 molecule is capable of cleaving a target nucleic acid molecule, which may be referred to herein as an active Cas9 molecule. In an embodiment, an active Cas9 molecule, comprises one or more of the following activities: a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which in an embodiment is the presence of two nickase activities; an endonuclease activity; an exonuclease activity; and a helicase activity, i.e., the ability to unwind the helical structure of a double stranded nucleic acid.

In an embodiment, an enzymatically active Cas9 molecule cleaves both DNA strands and results in a double stranded break. In an embodiment, a Cas9 molecule cleaves only one strand, e.g., the strand to which the gRNA hybridizes to, or the strand complementary to the strand the gRNA hybridizes with. In an embodiment, an active Cas9 molecule comprises cleavage activity associated with an HNH-like domain. In an embodiment, an active Cas9 molecule comprises cleavage activity associated with an N-terminal RuvC-like domain. In an embodiment, an active Cas9 molecule comprises cleavage activity associated with an HNH-like domain and cleavage activity associated with an N-terminal RuvC-like domain. In an embodiment, an active Cas9 molecule comprises an active, or cleavage competent, HNH-like domain and an inactive, or cleavage incompetent, N-terminal RuvC-like domain. In an embodiment, an active Cas9 molecule comprises an inactive, or cleavage incompetent, HNH-like domain and an active, or cleavage competent, N-terminal RuvC-like domain.

In an embodiment, the ability of an active Cas9 molecule to interact with and cleave a target nucleic acid is PAM sequence dependent. A PAM sequence is a sequence in the target nucleic acid. In an embodiment, cleavage of the target nucleic acid occurs upstream from the PAM sequence. Active Cas9 molecules from different bacterial species can recognize different sequence motifs (e.g., PAM sequences). In an embodiment, an active Cas9 molecule of *S. pyogenes* recognizes the sequence motif NGG and directs cleavage of a target nucleic acid sequence 1 to 10, e.g., 3 to 5, base pairs upstream from that sequence. See, e.g., Mali el ai, SCIENCE 2013; 339(6121): 823-826. In an embodiment, an active Cas9 molecule of *S. thermophilus* recognizes the sequence motif NGGNG and NNAG AAW (W=A or T) and directs cleavage of a core target nucleic acid sequence 1 to 10, e.g., 3 to 5, base pairs upstream from these sequences. See, e.g., Horvath et al., SCIENCE 2010; 327(5962): 167-170, and Deveau et al, J BACTERIOL 2008; 190(4): 1390-1400. In an embodiment, an active Cas9 molecule of S mulans recognizes the sequence motif NGG or NAAR (R-A or G) and directs cleavage of a core target nucleic acid sequence 1 to 10, e.g., 3 to 5 base pairs, upstream from this sequence. See, e.g., Deveau et al., J BACTERIOL 2008; 190(4): 1 390-1400.

In an embodiment, an active Cas9 molecule of *S. aureus* recognizes the sequence motif NNGRR (R=A or G) and directs cleavage of a target nucleic acid sequence 1 to 10, e.g., 3 to 5, base pairs upstream from that sequence. See, e.g., Ran F. et al., NATURE, vol. 520, 2015, pp. 186-191. In an embodiment, an active Cas9 molecule of *N. meningitidis* recognizes the sequence motif NNNNGATT and directs cleavage of a target nucleic acid sequence 1 to 10, e.g., 3 to 5, base pairs upstream from that sequence. See, e.g., Hou et al., PNAS EARLY EDITION 2013, 1-6. The ability of a Cas9 molecule to recognize a PAM sequence can be determined, e.g., using a transformation assay described in Jinek et al, SCIENCE 2012, 337:816.

Some Cas9 molecules have the ability to interact with a gRNA molecule, and in conjunction with the gRNA molecule home (e.g., targeted or localized) to a core target domain, but are incapable of cleaving the target nucleic acid, or incapable of cleaving at efficient rates. Cas9 molecules having no, or no substantial, cleavage activity may be referred to herein as an inactive Cas9 (an enzymatically inactive Cas9), a dead Cas9, or a dCas9 molecule. For example, an inactive Cas9 molecule can lack cleavage activity or have substantially less, e.g., less than 20, 10, 5, 1 or 0.1% of the cleavage activity of a reference Cas9 molecule, as measured by an assay described herein.

Exemplary naturally occurring Cas9 molecules are described in Chylinski et al, RNA Biology 2013; 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 1 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. pyogenes* (e.g., strain SF370, MGAS 10270, MGAS 10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA 159, NN2025), *S. macacae* (e.g., strain NCTC1 1558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. cmginosus* (e.g.; strain F021 1), *S. agalactia*\* (e.g., strain NEM316, A909), *Listeria monocytogenes* (e.g., strain F6854), *Listeria innocua* (*L. innocua*, e.g., strain Clip 1 1262), *Etuerococcus italicus* (e.g., strain DSM 15952), or *Enterococcus faecium* (e.g., strain 1,231,408). Additional exemplary Cas9 molecules are a Cas9 molecule of *Neisseria meningitidis* (Hou et al. PNAS Early Edition 2013, 1-6) and a *S. aureus* Cas9 molecule.

In an embodiment, a Cas9 molecule, e.g., an active Cas9 molecule or inactive Cas9 molecule, comprises an amino acid sequence: having 60%, 65%, 70%, 75%, 80%, 85%, 90%, 95%, 96%, 97%, 98%, or 99% homology with; differs at no more than 1%, 2%, 5%, 10%, 15%, 20%, 30%, or 40% of the amino acid residues when compared with; differs by at least 1, 2, 5, 10 or 20 amino acids but by no more than 100, 80, 70, 60, 50, 40 or 30 amino acids from; or is identical to; any Cas9 molecule sequence described herein or a naturally occurring Cas9 molecule sequence, e.g., a Cas9 molecule from a species listed herein or described in Chylinski et al., RNA Biology 2013, 10:5,Г2Г-Т,1 Hou et al. PNAS Early Edition 2013, 1-6.

In an embodiment, a Cas9 molecule comprises an amino acid sequence having 60%, 65%, 70%, 75%, 80%, 85%, 90%, 95%, 96%, 97%, 98%, or 99% homology with; differs at no more than 1%, 2%, 5%, 10%, 15%, 20%, 30%, or 40% of the amino acid residues when compared with; differs by at least 1, 2, 5, 10 or 20 amino acids but by no more than 100, 80, 70, 60, 50, 40 or 30 amino acids from; or is identical to; *S. pyogenes* Cas9:

(SEQ ID NO: 205)

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
                35                  40                  45

Gly Ala Leu Leu Phe Asp Ser Gly Glu Thr Ala Glu Ala Thr Arg Leu
            50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205
```

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
    355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640
```

-continued

```
His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
            1060                1065                1070
```

```
Val Trp Asp Lys Gly Arg Asp Phe Ala Thr Val Arg Lys Val Leu Ser
        1075            1080            1085

Met Pro Gln Val Asn Ile Val Lys Lys Thr Glu Val Gln Thr Gly Gly
        1090            1095            1100

Phe Ser Lys Glu Ser Ile Leu Pro Lys Arg Asn Ser Asp Lys Leu Ile
1105            1110            1115            1120

Ala Arg Lys Lys Asp Trp Asp Pro Lys Lys Tyr Gly Gly Phe Asp Ser
            1125            1130            1135

Pro Thr Val Ala Tyr Ser Val Leu Val Val Ala Lys Val Glu Lys Gly
            1140            1145            1150

Lys Ser Lys Lys Leu Lys Ser Val Lys Glu Leu Leu Gly Ile Thr Ile
        1155            1160            1165

Met Glu Arg Ser Ser Phe Glu Lys Asn Pro Ile Asp Phe Leu Glu Ala
        1170            1175            1180

Lys Gly Tyr Lys Glu Val Lys Lys Asp Leu Ile Ile Lys Leu Pro Lys
1185            1190            1195            1200

Tyr Ser Leu Phe Glu Leu Glu Asn Gly Arg Lys Arg Met Leu Ala Ser
            1205            1210            1215

Ala Gly Glu Leu Gln Lys Gly Asn Glu Leu Ala Leu Pro Ser Lys Tyr
            1220            1225            1230

Val Asn Phe Leu Tyr Leu Ala Ser His Tyr Glu Lys Leu Lys Gly Ser
            1235            1240            1245

Pro Glu Asp Asn Glu Gln Lys Gln Leu Phe Val Glu Gln His Lys His
        1250            1255            1260

Tyr Leu Asp Glu Ile Ile Glu Gln Ile Ser Glu Phe Ser Lys Arg Val
1265            1270            1275            1280

Ile Leu Ala Asp Ala Asn Leu Asp Lys Val Leu Ser Ala Tyr Asn Lys
            1285            1290            1295

His Arg Asp Lys Pro Ile Arg Glu Gln Ala Glu Asn Ile Ile His Leu
            1300            1305            1310

Phe Thr Leu Thr Asn Leu Gly Ala Pro Ala Ala Phe Lys Tyr Phe Asp
        1315            1320            1325

Thr Thr Ile Asp Arg Lys Arg Tyr Thr Ser Thr Lys Glu Val Leu Asp
        1330            1335            1340

Ala Thr Leu Ile His Gln Ser Ile Thr Gly Leu Tyr Glu Thr Arg Ile
1345            1350            1355            1360

Asp Leu Ser Gln Leu Gly Gly Asp
            1365
```

In embodiments, the Cas9 molecule is a *S. pyogenes* Cas9 variant of SEQ ID NO: 205 that includes one or more mutations to positively charged amino acids (e.g., lysine, arginine or histidine) that introduce an uncharged or non-polar amino acid, e.g., alanine, at said position. In embodiments, the mutation is to one or more positively charged amino acids in the nt-groove of Cas9. In embodiments, the Cas9 molecule is a *S. pyogenes* Cas9 variant of SEQ ID NO: 205 that includes a mutation at position 855 of SEQ ID NO: 205, for example a mutation to an uncharged amino acid, e.g., alanine, at position 855 of SEQ ID NO: 205. In embodiments, the Cas9 molecule has a mutation only at position 855 of SEQ ID NO: 205, relative to SEQ ID NO: 205, e.g., to an uncharged amino acid, e.g., alanine. In embodiments, the Cas9 molecule is a *S. pyogenes* Cas9 variant of SEQ ID NO: 205 that includes a mutation at position 810, a mutation at position 1003, and/or a mutation at position 1060 of SEQ ID NO: 205, for example a mutation to alanine at position 810, position 1003, and/or position 1060 of SEQ ID NO: 205. In embodiments, the Cas9 molecule has a mutation only at position 810, position 1003, and position 1060 of SEQ ID NO: 205, relative to SEQ ID NO: 205, e.g., where each mutation is to an uncharged amino acid, for example, alanine. In embodiments, the Cas9 molecule is a *S. pyogenes* Cas9 variant of SEQ ID NO: 205 that includes a mutation at position 848, a mutation at position 1003, and/or a mutation at position 1060 of SEQ ID NO: 205, for example a mutation to alanine at position 848, position 1003, and/or position 1060 of SEQ ID NO: 205. In embodiments, the Cas9 molecule has a mutation only at position 848, position 1003, and position 1060 of SEQ ID NO: 205, relative to SEQ ID NO: 205, e.g., where each mutation is to an uncharged amino acid, for example, alanine. In embodiments, the Cas9 molecule is a Cas9 molecule as described in Slaymaker et al., *Science Express*, available online Dec. 1, 2015 at Science DOI: 10.1126/science.aad5227.

In embodiments, the Cas9 molecule is a *S. pyogenes* Cas9 variant of SEQ ID NO: 205 that includes one or more mutations. In embodiments, the Cas9 variant comprises a mutation at position 80 of SEQ ID NO: 205, e.g., includes a leucine at position 80 of SEQ ID NO: 205 (i.e., comprises, e.g., consists of, SEQ ID NO: 205 with a C80L mutation). In embodiments, the Cas9 variant comprises a mutation at position 574 of SEQ ID NO: 205, e.g., includes a glutamic acid at position 574 of SEQ ID NO: 205 (i.e., comprises, e.g., consists of, SEQ ID NO: 205 with a C574E mutation). In embodiments, the Cas9 variant comprises a mutation at position 80 and a mutation at position 574 of SEQ ID NO: 205, e.g., includes a leucine at position 80 of SEQ ID NO: 205, and a glutamic acid at position 574 of SEQ ID NO: 205 (i.e., comprises, e.g., consists of, SEQ ID NO: 205 with a C80L mutation and a C574E mutation). Without being bound by theory, it is believed that such mutations improve the solution properties of the Cas9 molecule.

In embodiments, the Cas9 molecule is a *S. pyogenes* Cas9 variant of SEQ ID NO: 205 that includes one or more mutations. In embodiments, the Cas9 variant comprises a mutation at position 147 of SEQ ID NO: 205, e.g., includes a tyrosine at position 147 of SEQ ID NO: 205 (i.e., comprises, e.g., consists of, SEQ ID NO: 205 with a D147Y mutation). In embodiments, the Cas9 variant comprises a mutation at position 411 of SEQ ID NO: 205, e.g., includes a threonine at position 411 of SEQ ID NO: 205 (i.e., comprises, e.g., consists of, SEQ ID NO: 205 with a P411T mutation). In embodiments, the Cas9 variant comprises a mutation at position 147 and a mutation at position 411 of SEQ ID NO: 205, e.g., includes a tyrosine at position 147 of SEQ ID NO: 205, and a threonine at position 411 of SEQ ID NO: 205 (i.e., comprises, e.g., consists of, SEQ ID NO: 205 with a D147Y mutation and a P411T mutation). Without being bound by theory, it is believed that such mutations improve the targeting efficiency of the Cas9 molecule, e.g., in yeast.

In embodiments, the Cas9 molecule is a *S. pyogenes* Cas9 variant of SEQ ID NO: 205 that includes one or more mutations. In embodiments, the Cas9 variant comprises a mutation at position 1135 of SEQ ID NO: 205, e.g., includes a glutamic acid at position 1135 of SEQ ID NO: 205 (i.e., comprises, e.g., consists of, SEQ ID NO: 205 with a D1135E mutation). Without being bound by theory, it is believed that such mutations improve the selectivity of the Cas9 molecule for the NGG PAM sequence versus the NAG PAM sequence.

In embodiments, the Cas9 molecule is a *S. pyogenes* Cas9 variant of SEQ ID NO: 205 that includes one or more mutations that introduce an uncharged or nonpolar amino acid, e.g., alanine, at certain positions. In embodiments, the Cas9 molecule is a *S. pyogenes* Cas9 variant of SEQ ID NO: 205 that includes a mutation at position 497, a mutation at position 661, a mutation at position 695 and/or a mutation at position 926 of SEQ ID NO: 205, for example a mutation to alanine at position 497, position 661, position 695 and/or position 926 of SEQ ID NO: 205. In embodiments, the Cas9 molecule has a mutation only at position 497, position 661, position 695, and position 926 of SEQ ID NO: 205, relative to SEQ ID NO: 205, e.g., where each mutation is to an uncharged amino acid, for example, alanine Without being bound by theory, it is believed that such mutations reduce the cutting by the Cas9 molecule at off-target sites It will be understood that the mutations described herein to the Cas9 molecule may be combined, and may be combined with any of the fusions or other modifications described herein, and the Cas9 molecule tested in the assays described herein.

Various types of Cas molecules can be used to practice the inventions disclosed herein. In some embodiments, Cas molecules of Type II Cas systems are used. In other embodiments, Cas molecules of other Cas systems are used. For example, Type I or Type III Cas molecules may be used. Exemplary Cas molecules (and Cas systems) are described, e.g., in Haft et ai, PLoS COMPUTATIONAL BIOLOGY 2005, 1(6): e60 and Makarova et al, NATURE REVIEW MICROBIOLOGY 2011, 9:467-477, the contents of both references are incorporated herein by reference in their entirety.

In an embodiment, the Cas9 molecule comprises one or more of the following activities: a nickase activity; a double stranded cleavage activity (e.g., an endonuclease and/or exonuclease activity); a helicase activity; or the ability, together with a gRNA molecule, to localize to a target nucleic acid.

Altered Cas9 Molecules

Naturally occurring Cas9 molecules possess a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In an embodiment, a Cas9 molecules can include all or a subset of these properties. In typical embodiments, Cas9 molecules have the ability to interact with a gRNA molecule and, in concert with the gRNA molecule, localize to a site in a nucleic acid. Other activities, e.g., PAM specificity, cleavage activity, or helicase activity can vary more widely in Cas9 molecules.

Cas9 molecules with desired properties can be made in a number of ways, e.g., by alteration of a parental, e.g., naturally occurring Cas9 molecules to provide an altered Cas9 molecule having a desired property. For example, one or more mutations or differences relative to a parental Cas9 molecule can be introduced. Such mutations and differences comprise: substitutions (e.g., conservative substitutions or substitutions of non-essential amino acids); insertions; or deletions. In an embodiment, a Cas9 molecule can comprises one or more mutations or differences, e.g., at least 1, 2, 3, 4, 5, 10, 15, 20, 30, 40 or 50 mutations but less than 200, 100, or 80 mutations relative to a reference Cas9 molecule.

In an embodiment, a mutation or mutations do not have a substantial effect on a Cas9 activity, e.g. a Cas9 activity described herein. In an embodiment, a mutation or mutations have a substantial effect on a Cas9 activity, e.g. a Cas9 activity described herein. In an embodiment, exemplary activities comprise one or more of PAM specificity, cleavage activity, and helicase activity. A mutation(s) can be present, e.g., in: one or more RuvC-like domain, e.g., an N-terminal RuvC-like domain; an HNH-like domain; a region outside the RuvC-like domains and the HNH-like domain. In some embodiments, a mutation(s) is present in an N-terminal RuvC-like domain. In some embodiments, a mutation(s) is present in an HNH-like domain. In some embodiments, mutations are present in both an N-terminal RuvC-like domain and an HNH-like domain.

Whether or not a particular sequence, e.g., a substitution, may affect one or more activity, such as targeting activity, cleavage activity, etc, can be evaluated or predicted, e.g., by evaluating whether the mutation is conservative or by the method described in Section III. In an embodiment, a "non-essential" amino acid residue, as used in the context of a Cas9 molecule, is a residue that can be altered from the wild-type sequence of a Cas9 molecule, e.g., a naturally occurring Cas9 molecule, e.g., an active Cas9 molecule, without abolishing or more preferably, without substantially altering a Cas9 activity (e.g., cleavage activity), whereas changing an "essential" amino acid residue results in a substantial loss of activity (e.g., cleavage activity).

Cas9 Molecules with Altered PAM Recognition or No PAM Recognition

Naturally occurring Cas9 molecules can recognize specific PAM sequences, for example the PAM recognition sequences described above for S. pyogenes, S. thermophilus, S. mutans, S. aureus and N. meningitidis.

In an embodiment, a Cas9 molecule has the same PAM specificities as a naturally occurring Cas9 molecule. In other embodiments, a Cas9 molecule has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule recognizes to decrease off target sites and/or improve specificity; or eliminate a PAM recognition requirement. In an embodiment, a Cas9 molecule can be altered, e.g., to increase length of PAM recognition sequence and/or improve Cas9 specificity to high level of identity to decrease off target sites and increase specificity. In an embodiment, the length of the PAM recognition sequence is at least 4, 5, 6, 7, 8, 9, 10 or 15 amino acids in length. Cas9 molecules that recognize different PAM sequences and/or have reduced off-target activity can be generated using directed evolution. Exemplary methods and systems that can be used for directed evolution of Cas9 molecules are described, e.g., in Esvelt el al, Nature 2011, 472(7344): 499-503. Candidate Cas9 molecules can be evaluated, e.g., by methods described herein.

Non-Cleaving and Modified-Cleavage Cas9 Molecules

In an embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of S. pyogenes, as follows: its ability to modulate, e.g., decreased or increased, cleavage of a double stranded break (endonuclease and/or exonuclease activity), e.g., as compared to a naturally occurring Cas9 molecule (e.g., a Cas9 molecule of S. pyogenes); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of S. pyogenes); or the ability to cleave a nucleic acid molecule, e.g., a double stranded or single stranded nucleic acid molecule, can be eliminated.

Modified Cleavage active Cas9 Molecules

In an embodiment, an active Cas9 molecule comprises one or more of the following activities: cleavage activity associated with an N-terminal RuvC-like domain; cleavage activity associated with an HNH-like domain; cleavage activity associated with an HNH domain and cleavage activity associated with an N-terminal RuvC-like domain.

In an embodiment, the Cas9 molecule is a Cas9 nickase, e.g., cleaves only a single strand of DNA. In an embodiment, the Cas9 nickase includes a mutation at position 10 and/or a mutation at position 840 of SEQ ID NO: 205, e.g., comprises a D10A and/or H840A mutation to SEQ ID NO: 205.

Non-Cleaving Inactive Cas9 Molecules

In an embodiment, the altered Cas9 molecule is an inactive Cas9 molecule which does not cleave a nucleic acid molecule (either double stranded or single stranded nucleic acid molecules) or cleaves a nucleic acid molecule with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of S. pyogenes, S. thermophilus, S. aureus or N. meningitidis. In an embodiment, the reference Cas9 molecule is the naturally occurring Cas9 molecule having the closest sequence identity or homology. In an embodiment, the inactive Cas9 molecule lacks substantial cleavage activity associated with an N-terminal RuvC-like domain and cleavage activity associated with an HNH-like domain.

In an embodiment, the Cas9 molecule is dCas9. Tsai et al. (2014), Nat. Biotech. 32:569-577.

A catalytically inactive Cas9 molecule may be fused with a transcription repressor. An inactive Cas9 fusion protein complexes with a gRNA and localizes to a DNA sequence specified by gRNA's targeting domain, but, unlike an active Cas9, it will not cleave the target DNA. Fusion of an effector domain, such as a transcriptional repression domain, to an inactive Cas9 enables recruitment of the effector to any DNA site specified by the gRNA. Site specific targeting of a Cas9 fusion protein to a promoter region of a gene can block or affect polymerase binding to the promoter region, for example, a Cas9 fusion with a transcription factor (e.g., a transcription activator) and/or a transcriptional enhancer binding to the nucleic acid to increase or inhibit transcription activation. Alternatively, site specific targeting of a Cas9-fusion to a transcription repressor to a promoter region of a gene can be used to decrease transcription activation.

Transcription repressors or transcription repressor domains that may be fused to an inactive Cas9 molecule can include ruppel associated box (KRAB or SKD), the Mad mSIN3 interaction domain (SID) or the ERF repressor domain (ERD).

In another embodiment, an inactive Cas9 molecule may be fused with a protein that modifies chromatin. For example, an inactive Cas9 molecule may be fused to heterochromatin protein 1 (HP1), a histone lysine methyltransferase (e.g., SUV39H 1, SUV39H2, G9A, ESET/SETDB 1, Pr-SET7/8, SUV4-20H 1,RIZ1), a histone lysine demethylates (e.g., LSD1/BHC1 10, SpLsdl/Sw, 1/Safl 10, Su(var)3-3, JMJD2A/JHDM3A, JMJD2B, JMJD2C/GASC1, JMJD2D, Rphl, JARID 1 A/RBP2, JARI DIB/PLU-I, JAR1D 1C/SMCX, JARID1 D/SMCY, Lid, Jhn2, Jmj2), a histone lysine deacetylases (e.g., HDAC1, HDAC2, HDAC3, HDAC8, Rpd3, Hos 1, Cir6, HDAC4, HDAC5, HDAC7, HDAC9, Hdal, Cir3, SIRT 1, SIRT2, Sir2, Hst 1, Hst2, Hst3, Hst4, HDAC 11) and a DNA methylases (DNMTLDNMT2a/DMNT3b, MET1). An inactive Cas9-chomatin modifying molecule fusion protein can be used to alter chromatin status to reduce expression a target gene.

The heterologous sequence (e.g., the transcription repressor domain) may be fused to the N- or C-terminus of the inactive Cas9 protein. In an alternative embodiment, the heterologous sequence (e.g., the transcription repressor domain) may be fused to an internal portion (i.e., a portion other than the N-terminus or C-terminus) of the inactive Cas9 protein.

The ability of a Cas9 molecule/gRNA molecule complex to bind to and cleave a target nucleic acid can be evaluated, e.g., by the methods described herein in Section III. The activity of a Cas9 molecule, e.g., either an active Cas9 or a inactive Cas9, alone or in a complex with a gRNA molecule may also be evaluated by methods well-known in the art, including, gene expression assays and chromatin-based assays, e.g., chromatin immunoprecipitation (ChiP) and chromatin in vivo assay (CiA).

Other Cas9 Molecule Fusions

In embodiments, the Cas9 molecule, e.g, a Cas9 of *S. pyogenes*, may additionally comprise one or more amino acid sequences that confer additional activity.

In some aspects, the Cas9 molecule may comprise one or more nuclear localization sequences (NLSs), such as at least 1, 2, 3, 4, 5, 6, 7, 8, 9, 10, or more NLSs. In some embodiments, the Cas9 molecule comprises at least 1, 2, 3, 4, 5, 6, 7, 8, 9, 10, or more NLSs at or near the amino-terminus, at least 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence comprising or derived from: the NLS of the SV40 virus large T-antigen, having the amino acid sequence PKKKRKV (SEQ ID NO: 206); the NLS from nucleoplasmin (e.g. the nucleoplasmin bipartite NLS with the sequence KRPAATKKAGQAKKKK (SEQ ID NO: 207); the c-myc NLS having the amino acid sequence PAAKRVKLD (SEQ ID NO: 208) or RQRR-NELKRSP (SEQ ID NO: 209); the hRNPA1 M9 NLS having the sequence NQSSNFGPMKGGNFG-GRSSGPYGGGGQYFAKPRNQGGY (SEQ ID NO: 210); the sequence RMRIZFKNKGKDTAELRRRRVEVS-VELRKAKKDEQILKRRNV (SEQ ID NO: 211) of the IBB domain from importin-alpha; the sequences VSRKRPRP (SEQ ID NO: 212) and PPKKARED (SEQ ID NO: 213) of the myoma T protein; the sequence PQPKKKPL (SEQ ID NO: 214) of human p53; the sequence SALIKKKKKMAP (SEQ ID NO: 215) of mouse c-ab1 IV; the sequences DRLRR (SEQ ID NO: 216) and PKQKKRK (SEQ ID NO: 217) of the influenza virus NS1; the sequence RKLKK-KIKKL (SEQ ID NO: 218) of the Hepatitis virus delta antigen; the sequence REKKKFLKRR (SEQ ID NO: 219) of the mouse Mx1 protein; the sequence KRKGDEVDGVDEVAKKKSKK (SEQ ID NO: 220) of the human poly(ADP-ribose) polymerase; and the sequence RKCLQAGMNLEARKTKK (SEQ ID NO: 221) of the steroid hormone receptors (human) glucocorticoid. Other suitable NLS sequences are known in the art (e.g., Sorokin, Biochemistry (Moscow) (2007) 72:13, 1439-1457; Lange J Biol Chem. (2007) 282:8, 5101-5).

In an embodiment, the Cas9 molecule, e.g., *S. pyogenes* Cas9 molecule, comprises a NLS sequence of SV40, e.g., disposed N terminal to the Cas9 molecule. In an embodiment, the Cas9 molecule, e.g., *S. pyogenes* Cas9 molecule, comprises a NLS sequence of SV40 disposed N-terminal to the Cas9 molecule and a NLS sequence of SV40 disposed C terminal to the Cas9 molecule. In an embodiment, the Cas9 molecule, e.g., *S. pyogenes* Cas9 molecule, comprises a NLS sequence of SV40 disposed N-terminal to the Cas9 molecule and a NLS sequence of nucleoplasmin disposed C-terminal to the Cas9 molecule. In any of the aforementioned embodiments, the molecule may additionally comprise a tag, e.g., a His tag, e.g., a His(6) tag (SEQ ID NO: 247) or His(8) tag (SEQ ID NO: 248), e.g., at the N terminus or the C terminus.

In some aspects, the Cas9 molecule may comprise one or more amino acid sequences that allow the Cas9 molecule to be specifically recognized, for example a tag. In one embodiment, the tag is a Histidine tag, e.g., a histidine tag comprising at least 3, 4, 5, 6, 7, 8, 9, 10 or more histidine amino acids. In embodiments, the histidine tag is a His6 tag (six histidines) (SEQ ID NO: 247). In other embodiments, the histidine tag is a His8 tag (eight histidines) (SEQ ID NO: 248). In embodiments, the histidine tag may be separated from one or more other portions of the Cas9 molecule by a linker. In embodiments, the linker is GGS. An example of such a fusion is the Cas9 molecule iProt106520.

In some aspects, the Cas9 molecule may comprise one or more amino acid sequences that are recognized by a protease (e.g., comprise a protease cleavage site). In embodiments, the cleavage site is the tobacco etch virus (TEV) cleavage site, e.g., comprises the sequence ENLYFQG (SEQ ID NO: 230). In some aspects the protease cleavage site, e.g., the TEV cleavage site is disposed between a tag, e.g., a His tag, e.g., a His6 (SEQ ID NO: 247) or His8 tag (SEQ ID NO: 248), and the remainder of the Cas9 molecule. Without being bound by theory it is believed that such introduction will allow for the use of the tag for, e.g., purification of the Cas9 molecule, and then subsequent cleavage so the tag does not interfere with the Cas9 molecule function.

In embodiments, the Cas9 molecule (e.g., a Cas9 molecule as described herein) comprises an N-terminal NLS, and a C-terminal NLS (e.g., comprises, from N- to C-terminal NLS-Cas9-NLS), e.g., wherein each NLS is an SV40 NLS (PKKKRKV (SEQ ID NO: 206)). In embodiments, the Cas9 molecule (e.g., a Cas9 molecule as described herein) comprises an N-terminal NLS, a C-terminal NLS, and a C-terminal His6 tag (SEQ ID NO: 247) (e.g., comprises, from N- to C-terminal NLS-Cas9-NLS-His tag), e.g., wherein each NLS is an SV40 NLS (PKKKRKV (SEQ ID NO: 206)). In embodiments, the Cas9 molecule (e.g., a Cas9 molecule as described herein) comprises an N-terminal His tag (e.g., His6 tag (SEQ ID NO: 247)), an N-terminal NLS, and a C-terminal NLS (e.g., comprises, from N- to C-terminal His tag-NLS-Cas9-NLS), e.g., wherein each NLS is an SV40 NLS (PKKKRKV (SEQ ID NO: 206)). In embodiments, the Cas9 molecule (e.g., a Cas9 molecule as described herein) comprises an N-terminal NLS and a C-terminal His tag (e.g., His6 tag (SEQ ID NO: 247)) (e.g., comprises from N- to C-terminal His tag-Cas9-NLS), e.g., wherein the NLS is an SV40 NLS (PKKKRKV (SEQ ID NO: 206)). In embodiments, the Cas9 molecule (e.g., a Cas9 molecule as described herein) comprises an N-terminal NLS and a C-terminal His tag (e.g., His6 tag (SEQ ID NO: 247)) (e.g., comprises from N- to C-terminal NLS-Cas9-His tag), e.g., wherein the NLS is an SV40 NLS (PKKKRKV (SEQ ID NO: 206)). In embodiments, the Cas9 molecule (e.g., a Cas9 molecule as described herein) comprises an N-terminal His tag (e.g., His8 tag (SEQ ID NO: 248)), an N-terminal cleavage domain (e.g., a tobacco etch virus (TEV) cleavage domain (e.g., comprises the sequence ENLYFQG (SEQ ID NO: 230))), an N-terminal NLS (e.g., an SV40 NLS; SEQ ID NO: 206), and a C-terminal NLS (e.g., an SV40 NLS; SEQ ID NO: 206) (e.g., comprises from N- to C-terminal His tag-TEV-NLS-Cas9-NLS). In any of the aforementioned embodiments the Cas9 has the sequence of SEQ ID NO: 205. Alternatively, in any of the aforementioned embodiments, the Cas9 has a sequence of a Cas9 variant of SEQ ID NO: 205, e.g., as described herein. In any of the aforementioned embodiments, the Cas9 molecule comprises a linker between the His tag and another portion of the molecule, e.g., a GGS linker. Amino acid sequences of exemplary Cas9 molecules described above are provided below. "iProt" identifiers match those in FIG. 60.

```
iProt105026 (also referred to as iProt106154,
iProt106331, iProt106545, and PID426303,
depending on the preparation of the protein)
(SEQ ID NO: 233):
MAPKKKRKVD KKYSIGLDIG TNSVGWAVIT DEYKVPSKKF

KVLGNTDRHS IKKNLIGALL FDSGETAEAT RLKRTARRRY

TRRKNRICYL QEIFSNEMAK VDDSFFHRLE ESFLVEEDKK

HERHPIFGNI VDEVAYHEKY PTIYHLRKKL VDSTDKADLR

LIYLALAHMI KFRGHFLIEG DLNPDNSDVD KLFIQLVQTY

NQLFEENPIN ASGVDAKAIL SARLSKSRRL ENLIAQLPGE

KKNGLFGNLI ALSLGLTPNF KSNFDLAEDA KLQLSKDTYD

DDLDNLLAQI GDQYADLFLA AKNLSDAILL SDILRVNTEI

TKAPLSASMI KRYDEHHQDL TLLKALVRQQ LPEKYKEIFF

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTNFDKNL PNEKVLPKHS

LLYEYFTVYN ELTKVKYVTE GMRKPAFLSG EQKKAIVDLL

FKTNRKVTVK QLKEDYFKKI ECFDSVEISG VEDRFNASLG

TYHDLLKIIK DKDFLDNEEN EDILEDIVLT LTLFEDREMI

EERLKTYAHL FDDKVMKQLK RRRYTGWGRL SRKLINGIRD

KQSGKTILDF LKSDGFANRN FMQLIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEKLY LYYLQNGRDM YVDQELDINR

LSDYDVDHIV PQSFLKDDSI DNKVLTRSDK NRGKSDNVPS

EEVVKKMKNY WRQLLNAKLI TQRKFDNLTK AERGGLSELD

KAGFIKRQLV ETRQITKHVA QILDSRMNTK YDENDKLIRE

VKVITLKSKL VSDFRKDFQF YKVREINNYH HAHDAYLNAV

VGTALIKKYP KLESEFVYGD YKVYDVRKMI AKSEQEIGKA

TAKYFFYSNI MNFFKTEITL ANGEIRKRPL IETNGETGEI

VWDKGRDFAT VRKVLSMPQV NIVKKTEVQT GGFSKESILP

KRNSDKLIAR KKDWDPKKYG GFDSPTVAYS VLVVAKVEKG

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI

TGLYETRIDL SQLGGDSRAD PKKKRKVHHH HHH iProt106518 (SEQ ID NO: 234):
MAPKKKRKVD KKYSIGLDIG TNSVGWAVIT DEYKVPSKKF

KVLGNTDRHS IKKNLIGALL FDSGETAEAT RLKRTARRRY

TRRKNRILYL QEIFSNEMAK VDDSFFHRLE ESFLVEEDKK

HERHPIFGNI VDEVAYHEKY PTIYHLRKKL VDSTDKADLR

LIYLALAHMI KFRGHFLIEG DLNPDNSDVD KLFIQLVQTY

NQLFEENPIN ASGVDAKAIL SARLSKSRRL ENLIAQLPGE

KKNGLFGNLI ALSLGLTPNF KSNFDLAEDA KLQLSKDTYD

DDLDNLLAQI GDQYADLFLA AKNLSDAILL SDILRVNTEI

TKAPLSASMI KRYDEHHQDL TLLKALVRQQ LPEKYKEIFF

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTNFDKNL PNEKVLPKHS

LLYEYFTVYN ELTKVKYVTE GMRKPAFLSG EQKKAIVDLL

FKTNRKVTVK QLKEDYFKKI EEFDSVEISG VEDRFNASLG

TYHDLLKIIK DKDFLDNEEN EDILEDIVLT LTLFEDREMI

EERLKTYAHL FDDKVMKQLK RRRYTGWGRL SRKLINGIRD

KQSGKTILDF LKSDGFANRN FMQLIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEKLY LYYLQNGRDM YVDQELDINR

LSDYDVDHIV PQSFLKDDSI DNKVLTRSDK NRGKSDNVPS

EEVVKKMKNY WRQLLNAKLI TQRKFDNLTK AERGGLSELD

KAGFIKRQLV ETRQITKHVA QILDSRMNTK YDENDKLIRE

VKVITLKSKL VSDFRKDFQF YKVREINNYH HAHDAYLNAV

VGTALIKKYP KLESEFVYGD YKVYDVRKMI AKSEQEIGKA

TAKYFFYSNI MNFFKTEITL ANGEIRKRPL IETNGETGEI

VWDKGRDFAT VRKVLSMPQV NIVKKTEVQT GGFSKESILP

KRNSDKLIAR KKDWDPKKYG GFDSPTVAYS VLVVAKVEKG

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI
``` iProt106519 (SEQ ID NO: 235):
MGSSHHHHHH HHENLYFQGS MDKKYSIGLD IGTNSVGWAV
ITDEYKVPSK KFKVLGNTDR HSIKKNLIGA LLFDSGETAE
ATRLKRTARR RYTRRKNRIC YLQEIFSNEM AKVDDSFFHR
LEESFLVEED KKHERHPIFG NIVDEVAYHE KYPTIYHLRK
KLVDSTDKAD LRLIYLALAH MIKFRGHFLI EGDLNPDNSD
VDKLFIQLVQ TYNQLFEENP INASGVDAKA ILSARLSKSR
RLENLIAQLP GEKKNGLFGN LIALSLGLTP NFKSNFDLAE
DAKLQLSKDT YDDDLDNLLA QIGDQYADLF LAAKNLSDAI
LLSDILRVNT EITKAPLSAS MIKRYDEHHQ DLTLLKALVR
QQLPEKYKEI FFDQSKNGYA GYIDGGASQE EFYKFIKPIL
EKMDGTEELL VKLNREDLLR KQRTFDNGSI PHQIHLGELH
AILRRQEDFY PFLKDNREKI EKILTFRIPY YVGPLARGNS
RFAWMTRKSE ETITPWNFEE VVDKGASAQS FIERMTNFDK
NLPNEKVLPK HSLLYEYFTV YNELTKVKYV TEGMRKPAFL
SGEQKKAIVD LLFKTNRKVT VKQLKEDYFK KIECFDSVEI
SGVEDRFNAS LGTYHDLLKI IKDKDFLDNE ENEDILEDIV
LTLTLFEDRE MIEERLKTYA HLFDDKVMKQ LKRRRYTGWG
RLSRKLINGI RDKQSGKTIL DFLKSDGFAN RNFMQLIHDD
SLTFKEDIQK AQVSGQGDSL HEHIANLAGS PAIKKGILQT
VKVVDELVKV MGRHKPENIV IEMARENQTT QKGQKNSRER
MKRIEEGIKE LGSQILKEHP VENTQLQNEK LYLYYLQNGR
DMYVDQELDI NRLSDYDVDH IVPQSFLKDD SIDNKVLTRS
DKNRGKSDNV PSEEVVKKMK NYWRQLLNAK LITQRKFDNL
TKAERGGLSE LDKAGFIKRQ LVETRQITKH VAQILDSRMN
TKYDENDKLI REVKVITLKS KLVSDFRKDF QFYKVREINN
YHHAHDAYLN AVVGTALIKK YPKLESEFVY GDYKVYDVRK
MIAKSEQEIG KATAKYFFYS NIMNFFKTEI TLANGEIRKR
PLIETNGETG EIWVDKGRDF ATVRKVLSMP QVNIVKKTEV
QTGGFSKESI LPKRNSDKLI ARKKDWDPKK YGGFDSPTVA
YSVLVVAKVE KGKSKKLKSV KELLGITIME RSSFEKNPID
FLEAKGYKEV KKDLIIKLPK YSLFELENGR KRMLASAGEL
QKGNELALPS KYVNFLYLAS HYEKLKGSPE DNEQKQLFVE
QHKHYLDEII EQISEFSKRV ILADANLDKV LSAYNKHRDK
PIREQAENII HLFTLTNLGA PAAFKYFDTT IDRKRYTSTK
EVLDATLIHQ SITGLYETRI DLSQLGGDGG GSPKKKRKV iProt106520 (SEQ ID NO: 236):
MAHHHHHHGG SPKKKRKVDK KYSIGLDIGT NSVGWAVITD
EYKVPSKKFK VLGNTDRHSI KKNLIGALLF DSGETAEATR
LKRTARRRYT RRKNRICYLQ EIFSNEMAKV DDSFFHRLEE
SFLVEEDKKH ERHPIFGNIV DEVAYHEKYP TIYHLRKKLV
DSTDKADLRL IYLALAHMIK FRGHFLIEGD LNPDNSDVDK
LFIQLVQTYN QLFEENPINA SGVDAKAILS ARLSKSRRLE
NLIAQLPGEK KNGLFGNLIA LSLGLTPNFK SNFDLAEDAK
LQLSKDTYDD DLDNLLAQIG DQYADLFLAA KNLSDAILLS
DILRVNTEIT KAPLSASMIK RYDEHHQDLT LLKALVRQQL
PEKYKEIFFD QSKNGYAGYI DGGASQEEFY KFIKPILEKM
DGTEELLVKL NREDLLRKQR TFDNGSIPHQ IHLGELHAIL
RRQEDFYPFL KDNREKIEKI LTFRIPYYVG PLARGNSRFA
WMTRKSEETI TPWNFEEVVD KGASAQSFIE RMTNFDKNLP
NEKVLPKHSL LYEYFTVYNE LTKVKYVTEG MRKPAFLSGE
QKKAIVDLLF KTNRKVTVKQ LKEDYFKKIE CFDSVEISGV
EDRFNASLGT YHDLLKIIKD KDFLDNEENE DILEDIVLTL
TLFEDREMIE ERLKTYAHLF DDKVMKQLKR RRYTGWGRLS
RKLINGIRDK QSGKTILDFL KSDGFANRNF MQLIHDDSLT
FKEDIQKAQV SGQGDSLHEH IANLAGSPAI KKGILQTVKV
VDELVKVMGR HKPENIVIEM ARENQTTQKG QKNSRERMKR
IEEGIKELGS QILKEHPVEN TQLQNEKLYL YYLQNGRDMY
VDQELDINRL SDYDVDHIVP QSFLKDDSID NKVLTRSDKN
RGKSDNVPSE EVVKKMKNYW RQLLNAKLIT QRKFDNLTKA
ERGGLSELDK AGFIKRQLVE TRQITKHVAQ ILDSRMNTKY
DENDKLIREV KVITLKSKLV SDFRKDFQFY KVREINNYHH
AHDAYLNAVV GTALIKKYPK LESEFVYGDY KVYDVRKMIA
KSEQEIGKAT AKYFFYSNIM NFFKTEITLA NGEIRKRPLI
ETNGETGEIV WDKGRDFATV RKVLSMPQVN IVKKTEVQTG
GFSKESILPK RNSDKLIARK KDWDPKKYGG FDSPTVAYSV
LVVAKVEKGK SKKLKSVKEL LGITIMERSS FEKNPIDFLE
AKGYKEVKKD LIIKLPKYSL FELENGRKRM LASAGELQKG
NELALPSKYV NFLYLASHYE KLKGSPEDNE QKQLFVEQHK
HYLDEIIEQI SEFSKRVILA DANLDKVLSA YNKHRDKPIR
EQAENIIHLF TLTNLGAPAA FKYFDTTIDR KRYTSTKEVL
DATLIHQSIT GLYETRIDLS QLGGDSRADP KKKRKV iProt106521 (SEQ ID NO: 237):
MAPKKKRKVD KKYSIGLDIG TNSVGWAVIT DEYKVPSKKF
KVLGNTDRHS IKKNLIGALL FDSGETAEAT RLKRTARRRY
TRRKNRICYL QEIFSNEMAK VDDSFFHRLE ESFLVEEDKK
HERHPIFGNI VDEVAYHEKY PTIYHLRKKL VDSTDKADLR
LIYLALAHMI KFRGHFLIEG DLNPDNSDVD KLFIQLVQTY
NQLFEENPIN ASGVDAKAIL SARLSKSRRL ENLIAQLPGE
KKNGLFGNLI ALSLGLTPNF KSNFDLAEDA KLQLSKDTYD
DDLDNLLAQI GDQYADLFLA AKNLSDAILL SDILRVNTEI
TKAPLSASMI KRYDEHHQDL TLLKALVRQQ LPEKYKEIFF -continued

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTNFDKNL PNEKVLPKHS

LLYEYFTVYN ELTKVKYVTE GMRKPAFLSG EQKKAIVDLL

FKTNRKVTVK QLKEDYFKKI ECFDSVEISG VEDRFNASLG

TYHDLLKIIK DKDFLDNEEN EDILEDIVLT LTLFEDREMI

EERLKTYAHL FDDKVMKQLK RRRYTGWGRL SRKLINGIRD

KQSGKTILDF LKSDGFANRN FMQLIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEKLY LYYLQNGRDM YVDQELDINR

LSDYDVDHIV PQSFLKDDSI DNKVLTRSDK NRGKSDNVPS

EEVVKKMKNY WRQLLNAKLI TQRKFDNLTK AERGGLSELD

KAGFIKRQLV ETRQITKHVA QILDSRMNTK YDENDKLIRE

VKVITLKSKL VSDFRKDFQF YKVREINNYH HAHDAYLNAV

VGTALIKKYP KLESEFVYGD YKVYDVRKMI AKSEQEIGKA

TAKYFFYSNI MNFFKTEITL ANGEIRKRPL IETNGETGEI

VWDKGRDFAT VRKVLSMPQV NIVKKTEVQT GGFSKESILP

KRNSDKLIAR KKDWDPKKYG GFDSPTVAYS LVVVAKEKG

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI

TGLYETRIDL SQLGGDSRAD HHHHHH iProt106522 (SEQ ID NO: 238):
MAHHHHHGG SDKKYSIGLD IGTNSVGWAV ITDEYKVPSK

KFKVLGNTDR HSIKKNLIGA LLFDSGETAE ATRLKRTARR

RYTRRKNRIC YLQEIFSNEM AKVDDSFFHR LEESFLVEED

KKHERHPIFG NIVDEVAYHE KYPTIYHLRK KLVDSTDKAD

LRLIYLALAH MIKFRGHFLI EGDLNPDNSD VDKLFIQLVQ

TYNQLFEENP INASGVDAKA ILSARLSKSR RLENLIAQLP

GEKKNGLFGN LIALSLGLTP NFKSNFDLAE DAKLQLSKDT

YDDDLDNLLA QIGDQYADLF LAAKNLSDAI LLSDILRVNT

EITKAPLSAS MIKRYDEHHQ DLTLLKALVR QQLPEKYKEI

FFDQSKNGYA GYIDGGASQE EFYKFIKPIL EKMDGTEELL

VKLNREDLLR KQRTFDNGSI PHQIHLGELH AILRRQEDFY

PFLKDNREKI EKILTFRIPY YVGPLARGNS RFAWMTRKSE

ETITPWNFEE VVDKGASAQS FIERMTNFDK NLPNEKVLPK

HSLLYEYFTV YNELTKVKYV TEGMRKPAFL SGEQKKAIVD

LLFKTNRKVT VKQLKEDYFK KIECFDSVEI SGVEDRFNAS

LGTYHDLLKI IKDKDFLDNE ENEDILEDIV LTLTLFEDRE

MIEERLKTYA HLFDDKVMKQ LKRRRYTGWG RLSRKLINGI

RDKQSGKTIL DFLKSDGFAN RNFMQLIHDD SLTFKEDIQK

AQVSGQGDSL HEHIANLAGS PAIKKGILQT VKVVDELVKV

MGRHKPENIV IEMARENQTT QKGQKNSRER MKRIEEGIKE

LGSQILKEHP VENTQLQNEK LYLYYLQNGR DMYVDQELDI

NRLSDYDVDH IVPQSFLKDD SIDNKVLTRS DKNRGKSDNV

PSEEVVKKMK NYWRQLLNAK LITQRKFDNL TKAERGGLSE

LDKAGFIKRQ LVETRQITKH VAQILDSRMN TKYDENDKLI

REVKVITLKS KLVSDFRKDF QFYKVREINN YHHAHDAYLN

AVVGTALIKK YPKLESEFVY GDYKVYDVRK MIAKSEQEIG

KATAKYFFYS NIMNFFKTEI TLANGEIRKR PLIETNGETG

EIVWDKGRDF ATVRKVLSMP QVNIVKKTEV QTGGFSKESI

LPKRNSDKLI ARKKDWDPKK YGGFDSPTVA YSVLVVAKVE

KGKSKKLKSV KELLGITIME RSSFEKNPID FLEAKGYKEV

KKDLIIKLPK YSLFELENGR KRMLASAGEL QKGNELALPS

KYVNFLYLAS HYEKLKGSPE DNEQKQLFVE QHKHYLDEII

EQISEFSKRV ILADANLDKV LSAYNKHRDK PIREQAENII

HLFTLTNLGA PAAFKYFDTT IDRKRYTSTK EVLDATLIHQ

SITGLYETRI DLSQLGGDSR ADPKKKRKV iProt106658 (SEQ ID NO: 239):
MGSSHHHHHH HHENLYFQGS MDKKYSIGLD IGTNSVGWAV

ITDEYKVPSK KFKVLGNTDR HSIKKNLIGA LLFDSGETAE

ATRLKRTARR RYTRRKNRIC YLQEIFSNEM AKVDDSFFHR

LEESFLVEED KKHERHPIFG NIVDEVAYHE KYPTIYHLRK

KLVDSTDKAD LRLIYLALAH MIKFRGHFLI EGDLNPDNSD

VDKLFIQLVQ TYNQLFEENP INASGVDAKA ILSARLSKSR

RLENLIAQLP GEKKNGLFGN LIALSLGLTP NFKSNFDLAE

DAKLQLSKDT YDDDLDNLLA QIGDQYADLF LAAKNLSDAI

LLSDILRVNT EITKAPLSAS MIKRYDEHHQ DLTLLKALVR

QQLPEKYKEI FFDQSKNGYA GYIDGGASQE EFYKFIKPIL

EKMDGTEELL VKLNREDLLR KQRTFDNGSI PHQIHLGELH

AILRRQEDFY PFLKDNREKI EKILTFRIPY YVGPLARGNS

RFAWMTRKSE ETITPWNFEE VVDKGASAQS FIERMTNFDK

NLPNEKVLPK HSLLYEYFTV YNELTKVKYV TEGMRKPAFL

SGEQKKAIVD LLFKTNRKVT VKQLKEDYFK KIECFDSVEI

SGVEDRFNAS LGTYHDLLKI IKDKDFLDNE ENEDILEDIV

LTLTLFEDRE MIEERLKTYA HLFDDKVMKQ LKRRRYTGWG

RLSRKLINGI RDKQSGKTIL DFLKSDGFAN RNFMQLIHDD

SLTFKEDIQK AQVSGQGDSL HEHIANLAGS PAIKKGILQT

```
VKVVDELVKV MGRHKPENIV IEMARENQTT QKGQKNSRER

MKRIEEGIKE LGSQILKEHP VENTQLQNEK LYLYYLQNGR

DMYVDQELDI NRLSDYDVDH IVPQSFLKDD SIDNKVLTRS

DKNRGKSDNV PSEEVVKKMK NYWRQLLNAK LITQRKFDNL

TKAERGGLSE LDKAGFIKRQ LVETRQITKH VAQILDSRMN

TKYDENDKLI REVKVITLKS KLVSDFRKDF QFYKVREINN

YHHAHDAYLN AVVGTALIKK YPKLESEFVY GDYKVYDVRK

MIAKSEQEIG KATAKYFFYS NIMNFFKTEI TLANGEIRKR

PLIETNGETG EIWVDKGRDF ATVRKVLSMP QVNIVKKTEV

QTGGFSKESI LPKRNSDKLI ARKKDWDPKK YGGFDSPTVA

YSVLVVAKVE KGKSKKLKSV KELLGITIME RSSFEKNPID

FLEAKGYKEV KKDLIIKLPK YSLFELENGR KRMLASAGEL

QKGNELALPS KYVNFLYLAS HYEKLKGSPE DNEQKQLFVE

QHKHYLDEII EQISEFSKRV ILADANLDKV LSAYNKHRDK

PIREQAENII HLFTLTNLGA PAAFKYFDTT IDRKRYTSTK

EVLDATLIHQ SITGLYETRI DLSQLGGDGG GSPKKKRKV iProt106745 (SEQ ID NO: 240):
MAPKKKRKVD KKYSIGLDIG TNSVGWAVIT DEYKVPSKKF

KVLGNTDRHS IKKNLIGALL FDSGETAEAT RLKRTARRRY

TRRKNRICYL QEIFSNEMAK VDDSFFHRLE ESFLVEEDKK

HERHPIFGNI VDEVAYHEKY PTIYHLRKKL VDSTDKADLR

LIYLALAHMI KFRGHFLIEG DLNPDNSDVD KLFIQLVQTY

NQLFEENPIN ASGVDAKAIL SARLSKSRRL ENLIAQLPGE

KKNGLFGNLI ALSLGLTPNF KSNFDLAEDA KLQLSKDTYD

DDLDNLLAQI GDQYADLFLA AKNLSDAILL SDILRVNTEI

TKAPLSASMI KRYDEHHQDL TLLKALVRQQ LPEKYKEIFF

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTNFDKNL PNEKVLPKHS

LLYEYFTVYN ELTKVKYVTE GMRKPAFLSG EQKKAIVDLL

FKTNRKVTVK QLKEDYFKKI ECFDSVEISG VEDRFNASLG

TYHDLLKIIK DKDFLDNEEN EDILEDIVLT LTLFEDREMI

EERLKTYAHL FDDKVMKQLK RRRYTGWGRL SRKLINGIRD

KQSGKTILDF LKSDGFANRN FMQLIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEALY LYYLQNGRDM YVDQELDINR

LSDYDVDHIV PQSFLKDDSI DNAVLTRSDK NRGKSDNVPS

EEVVKKMKNY WRQLLNAKLI TQRKFDNLTK AERGGLSELD

KAGFIKRQLV ETRQITKHVA QILDSRMNTK YDENDKLIRE

VKVITLKSKL VSDFRKDFQF YKVREINNYH HAHDAYLNAV

VGTALIKKYP KLESEFVYGD YKVYDVRKMI AKSEQEIGKA

TAKYFFYSNI MNFFKTEITL ANGEIRKRPL IETNGETGEI

VWDKGRDFAT VRKVLSMPQV NIVKKTEVQT GGFSKESILP

KRNSDKLIAR KKDWDPKKYG GFDSPTVAYS VLVVAKVEKG

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI

TGLYETRIDL SQLGGDSRAD PKKKRKVHHH HHH iProt106746 (SEQ ID NO: 241):
MAPKKKRKVD KKYSIGLDIG TNSVGWAVIT DEYKVPSKKF

KVLGNTDRHS IKKNLIGALL FDSGETAEAT RLKRTARRRY

TRRKNRICYL QEIFSNEMAK VDDSFFHRLE ESFLVEEDKK

HERHPIFGNI VDEVAYHEKY PTIYHLRKKL VDSTDKADLR

LIYLALAHMI KFRGHFLIEG DLNPDNSDVD KLFIQLVQTY

NQLFEENPIN ASGVDAKAIL SARLSKSRRL ENLIAQLPGE

KKNGLFGNLI ALSLGLTPNF KSNFDLAEDA KLQLSKDTYD

DDLDNLLAQI GDQYADLFLA AKNLSDAILL SDILRVNTEI

TKAPLSASMI KRYDEHHQDL TLLKALVRQQ LPEKYKEIFF

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTNFDKNL PNEKVLPKHS

LLYEYFTVYN ELTKVKYVTE GMRKPAFLSG EQKKAIVDLL

FKTNRKVTVK QLKEDYFKKI ECFDSVEISG VEDRFNASLG

TYHDLLKIIK DKDFLDNEEN EDILEDIVLT LTLFEDREMI

EERLKTYAHL FDDKVMKQLK RRRYTGWGRL SRKLINGIRD

KQSGKTILDF LKSDGFANRN FMQLIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEALY LYYLQNGRDM YVDQELDINR

LSDYDVDHIV PQSFLKDDSI DNKVLTRSDK NRGKSDNVPS

EEVVKKMKNY WRQLLNAKLI TQRKFDNLTK AERGGLSELD

KAGFIKRQLV ETRQITKHVA QILDSRMNTK YDENDKLIRE

VKVITLKSKL VSDFRKDFQF YKVREINNYH HAHDAYLNAV

VGTALIKKYP ALESEFVYGD YKVYDVRKMI AKSEQEIGKA

TAKYFFYSNI MNFFKTEITL ANGEIRKAPL IETNGETGEI

VWDKGRDFAT VRKVLSMPQV NIVKKTEVQT GGFSKESILP

KRNSDKLIAR KKDWDPKKYG GFDSPTVAYS VLVVAKVEKG
```

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI

TGLYETRIDL SQLGGDSRAD PKKKRKVHHH HHH iProt106747 (SEQ ID NO: 242):
MAPKKKRKVD KKYSIGLDIG TNSVGWAVIT DEYKVPSKKF

KVLGNTDRHS IKKNLIGALL FDSGETAEAT RLKRTARRRY

TRRKNRICYL QEIFSNEMAK VDDSFFHRLE ESFLVEEDKK

HERHPIFGNI VDEVAYHEKY PTIYHLRKKL VDSTDKADLR

LIYLALAHMI KFRGHFLIEG DLNPDNSDVD KLFIQLVQTY

NQLFEENPIN ASGVDAKAIL SARLSKSRRL ENLIAQLPGE

KKNGLFGNLI ALSLGLTPNF KSNFDLAEDA KLQLSKDTYD

DDLDNLLAQI GDQYADLFLA AKNLSDAILL SDILRVNTEI

TKAPLSASMI KRYDEHHQDL TLLKALVRQQ LPEKYKEIFF

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTNFDKNL PNEKVLPKHS

LLYEYFTVYN ELTKVKYVTE GMRKPAFLSG EQKKAIVDLL

FKTNRKVTVK QLKEDYFKKI ECFDSVEISG VEDRFNASLG

TYHDLLKIIK DKDFLDNEEN EDILEDIVLT LTLFEDREMI

EERLKTYAHL FDDKVMKQLK RRRYTGWGRL SRKLINGIRD

KQSGKTILDF LKSDGFANRN FMQLIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEKLY LYYLQNGRDM YVDQELDINR

LSDYDVDHIV PQSFLADDSI DNKVLTRSDK NRGKSDNVPS

EEVVKKMKNY WRQLLNAKLI TQRKFDNLTK AERGGLSELD

KAGFIKRQLV ETRQITKHVA QILDSRMNTK YDENDKLIRE

VKVITLKSKL VSDFRKDFQF YKVREINNYH HAHDAYLNAV

VGTALIKKYP ALESEFVYGD YKVYDVRKMI AKSEQEIGKA

TAKYFFYSNI MNFFKTEITL ANGEIRKAPL IETNGETGEI

VWDKGRDFAT VRKVLSMPQV NIVKKTEVQT GGFSKESILP

KRNSDKLIAR KKDWDPKKYG GFDSPTVAYS VLVVAKVEKG

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI

TGLYETRIDL SQLGGDSRAD PKKKRKVHHH HHH iProt106884 (SEQ ID NO: 243):
MAPKKKRKVD KKYSIGLDIG TNSVGWAVIT DEYKVPSKKF

KVLGNTDRHS IKKNLIGALL FDSGETAEAT RLKRTARRRY

TRRKNRICYL QEIFSNEMAK VDDSFFHRLE ESFLVEEDKK

HERHPIFGNI VDEVAYHEKY PTIYHLRKKL VDSTDKADLR

LIYLALAHMI KFRGHFLIEG DLNPDNSDVD KLFIQLVQTY

NQLFEENPIN ASGVDAKAIL SARLSKSRRL ENLIAQLPGE

KKNGLFGNLI ALSLGLTPNF KSNFDLAEDA KLQLSKDTYD

DDLDNLLAQI GDQYADLFLA AKNLSDAILL SDILRVNTEI

TKAPLSASMI KRYDEHHQDL TLLKALVRQQ LPEKYKEIFF

DQSKNGYAGY IDGGASQEEF YKFIKPILEK MDGTEELLVK

LNREDLLRKQ RTFDNGSIPH QIHLGELHAI LRRQEDFYPF

LKDNREKIEK ILTFRIPYYV GPLARGNSRF AWMTRKSEET

ITPWNFEEVV DKGASAQSFI ERMTAFDKNL PNEKVLPKHS

LLYEYFTVYN ELTKVKYVTE GMRKPAFLSG EQKKAIVDLL

FKTNRKVTVK QLKEDYFKKI ECFDSVEISG VEDRFNASLG

TYHDLLKIIK DKDFLDNEEN EDILEDIVLT LTLFEDREMI

EERLKTYAHL FDDKVMKQLK RRRYTGWGAL SRKLINGIRD

KQSGKTILDF LKSDGFANRN FMALIHDDSL TFKEDIQKAQ

VSGQGDSLHE HIANLAGSPA IKKGILQTVK VVDELVKVMG

RHKPENIVIE MARENQTTQK GQKNSRERMK RIEEGIKELG

SQILKEHPVE NTQLQNEKLY LYYLQNGRDM YVDQELDINR

LSDYDVDHIV PQSFLKDDSI DNKVLTRSDK NRGKSDNVPS

EEVVKKMKNY WRQLLNAKLI TQRKFDNLTK AERGGLSELD

KAGFIKRQLV ETRAITKHVA QILDSRMNTK YDENDKLIRE

VKVITLKSKL VSDFRKDFQF YKVREINNYH HAHDAYLNAV

VGTALIKKYP KLESEFVYGD YKVYDVRKMI AKSEQEIGKA

TAKYFFYSNI MNFFKTEITL ANGEIRKRPL IETNGETGEI

VWDKGRDFAT VRKVLSMPQV NIVKKTEVQT GGFSKESILP

KRNSDKLIAR KKDWDPKKYG GFDSPTVAYS VLVVAKVEKG

KSKKLKSVKE LLGITIMERS SFEKNPIDFL EAKGYKEVKK

DLIIKLPKYS LFELENGRKR MLASAGELQK GNELALPSKY

VNFLYLASHY EKLKGSPEDN EQKQLFVEQH KHYLDEIIEQ

ISEFSKRVIL ADANLDKVLS AYNKHRDKPI REQAENIIHL

FTLTNLGAPA AFKYFDTTID RKRYTSTKEV LDATLIHQSI

TGLYETRIDL SQLGGDSRAD PKKKRKVHHH HHH iProt 20109496
(SEQ ID NO: 244)
MAPKKKRKVDKKYSIGLDIGTNSVGWAVITDEYKVPSKKFKVLGNTDRHS

IKKNLIGALLFDSGETAEATRLKRTARRRYTRRKNRILYLQEIFSNEMAK

VDDSFFHRLEESFLVEEDKKHERHPIFGNIVDEVAYHEKYPTIYHLRKKL

-continued

VDSTDKADLRLIYLALAHMIKFRGHFLIEGDLNPDNSDVDKLFIQLVQTY

NQLFEENPINASGVDAKAILSARLSKSRRLENLIAQLPGEKKNGLFGNLI

ALSLGLTPNFKSNFDLAEDAKLQLSKDTYDDDLDNLLAQIGDQYADLFLL

AAKNLSDAILLSDILRVNTEITKAPLSASMIKRYDEHHQDLTLLKALVRQ

QLPEKYKEIFFDQSKNGYAGYIDGGASQEEFYKFIKPILEKMDGTEELLV

KLNREDLLRKQRTFDNGSIPHQIHLGELHAILRRQEDFYPFLKDNREKIE

KILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFLS

GEQKKAIVDLLFKTNRKVTVKQLKEDYFKKIEEFDSVEISGVEDRFNASL

GTYHDLLKIIKDKDFLDNEENEDILEDIVLTLTLFEDREMIEERLKTYAH

LFDDKVMKQLKRRRYTGWGRLSRKLINGIRDKQSGKTILDFLKSDGFANR

NFMQLIHDDSLTFKEDIQKAQVSGQGDSLHEHIANLAGSPAIKKGILQTV

KVVDELVKVMGRHKPENIVIEMARENQTTQKGQKNSRERMKRIEEGIKEL

GSQILKEHPVENTQLQNEKLYLYYLQNGRDMYVDQELDINRLSDYDVDHI

VPQSFLKDDSIDNKVLTRSDKNRGKSDNVPSEEVVKKMKNYWRQLLNAKL

ITQRKFDNLTKAERGGLSELDKAGFIKRQLVETRQITKHVAQILDSRMNT

KYDENDKLIREVKVITLKSKLVSDFRKDFQFYKVREINNYHHAHDAYLNA

VVGTALIKKYPKLESEFVYGDYKVYDVRKMIAKSEQEIGKATAKYFFYSN

IMNFFKTEITLANGEIRKRPLIETNGETGEIVWDKGRDFATVRKVLSMPQ

VNIVKKTEVQTGGFSKESILPKRNSDKLIARKKDWDPKKYGGFDSPTVAY

-continued

SVLVVAKVEKGSKKLKSVKELLGITIMERSSFEKNPIDFLEAKGYKEVKK

DLIIKLPKYSLFELENGRKRMLASAGELQKGNELALPSKYVNFLYLASHY

EKLKGSPEDNEQKQLFVEQHKHYLDEIIEQISEFSKRVILADANLDKVLS

AYNKHRDKPIREQAENIIHLFTLTNLGAPAAFKYFDTTIDRKRYTSTKEV

LDATLIHQSITGLYETRIDLSQLGGDSRADHHHHHH

Nucleic Acids Encoding Cas9 Molecules

Nucleic acids encoding the Cas9 molecules, e.g., an active Cas9 molecule or an inactive Cas9 molecule are provided herein.

Exemplary nucleic acids encoding Cas9 molecules are described in Cong et al, SCIENCE 2013, 399(6121):819-823; Wang et al, CELL 2013, 153(4):910-918; Mali et al., SCIENCE 2013, 399(6121):823-826; Jinek et al, SCIENCE 2012, 337(6096):816-821.

In an embodiment, a nucleic acid encoding a Cas9 molecule can be a synthetic nucleic acid sequence. For example, the synthetic nucleic acid molecule can be chemically modified, e.g., as described in Section XIII. In an embodiment, the Cas9 mRNA has one or more of, e.g., all of the following properties: it is capped, polyadenylated, substituted with 5-methylcytidine and/or pseudouridine.

In addition or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

Provided below is an exemplary codon optimized nucleic acid sequence encoding a Cas9 molecule of S. pyogenes.

(SEQ ID NO: 222)

```
atggataaaa agtacagcat cgggctggac atcggtacaa actcagtggg gtgggccgtg    60
attacggacg agtacaaggt accctccaaa aaatttaaag tgctgggtaa cacggacaga   120
cactctataa agaaaaatct tattggagcc ttgctgttcg actcaggcga gacagccgaa   180
gccacaaggt tgaagcggac cgccaggagg cggtatacca ggagaaagaa ccgcatatgc   240
tacctgcaag aaatcttcag taacgagatg gcaaaggttg acgatagctt tttccatcgc   300
ctggaagaat cctttcttgt tgaggaagac aagaagcacg aacggcaccc catctttggc   360
aatattgtcg acgaagtggc atatcacgaa aagtacccga ctatctacca cctcaggaag   420
aagctggtgg actctaccga taaggcggac ctcagactta tttatttggc actcgcccac   480
atgattaaat ttagaggaca tttcttgatc gagggcgacc tgaacccgga caacagtgac   540
gtcgataagc tgttcatcca acttgtgcag acctacaatc aactgttcga agaaaaccct   600
ataaatgctt caggagtcga cgctaaagca atcctgtccg cgcgcctctc aaaatctaga   660
agacttgaga atctgattgc tcagttgccc ggggaaaaga aaaatggatt gtttggcaac   720
ctgatcgccc tcagtctcgg actgacccca aatttcaaaa gtaacttcga cctggccgaa   780
gacgctaagc tccagctgtc caaggacaca tacgatgacg acctcgacaa tctgctggcc   840
cagattgggg atcagtacgc cgatctcttt ttggcagcaa agaacctgtc cgacgccatc   900
ctgttgagcg atatcttgag agtgaacacc gaaattacta agcacccct agcgcatct    960
atgatcaagc ggtacgacga gcatcatcag gatctgaccc tgctgaaggc tcttgtgagg  1020
caacagctcc ccgaaaaata caaggaaatc ttctttgacc agagcaaaaa cggctacgct  1080
```

-continued

| | | | | |
|---|---|---|---|---|
| ggctatatag | atggtggggc | cagtcaggag | gaattctata | aattcatcaa gcccattctc | 1140 |
| gagaaaatgg | acggcacaga | ggagttgctg | gtcaaactta | acagggagga cctgctgcgg | 1200 |
| aagcagcgga | cctttgacaa | cgggtctatc | ccccaccaga | ttcatctggg cgaactgcac | 1260 |
| gcaatcctga | ggaggcagga | ggattttttat | ccttttctta | aagataaccg cgagaaaata | 1320 |
| gaaaagattc | ttacattcag | gatcccgtac | tacgtgggac | ctctcgcccg gggcaattca | 1380 |
| cggtttgcct | ggatgacaag | gaagtcagag | gagactatta | cccttggaa cttcgaagaa | 1440 |
| gtggtggaca | agggtgcatc | tgcccagtct | ttcatcgagc | ggatgacaaa ttttgacaag | 1500 |
| aacctcccta | atgagaaggt | gctgcccaaa | cattctctgc | tctacgagta ctttaccgtc | 1560 |
| tacaatgaac | tgactaaagt | caagtacgtc | accgaggaa | tgaggaagcc ggcattcctt | 1620 |
| agtggagaac | agaagaaggc | gattgtagac | ctgttgttca | agaccaacag gaaggtgact | 1680 |
| gtgaagcaac | ttaagaaga | ctactttaag | aagatcgaat | gttttgacag tgtggaaatt | 1740 |
| tcaggggttg | aagaccgctt | caatgcgtca | ttggggactt | accatgatct tctcaagatc | 1800 |
| ataaaggaca | agacttcct | ggacaacgaa | gaaaatgagg | atattctcga agacatcgtc | 1860 |
| ctcaccctga | ccctgttcga | agacagggaa | atgatagaag | agcgcttgaa aacctatgcc | 1920 |
| cacctcttcg | acgataaagt | tatgaagcag | ctgaagcgca | ggagatacac aggatgggga | 1980 |
| agattgtcaa | ggaagctgat | caatggaatt | agggataaac | agagtggcaa gaccatactg | 2040 |
| gatttcctca | atctgatgg | cttcgccaat | aggaacttca | tgcaactgat tcacgatgac | 2100 |
| tctcttacct | tcaaggagga | cattcaaaag | gctcaggtga | gcgggcaggg agactccctt | 2160 |
| catgaacaca | tcgcgaattt | ggcaggttcc | cccgctatta | aaaagggcat ccttcaaact | 2220 |
| gtcaaggtgg | tggatgaatt | ggtcaaggta | atgggcagac | ataagccaga aaatattgtg | 2280 |
| atcgagatgc | cccgcgaaaa | ccagaccaca | cagaagggcc | agaaaatag tagagagcgg | 2340 |
| atgaagagga | tcgaggaggg | catcaaagag | ctgggatctc | agattctcaa gaacaccccc | 2400 |
| gtagaaaaca | cacagctgca | gaacgaaaaa | ttgtacttgt | actatctgca gaacggcaga | 2460 |
| gacatgtacg | tcgaccaaga | acttgatatt | aatagactgt | ccgactatga cgtagaccat | 2520 |
| atcgtgcccc | agtccttcct | gaaggacgac | tccattgata | acaaagtctt gacaagaagc | 2580 |
| gacaagaaca | ggggtaaaag | tgataatgtg | cctagcgagg | aggtggtgaa aaaaatgaag | 2640 |
| aactactggc | gacagctgct | taatgcaaag | ctcattacac | aacggaagtt cgataatctg | 2700 |
| acgaaagcag | agagaggtgg | cttgtctgag | ttggacaagg | cagggtttat taagcggcag | 2760 |
| ctggtggaaa | ctaggcagat | cacaaagcac | gtggcgcaga | ttttggacag ccggatgaac | 2820 |
| acaaaatacg | acgaaaatga | taaactgata | cgagaggtca | agttatcac gctgaaaagc | 2880 |
| aagctggtgt | ccgattttcg | gaaagacttc | cagttctaca | agttcgcga gattaataac | 2940 |
| taccatcatg | ctcacgatgc | gtacctgaac | gctgttgtcg | ggaccgcctt gataaagaag | 3000 |
| tacccaaagc | tggaatccga | gttcgtatac | ggggattaca | aagtgtacga tgtgaggaaa | 3060 |
| atgatagcca | agtccgagca | ggagattgga | aaggccacag | ctaagtactt cttttattct | 3120 |
| aacatcatga | atttttttaa | gacgaaatt | accctggcca | acggagagat cagaaagcgg | 3180 |
| cccttatag | agacaaatgg | tgaaacaggt | gaaatcgtct | gggataaggg cagggatttc | 3240 |
| gctactgtga | ggaaggtgct | gagtatgcca | caggtaaata | tcgtgaaaaa aaccgaagta | 3300 |
| cagaccggag | gattttccaa | ggaaagcatt | ttgcctaaaa | gaaactcaga caagctcatc | 3360 |
| gccccgcaaga | aagattggga | ccctaagaaa | tacgggggat | ttgactcacc caccgtagcc | 3420 |
| tattctgtgc | tggtggtagc | taaggtgaa | aaaggaaagt | ctaagaagct gaagtccgtg | 3480 |
| aaggaactct | tgggaatcac | tatcatggaa | agatcatcct | ttgaaaagaa ccctatcgat | 3540 |

```
ttcctggagg ctaagggtta caaggaggtc aagaaagacc tcatcattaa actgccaaaa   3600
tactctctct tcgagctgga aaatggcagg aagagaatgt tggccagcgc cggagagctg   3660
caaaagggaa acgagcttgc tctgccctcc aaatatgtta attttctcta tctcgcttcc   3720
cactatgaaa agctgaaagg gtctcccgaa gataacgagc agaagcagct gttcgtcgaa   3780
cagcacaagc actatctgga tgaaataatc gaacaaataa gcgagttcag caaaagggtt   3840
atcctggcgg atgctaattt ggacaaagta ctgtctgctt ataacaagca ccgggataag   3900
cctattaggg aacaagccga gaatataatt caccctcttta cactcacgaa tctcggagcc   3960
cccgccgcct tcaaatactt tgatacgact atcgaccgga aacggtatac cagtaccaaa   4020
gaggtcctcg atgccaccct catccaccag tcaattactg gcctgtacga aacacggatc   4080
gacctctctc aactgggcgg cgactag                                      4107
```

Provided below is an exemplary codon optimized nucleic acid sequence encoding a Cas9 molecule including SEQ ID NO: 244:

(SEQ ID NO: 223)
ATGGCTCCGAAGAAAAAGCGTAAAGTGGATAAAAAATACAGCATTGGTCT
GGACATTGGCACGAACTCAGTGGGTTGGGCGGTCATCACGGATGAATATA
AGGTCCCGTCAAAAAAGTTCAAAGTGCTGGGCAACACCGATCGCCATTCG
ATTAAAAAGAATCTGATCGGCGCGCTGCTGTTTGATAGCGGTGAAACCGC
GGAAGCAACGCGTCTGAAACGTACCGCACGTCGCCGTTACACGCGCCGTA
AAAATCGTATTCTGTATCTGCAGGAAATCTTTAGCAACGAAATGGCGAAA
GTTGATGACTCATTTTTCCACCGCCTGGAAGAATCGTTTCTGGTCGAAGA
AGACAAAAAGCATGAACGTCACCCGATTTTCGGTAATATCGTTGATGAAG
TCGCGTACCATGAAAAATATCCGACGATTTACCATCTGCGTAAAAAACTG
GTGGATTCAACCGACAAAGCCGATCTGCGCCTGATTTACCTGGCACTGGC
TCATATGATCAAATTTCGTGGCCACTTCCTGATTGAAGGTGACCTGAACC
CGGATAACTCTGACGTTGATAAGCTGTTCATCCAGCTGGTCCAAACCTAT
AATCAGCTGTTCGAAGAAAACCCGATCAATGCAAGTGGCGTTGATGCGAA
GGCCATTCTGTCCGCTCGCCTGAGTAAATCCCGCCGTCTGGAAAACCTGA
TTGCACAACTGCCGGGCGAAAAGAAAAACGGCCTGTTTGGTAATCTGATC
GCTCTGTCACTGGGTCTGACGCCGAACTTTAAATCGAATTTCGACCTGGC
AGAAGATGCTAAGCTGCAGCTGAGCAAAGATACCTACGATGACGATCTGG
ACAACCTGCTGGCGCAAATTGGTGACCAGTATGCCGACCTGTTTCTGGCG
GCCAAAAATCTGTCAGATGCCATTCTGCTGTCGGACATCCTGCGCGTGAA
CACCGAAATCACGAAAGCGCCGCTGTCAGCCTCGATGATTAAACGCTACG
ATGAACATCACCAGGACCTGACCCTGCTGAAAGCACTGGTTCGTCAGCAA
CTGCCGGAAAAGTACAAGGAAATTTTCTTTGACCAATCTAAGAACGGCTA
TGCAGGTTACATCGATGGCGGTGCTAGTCAGGAAGAATTCTACAAGTTCA
TCAAGCCGATCCTGGAAAAAATGGATGGCACGGAAGAACTGCTGGTGAAA
CTGAATCGTGAAGATCTGCTGCGTAAACAACGCACCTTTGACAACGGCAG
CATTCCGCATCAGATCCACCTGGGTGAACTGCATGCGATTCTGCGCCGTC

-continued

AGGAAGATTTTTATCCGTTCCTGAAAGACAACCGTGAAAAAATTGAAAAG
ATCCTGACGTTTCGCATCCCGTATTACGTTGGCCCGCTGGCGCGTGGTAA
TAGCCGCTTCGCCTGGATGACCCGCAAATCTGAAGAAACCATTACGCCGT
GGAACTTTGAAGAAGTGGTTGATAAAGGTGCAAGCGCTCAGTCTTTTATC
GAACGTATGACCAATTTCGATAAAAACCTGCCGAATGAAAAGGTCCTGCC
GAAACATAGCCTGCTGTATGAATACTTTACCGTGTACAACGAACTGACGA
AAGTGAAGTATGTTACCGAAGGCATGCGCAAACCGGCGTTTCTGTCTGGT
GAACAGAAAAAAGCCATTGTGGATCTGCTGTTCAAGACCAATCGTAAAGT
TACGGTCAAACAGCTGAAGGAAGATTACTTCAAAAAGATCGAAGAATTCG
ACAGCGTGGAAATTTCTGGCGTTGAAGATCGTTTCAACGCCAGTCTGGGT
ACCTATCATGACCTGCTGAAGATCATCAAGGACAAGGATTTTCTGGATAA
CGAAGAAAATGAAGACATTCTGGAAGATATCGTGCTGACCCTGACGCTGT
TCGAAGATCGTGAAATGATTGAAGAACGCCTGAAAACGTACGCACACCTG
TTTGACGATAAAGTTATGAAGCAGCTGAAACGCCGTCGCTATACCGGCTG
GGGTCGTCTGTCTCGCAAACTGATTAATGGCATCCGCGATAAGCAAAGTG
GTAAAACGATTCTGGATTTCCTGAAATCCGACGGCTTTGCCAACCGTAAT
TTCATGCAGCTGATCCATGACGATAGTCTGACCTTTAAGGAAGACATTCA
GAAAGCACAAGTGTCAGGCCAGGGTGATTCGCTGCATGAACACATTGCGA
ACCTGGCCGGCTCCCCGGCTATTAAAAAGGGTATCCTGCAGACCGTCAAA
GTCGTGGATGAACTGGTGAAGGTTATGGGCCGTCACAAACCGGAAAACAT
TGTGATCGAAATGGCGCGCGAAAATCAGACCACGCAAAAGGGTCAGAAAA
ACTCACGTGAACGCATGAAGCGCATTGAAGAAGGCATCAAAGAACTGGGT
TCGCAGATTCTGAAAGAACATCCGGTTGAAAACACCCAGCTGCAAAATGA
AAAACTGTACCTGTATTACCTGCAAAATGGCCGTGACATGTATGTCGATC
AGGAACTGGACATCAACCGCCTGAGCGACTATGATGTCGACCACATTGTG
CCGCAGAGCTTTCTGAAGGACGATTCTATCGATAATAAAGTGCTGACCCG
TTCTGATAAGAACCGCGGTAAAAGCGACAATGTTCCGTCTGAAGAAGTTG
TCAAAAAGATGAAGAACTACTGGCGTCAACTGCTGAATGCGAAGCTGATT
ACGCAGCGTAAATTCGATAACCTGACCAAGGCGGAACGCGGCGGTCTGAG

```
TGAACTGGATAAGGCCGGCTTTATCAAACGTCAACTGGTGGAAACCCGCC

AGATTACGAAACATGTTGCCCAGATCCTGGATTCCCGCATGAACACGAAA

TATGACGAAATGATAAGCTGATTCGTGAAGTCAAAGTGATCACCCTGAA

GAGTAAGCTGGTGTCCGATTTCCGTAAGGACTTTCAGTTCTACAAAGTTC

GCGAAATTAACAATTACCATCACGCACACGATGCTTATCTGAATGCAGTG

GTTGGCACCGCTCTGATCAAAAAGTATCCGAAACTGGAAAGCGAATTTGT

GTATGGTGATTACAAAGTCTATGACGTGCGCAAGATGATTGCGAAAAGTG

AACAGGAAATCGGCAAGGCGACCGCCAAGTACTTTTTCTATTCCAACATC

ATGAACTTTTTCAAGACCGAAATCACGCTGGCAAATGGCGAAATTCGTAA

ACGCCCGCTGATCGAAACCAACGGCGAAACGGGTGAAATTGTGTGGGATA

AAGGTCGTGACTTCGCGACCGTTCGCAAAGTCCTGTCAATGCCGCAAGTG

AATATCGTTAAAAAGACCGAAGTTCAGACGGGCGGTTTTAGTAAAGAATC

CATCCTGCCGAAGCGTAACTCGGATAAACTGATTGCGCGCAAAAAGGATT

GGGACCCGAAAAAGTACGGCGGTTTTGATAGTCCGACCGTTGCATATTCC

GTCCTGGTCGTGGCTAAAGTTGAAAAAGGCAAGAGTAAAAAGCTGAAGTC

CGTCAAAGAACTGCTGGGTATTACCATCATGGAACGTAGCTCTTTTGAAA

AGAACCCGATTGACTTCCTGGAAGCCAAGGGCTACAAAGAAGTGAAAAAG

GATCTGATTATCAAGCTGCCGAAATATTCGCTGTTCGAACTGGAAAACGG

TCGTAAACGCATGCTGGCAAGCGCTGGCGAACTGCAGAAGGGTAATGAAC

TGGCACTGCCGTCTAAATATGTGAACTTTCTGTACCTGGCTAGCCATTAT

GAAAAACTGAAGGGTTCTCCGGAAGATAACGAACAGAAGCAACTGTTCGT

TGAACAACATAAACACTACCTGGATGAAATCATCGAACAGATCTCAGAAT

TCTCGAAACGCGTCATTCTGGCGGATGCCAATCTGGACAAAGTGCTGAGC

GCGTATAACAAGCATCGTGATAAACCGATTCGCGAACAGGCCGAAAATAT

TATCCACCTGTTTACCCTGACGAACCTGGGCGCACCGGCAGCTTTTAAAT

ACTTCGATACCACGATCGACCGTAAGCGCTATACCAGCACGAAAGAAGTT

CTGGATGCTACCCTGATTCATCAGTCAATCACCGGTCTGTATGAAACGCG

TATTGACCTGAGCCAACTGGGCGGTGATAGCCGTGCCGACCATCACCATC

ACCATCACTAATAG
```

If the above Cas9 sequences are fused with a peptide or polypeptide at the C-terminus (e.g., an inactive Cas9 fused with a transcription repressor at the C-terminus), it is understood that the stop codon will be removed.

Also provided herein are nucleic acids, vectors and cells for production of a Cas9 molecule, for example a Cas9 molecule described herein. The recombinant production of polypeptide molecules can be accomplished using techniques known to a skilled artisan. Described herein are molecules and methods for the recombinant production of polypeptide molecules, such as Cas9 molecules, e.g., as described herein. As used in connection herewith, "recombinant" molecules and production includes all polypeptides (e.g., Cas9 molecules, for example as described herein) that are prepared, expressed, created or isolated by recombinant means, such as polypeptides isolated from an animal (e.g., a mouse) that is transgenic or transchromosomal for nucleic acid encoding the molecule of interest, a hybridoma prepared therefrom, molecules isolated from a host cell transformed to express the molecule, e.g., from a transfectoma, molecules isolated from a recombinant, combinatorial library, and molecules prepared, expressed, created or isolated by any other means that involve splicing of all or a portion of a gene encoding the molecule (or portion thereof) to other DNA sequences. Recombinant production may be from a host cell, for example, a host cell comprising nucleic acid encoding a molecule described herein, e.g., a Cas9 molecule, e.g., a Cas9 molecule described herein.

Provided herein are nucleic acid molecules encoding a molecule (e.g., Cas9 molecule and/or gRNA molecule), e.g., as described herein. Specifically provided are nucleic acid molecules comprising sequence encoding any one of SEQ ID NO: 233 to SEQ ID NO: 244, or encoding a fragment of any of SEQ ID NO: 233 to SEQ ID NO: 244, or encoding a polypeptide comprising at least 90%, at least 91%, at least 92%, at least 93%, at least 94%, at least 95%, at least 96%, at least 97%, at least 98%, or at least 99% sequence homology to any of SEQ ID NO: 233 to SEQ ID NO: 244.

Provided herein are vectors, e.g., as described herein, comprising any of the above-described nucleic acid molecules. In embodiments, said nucleic acid molecules are operably linked to a promoter, for example a promoter operable in the host cell into which the vector is introduced.

Provided herein are host cells comprising one or more nucleic acid molecules and/or vectors described herein. In embodiments, the host cell is a prokaryotic host cell. In embodiments, the host cell is a eukaryotic host cell. In embodiments, the host cell is a yeast or E. coli cell. In embodiments, the host cell is a mammalian cell, e.g., a human cell. Such host cells may be used for the production of a recombinant molecule described herein, e.g., a Cas9 or gRNA molecule, e.g., as described herein.

VI. Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule are described, e.g., in Jinek el al., SCIENCE 2012; 337(6096):816-821.

VII. Template Nucleic Acids (for Introduction of Nucleic Acids)

The term "template nucleic acid" or "donor template" as used herein refers to a nucleic acid to be inserted at or near a target sequence that has been modified, e.g., cleaved, by a CRISPR system of the present invention. In an embodiment, nucleic acid sequence at or near the target sequence is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In embodiments, the template nucleic acid comprises sequence encoding a globin protein, e.g., a beta globin, e.g., comprises a beta globin gene. In an embodiment, the beta globin encoded by the nucleic acid comprises one or more mutations, e.g., anti-sickling mutations. In an embodiment, the beta globin encoded by the nucleic acid comprises the mutation T87Q. In an embodiment, the beta globin encoded by the nucleic acid comprises the mutation G16D. In an embodiment, the beta globin encoded by the nucleic acid comprises the mutation E22A. In an embodiment, the beta globin gene comprises the mutations G16D, E22A and T87Q. In embodiments, the template nucleic acid further comprises one or more regulatory elements, e.g., a promoter (e.g., a human beta globin promoter), a 3' enhancer, and/or at least a portion of a globin locus control region (e.g., one or more DNAseI hypersensitivity sites (e.g., HS2, HS3 and/or HS4 of the human globin locus)).

In other embodiments, the template nucleic acid comprises sequence encoding a gamma globin, e.g., comprises a gamma globin gene. In embodiments, the template nucleic acid comprises sequence encoding more than one copy of a gamma globin protein, e.g., comprises two or more, e.g., two, gamma globin gene sequences. In embodiments, the template nucleic acid further comprises one or more regulatory elements, e.g., a promotor and/or enhancer.

In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring base into the target nucleic acid.

Mutations in a gene or pathway described herein may be corrected using one of the approaches discussed herein. In an embodiment, a mutation in a gene or pathway described herein is corrected by homology directed repair (HDR) using a template nucleic acid. In an embodiment, a mutation in a gene or pathway described herein is corrected by homologous recombination (HR) using a template nucleic acid. In an embodiment, a mutation in a gene or pathway described herein is corrected by Non-Homologous End Joining (NHEJ) repair using a template nucleic acid. In other embodiments, nucleic acid encoding molecules of interest may be inserted at or near a site modified by a CRISPR system of the present invention. In embodiments, the template nucleic acid comprises regulatory elements, e.g., one or more promoters and/or enhancers, operably linked to the nucleic acid sequence encoding a molecule of interest, e.g., as described herein.

HDR or HR Repair and Template Nucleic Acids

As described herein, nuclease-induced homology directed repair (HDR) or homologous recombination (HR) can be used to alter a target sequence and correct (e.g., repair or edit) a mutation in the genome. While not wishing to be bound by theory, it is believed that alteration of the target sequence occurs by repair based on a donor template or template nucleic acid. For example, the donor template or the template nucleic acid provides for alteration of the target sequence. It is contemplated that a plasmid donor or linear double stranded template can be used as a template for homologous recombination. It is further contemplated that a single stranded donor template can be used as a template for alteration of the target sequence by alternate methods of homology directed repair (e.g., single strand annealing) between the target sequence and the donor template. Donor template-effected alteration of a target sequence may depend on cleavage by a Cas9 molecule. Cleavage by Cas9 can comprise a double strand break, one single strand break, or two single strand breaks.

In an embodiment, a mutation can be corrected by either a single double-strand break or two single strand breaks. In an embodiment, a mutation can be corrected by providing a template and a CRISPR/Cas9 system that creates (1) one double strand break, (2) two single strand breaks, (3) two double stranded breaks with a break occurring on each side of the target sequence, (4) one double stranded break and two single strand breaks with the double strand break and two single strand breaks occurring on each side of the target sequence, (5) four single stranded breaks with a pair of single stranded breaks occurring on each side of the target sequence, or (6) one single strand break.

Double Strand Break Mediated Correction

In an embodiment, double strand cleavage is effected by a Cas9 molecule having cleavage activity associated with an HNH-like domain and cleavage activity associated with a RuvC-like domain, e.g., an N-terminal RuvC-like domain, e.g., a wild type Cas9. Such embodiments require only a single gRNA.

Single Strand Break Mediated Correction

In other embodiments, two single strand breaks, or nicks, are effected by a Cas9 molecule having nickase activity, e.g., cleavage activity associated with an HNH-like domain or cleavage activity associated with an N-terminal RuvC-like domain. Such embodiments require two gRNAs, one for placement of each single strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In an embodiment, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HN H activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA).

In an embodiment, in which a nickase and two gRNAs are used to position two single strand nicks, one nick is on the + strand and one nick is on the − strand of the target nucleic acid. The PAMs are outwardly facing. The gRNAs can be selected such that the gRNAs are separated by, from about 0-50, 0-100, or 0-200 nucleotides. In an embodiment, there is no overlap between the target sequence that is complementary to the targeting domains of the two gRNAs. In an embodiment, the gRNAs do not overlap and are separated by as much as 50, 100, or 200 nucleotides. In an embodiment, the use of two gRNAs can increase specificity, e.g., by decreasing off-target binding (Ran el al., CELL 2013).

In an embodiment, a single nick can be used to induce HDR. It is contemplated herein that a single nick can be used to increase the ratio of HDR, HR or NHEJ at a given cleavage site.

Placement of the Double Strand Break or a Single Strand Break Relative to Target Position The double strand break or single strand break in one of the strands should be sufficiently close to target position such that correction occurs. In an embodiment, the distance is not more than 50, 100, 200, 300, 350 or 400 nucleotides. While not wishing to be bound by theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as donor sequence may only be used to correct sequence within the end resection region.

In an embodiment, in which a gRNA (unimolecular (or chimeric) or modular gRNA) and Cas9 nuclease induce a double strand break for the purpose of inducing HDR- or HR-mediated correction, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In an embodiment, in which two gRNAs (independently, unimolecular (or chimeric) or modular gRNA) complexing with Cas9 nickases induce two single strand breaks for the purpose of inducing HDR-mediated correction, the closer nick is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position and the two nicks will ideally be within 25-55 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp) and no more than 100 bp away from each other (e.g., no more than 90, 80, 70, 60, 50, 40, 30, 20, 10 or 5 bp away from each other). In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on either side of the target position (e.g., the first gRNA is used to target upstream (i.e., 5') of the target position and the second gRNA is used to target downstream (i.e., 3') of the target position). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the target position and the second gRNA is used to target downstream (i.e., 3') of the target position). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35. to 50, 40 to 50, 45 to 50, 35 to 45, or 40 to 45 bp) and no more than 100 bp away from each other (e.g., no more than 90, 80, 70, 60, 50, 40, 30, 20 or 10 bp).

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on two target sequences (e.g., the first gRNA is used to target an upstream (i.e., 5') target sequence and the second gRNA is used to target a downstream (i.e., 3') target sequence of an insertion site. In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of an insertion site (e.g., the first gRNA is used to target an upstream (i.e., 5') target sequence described herein, and the second gRNA is used to target a downstream (i.e., 3') target sequence described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

Length of the Homology Arms

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm does not extend into repeated elements, e.g., ALU repeats, LINE repeats. A template may have two homology arms of the same or different lengths.

Exemplary homology arm lengths include at least 25, 50, 100, 250, 500, 750 or 1000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the gRN A binds) In an embodiment, a target position is upstream or downstream of a target sequence (e.g., the sequence to which the gRNA binds).

Typically, the template sequence undergoes a breakage mediated or catalyzed recombination with the target sequence. In an embodiment, the template nucleic acid includes sequence that corresponds to a site on the target sequence that is cleaved by a Cas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

The template nucleic acid can include sequence which, when integrated, results in:
decreasing the activity of a positive control element;
increasing the activity of a positive control element;
decreasing the activity of a negative control element;
increasing the activity of a negative control element;
decreasing the expression of a gene;
increasing the expression of a gene;
increasing resistance to a disorder or disease;
increasing resistance to viral entry;
correcting a mutation or altering an unwanted amino acid residue;
conferring, increasing, abolishing or decreasing a biological property of a gene product, e.g., increasing the enzymatic activity of an enzyme, or increasing the ability of a gene product to interact with another molecule.

The template nucleic acid can include sequence which results in:
a change in sequence of 1, 2, 3, 4, 5, 6, 7, 8, 9, 10, 11, 12 or more nucleotides of the target sequence.

In an embodiment, the template nucleic acid is 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, 220+/−10, 200-300, 300-400, 400-500, 500-600, 600-700, 700-800, 800-900, 900-1000, 1000-2000, 2000-3000 or more than 3000 nucleotides in length.

A template nucleic acid comprises the following components:

[5' homology arm]-[insertion sequence]-[3' homology arm].

The homology arms provide for recombination into the chromosome, which can replace the undesired element, e.g., a mutation or signature, with the replacement sequence. In an embodiment, the homology arms flank the most distal cleavage sites.

In an embodiment, the 3' end of the 5' homology arm is the position next to the 5' end of the replacement sequence. In an embodiment, the 5' homology arm can extend at least 10, 20, 30, 40, 50, 60, 70, 80, 90, 100, 120, 150, 180, 200, 300, 400, 500, 600, 700, 800, 900, 1000, 1500, or 2000 nucleotides 5' from the 5' end of the replacement sequence.

In an embodiment, the 5' end of the 3' homology arm is the position next to the 3' end of the replacement sequence. In an embodiment, the 3' homology arm can extend at least 10, 20, 30, 40, 50, 60, 70, 80, 90, 100, 120, 150, 180, 200, 300, 400, 500, 600, 700, 800, 900, 1000, 1500, or 2000 nucleotides 3' from the 3' end of the replacement sequence.

It is contemplated herein that one or both homology arms may be shortened to avoid including certain sequence repeat elements, e.g., Alu repeats, LINE elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

It is contemplated herein that template nucleic acids for correcting a mutation may designed for use as a single-stranded oligonucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made.

NHEJ Approaches for Gene Targeting.

As described herein, nuclease-induced non-homologous end joining (NHEJ) can be used to target gene-specific knockouts. Nuclease-induced NHEJ can also be used to remove (e.g., delete) sequence in a gene of interest.

While not wishing to be bound by theory, it is believed that, in an embodiment, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations may alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population. The lengths of deletions can vary widely; most commonly in the 1-50 bp range, but they can easily reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Cas9 molecules and single strand, or nickase, Cas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

Placement of Double Strand or Single Strand Breaks Relative to the Target Position In an embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In an embodiment, the cleavage site is between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In an embodiment, the gRNAs are configured to position cuts at the same position, or within a few nucleotides of one another, on different strands, essentially mimicking a double strand break. In an embodiment, the closer nick is between 0-30 bp away from the target position (e.g., less than 30, 25, 20, 1, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In an embodiment, the gRNAs are configured to place a single strand break on either side of a nucleotide of the target position.

Both double strand cleaving Cas9 molecules and single strand, or nickase, Cas9 molecules can be used in the methods and compositions described herein to generate breaks both sides of a target position. Double strand or paired single strand breaks may be generated on both sides of a target position to remove the nucleic acid sequence between the two cuts (e.g., the region between the two breaks is deleted). In one embodiment, two gRNAs, e.g., independently, unimolecular (or chimeric) or modular gRNA, are configured to position a double-strand break on both sides of a target position (e.g., the first gRNA is used to target upstream (i.e., 5') of the mutation in a gene or pathway described herein, and the second gRNA is used to target downstream (i.e., 3') of the mutation in a gene or pathway described herein). In an alternate embodiment, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on either side of a target position (e.g., the first gRNA is used to target upstream (i.e., 5') of the mutation in a gene or pathway described herein, and the second gRNA is used to target downstream (i.e., 3') of the mutation in a gene or pathway described herein). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the mutation in a gene or pathway described herein, and the second gRNA is used to target downstream (i.e., 3') of the mutation in a gene or pathway described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

In other embodiments, the insertion of template nucleic acid may be mediated by microhomology end joining (MMEJ). See, e.g., Saksuma et al., "MMEJ-assisted gene knock-in using TALENs and CRISPR-Cas9 with the PITCh systems." *Nature Protocols* 11, 118-133 (2016) doi:10.1038/nprot.2015.140 Published online 17 Dec. 2015, the contents of which are incorporated by reference in their entirety.

VIII. Systems Comprising More than One gRNA Molecule

While not intending to be bound by theory, it has been surprisingly shown herein that the targeting of two target sequences (e.g., by two gRNA molecule/Cas9 molecule complexes which each induce a single- or double-strand break at or near their respective target sequences) located in close proximity on a continuous nucleic acid induces excision (e.g., deletion) of the nucleic acid sequence (or at least 80%, 85%, 90%, 95%, 96%, 97%, 98%, 99% of the nucleic acid sequence) located between the two target sequences. In some aspects, the present disclosure provides for the use of two or more gRNA molecules that comprise targeting domains targeting target sequences in close proximity on a continuous nucleic acid, e.g., a chromosome, e.g., a gene or gene locus, including its introns, exons and regulatory elements. The use may be, for example, by introduction of the two or more gRNA molecules, together with one or more Cas9 molecules (or nucleic acid encoding the two or more gRNA molecules and/or the one or more Cas9 molecules) into a cell.

In some aspects, the target sequences of the two or more gRNA molecules are located at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 11,000, 12,000, 13,000, 14,000, or 15,000 nucleotides apart on a continuous nucleic acid, but not more than 25,000 nucleotides apart on a continuous nucleic acid. In embodiments, the target sequences are located between about 4000 and about 6000 nucleotides apart. In an embodiment, the target sequences are located about 4000 nucleotides apart. In an embodiment, the target sequences are located about 5000 nucleotides apart. In an embodiment, the target sequences are located about 6000 nucleotides apart.

In some aspects, the plurality of gRNA molecules each target sequences within the same gene or gene locus. In an exemplary aspect, the target sequences of the two or more gRNA molecules are located in the HBG1 promoter region. In an exemplary aspect, the target sequences of the two or more gRNA molecules are located in the HBG2 promoter region. In another aspect, the plurality of gRNA molecules each target sequences within 2 or more different genes or gene loci. In an exemplary aspect, the target sequence of one or more of the gRNA molecules is located in the HBG1 promoter region, and the target sequence of one or more of the other gRNA molecules is located in the HBG2 promoter region.

In some aspects, the invention provides compositions and cells comprising a plurality, for example, 2 or more, for example, 2, gRNA molecules of the invention, wherein the plurality of gRNA molecules target sequences less than 15,000, less than 14,000, less than 13,000, less than 12,000, less than 11,000, less than 10,000, less than 9,000, less than 8,000, less than 7,000, less than 6,000, less than 5,000, less than 4,000, less than 3,000, less than 2,000, less than 1,000, less than 900, less than 800, less than 700, less than 600, less than 500, less than 400, less than 300, less than 200, less than 100, less than 90, less than 80, less than 70, less than 60, less than 50, less than 40, or less than 30 nucleotides apart. In an embodiment, the target sequences are on the same strand of duplex nucleic acid. In an embodiment, the target sequences are on different strands of duplex nucleic acid.

In one embodiment, the invention provides a method for excising (e.g., deleting) nucleic acid disposed between two gRNA binding sites disposed less than 25,000, less than 20,000, less than 15,000, less than 14,000, less than 13,000, less than 12,000, less than 11,000, less than 10,000, less than 9,000, less than 8,000, less than 7,000, less than 6,000, less than 5,000, less than 4,000, less than 3,000, less than 2,000, less than 1,000, less than 900, less than 800, less than 700, less than 600, less than 500, less than 400, less than 300, less than 200, less than 100, less than 90, less than 80, less than 70, less than 60, less than 50, less than 40, or less than 30 nucleotides apart on the same or different strands of duplex nucleic acid. In an embodiment, the method provides for deletion of more than 50%, more than 60%, more than 70%, more than 80%, more than 85%, more than 86%, more than 87%, more than 88%, more than 89%, more than 90%, more than 91%, more than 92%, more than 93%, more than 94%, more than 95%, more than 96%, more than 97%, more than 98%, more than 99%, or 100% of the nucleotides disposed between the PAM sites associated with each gRNA binding site. In embodiments, the deletion further comprises of one or more nucleotides within one or more of the PAM sites associated with each gRNA binding site. In embodiments, the deletion also comprises one or more nucleotides outside of the region between the PAM sites associated with each gRNA binding site.

In one aspect, the two or more gRNA molecules comprise targeting domains targeting target sequences flanking a gene regulatory element, e.g., a promotor binding site, an enhancer region, or a repressor region, such that excision of the intervening sequence (or a portion of the intervening sequence) causes up- or down-regulation of a gene of interest. In other embodiments, the two or more gRNA molecules comprise targeting domains that target sequences flanking a gene, such that excision of the intervening sequence (or portion thereof) causes deletion of the gene of interest.

In an embodiment, the two or more gRNA molecules each include a targeting domain comprising, e.g., consisting of, a targeting domain sequence of Table 1, e.g., of Table 2 or, e.g., of Table 3a or Table 3b. In embodiments, the two or more gRNA molecules each include a targeting domain comprising, e.g., consisting of, the targeting domain of a gRNA molecule which results in at least 15% upregulation in the number of F cells in a population of red blood cells differentiated (e.g., at day 7 following editing) from HSPCs edited by said gRNA ex vivo by the methods described herein. In aspects, the two or more gRNA molecules comprise targeting domains that are complementary with sequences in the same gene or region, e.g., the HBG1 promoter region or the HBG2 promoter region. In aspects, the two or more gRNA molecules comprise targeting domains that are complementary with sequences of different genes or regions, for example one in the HBG1 promoter region and one in the HBG2 promoter region.

In one aspect, the two or more gRNA molecules comprise targeting domains targeting target sequences flanking a gene regulatory element, e.g., a promotor binding site, an enhancer region, or a repressor region, such that excision of the intervening sequence (or a portion of the intervening sequence) causes up- or down-regulation of a gene of interest. In another aspect, the two or more gRNA molecules comprise targeting domains targeting target sequences flanking a gene, such that excision of the intervening sequence (or a portion of the intervening sequence) causes deletion of the gene of interest. By way of example, the two or more gRNA molecules comprise targeting domains targeting target sequences flanking the HBG1 gene (for example, one gRNA molecule targeting a target sequence in the HBG1 promoter region, and a second gRNA molecule targeting a target sequence in the HBG2 promoter region), such that the HBG1 gene is excised.

In an embodiment, the two or more gRNA molecules comprise targeting domains that comprise, e.g., consist of, targeting domains selected from Table 1.

In aspects, the two or more gRNA molecules comprise targeting domains comprising, e.g., consisting of, targeting domain sequences listed in Table 2, above. In aspects, the two or more gRNA molecules comprise targeting domains comprising, e.g., consisting of, targeting domain sequences of gRNAs listed in Table 3a, above. In aspects, the two or more gRNA molecules comprise targeting domains comprising, e.g., consisting of, targeting domain sequences listed in Table 3b, above.

The gRNA molecules comprising targeting domains which target sequences of within a nondeletional HPFH region, e.g., an HBG1 and/or HBG2 promoter region, may additionally be used with a gRNA molecule comprising a targeting domain complementary to a target sequence within, for example, a BCL11a enhancer region (e.g., a +55, +58 or +62 BCL11a enhancer region) and/or a gRNA molecule comprising a targeting domain complementary to a target sequence of a deletional HPFH locus. Such deletional HPFH loci are known in the art, for example, those described in Sankaran V G et al. NEJM (2011) 365:807-814 (hereby incorporated by reference in its entirety).

IX. Properties of the gRNA

It has further been surprisingly shown herein that single gRNA molecules may have target sequences in more than one loci (for example, loci with high sequence homology), and that, when such loci are present on the same chromosome, for example, within less than about 15,000 nucleotides, less than about 14,000 nucleotides, less than about 13,000 nucleotides, less than about 12,000 nucleotides, less than about 11,000 nucleotides, less than about 10,000 nucleotides, less than about 9,000 nucleotides, less than about 8,000 nucleotides, less than about 7,000 nucleotides, less than about 6,000 nucleotides, less than about 5,000 nucleotides, less than about 4,000 nucleotides, or less than about 3,000 nucleotides, (e.g., from about 4,000 to about 6,000 nucleotides apart) such a gRNA molecule may result in excision of the intervening sequence (or portion thereof), thereby resulting in a beneficial effect, for example, upregulation of fetal hemoglobin in erythroid cells differentiated from modified HSPCs (as described herein). Thus, in an aspect, the invention provides gRNA molecules which have target sequences at two loci, for example, to loci on the same chromosome, for example, which have target sequences at an HBG1 promoter region and at an HBG2 promoter region (for example as described in Table 1). Without begin bound by theory, it is believed that such gRNAs may result in the cutting of the genome at more than one location (e.g., at the target sequence in each of two regions), and that subsequent repair may result in a deletion of the intervening nucleic acid sequence. Again, without being bound by theory, deletion of said intervening sequence may have a desired effect on the expression or function of one or more proteins.

It has further been surprisingly shown that gRNA molecules which comprise a targeting domain complementary to a sequence only in one gene or region, for example, which is complementary to a target sequence in the HBG1 promoter region (but not the HBG2 promoter region), or which is complementary to a target sequence in the HBG2 promoter region (but not the HBG1 promoter region), can result in significant upregulation of fetal hemoglobin in erythroid cells differentiated from modified HSPCs (as described herein). In aspects, the invention thus provides gRNA molecules which comprise a targeting domain which is complementary to a target sequence in a single nondeletional HPFH region, for example within a HBG1 or HBG2 promoter region (for example as described in Table 1), but which does not have a fully (e.g., 100%) complementary target sequence match in any other gene or region.

It has further been surprisingly shown herein that gRNA molecules and CRISPR systems comprising said gRNA molecules produce similar or identical indel patterns across multiple experiments using the same cell type, method of delivery and crRNA/tracr components. Without being bound by theory, it is believed that some indel patterns may be more advantageous than others. For example, indels which predominantly include insertions and/or deletions which result in a "frameshift mutation" (e.g., 1- or 2-base pair insertion or deletions, or any insertion or deletion where n/3 is not a whole number (where n=the number of nucleotides in the insertion or deletion)) may be beneficial in reducing or eliminating expression of a functional protein. Likewise, indels which predominantly include "large deletions" (deletions of more than 10, 11, 12, 13, 14, 15, 20, 25, or 30 nucleotides, for example, more than 1 kb, more than 2 kb, more than 3 kb, more than 5 kb or more than 10 kb, for example, comprising sequence disposed between a first and second binding site for a gRNA, e.g., as described herein) may also be beneficial in, for example, removing critical regulatory sequences such as promoter binding sites, or altering the structure or function of a locus, which may similarly have an effect on expression of functional protein. While the indel patterns induced by a given gRNA/CRISPR system have surprisingly been found to be consistently reproduced for a given cell type, gRNA and CRISPR system, as described herein, not any single indel structure will inevitably be produced in a given cell upon introduction of a gRNA/CRISPR system.

The invention thus provides for gRNA molecules which create a beneficial indel pattern or structure, for example, which have indel patterns or structures predominantly composed of large deletions. Such gRNA molecules may be selected by assessing the indel pattern or structure created by a candidate gRNA molecule in a test cell (for example, a HEK293 cell) or in the cell of interest, e.g., a HSPC cell by NGS, as described herein. As shown in the Examples, gRNA molecules have been discovered, which, when introduced into the desired cell population, result in a population of cells comprising a significant fraction of the cells having a large deletion at or near the target sequence of the gRNA. In some cases, the rate of large deletion indel formation is as high as 75%, 80%, 85%, 90% or more. The invention thus provides for populations of cells which comprise at least about 40% of cells (e.g., at least about 45%, at least about 50%, at least about 55%, at least about 60%, at least about 65%, at least about 70%, at least about 75%, at least about 80%, at least about 85%, at least about 90%, at least about 95%, or at least about 99%) having a large deletion, e.g., as described herein, at or near the target site of a gRNA molecule described herein. The invention also provides for populations of cells which comprise at least about 50% of cells (e.g., at least about 55%, at least about 60%, at least about 65%, at least about 70%, at least about 75%, at least about 80%, at least about 85%, at least about 90%, at least about 95%, or at least about 99%) having a large deletion, e.g., as described herein, at or near the target site of a gRNA molecule described herein.

The invention thus provides methods of selecting gRNA molecules for use in the therapeutic methods of the invention comprising: 1) providing a plurality of gRNA molecules to a target of interest, 2) assessing the indel pattern or structure created by use of said gRNA molecules, 3) selecting a gRNA molecule that forms an indel pattern or structure composed predominantly of frameshift mutations, large deletions or a combination thereof, and 4) using said selected gRNA in a methods of the invention.

The invention thus provides methods of selecting gRNA molecules for use in the therapeutic methods of the invention comprising: 1) providing a plurality of gRNA molecules to a target of interest, e.g., which have target sequences at more than one location 2) assessing the indel pattern or structure created by use of said gRNA molecules, 3) selecting a gRNA molecule that forms an excision of sequence comprising nucleic acid sequence located between the two target sequences, e.g., in at least about 25% or more of the cells of a population of cells which are exposed to said gRNA molecules, and 4) using said selected gRNA molecule in a methods of the invention.

The invention further provides methods of altering cells, and altered cells, wherein a particular indel pattern is constantly produced with a given gRNA/CRISPR system in that cell type. The indel patterns, including the top 5 most frequently occurring indels observed with the gRNA/CRISPR systems described herein can be determined using the methods of the examples, and are disclosed, for example, in the Examples. As shown in the Examples, populations of cells are generated, wherein a significant fraction of the cells comprises one of the top 5 indels (for example, populations of cells wherein one of the top 5 indels is present in more than 30%, more than 40%, more than 50%, more than 60% or more of the cells of the population. Thus, the invention provides cells, e.g., HSPCs (as described herein), which comprise an indel of any one of the top 5 indels observed with a given gRNA/CRISPR system. Further, the invention provides populations of cells, e.g., HSPCs (as described herein), which when assessed by, for example, NGS, comprise a high percentage of cells comprising one of the top 5 indels described herein for a given gRNA/CRISPR system. When used in connection with indel pattern analysis, a "high percentage" refers to at least about 50% (e.g., at least about 55%, at least about 60%, at least about 65%, at least about 70%, at least about 75%, at least about 80%, at least about 85%, at least about 90%, at least about 95%, or at least about 99%) of the cells of the population comprising one of the top 5 indels described herein for a given gRNA/CRISPR system. In other embodiments, the population of cells comprises at least about 25% (e.g., from about 25% to about 60%, e.g., from about 25% to about 50%, e.g., from about 25% to about 40%, e.g., from about 25% to about 35%) of cells which have one of the top 5 indels described herein for a given gRNA/CRISPR system.

It has also been discovered that certain gRNA molecules do not create indels at off-target sequences (e.g., off-target sequences outside of the HBG1 and/or HBG2 promoter region) within the genome of the target cell type, or produce indels at off target sites (e.g., off-target sequences outside of the HBG1 and/or HBG2 promoter region) at very low frequencies (e.g., <5% of cells within a population) relative to the frequency of indel creation at the target site. Thus, the invention provides for gRNA molecules and CRISPR systems which do not exhibit off-target indel formation in the target cell type, or which produce a frequency of off-target indel formation of less than 5%, for example, an indel at any off-target site outside of the HBG1 and/or HBG2 promoter region at a frequency of less than 5%. In embodiments, the invention provides gRNA molecules and CRISPR systems which do not exhibit any off target indel formation in the target cell type. Thus, the invention further provides a cell, e.g., a population of cells, e.g., HSPCs, e.g., as described herein, which comprise an indel at or near a target site of a gRNA molecule described herein (e.g., a frameshift indel, or any one of the top 5 indels produced by a given gRNA/CRISPR system, e.g., as described herein), but does not comprise an indel at any off-target site of the gRNA molecule, for example, an indel at any off-target site outside of the HBG1 and/or HBG2 promoter region. In other embodiments, the invention further provides a population of cells, e.g., HSPCs, e.g., as described herein, which comprises at least 20%, for example at least 30%, for example at least 40%, for example at least 50%, for example at least 60%, for example at least 70%, for example at least 75% of cells which have an indel at or near a target site of a gRNA molecule described herein (e.g., a frameshift indel, or any one of the top 5 indels produced by a given gRNA/CRISPR system, e.g., as described herein), but which comprises less than 5%, e.g., less than 4%, less than 3%, less than 2% or less than 1%, of cells comprising an indel at any off-target site of the gRNA molecule, for example, an indel at any off-target site outside of the HBG1 and/or HBG2 promoter region. In other embodiments, the invention further provides a population of cells, e.g., HSPCs, e.g., as described herein, which comprises at least 20%, for example at least 30%, for example at least 40%, for example at least 50%, for example at least 60%, for example at least 70%, for example at least 75%, for example at least 80%, for example at least 90%, for example at least 95%, of cells which have an indel within the HBG1 and/or HBG2 promoter region (e.g., at or near a sequence which is as least 90% homologous to the target sequence of the gRNA), but which comprises less than 5%, e.g., less than 4%, less than 3%, less than 2% or less than 1%, of cells comprising an indel at or near any off-target site outside of the HBG1 and/or HBG2 promoter region.

In embodiments, the off-target indel is formed within a sequence of a gene, e.g., within a coding sequence of a gene. In embodiments no off-target indel is formed within a sequence of a gene, e.g., within a coding sequence of a gene, in the cell of interest, e.g., as described herein.

X. Delivery/Constructs

The components, e.g., a Cas9 molecule or gRNA molecule, or both, can be delivered, formulated, or administered in a variety of forms. As a non-limiting example, the gRNA molecule and Cas9 molecule can be formulated (in one or more compositions), directly delivered or administered to a cell in which a genome editing event is desired. Alternatively, nucleic acid encoding one or more components, e.g., a Cas9 molecule or gRNA molecule, or both, can be formulated (in one or more compositions), delivered or administered. In one aspect, the gRNA molecule is provided as DNA encoding the gRNA molecule and the Cas9 molecule is provided as DNA encoding the Cas9 molecule. In one embodiment, the gRNA molecule and Cas9 molecule are encoded on separate nucleic acid molecules. In one embodiment, the gRNA molecule and Cas9 molecule are encoded on the same nucleic acid molecule. In one aspect, the gRNA molecule is provided as RNA and the Cas9 molecule is provided as DNA encoding the Cas9 molecule. In one embodiment, the gRNA molecule is provided with one or more modifications, e.g., as described herein. In one aspect, the gRNA molecule is provided as RNA and the Cas9 molecule is provided as mRNA encoding the Cas9 molecule. In one aspect, the gRNA molecule is provided as RNA and the Cas9 molecule is provided as a protein. In one embodiment, the gRNA and Cas9 molecule are provided as a ribonuclear protein complex (RNP). In one aspect, the gRNA molecule is provided as DNA encoding the gRNA molecule and the Cas9 molecule is provided as a protein.

Delivery, e.g., delivery of the RNP, (e.g., to HSPC cells as described herein) may be accomplished by, for example, electroporation (e.g., as known in the art) or other method that renders the cell membrane permeable to nucleic acid and/or polypeptide molecules. In embodiments, the CRISPR system, e.g., the RNP as described herein, is delivered by electroporation using a 4D-Nucleofector (Lonza), for example, using program CM-137 on the 4D-Nucleofector (Lonza). In embodiments, the CRISPR system, e.g., the RNP as described herein, is delivered by electroporation using a voltage from about 800 volts to about 2000 volts, e.g., from about 1000 volts to about 1800 volts, e.g., from about 1200 volts to about 1800 volts, e.g., from about 1400 volts to about 1800 volts, e.g., from about 1600 volts to about 1800 volts, e.g., about 1700 volts, e.g., at a voltage of 1700 volts. In embodiments, the pulse width/length is from about 10 ms to about 50 ms, e.g., from about 10 ms to about 40 ms, e.g., from about 10 ms to about 30 ms, e.g., from about 15 ms to about 25 ms, e.g., about 20 ms, e.g., 20 ms. In embodiments, 1, 2, 3, 4, 5, or more, e.g., 2, e.g., 1 pulses are used. In an embodiment, the CRISPR system, e.g., the RNP as described herein, is delivered by electroporation using a voltage of about 1700 volts (e.g., 1700 volts), a pulse width of about 20 ms (e.g., 20 ms), using a single (1) pulse. In embodiments, electroporation is accomplished using a Neon electroporator. Additional techniques for rendering the membrane permeable are known in the art and include, for example, cell squeezing (e.g., as described in WO2015/023982 and WO2013/059343, the contents of which are hereby incorporated by reference in their entirety), nanoneedles (e.g., as described in Chiappini et al., Nat. Mat., 14; 532-39, or US2014/0295558, the contents of which are hereby incorporated by reference in their entirety) and nanostraws (e.g., as described in Xie, ACS Nano, 7(5); 4351-58, the contents of which are hereby incorporated by reference in their entirety).

When a component is delivered encoded in DNA the DNA will typically include a control region, e.g., comprising a promoter, to effect expression. Useful promoters for Cas9 molecule sequences include CMV, EF-1alpha, MSCV, PGK, CAG control promoters. Useful promoters for gRNAs include H1, EF-1a and U6 promoters. Promoters with similar or dissimilar strengths can be selected to tune the expression of components. Sequences encoding a Cas9 molecule can comprise a nuclear localization signal (NLS), e.g., an SV40 NLS. In an embodiment, a promoter for a Cas9 molecule or a gRNA molecule can be, independently, inducible, tissue specific, or cell specific.

DNA-Based Delivery of a Cas9 Molecule and or a gRNA Molecule

DNA encoding Cas9 molecules and/or gRNA molecules, can be administered to subjects or delivered into cells by art-known methods or as described herein. For example, Cas9-encoding and/or gRNA-encoding DNA can be delivered, e.g., by vectors (e.g., viral or non-viral vectors), non-vector based methods (e.g., using naked DNA or DNA complexes), or a combination thereof.

In some embodiments, the Cas9- and/or gRNA-encoding DNA is delivered by a vector (e.g., viral vector/virus, plasmid, minicircle or nanoplasmid).

A vector can comprise a sequence that encodes a Cas9 molecule and/or a gRNA molecule. A vector can also comprise a sequence encoding a signal peptide (e.g., for nuclear localization, nucleolar localization, mitochondrial localization), fused, e.g., to a Cas9 molecule sequence. For example, a vector can comprise one or more nuclear localization sequence (e.g., from SV40) fused to the sequence encoding the Cas9 molecule.

One or more regulatory/control elements, e.g., a promoter, an enhancer, an intron, a polyadenylation signal, a Kozak consensus sequence, internal ribosome entry sites (IRES), a 2A sequence, and a splice acceptor or donor can be included in the vectors. In some embodiments, the promoter is recognized by RNA polymerase II (e.g., a CMV promoter). In other embodiments, the promoter is recognized by RNA polymerase III (e.g., a U6 promoter). In some embodiments, the promoter is a regulated promoter (e.g., inducible promoter). In other embodiments, the promoter is a constitutive promoter. In some embodiments, the promoter is a tissue specific promoter. In some embodiments, the promoter is a viral promoter. In other embodiments, the promoter is a non-viral promoter.

In some embodiments, the vector or delivery vehicle is a minicircle. In some embodiments, the vector or delivery vehicle is a nanoplasmid.

In some embodiments, the vector or delivery vehicle is a viral vector (e.g., for generation of recombinant viruses). In some embodiments, the virus is a DNA virus (e.g., dsDNA or ssDNA virus). In other embodiments, the virus is an RNA virus (e.g., an ssRNA virus).

Exemplary viral vectors/viruses include, e.g., retroviruses, lentiviruses, adenovirus, adeno-associated virus (AAV), vaccinia viruses, poxviruses, and herpes simplex viruses. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals.

In some embodiments, the virus infects dividing cells. In other embodiments, the virus infects non-dividing cells. In some embodiments, the virus infects both dividing and non-dividing cells. In some embodiments, the virus can integrate into the host genome. In some embodiments, the virus is engineered to have reduced immunity, e.g., in human. In some embodiments, the virus is replication-competent. In other embodiments, the virus is replication-defective, e.g., having one or more coding regions for the genes necessary for additional rounds of virion replication and/or packaging replaced with other genes or deleted. In some embodiments, the virus causes transient expression of the Cas9 molecule and/or the gRNA molecule. In other embodiments, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In some embodiments, the Cas9- and/or gRNA-encoding DNA is delivered by a recombinant retrovirus. In some embodiments, the retrovirus (e.g., Moloney murine leukemia virus) comprises a reverse transcriptase, e.g., that allows integration into the host genome. In some embodiments, the retrovirus is replication-competent. In other embodiments, the retrovirus is replication-defective, e.g., having one of more coding regions for the genes necessary for additional rounds of virion replication and packaging replaced with other genes, or deleted.

In some embodiments, the Cas9- and/or gRNA-encoding DNA is delivered by a recombinant lentivirus. For example, the lentivirus is replication-defective, e.g., does not comprise one or more genes required for viral replication.

In some embodiments, the Cas9- and/or gRNA-encoding DNA is delivered by a recombinant adenovirus. In some embodiments, the adenovirus is engineered to have reduced immunity in human.

In some embodiments, the Cas9- and/or gRNA-encoding DNA is delivered by a recombinant AAV. In some embodiments, the AAV can incorporate its genome into that of a host cell, e.g., a target cell as described herein. In some embodiments, the AAV is a self-complementary adeno-associated virus (scAAV), e.g., a scAAV that packages both strands which anneal together to form double stranded DNA. AAV serotypes that may be used in the disclosed methods include, e.g., AAV1, AAV2, modified AAV2 (e.g., modifications at Y444F, Y500F, Y730F and/or S662V), AAV3, modified AAV3 (e.g., modifications at Y705F, Y73 1 F and/or. T492V), AAV4, AAV5, AAV6, modified AAV6 (e.g., modifications at S663V and/or T492V), AAV8. AAV 8.2, AAV9, AAV rh 10, and pseudotyped AAV, such as AAV2/8, AAV2/5 and AAV2/6 can also be used in the disclosed methods.

In some embodiments, the Cas9- and/or gRNA-encoding DNA is delivered by a hybrid virus, e.g., a hybrid of one or more of the viruses described herein.

A Packaging cell is used to form a virus particle that is capable of infecting a host or target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In an embodiment, the viral vector has the ability of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibodies, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In an embodiment, the viral vector achieves cell type specific expression. For example, a tissue-specific promoter can be constructed to restrict expression of the transgene (Cas 9 and gRNA) in only the target cell. The specificity of the vector can also be mediated by microRNA-dependent control of transgene expression. In an embodiment, the viral vector has increased efficiency of fusion of the viral vector and a target cell membrane. For example, a fusion protein such as fusion-competent hemaglutinin (HA) can be incorporated to increase viral uptake into cells. In an embodiment, the viral vector has the ability of nuclear localization. For example, a virus that requires the breakdown of the cell wall (during cell division) and therefore will not infect a non-diving cell can be altered to incorporate a nuclear localization peptide in the matrix protein of the virus thereby enabling the transduction of non-proliferating cells.

In some embodiments, the Cas9- and/or gRNA-encoding DNA is delivered by a non-vector based method (e.g., using naked DNA or DNA complexes). For example, the DNA can be delivered, e.g., by organically modified silica or silicate (Ormosil), electroporation, gene gun, sonoporation, magnetofection, lipid-mediated transfection, dendrimers, inorganic nanoparticles, calcium phosphates, or a combination thereof.

In some embodiments, the Cas9- and/or gRNA-encoding DNA is delivered by a combination of a vector and a non-vector based method. For example, a virosome comprises a liposome combined with an inactivated virus (e.g., HIV or influenza virus), which can result in more efficient gene transfer, e.g., in a respiratory epithelial cell than either a viral or a liposomal method alone.

In an embodiment, the delivery vehicle is a non-viral vector. In an embodiment, the non-viral vector is an inorganic nanoparticle (e.g., attached to the payload to the surface of the nanoparticle). Exemplary inorganic nanoparticles include, e.g., magnetic nanoparticles (e.g., Fe $1v1n0_2$), or silica. The outer surface of the nanoparticle can be conjugated with a positively charged polymer (e.g., polyethylenimine, polylysine, polyserine) which allows for attachment (e.g., conjugation or entrapment) of payload. In an embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids and/or polymers for transfer of CRISPR systems or nucleic acid, e.g., vectors, encoding CRISPR systems or components thereof include, for example, those described in WO2011/076807, WO2014/136086, WO2005/060697, WO2014/140211, WO2012/031046, WO2013/103467, WO2013/006825, WO2012/006378, WO2015/095340, and WO2015/095346, the contents of each of the foregoing are hereby incorporated by reference in their entirety. In an embodiment, the vehicle has targeting modifications to increase target cell update of nanoparticles and liposomes, e.g., cell specific antigens, monoclonal antibodies, single chain antibodies, aptamers, polymers, sugars, and cell penetrating peptides. In an embodiment, the vehicle uses fusogenic and endosome-destabilizing peptides/polymers. In an embodiment, the vehicle undergoes acid-triggered conformational changes (e.g., to accelerate endosomal escape of the cargo). In an embodiment, a stimuli-cleavable polymer is used, e.g., for release in a cellular compartment. For example, disulfide-based cationic polymers that are cleaved in the reducing cellular environment can be used.

In an embodiment, the delivery vehicle is a biological non-viral delivery vehicle. In an embodiment, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In an embodiment, the vehicle is a genetically modified bacteriophage (e.g., engineered phages having large packaging capacity, less immunogenic, containing mammalian plasmid maintenance sequences and having incorporated targeting ligands) In an embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In an embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject (i.e., patient) derived membrane-bound nanovesicle (30-100 nm) of endocytic origin (e.g., can be produced from various cell types and can therefore be taken up by cells without the need of for targeting ligands).

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas9 system are delivered. In an embodiment, the nucleic acid molecule is delivered by a different means than one or more of the components of the Cas9 system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein. Delivery of RNA encoding a Cas9 molecule RNA encoding Cas9 molecules (e.g., active Cas9 molecules, inactive Cas9 molecules or inactive Cas9 fusion proteins) and/or gRNA molecules, can be delivered into cells, e.g., target cells described herein, by art-known methods or as described herein. For example, Cas9-encoding and/or gRNA-encoding RNA can be delivered, e.g., by microinjection, electroporation, lipid-mediated transfection, peptide-mediated delivery, or a combination thereof.

Delivery of Cas9 Molecule as Protein

Cas9 molecules (e.g., active Cas9 molecules, inactive Cas9 molecules or inactive Cas9 fusion proteins) can be delivered into cells by art-known methods or as described herein. For example, Cas9 protein molecules can be delivered, e.g., by microinjection, electroporation, lipid-mediated transfection, peptide-mediated delivery, cell squeezing or abrasion (e.g., by nanoneedles) or a combination thereof. Delivery can be accompanied by DNA encoding a gRNA or by a gRNA, e.g., by precomplexing the gRNA and the Cas9 protein in a ribonuclear protein complex (RNP).

In an aspect the Cas9 molecule, e.g., as described herein, is delivered as a protein and the gRNA molecule is delivered as one or more RNAs (e.g., as a dgRNA or sgRNA, as described herein). In embodiments, the Cas9 protein is complexed with the gRNA molecule prior to delivery to a cell, e.g., as described herein, as a ribonuclear protein complex ("RNP"). In embodiments, the RNP can be delivered into cells, e.g., described herein, by any art-known method, e.g., electroporation. As described herein, and without being bound by theory, it can be preferable to use a gRNA molecule and Cas9 molecule which result in high % editing at the target sequence (e.g., >85%, >90%, >95%, >98%, or >99%) in the target cell, e.g., described herein, even when the concentration of RNP delivered to the cell is reduced. Again, without being bound by theory, delivering a reduced or low concentration of RNP comprising a gRNA molecule that produces a high % editing at the target sequence in the target cell (including at the low RNP concentration), can be beneficial because it may reduce the frequency and number of off-target editing events. In one aspect, where a low or reduced concentration of RNP is to be used, the following exemplary procedure can be used to generate the RNP with a dgRNA molecule:

1. Provide the Cas9 molecule and the tracr in solution at a high concentration (e.g., a concentration higher than the final RNP concentration to be delivered to the cell), and allow the two components to equilibrate;
2. Provide the crRNA molecule, and allow the components to equilibrate (thereby forming a high-concentration solution of the RNP);
3. Dilute the RNP solution to the desired concentration;
4. Deliver said RNP at said desired concentration to the target cells, e.g., by electroporation.

The above procedure may be modified for use with sgRNA molecules by omitting step 2, above, and in step 1, providing the Cas9 molecule and the sgRNA molecule in solution at high concentration, and allowing the components to equilibrate. In embodiments, the Cas9 molecule and each gRNA component are provided in solution at a 1:2 ratio (Cas9:gRNA), e.g., a 1:2 molar ratio of Cas9:gRNA molecule. Where dgRNA molecules are used, the ratio, e.g., molar ratio, is 1:2:2 (Cas9:tracr:crRNA). In embodiments, the RNP is formed at a concentration of 20 uM or higher, e.g., a concentration from about 20 uM to about 50 uM. In embodiments, the RNP is formed at a concentration of 10 uM or higher, e.g., a concentration from about 10 uM to about 30 uM. In embodiments, the RNP is diluted to a final concentration of 10 uM or less (e.g., a concentration from about 0.01 uM to about 10 uM) in a solution comprising the target cell (e.g., described herein) for delivery to said target cell. In embodiments, the RNP is diluted to a final concentration of 3 uM or less (e.g., a concentration from about 0.01 uM to about 3 uM) in a solution comprising the target cell (e.g., described herein) for delivery to said target cell. In embodiments, the RNP is diluted to a final concentration of 1 uM or less (e.g., a concentration from about 0.01 uM to about 1 uM) in a solution comprising the target cell (e.g., described herein) for delivery to said target cell. In embodiments, the RNP is diluted to a final concentration of 0.3 uM or less (e.g., a concentration from about 0.01 uM to about 0.3 uM) in a solution comprising the target cell (e.g., described herein) for delivery to said target cell. In embodiments, the RNP is provided at a final concentration of about 3 uM in a solution comprising the target cell (e.g., described herein) for delivery to said target cell. In embodiments, the RNP is provided at a final concentration of about 2 uM in a solution comprising the target cell (e.g., described herein) for delivery to said target cell. In embodiments, the RNP is provided at a final concentration of about 1 uM in a solution comprising the target cell (e.g., described herein) for delivery to said target cell. In embodiments, the RNP is provided at a final concentration of about 0.3 uM in a solution comprising the target cell (e.g., described herein) for delivery to said target cell. In embodiments, the RNP is provided at a final concentration of about 0.1 uM in a solution comprising the target cell (e.g., described herein) for delivery to said target cell. In embodiments, the RNP is provided at a final concentration of about 0.05 uM in a solution comprising the target cell (e.g., described herein) for delivery to said target cell. In embodiments, the RNP is provided at a final concentration of about 0.03 uM in a solution comprising the target cell (e.g., described herein) for delivery to said target cell. In embodiments, the RNP is provided at a final concentration of about 0.01 uM in a solution comprising the target cell (e.g., described herein) for delivery to said target cell. In embodiments, the RNP is formulated in a medium suitable for electroporation. In embodiments, the RNP is delivered to cells, e.g., HSPC cells, e.g., as described herein, by electroporation, e.g., using electroporation conditions described herein.

In aspects, the components of the gene editing system (e.g., CRISPR system) and/or nucleic acid encoding one or more components of the gene editing system (e.g., CRISPR system) are introduced into the cells by mechanically perturbing the cells, for example, by passing said cells through a pore or channel which constricts the cells. Such perturbation may be accomplished in a solution comprising the components of the gene editing system (e.g., CRISPR system) and/or nucleic acid encoding one or more components of the gene editing system (e.g., CRISPR system), e.g., as described herein. In embodiments, the perturbation is accomplished using a TRIAMF system, e.g., as described herein, for example, in the Examples and in PCT patent application PCT/US17/54110 (incorporated herein by reference in its entirety).

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety.

In an embodiment, the Cas9 molecule and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule, gRNA molecule, or template nucleic acid. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result-in more persistent expression of and presence of a component.

XI. Methods of Treatment

The Cas9 systems, e.g., one or more gRNA molecules and one or more Cas9 molecules, described herein are useful for the treatment of disease in a mammal, e.g., in a human. The terms "treat," "treated," "treating," and "treatment," include the administration of cas9 systems, e.g., one or more gRNA molecules and one or more cas9 molecules, to cells to prevent or delay the onset of the symptoms, complications, or biochemical indicia of a disease, alleviating the symptoms or arresting or inhibiting further development of the disease, condition, or disorder. Treatment may also include the administration of one or more (e.g., a population of) cells, e.g., HSPCs, that have been modified by the introduction of a gRNA molecule (or more than one gRNA molecule) of the present invention, or by the introduction of a CRISPR system as described herein, or by any of the methods of preparing said cells described herein, to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease. Treatment can be measured by the therapeutic measures described herein. Thus, the methods of "treatment" of the present invention also include administration of cells altered by the introduction of a cas9 system (e.g., one or more gRNA molecules and one or more Cas9 molecules) into said cells to a subject in order to cure, reduce the severity of, or ameliorate one or more symptoms of a disease or condition, in order to prolong the health or survival of a subject beyond that expected in the absence of such treatment. For example, "treatment" includes the alleviation of a disease symptom in a subject by at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% or more.

Cas9 systems comprising gRNA molecules comprising the targeting domains described herein, e.g., in Table 1, and the methods and cells (e.g., as described herein) are useful for the treatment of hemoglobinopathies.

Hemoglobinopathies

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickle) hemoglobin (HbS). HbS is prone to polymerization, particularly under deoxygenated conditions. HbS RBCs are more fragile than normal RBCs and undergo hemolysis more readily, leading eventually to anemia.

In an embodiment, a genetic defect in alpha globin or beta globin is corrected, e.g., by homologous recombination, using the Cas9 molecules and gRNA molecules, e.g., CRISPR systems, described herein.

In an embodiment, a gene encoding a wild type (e.g., non-mutated) copy of alpha globin or beta globin is inserted into the genome of the cell, e.g., at a safe harbor site, e.g., at an AAVS1 safe harbor site, by homologous recombination, using a CRISPR system and methods described herein.

In an embodiment, a hemoglobinopathies-associated gene is targeted, using the Cas9 molecule and gRNA molecule described herein. Exemplary targets include, e.g., genes associated with control of the gamma-globin genes. In an embodiment, the target is a nondeletional HPFH region.

Fetal hemoglobin (also hemoglobin F or HbF or α2γ2) is a tetramer of two adult alpha-globin polypeptides and two fetal beta-like gamma-globin polypeptides. HbF is the main oxygen transport protein in the human fetus during the last seven months of development in the uterus and in the newborn until roughly 6 months old. Functionally, fetal hemoglobin differs most from adult hemoglobin in that it is able to bind oxygen with greater affinity than the adult form, giving the developing fetus better access to oxygen from the mother's bloodstream.

In newborns, fetal hemoglobin is nearly completely replaced by adult hemoglobin by approximately 6 months postnatally. In adults, fetal hemoglobin production can be reactivated pharmacologically, which is useful in the treatment of diseases such as hemoglobinopathies. For example, in certain patients with hemoglobinopathies, higher levels of gamma-globin expression can partially compensate for defective or impaired beta-globin gene production, which can ameliorate the clinical severity in these diseases. Increased HbF levels or F-cell (HbF containing erythrocyte) numbers can ameliorate the disease severity of hemoglobinopathies, e.g., beta-thalassemia major and sickle cell anemia.

As was surprisingly discovered, increased HbF levels or F-cell counts can be associated indel formation at one or more nondeltional HPFH regions in cells, for example, HSPCs and/or cells differentiated from HSPCs (e.g., HSPCs modified by one or more gRNA molecules described herein). In an embodiment, the cell is a hemopoietic stem cell or progenitor cell.

Sickle Cell Diseases

Sickle cell disease is a group of disorders that affects hemoglobin. People with this disorder have atypical hemoglobin molecules (hemoglobin S), which can distort red blood cells into a sickle, or crescent, shape. Characteristic features of this disorder include a low number of red blood cells (anemia), repeated infections, and periodic episodes of pain.

Mutations in the HBB gene cause sickle cell disease. The HBB gene provides instructions for making beta-globin. Various versions of beta-globin result from different mutations in the HBB gene. One particular HBB gene mutation produces an abnormal version of beta-globin known as hemoglobin S (HbS). Other mutations in the HBB gene lead to additional abnormal versions of beta-globin such as hemoglobin C (HbC) and hemoglobin E (HbE). HBB gene mutations can also result in an unusually low level of beta-globin, i.e., beta thalassemia.

In people with sickle cell disease, at least one of the beta-globin subunits in hemoglobin is replaced with hemoglobin S. In sickle cell anemia, which is a common form of sickle cell disease, hemoglobin S replaces both beta-globin subunits in hemoglobin. In other types of sickle cell disease, just one beta-globin subunit in hemoglobin is replaced with hemoglobin S. The other beta-globin subunit is replaced with a different abnormal variant, such as hemoglobin C. For example, people with sickle-hemoglobin C (HbSC) disease have hemoglobin molecules with hemoglobin S and hemoglobin C instead of beta-globin. If mutations that produce hemoglobin S and beta thalassemia occur together, individuals have hemoglobin S-beta thalassemia (HbSBetaThal) disease.

Beta Thalassemia

Beta thalassemia is a blood disorder that reduces the production of hemoglobin. In people with beta thalassemia, low levels of hemoglobin lead to a lack of oxygen in many parts of the body. Affected individuals also have a shortage of red blood cells (anemia), which can cause pale skin, weakness, fatigue, and more serious complications. People with beta thalassemia are at an increased risk of developing abnormal blood clots.

Beta thalassemia is classified into two types depending on the severity of symptoms: thalassemia major (also known as Cooley's anemia) and thalassemia intermedia. Of the two types, thalassemia major is more severe.

Mutations in the HBB gene cause beta thalassemia. The HBB gene provides instructions for making beta-globin. Some mutations in the HBB gene prevent the production of any beta-globin. The absence of beta-globin is referred to as beta-zero (B°) thalassemia. Other HBB gene mutations allow some beta-globin to be produced but in reduced amounts, i.e., beta-plus (B⁺) thalassemia. People with both types have been diagnosed with thalassemia major and thalassemia intermedia.

In an embodiment, a Cas9 molecule/gRNA molecule complex targeting a first gene or locus is used to treat a disorder characterized by a second gene, e.g., a mutation in a second gene. By way of example, targeting of the first gene, e.g., by editing or payload delivery, can compensate for, or inhibit further damage from, the affect of a second gene, e.g., a mutant second gene. In an embodiment the allele(s) of the first gene carried by the subject is not causative of the disorder. For example, as shown herein, gRNA molecules which induce indel formation at a nondeletional HPFH region, for example an HBG1 and/or HBG2 promoter region, can result in upregulation of fetal hemoglobin in erythroid cells differentiated from modified HSPCs (as described herein), and without being bound by theory, such fetal hemoglobin upregulation compensates and corrects for the HBB gene harboring a sickle mutation.

In one aspect, the invention relates to the treatment of a mammal, e.g., a human, in need of increased fetal hemoglobin (HbF).

In one aspect, the invention relates to the treatment of a mammal, e.g., a human, that has been diagnosed with, or is at risk of developing, a hemoglobinopathy.

In one aspect, the hemoglobinopathy is a β-hemoglobinopathy. In one aspect, the hemoglobinopathy is sickle cell disease. In one aspect, the hemoglobinopathy is beta thalassemia.

Methods of Treatment of Hemoglobinopathies

In another aspect the invention provides methods of treatment. In aspects, the gRNA molecules, CRISPR systems and/or cells of the invention are used to treat a patient in need thereof. In aspects, the patient is a mammal, e.g., a human. In aspects, the patient has a hemoglobinopathy. In embodiments, the patient has sickle cell disease. In embodiments, the patient has beta thalassemia.

In one aspect, the method of treatment comprises administering to a mammal, e.g., a human, one or more gRNA molecules, e.g., one or more gRNA molecules comprising a targeting domain described in Table 1, and one or more cas9 molecules described herein.

In one aspect, the method of treatment comprises administering to a mammal a cell population, wherein the cell population is a cell population from a mammal, e.g., a human, that has been administered one or more gRNA molecules, e.g., one or more gRNA molecules comprising a targeting domain described in Table 1, and one or more cas9 molecules described herein, e.g., a CRISPR system as described herein. In one embodiment, the administration of the one or more gRNA molecules or CRISPR systems to the cell is accomplished in vivo. In one embodiment the administration of the one or more gRNA molecules or CRISPR systems to the cell is accomplished ex vivo.

In one aspect, the method of treatment comprises administering to the mammal, e.g., the human, an effective amount of a cell population comprising cells which comprise or at one time comprised one or more gRNA molecules, e.g., one or more gRNA molecules comprising a targeting domain described in Table 1, and one or more cas9 molecules described herein, or the progeny of said cells. In one embodiment, the cells are allogeneic to the mammal. In one embodiment, the cells are autologous to the mammal. In one embodiment the cells are harvested from the mammal, manipulated ex vivo, and returned to the mammal.

In aspects, the cells comprising or which at one time comprised one or more gRNA molecules, e.g., one or more gRNA molecules comprising a targeting domain described in Table 1, and one or more cas9 molecules described herein, or the progeny of said cells, comprise stem cells or progenitor cells. In one aspect, the stem cells are hematopoietic stem cells. In one aspect, the progenitor cells are hematopoietic progenitor cells. In one aspect, the cells comprise both hematopoietic stem cells and hematopoietic progenitor cells, e.g., are HSPCs. In one aspect, the cells comprise, e.g., consist of, CD34+ cells. In one aspect the cells are substantially free of CD34− cells. In one aspect, the cells comprise, e.g., consist of, CD34+/CD90+ stem cells. In one aspect, the cells comprise, e.g., consist of, CD34+/CD90− cells. In an aspect, the cells are a population comprising one or more of the cell types described above or described herein.

In one embodiment, the disclosure provides a method for treating a hemoglobinopathy, e.g., sickle cell disease or beta-thalassemia, or a method for increasing fetal hemoglobin expression in a mammal, e.g., a human, in need thereof, the method comprising:

a) providing, e.g., harvesting or isolating, a population of HSPCs (e.g., CD34+ cells) from a mammal;

b) providing said cells ex vivo, e.g., in a cell culture medium, optionally in the presence of an effective amount of a composition comprising at least one stem cell expander, whereby said population of HSPCs (e.g., CD34+ cells) expands to a greater degree than an untreated population;

c) contacting the population of HSPCs (e.g., CD34+ cells) with an effective amount of: a composition comprising at least one gRNA molecule comprising a targeting domain described herein, e.g., a targeting domain described in Table 1, or a nucleic acid encoding said gRNA molecule, and at least one cas9 molecule, e.g., described herein, or a nucleic acid encoding said cas9 molecule, e.g., one or more RNPs as described herein, e.g., with a CRISPR system described herein;

d) causing at least one modification in at least a portion of the cells of the population (e.g., at least a portion of the HSPCs, e.g., CD34+ cells, of the population), whereby, e.g., when said HSPCs are differentiated into cells of an erythroid lineage, e.g., red blood cells, fetal hemoglobin expression is increased, e.g., relative to cells not contacted according to step c); and f) returning a population of cells comprising said modified HSPCs (e.g., CD34+ cells) to the mammal.

In an aspect, the HSPCs are allogeneic to the mammal to which they are returned. In an aspect, the HSPCs are autologous to the mammal to which they are returned. In aspects, the HSPCs are isolated from bone marrow. In aspects, the HSPCs are isolated from peripheral blood, e.g., mobilized peripheral blood. In aspects, the mobilized peripheral blood is isolated from a subject who has been administered a G-CSF. In aspects, the mobilized peripheral blood is isolated from a subject who has been administered a mobilization agent other than G-CSF, for example, Plerixafor® (AMD3100). In other aspects, the mobilized peripheral blood is isolated from a subject who has been administered a combination of G-CSF and Plerixafor® (AMD3100)). In aspects, the HSPCs are isolated from umbilical cord blood. In embodiments, the cells are derived from a hemoglobinopathy patient, for example a patient with sickle cell disease or a patient with a thalassemia, e.g., beta-thalassemia.

In further embodiments of the method, the method further comprises, after providing a population of HSPCs (e.g., CD34+ cells), e.g., from a source described above, the step of enriching the population of cells for HSPCs (e.g., CD34+ cells). In embodiments of the method, after said enriching, the population of cells, e.g., HSPCs, is substantially free of CD34– cells.

In embodiments, the population of cells which is returned to the mammal includes at least 70% viable cells. In embodiments, the population of cells which is returned to the mammal includes at least 75% viable cells. In embodiments, the population of cells which is returned to the mammal includes at least 80% viable cells. In embodiments, the population of cells which is returned to the mammal includes at least 85% viable cells. In embodiments, the population of cells which is returned to the mammal includes at least 90% viable cells. In embodiments, the population of cells which is returned to the mammal includes at least 95% viable cells. In embodiments, the population of cells which is returned to the mammal includes at least 99% viable cells. Viability can be determined by staining a representative portion of the population of cells for a cell viability marker, e.g., as known in the art.

In another embodiment, the disclosure provides a method for treating a hemoglobinopathy, e.g., sickle cell disease or beta-thalassemia, or a method for increasing fetal hemoglobin expression in a mammal, e.g., a human, in need thereof, the method comprising the steps of:

a) providing, e.g., harvesting or isolating, a population of HSPCs (e.g., CD34+ cells) of a mammal, e.g., from the bone marrow of a mammal;

b) isolating the CD34+ cells from the population of cells of step a);

c) providing said CD34+ cells ex vivo, and culturing said cells, e.g., in a cell culture medium, in the presence of an effective amount of a composition comprising at least one stem cell expander, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.5 to about 0.75 micromolar, whereby said population of CD34+ cells expands to a greater degree than an untreated population;

d) introducing into the cells of the population CD34+ cells an effective amount of: a composition comprising a Cas9 molecule, e.g., as described herein, and a gRNA molecule, e.g., as described herein, e.g., optionally where the Cas9 molecule and the gRNA molecule are in the form of an RNP, e.g., as described herein, and optionally where said introduction is by electroporation, e.g., as described herein, of said RNP into said cells;

e) causing at least one genetic modification in at least a portion of the cells of the population (e.g., at least a portion of the HSPCs, e.g., CD34+ cells, of the population), whereby an indel, e.g., as described herein, is created at or near the genomic site complementary to the targeting domain of the gRNA introduced in step d);

f) optionally, additionally culturing said cells after said introducing, e.g., in a cell culture medium, in the presence of an effective amount of a composition comprising at least one stem cell expander, e.g., (S)-2-(6-(2-(1H-indol-3-yl) ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.5 to about 0.75 micromolar, such that the cells expand at least 2-fold, e.g., at least 4-fold, e.g., at least 5-fold;

g) cryopreserving said cells; and h) returning the cells to the mammal, wherein,
the cells returned to the mammal comprise cells that 1) maintain the ability to differentiate into cells of the erythroid lineage, e.g., red blood cells; 2) when differentiated into red blood cells, produce an increased level of fetal hemoglobin, e.g., relative to cells unmodified by the gRNA of step e), e.g., produce at least 6 picograms fetal hemoglobin per cell.

In an aspect, the HSPCs are allogeneic to the mammal to which they are returned. In an aspect, the HSPCs are autologous to the mammal to which they are returned. In aspects, the HSPCs are isolated from bone marrow. In aspects, the HSPCs are isolated from peripheral blood, e.g., mobilized peripheral blood. In aspects, the mobilized peripheral blood is isolated from a subject who has been administered a G-CSF. In aspects, the mobilized peripheral blood is isolated from a subject who has been administered a mobilization agent other than G-CSF, for example, Plerixafor® (AMD3100). In other aspects, the mobilized peripheral blood is isolated from a subject who has been administered a combination of G-CSF and Plerixafor® (AMD3100)). In aspects, the HSPCs are isolated from umbilical cord blood. In embodiments, the cells are derived from a hemoglobinopathy patient, for example a patient with sickle cell disease or a patient with a thalassemia, e.g., beta-thalassemia.

In embodiments of the method above, the recited step b) results in a population of cells which is substantially free of CD34– cells.

In further embodiments of the method, the method further comprises, after providing a population of HSPCs (e.g., CD34+ cells), e.g., from a source described above, the population of cells is enriched for HSPCs (e.g., CD34+ cells).

In a further embodiments of these methods, the population of modified HSPCs (e.g., CD34+ stem cells) having the ability to differentiate increased fetal hemoglobin expression is cryopreserved and stored prior to being reintroduced into the mammal. In embodiments, the cryopreserved population of HSPCs having the ability to differentiate into cells of the erythroid lineage, e.g., red blood cells, and/or when differentiated into cells of the erythroid lineage, e.g., red blood cells, produce an increased level of fetal hemoglobin is thawed and then reintroduced into the mammal. In a further embodiment of these methods, the method comprises chemotherapy and/or radiation therapy to remove or reduce the endogenous hematopoietic progenitor or stem cells in the mammal. In a further embodiment of these methods, the method does not comprise a step of chemotherapy and/or radiation therapy to remove or reduce the endogenous hematopoietic progenitor or stem cells in the mammal. In a further embodiment of these methods, the method comprises a chemotherapy and/or radiation therapy to reduce partially (e.g., partial lymphodepletion) the endogenous hematopoietic progenitor or stem cells in the mammal. In embodiments the patient is treated with a fully lymphodepleting dose of busulfan prior to reintroduction of the modified HSPCs to the mammal. In embodiments, the patient is treated with a partially lymphodepleting dose of busulfan prior to reintroduction of the modified HSPCs to the mammal.

In embodiments, the cells are contacted with RNP comprising a Cas9 molecule, e.g., as described herein, complexed with a gRNA to a nondeletional HPFH region, e.g., as described herein (e.g., comprising a targeting domain listed in Table 1.

In embodiments, the stem cell expander is Compound 1. In embodiments, the stem cell expander is Compound 2. In embodiments, the stem cell expander is Compound 3. In embodiments, the stem cell expander is (S)-2-(6-(2-(1H-indol-3-yl)ethylamino)-2-(5-fluoropyridin-3-yl)-9H-purin-9-yl)propan-1-ol. In embodiments, the stem cell expander is (S)-2-(6-(2-(1H-indol-3-yl)ethylamino)-2-(5-fluoropyridin-3-yl)-9H-purin-9-yl)propan-1-ol and is present at a concentration of 2-0.1 micromolar, e.g., 1-0.25 micromolar, e.g., 0.75-0.5 micromolar. In embodiments, the stem cell expander is a molecule described in WO2010/059401 (e.g., the molecule described in Example 1 of WO2010/059401).

In embodiments, the cells, e.g., HSPCs, e.g., as described herein, are cultured ex vivo for a period of about 1 hour to about 15 days, e.g., a period of about 12 hours to about 12 days, e.g., a period of about 12 hours to 4 days, e.g., a period of about 1 day to about 4 days, e.g., a period of about 1 day to about 2 days, e.g., a period of about 1 day or a period of about 2 days, prior to the step of contacting the cells with a CRISPR system, e.g., described herein. In embodiments, said culturing prior to said contacting step is in a composition (e.g., a cell culture medium) comprising a stem cell expander, e.g., described herein, e.g., (S)-2-(6-(2-(1H-indol-3-yl)ethylamino)-2-(5-fluoropyridin-3-yl)-9H-purin-9-yl) propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.25 uM to about 1 uM, e.g., (S)-2-(6-(2-(1H-indol-3-yl)ethylamino)-2-(5-fluoropyridin-3-yl)-9H-purin-9-yl)propan-1-ol at a concentration of about 0.75-0.5 micromolar. In embodiments, the cells are cultured ex vivo for a period of no more than about about 1 day, e.g., no more than about 18, 17, 16, 15, 14, 13, 12, 11, 10, 9, 8, 7, 6, 5, 4, 3, 2, or 1 hour(s) after the step of contacting the cells with a CRISPR system, e.g., described herein, e.g., in a cell culture medium which comprises a stem cell expander, e.g., described herein, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.25 uM to about 1 uM, e.g., (S)-2-(6-(2-(1H-indol-3-yl)ethylamino)-2-(5-fluoropyridin-3-yl)-9H-purin-9-yl) propan-1-ol at a concentration of about 0.75-0.5 micromolar.

In other embodiments, the cells are cultured ex vivo for a period of about 1 hour to about 15 days, e.g., a period of about 12 hours to about 10 days, e.g., a period of about 1 day to about 10 days, e.g., a period of about 1 day to about 5 days, e.g., a period of about 1 day to about 4 days, e.g., a period of about 2 days to about 4 days, e.g., a period of about 2 days, about 3 days or about 4 days, after the step of contacting the cells with a CRISPR system, e.g., described herein, in a cell culture medium, e.g., which comprises a stem cell expander, e.g., described herein, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.25 uM to about 1 uM, e.g., (S)-2-(6-(2-(1H-indol-3-yl)ethylamino)-2-(5-fluoropyridin-3-yl)-9H-purin-9-yl)propan-1-ol at a concentration of about 0.75-0.5 micromolar. In embodiments, the cells are cultured ex vivo (e.g., cultured prior to said contacting step and/or cultured after said contacting step) for a period of about 1 hour to about 20 days, e.g., a period of about 6-12 days, e.g., a period of about 6, about 7, about 8, about 9, about 10, about 11, or about 12 days.

In embodiments, the population of cells comprising the modified HSPCs returned to the mammal comprises at least about 1 million cells (e.g., at least about 1 million CD34+ cells) per kg. In embodiments, the population of cells comprising the modified HSPCs returned to the mammal comprises at least about 2 million cells (e.g., at least about 2 million CD34+ cells) per kg. In embodiments, the population of cells comprising the modified HSPCs returned to the mammal comprises at least about 3 million cells (e.g., at least about 3 million CD34+ cells) per kg. In embodiments, the population of cells comprising the modified HSPCs returned to the mammal comprises at least about 4 million cells (e.g., at least about 4 million CD34+ cells) per kg. In embodiments, the population of cells comprising the modified HSPCs returned to the mammal comprises at least about 5 million cells (e.g., at least about 5 million CD34+ cells) per kg. In embodiments, the population of cells comprising the modified HSPCs returned to the mammal comprises at least about 6 million cells (e.g., at least about 6 million CD34+ cells) per kg. In embodiments, the population of cells comprising the modified HSPCs returned to the mammal comprises at least 1 million cells (e.g., at least 1 million CD34+ cells) per kg. In embodiments, the population of cells comprising the modified HSPCs returned to the mammal comprises at least 2 million cells (e.g., at least 2 million CD34+ cells) per kg. In embodiments, the population of cells comprising the modified HSPCs returned to the mammal comprises at least 3 million cells (e.g., at least 3 million CD34+ cells) per kg. In embodiments, the population of cells comprising the modified HSPCs returned to the mammal comprises at least 4 million cells (e.g., at least 4 million CD34+ cells) per kg. In embodiments, the population of cells comprising the modified HSPCs returned to the mammal comprises at least 5 million cells (e.g., at least 5 million CD34+ cells) per kg. In embodiments, the population of cells comprising the modified HSPCs returned to the mammal comprises at least 6 million cells (e.g., at least 6 million CD34+ cells) per kg. In embodiments, the population of cells comprising the modified HSPCs returned to the mammal comprises about 1 million cells (e.g., about 1 million CD34+ cells) per kg. In embodiments, the population of cells comprising the modified HSPCs returned to the mammal comprises about 2 million cells (e.g., about 2 million CD34+ cells) per kg. In embodiments, the population of cells comprising the modified HSPCs returned to the mammal comprises about 3 million cells (e.g., about 3 million CD34+ cells) per kg. In embodiments, the population of cells comprising the modified HSPCs returned to the mammal comprises about 4 million cells (e.g., about 4 million CD34+ cells) per kg. In embodiments, the population of cells comprising the modified HSPCs returned to the mammal comprises about 5 million cells (e.g., about 5 million CD34+ cells) per kg. In embodiments, the population of cells comprising the modified HSPCs returned to the mammal comprises about 6 million cells (e.g., about 6 million CD34+ cells) per kg. In embodiments, the population of cells comprising the modified HSPCs returned to the mammal comprises about $2 \times 10^6$ cells (e.g., about $2 \times 10^6$ CD34+ cells) per kg body weight of the patient. In embodiments, the population of cells comprising the modified HSPCs returned to the mammal comprises at least $2 \times 10^6$ cells (e.g., about $2 \times 10^6$ CD34+ cells) per kg body weight of the patient. In embodiments, the population of cells comprising the modified HSPCs returned to the mammal comprises between $2 \times 10^6$ cells (e.g., about $2 \times 10^6$ CD34+ cells) per kg body weight of the patient and $10 \times 10^6$ cells (e.g., about $2 \times 10^6$ CD34+ cells) per kg body weight of the patient. In embodiments, the cells comprising the modified cells are infused into the patient. In embodiments, before the cells comprising the modified HSPCs are infused into the patient, the patient is treated with a lymphodepleting therapy, for example, is treated with busulphan, for example is treated with a full lymphodepleting busulphan regimen, or for example is treated with a reduced intensity busulphan lymphodepleting regimen.

In embodiments, any of the methods described above results in the patient having at least 80% of its circulating CD34+ cells comprising an indel at or near the genomic site complementary to the targeting domain of the gRNA molecule used in the method, e.g., as measured at least 15 days, e.g., at least 20, at least 30, at least 40 at least 50 or at least 60 days after reintroduction of the cells into the mammal Without being bound by theory, it has surprisingly been discovered herein that indels and indel patterns (including large deletions) observed when gene editing systems, e.g., CRISPR systems, e.g., CRISPR systems comprising a gRNA molecule targeting the HBG1 and/or HBG2 region, e.g., as described herein, are introduced into HSPCs, and those cells are transplanted into organisms, certain gRNAs produce cells comprising indels and indel patterns (including large indels) that remain detectable in the edited cell population and its progeny, in the organism, and persist for more than 8 weeks, 12 weeks, 16 weeks or 20 weeks. Without being bound by theory, a cell population comprising an indel pattern or particular indel (including large deletion) that persists within a detectible cell population, for example, longer than 16 weeks or longer than 20 weeks after introduction into an organism (e.g., a patient), could be beneficial to producing a longer-term amelioration of a disease or condition, e.g. described herein (e.g., a hemoglobinopathy, e.g., sickle cell disease or a thalassemia) than cells (or their progeny) that upon introduction into an organism or patient lose one or more indels (including large deletions). In embodiments, the persisting indel or indel pattern is associated with upregulated fetal hemoglobin (e.g., in erythroid progeny of said cells). Thus, in embodiments, the present disclosure provides populations of cells, e.g., HSPCs, e.g., as described herein, which comprise one or more indels (including large deletions) which persist (e.g., remain detectible, e.g., in a cell population or its progeny) in the blood and/or bone marrow) for more than 8 weeks, more than 12 weeks, more than 16 weeks or more than 20 weeks after introduction into an organism, e.g., patient.

In embodiments, any of the methods described above results in the patient having at least 20% of its bone marrow CD34+ cells comprising an indel at or near the genomic site complementary to the targeting domain of the gRNA molecule used in the method, e.g., as measured at least 15 days, e.g., at least 20, at least 30, at least 40 at least 50 or at least 60 days after reintroduction of the cells into the mammal.

In embodiments, the HSPCs that are reintroduced into the mammal are able to differentiate in vivo into cells of the erythroid lineage, e.g., red blood cells, and said differentiated cells exhibit increased fetal hemoglobin levels, e.g., produce at least 6 picograms fetal hemoglobin per cell, e.g., at least 7 picograms fetal hemoglobin per cell, at least 8 picograms fetal hemoglobin per cell, at least 9 picograms fetal hemoglobin per cell, at least 10 picograms fetal hemoglobin per cell, e.g., between about 9 and about 10 picograms fetal hemoglobin per cell, e.g., such that the hemoglobinopathy is treated the mammal.

It will be understood that when a cell is characterized as having increased fetal hemoglobin, that includes embodiments in which a progeny, e.g., a differentiated progeny, of that cell exhibits increased fetal hemoglobin. For example, in the methods described herein, the altered or modified CD34+ cell (or cell population) may not express increased fetal hemoglobin, but when differentiated into cells of erythroid lineage, e.g., red blood cells, the cells express increased fetal hemoglobin, e.g., increased fetal hemoglobin relative to an unmodified or unaltered cell under similar conditions.

XII. Culture Methods and Methods of Manufacturing Cells

The disclosure provides methods of culturing cells, e.g., HSPCs, e.g., hematopoietic stem cells, e.g., CD34+ cells modified, or to be modified, with the gRNA molecules described herein.

DNA Repair Pathway Inhibitors

Without being bound by theory, it is believed that the pattern of indels produced by a given gRNA molecule at a particular target sequence is a product of each of the active DNA repair mechanisms within the cell (e.g., non-homologous end joining, microhomology-mediated end joining, etc.). Without being bound by theory, it is believed that a particularly favorable indel may be selected for or enriched for by contacting the cells to be edited with an inhibitor of a DNA repair pathway that does not produce the desired indel. Thus, the gRNA molecules, CRISPR systems, methods and other aspects of the invention may be performed in combination with such inhibitors. Examples of such inhibitors include those described in, e.g., WO2014/130955, the contents of which are hereby incorporated by reference in their entirety. In embodiment, the inhibitor is a DNAPKc inhibitor, e.g., NU7441.

Stem Cell Expanders

In one aspect the invention relates to culturing the cells, e.g., HSPCs, e.g., CD34+ cells modified, or to be modified, with the gRNA molecules described herein, with one or more agents that result in an increased expansion rate, increased expansion level, or increased engraftment relative to cells not treated with the agent. Such agents are referred to herein as stem cell expanders.

In an aspect, the one or more agents that result in an increased expansion rate or increased expansion level, relative to cells not treated with the agent, e.g., the stem cell expander, comprises an agent that is an inhibitor of the aryl hydrocarbon receptor (AHR) pathway. In aspects, the stem cell expander is a compound disclosed in WO2013/110198 or a compound disclosed in WO2010/059401, the contents of which are incorporated by reference in their entirety.

In one aspect, the one or more agents that result in an increased expansion rate or increased expansion level, relative to cells not treated with the agent, is a pyrimido[4,5-b] indole derivative, e.g., as disclosed in WO2013/110198, the contents of which are hereby incorporated by reference in their entirety. In one embodiment the agent is compound 1 ((1r,4r)—N$^1$-(2-benzyl-7-(2-methyl-2H-tetrazol-5-yl)-9H-pyrimido[4,5-b]indol-4-yl)cyclohexane-1,4-diamine):

Compound 1

In another aspect, the agent is Compound 2 (methyl 4-(3-piperidin-1-ylpropylamino)-9H-pyrimido[4,5-b]indole-7-carboxylate):

Compound 2

In another aspect, the one or more agents that result in an increased expansion rate or increased expansion level, relative to cells not treated with the agent, is an agent disclosed in WO2010/059401, the contents of which are hereby incorporated by reference in their entirety.

In one embodiment, the stem cell expander is compound 3: 4-(2-(2-(benzo[b]thiophen-3-yl)-9-isopropyl-9H-purin-6-ylamino)ethyl)phenol, i.e., is the compound from example 1 of WO2010/059401, having the following structure:

Compound 3

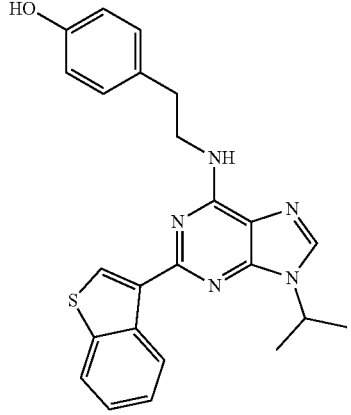

In another aspect, the stem cell expander is (S)-2-(6-(2-(1H-indol-3-yl)ethylamino)-2-(5-fluoropyridin-3-yl)-9H-purin-9-yl)propan-1-ol ((S)-2-(6-(2-(1H-indol-3-yl)ethylamino)-2-(5-fluoropyridin-3-yl)-9H-purin-9-yl)propan-1-ol, i.e., is the compound 157S according to WO2010/059401), having the following structure:

(S)-2-(6-(2-(1H-indol-3-yl)ethylamino)-2-(5-fluoropyridin-3-yl)-9H-purin-9-yl)propan-1-ol

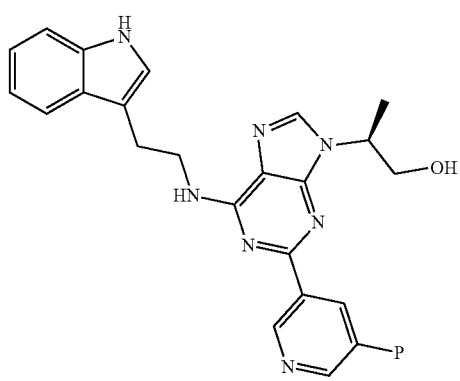

In embodiments the population of HSPCs is contacted with the stem cell expander, e.g., compound 1, compound 2, compound 3, (S)-2-(6-(2-(1H-indol-3-yl)ethylamino)-2-(5-fluoropyridin-3-yl)-9H-purin-9-yl)propan-1-ol, or combinations thereof (e.g., a combination of compound 1 and (S)-2-(6-(2-(1H-indol-3-yl)ethylamino)-2-(5-fluoropyridin-3-yl)-9H-purin-9-yl)propan-1-ol) before introduction of the CRISPR system (e.g., gRNA molecule and/or Cas9 molecule of the invention) to said HSPCs. In embodiments, the population of HSPCs is contacted with the stem cell expander, e.g., compound 1, compound 2, compound 3, (S)-2-(6-(2-(1H-indol-3-yl)ethylamino)-2-(5-fluoropyridin-3-yl)-9H-purin-9-yl)propan-1-ol, or combinations thereof (e.g., a combination of compound 1 and (S)-2-(6-(2-(1H-indol-3-yl)ethylamino)-2-(5-fluoropyridin-3-yl)-9H-purin-9-yl)propan-1-ol), after introduction of the CRISPR system (e.g., gRNA molecule and/or Cas9 molecule of the invention) to said HSPCs. In embodiments, the population of HSPCs is contacted with the stem cell expander, e.g., compound 1, compound 2, compound 3, (S)-2-(6-(2-(1H-indol-3-yl)ethylamino)-2-(5-fluoropyridin-3-yl)-9H-purin-

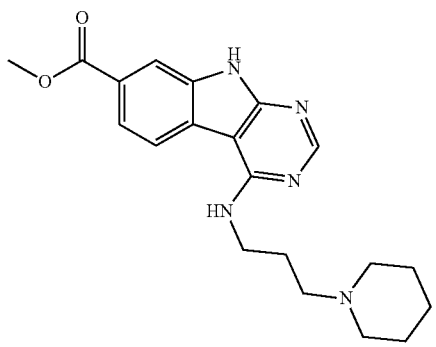

9-yl)propan-1-ol, or combinations thereof (e.g., a combination of compound 1 and (S)-2-(6-(2-(1H-indol-3-yl)ethylamino)-2-(5-fluoropyridin-3-yl)-9H-purin-9-yl)propan-1-ol), both before and after introduction of the CRISPR system (e.g., gRNA molecule and/or Cas9 molecule of the invention) to said HSPCs.

In embodiments, the stem cell expander is present in an effective amount to increase the expansion level of the HSPCs, relative to HSPCs in the same media but for the absence of the stem cell expander. In embodiments, the stem cell expander is present at a concentration ranging from about 0.01 to about 10 uM, e.g., from about 0.1 uM to about 1 uM. In embodiments, the stem cell expander is present in the cell culture medium at a concentration of about 1 uM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 25 nM, or about 10 nM. In embodiments, the stem cell expander is present at a concentration ranging from about 500 nM to about 750 nM.

In embodiments, the stem cell expander is (S)-2-(6-(2-(1H-indol-3-yl)ethylamino)-2-(5-fluoropyridin-3-yl)-9H-purin-9-yl)propan-1-ol, which is present in the cell culture medium at a concentration ranging from about 0.01 to about 10 micromolar (uM). In embodiments, the stem cell expander is (S)-2-(6-(2-(1H-indol-3-yl)ethylamino)-2-(5-fluoropyridin-3-yl)-9H-purin-9-yl)propan-1-ol, which is present in the cell culture medium at a concentration ranging from about 0.1 to about 1 micromolar (uM). In embodiments, the stem cell expander is (S)-2-(6-(2-(1H-indol-3-yl)ethylamino)-2-(5-fluoropyridin-3-yl)-9H-purin-9-yl)propan-1-ol, which is present in the cell culture medium at a concentration of about 0.75 micromolar (uM). In embodiments, the stem cell expander is (S)-2-(6-(2-(1H-indol-3-yl)ethylamino)-2-(5-fluoropyridin-3-yl)-9H-purin-9-yl)propan-1-ol, which is present in the cell culture medium at a concentration of about 0.5 micromolar (uM). In embodiments of any of the foregoing, the cell culture medium additionally comprises compound 1.

In embodiments, the stem cell expander is a mixture of compound 1 and (S)-2-(6-(2-(1H-indol-3-yl)ethylamino)-2-(5-fluoropyridin-3-yl)-9H-purin-9-yl)propan-1-ol.

In embodiments, the cells of the invention are contacted with one or more stem cell expander molecules for a sufficient time and in a sufficient amount to cause a 2 to 10,000-fold expansion of CD34+ cells, e.g., a 2-1000-fold expansion of CD34+ cells, e.g., a 2-100-fold expansion of CD34+ cells, e.g., a 20-200-fold expansion of CD34+ cells. As described herein, the contacting with the one or more stem cell expanders may be before the cells are contacted with a CRISPR system, e.g., as described herein, after the cells are contacted with a CRISPR system, e.g., as described herein, or a combination thereof. In an embodiment, the cells are contacted with one or more stem cell expander molecules, e.g., (S)-2-(6-(2-(1H-indol-3-yl)ethylamino)-2-(5-fluoropyridin-3-yl)-9H-purin-9-yl)propan-1-ol, for a sufficient time and in a sufficient amount to cause at least a 2-fold expansion of CD34+ cells, e.g., CD34+ cells comprising an indel at or near the target site having complementarity to the targeting domain of the gRNA of the CRISPR/Cas9 system introduced into said cell. In an embodiment, the cells are contacted with one or more stem cell expander molecules, e.g., (S)-2-(6-(2-(1H-indol-3-yl)ethylamino)-2-(5-fluoropyridin-3-yl)-9H-purin-9-yl)propan-1-ol, for a sufficient time and in a sufficient amount to cause at least a 4-fold expansion of CD34+ cells, e.g., CD34+ cells comprising an indel at or near the target site having complementarity to the targeting domain of the gRNA of the CRISPR/Cas9 system introduced into said cell. In an embodiment, the cells are contacted with one or more stem cell expander molecules, e.g., (S)-2-(6-(2-(1H-indol-3-yl)ethylamino)-2-(5-fluoropyridin-3-yl)-9H-purin-9-yl)propan-1-ol, for a sufficient time and in a sufficient amount to cause at least a 5-fold expansion of CD34+ cells, e.g., CD34+ cells comprising an indel at or near the target site having complementarity to the targeting domain of the gRNA of the CRISPR/Cas9 system introduced into said cell. In an embodiment, the cells are contacted with one or more stem cell expander molecules for a sufficient time and in a sufficient amount to cause at least a 10-fold expansion of CD34+ cells. In an embodiment, the cells are contacted with one or more stem cell expander molecules for a sufficient time and in a sufficient amount to cause at least a 20-fold expansion of CD34+ cells. In an embodiment, the cells are contacted with one or more stem cell expander molecules for a sufficient time and in a sufficient amount to cause at least a 30-fold expansion of CD34+ cells. In an embodiment, the cells are contacted with one or more stem cell expander molecules for a sufficient time and in a sufficient amount to cause at least a 40-fold expansion of CD34+ cells. In an embodiment, the cells are contacted with one or more stem cell expander molecules for a sufficient time and in a sufficient amount to cause at least a 50-fold expansion of CD34+ cells. In an embodiment, the cells are contacted with one or more stem cell expander molecules for a sufficient time and in a sufficient amount to cause at least a 60-fold expansion of CD34+ cells. In embodiments, the cells are contacted with the one or more stem cell expanders for a period of about 1-60 days, e.g., about 1-50 days, e.g., about 1-40 days, e.g., about 1-30 days, e.g., 1-20 days, e.g., about 1-10 days, e.g., about 7 days, e.g., about 1-5 days, e.g., about 2-5 days, e.g., about 2-4 days, e.g., about 2 days or, e.g., about 4 days.

In embodiments, the cells, e.g., HSPCs, e.g., as described herein, are cultured ex vivo for a period of about 1 hour to about 10 days, e.g., a period of about 12 hours to about 5 days, e.g., a period of about 12 hours to 4 days, e.g., a period of about 1 day to about 4 days, e.g., a period of about 1 day to about 2 days, e.g., a period of about 1 day or a period of about 2 days, prior to the step of contacting the cells with a CRISPR system, e.g., described herein. In embodiments, said culturing prior to said contacting step is in a composition (e.g., a cell culture medium) comprising a stem cell expander, e.g., described herein, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.25 uM to about 1 uM, e.g., (S)-2-(6-(2-(1H-indol-3-yl)ethylamino)-2-(5-fluoropyridin-3-yl)-9H-purin-9-yl)propan-1-ol at a concentration of about 0.75-0.5 micromolar. In embodiments, the cells are cultured ex vivo for a period of no more than about about 1 day, e.g., no more than about 18, 17, 16, 15, 14, 13, 12, 11, 10, 9, 8, 7, 6, 5, 4, 3, 2, or 1 hour(s) after the step of contacting the cells with a CRISPR system, e.g., described herein, e.g., in a cell culture medium which comprises a stem cell expander, e.g., described herein, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.25 uM to about 1 uM, e.g., (S)-2-(6-(2-(1H-indol-3-yl)ethylamino)-2-(5-fluoropyridin-3-yl)-9H-purin-9-yl)propan-1-ol at a concentration of about 0.75-0.5 micromolar.

In other embodiments, the cells are cultured ex vivo for a period of about 1 hour to about 14 days, e.g., a period of about 12 hours to about 10 days, e.g., a period of about 1 day to about 10 days, e.g., a period of about 1 day to about 5 days, e.g., a period of about 1 day to about 4 days, e.g., a period of about 2 days to about 4 days, e.g., a period of about 2 days, about 3 days or about 4 days, after the step of contacting the cells with a CRISPR system, e.g., described herein, in a cell culture medium, e.g., which comprises a stem cell expander, e.g., described herein, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of about 0.25 uM to about 1 uM, e.g., (S)-2-(6-(2-(1H-indol-3-yl)ethylamino)-2-(5-fluoropyridin-3-yl)-9H-purin-9-yl)propan-1-ol at a concentration of about 0.75-0.5 micromolar.

In embodiments, the cell culture medium is a chemically defined medium. In embodiments, the cell culture medium may additionally contain, for example, StemSpan SFEM (StemCell Technologies; Cat no. 09650). In embodiments, the cell culture medium may alternatively or additionally contain, for example, HSC Brew, GMP (Miltenyi). In embodiments, the cell culture media is serum free. In embodiments, the media may be supplemented with thrombopoietin (TPO), human Flt3 ligand (Flt-3L), human stem cell factor (SCF), human interleukin-6, L-glutamine, and/or penicillin/streptomycin. In embodiments, the media is supplemented with thrombopoietin (TPO), human Flt3 ligand (Flt-3L), human stem cell factor (SCF), human interleukin-6, and L-glutamine. In other embodiments, the media is supplemented with thrombopoietin (TPO), human Flt3 ligand (Flt-3L), human stem cell factor (SCF), and human interleukin-6. In other embodiments the media is supplemented with thrombopoietin (TPO), human Flt3 ligand (Flt-3L), and human stem cell factor (SCF), but not human interleukin-6. In other embodiments, the media is supplemented with human Flt3 ligand (Flt-3L), human stem cell factor (SCF), but not human thrombopoietin (TPO) or human interleukin-6. When present in the medium, the thrombopoietin (TPO), human Flt3 ligand (Flt-3L), human stem cell factor (SCF), human interleukin-6, and/or L-glutamine are each present in a concentration ranging from about 1 ng/mL to about 1000 ng/mL, e.g., a concentration ranging from about 10 ng/mL to about 500 ng/mL, e.g., a concentration ranging from about 10 ng/mL to about 100 ng/mL, e.g., a concentration ranging from about 25 ng/mL to about 75 ng/mL, e.g., a concentration of about 50 ng/mL. In embodiments, each of the supplemented components is at the same concentration. In other embodiments, each of the supplemented components is at a different concentration. In an embodiment, the medium comprises StemSpan SFEM (StemCell Technologies; Cat no. 09650), 50 ng/mL of thrombopoietin (Tpo), 50 ng/mL of human Flt3 ligand (Flt-3L), 50 ng/mL of human stem cell factor (SCF), and 50 ng/mL of human interleukin-6 (IL-6). In an embodiment, the medium comprises StemSpan SFEM (StemCell Technologies; Cat no. 09650), 50 ng/mL of thrombopoietin (Tpo), 50 ng/mL of human Flt3 ligand (Flt-3L), and 50 ng/mL of human stem cell factor (SCF), and does not comprise IL-6. In embodiments, the media further comprises a stem cell expander, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of 0.75 µM. In embodiments, the media further comprises a stem cell expander, e.g., (S)-2-(6-(2-(1H-indol-3-yl)ethylamino)-2-(5-fluoropyridin-3-yl)-9H-purin-9-yl)propan-1-ol, e.g., (S)-2-(6-(2-(1H-indol-3-yl)ethylamino)-2-(5-fluoropyridin-3-yl)-9H-purin-9-yl)propan-1-ol at a concentration of 0.5 µM. In embodiments, the media further comprises 1% L-glutamine and 2% penicillin/streptomycin. In embodiments, the cell culture medium is serum free.

XII. Combination Therapy

The present disclosure contemplates the use of the gRNA molecules described herein, or cells (e.g., hematopoietic stem cells, e.g., CD34+ cells) modified with the gRNA molecules described herein, in combination with one or more other therapeutic modalities and/or agents. Thus, in addition to the use of the gRNA molecules or cells modified with the gRNA molecules described herein, one may also administer to the subject one or more "standard" therapies for treating hemoglobinopathies.

The one or more additional therapies for treating hemoglobinopathies may include, for example, additional stem cell transplantation, e.g., hematopoietic stem cell transplantation. The stem cell transplantation may be allogeneic or autologous.

The one or more additional therapies for treating hemoglobinopathies may include, for example, blood transfusion and/or iron chelation (e.g., removal) therapy. Known iron chelation agents include, for example, deferoxamine and deferasirox.

The one or more additional therapies for treating hemoglobinopathies may include, for example, folic acid supplements, or hydroxyurea (e.g., 5-hydroxyurea). The one or more additional therapies for treating hemoglobinopathies may be hydroxyurea. In embodiments, the hydroxyurea may be administered at a dose of, for example, 10-35 mg/kg per day, e.g., 10-20 mg/kg per day. In embodiments, the hydroxyurea is adminstered at a dose of 10 mg/kg per day. In embodiments, the hydroxyurea is adminstered at a dose of 10 mg/kg per day. In embodiments, the hydroxyurea is adminstered at a dose of 20 mg/kg per day. In embodiments, the hydroxyurea is administered before and/or after the cell (or population of cells), e.g., CD34+ cell (or population of cells) of the invention, e.g., as described herein.

The one or more additional therapeutic agents may include, for example, an anti-p-selectin antibody, e.g., SelG1 (Selexys). P-selectin antibodies are described in, for example, PCT publication WO1993/021956, PCT publication WO1995/034324, PCT publication WO2005/100402, PCT publication WO2008/069999, US patent application publication US2011/0293617, U.S. Pat. Nos. 5,800,815, 6,667,036, 8,945,565, 8,377,440 and 9,068,001, the contents of each of which are incorporated herein in their entirety.

The one or more additional agents may include, for example, a small molecule which upregulates fetal hemoglobin. Examples of such molecules include TN1 (e.g., as described in Nam, T. et al., ChemMedChem 2011, 6, 777-780, DOI: 10.1002/cmdc.201000505, herein incorporated by reference).

The one or more additional therapies may also include irradiation or other bone marrow ablation therapies known in the art. An example of such a therapy is busulfan. Such additional therapy may be performed prior to introduction of the cells of the invention into the subject. In an embodiment the methods of treatment described herein (e.g., the methods of treatment that include administration of cells (e.g., HSPCs) modified by the methods described herein (e.g., modified with a CRISPR system described herein, e.g., to increase HbF production)), the method does not include the step of bone marrow ablation. In embodiments, the methods include a partial bone marrow ablation step.

The therapies described herein (e.g., comprising administering a population of HSPCs, e.g., HSPCs modified using a CRISPR system described herein) may also be combined with an additional therapeutic agent. In an embodiment, the additional therapeutic agent is an HDAC inhibitor, e.g., panobinostat. In an embodiment, the additional therapeutic is a compound described in PCT Publication No. WO2014/150256, e.g., a compound described in Table 1 of WO2014/150256, e.g., GBT440. Other examples of HDAC inhibitors include, for example, suberoylanilide hydroxamic acid (SAHA). The one or more additional agents may include, for example, a DNA methylation inhibitor.

Such agents have been shown to increase the HbF induction in cells having reduced BCL11a activity (e.g., Jian Xu et al, Science 334, 993 (2011); DOI: 0.1126/science.1211053, herein incorporated by reference). Other HDAC inhibitors include any HDAC inhibitor known in the art, for example, trichostatin A, HC toxin, DACI-2, FK228, DACI-14, depudicin, DACI-16, tubacin, NK57, MAZ1536, NK125, Scriptaid, Pyroxamide, MS-275, ITF-2357, MCG-D0103, CRA-024781, CI-994, and LBH589 (see, e.g., Bradner J E, et al., PNAS, 2010 (vol. 107:28), 12617-12622, herein incorporated by reference in its entirety).

The gRNA molecules described herein, or cells (e.g., hematopoietic stem cells, e.g., CD34+ cells) modified with the gRNA molecules described herein, and the co-therapeutic agent or co-therapy can be administered in the same formulation or separately. In the case of separate administration, the gRNA molecules described herein, or cells modified with the gRNA molecules described herein, can be administered before, after or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

XIII. Modified Nucleosides, Nucleotides, and Nucleic Acids

Modified nucleosides and modified nucleotides can be present in nucleic acids, e.g., particularly gRNA, but also other forms of RNA, e.g., mRNA, RNAi, or siRNA. As described herein "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:

(i) alteration, e.g., replacement, of one or both of the non-linking phosphate oxygens and/or of one or more of the linking phosphate oxygens in the phosphodiester backbone linkage;

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring nucleobase, including with a non-canonical nucleobase;

(v) replacement or modification of the ribose-phosphate backbone;

(vi) modification of the 3' end or 5' end of the oligonucleotide, e.g., removal, modification or replacement of a terminal phosphate group or conjugation of a moiety, cap or linker; and (vii) modification or replacement of the sugar.

The modifications listed above can be combined to provide modified nucleosides and nucleotides that can have two, three, four, or more modifications. For example, a modified nucleoside or nucleotide can have a modified sugar and a modified nucleobase. In an embodiment, every base of a gRNA is modified, e.g., all bases have a modified phosphate group, e.g., all are phosphorothioate groups. In an embodiment, all, or substantially all, of the phosphate groups of a unimolecular or modular gRNA molecule are replaced with phosphorothioate groups. In embodiments, one or more of the five 3'-terminal bases and/or one or more of the five 5'-terminal bases of the gRNA are modified with a phosphorothioate group.

In an embodiment, modified nucleotides, e.g., nucleotides having modifications as described herein, can be incorporated into a nucleic acid, e.g., a "modified nucleic acid." In some embodiments, the modified nucleic acids comprise one, two, three or more modified nucleotides. In some embodiments, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In some embodiments, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In some embodiments, the modified nucleosides, modified nucleotides, and modified nucleic acids described herein can disrupt binding of a major groove interacting partner with the nucleic acid.

In some embodiments, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "alkenyl" refers to an aliphatic group containing at least one double bond. As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

Phosphate Backbone Modifications

The Phosphate Group

In some embodiments, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In some embodiments, the modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidites, alkyl or aryl phosphonates and phosphotriesters. In some embodiments, one of the non-bridging phosphate oxygen atoms in the phosphate backbone moiety can be replaced by any of the following groups: sulfur (S), selenium (Se), BR$_3$ (wherein R can be, e.g., hydrogen, alkyl, or aryl), C (e.g., an alkyl group, an aryl group, and the like), H, NR$_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In some embodiments, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidites), sulfur (bridged phosphorothioates) and carbon (bridged methylenephosphonates). The replacement can occur at either linking oxygen or at both of the linking oxygens.

Replacement of the Phosphate Group

The phosphate group can be replaced by non-phosphorus containing connectors. In some embodiments, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetyl, oxime, methyleneimino, methylenemethylimino, methylenehydrazo, methylenedimethylhydrazo and methyleneoxymethylimino.

Replacement of the Ribophosphate Backbone

Scaffolds that can mimic nucleic acids can also be constructed wherein the phosphate linker and ribose sugar are replaced by nuclease resistant nucleoside or nucleotide surrogates. In some embodiments, the nucleobases can be tethered by a surrogate backbone. Examples can include, without limitation, the morpholino, cyclobutyl, pyrrolidine and peptide nucleic acid (PNA) nucleoside surrogates.

Sugar Modifications

The modified nucleosides and modified nucleotides can include one or more modifications to the sugar group. For example, the 2' hydroxyl group (OH) can be modified or replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In some embodiments, the "oxy"-2' hydroxyl group modification can include "locked" nucleic acids (LNA) in which the 2' hydroxyl can be connected, e.g., by a Ci-$_6$ alkylene or Cj-6 heteroalkylene bridge, to the 4' carbon of the same ribose sugar, where exemplary bridges can include methylene, propylene, ether, or amino bridges; O-amino (wherein amino can be, e.g., NH$_2$; alkylamino, dialkylamino, heterocyclyl, arylamino, diarylamino, heteroarylamino, or diheteroarylamino, ethylenediamine, or polyamino) and aminoalkoxy, $0(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH2CH_2$— amino (wherein amino can be, e.g., as described herein), —NHC(0)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the Γ position on the sugar, e.g., alpha-nucleosides. The modified nucleic acids can also include "abasic" sugars, which lack a nucleobase at C—. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In some embodiments, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with a-L-threofuranosyl-(3'-→2')).

Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In some embodiments, the nucleobase can include, for example, naturally-occurring and synthetic derivatives of a base.

Uracil

In some embodiments, the modified nucleobase is a modified uracil. Exemplary nucleobases and nucleosides having a modified uracil include without limitation pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s2U$), 5-aminomethyl-2-thio-uridine ($nm^5s2U$), 5-methylaminomethyl-uridine ($mnm^5U$), 5-methylaminomethyl-2-thio-uridine ($mnm^5s2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine (cmnm \s2U), 5-propynyl-uridine, 1-propynyl-pseudouridine, 5-taurinomethyl-uridine ($xcm^5U$), 1-taurinomethyl-pseudouridine, 5-taurinomethyl-2-thio-uridine($Trn^5s2U$), 1-taurinomethyl-4-thio-pseudouridine, 5-methyl-uridine ($m^5U$, i.e., having the nucleobase deoxythymine), 1-methyl-pseudouridine (ιτι'ψ). 5-methyl-2-thio-uridine ($m^5s2U$), 1-methyl-4-thio-pseudouridine (m's \l/), 4-thio-1-methyl-pseudouridine, 3-methyl-pseudouridine (m'V), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine ($acp^3U$), 1-methyl-3-(3-amino-3-carboxypropy pseudouridine 5-(isopentenylaminomethyl)uridine ($inm^5U$), 5-(isopentenylaminomethyp-2-thio-uridine ($inm^5s2U$), a-thio-uridine, 2'-0-methyl-uridine (Urn), 5,2'-0-dimethyl-uridine ($m^5Um$), 2'-0-methyl-pseudouridine (ψπι), 2-thio-2'-0-methyl-uridine (s2Um), 5-methoxycarbonylmethyl-2'-0-methyl-uridine ($mcm^5Um$), 5-carbamoylmethyl-2'-0-methyl-uridine ($ncm^5Um$), 5-carboxymethylaminomethyl-2'-0-methyl-uridine ($cmnm^5Um$), 3,2'-0-dimethyl-uridine ($m^3Um$), 5-(isopentenylaminomethyl)-2'-0-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

Cytosine

In some embodiments, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine ($m^3C$), N4-acetyl-cytidine (act), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k^2C$), a-thio-cytidine, 2'-0-methyl-cytidine (Cm), 5,2'-0-dimethyl-cytidine ($m^5Cm$), N4-acetyl-2'-0-methyl-cytidine ($ac^4Cm$), N4,2'-0-dimethyl-cytidine ($m^4Cm$), 5-formyl-2'-0- methyl-cytidine (f⁵Cm), N4,N4,2'-0-trimethyl-cytidine (m⁴₂Cm), 1-thio-cytidine, 2'-F-ara-cytidine, 2'-F-cytidine, and 2'-OH-ara-cytidine.

Adenine

In some embodiments, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m'A), 2-methyl-adenine (m A), N6-methyl-adenosine (m⁶A), 2-methylthio-N6-methyl-adenosine (ms2 m⁶A), N6-isopentenyl-adenosine (i⁶A), 2-methylthio-N6-isopentenyl-adenosine (ms²i⁶A), N6-(cis-hydroxyisopentanyl)adenosine (io⁶A), 2-methylthio-N6-(cis-hydroxyisopentanyl)adenosine (ms2io⁶A), N6-glycinylcarbamoyl-adenosine (g⁶A), N6-threonylcarbamoyl-adenosine (t⁶A), N6-methyl-N6-threonylcarbamoyl-adenosine (m⁶t⁶A), 2-methylthio-N6-threonylcarbamoyl-adenosine (ms2g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms2hn⁶A), N6-acetyl-adenosine (ac⁶A), 7-methyl-adenine, 2-methylthio-adenine, 2-methoxy-adenine, a-thio-adenosine, 2'-0-methyl-adenosine (Am), N⁶,2'-0-dimethyl-adenosine (m⁵Am), N⁶-Methyl-2'-deoxyadenosine, N6,N6,2'-0-trimethyl-adenosine (m⁶₂Am), 1,2'-0-dimethyl-adenosine (m' Am), 2'-0-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

Guanine

In some embodiments, the modified nucleobase is a modified guanine. Exemplary nucleobases and nucleosides having a modified guanine include without limitation inosine (I), 1-methyl-inosine (m'l), wyosine (imG), methylwyosine (mimG), 4-demethyl-wyo"sine (imG-14), isowyosine (imG2), wybutosine (yW), peroxywybutosine (o₂yW), hydroxywybutosine (OHyW), undemriodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ₀), 7-aminomethyl-7-deaza-guanosine (preQi), archaeosine (G), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m'G), N2-methyl-guanosine (m²G), N2,N2-dimethyl-guanosine (m²₂G), N2,7-dimethyl-guanosine (m²,7G), N2, N2,7-dimethyl-guanosine (m²,2,7G), 8-oxo-guanosine, 7-methyl-8-oxo-guanosine, 1-meth thio-guanosine, N2-methyl-6-thio-guanosine, N2,N2-dimethyl-6-thio-guanosine, a-thio-guanosine, 2'-0-methyl-guanosine (Gm), N2-methyl-2'-0-methyl-guanosine (m³⁄4m), N2,N2-dimethyl-2'-0-methyl-guanosine (m²₂Gm), 1-methyl-2'-0-methyl-guanosine (m'Gm), N2,7-dimethyl-2'-0-methyl-guanosine (m²,7Gm), 2'-0-methyl-inosine (Im), 1,2'-0-dimethyl-inosine (m'lm), 0⁶-phenyl-2'-deoxyinosine, 2'-0-ribosylguanosine (phosphate) (Gr(p)), 1-thio-guanosine, 0⁶-methyl]-guanosine, 0⁶-Methyl-2'-deoxyguanosine, 2'-F-ara-guanosine, and 2'-F-guanosine.

Modified gRNAs

In some embodiments, the modified nucleic acids can be modified gRNAs. In some embodiments, gRNAs can be modified at the 3' end. In this embodiment, the gRNAs can be modified at the 3' terminal U ribose. For example, the two terminal hydroxyl groups of the U ribose can be oxidized to aldehyde groups and a concomitant opening of the ribose ring to afford a modified nucleoside, wherein U can be an unmodified or modified uridine.

In another embodiment, the 3' terminal U can be modified with a 2' 3' cyclic phosphate, wherein U can be an unmodified or modified uridine. In some embodiments, the gRNA molecules may contain 3' nucleotides which can be stabilized against degradation, e.g., by incorporating one or more of the modified nucleotides described herein. In this embodiment, e.g., uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein. In some embodiments, deaza nucleotides, e.g., 7-deaza-adenosine, can be incorporated into the gRNA. In some embodiments, 0- and N-alkylated nucleotides, e.g., N6-methyl adenosine, can be incorporated into the gRNA. In some embodiments, sugar-modified ribonucleotides can be incorporated, e.g., wherein the 2' OH— group is replaced by a group selected from H, —OR, —R (wherein R can be, e.g., methyl, alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH₂; alkylamino, dialkylamino, heterocyclyl, acylamino, diarylamino, heteroarylamino, diheteroarylamino, or amino acid); or cyano (—CN). In some embodiments, the phosphate backbone can be modified as described herein, e.g., with a phosphothioate group. In some embodiments, the nucleotides in the overhang region of the gRNA can each independently be a modified or unmodified nucleotide including, but not limited to 2'-sugar modified, such as, 2-F 2'-0-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In an embodiment, a one or more or all of the nucleotides in single stranded overhang of an RNA molecule, e.g., a gRNA molecule, are deoxynucleotides.

Pharmaceutical Compositions

Pharmaceutical compositions of the present invention may comprise a gRNA molecule described herein, e.g., a plurality of gRNA molecules as described herein, or a cell (e.g., a population of cells, e.g., a population of hematopoietic stem cells, e.g., of CD34+ cells) comprising one or more cells modified with one or more gRNA molecules described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, mouse antibodies, pooled human serum, bovine serum albumin, bovine serum, culture media components, unwanted CRISPR system components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one aspect, the compositions of the present invention are administered to a patient by intradermal or subcutaneous injection. In one aspect, the cell compositions of the present invention are administered by i.v. injection.

The dosage of the above treatments to be administered to a patient will vary with the precise nature of the condition being treated and the recipient of the treatment. The scaling of dosages for human administration can be performed according to art-accepted practices.

Cells

The invention also relates to cells comprising a gRNA molecule of the invention, or nucleic acid encoding said gRNA molecules.

In an aspect the cells are cells made by a process described herein.

In embodiments, the cells are hematopoietic stem cells (e.g., hematopoietic stem and progenitor cells; HSPCs), for example, CD34+ stem cells. In embodiments, the cells are CD34+/CD90+ stem cells. In embodiments, the cells are CD34+/CD90− stem cells. In embodiments, the cells are human hematopoietic stem cells. In embodiments, the cells are autologous. In embodiments, the cells are allogeneic.

In embodiments, the cells are derived from bone marrow, e.g., autologous bone marrow. In embodiments, the cells are derived from peripheral blood, e.g., mobilized peripheral blood, e.g., autologous mobilized peripheral blood. In embodiments employing mobilized peripheral blood, the cells are isolated from patients who have been administered a mobilization agent. In embodiments, the mobilization agent is G-CSF. In embodiments, the mobilization agent is Plerixafor® (AMD3100). In embodiments, the mobilization agent comprises a combination of G-CSF and Plerixafor® (AMD3100)). In embodiments, the cells are derived from umbilical cord blood, e.g., allogeneic umbilical cord blood. In embodiments, the cells are derived from a hemoglobinopathy patient, for example a patient with sickle cell disease or a patient with a thalassemia, e.g., beta-thalassemia.

In embodiments, the cells are mammalian. In embodiments, the cells are human. In embodiments, the cells are derived from a hemoglobinopathy patient, for example a patient with sickle cell disease or a patient with a thalassemia, e.g., beta-thalassemia.

In an aspect, the invention provides a cell comprising a modification or alteration, e.g., an indel, at or near (e.g., within 20, 19, 18, 17, 16, 15, 14, 13, 12, 11, 10, 9, 8, 7, 6, 5, 4, 3, 2 or 1 nucleotides of) a nucleic acid sequence having complementarity to a gRNA molecule or gRNA molecules, e.g., as described herein, introduced into said cells, e.g., as part of a CRISPR system as described herein. In embodiments, the cell is a CD34+ cell. In embodiments, the altered or modified cell, e.g., CD34+ cell, maintains the ability to differentiate into cells of multiple lineages, e.g., maintains the ability to differentiate into cells of the erythroid lineage. In embodiments, the altered or modified cell, e.g., CD34+ cell, has undergone or is able to undergo at least 2, at least 3, at least 4, at least 5, at least 6, at least 7, at least 8, at least 9 or at least 10 or more doublings in culture, e.g., in culture comprising a stem cell expander, e.g., (S)-2-(6-(2-(1H-indol-3-yl)ethylamino)-2-(5-fluoropyridin-3-yl)-9H-purin-9-yl)propan-1-ol. In embodiments, the altered or modified cell, e.g., CD34+ cell, has undergone or is able to undergo at least 5, e.g., about 5, doublings in culture, e.g., in culture comprising a stem cell expander molecule, e.g., as described herein, e.g., (S)-2-(6-(2-(1H-indol-3-yl)ethylamino)-2-(5-fluoropyridin-3-yl)-9H-purin-9-yl)propan-1-ol. In embodiments the altered or modified cell, e.g., CD34+ cell, exhibits and/or is able to differentiate into a cell, e.g., into a cell of the erythroid lineage, e.g., into a red blood cell, that exhibits increased fetal hemoglobin level (e.g., expression level and/or protein level), e.g., at least a 20% increase in fetal hemoglobin protein level, relative to a similar unmodified or unaltered cell. In embodiments the altered or modified cell, e.g., CD34+ cell, exhibits and/or is able to differentiate into a cell, e.g., into a cell of the erythroid lineage, e.g., into a red blood cell, that exhibits increased fetal hemoglobin level (e.g., expression level and/or protein level), relative to a similar unmodified or unaltered cell, e.g., produces at least 6 picograms, e.g., at least 7 picograms, at least 8 picograms, at least 9 picograms, or at least 10 picograms of fetal hemoglobin. In embodiments the altered or modified cell, e.g., CD34+ cell, exhibits and/or is able to differentiate into a cell, e.g., into a cell of the erythroid lineage, e.g., into a red blood cell, that exhibits increased fetal hemoglobin level (e.g., expression level and/or protein level), relative to a similar unmodified or unaltered cell, e.g., produces about 6 to about 12, about 6 to about 7, about 7 to about 8, about 8 to about 9, about 9 to about 10, about 10 to about 11 or about 11 to about 12 picograms of fetal hemoglobin.

In an aspect, the invention provides a population of cells comprising cells having a modification or alteration, e.g., an indel, at or near (e.g., within 20, 19, 18, 17, 16, 15, 14, 13, 12, 11, 10, 9, 8, 7, 6, 5, 4, 3, 2 or 1 nucleotides of) a nucleic acid sequence having complementarity to a gRNA molecule or gRNA molecules, e.g., as described herein, introduced into said cells, e.g., as part of a CRISPR system as described herein. In embodiments, at least 50%, e.g., at least 60%, at least 70%, at least 80% or at least 90% of the cells of the population have the modification or alteration (e.g., have at least one modification or alteration), e.g., as measured by NGS, e.g., as described herein, e.g., at day two following introduction of the gRNA and/or CRISPR system of the invention. In embodiments, at least 90%, e.g., at least 91%, at least 92%, at least 93%, at least 94%, at least 95%, at least 96%, at least 97%, at least 98% or at least 99% of the cells of the population have the modification or alteration (e.g., have at least one modification or alteration), e.g., as measured by NGS, e.g., as described herein, e.g., at day two following introduction of the gRNA and/or CRISPR system of the invention. In embodiments, the population of cells comprise CD34+ cells, e.g., comprise at least about 50%, at least about 60%, at least about 70%, at least about 80%, at least about 90%, at least about 95% or at least about 98%

CD34+ cells. In embodiments, the population of cells comprising the altered or modified cells, e.g., CD34+ cells, maintain the ability to produce, e.g., differentiate into, cells of multiple lineages, e.g., maintains the ability to produce, e.g., differentiate into, cells of the erythroid lineage. In embodiments, the population of cells, e.g., population of CD34+ cells, has undergone or is able to undergo at least 2, at least 3, at least 4, at least 5, at least 6, at least 7, at least 8, at least 9 or at least 10 or more population doublings in culture, e.g., in culture comprising a stem cell expander, e.g., (S)-2-(6-(2-(1H-indol-3-yl)ethylamino)-2-(5-fluoropyridin-3-yl)-9H-purin-9-yl)propan-1-ol. In embodiments, the population of altered or modified cells, e.g., population of CD34+ cells, has undergone or is capable of undergoing at least 5, e.g., about 5, population doublings in culture, e.g., in culture comprising a stem cell expander molecule, e.g., as described herein, e.g., (S)-2-(6-(2-(1H-indol-3-yl)ethylamino)-2-(5-fluoropyridin-3-yl)-9H-purin-9-yl)propan-1-ol. In embodiments the population of cells comprising altered or modified cells, e.g., CD34+ cells, exhibits and/or is able to differentiate into a population of cells, e.g., into a population of cells of the erythroid lineage, e.g., into a population of red blood cells, that exhibits increased fetal hemoglobin level (e.g., expression level and/or protein level), e.g., at least a 20% increase in fetal hemoglobin protein level, relative to a similar unmodified or unaltered cells. In embodiments the population of cells comprising altered or modified cells, e.g., CD34+ cells, exhibits and/or is able to differentiate into a population of cells, e.g., into a population of cells of the erythroid lineage, e.g., into a population of red blood cells, that exhibits increased fetal hemoglobin level (e.g., expression level and/or protein level), relative to a similar unmodified or unaltered cells, e.g., comprises cells that produce at least 6 picograms, e.g., at least 7 picograms, at least 8 picograms, at least 9 picograms, or at least 10 picograms of fetal hemoglobin per cell. In embodiments the population of altered or modified cells, e.g., CD34+ cells, exhibits and/or is able to differentiate into a population of cells, e.g., into a population of cells of the erythroid lineage, e.g., into a population of red blood cells, that exhibits increased fetal hemoglobin level (e.g., expression level and/or protein level), relative to a similar unmodified or unaltered cell, e.g., comprises cells that produce about 6 to about 12, about 6 to about 7, about 7 to about 8, about 8 to about 9, about 9 to about 10, about 10 to about 11 or about 11 to about 12 picograms of fetal hemoglobin per cell.

In embodiments, the population of cells, e.g., as described herein, comprises at least about 1e3 cells. In embodiments, the population of cells, e.g., as described herein, comprises at least about 1e4 cells. In embodiments, the population of cells, e.g., as described herein, comprises at least about 1e5 cells. In embodiments, the population of cells, e.g., as described herein, comprises at least about 1e6 cells. In embodiments, the population of cells, e.g., as described herein, comprises at least about 1e7 cells. In embodiments, the population of cells, e.g., as described herein, comprises at least about 1e8 cells. In embodiments, the population of cells, e.g., as described herein, comprises at least about 1e9 cells. In embodiments, the population of cells, e.g., as described herein, comprises at least about 1e10 cells. In embodiments, the population of cells, e.g., as described herein, comprises at least about 1e11 cells. In embodiments, the population of cells, e.g., as described herein, comprises at least about 1e12 cells. In embodiments, the population of cells, e.g., as described herein, comprises at least about 1e13 cells per kilogram body weight of the patient to which they are to be administered. In embodiments, the population of cells, e.g., as described herein, comprises at least about 1e6 cells per kilogram body weight of the patient to which they are to be administered. In embodiments, the population of cells, e.g., as described herein, comprises at least about 2e6 cells per kilogram body weight of the patient to which they are to be administered. In embodiments, the population of cells, e.g., as described herein, comprises at least about 3e6 cells per kilogram body weight of the patient to which they are to be administered. In embodiments, the population of cells, e.g., as described herein, comprises at least about 4e6 cells per kilogram body weight of the patient to which they are to be administered. In embodiments, the population of cells, e.g., as described herein, comprises at least about 5e6 cells per kilogram body weight of the patient to which they are to be administered. In embodiments, the population of cells, e.g., as described herein, comprises at least about 6e6 cells per kilogram body weight of the patient to which they are to be administered. In embodiments, the population of cells, e.g., as described herein, comprises at least about 7e6 cells per kilogram body weight of the patient to which they are to be administered. In embodiments, the population of cells, e.g., as described herein, comprises at least about 8e6 cells per kilogram body weight of the patient to which they are to be administered. In embodiments, the population of cells, e.g., as described herein, comprises at least about 9e6 cells per kilogram body weight of the patient to which they are to be administered. In embodiments, the population of cells, e.g., as described herein, comprises at least about 1e7 cells per kilogram body weight of the patient to which they are to be administered. In embodiments, the population of cells, e.g., as described herein, comprises at least about 2e7 cells per kilogram body weight of the patient to which they are to be administered. In embodiments, the population of cells, e.g., as described herein, comprises at least about 3e7 cells per kilogram body weight of the patient to which they are to be administered. In embodiments, the population of cells, e.g., as described herein, comprises at least about 4e7 cells per kilogram body weight of the patient to which they are to be administered. In embodiments, the population of cells, e.g., as described herein, comprises at least about 5e7 cells per kilogram body weight of the patient to which they are to be administered. In embodiments, the population of cells, e.g., as described herein, comprises at least about 6e7 cells per kilogram body weight of the patient to which they are to be administered. In embodiments, the population of cells, e.g., as described herein, comprises at least about 7e7 cells per kilogram body weight of the patient to which they are to be administered. In embodiments, the population of cells, e.g., as described herein, comprises at least about 8e7 cells per kilogram body weight of the patient to which they are to be administered. In embodiments, the population of cells, e.g., as described herein, comprises at least about 9e7 cells per kilogram body weight of the patient to which they are to be administered. In embodiments, the population of cells, e.g., as described herein, comprises at least about 1e8 cells per kilogram body weight of the patient to which they are to be administered. In any of the aforementioned embodiments, the population of cells may comprise at least about 50% (for example, at least about 60%, at least about 70%, at least about 80%, at least about 90%, at least about 95% or at least about 99%) HSPCs, e.g., CD34+ cells. In any of the aforementioned embodiments, the population of cells may comprise about 60% HSPCs, e.g., CD34+ cells. In an embodiment, the population of cells, e.g., as described herein, comprises about 3e7 cells and comprises about 2e7 HSPCs, e.g., CD34+ cells. As used throughout this application, the scientific notation [number]e[number] is given its ordinary meaning. Thus, for example, 2e6 is equivalent to $2\times10^6$ or 2,000,000.

In embodiments, the population of cells, e.g., as described herein, comprises at least about 1e6 HSPCs, e.g., CD34+ cells, per kilogram body weight of the patient to which they are to be administered. In embodiments, the population of cells, e.g., as described herein, comprises at least about 1.5e6 HSPCs, e.g., CD34+ cells, per kilogram body weight of the patient to which they are to be administered. In embodiments, the population of cells, e.g., as described herein, comprises at least about 2e6 HSPCs, e.g., CD34+ cells, per kilogram body weight of the patient to which they are to be administered. In embodiments, the population of cells, e.g., as described herein, comprises at least about 3e6 HSPCs, e.g., CD34+ cells, per kilogram body weight of the patient to which they are to be administered. In embodiments, the population of cells, e.g., as described herein, comprises at least about 4e6 HSPCs, e.g., CD34+ cells, per kilogram body weight of the patient to which they are to be administered. In embodiments, the population of cells, e.g., as described herein, comprises at least about 5e6 HSPCs, e.g., CD34+ cells, per kilogram body weight of the patient to which they are to be administered. In embodiments, the population of cells, e.g., as described herein, comprises at least about 6e6 HSPCs, e.g., CD34+ cells, per kilogram body weight of the patient to which they are to be administered. In embodiments, the population of cells, e.g., as described herein, comprises at least about 7e6 HSPCs, e.g., CD34+ cells, per kilogram body weight of the patient to which they are to be administered. In embodiments, the population of cells, e.g., as described herein, comprises at least about 8e6 HSPCs, e.g., CD34+ cells, per kilogram body weight of the patient to which they are to be administered. In embodiments, the population of cells, e.g., as described herein, comprises at least about 9e6 HSPCs, e.g., CD34+ cells, per kilogram body weight of the patient to which they are to be administered. In embodiments, the population of cells, e.g., as described herein, comprises at least about 1e7 HSPCs, e.g., CD34+ cells, per kilogram body weight of the patient to which they are to be administered. In embodiments, the population of cells, e.g., as described herein, comprises at least about 2e7 HSPCs, e.g., CD34+ cells, per kilogram body weight of the patient to which they are to be administered. In embodiments, the population of cells, e.g., as described herein, comprises at least about 3e7 HSPCs, e.g., CD34+ cells, per kilogram body weight of the patient to which they are to be administered. In embodiments, the population of cells, e.g., as described herein, comprises at least about 4e7 HSPCs, e.g., CD34+ cells, per kilogram body weight of the patient to which they are to be administered. In embodiments, the population of cells, e.g., as described herein, comprises at least about 5e7 HSPCs, e.g., CD34+ cells, per kilogram body weight of the patient to which they are to be administered. In embodiments, the population of cells, e.g., as described herein, comprises at least about 6e7 HSPCs, e.g., CD34+ cells, per kilogram body weight of the patient to which they are to be administered. In embodiments, the population of cells, e.g., as described herein, comprises at least about 7e7 HSPCs, e.g., CD34+ cells, per kilogram body weight of the patient to which they are to be administered. In embodiments, the population of cells, e.g., as described herein, comprises at least about 8e7 HSPCs, e.g., CD34+ cells, per kilogram body weight of the patient to which they are to be administered. In embodiments, the population of cells, e.g., as described herein, comprises at least about 9e7 HSPCs, e.g., CD34+ cells, per kilogram body weight of the patient to which they are to be administered. In embodiments, the population of cells, e.g., as described herein, comprises at least about 1e8 HSPCs, e.g., CD34+ cells, per kilogram body weight of the patient to which they are to be administered. In embodiments, the population of cells, e.g., as described herein, comprises at least about 2e8 HSPCs, e.g., CD34+ cells, per kilogram body weight of the patient to which they are to be administered. In embodiments, the population of cells, e.g., as described herein, comprises at least about 3e8 HSPCs, e.g., CD34+ cells, per kilogram body weight of the patient to which they are to be administered. In embodiments, the population of cells, e.g., as described herein, comprises at least about 4e8 HSPCs, e.g., CD34+ cells, per kilogram body weight of the patient to which they are to be administered. In embodiments, the population of cells, e.g., as described herein, comprises at least about 5e8 HSPCs, e.g., CD34+ cells, per kilogram body weight of the patient to which they are to be administered.

In embodiments, the population of cells, e.g., as described herein, comprises about 1e6 HSPCs, e.g., CD34+ cells, per kilogram body weight of the patient to which they are to be administered. In embodiments, the population of cells, e.g., as described herein, comprises about 1.5e6 HSPCs, e.g., CD34+ cells, per kilogram body weight of the patient to which they are to be administered. In embodiments, the population of cells, e.g., as described herein, comprises about 2e6 HSPCs, e.g., CD34+ cells, per kilogram body weight of the patient to which they are to be administered. In embodiments, the population of cells, e.g., as described herein, comprises about 3e6 HSPCs, e.g., CD34+ cells, per kilogram body weight of the patient to which they are to be administered. In embodiments, the population of cells, e.g., as described herein, comprises about 4e6 HSPCs, e.g., CD34+ cells, per kilogram body weight of the patient to which they are to be administered. In embodiments, the population of cells, e.g., as described herein, comprises about 5e6 HSPCs, e.g., CD34+ cells, per kilogram body weight of the patient to which they are to be administered. In embodiments, the population of cells, e.g., as described herein, comprises about 6e6 HSPCs, e.g., CD34+ cells, per kilogram body weight of the patient to which they are to be administered. In embodiments, the population of cells, e.g., as described herein, comprises about 7e6 HSPCs, e.g., CD34+ cells, per kilogram body weight of the patient to which they are to be administered. In embodiments, the population of cells, e.g., as described herein, comprises about 8e6 HSPCs, e.g., CD34+ cells, per kilogram body weight of the patient to which they are to be administered. In embodiments, the population of cells, e.g., as described herein, comprises about 9e6 HSPCs, e.g., CD34+ cells, per kilogram body weight of the patient to which they are to be administered. In embodiments, the population of cells, e.g., as described herein, comprises about 1e7 HSPCs, e.g., CD34+ cells, per kilogram body weight of the patient to which they are to be administered. In embodiments, the population of cells, e.g., as described herein, comprises about 2e7 HSPCs, e.g., CD34+ cells, per kilogram body weight of the patient to which they are to be administered. In embodiments, the population of cells, e.g., as described herein, comprises about 3e7 HSPCs, e.g., CD34+ cells, per kilogram body weight of the patient to which they are to be administered. In embodiments, the population of cells, e.g., as described herein, comprises about 4e7 HSPCs, e.g., CD34+ cells, per kilogram body weight of the patient to which they are to be administered. In embodiments, the population of cells, e.g., as described herein, comprises about 5e7 HSPCs, e.g., CD34+ cells, per kilogram body weight of the patient to which they are to be administered. In embodiments, the population of cells, e.g., as described herein, comprises about 6e7 HSPCs, e.g., CD34+ cells, per kilogram body weight of the patient to which they are to be administered. In embodiments, the population of cells, e.g., as described herein, comprises about 7e7 HSPCs, e.g., CD34+ cells, per kilogram body weight of the patient to which they are to be administered. In embodiments, the population of cells, e.g., as described herein, comprises about 8e7 HSPCs, e.g., CD34+ cells, per kilogram body weight of the patient to which they are to be administered. In embodiments, the population of cells, e.g., as described herein, comprises about 9e7 HSPCs, e.g., CD34+ cells, per kilogram body weight of the patient to which they are to be administered. In embodiments, the population of cells, e.g., as described herein, comprises about 1e8 HSPCs, e.g., CD34+ cells, per kilogram body weight of the patient to which they are to be administered. In embodiments, the population of cells, e.g., as described herein, comprises about 2e8 HSPCs, e.g., CD34+ cells, per kilogram body weight of the patient to which they are to be administered. In embodiments, the population of cells, e.g., as described herein, comprises about 3e8 HSPCs, e.g., CD34+ cells, per kilogram body weight of the patient to which they are to be administered. In embodiments, the population of cells, e.g., as described herein, comprises about 4e8 HSPCs, e.g., CD34+ cells, per kilogram body weight of the patient to which they are to be administered. In embodiments, the population of cells, e.g., as described herein, comprises about 5e8 HSPCs, e.g., CD34+ cells, per kilogram body weight of the patient to which they are to be administered.

In embodiments, the population of cells, e.g., as described herein, comprises from about 2e6 to about 10e6 HSPCs, e.g., CD34+ cells, per kilogram body weight of the patient to which they are to be administered. In embodiments, the population of cells, e.g., as described herein, comprises from 2e6 to 10e6 HSPCs, e.g., CD34+ cells, per kilogram body weight of the patient to which they are to be administered.

The cells of the invention may comprise a gRNA molecule of the present invention, or nucleic acid encoding said gRNA molecule, and a Cas9 molecule of the present invention, or nucleic acid encoding said Cas9 molecule. In an embodiment, the cells of the invention may comprise a ribonuclear protein (RNP) complex which comprises a gRNA molecule of the invention and a Cas9 molecule of the invention.

The cells of the invention are preferably modified to comprise a gRNA molecule of the invention ex vivo, for example by a method described herein, e.g., by electroporation or by TRIAMF (as described in patent application PCT/US2017/54110, incorporated herein by reference in its entirety).

The cells of the invention include cells in which expression of one or more genes has been altered, for example, reduced or inhibited, by introduction of a CRISPR system comprising a gRNA of the invention. For example, the cells of the present invention may have a reduced level of beta globin (e.g., hemoglobin beta comprising a sickling mutation) expression relative to unmodified cells. As another example, the cells of the present invention may have an increased level of fetal hemoglobin expression relative to unmodified cells. Alternatively, or in addition, a cell of the invention may give rise, e.g., differentiate into, another type of cell, e.g., an erythrocyte, that has an increased level of fetal hemoglobin expression relative to cells differentiated from unmodified cells. In embodiments, the increase in level of fetal hemoglobin is at least about 20%, at least about 30%, at least about 40% or at least about 50%. Alternatively, or in addition, a cell of the invention may give rise, e.g., differentiate into, another type of cell, e.g., an erythrocyte, that has a reduced level of beta globin (e.g., hemoglobin beta comprising a sickling mutation, also referred to herein as sickle beta globin) expression relative to cells differentiated from unmodified cells. In embodiments, the decrease in level of sickle beta-globin is at least about 20%, at least about 30%, at least about 40% or at least about 50%.

The cells of the invention include cells in which expression of one or more genes has been altered, for example, reduced or inhibited, by introduction of a CRISPR system comprising a gRNA of the invention. For example, the cells of the present invention may have a reduced level of hemoglobin beta, for example a mutated or wild-type hemoglobin beta, expression relative to unmodified cells. In another aspect, the invention provides cells which are derived from, e.g., differentiated from, cells in which a CRISPR system comprising a gRNA of the invention has been introduced. In such aspects, the cells in which the CRISPR system comprising the gRNA of the invention has been introduced may not exhibit the reduced level of hemoglobin beta, for example a mutated or wild-type hemoglobin beta, but the cells derived from, e.g., differentiated from, said cells exhibit the reduced level of hemoglobin beta, for example a mutated or wild-type hemoglobin beta. In embodiments, the derivation, e.g., differentiation, is accomplished in vivo (e.g., in a patient, e.g., in a hemoglobinopathy patient, e.g., in a patient with sickle cell disease or a thalassemia, e.g., beta thalassemia). In embodiments the cells in which the CRISPR system comprising the gRNA of the invention has been introduced are CD34+ cells and the cells derived, e.g., differentiated, therefrom are of the erythroid lineage, e.g., red blood cells.

The cells of the invention include cells in which expression of one or more genes has been altered, for example, increased or promoted, by introduction of a CRISPR system comprising a gRNA of the invention. For example, the cells of the present invention may have an increased level of fetal hemoglobin expression relative to unmodified cells. In another aspect, the invention provides cells which are derived from, e.g., differentiated from, cells in which a CRISPR system comprising a gRNA of the invention has been introduced. In such aspects, the cells in which the CRISPR system comprising the gRNA of the invention has been introduced may not exhibit the increased level of fetal hemoglobin but the cells derived from, e.g., differentiated from, said cells exhibit the increased level of fetal hemoglobin. In embodiments, the derivation, e.g., differentiation, is accomplished in vivo (e.g., in a patient, e.g., in a hemoglobinopathy patient, e.g., in a patient with sickle cell disease or a thalassemia, e.g., beta thalassemia). In embodiments the cells in which the CRISPR system comprising the gRNA of the invention has been introduced are CD34+ cells and the cells derived, e.g., differentiated, therefrom are of the erythroid lineage, e.g., red blood cells.

In another aspect, the invention relates to cells which include an indel at (e.g., within) or near (e.g., within 20, 19, 18, 17, 16, 15, 14, 13, 12, 11, 10, 9, 8, 7, 6, 5, 4, 3, 2 or 1 nucleotides of) a nucleic acid sequence having complementarity to the gRNA molecule (e.g., the target sequence of the gRNA molecule) or gRNA molecules introduced into said cells. In embodiments, the indel is a frameshift indel. In embodiments, the cell includes a large deletion, for example a deletion of 1 kb, 2 kb, 3 kb, 4 kb, 5 kb, 6 kb or more. In embodiments, the large deletion comprises nucleic acids disposed between two binding sites for the gRNA molecule or gRNA molecules introduced into said cells. In embodiments, the deletion comprises, e.g., consists of, the about 4900 nt disposed between the target sequence of a gRNA described herein disposed in the HBG1 promoter region and the target sequence of a gRNA described herein disposed in the HBG2 promoter region. In embodiments, the indel, e.g., deletion, does not comprise a nucleotide disposed between 5,250,092 and 5,249,833, − strand (hg38).

In an aspect, the invention relates to a population of cells (e.g., as described herein), e.g., a population of HSPCs, which comprises cells which include an indel at or near (e.g., within 20, 19, 18, 17, 16, 15, 14, 13, 12, 11, 10, 9, 8, 7, 6, 5, 4, 3, 2 or 1 nucleotides of) a nucleic acid sequence having complementarity to a gRNA molecule or gRNA molecules, e.g., as described herein, introduced into said cells, e.g., as described herein. In embodiments, the indel is a frameshift indel. In embodiments, the cell population includes cells which comprise a large deletion, for example a deletion of 1 kb, 2 kb, 3 kb, 4 kb, 5 kb, 6 kb or more. In embodiments, the large deletion comprises nucleic acids disposed between two binding sites for the gRNA molecule or gRNA molecules introduced into said cells. In embodiments, the deletion comprises, e.g., consists of, the about 4900 nt disposed between the target sequence of a gRNA described herein disposed in the HBG1 promoter region and the target sequence of a gRNA described herein disposed in the HBG2 promoter region. In embodiments, less than 1%, 0.5%, 0.1% or 0.001% of the cells of the population (e.g., no cell of the population) comprises a deletion of a nucleotide disposed between 5,250,092 and 5,249,833, − strand (hg38). In embodiments, 20%-100% of the cells of the population include said large deletion, indel or indels. In embodiments, 30%-100% of the cells of the population include said large deletion, indel or indels. In embodiments, 40%-100% of the cells of the population include said large deletion, indel or indels. In embodiments, 50%-100% of the cells of the population include said large deletion, indel or indels. In embodiments, 60%-100% of the cells of the population include said large deletion, indel or indels. In embodiments, 70%-100% of the cells of the population include said large deletion, indel or indels. In embodiments, 80%-100% of the cells of the population include said large deletion, indel or indels. In embodiments, 90%-100% of the cells of the population include said large deletion, indel or indels. In embodiments, the population of cells retains the ability to differentiate into multiple cell types, e.g., maintains the ability to differentiate into cells of erythroid lineage, e.g., red blood cells, e.g., in a subject, e.g., a human. In embodiments, the edited cells (e.g., HSPC cells, e.g., CD34+ cell, e.g., any subpopulation of CD34+ cell, e.g., as described herein) maintain the ability (and/or do) to proliferate, e.g., in cell culture, e.g., proliferate at least 5-fold, at least 10-fold, at least 15-fold, at least 20-fold, at least 25-fold, at least 30-fold, at least 35-fold, at least 40-fold, at least 45-fold, at least 50-fold or more, e.g., after 1, 2, 3, 4, 5, 6, 7 or more days (e.g., after about 1 or about 2 days) in cell culture, e.g., in a cell culture medium described herein, e.g., a cell culture medium comprising one or more stem cell expanders, e.g., compound 4. In embodiments, the edited and differentiated cells (e.g., red blood cells) maintain the ability to proliferate, e.g., proliferate at least 5-fold, at least 10-fold, at least 15-fold, at least 20-fold, at least 25-fold, at least 30-fold, at least 35-fold, at least 40-fold, at least 45-fold, at least 50-fold or more after 7 days in erythroid differentiation medium (EDM), e.g., as described in the Examples, and/or, proliferate at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, at least 100-fold, at least 110-fold, at least 120-fold, at least 130-fold, at least 140-fold, at least 150-fold, at least 200-fold, at least 300-fold, at least 400-fold, at least 500-fold, at least 600-fold, at least 700-fold, at least 800-fold, at least 900-fold, at least 1000-fold, at least 1100-fold, at least 1200-fold, at least 1300-fold, at least 1400-fold, at least 1500-fold or more after 21 days, e.g., in erythroid differentiation medium (EDM), e.g., as described in the Examples or in a subject (e.g., a mammal, e.g., a human)

In an embodiment, the invention provides a population of cells, e.g., CD34+ cells, of which at least 90%, e.g., at least 95%, e.g., at least 98%, of the cells of the population comprise a large deletion or one or more indels, e.g., as described herein. Without being bound by theory, it is believed that introduction of a gRNA molecule or CRISPR system as described herein into a population of cells produces a pattern of indels and/or large deletions in said population, and thus, each cell of the population which comprises an indel and/or large deletion may not exhibit the same indel and/or large deletion. In embodiments, the indel and/or large deletion comprises one or more nucleic acids at or near a site complementary to the targeting domain of a gRNA molecule described herein; wherein said cells maintain the ability to differentiate into cells of an erythroid lineage, e.g., red blood cells; and/or wherein said cells differentiated from the population of cells have an increased level of fetal hemoglobin (e.g., the population has a higher % F cells) relative to cells differentiated from a similar population of unmodified cells. In embodiments, the population of cells has undergone at least a 2-fold expansion ex vivo, e.g., in the media comprising one or more stem cell expanders, e.g., comprising (S)-2-(6-(2-(1H-indol-3-yl)ethylamino)-2-(5-fluoropyridin-3-yl)-9H-purin-9-yl)propan-1-ol. In embodiments, the population of cells has undergone at least a 5-fold expansion ex vivo, e.g., in the media comprising one or more stem cell expanders, e.g., comprising (S)-2-(6-(2-(1H-indol-3-yl)ethylamino)-2-(5-fluoropyridin-3-yl)-9H-purin-9-yl)propan-1-ol.

In embodiments, the indel is less than about 50 nucleotides, e.g., less than about 45, less than about 40, less than about 35, less than about 30 or less than about 25 nucleotides. In embodiments, the indel is less than about 25 nucleotides. In embodiments, the indel is less than about 20 nucleotides. In embodiments, the indel is less than about 15 nucleotides. In embodiments, the indel is less than about 10 nucleotides. In embodiments, the indel is less than about 9 nucleotides. In embodiments, the indel is less than about 9 nucleotides. In embodiments, the indel is less than about 7 nucleotides. In embodiments, the indel is less than about 6 nucleotides. In embodiments, the indel is less than about 5 nucleotides. In embodiments, the indel is less than about 4 nucleotides. In embodiments, the indel is less than about 3 nucleotides. In embodiments, the indel is less than about 2 nucleotides. In any of the aforementioned embodiments, the indel is at least 1 nucleotide. In embodiments, the indel is 1 nucleotide. In embodiments, the large deletion comprises about 1 kb of DNA. In embodiments, the large deletion comprises about 2 kb of DNA. In embodiments, the large deletion comprises about 3 kb of DNA. In embodiments, the large deletion comprises about 4 kb of DNA. In embodiments, the large deletion comprises about 5 kb of DNA. In embodiments, the large deletion comprises about 6 kb of DNA. In embodiments, the large deletion comprises about 4.9 kb of DNA, for example, disposed between a target sequence in the HBG1 promoter region and a target sequence in the HBG2 promoter region.

In embodiments, a population of cells (e.g., as described herein) comprises a pattern of indels and/or large deletions comprising any 1, 2, 3, 4, 5, or 6 of the most frequently detected indels associated with a CRISPR system comprising a gRNA molecule described herein, e.g., comprises 1, 2, 3, 4, 5, or 6 of the indels and large deletions described in Table 7-2 (e.g., comprises 1, 2, 3, 4, 5 or 6 of the indels and large deletions detected at or near the HBG1 target sequence and/or comprises 1, 2, 3, 4, 5 or 6 of the indels and large deletions detected at or near the HBG2 target sequence). In embodiments, the indels and/or large deletions are detected by a method described herein, e.g., by NGS or qPCR.

In an aspect, the cell or population of cells (e.g., as described herein) does not comprise an indel or large deletion at an off-target site, e.g., as detected by a method described herein.

In embodiments, the progeny, e.g., differentiated progeny, e.g., erythroid (e.g., red blood cell) progeny of the cell or population of cells described herein (e.g., derived from a sickle cell disease patient) produce a lower level of sickle beta globin and/or a higher level of gamma globin than unmodified cells. In embodiments, the progeny, e.g., differentiated progeny, e.g., erythroid (e.g., red blood cell) progeny of the cell or population of cells described herein (e.g., derived from a sickle cell disease patient) produce a lower level of sickle beta globin and a higher level of gamma globin than unmodified cells. In embodiments, sickle beta globin is produced at a level at least about 20%, at least about 30%, at least about 40% or at least about 50% lower than unmodified cells. In embodiments, gamma globin is produced at a level at least about 20%, at least about 30%, at least about 40%, at least about 50%, at least about 60% or at least about 70% higher than unmodified cells.

In an aspect, the invention provides a population of modified HSPCs or erythroid cells differentiated from said HSPCs (e.g., differentiated ex vivo or in a patient), e.g., as described herein, wherein at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the cells are F cells. In embodiments, the population of cells contains (or is capable of differentiating, e.g., in vivo, into a population of erythrocytes that contains) a higher percent of F cells than a similar population of cells which have not had a gRNA molecule or gRNA molecules, e.g., as described herein, introduced into said cells. In embodiments, the population of cells has (or is capable of differentiating, e.g., in vivo, into a population of erythrocytes that has) at least a 20% increase, e.g, at least 21% increase, at least 22% increase, at least 23% increase, at least 24% increase, at least 25% increase, at least 26% increase, at least 27% increase, at least 28% increase, or at least 29% increase, in F cells relative to the similar population of cells which have not had a gRNA molecule or gRNA molecules, e.g., as described herein, introduced into said cells. In embodiments, the population of cells has (or is capable of differentiating, e.g., in vivo, into a population of erythrocytes that has) at least a 30% increase, e.g., at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase or at least a 95% increase, in F cells relative to the similar population of cells which have not had a gRNA molecule or gRNA molecules, e.g., as described herein, introduced into said cells. In embodiments, the population of cells has (or is capable of differentiating, e.g., in vivo, into a population of erythrocytes that has) a 10-90%, a 20%-80%, a 20%-70%, a 20%-60%, a 20%-50%, a 20%-40%, a 20%-30%, a 25%-80%, a 25%-70%, a 25%-60%, a 25%-50%, a 25%-40%, a 25%-35%, a 25%-30%, a 30%-80%, a 30%-70%, a 30%-60%, a 30%-50%, a 30%-40%, or a 30%-35% increase in F cells relative to the similar population of cells which have not had a gRNA molecule or gRNA molecules, e.g., as described herein, introduced into said cells. In embodiments, the population of cells, e.g., as produced by a method described herein, comprises a sufficient number or cells and/or a sufficient increase in % F cells to treat a hemoglobinopathy, e.g., as described herein, e.g., sickle cell disease and/or beta thalassemia, in a patient in need thereof when introduced into said patient, e.g., in a therapeutically effective amount. In embodiments, the increase in F cells is as measured in an erythroid differentiation assay, e.g., as described herein.

In embodiments, including in any of the embodiments and aspects described herein, the invention relates to a cell, e.g., a population of cells, e.g., as modified by any of the gRNA, methods and/or CRISPR systems described herein, comprising F cells that produce at least 6 picograms fetal hemoglobin per cell. In embodiments, the F cells produce at least 7 picograms fetal hemoglobin per cell. In embodiments, the F cells produce at least 8 picograms fetal hemoglobin per cell. In embodiments, the F cells produce at least 9 picograms fetal hemoglobin per cell. In embodiments, the F cells produce at least 10 picograms fetal hemoglobin per cell. In embodiments, the F cells produce an average of between 6.0 and 7.0 picograms, between 7.0 and 8.0, between 8.0 and 9.0, between 9.0 and 10.0, between 10.0 and 11.0, or between 11.0 and 12.0 picograms of fetal hemoglobin per cell.

In embodiments, a cell or population of cells, e.g., as described herein (for example, comprising an indel, e.g., a large deletion or indel described in Table 7-2) (or its progeny), is detectable in the cells of a subject to which it is introduced, for example, remains detectable by detecting the indel, for example, using a method described herein. In embodiments, the cell or population of cells (or its progeny) is detectable in a subject to which it is introduced for at least 10 weeks, at least 14 weeks, at least 16 weeks, at least 18 weeks, at least 20 weeks, at least 30 weeks at least 40 weeks, at least 50 weeks, or longer after said cell or population of cells is introduced into said subject.

In embodiments, one or more indels (e.g., a large deletion or indel described in Table 7-2), is detectable in the cells (e.g., the cells, e.g., CD34+ cells, of the bone marrow and/or peripheral blood) of a subject to which the cells or population of cells described herein have been introduced, for example, remains detectable by a method described herein, e.g., NGS. In embodiments, the one or more indels is detectable in the cells (e.g., the cells, e.g., CD34+ cells, of the bone marrow and/or peripheral blood) of a subject to which the cells or population of cells described herein have been introduced for at least 10 weeks, at least 14 weeks, at least 16 weeks, at least 18 weeks, at least 20 weeks, at least 30 weeks at least 40 weeks, at least 50 weeks, or longer after the cell or population of cells described herein is introduced into said subject. In embodiments, the level of detection of said one or more indels does not decrease over time, or decreases by less than 5%, less than 10%, less than 15%, less than 20%, less than 30%, less than 40% or less than 50% (for example relative to the level of indel detection pre-transplant or relative to the level of detection at week 2 post-transplant or at week 8 post transplant), for example when measured at week 20 post-transplant relative to the level of detection (e.g., percentage of cells comprising the one or more indels) measured pre-transplant or measured at week 2 post transplant or at week 8 post transplant.

In embodiments, including in any of the aforementioned embodiments, the cell and/or population of cells of the invention includes, e.g., consists of, cells which do not comprise nucleic acid encoding a Cas9 molecule.

Methods of Treatment

Delivery Timing

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In an embodiment, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g, an RNA molecule described herein.

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety. In an embodiment, the Cas9 molecule and the gRNA molecule are delivered by different modes, or as sometimes referred to herein as differential modes. Different or differential modes, as used herein, refer modes of delivery, that confer different pharmacodynamic or pharmacokinetic properties on the subject component molecule, e.g., a Cas9 molecule, gRNA molecule, template nucleic acid, or payload. E.g., the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adeno associated virus or lentivirus, delivery.

By way of example, the components, e.g., a Cas9 molecule and a gRNA molecule, can be delivered by modes that differ in terms of resulting half life or persistent of the delivered component the body, or in a particular compartment, tissue or organ. In an embodiment, a gRNA molecule can be delivered by such modes. The Cas9 molecule component can be delivered by a mode which results in less persistence or less exposure of its to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In an embodiment, the first pharmacodynamic or pharmacokinetic property, e.g., distribution, persistence or exposure, is more limited than the second pharmacodynamic or pharmacokinetic property.

In an embodiment, the first mode of delivery is selected to optimize, e.g., minimize, a pharmacodynamic or pharmacokinetic property, e.g., distribution, persistence or exposure.

In an embodiment, the second mode of delivery is selected to optimize, e.g., maximize, a pharmacodynamic or pharmcokinetic property, e.g., distribution, persistence or exposure.

In an embodiment, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In an embodiment, the second mode of delivery comprises a relatively transient element, e.g., an RNA or protein.

In an embodiment, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRAs are incapable of acting in isolation. The second component, a Cas9 molecule, is delivered in a transient manner, for example as mRNA or as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and efficacy. For example, the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA molecule is delivered by a first delivery mode that results in a first spatial, e.g., tissue, distribution. A second component, e.g., a Cas9 molecule is delivered by a second delivery mode that results in a second spatial, e.g., tissue, distribution. In an embodiment, the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In an embodiment, the second mode of delivery comprises a second targeting element, e.g., a second cell specific receptor or second antibody.

When the Cas9 molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 molecule are packaged in separated delivery vehicles with distinct but overlapping tissue tropism, the fully functional complex is only be formed in the tissue that is targeted by both vectors.

Candidate Cas molecules, e.g., Cas9 molecules, candidate gRNA molecules, candidate Cas9 molecule/gRNA molecule complexes, and candidate CRISPR systems, can be evaluated by art-known methods or as described herein. For example, exemplary methods for evaluating the endonuclease activity of Cas9 molecule are described, e.g., in Jinek el al., SCIENCE 2012; 337(6096):816-821.

Additional aspects are described in the enumerated embodiments, below.

EMBODIMENTS

1. A gRNA molecule comprising a tracr and crRNA, wherein the crRNA comprises a targeting domain that:
   a) is complementary with a target sequence of a nondeletional HFPH region (e.g., a human nondeletional HPFH region);
   b) is complementary with a target sequence within the genomic nucleic acid sequence at Chr11:5,249,833 to Chr11:5,250,237, – strand, hg38;
   c) is complementary with a target sequence within the genomic nucleic acid sequence at Chr11:5,254,738 to Chr11:5,255,164, – strand, hg38;
   d) is complementary with a target sequence within the genomic nucleic acid sequence at Chr11:5,250,094-5,250, 237, – strand, hg38;
   e) is complementary with a target sequence within the genomic nucleic acid sequence at Chr11:5,255,022-5,255, 164, – strand, hg38;
   f) is complementary with a target sequence within the genomic nucleic acid sequence at Chr11:5,249,833-5,249, 927, – strand, hg38;
   g) is complementary with a target sequence within the genomic nucleic acid sequence at Chr11:5,254,738-5,254, 851, – strand, hg38;
   h) is complementary with a target sequence within the genomic nucleic acid sequence at Chr11:5,250,139-5,250, 237, – strand, hg38; or
   i) combinations thereof.

2. A gRNA molecule of embodiment 1, wherein the targeting domain comprises, e.g., consists of, any one of SEQ ID NO: 1 to SEQ ID NO: 72, or a fragment thereof.

3. A gRNA molecule of embodiment 2, wherein the targeting domain comprises, e.g., consists of, any one of SEQ ID NO: 1, SEQ ID NO: 6, SEQ ID NO: 8, SEQ ID NO: 9, SEQ ID NO: 10, SEQ ID NO: 11, SEQ ID NO: 12, SEQ ID NO: 28, SEQ ID NO: 34, SEQ ID NO: 45, SEQ ID NO: 46, SEQ ID NO: 47, SEQ ID NO: 48, SEQ ID NO: 50, SEQ ID NO: 51, SEQ ID NO: 53, SEQ ID NO: 54, SEQ ID NO: 58, SEQ ID NO: 62, SEQ ID NO: 63, SEQ ID NO: 67, or a fragment thereof.

4. A gRNA molecule of embodiment 2, wherein the targeting domain comprises, e.g., consists of, any one of
   a) SEQ ID NO: 6, SEQ ID NO: 8, SEQ ID NO: 28, SEQ ID NO: 34, SEQ ID NO: 48, SEQ ID NO: 51, SEQ ID NO: 67, or a fragment thereof; or
   b) SEQ ID NO: 1, SEQ ID NO: 8, SEQ ID NO: 9, SEQ ID NO: 10, SEQ ID NO: 12, SEQ ID NO: 54, or a fragment thereof.

5. The gRNA molecule of any of embodiments 2-4, wherein the targeting domain comprises, e.g., consists of, 17, 18, 19, or 20 consecutive nucleic acids of any one of the recited targeting domain sequences.

6. The gRNA molecule of embodiment 5, wherein the 17, 18, 19, or 20 consecutive nucleic acids of any one of the recited targeting domain sequences are the 17, 18, 19, or 20 consecutive nucleic acids disposed at the 3' end of the recited targeting domain sequence.

7. The gRNA molecule of embodiment 5, wherein the 17, 18, 19, or 20 consecutive nucleic acids of any one of the recited targeting domain sequences are the 17, 18, 19, or 20 consecutive nucleic acids disposed at the 5' end of the recited targeting domain sequence.

8. The gRNA molecule of embodiment 5, wherein the 17, 18, 19, or 20 consecutive nucleic acids of any one of the recited targeting domain sequences do not comprise either the 5' or 3' nucleic acid of the recited targeting domain sequence.

9. The gRNA molecule of any of embodiments 2-8, wherein the targeting domain consists of the recited targeting domain sequence.

10. The gRNA molecule of any of the previous embodiments, wherein a portion of the crRNA and a portion of the tracr hybridize to form a flagpole comprising SEQ ID NO: 182 or 183.

11. The gRNA molecule of embodiment 10, wherein the flagpole further comprises a first flagpole extension, located 3' to the crRNA portion of the flagpole, wherein said first flagpole extension comprises SEQ ID NO: 184.

12. The gRNA molecule of embodiment 10 or 11, wherein the flagpole further comprises a second flagpole extension located 3' to the crRNA portion of the flagpole and, if present, the first flagpole extension, wherein said second flagpole extension comprises SEQ ID NO: 185.

13. The gRNA molecule of any of embodiments 1-12, wherein the tracr comprises SEQ ID NO: 224 or SEQ ID NO: 225.

14. The gRNA molecule of any of embodiments 1-13, wherein the tracr comprises SEQ ID NO: 232, optionally further comprising, at the 3' end, an additional 1, 2, 3, 4, 5, 6, or 7 uracil (U) nucleotides.

15. The gRNA molecule of any of embodiments 1-14, wherein the crRNA comprises, from 5' to 3', [targeting domain]–:
   a) SEQ ID NO: 182;
   b) SEQ ID NO: 183;
   c) SEQ ID NO: 199;
   d) SEQ ID NO: 200;
   e) SEQ ID NO: 201;
   f) SEQ ID NO: 202; or
   g) SEQ ID NO: 226.

16. The gRNA molecule of any of embodiments 1-9 or 15, wherein the tracr comprises, from 5' to 3':
   a) SEQ ID NO: 187;
   b) SEQ ID NO: 188;

c) SEQ ID NO: 203;
d) SEQ ID NO: 204;
e) SEQ ID NO: 224;
f) SEQ ID NO: 225;
g) SEQ ID NO: 232;
h) SEQ ID NO: 227;
i) (SEQ ID NO: 228;
j) SEQ ID NO: 229;
k) any of a) to j), above, further comprising, at the 3' end, at least 1, 2, 3, 4, 5, 6 or 7 uracil (U) nucleotides, e.g., 1, 2, 3, 4, 5, 6, or 7 uracil (U) nucleotides;
l) any of a) to k), above, further comprising, at the 3' end, at least 1, 2, 3, 4, 5, 6 or 7 adenine (A) nucleotides, e.g., 1, 2, 3, 4, 5, 6, or 7 adenine (A) nucleotides; or
m) any of a) to l), above, further comprising, at the 5' end (e.g., at the 5' terminus), at least 1, 2, 3, 4, 5, 6 or 7 adenine (A) nucleotides, e.g., 1, 2, 3, 4, 5, 6, or 7 adenine (A) nucleotides.

17. The gRNA molecule of any of embodiments 1-9, wherein the targeting domain and the tracr are disposed on separate nucleic acid molecules, and wherein the nucleic acid molecule comprising the targeting domain comprises SEQ ID NO: 201, optionally disposed immediately 3' to the targeting domain, and the nucleic acid molecule comprising the tracr comprises, e.g., consists of, SEQ ID NO: 224.

18. The gRNA molecule of any of embodiments 13-14, wherein the crRNA portion of the flagpole comprises SEQ ID NO: 201 or SEQ ID NO: 202.

19. The gRNA molecule of any of embodiments 1-12, wherein the tracr comprises SEQ ID NO: 187 or 188, and optionally, if a first flagpole extension is present, a first tracr extension, disposed 5' to SEQ ID NO: 187 or 188, said first tracr extension comprising SEQ ID NO: 189.

20. The gRNA molecule of any of embodiments 1-19, wherein the targeting domain and the tracr are disposed on separate nucleic acid molecules.

21. The gRNA molecule of any of embodiments 1-19, wherein the targeting domain and the tracr are disposed on a single nucleic acid molecule, and wherein the tracr is disposed 3' to the targeting domain.

22. The gRNA molecule of embodiment 21, further comprising a loop, disposed 3' to the targeting domain and 5' to the tracr.

23. The gRNA molecule of embodiment 22, wherein the loop comprises SEQ ID NO: 186.

24. The gRNA molecule of any of embodiments 1-9, comprising, from 5' to 3', [targeting domain]–:
(a) SEQ ID NO: 195;
(b) SEQ ID NO: 196;
(c) SEQ ID NO: 197;
(d) SEQ ID NO: 198;
(e) SEQ ID NO: 231; or
(f) any of (a) to (e), above, further comprising, at the 3' end, 1, 2, 3, 4, 5, 6 or 7 uracil (U) nucleotides.

25. The gRNA molecule of any of embodiments 1-9 or 21-24, wherein the targeting domain and the tracr are disposed on a single nucleic acid molecule, and wherein said nucleic acid molecule comprises, e.g., consists of, said targeting domain and SEQ ID NO: 231, optionally disposed immediately 3' to said targeting domain.

26. The gRNA molecule of any of embodiments 1-25 wherein one, or optionally more than one, of the nucleic acid molecules comprising the gRNA molecule comprises:
a) one or more, e.g., three, phosphorothioate modifications at the 3' end of said nucleic acid molecule or molecules;
b) one or more, e.g., three, phosphorothioate modifications at the 5' end of said nucleic acid molecule or molecules;
c) one or more, e.g., three, 2'-O-methyl modifications at the 3' end of said nucleic acid molecule or molecules;
d) one or more, e.g., three, 2'-O-methyl modifications at the 5' end of said nucleic acid molecule or molecules;
e) a 2' O-methyl modification at each of the $4^{th}$-to-terminal, $3^{rd}$-to-terminal, and $2^{nd}$-to-terminal 3' residues of said nucleic acid molecule or molecules;
f) a 2' O-methyl modification at each of the $4^{th}$-to-terminal, $3^{rd}$-to-terminal, and $2^{nd}$-to-terminal 5' residues of said nucleic acid molecule or molecules; or
f) any combination thereof.

27. A gRNA molecule of embodiment 1, comprising, e.g., consisting of, the sequence:
(a) SEQ ID NO: 74;
(b) SEQ ID NO: 75; or
(c) SEQ ID NO: 76.

28. A gRNA molecule of embodiment 1, comprising, e.g., consisting of:
(a) a crRNA comprising, e.g., consisting of, SEQ ID NO: 77, and a tracr comprising, e.g., consisting of, SEQ ID NO: 224;
(b) a crRNA comprising, e.g., consisting of, SEQ ID NO: 77, and a tracr comprising, e.g., consisting of, SEQ ID NO: 73;
(c) a crRNA comprising, e.g., consisting of, SEQ ID NO: 78, and a tracr comprising, e.g., consisting of, SEQ ID NO: 224; or
(d) a crRNA comprising, e.g., consisting of, SEQ ID NO: 78, and a tracr comprising, e.g., consisting of, SEQ ID NO: 73.

29. A gRNA molecule of embodiment 1, comprising, e.g., consisting of, the sequence:
(a) SEQ ID NO: 79;
(b) SEQ ID NO: 80; or
(c) SEQ ID NO: 81.

30. A gRNA molecule of embodiment 1, comprising, e.g., consisting of:
(a) a crRNA comprising, e.g., consisting of, SEQ ID NO: 82, and a tracr comprising, e.g., consisting of, SEQ ID NO: 224;
(b) a crRNA comprising, e.g., consisting of, SEQ ID NO: 82, and a tracr comprising, e.g., consisting of, SEQ ID NO: 73;
(c) a crRNA comprising, e.g., consisting of, SEQ ID NO: 83, and a tracr comprising, e.g., consisting of, SEQ ID NO: 224; or
(d) a crRNA comprising, e.g., consisting of, SEQ ID NO: 83, and a tracr comprising, e.g., consisting of, SEQ ID NO: 73.

31. A gRNA molecule of embodiment 1, comprising, e.g., consisting of, the sequence:
(a) SEQ ID NO: 84;
(b) SEQ ID NO: 85; or
(c) SEQ ID NO: 86.

32. A gRNA molecule of embodiment 1, comprising, e.g., consisting of:
(a) a crRNA comprising, e.g., consisting of, SEQ ID NO: 87, and a tracr comprising, e.g., consisting of, SEQ ID NO: 224;
(b) a crRNA comprising, e.g., consisting of, SEQ ID NO: 87, and a tracr comprising, e.g., consisting of, SEQ ID NO: 73;

(c) a crRNA comprising, e.g., consisting of, SEQ ID NO: 88, and a tracr comprising, e.g., consisting of, SEQ ID NO: 224; or (d) a crRNA comprising, e.g., consisting of, SEQ ID NO: 88, and a tracr comprising, e.g., consisting of, SEQ ID NO: 73.

33. A gRNA molecule of embodiment 1, comprising, e.g., consisting of, the sequence:
    (a) SEQ ID NO: 89;
    (b) SEQ ID NO: 90; or
    (c) SEQ ID NO: 91.

34. A gRNA molecule of embodiment 1, comprising, e.g., consisting of:
    (a) a crRNA comprising, e.g., consisting of, SEQ ID NO: 92, and a tracr comprising, e.g., consisting of, SEQ ID NO: 224;
    (b) a crRNA comprising, e.g., consisting of, SEQ ID NO: 92, and a tracr comprising, e.g., consisting of, SEQ ID NO: 73;
    (c) a crRNA comprising, e.g., consisting of, SEQ ID NO: 93, and a tracr comprising, e.g., consisting of, SEQ ID NO: 224; or
    (d) a crRNA comprising, e.g., consisting of, SEQ ID NO: 93, and a tracr comprising, e.g., consisting of, SEQ ID NO: 73.

35. A gRNA molecule of embodiment 1, comprising, e.g., consisting of, the sequence:
    (a) SEQ ID NO: 94;
    (b) SEQ ID NO: 95; or
    (c) SEQ ID NO: 96.

36. A gRNA molecule of embodiment 1, comprising, e.g., consisting of:
    (a) a crRNA comprising, e.g., consisting of, SEQ ID NO: 97, and a tracr comprising, e.g., consisting of, SEQ ID NO: 224;
    (b) a crRNA comprising, e.g., consisting of, SEQ ID NO: 97, and a tracr comprising, e.g., consisting of, SEQ ID NO: 73;
    (c) a crRNA comprising, e.g., consisting of, SEQ ID NO: 98, and a tracr comprising, e.g., consisting of, SEQ ID NO: 224; or
    (d) a crRNA comprising, e.g., consisting of, SEQ ID NO: 98, and a tracr comprising, e.g., consisting of, SEQ ID NO: 73.

37. A gRNA molecule of embodiment 1, comprising, e.g., consisting of, the sequence:
    (a) SEQ ID NO: 99;
    (b) SEQ ID NO: 100; or
    (c) SEQ ID NO: 101.

38. A gRNA molecule of embodiment 1, comprising, e.g., consisting of:
    (a) a crRNA comprising, e.g., consisting of, SEQ ID NO: 102, and a tracr comprising, e.g., consisting of, SEQ ID NO: 224;
    (b) a crRNA comprising, e.g., consisting of, SEQ ID NO: 102, and a tracr comprising, e.g., consisting of, SEQ ID NO: 73;
    (c) a crRNA comprising, e.g., consisting of, SEQ ID NO: 103, and a tracr comprising, e.g., consisting of, SEQ ID NO: 224; or
    (d) a crRNA comprising, e.g., consisting of, SEQ ID NO: 103, and a tracr comprising, e.g., consisting of, SEQ ID NO: 73.

39. A gRNA molecule of embodiment 1, comprising, e.g., consisting of, the sequence:
    (a) SEQ ID NO: 104;
    (b) SEQ ID NO: 105; or
    (c) SEQ ID NO:106.

40. A gRNA molecule of embodiment 1, comprising, e.g., consisting of:
    (a) a crRNA comprising, e.g., consisting of, SEQ ID NO: 107, and a tracr comprising, e.g., consisting of, SEQ ID NO: 224;
    (b) a crRNA comprising, e.g., consisting of, SEQ ID NO: 107, and a tracr comprising, e.g., consisting of, SEQ ID NO: 73;
    (c) a crRNA comprising, e.g., consisting of, SEQ ID NO: 108, and a tracr comprising, e.g., consisting of, SEQ ID NO: 224; or
    (d) a crRNA comprising, e.g., consisting of, SEQ ID NO: 108, and a tracr comprising, e.g., consisting of, SEQ ID NO: 73.

41. A gRNA molecule of embodiment 1, comprising, e.g., consisting of, the sequence:
    (a) SEQ ID NO: 109;
    (b) SEQ ID NO: 110; or
    (c) SEQ ID NO: 111.

42. A gRNA molecule of embodiment 1, comprising, e.g., consisting of:
    (a) a crRNA comprising, e.g., consisting of, SEQ ID NO: 112, and a tracr comprising, e.g., consisting of, SEQ ID NO: 224;
    (b) a crRNA comprising, e.g., consisting of, SEQ ID NO: 112, and a tracr comprising, e.g., consisting of, SEQ ID NO: 73;
    (c) a crRNA comprising, e.g., consisting of, SEQ ID NO: 113, and a tracr comprising, e.g., consisting of, SEQ ID NO: 224; or
    (d) a crRNA comprising, e.g., consisting of, SEQ ID NO: 113, and a tracr comprising, e.g., consisting of, SEQ ID NO: 73.

43. A gRNA molecule of embodiment 1, comprising, e.g., consisting of, the sequence:
    (a) SEQ ID NO: 114;
    (b) SEQ ID NO: 115; or
    (c) SEQ ID NO:116.

44. A gRNA molecule of embodiment 1, comprising, e.g., consisting of:
    (a) a crRNA comprising, e.g., consisting of, SEQ ID NO: 117, and a tracr comprising, e.g., consisting of, SEQ ID NO: 224;
    (b) a crRNA comprising, e.g., consisting of, SEQ ID NO: 117, and a tracr comprising, e.g., consisting of, SEQ ID NO: 73;
    (c) a crRNA comprising, e.g., consisting of, SEQ ID NO: 118, and a tracr comprising, e.g., consisting of, SEQ ID NO: 224; or
    (d) a crRNA comprising, e.g., consisting of, SEQ ID NO: 118, and a tracr comprising, e.g., consisting of, SEQ ID NO: 73.

45. A gRNA molecule of embodiment 1, comprising, e.g., consisting of, the sequence:
    (a) SEQ ID NO: 119;
    (b) SEQ ID NO: 120; or
    (c) SEQ ID NO: 121.

46. A gRNA molecule of embodiment 1, comprising, e.g., consisting of:
    (a) a crRNA comprising, e.g., consisting of, SEQ ID NO: 122, and a tracr comprising, e.g., consisting of, SEQ ID NO: 224;

(b) a crRNA comprising, e.g., consisting of, SEQ ID NO: 122, and a tracr comprising, e.g., consisting of, SEQ ID NO: 73;

(c) a crRNA comprising, e.g., consisting of, SEQ ID NO: 123, and a tracr comprising, e.g., consisting of, SEQ ID NO: 224; or (d) a crRNA comprising, e.g., consisting of, SEQ ID NO: 123, and a tracr comprising, e.g., consisting of, SEQ ID NO: 73.

47. A gRNA molecule of embodiment 1, comprising, e.g., consisting of, the sequence:
    (a) SEQ ID NO: 124;
    (b) SEQ ID NO: 125; or
    (c) SEQ ID NO:126.

48. A gRNA molecule of embodiment 1, comprising, e.g., consisting of:
    (a) a crRNA comprising, e.g., consisting of, SEQ ID NO: 127, and a tracr comprising, e.g., consisting of, SEQ ID NO: 224;
    (b) a crRNA comprising, e.g., consisting of, SEQ ID NO: 127, and a tracr comprising, e.g., consisting of, SEQ ID NO: 73;
    (c) a crRNA comprising, e.g., consisting of, SEQ ID NO: 128, and a tracr comprising, e.g., consisting of, SEQ ID NO: 224; or
    (d) a crRNA comprising, e.g., consisting of, SEQ ID NO: 128, and a tracr comprising, e.g., consisting of, SEQ ID NO: 73.

49. A gRNA molecule of embodiment 1, comprising, e.g., consisting of, the sequence:
    (a) SEQ ID NO: 129;
    (b) SEQ ID NO: 130; or
    (c) SEQ ID NO: 131.

50. A gRNA molecule of embodiment 1, comprising, e.g., consisting of:
    (a) a crRNA comprising, e.g., consisting of, SEQ ID NO: 132, and a tracr comprising, e.g., consisting of, SEQ ID NO: 224;
    (b) a crRNA comprising, e.g., consisting of, SEQ ID NO: 132, and a tracr comprising, e.g., consisting of, SEQ ID NO: 73;
    (c) a crRNA comprising, e.g., consisting of, SEQ ID NO: 133, and a tracr comprising, e.g., consisting of, SEQ ID NO: 224; or
    (d) a crRNA comprising, e.g., consisting of, SEQ ID NO: 133, and a tracr comprising, e.g., consisting of, SEQ ID NO: 73.

51. A gRNA molecule of embodiment 1, comprising, e.g., consisting of, the sequence:
    (a) SEQ ID NO: 134;
    (b) SEQ ID NO: 135; or
    (c) SEQ ID NO:136.

52. A gRNA molecule of embodiment 1, comprising, e.g., consisting of:
    (a) a crRNA comprising, e.g., consisting of, SEQ ID NO: 137, and a tracr comprising, e.g., consisting of, SEQ ID NO: 224;
    (b) a crRNA comprising, e.g., consisting of, SEQ ID NO: 137, and a tracr comprising, e.g., consisting of, SEQ ID NO: 73;
    (c) a crRNA comprising, e.g., consisting of, SEQ ID NO: 138, and a tracr comprising, e.g., consisting of, SEQ ID NO: 224; or
    (d) a crRNA comprising, e.g., consisting of, SEQ ID NO: 138, and a tracr comprising, e.g., consisting of, SEQ ID NO: 73.

53. A gRNA molecule of embodiment 1, comprising, e.g., consisting of, the sequence:
    (a) SEQ ID NO: 139;
    (b) SEQ ID NO: 140; or
    (c) SEQ ID NO: 141.

54. A gRNA molecule of embodiment 1, comprising, e.g., consisting of:
    (a) a crRNA comprising, e.g., consisting of, SEQ ID NO: 142, and a tracr comprising, e.g., consisting of, SEQ ID NO: 224;
    (b) a crRNA comprising, e.g., consisting of, SEQ ID NO: 142, and a tracr comprising, e.g., consisting of, SEQ ID NO: 73;
    (c) a crRNA comprising, e.g., consisting of, SEQ ID NO: 143, and a tracr comprising, e.g., consisting of, SEQ ID NO: 224; or
    (d) a crRNA comprising, e.g., consisting of, SEQ ID NO: 143, and a tracr comprising, e.g., consisting of, SEQ ID NO: 73.

55. A gRNA molecule of embodiment 1, comprising, e.g., consisting of, the sequence:
    (a) SEQ ID NO: 144;
    (b) SEQ ID NO: 145; or
    (c) SEQ ID NO:146.

56. A gRNA molecule of embodiment 1, comprising, e.g., consisting of:
    (a) a crRNA comprising, e.g., consisting of, SEQ ID NO: 147, and a tracr comprising, e.g., consisting of, SEQ ID NO: 224;
    (b) a crRNA comprising, e.g., consisting of, SEQ ID NO: 147, and a tracr comprising, e.g., consisting of, SEQ ID NO: 73;
    (c) a crRNA comprising, e.g., consisting of, SEQ ID NO: 148, and a tracr comprising, e.g., consisting of, SEQ ID NO: 224; or
    (d) a crRNA comprising, e.g., consisting of, SEQ ID NO: 148, and a tracr comprising, e.g., consisting of, SEQ ID NO: 73.

57. A gRNA molecule of embodiment 1, comprising, e.g., consisting of, the sequence:
    (a) SEQ ID NO: 149;
    (b) SEQ ID NO: 150; or
    (c) SEQ ID NO: 151.

58. A gRNA molecule of embodiment 1, comprising, e.g., consisting of:
    (a) a crRNA comprising, e.g., consisting of, SEQ ID NO: 152, and a tracr comprising, e.g., consisting of, SEQ ID NO: 224;
    (b) a crRNA comprising, e.g., consisting of, SEQ ID NO: 152, and a tracr comprising, e.g., consisting of, SEQ ID NO: 73;
    (c) a crRNA comprising, e.g., consisting of, SEQ ID NO: 153, and a tracr comprising, e.g., consisting of, SEQ ID NO: 224; or
    (d) a crRNA comprising, e.g., consisting of, SEQ ID NO: 153, and a tracr comprising, e.g., consisting of, SEQ ID NO: 73.

59. A gRNA molecule of embodiment 1, comprising, e.g., consisting of, the sequence:
    (a) SEQ ID NO: 154;
    (b) SEQ ID NO: 155; or
    (c) SEQ ID NO:156.

60. A gRNA molecule of embodiment 1, comprising, e.g., consisting of:
    (a) a crRNA comprising, e.g., consisting of, SEQ ID NO: 157, and a tracr comprising, e.g., consisting of, SEQ ID NO: 224;

(b) a crRNA comprising, e.g., consisting of, SEQ ID NO: 157, and a tracr comprising, e.g., consisting of, SEQ ID NO: 73;

(c) a crRNA comprising, e.g., consisting of, SEQ ID NO: 158, and a tracr comprising, e.g., consisting of, SEQ ID NO: 224; or (d) a crRNA comprising, e.g., consisting of, SEQ ID NO: 158, and a tracr comprising, e.g., consisting of, SEQ ID NO: 73.

61. A gRNA molecule of embodiment 1, comprising, e.g., consisting of, the sequence:
    (a) SEQ ID NO: 159;
    (b) SEQ ID NO: 160; or
    (c) SEQ ID NO: 161.

62. A gRNA molecule of embodiment 1, comprising, e.g., consisting of:
    (a) a crRNA comprising, e.g., consisting of, SEQ ID NO: 162, and a tracr comprising, e.g., consisting of, SEQ ID NO: 224;
    (b) a crRNA comprising, e.g., consisting of, SEQ ID NO: 162, and a tracr comprising, e.g., consisting of, SEQ ID NO: 73;
    (c) a crRNA comprising, e.g., consisting of, SEQ ID NO: 163, and a tracr comprising, e.g., consisting of, SEQ ID NO: 224; or
    (d) a crRNA comprising, e.g., consisting of, SEQ ID NO: 163, and a tracr comprising, e.g., consisting of, SEQ ID NO: 73.

63. A gRNA molecule of embodiment 1, comprising, e.g., consisting of, the sequence:
    (a) SEQ ID NO: 164;
    (b) SEQ ID NO: 165; or
    (c) SEQ ID NO:166.

64. A gRNA molecule of embodiment 1, comprising, e.g., consisting of:
    (a) a crRNA comprising, e.g., consisting of, SEQ ID NO: 167, and a tracr comprising, e.g., consisting of, SEQ ID NO: 224;
    (b) a crRNA comprising, e.g., consisting of, SEQ ID NO: 167, and a tracr comprising, e.g., consisting of, SEQ ID NO: 73;
    (c) a crRNA comprising, e.g., consisting of, SEQ ID NO: 168, and a tracr comprising, e.g., consisting of, SEQ ID NO: 224; or
    (d) a crRNA comprising, e.g., consisting of, SEQ ID NO: 168, and a tracr comprising, e.g., consisting of, SEQ ID NO: 73.

65. A gRNA molecule of embodiment 1, comprising, e.g., consisting of, the sequence:
    (a) SEQ ID NO: 169;
    (b) SEQ ID NO: 170; or
    (c) SEQ ID NO: 171.

66. A gRNA molecule of embodiment 1, comprising, e.g., consisting of:
    (a) a crRNA comprising, e.g., consisting of, SEQ ID NO: 172, and a tracr comprising, e.g., consisting of, SEQ ID NO: 224;
    (b) a crRNA comprising, e.g., consisting of, SEQ ID NO: 172, and a tracr comprising, e.g., consisting of, SEQ ID NO: 73;
    (c) a crRNA comprising, e.g., consisting of, SEQ ID NO: 173, and a tracr comprising, e.g., consisting of, SEQ ID NO: 224; or
    (d) a crRNA comprising, e.g., consisting of, SEQ ID NO: 173, and a tracr comprising, e.g., consisting of, SEQ ID NO: 73.

67. A gRNA molecule of embodiment 1, comprising, e.g., consisting of, the sequence:
    (a) SEQ ID NO: 174;
    (b) SEQ ID NO: 175; or
    (c) SEQ ID NO:176.

68. A gRNA molecule of embodiment 1, comprising, e.g., consisting of:
    (a) a crRNA comprising, e.g., consisting of, SEQ ID NO: 177, and a tracr comprising, e.g., consisting of, SEQ ID NO: 224;
    (b) a crRNA comprising, e.g., consisting of, SEQ ID NO: 177, and a tracr comprising, e.g., consisting of, SEQ ID NO: 73;
    (c) a crRNA comprising, e.g., consisting of, SEQ ID NO: 178, and a tracr comprising, e.g., consisting of, SEQ ID NO: 224; or
    (d) a crRNA comprising, e.g., consisting of, SEQ ID NO: 178, and a tracr comprising, e.g., consisting of, SEQ ID NO: 73.

69. A gRNA molecule of any of embodiments 1-68, wherein
    a) when a CRISPR system (e.g., an RNP as described herein) comprising the gRNA molecule is introduced into a cell, an indel is formed at or near the target sequence complementary to the targeting domain of the gRNA molecule; and/or
    b) when a CRISPR system (e.g., an RNP as described herein) comprising the gRNA molecule is introduced into a cell, a deletion is created comprising sequence, e.g., comprising substantially all the sequence, between a sequence complementary to the gRNA targeting domain (e.g., at least 90% complementary to the gRNA targeting domain, e.g., fully complementary to the gRNA targeting domain) in the HBG1 promoter region and a sequence complementary to the gRNA targeting domain (e.g., at least 90% complementary to the gRNA targeting domain, e.g., fully complementary to the gRNA targeting domain) in the HBG2 promoter region.

70. The gRNA molecule of embodiment 69, wherein the indel does not comprise a nucleotide disposed between 5,250,092 and 5,249,833, – strand (hg38), optionally wherein the indel does not comprise a nucleotide of a nondeletional HPFH or transcription factor binding site.

71. A gRNA molecule of any of embodiments 1-70, wherein when a CRISPR system (e.g., an RNP as described herein) comprising the gRNA molecule is introduced into a population of cells, an indel is formed at or near the target sequence complementary to the targeting domain of the gRNA molecule in at least about 15%, e.g., at least about 17%, e.g., at least about 20%, e.g., at least about 30%, e.g., at least about 40%, e.g., at least about 50%, e.g., at least about 55%, e.g., at least about 60%, e.g., at least about 70%, e.g., at least about 75%, e.g., at least about 80%, e.g., at least about 85%, e.g., at least about 90%, e.g., at least about 95%, of the cells of the population.

72. A gRNA molecule of any of embodiments 69-71, wherein the indel comprises at least one nucleotide of an HBG1 promoter region or at least one nucleotide of an HBG2 promoter region.

73. A gRNA molecule of any of embodiments 71-72, wherein at least about 15% of the cells of the population comprise an indel which comprises at least one nucleotide of an HBG1 promoter region and an indel which comprises at least one nucleotide of an HBG2 promoter region.

74. A gRNA molecule of embodiment 71-73, wherein the percentage of the cells of the population which comprise an indel which comprises at least one nucleotide of an HBG1 promoter region differs from percentage of the cells of the population which comprise an indel which comprises at least one nucleotide of an HBG2 promoter region by at least about 5%, e.g., at least about 10%, e.g., at least about 20%, e.g., at least about 30%.

75. The gRNA molecule of any of embodiments 69-74, wherein the indel is as measured by next generation sequencing (NGS).

76. A gRNA molecule of any of embodiments 1-75, wherein when a CRISPR system (e.g., an RNP as described herein) comprising the gRNA molecule is introduced into a cell, expression of fetal hemoglobin is increased in said cell or its progeny, e.g., its erythroid progeny, e.g., its red blood cell progeny.

77. A gRNA molecule of embodiment 76, wherein when a CRISPR system (e.g., an RNP as described herein) comprising the gRNA molecule is introduced into a population of cells, the percentage of F cells in said population or population of its progeny, e.g., its erythroid progeny, e.g., its red blood cell progeny, is increased by at least about 15%, e.g., at least about 17%, e.g., at least about 20%, e.g., at least about 25%, e.g., at least about 30%, e.g., at least about 35%, e.g., at least about 40%, relative to the percentage of F cells in a population of cells to which the gRNA molecule was not introduced or a population of its progeny, e.g., its erythroid progeny, e.g., its red blood cell progeny.

78. A gRNA molecule of any of embodiments 76, wherein said cell or its progeny, e.g., its erythroid progeny, e.g., its red blood cell progeny, produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell.

79. The gRNA molecule of any of embodiments 1-78, wherein when a CRISPR system (e.g., an RNP as described herein) comprising the gRNA molecule is introduced into a cell, no off-target indels are formed in said cell, e.g., no off-target indels are formed outside of the HBG1 and/or HBG2 promoter regions, e.g., as detectible by next generation sequencing and/or a nucleotide insertional assay.

80. The gRNA molecule of any of embodiments 1-78, wherein when a CRISPR system (e.g., an RNP as described herein) comprising the gRNA molecule is introduced into a population of cells, no off-target indel, e.g., no off-target indel outside of the HBG1 and/or HBG2 promoter regions, is detected in more than about 5%, e.g., more than about 1%, e.g., more than about 0.1%, e.g., more than about 0.01%, of the cells of the population of cells, e.g., as detectible by next generation sequencing and/or a nucleotide insertional assay.

81. The gRNA molecule of any of embodiments 69-80, wherein the cell is (or population of cells comprises) a mammalian, primate, or human cell, e.g., is a human cell.

82. The gRNA molecule of embodiment 81, wherein the cell is (or population of cells comprises) an HSPC.

83. The gRNA molecule of embodiment 82, wherein the HSPC is CD34+.

84. The gRNA molecule of embodiment 83, wherein the HSPC is CD34+CD90+.

85. The gRNA molecule of any of embodiments 69-84, wherein the cell is autologous with respect to a patient to be administered said cell.

86. The gRNA molecule of any of embodiments 69-84, wherein the cell is allogeneic with respect to a patient to be administered said cell.

87. A composition comprising:
  1) one or more gRNA molecules (including a first gRNA molecule) of any of embodiments 1-86 and a Cas9 molecule;
  2) one or more gRNA molecules (including a first gRNA molecule) of any of embodiments 1-86 and nucleic acid encoding a Cas9 molecule;
  3) nucleic acid encoding one or more gRNA molecules (including a first gRNA molecule) of any of embodiments 1-86 and a Cas9 molecule;
  4) nucleic acid encoding one or more gRNA molecules (including a first gRNA molecule) of any of embodiments 1-86 and nucleic acid encoding a Cas9 molecule; or
  5) any of 1) to 4), above, and a template nucleic acid; or
  6) any of 1) to 4), above, and nucleic acid comprising sequence encoding a template nucleic acid.

88. A composition comprising a first gRNA molecule of any of embodiments 1-86, optionally further comprising a Cas9 molecule.

89. The composition of embodiment 87 or 88, wherein the Cas9 molecule is an active or inactive s. *pyogenes* Cas9.

90. The composition of embodiment 87-89, wherein the Cas9 molecule comprises SEQ ID NO: 205.

91. The composition of embodiment 87-89, wherein the Cas9 molecule comprises, e.g., consists of:
  (a) SEQ ID NO: 233;
  (b) SEQ ID NO: 234;
  (c) SEQ ID NO: 235;
  (d) SEQ ID NO: 236;
  (e) SEQ ID NO: 237;
  (f) SEQ ID NO: 238;
  (g) SEQ ID NO: 239;
  (h) SEQ ID NO: 240;
  (i) SEQ ID NO: 241;
  (j) SEQ ID NO: 242;
  (k) SEQ ID NO: 243; or
  (l) SEQ ID NO: 244.

92. The composition of any of embodiments 88-91, wherein the first gRNA molecule and Cas9 molecule are present in a ribonuclear protein complex (RNP).

93. The composition of any of embodiments 87-92, further comprising a second gRNA molecule; a second gRNA molecule and a third gRNA molecule; or a second gRNA molecule, optionally, a third gRNA molecule, and, optionally, a fourth gRNA molecule, wherein the second gRNA molecule, the optional third gRNA molecule, and the optional fourth gRNA molecule are a gRNA molecule of any of embodiments 1-68, and wherein each gRNA molecule of the composition is complementary to a different target sequence.

94. The composition of embodiment 93, wherein two or more of the first gRNA molecule, the second gRNA molecule, the optional third gRNA molecule, and the optional fourth gRNA molecule are complementary to target sequences within the same gene or region.

95. The composition of embodiment 93 or 94, wherein the first gRNA molecule, the second gRNA molecule, the optional third gRNA molecule, and the optional fourth gRNA molecule are complementary to target sequences not more than 6000 nucleotides, not more than 5000 nucleotides, not more than 500, not more than 400 nucleotides, not more than 300, not more than 200 nucleotides, not more than 100 nucleotides, not more than 90 nucleotides, not more than 80 nucleotides, not more than 70 nucleotides, not more than 60 nucleotides, not more than 50 nucleotides, not more than 40 nucleotides, not more than 30 nucleotides, not more than 20 nucleotides or not more than 10 nucleotides apart.

96. The composition of embodiment 93, wherein two or more of the first gRNA molecule, the second gRNA molecule, the optional third gRNA molecule, and the optional fourth gRNA molecule comprise at least one gRNA molecule which comprises a targeting domain complementary to a target sequence of an HBG1 promoter region and at least one gRNA molecule which comprises a targeting domain complementary to a target sequence of an HBG2 promoter region.

97. The composition of any of embodiments 94-95, comprising a first gRNA molecule and a second gRNA molecule, wherein the first gRNA molecule and second gRNA molecule are:

(a) independently selected from the gRNA molecules of embodiment 1, and are complementary to different target sequences;

(b) independently selected from the gRNA molecules of embodiment 2, and are complementary to different target sequences;

c) independently selected from the gRNA molecules of embodiment 3, and are complementary to different target sequences; or (d) independently selected from the gRNA molecules of embodiment 4, and are complementary to different target sequences; or (e) independently selected from the gRNA molecules of any of embodiments 27-68, and are complementary to different target sequences.

98. The composition of any of embodiments 94-96, comprising a first gRNA molecule and a second gRNA molecule, wherein:

a) the first gRNA molecule is complementary to a target sequence comprising at least 1 nucleotide (e.g., comprising 20 consecutive nucleotides) within:
  i) Chr11:5,249,833 to Chr11:5,250,237 (hg38);
  ii) Chr11:5,250,094-5,250,237 (hg38);
  iii) Chr11:5,249,833-5,249,927 (hg38); or
  iv) Chr11:5,250,139-5,250,237 (hg38);

b) the second gRNA molecule is complementary to a target sequence comprising at least 1 nucleotide (e.g., comprising 20 consecutive nucleotides) within:
  i) Chr11:5,254,738 to Chr11:5,255,164 (hg38);
  ii) Chr11:5,255,022-5,255,164 (hg38); or
  iii) Chr11:5,254,738-5,254,851 (hg38).

99. The composition of any of embodiments 87-108, wherein with respect to the gRNA molecule components of the composition, the composition consists of a first gRNA molecule and a second gRNA molecule.

100. The composition of any one of embodiments 87-109, wherein each of said gRNA molecules is in a ribonuclear protein complex (RNP) with a Cas9 molecule described herein, e.g., a Cas9 molecule of any of embodiments 90 or 91.

101. The composition of any of embodiments 87-100, comprising a template nucleic acid, wherein the template nucleic acid comprises a nucleotide that corresponds to a nucleotide at or near the target sequence of the first gRNA molecule.

102. The composition of any of embodiments 101, wherein the template nucleic acid comprises nucleic acid encoding:

(a) human beta globin, e.g., human beta globin comprising one or more of the mutations G16D, E22A and T87Q, or fragment thereof; or (b) human gamma globin, or fragment thereof.

103. The composition of any of embodiments 87-102, formulated in a medium suitable for electroporation.

104. The composition of any of embodiments 87-103, wherein each of said gRNA molecules is in a RNP with a Cas9 molecule described herein, and wherein each of said RNP is at a concentration of less than about 10 uM, e.g., less than about 3 uM, e.g., less than about 1 uM, e.g., less than about 0.5 uM, e.g., less than about 0.3 uM, e.g., less than about 0.1 uM, optionally wherein the concentration of said RNP is about 2 uM or is about 1 uM, optionally wherein the composition further comprises a population of cells, e.g., HSPCs.

105. A nucleic acid sequence that encodes one or more gRNA molecules of any of embodiments 1-68.

106. The nucleic acid sequence of embodiment 105, wherein the nucleic acid comprises a promoter operably linked to the sequence that encodes the one or more gRNA molecules.

107. The nucleic acid sequence of embodiment 106, wherein the promoter is a promoter recognized by an RNA polymerase II or RNA polymerase III.

108. The nucleic acid sequence of embodiment 107, wherein the promoter is a U6 promoter or an HI promoter.

109. The nucleic acid sequence of any of embodiments 105-108, wherein the nucleic acid further encodes a Cas9 molecule.

110. The nucleic acid sequence of embodiment 109, wherein the Cas9 molecule comprises any of SEQ ID NO: 205, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243 or SEQ ID NO: 244.

111. The nucleic acid sequence of any of embodiments 109-110, wherein said nucleic acid comprises a promoter operably linked to the sequence that encodes a Cas9 molecule.

112. The nucleic acid sequence of embodiment 111, wherein the promoter is an EF-1 promoter, a CMV IE gene promoter, an EF-1α promoter, an ubiquitin C promoter, or a phosphoglycerate kinase (PGK) promoter.

113. A vector comprising the nucleic acid of any of embodiments 105-112.

114. The vector of embodiment 113, wherein in the vector is selected from the group consisting of a lentiviral vector, an adenoviral vector, an adeno-associated viral (AAV) vector, a herpes simplex virus (HSV) vector, a plasmid, a minicircle, a nanoplasmid, and an RNA vector.

115. A method of altering a cell (e.g., a population of cells), (e.g., altering the structure (e.g., sequence) of nucleic acid) at or near a target sequence within said cell, comprising contacting (e.g., introducing into) said cell (e.g., population of cells) with:

1) one or more gRNA molecules of any of embodiments 1-68 and a Cas9 molecule;

2) one or more gRNA molecules of any of embodiments 1-68 and nucleic acid encoding a Cas9 molecule;

3) nucleic acid encoding one or more gRNA molecules of any of embodiments 1-68 and a Cas9 molecule;

4) nucleic acid encoding one or more gRNA molecules of any of embodiments 1-68 and nucleic acid encoding a Cas9 molecule;

5) any of 1) to 4), above, and a template nucleic acid;

6) any of 1) to 4) above, and nucleic acid comprising sequence encoding a template nucleic acid;

7) the composition of any of embodiments 87-104; or 8) the vector of any of embodiments 113-114.

116. The method of embodiment 115, wherein the gRNA molecule or nucleic acid encoding the gRNA molecule, and the Cas9 molecule or nucleic acid encoding the Cas9 molecule, are formulated in a single composition.

117. The method of embodiment 115, wherein the gRNA molecule or nucleic acid encoding the gRNA molecule, and the Cas9 molecule or nucleic acid encoding the Cas9 molecule, are formulated in more than one composition.

118. The method of embodiment 117, wherein the more than one composition are delivered simultaneously or sequentially.

119. The method of any of embodiments 115-118, wherein the cell is an animal cell.

120. The method of any of embodiments 115-118, wherein the cell is a mammalian, primate, or human cell.

121. The method of embodiment 120, wherein the cell is a hematopoietic stem or progenitor cell (HSPC) (e.g., a population of HSPCs).

122. The method of any of embodiments 115-121, wherein the cell is a CD34+ cell.

123. The method of any of embodiments 115-122, wherein the cell is a CD34+CD90+ cell.

124. The method of any of embodiments 115-123, wherein the cell is disposed in a composition comprising a population of cells that has been enriched for CD34+ cells.

125. The method of any of embodiments 115-124, wherein the cell (e.g. population of cells) has been isolated from bone marrow, mobilized peripheral blood, or umbilical cord blood.

126. The method of any of embodiments 115-125, wherein the cell is autologous or allogeneic with respect to a patient to be administered said cell, optionally wherein the patient is a hemoglobinopathy patient, optionally wherein the patient has sickle cell disease or a thalassemia, optionally beta thalassemia.

127. The method of any of embodiments 115-126, wherein:
a) the altering results in an indel at or near a genomic DNA sequence complementary to the targeting domain of the one or more gRNA molecules; and/or
b) the altering results in a deletion comprising sequence, e.g., substantially all the sequence, between a sequence complementary to the targeting domain of the one or more gRNA molecules (e.g., at least 90% complementary to the gRNA targeting domain, e.g., fully complementary to the gRNA targeting domain) in the HBG1 promoter region and a sequence complementary to the targeting domain of the one or more gRNA molecules (e.g., at least 90% complementary to the gRNA targeting domain, e.g., fully complementary to the gRNA targeting domain) in the HBG2 promoter region, optionally wherein the deletion does not comprise a nucleotide disposed between 5,250,092 and 5,249,833, − strand (hg38).

128. The method of embodiment 127, wherein the indel is an insertion or deletion of less than about 40 nucleotides, e.g., less than 30 nucleotides, e.g., less than 20 nucleotides, e.g., less than 10 nucleotides.

129. The method of embodiment 128, wherein the indel is a single nucleotide deletion.

130. The method of any of embodiments 127-129, wherein the method results in a population of cells wherein at least about 15%, e.g., at least about 17%, e.g., at least about 20%, e.g., at least about 30%, e.g., at least about 40%, e.g., at least about 50%, e.g., at least about 55%, e.g., at least about 60%, e.g., at least about 70%, e.g., at least about 75%, e.g., at least about 80%, e.g., at least about 85%, e.g., at least about 90%, e.g., at least about 95%, of the population have been altered, e.g., comprise an indel, optionally wherein the indel is selected from an indel listed in Table 2-7, optionally wherein the cells of the population do not comprise a deletion of a nucleotide disposed between 5,250,092 and 5,249,833, − strand (hg38).

131. The method of any of embodiments 115-130, wherein the altering results in a cell (e.g., population of cells) that is capable of differentiating into a differentiated cell of an erythroid lineage (e.g., a red blood cell), and wherein said differentiated cell exhibits an increased level of fetal hemoglobin, e.g., relative to an unaltered cell (e.g., population of cells).

132. The method of any of embodiments 115-131, wherein the altering results in a population of cells that is capable of differentiating into a population of differentiated cells, e.g., a population of cells of an erythroid lineage (e.g., a population of red blood cells), and wherein said population of differentiated cells has an increased percentage of F cells (e.g., at least about 15%, at least about 20%, at least about 25%, at least about 30%, or at least about 40% higher percentage of F cells) e.g., relative to a population of unaltered cells.

133. The method of any of embodiments 115-131, wherein the altering results in a cell that is capable of differentiating into a differentiated cell, e.g., a cell of an erythroid lineage (e.g., a red blood cell), and wherein said differentiated cell produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell.

134. A cell, altered by the method of any of embodiments 115-133, or a cell obtainable by the method of any of embodiments 115-133.

135. A cell, comprising an indel described in Table 7-2, optionally wherein the cell does not comprise a deletion of a nucleotide disposed between 5,250,092 and 5,249,833, − strand (hg38).

136. A cell, comprising a first gRNA molecule of any of embodiments 1-68, or a composition of any of embodiments 87-104, a nucleic acid of any of embodiments 105-112, or a vector of any of embodiments 113-114.

137. The cell of embodiment 136, comprising a Cas9 molecule.

138. The cell of embodiment 137, wherein the Cas9 molecule comprises any of SEQ ID NO: 205, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243 or SEQ ID NO: 244.

139. The cell of any of embodiments 134-138, wherein the cell comprises, has comprised, or will comprise a second gRNA molecule of any of embodiments 1-68, or a nucleic acid encoding a second gRNA molecule of any of embodiments 1-68, wherein the first gRNA molecule and second gRNA molecule comprise nonidentical targeting domains.

140. The cell of any of embodiments 134-139, wherein expression of fetal hemoglobin is increased in said cell or its progeny (e.g., its erythroid progeny, e.g., its red blood cell progeny) relative to a cell or its progeny of the same cell type that has not been modified to comprise a gRNA molecule.

141. The cell of any of embodiments 134-139, wherein the cell is capable of differentiating into a differentiated cell, e.g., a cell of an erythroid lineage (e.g., a red blood cell), and wherein said differentiated cell exhibits an increased level of fetal hemoglobin, e.g., relative to a cell of the same type that has not been modified to comprise a gRNA molecule.

142. The cell of any of embodiments 140-141, wherein the differentiated cell (e.g., cell of an erythroid lineage, e.g., red blood cell) produces at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin, e.g., relative to a differentiated cell of the same type that has not been modified to comprise a gRNA molecule.

143. The cell of any of embodiments 134-142, that has been contacted with a stem cell expander.

144. The cell of embodiment 143, wherein the stem cell expander is:

a) (1r,4r)—$N^1$-(2-benzyl-7-(2-methyl-2H-tetrazol-5-yl)-9H-pyrimido[4,5-b]indol-4-yl)cyclohexane-1,4-diamine;

b) methyl 4-(3-piperidin-1-ylpropylamino)-9H-pyrimido[4,5-b]indole-7-carboxylate;

c) 4-(2-(2-(benzo[b]thiophen-3-yl)-9-isopropyl-9H-purin-6-ylamino)ethyl)phenol;

d) (S)-2-(6-(2-(1H-indol-3-yl)ethylamino)-2-(5-fluoropyridin-3-yl)-9H-purin-9-yl)propan-1-ol; or e) combinations thereof (e.g., a combination of (1r,4r)—$N^1$-(2-benzyl-7-(2-methyl-2H-tetrazol-5-yl)-9H-pyrimido[4,5-b]indol-4-yl)cyclohexane-1,4-diamine and (S)-2-(6-(2-(1H-indol-3-yl)ethylamino)-2-(5-fluoropyridin-3-yl)-9H-purin-9-yl)propan-1-ol).

145. The cell of embodiment 144, wherein the stem cell expander is (S)-2-(6-(2-(1H-indol-3-yl)ethylamino)-2-(5-fluoropyridin-3-yl)-9H-purin-9-yl)propan-1-ol.

146. A cell, e.g., a cell of any of embodiments 134-145, comprising:

a) an indel at or near a genomic DNA sequence complementary to the targeting domain of a gRNA molecule of any of embodiments 1-68; and/or b) a deletion comprising sequence, e.g., substantially all the sequence, between a sequence complementary to the targeting domain of a gRNA molecule of any of embodiments 1-68 (e.g., at least 90% complementary to the gRNA targeting domain, e.g., fully complementary to the gRNA targeting domain) in the HBG1 promoter region and a sequence complementary to the targeting domain of a gRNA molecule of any of embodiments 1-68 (e.g., at least 90% complementary to the gRNA targeting domain, e.g., fully complementary to the gRNA targeting domain) in the HBG2 promoter region, optionally wherein the deletion, does not comprise a nucleotide disposed between 5,250,092 and 5,249,833, – strand (hg38).

147. The cell of embodiment 146, wherein the indel is an insertion or deletion of less than about 40 nucleotides, e.g., less than 30 nucleotides, e.g., less than 20 nucleotides, e.g., less than 10 nucleotides.

148. The cell of any of embodiments 146-147, wherein the indel is a single nucleotide deletion.

149. The cell of any of embodiments 134-148, wherein the cell is an animal cell.

150. The cell of embodiment 149, wherein the cell is a mammalian, a primate, or a human cell.

151. The cell of any of embodiments 134-150, wherein the cell is a hematopoietic stem or progenitor cell (HSPC) (e.g., a population of HSPCs).

152. The cell of any of embodiments 134-151, wherein the cell is a CD34+ cell.

153. The cell of embodiment 152, wherein the cell is a CD34+CD90+ cell.

154. The cell of any of embodiments 134-153, wherein the cell (e.g. population of cells) has been isolated from bone marrow, mobilized peripheral blood, or umbilical cord blood.

155. The cell of any of embodiments 134-154, wherein the cell is autologous with respect to a patient to be administered said cell, optionally wherein the patient is a hemoglobinopathy patients, optionally wherein the patient has sickle cell disease or a thalassemia, optionally beta thalassemia.

156. The cell of any of embodiments 134-154, wherein the cell is allogeneic with respect to a patient to be administered said cell.

157. A population of cells comprising the cell of any of embodiments 134-156.

158. The population of cells of embodiment 157, wherein at least about 50%, e.g., at least about 60%, e.g., at least about 70%, e.g., at least about 80%, e.g., at least about 90% (e.g., at least about 95%, at least about 96%, at least about 97%, at least about 98%, or at least about 99%) of the cells of the population are a cell according to any one of embodiments 134-156.

159. The population of cells of any of embodiments 157-158, wherein the population of cells is capable of differentiating into a population of differentiated cells, e.g., a population of cells of an erythroid lineage (e.g., a population of red blood cells), and wherein said population of differentiated cells has an increased percentage of F cells (e.g., at least about 15%, at least about 17%, at least about 20%, at least about 25%, at least about 30%, or at least about 40% higher percentage of F cells) e.g., relative to a population of unmodified cells of the same type.

160. The population of cells of embodiment 159, wherein the F cells of the population of differentiated cells produce an average of at least about 6 picograms (e.g., at least about 7 picograms, at least about 8 picograms, at least about 9 picograms, at least about 10 picograms, or from about 8 to about 9 picograms, or from about 9 to about 10 picograms) fetal hemoglobin per cell.

161. The population of cells of any of embodiments 157-160, comprising:

1) at least 1e6 CD34+ cells/kg body weight of the patient to whom the cells are to be administered;

2) at least 2e6 CD34+ cells/kg body weight of the patient to whom the cells are to be administered;

3) at least 3e6 CD34+ cells/kg body weight of the patient to whom the cells are to be administered;

4) at least 4e6 CD34+ cells/kg body weight of the patient to whom the cells are to be administered; or 5) from 2e6 to 10e6 CD34+ cells/kg body weight of the patient to whom the cells are to be administered.

162. The population of cells of any of embodiments 157-161, wherein at least about 40%, e.g., at least about 50%, (e.g., at least about 60%, at least about 70%, at least about 80%, or at least about 90%) of the cells of the population are CD34+ cells.

163. The population of cells of embodiment 162, wherein at least about 10%, e.g., at least about 15%, e.g., at least about 20%, e.g., at least about 30% of the cells of the population are CD34+CD90+ cells.

164. The population of cells of any of embodiments 157-163, wherein the population of cells is derived from umbilical cord blood, peripheral blood (e.g., mobilized peripheral blood), or bone marrow, e.g., is derived from bone marrow.

165. The population of cells of any of embodiments 157-164, wherein the population of cells comprises, e.g., consists of, mammalian cells, e.g., human cells, optionally wherein the population of cells is obtained from a patient suffering from a hemoglobinopathy, e.g., sickle cell disease or a thalassemia, e.g., beta-thalassemia.

166. The population of cells of any of embodiments 157-165, wherein the population of cells is (i) autologous relative to a patient to which it is to be administered, or (ii) allogeneic relative to a patient to which it is to be administered.

167. The population of cells (e.g., CD34+ cells), e.g., of any of embodiments 157-165, comprising an indel pattern as described in Table 7-2, optionally wherein the indels of an indel pattern described in Table 7-2 are detectible in at least 20%, at least 30%, at least 40%, at least 50%, at least 60%, at least 70%, at least 80%, at least 90% or at least 95% of the cells of the population.

168. A composition comprising a cell of any of embodiments 134-156, or the population of cells of any of embodiments 157-167.

169. The composition of embodiment 168, comprising a pharmaceutically acceptable medium, e.g., a pharmaceutically acceptable medium suitable for cryopreservation.

170. A method of treating a hemoglobinopathy, comprising administering to a patient a cell of any of embodiments 134-156, a population of cells of any of embodiments 157-167, or a composition of any of embodiments 168-169.

171. A method of increasing fetal hemoglobin expression in a mammal, comprising administering to a patient a cell of any of embodiments 134-156, a population of cells of any of embodiments 157-167, or a composition of any of embodiments 168-169.

172. The method of embodiment 170, wherein the hemoglobinopathy is beta-thalassemia or sickle cell disease.

173. A method of preparing a cell (e.g., a population of cells) comprising:
(a) providing a cell (e.g., a population of cells) (e.g., a HSPC (e.g., a population of HSPCs));
(b) culturing said cell (e.g., said population of cells) ex vivo in a cell culture medium comprising a stem cell expander; and
(c) introducing into said cell a first gRNA molecule of any of embodiments 1-86, a nucleic acid molecule encoding a first gRNA molecule of any of embodiments 1-86, a composition of any of embodiments 87-104 or 168-169, a nucleic acid of any of embodiments 105-112, or a vector of any of embodiments 113-114.

174. The method of embodiment 173, wherein after said introducing of step (c), said cell (e.g., population of cells) is capable of differentiating into a differentiated cell (e.g., population of differentiated cells), e.g., a cell of an erythroid lineage (e.g., population of cells of an erythroid lineage), e.g., a red blood cell (e.g., a population of red blood cells), and wherein said differentiated cell (e.g., population of differentiated cells) produces increased fetal hemoglobin, e.g., relative to the same cell which has not been subjected to step (c).

175. The method of any of embodiments 173-174, wherein the stem cell expander is:
a) (1r,4r)—N1-(2-benzyl-7-(2-methyl-2H-tetrazol-5-yl)-9H-pyrimido[4,5-b]indol-4-yl)cyclohexane-1,4-diamine;
b) methyl 4-(3-piperidin-1-ylpropylamino)-9H-pyrimido[4,5-b]indol-7-carboxylate;
c) 4-(2-(2-(benzo[b]thiophen-3-yl)-9-isopropyl-9H-purin-6-ylamino)ethyl)phenol;
d) (S)-2-(6-(2-(1H-indol-3-yl)ethylamino)-2-(5-fluoropyridin-3-yl)-9H-purin-9-yl)propan-1-ol; or
e) combinations thereof (e.g., a combination of (1r,4r)—N1-(2-benzyl-7-(2-methyl-2H-tetrazol-5-yl)-9H-pyrimido[4,5-b]indol-4-yl)cyclohexane-1,4-diamine and (S)-2-(6-(2-(1H-indol-3-yl)ethylamino)-2-(5-fluoropyridin-3-yl)-9H-purin-9-yl)propan-1-ol).

176. The method of embodiment 175, wherein the stem cell expander is (S)-2-(6-(2-(1H-indol-3-yl)ethylamino)-2-(5-fluoropyridin-3-yl)-9H-purin-9-yl)propan-1-ol.

177. The method of any of embodiments 173-176, wherein the cell culture medium comprises thrombopoietin (Tpo), Flt3 ligand (Flt-3L), and human stem cell factor (SCF).

178. The method of embodiment 177, wherein the cell culture medium further comprises human interleukin-6 (IL-6).

179. The method of embodiment 177-178, wherein the cell culture medium comprises thrombopoietin (Tpo), Flt3 ligand (Flt-3L), and human stem cell factor (SCF) each at a concentration ranging from about 10 ng/mL to about 1000 ng/mL.

180. The method of embodiment 179, wherein the cell culture medium comprises thrombopoietin (Tpo), Flt3 ligand (Flt-3L), and human stem cell factor (SCF) each at a concentration of about 50 ng/mL, e.g, at a concentration of 50 ng/mL.

181. The method of any of embodiments 178-180, wherein the cell culture medium comprises human interleukin-6 (IL-6) at a concentration ranging from about 10 ng/mL to about 1000 ng/mL.

182. The method of embodiment 181, wherein the cell culture medium comprises human interleukin-6 (IL-6) at a concentration of about 50 ng/mL, e.g, at a concentration of 50 ng/mL.

183. The method of any of embodiments 173-182, wherein the cell culture medium comprises a stem cell expander at a concentration ranging from about 1 nM to about 1 mM.

184. The method of embodiment 183, wherein the cell culture medium comprises a stem cell expander at a concentration ranging from about 1 uM to about 100 nM.

185. The method of embodiment 184, wherein the cell culture medium comprises a stem cell expander at a concentration ranging from about 500 nM to about 750 nM.

186. The method of embodiment 185, wherein the cell culture medium comprises a stem cell expander at a concentration of about 500 nM, e.g., at a concentration of 500 nM.

187. The method of embodiment 186, wherein the cell culture medium comprises a stem cell expander at a concentration of about 750 nM, e.g., at a concentration of 750 nM.

188. The method of any of embodiments 173-187, wherein the culturing of step (b) comprises a period of culturing before the introducing of step (c).

189. The method of embodiment 188, wherein the period of culturing before the introducing of step (c) is at least 12 hours, e.g., is for a period of about 1 day to about 12 days, e.g., is for a period of about 1 day to about 6 days, e.g., is for a period of about 1 day to about 3 days, e.g., is for a period of about 1 day to about 2 days, e.g., is for a period of about 2 days or for a period of about 1 day.

190. The method of any of embodiments 173-189, wherein the culturing of step (b) comprises a period of culturing after the introducing of step (c).

191. The method of embodiment 190, wherein the period of culturing after the introducing of step (c) is at least 12 hours, e.g., is for a period of about 1 day to about 12 days, e.g., is for a period of about 1 day to about 6 days, e.g., is for a period of about 2 days to about 4 days, e.g., is for a period of about 2 days or is for a period of about 3 days or is for a period of about 4 days.

192. The method of any of embodiments 173-191, wherein the population of cells is expanded at least 4-fold, e.g., at least 5-fold, e.g, at least 10-fold, e.g., relative to cells which are not cultured according to step (b).

193. The method of any of embodiments 173-192, wherein the introducing of step (c) comprises an electroporation.

194. The method of embodiment 193, wherein the electroporation comprises 1 to 5 pulses, e.g., 1 pulse, and wherein each pulse is at a pulse voltage ranging from 700 volts to 2000 volts and has a pulse duration ranging from 10 ms to 100 ms.

195. The method of embodiment 194, wherein the electroporation comprises 1 pulse.

196. The method of any of embodiments 194-195, wherein the pulse voltage ranges from 1500 to 1900 volts, e.g., is 1700 volts.

197. The method of any of embodiments 194-196, wherein the pulse duration ranges from 10 ms to 40 ms, e.g., is 20 ms.

198. The method of any of embodiments 173-197, wherein the cell (e.g., population of cells) provided in step (a) is a human cell (e.g., a population of human cells).

199. The method of embodiment 198, wherein the cell (e.g., population of cells) provided in step (a) is isolated from bone marrow, peripheral blood (e.g., mobilized peripheral blood) or umbilical cord blood.

200. The method of embodiment 199, wherein (i) the cell (e.g., population of cells) provided in step (a) is isolated from bone marrow, e.g., is isolated from bone marrow of a patient suffering from a hemoglobinopathy, optionally wherein the hemoglobinopathy is sickle cell disease or a thalassemia, optionally wherein the thalassemia is beta thalassemia; or (ii) the cell (e.g., population of cells) provided in step (a) is isolated from peripheral blood, e.g., is isolated from peripheral blood of a patient suffering from a hemoglobinopathy, optionally wherein the hemoglobinopathy is sickle cell disease or a thalassemia, optionally wherein the thalassemia is beta thalassemia; optionally wherein the peripheral blood is mobilized peripheral blood, optionally wherein the mobilized peripheral blood is mobilized using Plerixafor, G-CSF, or a combination thereof.

201. The method of any of embodiments 173-200, wherein the population of cells provided in step (a) is enriched for CD34+ cells.

202. The method of any of embodiments 173-201, wherein subsequent to the introducing of step (c), the cell (e.g., population of cells) is cryopreserved.

203. The method of any of embodiments 173-202, wherein subsequent to the introducing of step (c), the cell (e.g., population of cells) comprises:

a) an indel at or near a genomic DNA sequence complementary to the targeting domain of the first gRNA molecule; and/or b) a deletion comprising sequence, e.g., substantially all the sequence, between a sequence complementary to the targeting domain of the first gRNA molecule (e.g., at least 90% complementary to the gRNA targeting domain, e.g., fully complementary to the gRNA targeting domain) in the HBG1 promoter region and a sequence complementary to the targeting domain of the first gRNA molecule (e.g., at least 90% complementary to the gRNA targeting domain, e.g., fully complementary to the gRNA targeting domain) in the HBG2 promoter region, optionally wherein the indel, e.g., deletion, does not comprise a nucleotide disposed between 5,250,092 and 5,249,833, – strand (hg38).

204. The method of any of embodiments 173-203, wherein after the introducing of step (c), at least about 40%, at least about 50%, at least about 60%, at least about 70%, at least about 80%, at least about 90%, at least about 95%, at least about 96%, at least about 97%, at least about 98% or at least about 99% of the cells of the population of cells comprise an indel at or near a genomic DNA sequence complementary to the targeting domain of the first gRNA molecule, optionally wherein no cell of the population comprises a deletion of a nucleotide disposed between 5,250,092 and 5,249,833, – strand (hg38).

205. A cell (e.g., population of cells), obtainable by the method of any of embodiments 173-204.

206. A method of treating a hemoglobinopathy, comprising administering to a human patient a composition comprising a cell of any of embodiments 134-156, a population of cells of any of embodiments 157-167, or a cell (e.g., a population of cells) of embodiment 205.

207. A method of increasing fetal hemoglobin expression in a human patient, comprising administering to said human patient a composition comprising a cell of any of embodiments 134-156, a population of cells of any of embodiments 157-167, or a cell (e.g., a population of cells) of embodiment 205.

208. The method of embodiment 206, wherein the hemoglobinopathy is beta-thalassemia or sickle cell disease.

209. The method of any of embodiments 206-208, wherein the human patient is administered a composition comprising at least about 1e6 cells of embodiment 205 per kg body weight of the human patient, e.g., at least about 1e6 CD34+ cells of embodiment 205 per kg body weight of the human patient.

210. The method embodiment 209, wherein the human patient is administered a composition comprising at least about 2e6 cells of embodiment 205 per kg body weight of the human patient, e.g., at least about 2e6 CD34+ cells of embodiment 205 per kg body weight of the human patient.

211. The method embodiment 209, wherein the human patient is administered a composition comprising from about 2e6 to about 10e6 cells of embodiment 205 per kg body weight of the human patient, e.g., at least about 2e6 to about 10e6 CD34+ cells of embodiment 205 per kg body weight of the human patient.

212. A gRNA molecule of any of embodiments 1-86, a composition of any of embodiments 87-114 or 168-169, a nucleic acid of any of embodiments 105-112, a vector of any of embodiments 113-114, a cell of any of embodiments 134-156 or 205, or a population of cells of any of embodiments 157-167, for use as a medicament.

213. A gRNA molecule of any of embodiments 1-86, a composition of any of embodiments 87-114 or 168-169, a nucleic acid of any of embodiments 105-112, a vector of any of embodiments 113-114, a cell of any of embodiments 134-156 or 205, or a population of cells of any of embodiments 157-167, for use in the manufacture of a medicament.

214. A gRNA molecule of any of embodiments 1-86, a composition of any of embodiments 87-114 or 168-169, a nucleic acid of any of embodiments 105-112, a vector of any of embodiments 113-114, a cell of any of embodiments 134-156 or 205, or a population of cells of any of embodiments 157-167, for use in the treatment of a disease.

215. A gRNA molecule of any of embodiments 1-86, a composition of any of embodiments 87-114 or 168-169, a nucleic acid of any of embodiments 105-112, a vector of any of embodiments 113-114, a cell of any of embodiments 134-156 or 205, or a population of cells of any of embodiments 157-167, for use in the treatment of a disease, wherein the disease is a hemoglobinopathy.

216. A gRNA molecule of any of embodiments 1-86, a composition of any of embodiments 87-114 or 168-169, a nucleic acid of any of embodiments 105-112, a vector of any of embodiments 113-114, a cell of any of embodiments 134-156 or 205, or a population of cells of any of embodiments 157-167, for use in the treatment of a disease, wherein the hemoglobinopathy is beta-thalassemia or sickle cell disease.

EXAMPLES

Example 1—Exemplary General Methods

Guide Selection and Design

Initial guide selection was performed in silico using a human reference genome and user defined genomic regions of interest (e.g., a gene, an exon of a gene, non-coding regulatory region, etc), for identifying PAMs in the regions of interest. For each identified PAM, analyses were performed and statistics reported. gRNA molecules were further selected and rank-ordered based on a number of methods for determining efficiency and efficacy, e.g., as described herein. This example provides the experimental details for procedures that can be used to assay the CRISPR systems, gRNAs and other aspects of the invention described herein. Any modifications to these general procedures that were employed in a particular experiment are noted in that example.

Throughout the Examples, in the experiments below, either sgRNA molecules or dgRNA molecules were used. Unless indicated otherwise, where dgRNA molecules were used, the gRNA includes the following:

```
crRNA:
                              [SEQ ID NO: 201]
[targeting domain]

tracr (trRNA):
                     SEQ ID NO: 224
```

Unless indicated otherwise, in experiments employing a sgRNA molecule, the following sequence was used:

```
[targeting domain]
                              [SEQ ID NO: 195]
UUUU
```

Next-Generation Sequencing (NGS) and Analysis for On-Target Cleavage Efficiency and Indel Formation To determine the efficiency of editing (e.g., cleaving) the target location in the genome, deep sequencing was utilized to identify the presence of insertions and deletions introduced by non-homologous end joining.

In summary PCR primers were designed around the target site, and the genomic area of interest were PCR amplified in edited and unedited samples. Resulting amplicons were converted into Illumina sequencing libraries and sequenced. Sequencing reads were aligned to the human genome reference and subjected to variant calling analysis allowing us to the determine sequence variants and their frequency at the target region of interest. Data were subjected to various quality filters and known variants or variants identified only in the unedited samples were excluded. The editing percentage was defined as the percentage of all insertions or deletions events occurring at the on-target site of interest (i.e. insertion and deletion reads at the on-target site over the total number of reads (wild type and mutant reads) at on-target site. A detailed description of the NGS analysis process is described in Example 2.1.

RNP Generation

The addition of crRNA and trRNA to Cas9 protein results in the formation of the active Cas9 ribonucleoprotein complex (RNP), which mediates binding to the target region specified by the crRNA and specific cleavage of the targeted genomic DNA. This complex was formed by loading trRNA and crRNA into Cas9, which is believed to cause conformational changes to Cas9 allowing it to bind and cleave dsDNA.

The crRNA and trRNA were separately denatured at 95° C. for 2 minutes, and allowed to come to room temperature. Cas9 protein (10 mg/ml) was added to 5×CCE buffer (20 mM HEPES, 100 mM KCl, 5 mM $MgCl_2$, 1 mM DTT, 5% glycerol), to which trRNA and the various crRNAs were then added (in separate reactions) and incubated at 37° C. for 10 minutes, thereby forming the active RNP complex. The complex was delivered by electroporation and other methods into a wide variety of cells, including HEK-293 and CD34+ hematopoietic cells.

Delivery of RNPs to CD34+ HSCs

Cas9 RNPs were Delivered into CD34+ HSCs.

CD34+ HSCs were thawed and cultured (at 500,000 cells/ml) overnight in StemSpan SFEM (StemCell Technologies) media with IL12, SCF, TPO, Flt3L and Pen/Strep added. Roughly 90,000 cells were aliquoted and pelleted per each RNP delivery reaction. The cells were then resuspended in 60 ul P3 nucleofection buffer (Lonza), to which active RNP was subsequently added. The HSCs were then electroporated (e.g., nucleofected using program CA-137 on a Lonza Nucleofector) in triplicate (20 uL/electroporation) Immediately following electroporation, StemSpan SFEM media (with IL12, SCF, TPO, Flt3L and Pen/Strep) was added to the HSCs, which were cultured for at least 24 hours. HSCs were then harvested and subjected to T7E1, NGS, and/or surface marker expression analyses.

HSC Functional Assay

CD34+ HSCs may be assayed for stem cell phenotype using known techniques such as flow cytometry or the in vitro colony forming assay. By way of example, cells were assayed by the in vitro colony forming assay (CFC) using the Methocult H4034 Optimum kit (StemCell Technologies) using the manufacturer's protocol. Briefly, 500-2000 CD34+ cells in <=100 ul volume are added to 1-1.25 ml methocult. The mixture was vortexed vigorously for 4-5 seconds to mix thoroughly, then allowed to rest at room temperature for at least 5 minutes. Using a syringe, 1-1.25 ml of MethoCult+ cells was transferred to a 35 mm dish or well of a 6-well plate. Colony number and morphology was assessed after 12-14 days as per the manufacturer's protocol.

In Vivo Xeno-Transplantation

HSCs are functionally defined by their ability to self-renew and for multi-lineage differentiation. This functionality can only be assessed in vivo. The gold-standard for determining human HSC function is through xeno-transplantation into the NOD-SCID gamma mouse (NSG) that through a series of mutations is severely immunocompromised and thus can act as a recipient for human cells. HSCs following editing were transplanted into NSG mice to validate that the induced edit does not impact HSC function. Periodic peripheral blood analysis were used to assess human chimerism and lineage development and secondary transplantation following 20 weeks was used to establish the presence of functional HSCs, as described more fully in these examples.

Example 2.1 Non-Deletional HPFH Region Editing in Hematopoietic Stem and Progenitor Cells (HSPCs) Using CRISPR-Cas9 for De-Repression of Fetal Globin Expression in Adult Erythroid Cells Methods:

Human CD34+ cell culture. Human CD34+ cells were isolated from G-CSF mobilized peripheral blood from adult donors (AllCells) using immunoselection (Miltenyi) according to the manufacturer's instructions and expanded for 4 to 6 days using StemSpan SFEM (StemCell Technologies; Cat no. 09650) supplemented with 50 ng/mL each of thrombopoietin (Tpo, Life Technologies, Cat. #PHC9514), Flt3 ligand (Flt-3L, Life Technologies, Cat. #PHC9413), human stem cell factor (SCF, Life Technologies, Cat. #PHC2113) and human interleukin-6 (IL-6, Life Technologies, Cat. #PHC0063), as well as 1× antibiotic/antimycotic (Gibco, Cat. #10378-016) and 500 nM Compound 4. Throughout this example (including its subexamples), where the protocol indicates that cells were "expanded," this medium was used. This medium is also referred to as "stem cell expansion medium," or "expansion medium" throughout this example (including its subexamples).

Assembly of Cas9 and guide RNA ribonucleoprotein (RNP) complexes, preparation of HSPC, and electroporation of RNP into HSPC. Cas9-guide RNA ribonucleoprotein complexes (RNPs) were prepared immediately prior to electroporation. For formation of RNP using dual guide RNAs (dgRNAs), 6 µg of each of crRNA (in 4.5 µL) and tracr (in 2.52 µL) are first denatured at 95° C. for 2 min in separate tubes and then cooled to room temperature. For preparation of Cas9 protein, 12 µg of CAS9 protein (in 2 µL) was mixed with 1 µL of 10×CCE buffer (20 mM HEPES, 100 mM KCL, 5 mM MgCL2, 5% Glycerol and freshly added 1 mM DTT). Tracr was first mixed with the Cas9 preparation and incubated at 37° C. for 5 min. The crRNA was then added to Tracr/CAS9 complexes and incubated for 5 min at 37° C. For the None/control condition, vehicle rather than crRNA was added to the Tracr/CAS9 complexes. The HSPC were collected by centrifugation and resuspended in P3 buffer + supplement that comes with Lonza electroporation kit (Cat #V4XP-3032 Lonza Amaxa P3 primary cell 4-D nucleofection X Kit S) at a cell density of $2.8 \times 10^6$/mL. The RNP was mixed with 40 µL of cells by pipetting up and down and incubated at RT for 2 min. For each replicate 21 µL of the RNP/cell mixture was transferred into the Lonza Amaxa P3 primary cell 4-D nucleofection X Kit S. The electroporation was performed with a Lonza transfection system (4D-Nucleofector X Unit) using protocol CM-137. Duplicate 21 µL electroporations were performed.

In vitro erythropoiesis and FACS analysis for HbF containing erythroid cells. After electroporation, the cells were immediately transferred into 250 µL pre-warmed erythroid differentiation medium (EDM) consisting of IMDM (GE Life Sciences, Cat. #SH30228.01). 330 µg/mL human holotransferrin (Invitria Cat #777TRF029), 10 µg/mL recombinant human insulin (Gibco Cat #A1138211), 2 IU/mL heparin (Sigma, part #H3393), 5% human AB serum (Sigma, Cat #H4522), 2.5 U/mL human erythropoietin (Peprotech #100-064), and 1× antibiotic/antimycotic (Gibco, Cat. #10378-016). During the initial culture period up to day 7, EDM was further supplemented with 1.38 µM hydrocortisone (Sigma H8672), 100 ng/mL human SCF (Life Technologies, Cat. #PHC2113), and 5 ng/mL human IL-3 (Peprotech #10779-598) to make EDM-I. After 4 days, the cell culture was diluted in fresh medium. Cultures were maintained for a total of 7 days in the culture conditions described above, at which time half of the cells were analyzed by intracellular staining for HbF expression. Briefly, the cells were washed once with PBS, resuspended in LIVE/DEAD® Fixable Violet Dead Cell Stain (ThermoFisher L34963; 1:1000 in PBS) and incubated for 30 min. Cell were then washed and stained with 1/50 dilutions of anti-CD71-BV711 (Fisher Scientific Company Llc. BD 563767) and anti-CD235a-APC (BD 551336) antibodies for 30 min. The cells were then washed, followed by fixation with fixation buffer (Biolegend, Cat #420801) and permeabilized with 1× intracellular staining permeabilization wash buffer (Biolegend, Cat #421002) according to the manufacturers instructions. The cells were then incubated with a 1/40 dilution of anti-HbF-PE antibody (Life Technologies, part #MHFH04) in 50 µL of 1× intracellular staining perm wash buffer for 20 min at room temperature. The cells were washed twice with 0.2 mL of 1× intracellular staining Perm wash buffer and resuspend in staining buffer and analyzed on an LSRFortessa flow cytometer (BD Biosciences) for HbF expression. The results were analyzed using Flowjo and data were presented as % of HbF positive cells (F-cells) in the viable CD71 positive erythroid cell population.

From the remaining day 7 cultured cells 80,000 per condition were transferred into a EDM-II culture medium for further differentiation until day 11. EDM-II consists of EDM-I supplemented with only 100 ng/mL SCF. On day 11 cells were counted and 200,000 cells per condition were transferred into EDM without further supplements. On day 14 cells were stained for analysis of HbF expression similar to day 7 but surface markers were excluded from the staining to prevent aggregation of cells.

Genomic DNA preparation and next generation sequencing (NGS). Genomic DNA was prepared from edited and unedited HSPC at 7 days post-electroporation using Quick Extract DNA Extraction Solution (Epicentre Cat #QE09050). To determine editing efficiency and patterns of insertions and deletions (indels), PCR products were generated using primers flanking the target sites, which were then subjected to next generation sequencing (NGS) as described in the literature. Percent editing of corresponding sequences in unedited samples (electroporated with RNPs consisting of Cas9 and Tracr only) was typically less than 1% and never exceeded 3%.

NGS library preparation and sequencing of amplicons. PCR amplicons were purified using 1.8× Agencourt AmpureXP beads (Beckman Coulter) following the manufactures recommendations. Amplicons were quantified using the Quant-iT PicoGreen dsDNA assay (Life Technologies) following the manufacture's recommendations Illumina sequencing libraries were generated using the Nextera DNA Library Prep Kit (Illumina) following the manufacture's recommendations with the following changes. Tagmentation was performed in a final volume of 5 ul using 5 ng of purified PCR product, 0.15 ul of Nextera tagment enzyme and tagmentation buffer previously described by Wang et al (PMID: 24071908; incorporated herein by reference). Tagmented amplicons were then PCR amplified in a final volume of 50 ul using a final concentration of 0.2 mM dNTP (Life Technologies), 0.2 uM Illumina index PCR primers (Integrated DNA Technologies), 1× Phusion DNA polymerase buffer (New England Biolabs) and 1 U of Phusion DNA polymerase (New England Biolabs). PCR cycling conditions used were as follows: 72° C. for 3 min, 98° C. for 2 min and 15 cycles of 98° C. for 10 sec, 63° C. for 30 sec, and 72° C. for 3 min. Sequencing libraries were then purified using 1.0× Agencourt AmpureXP beads (Beckman Coulter) following the manufactures recommendations. Sequencing libraries were quantified using the Quant-iT PicoGreen dsDNA assay (Life Technologies) following the manufactures recommendations and pooled equimolar for sequencing. Sequencing libraries were sequenced with 150 base paired-end reads on a MiSeq sequencer following the manufactures recommendations (Illumina) A minimum of a 1000-fold sequencing coverage was generated per amplicon.

NGS sequencing data QC and variant analysis. Using default parameters, the Illumina MiSeq analysis software (MiSeq reporter, version 2.6.2, Illumina) was used to generate amplicon specific FASTQ sequencing data files (Cock et al, Nucleic Acids Res. 2010, 38(6):1767-71, PMID: 20015970). FASTQ files were then processed through an internally developed variant analysis pipeline consisting of a series of public domain software packages joined together using a standard Perl script wrapper. The workflow used was divided into five stages.

Stage 1, PCR primer and on- and off-target sequence QC: For both on- and off-target sites the 20 nucleotide gRNA targeting domain sequence plus PAM sequence and target specific PCR primer sequences (left and right without the additional Illumina sequences) were aligned to the human genome reference sequence (build GRCh38) using a BLAST search (version 2.2.29+, Altschul et al, J Mol Biol., 1990, 215(3):403-10, PMID: 2231712). On- and off-target sites with multiple genomic locations were flagged.

Stage 2, sequencer file decompression: Illumina sequencer generated FASTQ.GZ files were decompressed to FASTQ files using the gzip script (version 1.3.12) and number of reads per file was calculated. Files with no reads were excluded from further analysis.

Stage 3, sequence read alignment and quality trimming: Sequencing reads in FASTQ files were aligned to the human genome reference sequence (build GRCh38) using the BWA-MEM aligner (version 0.7.4-r385, Li and Durbin, Bioinformatics, 2009, 25(14):1754-60, PMID: 19451168) using 'hard-clipping' to trim 3' ends of reads of Illumina sequences and low quality bases. Resulting aligned reads, in the BAM file format (Li et al, Bioinformatics, 2009 25(16): 2078-9, PMID: 19505943), were converted to FASTQ files using the SAMtools script (version 0.1.19-44428cd, Li et al, Bioinformatics, 2009 25(16):2078-9, PMID: 19505943). FASTQ files were then aligned again to the human genome reference sequence (build GRCh38) using the BWA-MEM aligner, this time without 'hard-clipping'.

Stage 4, variant (SNP and INDEL) analysis: BAM files of aligned reads were processed using the VarDict variant caller (version 1.0 'Cas9 aware' modified by developer ZhongWu Lai, Lai et al, Nucleic Acids Res., 2016, 44(11): e108, PMID: 27060149) with allele frequency detection limit set at >=0.0001 to identify variants (SNPs and indels). The Cas9 aware VarDict caller is based on a public domain package but able to move ambiguous variant calls, generated due to repetitive sequences in the alignment region of the variant events, toward the potential Cas9 nuclease cut site in the gRNA targeting domain sequence located 3 bases 5' of the PAM sequence. The SAMtools script was used to calculate read coverage per sample amplicon to determine whether the on- and off-target sites were covered at >1000-fold sequence coverage. Sites with <1000-fold sequence coverage were flagged.

Stage 5, dbSNP filtering and treated/untreated differential analysis: Variants identified were filtered for known variants (SNPs and indels) found in dbSNP (build 142, Shery et al, Nucleic Acids Res. 2001, 29(1):308-11, PMID: 11125122). Variants in the treated samples were further filtered to exclude: 1) variants identified in the unedited control samples; 2) variants with a VarDict strand bias of 2:1 (where forward and reverse read counts supporting the reference sequence are balanced but imbalanced for the non-reference variant call); 3) variants located >5 bp either side of the potential Cas9 cut site; 4) single nucleotide variants.

Results:

We have shown here the surprising result that targeted disruption of specific sequences (e.g., by indel creation at or near those sequences) within the HBG1 or HBG2 promoter regions relieves repression of γ-globin expression, allowing production of the red blood cells containing elevated HbF protein, (cells expressing fetal hemoglobin are sometimes referred to herein as "F-cells"). The elevated HbF prevents sickling of the red blood cells under deoxygenated conditions and will be therapeutic/curative for the patients of both β-thalassemia and SCD. Here, autologous hematopoietic stem cell transplantation (HSCT) with ex vivo genome edited HSC from SCD patients was also combined with stem cell expansion enhancing technology, e.g., an aryl hydrocarbon receptor (AHR) inhibitor, e.g., as described in WO2010/059401 (the contents of which are incorporated by reference in their entirety), e.g., Compound 4, to improve ex vivo expansion and increase the dose of gene modified HSC delivered.

For efficient genome editing via programmable nuclease, Cas9, the successful delivery of guide RNA (gRNA) and Cas9 protein into target cells and tissues is essential. Here, we show delivery of precomplexed gRNA/Cas9 ribonucleoprotein (RNP) complexes by electroporation leads to efficient and specific genome editing almost immediately after delivery and are degraded in cells, reducing off-target effects. In contrast, use of plasmid and viral vector systems used to deliver Cas9 results in prolonged expression of the enzyme which may aggravate off-target effects associated with the system. Additionally, delivery of RNPs into the target cells requires no additional tools which would greatly facilitate translation of genome editing for therapeutic purposes in the clinic.

Recombinant *S. pyogenes* Cas9 protein (SEQ ID NO: 236) was purified from *Escherichia coli* and complexed with synthetic dual gRNAs (dgRNA) that consist of crRNA and tracr to generate ribonucleoprotein (RNP) complexes. The list and sequences of gRNA targeting domains used in the study are shown in Table 1. Most of the gRNA sequences have perfect targets or only 1 or 2 mismatches in both the HBG1 and HBG2 promoter areas. This situation is owed to the duplication of the HBG genes within the human beta globin locus. The RNP complexes were electroporated into CD34+ HSPC via electroporation as described under materials and methods. The cells were expanded prior to the delivery of RNP complexes. Without begin bound by theory, actively dividing cells may facilitate uptake of RNP complexes delivered by electroporation.

TABLE 4

List of gRNAs targeting the HBG1 and HBG2 promoter region used in the current study. All gRNA molecules were tested in duplicate in the dgRNA format described above.

| Guide RNA targeting domain ID | Av % CD71+ day 7) | Std % CD71+ day 7) | % (HbF+ (F cells), average of replicates day 7 | % HbF+ (F cells), standard deviation day 7 | % HbF+ (F cells), average of replicates day 14 | % HbF+ (F cells), standard deviation day 14 | % edited HBG1, Average of replicates | % edited HBG1, standard deviation | % edited HBG2, Average of replicates | % edited HBG2, standard deviation |
|---|---|---|---|---|---|---|---|---|---|---|
| mock | 78.95 | 0.21 | 16.90 | 0.71 | 29.15 | 2.19 | n/a | n/a | n/a | n/a |
| g8 | 73.15 | 1.20 | 49.25 | 0.64 | 66.95 | 1.48 | n/a | n/a | n/a | n/a |
| GCR-0001 | 76.05 | 0.78 | 50.45 | 1.63 | 50.90 | 1.13 | 20.77 | 4.48 | 0.40 | 0.11 |
| GCR-0002 | 73.5 | 1.41 | 24.50 | 0.42 | 33.85 | 1.91 | 1.37 | 0.04 | 1.54 | 0.16 |
| GCR-0003 | 72.85 | 3.32 | 29.05 | 1.63 | 36.00 | 0.42 | 2.77 | 0.67 | 0.21 | 0.05 |
| GCR-0004 | 72.4 | 0.42 | 24.60 | 0.14 | 32.55 | 0.21 | 0.82 | 0.04 | 0.82 | 0.04 |
| GCR-0005 | 71.15 | 2.76 | 24.40 | 0.71 | 33.00 | 1.27 | 0.79 | 0.02 | 0.85 | 0.07 |
| GCR-0006 | 76.25 | 2.33 | 43.40 | 0.00 | 43.90 | 2.40 | 4.95 | 0.76 | 5.92 | 1.10 |
| GCR-0007 | 76.85 | 1.91 | 29.70 | 1.98 | 31.25 | 0.07 | 3.94 | 0.81 | 0.29 | 0.01 |
| GCR-0008 | 70.75 | 6.15 | 61.60 | 2.12 | 55.75 | 2.90 | 57.72 | 4.53 | 75.09 | 1.96 |
| GCR-0009 | 78.35 | 0.21 | 39.95 | 2.90 | 41.70 | 3.54 | 11.99 | 2.60 | 0.24 | 0.02 |
| GCR-00010 | 73.1 | 5.52 | 46.15 | 2.19 | 43.30 | 0.85 | 5.42 | 0.17 | 9.58 | 0.63 |
| GCR-0011 | 72.2 | 0.28 | 43.15 | 0.07 | 43.65 | 1.48 | 33.62 | 1.92 | 11.15 | 1.42 |
| GCR-0012 | 69.3 | 0.42 | 51.00 | 0.00 | 49.05 | 0.07 | 44.34 | 4.16 | 5.39 | 0.08 |
| GCR-0013 | 71.95 | 3.89 | 23.95 | 0.21 | 32.35 | 0.78 | 1.02 | 0.52 | 0.99 | 0.50 |
| GCR-0014 | 76.55 | 0.64 | 28.95 | 0.49 | 33.65 | 2.33 | 5.26 | 0.37 | 0.25 | 0.04 |
| GCR-0015 | 76.1 | 1.56 | 30.95 | 0.64 | 36.45 | 0.92 | 5.58 | 0.01 | 0.29 | 0.05 |
| GCR-0016 | 77.35 | 0.64 | 23.75 | 0.07 | 30.90 | 2.12 | 0.59 | 0.08 | nd | nd |
| GCR-0017 | 77.7 | 2.97 | 25.35 | 0.78 | 29.80 | 0.42 | 2.27 | 0.56 | 2.00 | 0.05 |
| GCR-0018 | 79.3 | 0.14 | 28.05 | 2.05 | 33.15 | 1.77 | 3.32 | 0.74 | nd | nd |
| GCR-0019 | 79.2 | 0.99 | 28.30 | 1.70 | 34.65 | 0.92 | 4.47 | 0.14 | 6.17 | 1.19 |
| GCR-0020 | 78.7 | 0.57 | 25.30 | 1.56 | 31.05 | 0.07 | 1.25 | 0.64 | nd | nd |
| GCR-0021 | 76.05 | 0.07 | 24.75 | 0.64 | 30.70 | 2.69 | 1.09 | 0.01 | 1.41 | 0.20 |
| GCR-0022 | 75.75 | 1.06 | 25.00 | 1.56 | 32.25 | 0.92 | 0.24 | 0.02 | 2.01 | 0.16 |
| GCR-0023 | 76.95 | 2.76 | 23.00 | 0.57 | 31.80 | 0.85 | 0.31 | 0.05 | nd | nd |
| GCR-0024 | 77.7 | 1.56 | 22.90 | 0.28 | 30.50 | 1.41 | 0.47 | 0.25 | nd | nd |
| GCR-0025 | 77 | 0.71 | 26.70 | 0.85 | 32.80 | 0.71 | 1.59 | 0.01 | nd | nd |
| GCR-0026 | 76.85 | 2.05 | 24.15 | 0.49 | 30.95 | 0.35 | 0.95 | 0.18 | 1.43 | 0.11 |
| GCR-0027 | 78.65 | 0.35 | 25.80 | 0.00 | 29.00 | 1.13 | nd | nd | 0.78 | 0.01 |
| GCR-0028 | 79 | 2.97 | 50.60 | 0.71 | 47.90 | 0.85 | 24.90 | 2.02 | nd | nd |
| GCR-0029 | 74.7 | 0.99 | 28.90 | 1.13 | 32.50 | 1.70 | 0.19 | 0.10 | 4.09 | 1.00 |
| GCR-0030 | 77 | 3.25 | 24.95 | 0.92 | 32.20 | 0.57 | 0.96 | 0.08 | nd | nd |
| GCR-0031 | 79 | 0.99 | 30.40 | 0.71 | 36.00 | 1.70 | 2.87 | 0.93 | 2.98 | 0.84 |
| GCR-0032 | 78.55 | 0.21 | 26.30 | 0.28 | 33.00 | 0.71 | 4.25 | 0.56 | 4.61 | 0.66 |

TABLE 4-continued

List of gRNAs targeting the HBG1 and HBG2 promoter region used in the current study. All gRNA molecules were tested in duplicate in the dgRNA format described above.

| Guide RNA targeting domain ID | Av % CD71+ day 7) | Std % CD71+ day 7) | % (HbF+ (F cells), average of replicates day 7 | % HbF+ (F cells), standard deviation day 7 | % HbF+ (F cells), average of replicates day 14 | % HbF+ (F cells), standard deviation day 14 | % edited HBG1, Average of replicates | % edited HBG1, standard deviation | % edited HBG2, Average of replicates | % edited HBG2, standard deviation |
|---|---|---|---|---|---|---|---|---|---|---|
| GCR-0033 | 78.75 | 0.92 | 27.20 | 1.56 | 32.95 | 1.91 | 3.00 | 0.68 | 3.58 | 0.28 |
| GCR-0034 | 80.05 | 0.49 | 50.55 | 1.48 | 50.35 | 1.48 | 6.31 | 0.24 | 12.68 | 0.64 |
| GCR-0035 | 79.75 | 0.35 | 23.30 | 0.00 | 31.30 | 0.71 | 3.68 | 0.16 | nd | nd |
| GCR-0036 | 79.7 | 0.57 | 23.50 | 0.28 | 30.95 | 0.07 | 0.71 | 0.21 | 1.51 | 0.36 |
| GCR-0037 | 74.9 | 2.26 | 34.85 | 0.49 | 34.55 | 0.64 | 4.30 | 0.67 | 7.95 | 0.83 |
| GCR-0038 | 77 | 0.14 | 25.20 | 0.28 | 30.55 | 2.19 | 1.61 | 0.13 | nd | nd |
| GCR-0039 | 75.35 | 1.06 | 25.50 | 0.28 | 34.40 | 0.99 | 2.66 | 0.62 | 0.43 | 0.01 |
| GCR-0040 | 76.35 | 1.06 | 28.20 | 0.71 | 33.50 | 0.57 | 2.66 | 0.51 | 2.61 | 0.21 |
| GCR-0041 | 74.8 | 3.68 | 24.30 | 0.99 | 33.80 | 0.71 | 0.90 | 0.14 | nd | nd |
| GCR-0042 | 73.6 | 4.10 | 26.45 | 0.49 | 33.65 | 2.76 | 1.75 | 0.22 | 2.43 | 0.13 |
| GCR-0043 | 70.4 | 0.00 | 25.45 | 0.21 | 33.25 | 0.21 | 1.17 | 0.02 | 1.66 | 0.17 |
| GCR-0044 | 74.7 | 0.00 | 26.10 | 0.85 | 34.25 | 2.19 | 2.40 | 0.14 | 3.65 | 0.01 |
| GCR-0045 | 75.75 | 1.91 | 41.30 | 1.70 | 41.55 | 1.34 | 7.46 | 0.71 | 11.75 | 2.79 |
| GCR-0046 | 77.85 | 1.91 | 41.30 | 1.70 | 42.40 | 0.71 | 1.69 | 0.03 | 13.10 | 0.15 |
| GCR-0047 | 74.6 | 2.40 | 49.15 | 4.03 | 39.90 | 2.12 | 24.89 | 6.43 | 45.59 | 10.58 |
| GCR-0048 | 76.85 | 4.88 | 60.75 | 1.77 | 52.95 | 2.62 | 28.49 | 10.88 | 47.10 | 15.49 |
| GCR-0049 | 78.05 | 0.21 | 34.50 | 0.57 | 37.45 | 1.77 | 3.39 | 0.55 | nd | nd |
| GCR-0050 | 76.25 | 6.72 | 45.90 | 2.12 | 41.20 | 0.57 | 21.36 | 8.74 | 30.16 | 1.60 |
| GCR-0051 | 81.55 | 2.19 | 54.55 | 0.92 | 51.35 | 1.77 | 25.09 | 0.33 | 77.84 | 1.39 |
| GCR-0052 | 80.6 | 0.14 | 37.25 | 1.77 | 42.35 | 0.35 | 0.31 | 0.04 | 20.52 | 1.70 |
| GCR-0053 | 80.35 | 0.64 | 39.75 | 1.20 | 43.45 | 1.63 | 6.81 | 0.57 | 10.47 | 2.01 |
| GCR-0054 | 81.05 | 0.21 | 44.55 | 0.78 | 46.55 | 1.48 | 0.48 | 0.10 | 23.91 | 2.87 |
| GCR-0055 | 81.4 | 0.71 | 22.95 | 0.35 | 31.70 | 0.42 | 1.79 | 0.62 | 2.40 | 0.47 |
| GCR-0056 | 81.1 | 0.85 | 31.70 | 0.14 | 37.00 | 0.28 | 2.63 | 0.46 | 5.24 | 0.66 |
| GCR-0057 | 72.4 | 6.08 | 25.25 | 0.78 | 30.25 | 1.20 | 0.88 | 0.56 | nd | nd |
| GCR-0058 | 70.95 | 3.04 | 40.00 | 0.71 | 39.25 | 0.49 | 0.54 | 0.13 | 17.84 | 1.33 |
| GCR-0059 | 73.85 | 2.76 | 29.75 | 0.64 | 33.85 | 0.07 | 3.36 | 0.18 | 5.56 | 0.91 |
| GCR-0060 | 67 | 8.20 | 24.70 | 0.14 | 30.95 | 0.07 | 0.99 | 0.06 | 1.06 | 0.38 |
| GCR-0061 | 71.1 | 3.82 | 30.05 | 0.49 | 35.80 | 0.42 | 2.91 | 0.67 | 2.07 | nd |
| GCR-0062 | 74.9 | 4.67 | 43.95 | 3.46 | 43.60 | 2.26 | 7.77 | 1.89 | 13.23 | 2.01 |
| GCR-0063 | 77.05 | 2.62 | 42.20 | 1.13 | 43.80 | 1.13 | 11.32 | 0.84 | 17.89 | 1.55 |
| GCR-0064 | 78.85 | 0.21 | 21.85 | 0.92 | 31.60 | 1.41 | 0.83 | 0.12 | 0.81 | 0.08 |
| GCR-0065 | 78.15 | 0.21 | 26.35 | 2.05 | 34.75 | 0.49 | nd | nd | nd | nd |

TABLE 4-continued

List of gRNAs targeting the HBG1 and HBG2 promoter region used in the current study. All gRNA molecules were tested in duplicate in the dgRNA format described above.

| Guide RNA targeting domain ID | Av % CD71+ day 7) | Std % CD71+ day 7) | % (HbF+ (F cells), average of replicates day 7 | % HbF+ (F cells), standard deviation day 7 | % HbF+ (F cells), average of replicates day 14 | % HbF+ (F cells), standard deviation day 14 | % edited HBG1, Average of replicates | % edited HBG1, standard deviation | % edited HBG2, Average of replicates | % edited HBG2, standard deviation |
|---|---|---|---|---|---|---|---|---|---|---|
| GCR-0066 | 78.85 | 1.77 | 23.85 | 0.07 | 31.55 | 0.64 | 4.86 | 0.18 | 4.89 | 0.08 |
| GCR-0067 | 69 | 7.07 | 62.75 | 0.92 | 53.85 | 2.19 | 16.54 | 4.20 | 29.61 | 7.91 |
| GCR-0068 | 78.1 | 1.84 | 27.75 | 1.77 | 34.40 | 0.71 | 3.77 | 0.12 | 0.39 | 0.07 |
| GCR-0069 | 79.15 | 2.19 | 30.00 | 0.14 | 35.40 | 1.56 | 4.28 | 0.10 | 6.23 | 1.40 |
| GCR-0070 | 77.9 | 0.14 | 30.70 | 0.42 | 36.05 | 1.20 | 3.47 | 0.56 | nd | nd |
| GCR-0071 | 79.2 | 0.42 | 36.80 | 2.55 | 39.80 | 2.12 | 67.16 | 8.10 | nd | nd |
| GCR-0072 | 79.25 | 1.20 | 26.20 | 0.28 | 34.60 | 1.13 | 2.89 | 0.88 | 3.48 | 0.64 |

Figure 2:
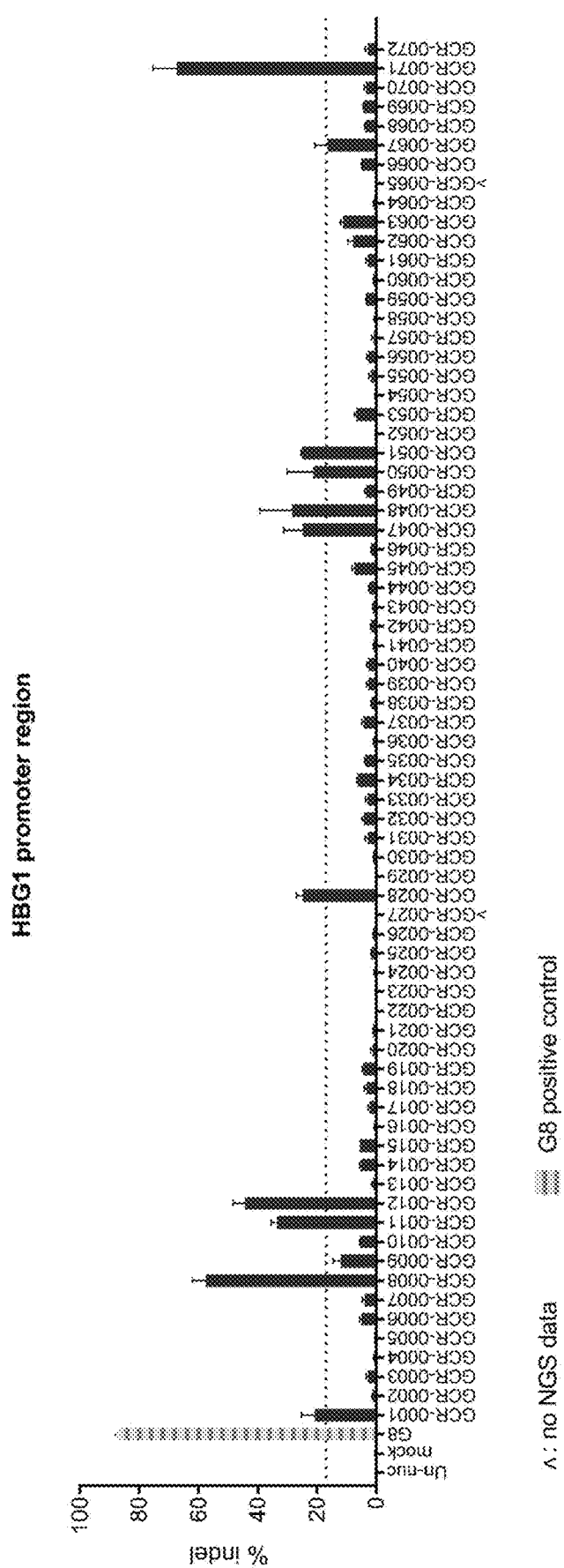
FIG. 2: Editing efficiency at the HBG1 target locus. For each gRNA tested the percentage of indels detected by NGS is shown as mean with error bar indicating standard deviation. The gRNA G8 against exon 2 of BCL11A serves as a positive control. Two guides for which no NGS data was obtained are indicated by arrowheads.
Figure 3:
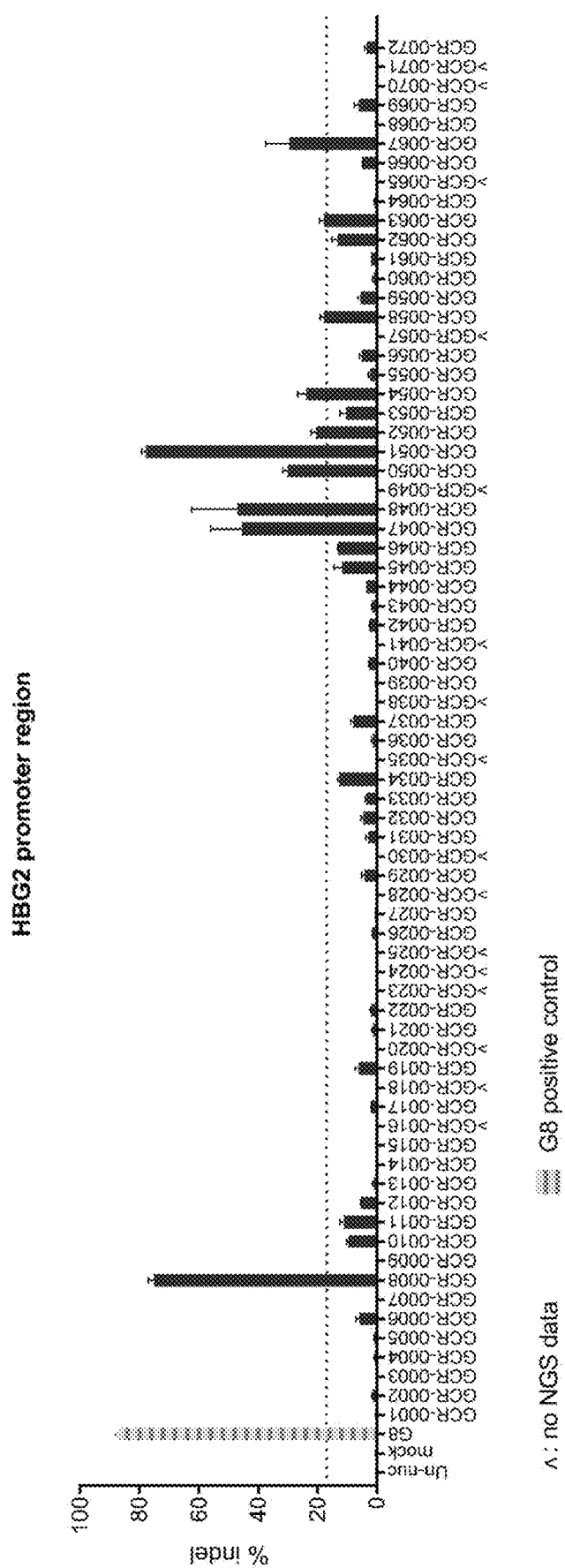
FIG. 3: Editing efficiency at the HBG2 target locus. For each gRNA tested the percentage of indels detected by NGS is shown as mean with error bar indicating standard deviation. The gRNA G8 against exon 2 of BCL11A serves as a positive control. Sixteen guides for which no NGS data was obtained are indicated by arrowheads.
Figure 4A:
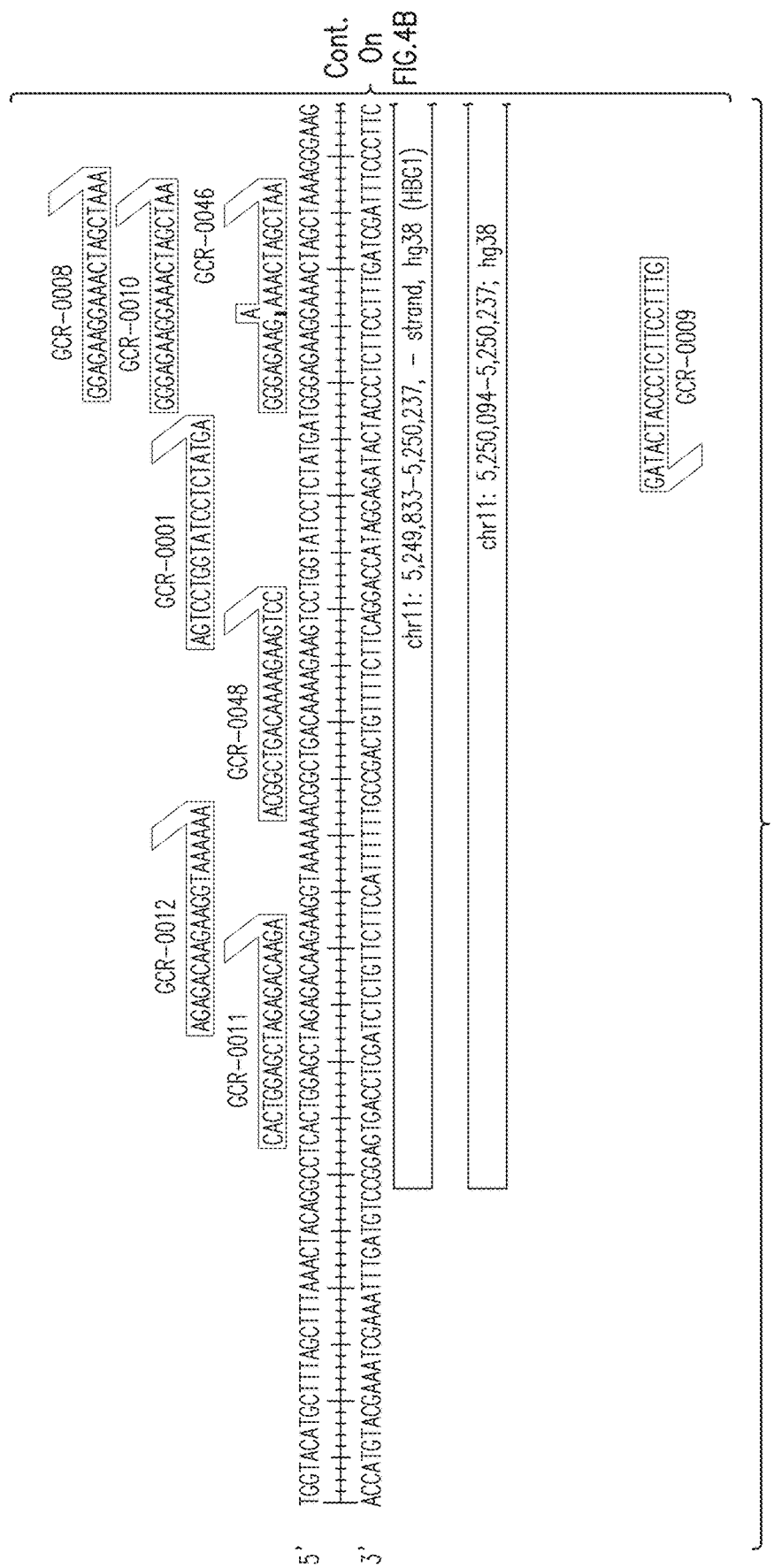
Figure 4B:
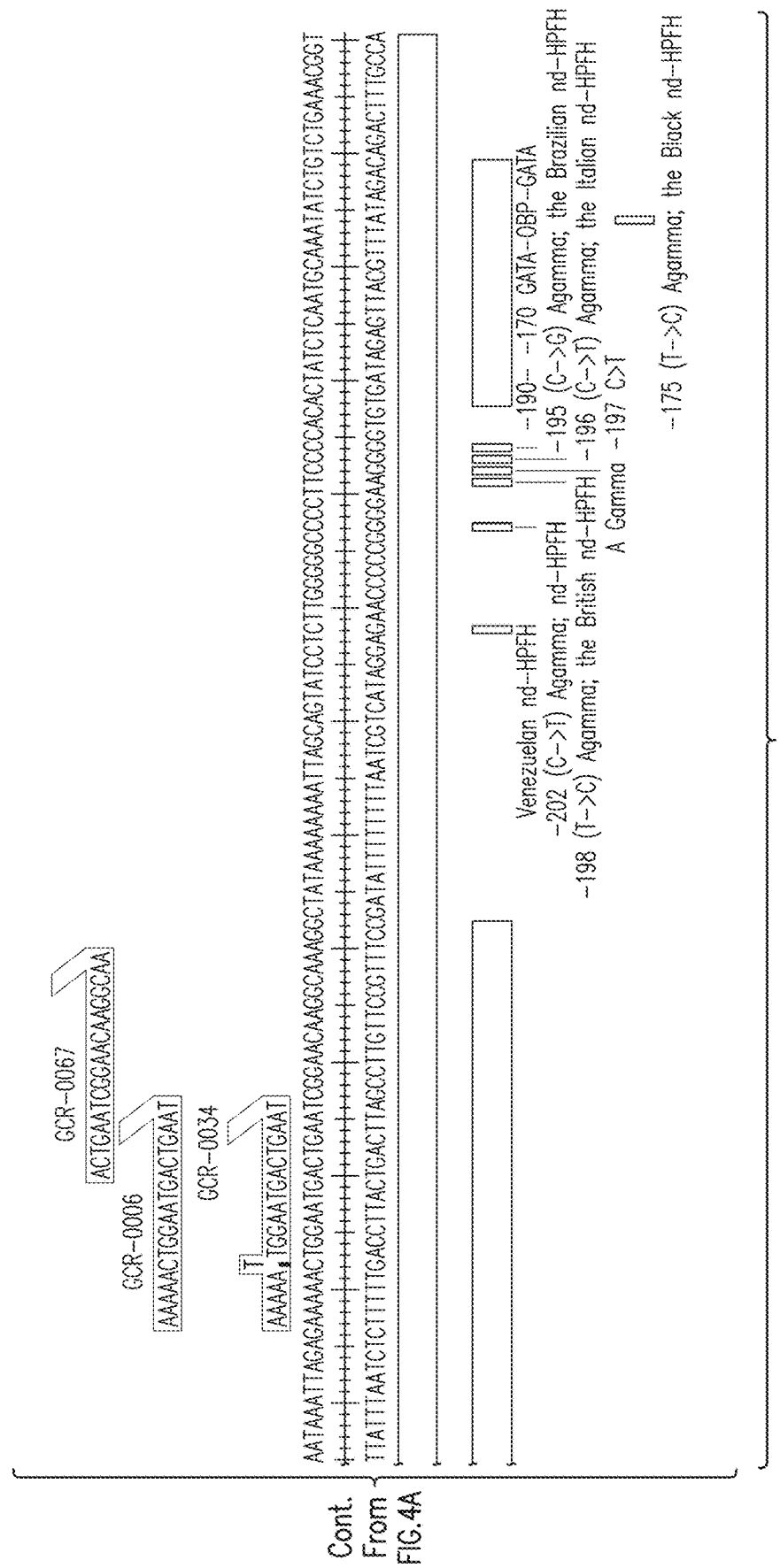
Figure 4C:
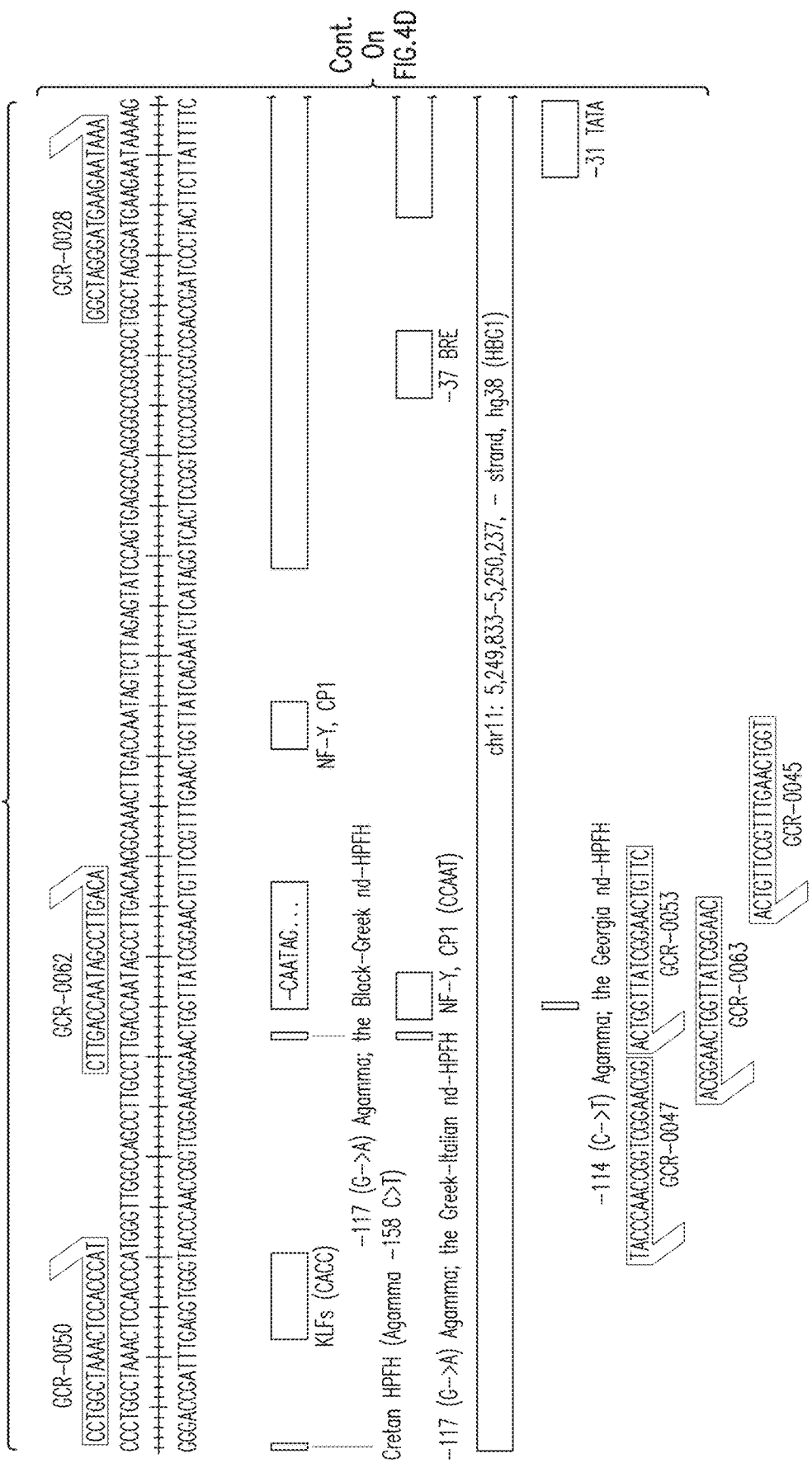
Figure 5A:
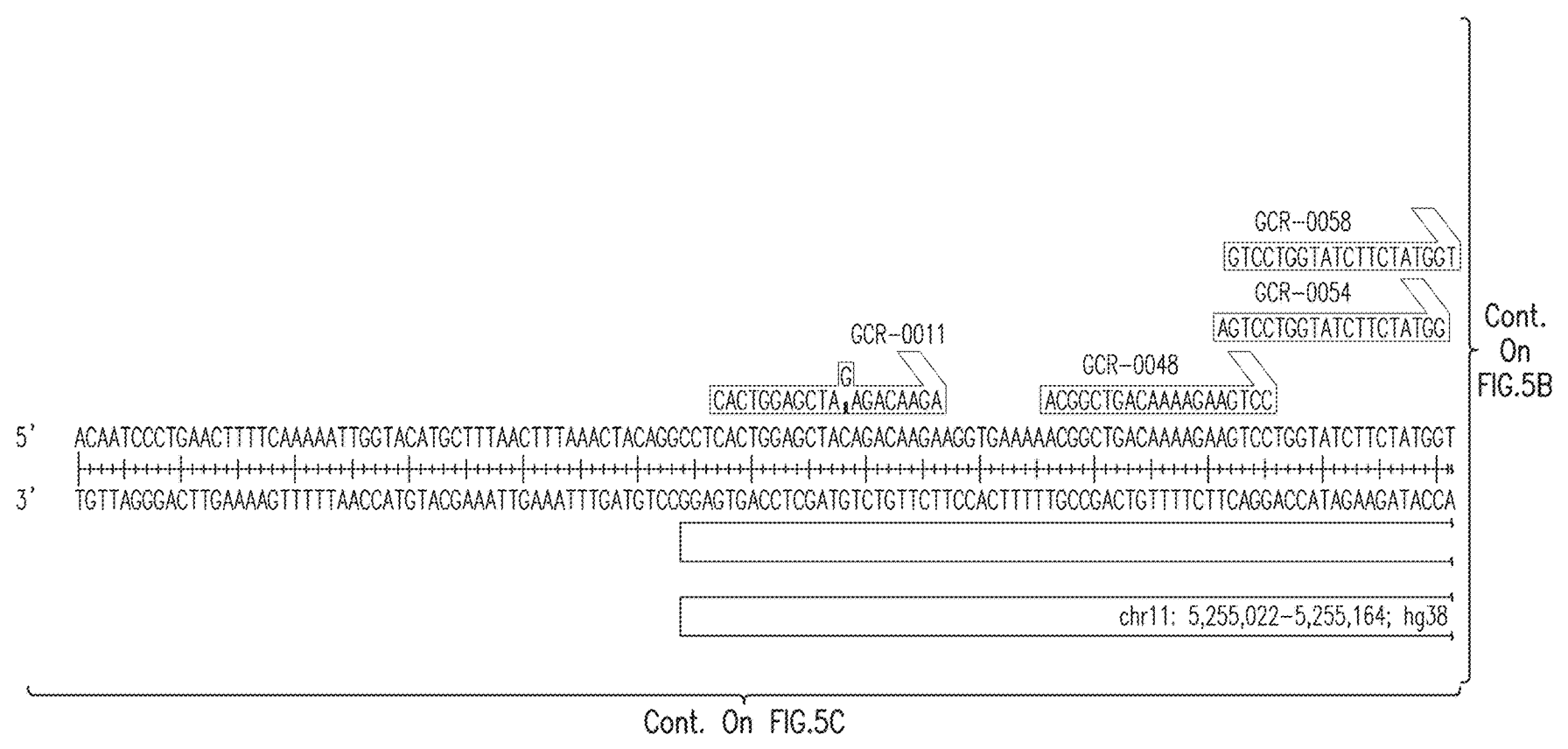
Figure 5B:
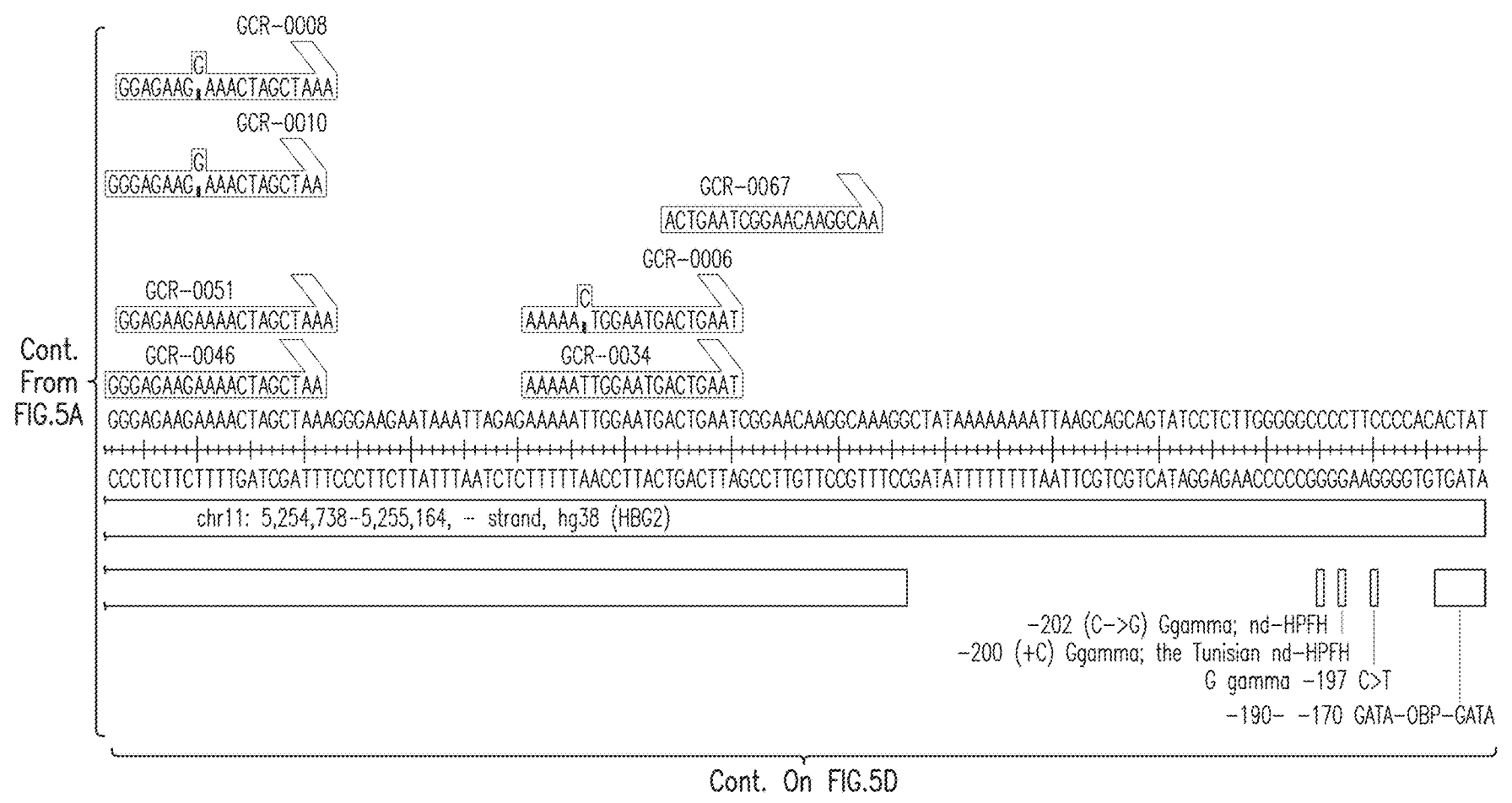
Figure 5C:
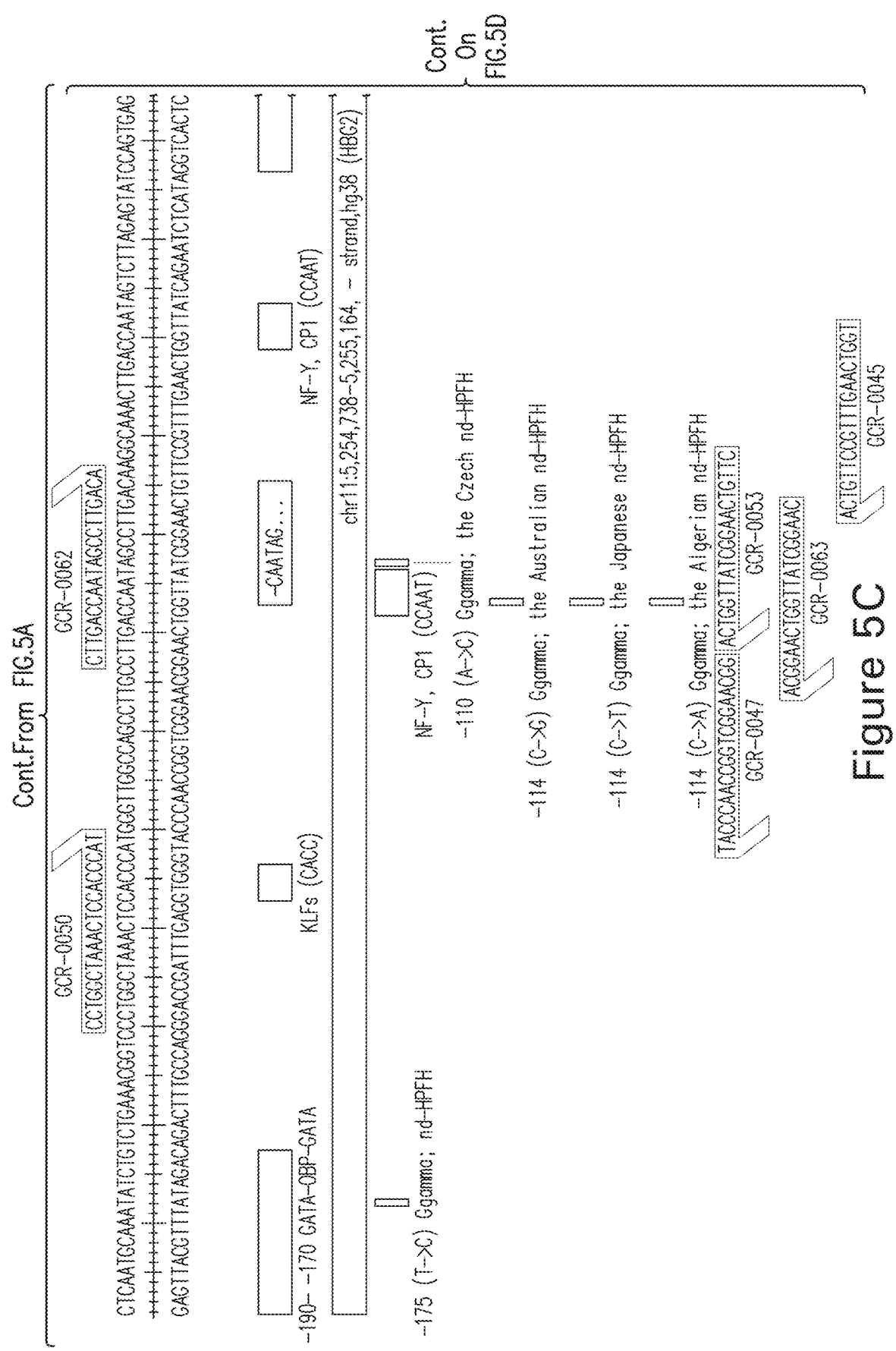
Figure 5D:
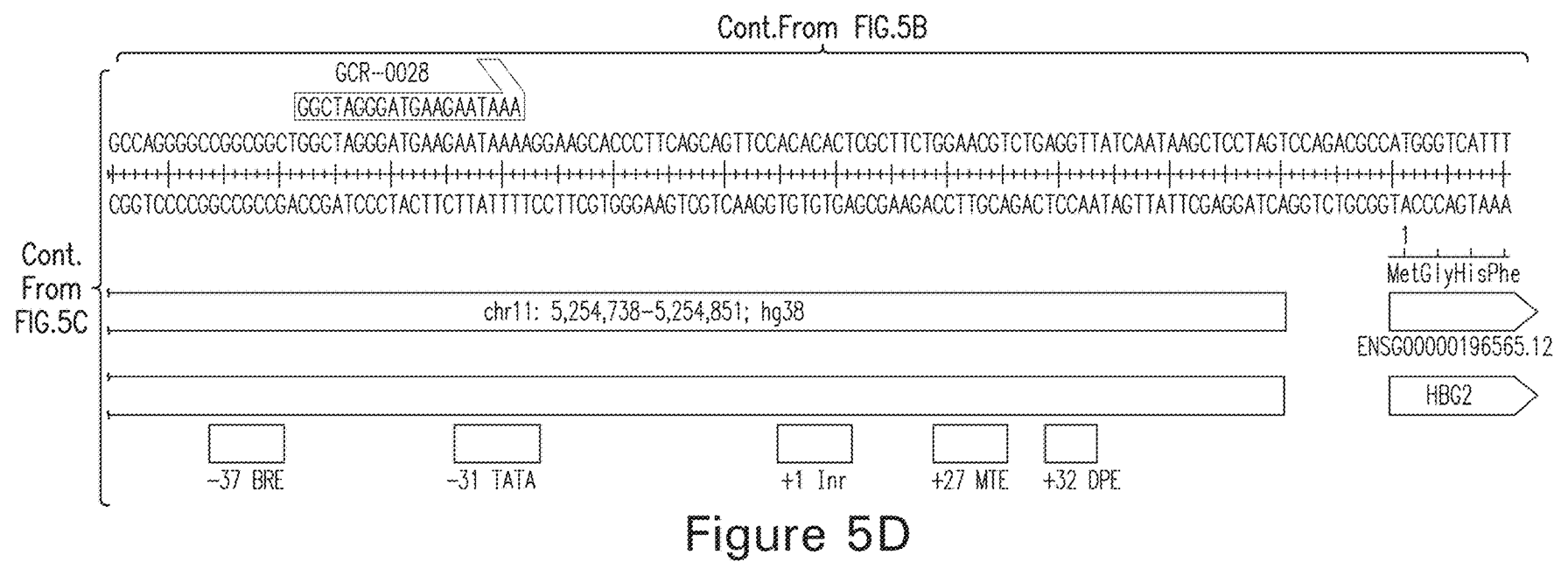

The genome edited and unedited HSPC were analyzed by flow cytometry for expression levels of fetal globin and the erythroid cell surface marker transferrin receptor (CD71) using antibodies conjugated to fluorescent dyes. The live cells were identified and gated by exclusion of Live Dead Violet. Genome editing did not adversely affect erythroid differentiation as the cultured cells showed percentages of CD71+ cells consistent with erythroblasts similar to unedited cells. Delivery of these gRNA RNPs to HSPCs resulted in an increased percentage of progeny erythroid cells containing HbF (up to 62.75%) compared to mock electroporated cells (16.9%) at day 7 following electroporation (Table 4). Additional evaluation of HbF induction levels on day 14 confirmed high induction levels for the best performing dgRNA sequences (table 4), although background HbF levels detected in controls were higher compared to day 7. Induction of HbF positive cells by dgRNA including the targeting domain of g8 targeting exon 2 of BCL11A was also observed in parallel, and several of the gRNAs to the HBG1 or HBG2 regions resulted in higher % F cell levels than g8. PCR products from genomic DNA of the HBG1 and HBG2 promoter region isolated on day 7 after electroporation were also subjected to next generation sequencing (NGS) to determine the percentage of edited alleles in the cell population. High genome editing percentages at the HBG1 and HBG2 promoter region was observed in many of the cell cultures electroporated with RNPs containing Cas9, crRNA of the given targeting domain and Tracr (Table 4, FIG. 1), but not in control cells with no targeting domain delivered (RNPs containing only Cas9 and Tmcr). In particular, the dgRNA treatments that resulted in greater than 17% HbF+ cells above mock transfected control background on Day 7 had a range of 5.92% to 77.84% edited alleles in either the HBG1 or HBG2 target loci (Table 4, FIG. 2 and FIG. 3). Some guides with selective specificity for either the HBG1 or HBG2 promoter area showed preferential editing at the locus they are specific for (for example GCR-0001, GCR-0011 and GCR-0012 edit HBG1 more efficiently and GCR-0034, GCR-0046, GCR-0051, GCR-0052, GCR-0054 and GCR-0058 edit HBG2 more efficiently). A notable and surprising exception to this correlation is GCR-0008 which, although specific to a target sequence of the HBG1 locus, edits both HBG1 and HBG2 loci efficiently and also results in high HbF induction. GCR-0008 has a single mismatch with the target sequence in the HBG2 locus suggesting that efficient off-target editing occurs at this site. The target sequence of some of the 72 gRNAs tested map to regions overlapping or near several annotated human mutations associated with hereditary persistence of fetal hemoglobin (HPFH) expression as well as to known binding sites for transcription factors in the proximal promoter areas of both HBG1 and HBG2 (FIGS. 4A-4D and FIGS. 5A-5D). Surprisingly, a cluster of the best performing gRNAs target sequences outside of these known areas of promoter function in the HBG1 and HBG2 genes (e.g., map to chr11:5, 250,094-5,250,237; hg38 and chr11:5,255,022-5,255,164; hg38 (FIGS. 4A-4D and FIGS. 5A-5D), respectively). These gRNAs include GCR-0001, GCR-0006, GCR-0008, GCR-0009, GCR-0010, GCR-0011, GCR-0012, GCR-0034, GCR-0046, GCR-0048, GCR-0051, GCR-0054, GCR-0058 and GCR-0067. Another well performing gRNA (GCR-0028) targets a transcription factor binding site (TATA box) in the proximal promoter area both of HBG1 and HBG2 that is not associated with non-deletional HPFH mutations (chr11:5,249,833-5,249,927; hg38 and chr11:5,254,738-5, 254,851; hg38 (FIGS. 4A-4D and FIGS. 5A-5D), respectively).

Example 2.2—Gamma Globin Promoter Region Editing in HSPCs for De-Repression of Fetal Globin Expression in Adult Erythroid Cell—Evaluation at Select Sites Using CRISPR-Cas9 with sgRNA Format Methods:
Methods are as in Example 2.1, with the following modifications.

Human CD34+ cell culture Human CD34+ cells were derived from adult healthy donor bone marrow (Lonza catalog #2M-101D). Cells were thawed then expanded for 6 days.

Assembly of Cas9 and guide RNA ribonucleoprotein (RNP) complexes, preparation of HSPC, and electroporation of RNP into HSPC. For formation of RNP using single guide RNAs (sgRNAs), 12 µg of each of sgRNA, 12 µg of CAS9 protein and 1 µL of 10×CCE buffer (20 mM HEPES, 100 mM KCL, 5 mM MgCL2, 5% Glycerol and freshly added 1 mM DTT) were combined in a total volume of 10 ul, then incubated at 37° C. for 5 min. For the None/control condition, vehicle rather than sgRNA was added. Cell density in P3 buffer + supplement was $3.9 \times 10^6$/mL.

In vitro erythropoiesis and FACS analysis for HbF containing erythroid cells. On day 11 cells were transferred into EDM without further supplements. On day 14 and day 18 cells were pelleted and resuspended in fresh EDM without further supplements. An aliquot of cells was taken for analysis of HbF expression at day 14 and day 21. Cells were stained similar to day 7, but surface markers were excluded from the staining to prevent aggregation of cells and anti-HbF antibody was used at 1:20 dilution.

Genomic DNA preparation and next generation sequencing (NGS). Genomic DNA was prepared from edited and unedited HSPC at 3 days post-electroporation using Quick Extract DNA Extraction Solution (Epicentre Cat #QE09050). NGS analysis described below showed no significant editing in control samples electroporated with Cas9 alone.

NGS library preparation and sequencing of amplicons was carried out as described in Example 2.1. NGS sequencing data QC and variant analysis was performed as described in Example 2.1.

Results:

We have shown here that the targeted disruption of specific sequences within the HBG1 or HBG2 promoter regions leading to the production of F-cells can also be accomplished by utilizing gRNA of the sgRNA format.

TABLE 5

List of select gRNAs targeting the HBG1 and HBG2 promoter region used in the current study. All gRNA molecules were tested in duplicate in the sgRNA format described above.

| Guide RNA targeting domain ID | % HbF+ (F cells), average of replicates day 7 | % HbF+ (F cells), standard deviation day 7 | % (HbF+ (F cells), average of replicates day 14 | % HbF+ (F cells), standard deviation day 14 | % HbF+ (F cells), average of replicates day 21 | % HbF+ (F cells), standard deviation day 21 | % edited HBG1, Average of replicates | % edited HBG1, standard deviation | % edited HBG2, Average of replicates | % edited HBG2, standard deviation |
|---|---|---|---|---|---|---|---|---|---|---|
| None/control | 39.0 | 1.8 | 32.7 | 0.6 | 14.4 | 4.9 | n/a | n/a | n/a | n/a |
| GCR-0001 | 60.8 | 2.5 | 49.2 | 0.4 | 20.5 | 7.6 | 15.8 | 3.0 | 0.0 | 0.0 |
| GCR-0008 | 67.1 | 0.8 | 55.2 | 2.3 | 25.6 | 9.3 | 55.2 | 2.0 | 40.9 | 2.8 |
| GCR-0010 | 61.3 | 0.8 | 52.3 | 1.0 | 14.0 | 0.8 | 4.8 | 0.8 | 3.0 | 0.0 |
| GCR-0028 | 58.7 | 1.6 | 49.2 | 0.1 | 14.1 | 2.1 | nd | nd | nd | nd |
| GCR-0047 | 52.6 | 1.6 | 41.2 | 4.1 | 16.7 | 3.3 | nd | nd | nd | nd |
| GCR-0048 | 64.3 | 2.3 | 57.5 | 2.3 | 28.8 | 11.0 | 53.7 | 5.3 | 57.2 | 5.3 |
| GCR-0051 | 65.3 | 3.0 | 59.1 | 2.0 | 20.6 | 5.7 | 27.3 | 0.3 | 50.6 | 3.8 |
| GCR-0053 | 71.7 | 3.3 | 73.7 | 3.3 | 26.2 | 2.6 | 11.9 | 4.2 | 28.0 | 6.1 |
| GCR-0054 | 67.3 | 2.0 | 61.4 | 4.0 | 23.4 | 3.5 | nd | nd | 18.4 | 1.9 |
| GCR-0062 | 61.1 | 5.2 | 54.8 | 1.1 | 16.7 | 1.7 | 2.5 | 1.8 | 3.9 | 2.7 |
| GCR-0063 | 63.6 | 3.7 | 58.0 | 1.7 | 24.6 | 1.3 | 16.4 | 0.2 | 29.9 | 2.9 |
| GCR-0067 | 74.6 | 0.4 | 70.4 | 3.7 | 36.6 | 0.6 | 23.7 | 0.0 | 37.5 | 4.4 |

Adult bone marrow-derived HSPC were electroporated with RNP complexes formed from recombinant S. pyogenes Cas9 protein (SEQ ID NO: 236) and the indicated gRNA of the sgRNA format. The resulting genome edited and unedited HSPC were analyzed by flow cytometry for expression levels of fetal globin and the erythroid cell surface marker transferrin receptor (CD71) using antibodies conjugated to fluorescent dyes. The live cells were identified and gated by exclusion of Live Dead Violet. Delivery of these gRNA RNPs to HSPCs resulted in an increased percentage of progeny erythroid cells containing HbF (up to 74.6%) compared to mock electroporated cells (39.0%) at day 7 following electroporation (Table 5). Additional evaluation of HbF induction levels on day 14 and day 21 confirmed high induction levels for the best performing sgRNA sequences (Table 5). PCR products from genomic DNA of the HBG1 and HBG2 promoter region isolated on day 3 after electroporation were also subjected to next generation sequencing (NGS) to determine the percentage of edited alleles in the cell population. High genome editing percentages (excluding large deletions) at the HBG1 and HBG2 promoter region was observed in many of the cell cultures electroporated with RNPs containing Cas9 and sgRNA of the given targeting domain (Table 5), but not in control cells with no sgRNA delivered (Cas9 only).

Figure 7:
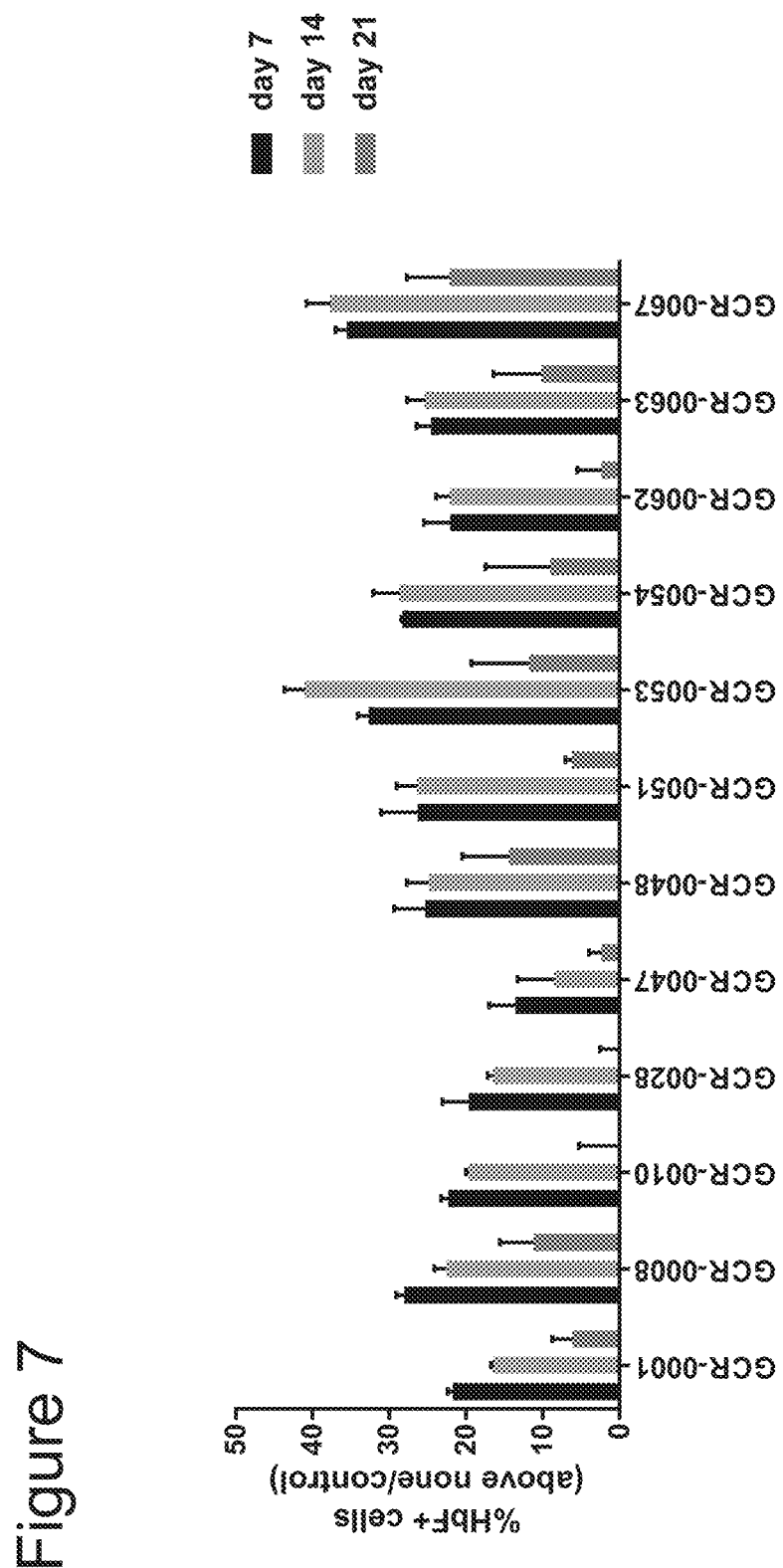
FIG. 7: Detection and quantification of HbF positive cells by flow cytometry at 7 (black bars), 14 (light gray bars) or 21 (dark gray bars) days after erythroid differentiation following electroporation of HSPCs with RNPs containing sgRNA of the indicated targeting domain. The percentage HbF+ cells for control cultures not treated with sgRNA at each time point has been subtracted. Mean+standard deviation is indicated (n=2 technical replicates).

Select targeting sites with a >17% increase in HbF+ erythroid cells at day 7 in Example 2.1 were included in this study. The experimental design differed in two significant ways from that previously described in Example 2.1: the gRNA format (sgRNA rather than dgRNA) and the HSPC source (different donor and bone marrow-derived rather than mobilized peripheral blood-derived). Without being bound by theory, the differences in baseline percentages of HbF+ cells in unedited cell cultures between studies may be caused by the inherent differences between HSPC sources. Despite these differences, all targeting sites with the exception of GCR-47 remained associated with a >17% increase in HbF+ erythroid cells at day 7 (FIG. 7). This increase was maintained out to day 21 for GCR-0067 (FIG. 7). Additionally, indel formation of >25% at HBG1, HBG2 or both was observed with GCR-0008, GCR-0048, GCR-0051, GCR-0053, GCR-0063 and GCR-0067 (Table 5). As with the dgRNA format (Table 4), GCR-0008 in the sgRNA format was associated with efficient editing at both the on-target HBG1 site and the off-target HBG2 site (Table 5). It was undetermined whether the lower HbF+ cell induction with GCR-0047 in this study was associated with reduced editing. Notably, day 7 and day 14 HbF+ cell induction of >17% was associated with targeting sequences outside of the known areas of promoter function in the HBG1 and HBG2 genes (e.g., map to chr11:5,250,094-5,250,237; hg38 and chr11:5,255,022-5,255,164; hg38 (FIGS. 4A-4D and FIGS. 5A-5D), respectively), specifically GCR-0001, GCR-0008, GCR-0010, GCR-0048, GCR-0051, GCR-0054 and GCR-0067 (FIG. 7). Of these, GCR-0008, GCR-0048 and GCR-0067 also had a >10% increase in HbF+ cells at day 21 and >25% indels at HBG1, HBG2 or both (Table 5 and FIG. 7).

Example 2.3—Gamma Globin Promoter Region Editing in HSPCs for De-Repression of Fetal Globin Expression in Adult Erythroid Cells—Additional Analysis of Editing Patterns Using CRISPR-Cas9 with sgRNA Format Methods:
Methods are as in Example 2.1, with the following modifications.

Human CD34+ cell culture. Human CD34+ cells were derived from bone marrow from adult healthy donors (Lonza catalog #2M-101D and Hemacare catalog #BM34-C). Cells were thawed then expanded for 6 days.

Assembly of Cas9 and guide RNA ribonucleoprotein (RNP) complexes, preparation of HSPC, and electroporation of RNP into HSPC. For formation of RNP using single guide RNAs (sgRNAs), 12 µg of each of sgRNA, 12 µg of CAS9 protein and 1 µL of 10×CCE buffer (20 mM HEPES, 100 mM KCL, 5 mM MgCL2, 5% Glycerol and freshly added 1 mM DTT) were combined in a total volume of 10 ul, then incubated at 37° C. for 5 min. For the None/control condition, vehicle rather than sgRNA was added. Cell density in P3 buffer + supplement was $3.9 \times 10^6$/mL.

In vitro erythropoiesis and FACS analysis for HbF containing erythroid cells. On day 11 cells were transferred into EDM without further supplements. On day 14 and day 18 cells were pelleted and resuspended in fresh EDM without further supplements. An aliquot of cells was taken for analysis of HbF expression at day 14 and day 21. Cells were stained similar to day 7, but surface markers were excluded from the staining to prevent aggregation of cells and anti-HbF antibody was used at 1:20 dilution.

Genomic DNA preparation and next generation sequencing (NGS). Genomic DNA was prepared from edited and unedited HSPC at 3 days post-electroporation using Quick Extract DNA Extraction Solution (Epicentre Cat #QE09050). NGS analysis described below showed no significant editing in control samples electroporated with Cas9 alone.

NGS library preparation and sequencing of amplicons was carried out as described in Example 2.1. NGS sequencing data QC and variant analysis was performed as described in Example 2.1.

Non-quantitative PCR for detection of inversions and large deletions. The following primer sets were used to amplify gDNA in the region of HBG1 and HBG2. P1: forward primer 5'-TGCTGAGATGAAACAGGCGT-3' (SEQ ID NO: 257), reverse primer 5'-TTAGGCATC-CACAAGGGCTG-3' (SEQ ID NO: 258), expected ~2.8 kb product for deletion between HBG1 and HBG2 target/off-target sites, expected ~7.7 kb product for inversion between HBG1 and HBG2 target/off-target sites, expected ~7.7 kb product for no large deletion or inversion (unedited or smaller indels at HBG1 and/or HBG2 target/off-target sites, individually). P2: forward primer 5'-GCTCTACAAATG-GAACCCAACC-3' (SEQ ID NO: 259), reverse primer 5'-CTGCTCTGATCTCTAACACCTCA-3' (SEQ ID NO: 260), no product expected for deletion between HBG1 and HBG2 target/off-target sites, no product expected for inversion between HBG1 and HBG2 target/off-target sites, expected ~3.8 kb product for no large deletion or inversion (unedited or smaller indels at HBG1 and/or HBG2 target/off-target sites, individually). P3: forward primer 5'-GAA-GATACAGCTTGCCTCCGA-3' (SEQ ID NO: 261), reverse primer 5'-TTGCTGAGATGAAACAGGCGT-3' (SEQ ID NO: 262), no product expected for deletion between HBG1 and HBG2 target/off-target sites, expected ~1.75 kb product for inversion between HBG1 and HBG2 target/off-target sites, no product expected for no large deletion or inversion (unedited or smaller indels at HBG1 and/or HBG2 target/off-target sites, individually). PCR products were visualized on an agarose gel along with a reference ladder containing 0.5, 1, 1.5, 2, 3, 4, 5, 6, 8 and 10 kb bands (L; New England Biolabs catalog #N3232L). Select products were isolated as indicated and subjected to NGS as described in Example 2.1.

Quantification of large deletions. Large deletions between targeting sites at the HBG1 and HBG2 promotors were quantified by digital droplet PCR (ddPCR) in non-competitive assay format for copy number determination according to manufacturer's recommendations. Briefly, gDNA was combined with ddPCR SuperMix for Probes (no dUTPs) (BioRad Cat #1863024), HindIII-HF restriction enzyme (NEB Cat #R3104S) and each primer probe mix, transferred to a DG8 cartridge along with Droplet Generation Oil for Probes (BioRad Cat #1863005) and droplets generated with a QX200 droplet generator (BioRad). Droplets were subject to PCR on a C1000 Touch Thermal Cycler with 96-Deep Well Reaction Module (BioRad), followed by detection with QX200 droplet reader (BioRad). Copies per ul was determined by analysis with QuantaSoft software (BioRad). A custom primer probe set (Life Technologies Cat #APZW76R, PN4331348, Forward primer: ACGGA-TAAGTAGATATTGAGGTAAGC (SEQ ID NO: 263), Reverse primer: GTCTCTTTCAGTTAGCAGTGG (SEQ ID NO: 264), FAM TaqMan Probe: ACTGCGCT-GAAACTGTGGCTTTATAG (SEQ ID NO: 265)) used to amplify gDNA within the HBG1-HBG2 intergenic region. A TaqMan Copy Number Reference Assay, human, RNase P (Thermo Fisher cat #4403326) was used as a reference amplicon. Copies per ul for HBG1-HBG2 and RNase P amplicons were within the manufacturer's reported linear range. Percent deletion was reported as 100% times 1 minus the ratio of copies per ul for HBG1-HBG2 and RNase P amplicons. Unedited control samples had calculated percent deletions of 2.4%, which may reflect background in the assay.

Results:

We have shown here that the targeted disruption of specific sequences within the HBG1 and HBG2 promoter regions leading to the production of F-cells is associated with both indels at the HBG1 or HBG2 target or off-target site, as well as deletions and inversions of the intervening region. NGS analysis of amplicons confirms this observation.

TABLE 6

List of select gRNAs targeting the HBG1 and HBG2 promoter region used in the current study to edit cells from the first independent donor. All gRNA molecules were tested in duplicate in the sgRNA format described above.

| Guide RNA targeting domain ID | % HbF+ (F cells), average of replicates day 7 | % HbF+ (F cells), standard deviation day 7 | % HbF+ (F cells), average of replicates day 14 | % HbF+ (F cells), standard deviation day 14 | % HbF+ (F cells), average of replicates day 21 | % HbF+ (F cells), standard deviation day 21 | % edited HBG1, Average of replicates | % edited HBG1, standard deviation | % edited HBG2, Average of replicates | % edited HBG2, standard deviation |
|---|---|---|---|---|---|---|---|---|---|---|
| none/control | 37.6 | 3.0 | 17.1 | 0.4 | 32.4 | 5.9 | n/a | n/a | n/a | n/a |
| GCR-0001 | 61.3 | 1.1 | 45.6 | 0.4 | 75.1 | 2.1 | 59.1 | 3.9 | 1.0 | 0.4 |
| GCR-0008 | 62.9 | 1.3 | 42.8 | 2.1 | 67.3 | 1.3 | 86.3 | 6.2 | 85.6 | 5.5 |
| GCR-0010 | 69.5 | 3.0 | 53.4 | 0.9 | 75.0 | 0.4 | 19.5 | 6.2 | 25.1 | 1.0 |
| GCR-0048 | 59.2 | 4.2 | 43.8 | 0.8 | 66.2 | 3.6 | 73.5 | 9.2 | 80.4 | 3.6 |
| GCR-0051 | 61.9 | 0.4 | 49.7 | 1.7 | 70.1 | 6.2 | 53.0 | 0.5 | 86.4 | 0.6 |
| GCR-0067 | 72.2 | 1.8 | 58.1 | 1.7 | 77.4 | 4.2 | 68.8 | 1.2 | 77.5 | 1.6 |

TABLE 7

List of select gRNAs targeting the HBG1 and HBG2 promoter region used in the current study to edit cells from the second independent donor. All gRNA molecules were tested in duplicate in the sgRNA format described above.

| Guide RNA targeting domain ID | % HbF+ (F cells), average of replicates day 7 | % HbF+ (F cells), standard deviation day 7 | % HbF+ (F cells), average of replicates day 14 | % HbF+ (F cells), standard deviation day 14 | % HbF+ (F cells), average of replicates day 21 | % HbF+ (F cells), standard deviation day 21 | % edited HBG1, Average of replicates | % edited HBG1, standard deviation | % edited HBG2, Average of replicates | % edited HBG2, standard deviation |
|---|---|---|---|---|---|---|---|---|---|---|
| none/control | 39.3 | 0.2 | 23.1 | 0.8 | 52.7 | 0.3 | n/a | n/a | n/a | n/a |
| GCR-0001 | 58.8 | 0.7 | 44.7 | 3.0 | 80.2 | 0.8 | 62.7 | 10.0 | 1.0 | 0.0 |
| GCR-0008 | 61.6 | 2.2 | 44.4 | 0.7 | 75.0 | 0.5 | 92.1 | 5.7 | 86.4 | 5.5 |
| GCR-0010 | 65.5 | 2.5 | 47.7 | 3.0 | 79.4 | 0.0 | 17.7 | n/a | 28.5 | 9.0 |
| GCR-0048 | 60.5 | 0.3 | 46.1 | 3.3 | 79.3 | 1.2 | 68.4 | 6.6 | 76.9 | 9.3 |
| GCR-0051 | 64.5 | 1.7 | 47.1 | 4.2 | 78.1 | 0.4 | 62.7 | 7.8 | 86.4 | 3.0 |
| GCR-0067 | 68.8 | 4.6 | 54.9 | 0.4 | 84.5 | 3.1 | 77.4 | 8.7 | 78.0 | 4.2 |

Figure 8:
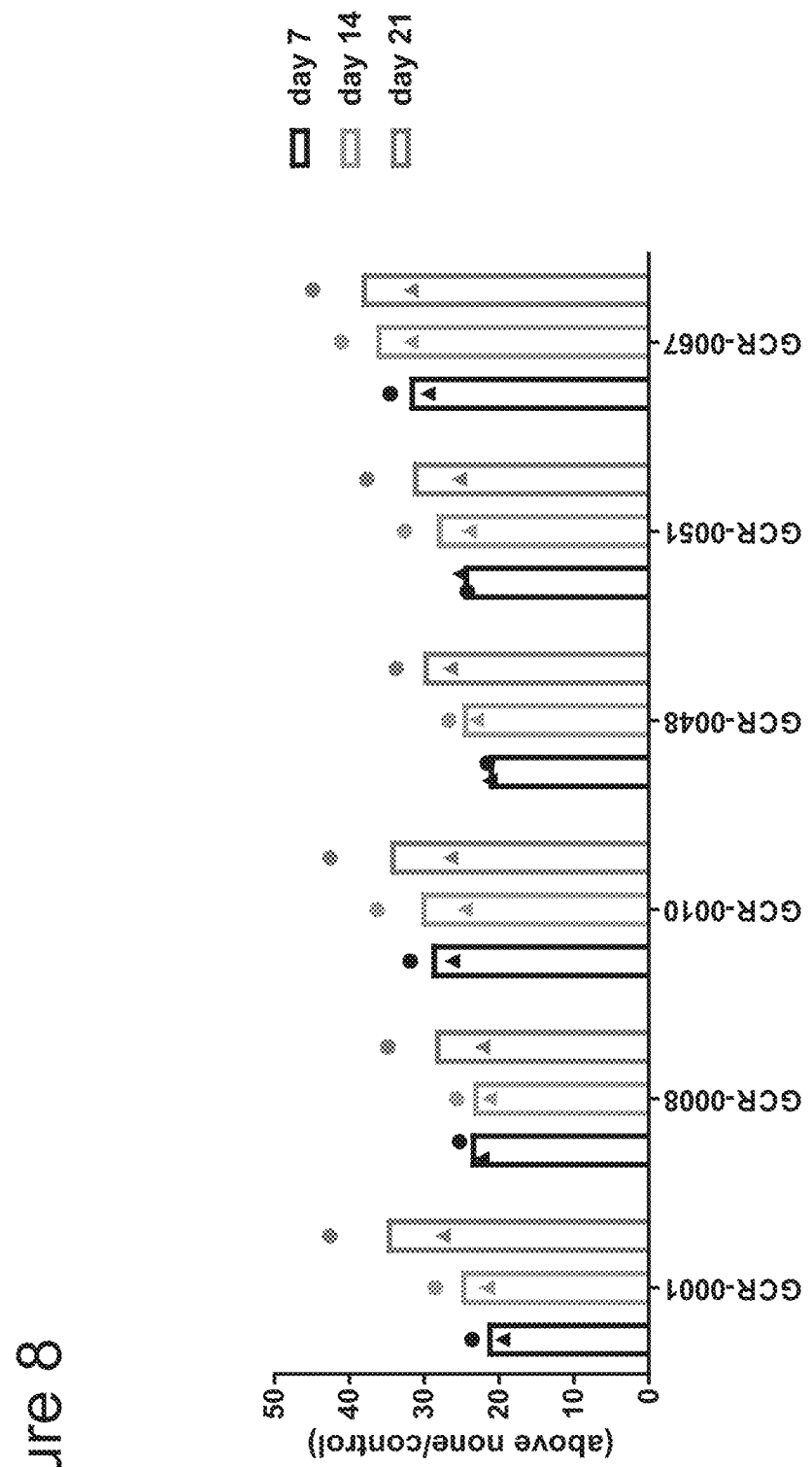
FIG. 8: Detection and quantification of HbF positive cells by flow cytometry at 7 (open black bars), 14 (open light gray bars) or 21 (open dark gray bars) days after erythroid differentiation following electroporation of HSPCs with RNPs containing sgRNA of the indicated targeting domain. The percentage HbF+ cells for control cultures not treated with sgRNA at each time point has been subtracted. Mean (bar) of two independent cell donors is shown, along with value for each donor (circle=first donor, triangle=second donor).

Adult bone marrow-derived HSPC from 2 independent donors were electroporated with RNP complexes formed from recombinant *S. pyogenes* Cas9 protein (SEQ ID NO: 236) and the indicated gRNA of the sgRNA format. Evaluated sgRNAs had targeting sequences outside of the known areas of promoter function in the HBG1 and HBG2 genes (e.g., map to chr11:5,250,094-5,250,237; hg38 and chr11:5, 255,022-5,255,164; hg38 (FIGS. 4A-4D and FIGS. 5A-5D), respectively). The resulting genome edited and unedited HSPC were analyzed by flow cytometry for expression levels of fetal globin and the erythroid cell surface marker transferrin receptor (CD71) using antibodies conjugated to fluorescent dyes. The live cells were identified and gated by exclusion of Live Dead Violet. Delivery of these gRNA RNPs to HSPCs resulted in an increased percentage of progeny erythroid cells containing HbF compared to mock electroporated cells at days 7, 14 and 21 following electroporation (Tables 6 and 7). All included targeting sites were associated with a >17% increase in HbF+ erythroid cells from both donors at all timepoints—days 7, 14 and 21 (FIG. 8). PCR products from genomic DNA of the HBG1 and HBG2 promoter region isolated on day 3 after electroporation were also subjected to next generation sequencing (NGS) to determine the percentage of edited alleles in the cell population. High genome editing percentages at both the HBG1 and HBG2 promoter region (53% to 92% indels) was observed in cell cultures from both donors electroporated with RNPs containing Cas9 and sgRNAs with targeting domains GCR-0008, GCR-0048, GCR-0051 and GCR-0067 (Tables 6 and 7), but not in control cells with no sgRNA delivered (Cas9 only). Targeting domain GCR-0010 was associated with reduced but sizable editing percentages at both the HBG1 and HBG2 promotor region (17% to 28% indels) in cell cultures from both donors; whereas, GCR-0001 was associated with efficient and selective editing at HBG1 (59% and 62%) compared with HBG2 (1% and 1%) in the two donors (Tables 6 and 7).

Figure 9:
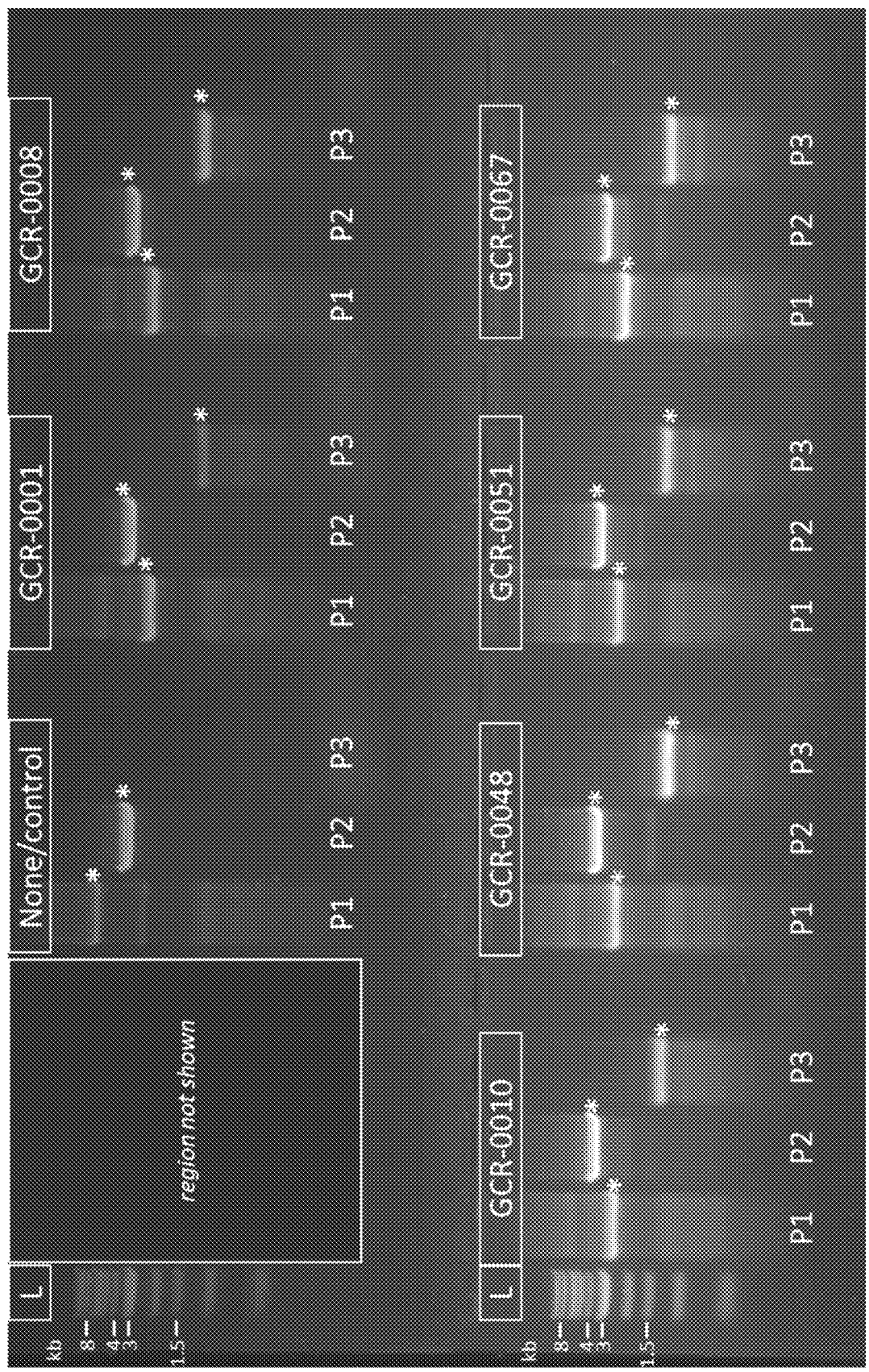
FIG. 9. Visualization of PCR products from the indicated reaction: P1, P2 or P3, as described in the Examples, from cells following electroporation with RNPs containing sgRNA of the indicated targeting domain or control cells not treated with sgRNA. Expected products are as follows. P1: 7.7 kb for wild type/small indel allele or 4.9 kb inversion allele, 2.8 kb for 4.9 kb deleted allele. P2: 3.8 kb for wild type/small indel allele, no product for 4.9 kb deletion or 4.9 kb inversion allele. P3: 1.8 kb for 4.9 kb inversion allele, no product for wild type/small indel allele or 4.9 kb deletion allele. L=DNA reference ladder. *=DNA from this band was isolated and subjected to next-generation sequencing.

The GCR-0048 and GCR-0067 targeting domains are present at both HBG1 and HBG2, and the other targeting domains are present at either HBG1 (GCR-0001, GCR-0008 and GCR-0010) or HBG2 (GCR-0051) with a potential mismatched off-target site at the other promoter. Simultaneous cleavage at both the HBG1 and HBG2 target/off-target sites has the potential to result in deletion and/or inversion of the intervening 4.9 kb genomic sequence; herein sometimes also referred to as '4.9 kb' or HBG1-HBG2' or 'large' inversion or deletion. Thus, a set of three different PCR reactions was used to detect the presence of genomes with deletion or inversion of this region. The P2 reaction was designed so that genomic sequences without the HBG1-HBG2 deletion or inversion would be amplified with a resulting 3.8 kb product, whereas sequences with the HBG1-HBG2 deletion or inversion would not be amplified. A band approximately of this size was detected in all samples (FIG. 9), consistent with the detection of smaller indels at each individual HBG1 or HBG2 targeting site (Tables 6 and 7). The P3 reaction was designed so that HBG1-HBG2 inverted genomic sequences would be amplified with a resulting 1.7 kb product, whereas sequences without this inversion or with/without the HBG1-HBG2 deletion would not be amplified. A band approximately of this size was detected in cultures electroporated with RNPs containing Cas9 and sgRNAs with the indicated targeting domains, but was undetectable in unedited control cultures (FIG. 9). Finally, the P1 reaction was designed to span both the HBG1 and HBG2 targeting region, so that amplification of sequences without the HBG1-HBG2 deletion as well as those with the HBG1-HBG2 region inverted would both produce a 7.7 kb product, while amplification of sequences containing the HBG1-HBG2 deletion would result in a 2.8 kb product. Indeed, unedited control samples had a prominent upper band at approximately 8 kb and a faint, potentially non-specific band at approximately 2.8 kb. In contrast, cultures electroporated with RNPs containing Cas9 and sgRNAs with the indicated targeting domains had a prominent band at approximately 2.8 kb and a faint band at approximately 8 kb (FIG. 9). DNA from each band indicated with an asterix was isolated and subject to next-generation sequencing to confirm its identity as amplification of the predicted sequence (with or without the HBG1-HBG2 inversion or deletion, as described).

For further sequence characterization of the region spanning the HBG1 and HBG2 editing sites, a fourth long range PCR condition (P4) was developed to amplify a 6192 bp region encompassing the HBG1 and HBG2 editing sites for gRNA GCR-0001, GCR-0008, GCR-0010, GCR-0048, GCR-0051 and GCR-0067. Amplification of genome edited samples results in two amplicon sizes (1.2 kb and a 6.2 kb), while unedited samples only generate one amplicon size (6.2 kb). Sequence analysis of the 6.2 kb and 1.2 kb amplicons shows that the 1.2 kb amplicons are a result of 4.9 kb deletions between the HBG1 and HBG2 cut sites, while the 6.2 kb amplicon consist of wildtype and various indel alleles at the HBG1 and HBG2 editing sites. Sequencing analysis also shows a low level of inversions between the HBG1 and HBG2 cut sites where the sequence excised between the two sites has been reincorporated into the genome in the opposite direction. This analysis is not quantitative, but the inversion is likely very rare as it is only detected in a small percentage (<1%) of sequencing reads spanning the HBG1 and HBG2 cut sites.

Figure 10:
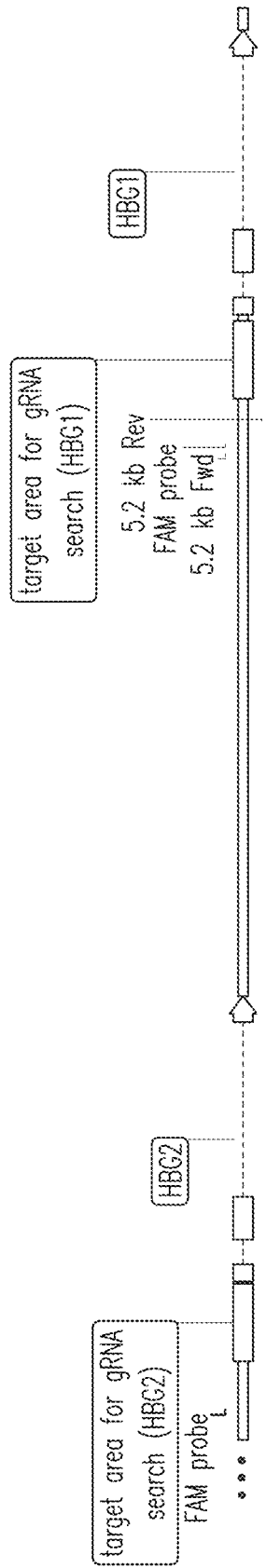
FIG. 10: Schematic indicating genomic location of primer and probe binding sites for the digital droplet PCR assay to quantify 4.9 kb deletions. The primers (5.2 kb Fwd and 5.2 kb Rev) and probe (FAM probe) bind to an intergenic site downstream of HBG2 and upstream of HBG1. The probe has a second binding site upstream of HBG2, but that region is not bound by the primers. The areas in which the targeting domains in the HBG1 and HBG2 promotors are located are indicated. If the sequence intervening the two targeting domain regions is deleted, the primer/probe binding site between HBG1 and HBG2 would be lost.

Together these results suggest that, in addition to indels at either HBG1 or HBG2 target/off-target site, cultures electroporated with RNPs containing Cas9 and sgRNAs with the indicated targeting domains contain edited alleles with deletion or inversion of the intervening HBG1-HBG2 region. Thus, a given allele post-editing could be an HBG1-HBG1 inversion, an HBG1-HBG2 deletion, a indel localized to the HBG1 site, an indel localized to the HBG2 site, or an indel localized to the HBG1 site along with an indel localized to the HBG2 site without modification of the intervening region. The most common on-target editing repair pattern variants generated by editing with gRNAs GCR-0001, GCR-0008, GCR-0010, GCR-0048, GCR-0051 and GCR-0067 are shown in Table 7-2. The variants shown are localized indels generated at the HBG1 and HBG2 loci and large 4.9 kb deletions caused by the excision of the sequence between the HBG1 and HBG2 cut sites. The localized indels were characterized using PCR and NGS analysis as described in Example 2.1. A quantitative ddPCR assay was developed to determine the frequency of alleles with the large 4.9 kb deletion of the intervening HBG1 to HBG2 region (FIG. 10). Briefly, copy number of the region upstream of the HBG1 promoter (between the 5.2 kb Fwd and Rev primers shown in FIG. 10) was defined in relation to copy number at the RPPH1 locus as described in the methods. Allele frequencies for the localized smaller indels are not relative to the total indel frequency, because the amplification of the HBG1 or HBG2 site for NGS would not occur in alleles containing the 4.9 kb inversion or deletion. For example, for gRNA GCR-0001 the frequency of the 4.9 kb deletion is 35.2%, with the remaining 64.8% (100%–35.2%, ignoring inversions) being a mixture of wildtype and smaller localized indels. Therefore the 9% single base pair A base deletion would be 5.8% of the total indel frequency i.e. 9% of 64.8%. Allele frequencies shown in Table 7-2 vary slightly between experiments and should not be considered as absolute values.

TABLE 7-2

Top on-target editing repair pattern (collectively for any gRNA molecule, also referred to herein as "indel pattern") variants generated by editing cells from the first donor with gRNAs GCR-0001, GCR-0008, GCR-0010, GCR-0048, GCR-0051 and GCR-0067. Variant size, variant type (Ins = insertion, Del = deletion), reference allele, variant allele, variant start and end position relative to chromosome 11 reference genome build hg38, and allele frequency are shown. The HBG2 locus edited with gRNA GCR-0001 shows no significant localized indels, but based on the qPCR results it does result in a 4.9kb deletion.

| gRNA name | Size (bp) | Type | Reference allele | Variant allele | Variant start and end position | Allele frequency |
|---|---|---|---|---|---|---|
| GCR-0001 (HBG1) | 4928 | Del | Not shown | Not shown | 5250172-5255100 | 35.2% |
| | -1 | Del | CA | C | 5250171-5250172 | 9.0% |
| | 1 | Ins | A | AT | 5250172-5250173 | 8.1% |
| | -1 | Del | AT | A | 5250172-5250173 | 8.0% |
| | -2 | Del | ATA | A | 5250172-5250174 | 5.1% |
| | 1 | Ins | A | AA | 5250172-5250172 | 2.6% |
| GCR-0008 (HBG1) | 4928 | Del | Not shown | Not shown | 5250150-5255078 | 40.4% |
| | 1 | Ins | T | TA | 5250150-5250151 | 50.5% |
| | -2 | Del | AGC | A | 5250151-5250153 | 3.4% |
| | -1 | Del | TA | T | 5250150-5250151 | 3.3% |
| | -1 | Del | AG | A | 5250151-5250152 | 2.4% |
| | -4 | Del | TAGCT | T | 5250150-5250154 | 2.2% |
| GCR-0008* (HBG2) | 4928 | Del | Not shown | Not shown | 5250150-5255078 | 40.4% |
| | 1 | Ins | T | TA | 5255078-5255079 | 55.8% |
| | -19 | Del | CCCTTTAGCTAGTTTTCTTC (SEQ ID NO: 266) | A | 5255073-5255092 | 5.6% |
| | -2 | Del | AGC | A | 5255079-5255081 | 2.9% |
| | -6 | Del | TTTAGCT | T | 5255076-5255082 | 2.8% |
| | -1 | Del | TA | T | 5255078-5255079 | 2.6% |
| GCR-0010 (HBG1) | 4928 | Del | Not shown | Not shown | 5250151-5255079 | 43.6% |
| | 1 | Ins | A | AG | 5250151-5250152 | 5.6% |
| | -4 | Del | AGCTA | A | 5250151-5250155 | 1.8% |
| | 1 | Ins | A | AA | 5250151-5250152 | 1.6% |
| GCR-0010* (HBG2) | 4928 | Del | Not shown | Not shown | 5250151-5255079 | 43.6% |
| | 1 | Ins | A | AG | 5255079-5255080 | 5.7% |
| | -19 | Del | CCCTTTAGCTAGTTTTCTTC (SEQ ID NO: 266) | A | 5255073-5255092 | 2.6% |
| | -52 | Del | GCCTTGTT.....TTCCCTTTA | G | 5255027-5255079 | 2.0% |
| | -4 | Del | TAGCT | T | 5255078-5255082 | 1.5% |
| | -6 | Del | TTTAGCT | T | 5255076-5255082 | 1.5% |
| GCR-0048 (HBG1) | 4928 | Del | Not shown | Not shown | 5250187-5255115 | 43.5% |
| | -1 | Del | AC | A | 5250187-5250188 | 40.0% |
| | -2 | Del | ACT | A | 5250187-5250189 | 10.1% |
| | -4 | Del | ACTTC | A | 5250187-5250191 | 5.2% |
| | 1 | Ins | A | AA | 5250187-5250188 | 1.9% |
| | -1 | Del | GA | G | 5250186-5250187 | 2.1% |
| GCR-0048 (HBG2) | 4928 | Del | Not shown | Not shown | 5250187-5255115 | 43.5% |
| | -1 | Del | AC | A | 5255115-5255116 | 42.4% |
| | -2 | Del | ACT | A | 5255115-5255117 | 8.9% |
| | -3 | Del | ACTT | A | 5255115-5255118 | 2.7% |
| | -4 | Del | ACTTC | A | 5255115-5255119 | 2.5% |
| | -15 | Del | GGACTTCTTTTGTCAG (SEQ ID NO: 267) | G | 5255113-5255128 | 2.5% |
| GCR-0051* (HBG1) | 4928 | Del | Not shown | Not shown | 5250150-5255078 | 44.9% |
| | 1 | Ins | T | TA | 5250150-5250151 | 39.4% |
| | -1 | Del | TA | A | 5250150-5250151 | 1.3% |
| | -2 | Del | AGC | A | 5250151-5250153 | 0.7% |
| | -14 | Del | TTAGCTAGTTTCCTT (SEQ ID NO: 268) | T | 5250149-5250163 | 0.9% |
| | -6 | Del | TTTAGCT | T | 5250148-5250154 | 0.6% |

TABLE 7-2-continued

Top on-target editing repair pattern (collectively for any gRNA molecule, also referred to herein as "indel pattern") variants generated by editing cells from the first donor with gRNAs GCR-0001, GCR-0008, GCR-0010, GCR-0048, GCR-0051 and GCR-0067. Variant size, variant type (Ins = insertion, Del = deletion), reference allele, variant allele, variant start and end position relative to chromosome 11 reference genome build hg38, and allele frequency are shown. The HBG2 locus edited with gRNA GCR-0001 shows no significant localized indels, but based on the qPCR results it does result in a 4.9kb deletion.

| gRNA name | Size (bp) | Type | Reference allele | Variant allele | Variant start and end position | Allele frequency |
|---|---|---|---|---|---|---|
| GCR-0051 (HBG2) | 4928 | Del | Not shown | Not shown | 5250150-5255078 | 44.9% |
| | 1 | Ins | T | TA | 5255078-5255079 | 52.5% |
| | -19 | Del | CCCTTTAGCTAGTTTTCT TC (SEQ ID NO: 269) | C | 5255073-5255092 | 4.9% |
| | -2 | Del | AGC | A | 5255079-5255081 | 3.2% |
| | -4 | Del | TAGCT | T | 5255078-5255082 | 2.4% |
| | -1 | Del | TA | T | 5255078-5255079 | 2.2% |
| GCR-0067 (HBG1) | 4928 | Del | Not shown | Not shown | 5250099-5255027 | 55.3% |
| | -6 | Del | GCCTTTG | G | 5250093-5250099 | 11.3% |
| | -1 | Del | TG | T | 5250098-5250099 | 9.4% |
| | -1 | Del | GC | G | 5250099-5250100 | 7.0% |
| | -5 | Del | GCCTTG | G | 5250099-5250104 | 5.4% |
| | -2 | Del | GCC | G | 5250099-5250101 | 3.4% |
| GCR-0067 (HBG2) | 4928 | Del | Not shown | Not shown | 5250099-5255027 | 55.3% |
| | -6 | Del | GCCTTTG | G | 5255021-5255027 | 36.1% |
| | -5 | Del | GCCTTG | G | 5255027-5255032 | 15.7% |
| | -1 | Del | TG | T | 5255026-5255027 | 4.0% |
| | -1 | Del | GC | G | 5255027-5255028 | 2.4% |
| | -2 | Del | GCC | G | 5255027-5255029 | 2.1% |

*HBG1/2 target site with mismatches.

High overall editing frequencies at the gamma globin locus, including high frequencies of large 4.9 kb deletions between the HBG1 and HBG2 promotor targeting sites, were observed after electroporating cells with RNPs containing sgRNA of the indicated targeting domain. The on-target editing patterns shown were identified in cells which generated increased F cells after erythroid differentiation, as described. In embodiments, the indel pattern for any gRNA molecule described herein includes the most frequent 1, 2, 3, 4, 5 or 6 indels detected at the HBG1 locus. In embodiments, the indel pattern for any gRNA molecule described herein includes the most frequent 1, 2, 3, 4, 5 or 6 indels detected at the HBG2 locus. In embodiments, the indel pattern for any gRNA molecule described herein includes the most frequent 1, 2, 3, 4, 5 or 6 indels detected at the HBG1 locus and the most frequent 1, 2, 3, 4, 5 or 6 indels detected at the HBG2 locus, e.g., as described in Table 7-2 (but not double-counting the approximately 4.9 kb deletion).

Example 2.4: Exemplary Editing Patterns in Isolated Sub-Populations of HSPCs after Gamma Globin Promoter Region Editing Methods:

Methods are as in Example 2.1, with the following modifications.

Human CD34+ cell culture. Human CD34+ cells were isolated from G-CSF mobilized peripheral blood from adult donors (Hemacare catalog #M001F-GCSF-3) using immunoselection (Miltenyi) according to the manufacturer's instructions and expanded for 2 days prior to electroporation with RNP complexes.

Assembly of Cas9 and guide RNA ribonucleoprotein (RNP) complexes, preparation of HSPC, and electroporation of RNP into HSPC. For formation of RNP using single guide RNAs (sgRNAs), 12 μg of each of sgRNA, 12 μg of CAS9 protein and 1 μL of 10×CCE buffer (20 mM HEPES, 100 mM KCL, 5 mM MgCL2, 5% Glycerol and freshly added 1 mM DTT) were combined in a total volume of 10 ul, then incubated at 37° C. for 5 min. Cell density in P3 buffer + supplement was $1.3 \times 10^8$/mL. Seven replicate electroporation were performed using GCR-0067, and cells were combined post-electroporation. For the None/control condition, cells were transferred directly from P3 buffer into expansion medium without electroporation or addition of Cas9. Following electroporation with RNP complexes, cells were expanded for an additional 3 days prior to flow cytometry cell sorting.

Flow cytometry cell sorting for analysis of editing efficiency in hematopoietic stem and progenitor subpopulations. Edited cell cultures at 3 days post-electroporation were harvested and incubated with anti-CD34 (BD Biosciences, Cat #348057), anti-CD38 (BD Biosciences, Cat #560677), anti-CD90 (BD Biosciences, Cat #559869), anti-CD45RA (BD Biosciences, Cat #563963), anti-CD49f (BD Biosciences, Cat #562598) in FACS staining buffer consisting of HBSS (GE Life Sciences, Cat. #SH30588.01) supplemented with 2% FBS (Omega Scientific, Cat. #FB-11) and 2 mM EDTA (Corning Cat. #46-034-CL). Cells were washed with FACS staining buffer, and cell viability was determined by addition of DAPI (4',6-Diamidino-2-Phenylindole). Multicolor FACS analysis was performed on a FACS Aria cell sorter (BD Biosciences). Discrimination between negative and positive cell populations was determined by gates set using control stained cell cultures, in which each antibody was individually replaced with an isotype and fluorochrome-conjugate matched non-specific control antibody (BD Biosciences Cat #550854, 554680, 563437, 557872, and 562602). Purity of sorted cells was confirmed by post-sort purity check.

Genomic DNA preparation and next generation sequencing (NGS). Genomic DNA was prepared from unedited HSPC and sorted subpopulations of edited HSPC at 3 days post-electroporation using the DNeasy Blood & Tissue Kit (Qiagen Cat #69504). NGS analysis described below showed no significant editing in control unedited samples.

NGS library preparation and sequencing of amplicons was carried out as described in Example 2.1. NGS sequencing data QC and variant analysis was performed as described in Example 2.1.

Quantification of large deletions. Large deletions between targeting sites at the HBG1 and HBG2 promotors were quantified by digital droplet PCR (ddPCR) in non-competitive assay format for copy number determination according to manufacturer's recommendations. Briefly, gDNA was combined with ddPCR SuperMix for Probes (no dUTPs) (BioRad Cat #1863024), HindIII-HF restriction enzyme (NEB Cat #R3104S) and each primer probe mix, transferred to a DG8 cartridge along with Droplet Generation Oil for Probes (BioRad Cat #1863005) and droplets generated with a QX200 droplet generator (BioRad). Droplets were subject to PCR on a C1000 Touch Thermal Cycler with 96-Deep Well Reaction Module (BioRad), followed by detection with QX200 droplet reader (BioRad). Copies per ul was determined by analysis with QuantaSoft software (BioRad). A custom primer probe set (Life Technologies Cat #APZW76R, PN4331348, Forward primer: ACGGA-TAAGTAGATATTGAGGTAAGC (SEQ ID NO: 270), Reverse primer: GTCTCTTTCAGTTAGCAGTGG (SEQ ID NO: 271), FAM TaqMan Probe: ACTGCGCT-GAAACTGTGGCTTTATAG (SEQ ID NO: 272)) used to amplify gDNA within the HBG1-HBG2 intergenic region. A TaqMan Copy Number Reference Assay, human, RNase P (Thermo Fisher cat #4403326) was used as a reference amplicon. Copies per ul for HBG1-HBG2 and RNase P amplicons were within the manufacturer's reported linear range. Percent deletion was reported as 100% times 1 minus the ratio of copies per ul for HBG1-HBG2 and RNase P amplicons. Unedited control samples had calculated percent deletions up to 13%, which may reflect background in the assay.

Figure 11:
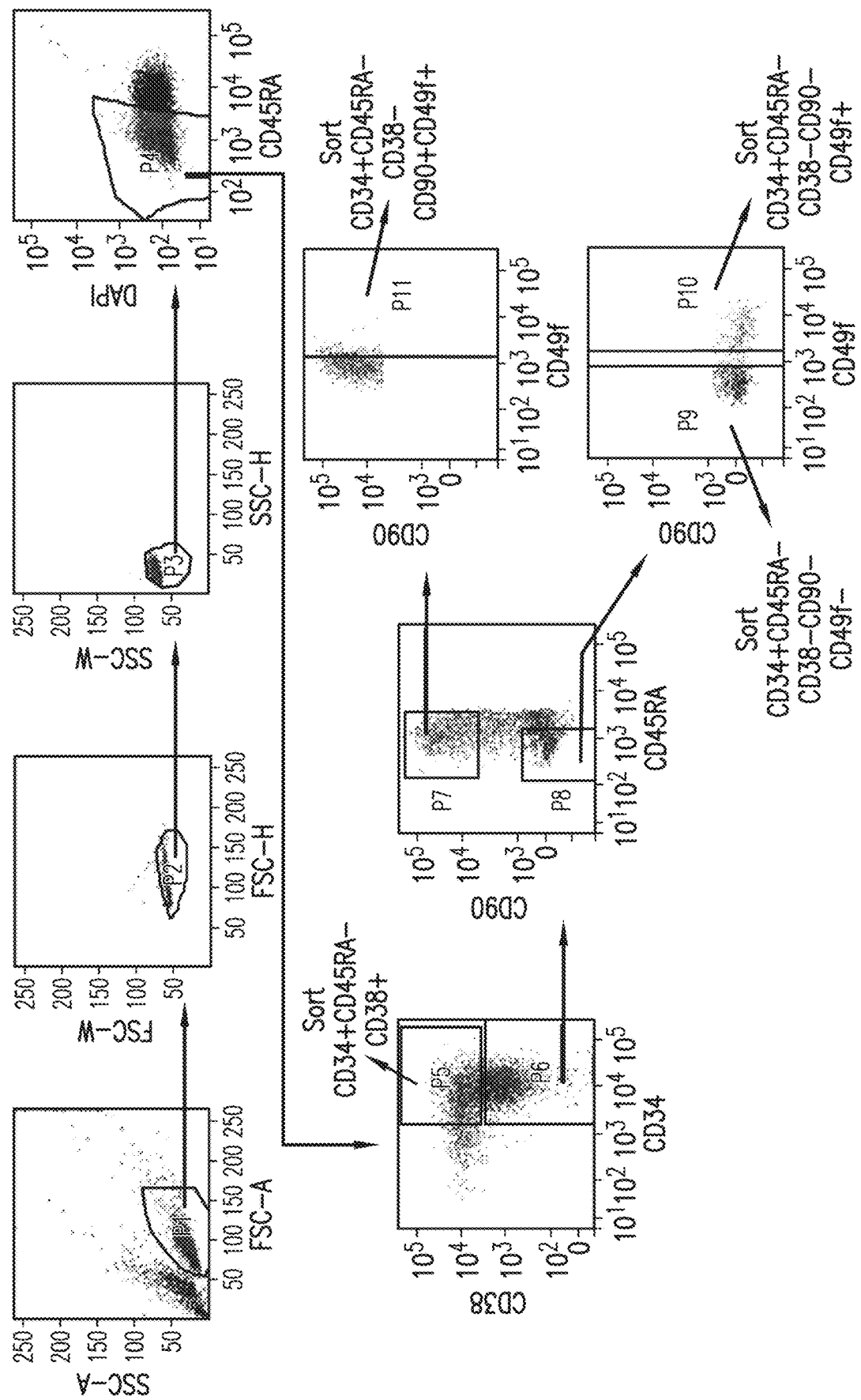
FIG. 11: Sorting scheme for HSPC subpopulations for the cell sample following electroporation with RNPs containing sgRNA of the GCR-0067 targeting domain. Dot plots of cellular fluorescence following immunostaining targeted to the indicated cell surface marker are shown. The following populations were sorted as shown: P5=CMP (CD34+ CD45RA−CD38+), P9=MPP (CD34+CD45RA−CD38− CD90−CD49f−), P10=ST-HSC (CD34+CD45RA−CD38− CD90−CD49f+), P11=LT-HSC (CD34+CD45RA−CD38− CD90+CD49f+). Total CD34+ cells were also sorted (not shown).

Results:

Without being bound by theory, the CD34+ HSPC population is thought to contain cells of various potential for engraftment, self-renewal and cell fate, with additional markers further enriching in cells with shared properties, including engrafting long-term hematopoietic stem cells (Notta, *Science*, 2011 Jul. 8; 333(6039):218-21. doi: 10.1126/science.1201219; Huntsman, Blood. 2015 Sep. 24; 126(13):1631-3. doi: 10.1182/blood-2015-07-660670; each incorporated herein by reference in their entirety). Without being bound by theory, such subpopulations may be of particular therapeutic benefit in gene edited cell transplant, as they may reconstitute the hematopoietic system at different times post-transplant. Thus, cells were subjected to flow cytometry to characterize editing efficiency in HSPC sub-populations. Five cell populations were isolated, first CD34+ cells, followed by a 4-way sort for CD34+CD45RA−CD38+, CD34+CD45RA−CD38−CD90−CD49f+, CD34+CD45RA−CD38−CD90+CD49f+ and CD34+CD45RA−CD38−CD90−CD49f− cells using the strategy shown (FIG. 11).

Figure 12:
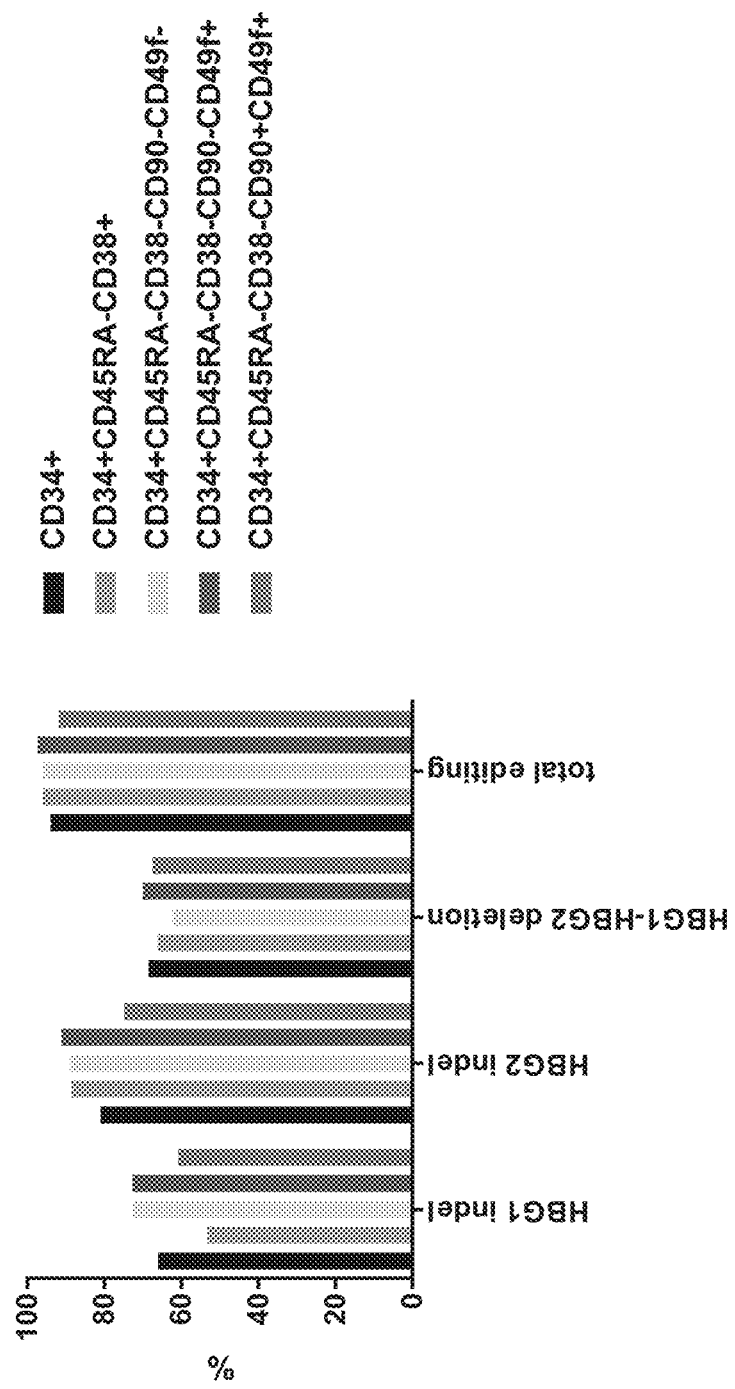
FIG. 12: Percent editing of sorted HSPC subpopulations following electroporation with RNPs containing sgRNA of the GCR-0067 targeting domain. HBG1 indel and HBG2 indel indicates the percentage of small insertions and deletions identified by next generation sequencing of PCR amplicons at or near the HBG1 or HBG2 promotor region targeting domain, respectively (note that alleles with the previously described 4.9 kb deletion or inversion are not amplified). HBG1-HBG2 deletion indicates the percentage of alleles with the 4.9 kb deletion, as determined by the digital droplet PCR assay described in the Examples. Total editing is an approximation calculated by the percentage of HBG1-HBG2 deletion added to the percentage without HBG1-HBG2 deletion times the percentage HBG2 indel.
Figure 13A:
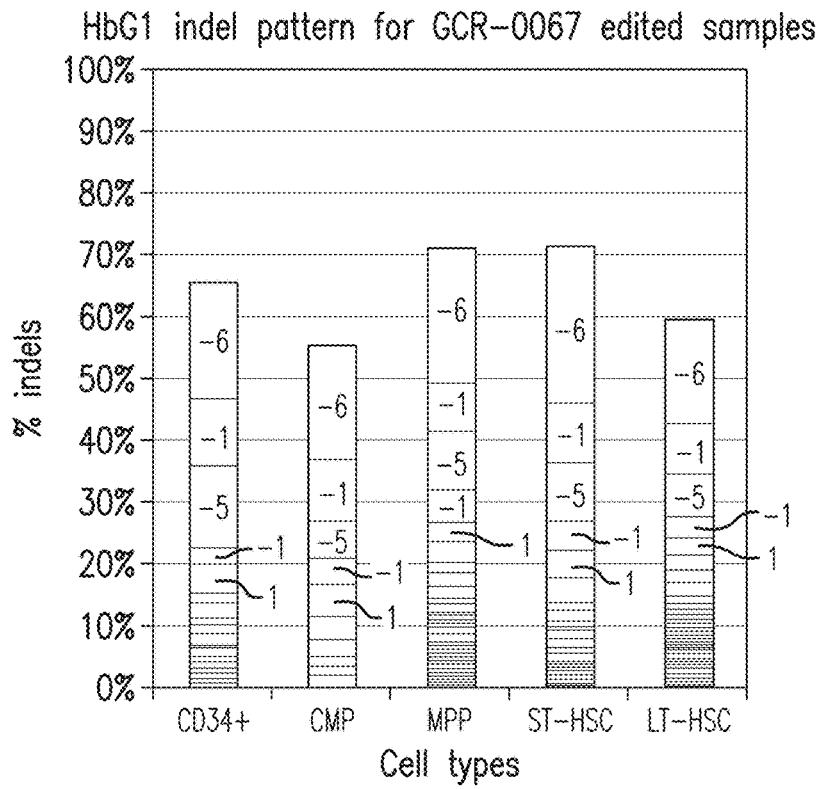
FIG. 13A shows the sum of all indels observed at the HBG1 locus in the stated cell type after introduction of sgRNA comprising the targeting domain of GCR-0067. Indels are arranged with most frequently observed indels at the top of each bar. Not quantified in this assay is the fraction of cells comprising the large 4.9 kb deletion between HBG1 and HBG2 loci. The number within the bar of each of the most prevalent indels indicates the number of nucleotide differences from the wild-type genomic sequence (− indicates deletion; + indicates insertion).
Figure 13B:
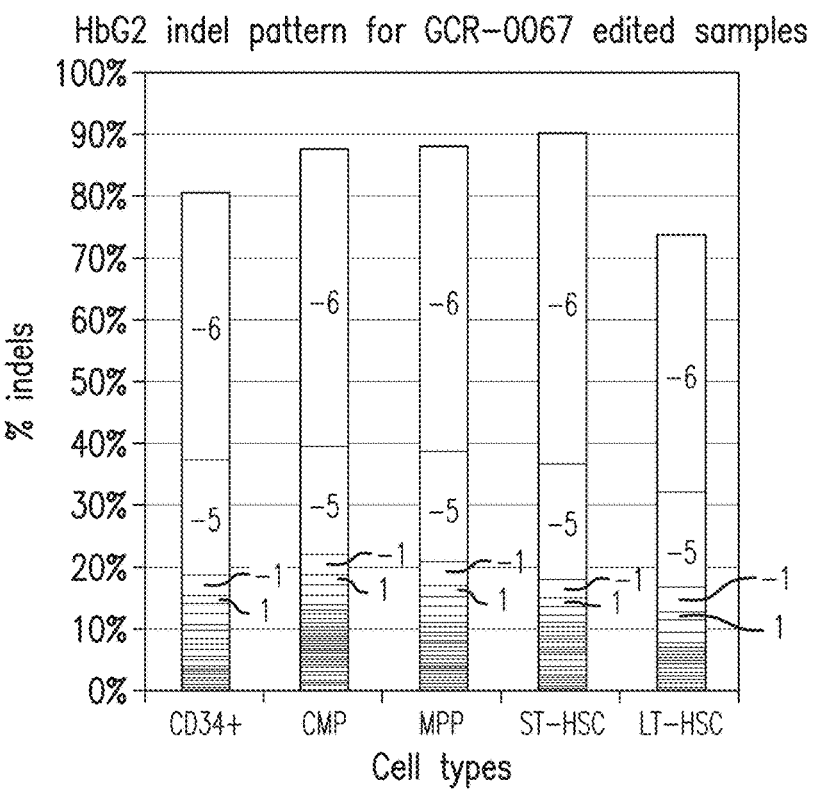
FIG. 13B shows the sum of all indels observed at the HBG2 locus in the stated cell type after introduction of sgRNA comprising the targeting domain of GCR-0067. Indels are arranged with most frequently observed indels at the top of each bar. Not quantified in this assay is the fraction of cells comprising the large 4.9 kb deletion between HBG1 and HBG2 loci. The number within the bar of each of the most prevalent indels indicates the number of nucleotide differences from the wild-type genomic sequence (− indicates deletion; + indicates insertion). CMP=CD34+CD45RA−CD38+ cells; MPP=CD34+CD45RA−CD38−CD90−CD49f− cells; ST-HSC=CD34+CD45RA−CD38−CD90−CD49f+ cells; and LT-HSC=CD34+CD45RA−CD38−CD90+CD49f+ cells.

Each of these sorted populations was analyzed for editing by individually sequencing the HBG1 and HBG2 target site localized regions, as well as by detection of deletion of the intervening HBG1-HBG2 region. HBG1-HBG2 deletion (i.e., excision) frequencies were consistently high across subpopulations, ranging from 69 to 81 percent (FIG. 12). Localized amplification at the HBG1 and HBG2 promotor, individually, and NGS was used to determine % editing at each site (small indels). Alleles with inversions or deletions caused by targeting at both promotors would not be amplified in the assay. Of the alleles without HBG1-HBG2 deletion or inversion, editing was similarly high across sub-populations, ranging from 53 to 73 percent for HBG1 and 75 to 91 percent for HBG2 Minimal total editing was estimated by combining the percentage of HBG1-HBG2 deleted genomes with the percentage of non-HBG1-HBG2 deleted genomes with editing at HBG2 (minimum total editing=deletion plus % undeleted [100 minus % deletion, ignoring inversions] times the % edited at HBG2). Localized small indels at HBG1 were not included, because we could not determine what proportion of % editing at HBG1 was an allele with indels localized to HBG1 only and what proportion was an allele with co-existing indels at both HBG1 and HBG2 Minimal total editing was estimated to range from 92 to 97 percent across sub-populations. Editing patterns for indels localized to the HBG1 and HBG2 target sites were also similar across sub-populations, with the most frequently observed editing patterns common across sub-populations. For all sub-populations and each site, HBG1 or HBG2, the top three indel patterns included a 6 bp deletion, a 5 bp deletion and a 1 bp deletion (FIG. 13A (HBG1 locus); FIG. 13B (HBG2 locus)). In summary, the consistent editing frequencies and patterns between total HSPC and sub-fractions, including defined CD34+CD45RA−CD38−CD90+CD49f+ long-term hematopoietic stem cells, supports the utility of the herein described gene editing approach for HSPC transplant.

Example 2.5: Colony Forming Ability of HSPCs after Gamma Globin Promoter Region Editing Methods:

Methods are as in Example 2.1, with the following modifications.

Human CD34$^+$ cell culture. Human CD34+ cells were derived from bone marrow from adult healthy donors (Lonza catalog #2M-101D). Cells were thawed then expanded for 2 days prior to electroporation with RNP complexes.

Assembly of Cas9 and guide RNA ribonucleoprotein (RNP) complexes, preparation of HSPC, and electroporation of RNP into HSPC. For formation of RNP using single guide RNAs (sgRNAs), 12 µg of each of sgRNA, 12 µg of CAS9 protein and 1 µL of 10×CCE buffer (20 mM HEPES, 100 mM KCL, 5 mM MgCL2, 5% Glycerol and freshly added 1 mM DTT) were combined in a total volume of 10 ul, then incubated at 37° C. for 5 min. Cell density in P3 buffer + supplement was 6.64×10$^6$/mL. Two electroporation replicates were performed with cells from each of two independent donors. For the None/control condition, vehicle rather than sgRNA was added. Following electroporation with RNP complexes, cells were returned to expansion medium.

Genomic DNA preparation and next generation sequencing (NGS). Genomic DNA was prepared from unedited HSPC and sorted subpopulations of edited HSPC at 3 days post-electroporation using the DNeasy Blood & Tissue Kit (Qiagen Cat #69504). NGS analysis described below showed no significant editing in control samples electroporated with Cas9 alone.

NGS library preparation and sequencing of amplicons was carried out as described in Example 2.1. NGS sequencing data QC and variant analysis was performed as described in Example 2.1.

Quantification of large deletions. Large deletions between targeting sites at the HBG1 and HBG2 promotors were quantified by digital droplet PCR (ddPCR) in non-competitive assay format for copy number determination according to manufacturer's recommendations. Briefly, gDNA was combined with ddPCR SuperMix for Probes (no dUTPs) (BioRad Cat #1863024), HindIII-HF restriction enzyme (NEB Cat #R3104S) and each primer probe mix, transferred to a DG8 cartridge along with Droplet Generation Oil for Probes (BioRad Cat #1863005) and droplets generated with a QX200 droplet generator (BioRad). Droplets were subject to PCR on a C1000 Touch Thermal Cycler with 96-Deep Well Reaction Module (BioRad), followed by detection with QX200 droplet reader (BioRad). Copies per ul was determined by analysis with QuantaSoft software (BioRad). A custom primer probe set (Life Technologies Cat #APZW76R, PN4331348, Forward primer: ACGGATAAGTAGATATTGAGGTAAGC (SEQ ID NO: 273), Reverse primer: GTCTCTTTCAGTTAGCAGTGG (SEQ ID NO: 274), FAM TaqMan Probe: ACTGCGCTGAAACTGTGGCTTTATAG (SEQ ID NO: 275)) used to amplify gDNA within the HBG1-HBG2 intergenic region. A TaqMan Copy Number Reference Assay, human, RNase P (Thermo Fisher cat #4403326) was used as a reference amplicon. Copies per ul for HBG1-HBG2 and RNase P amplicons were within the manufacturer's reported linear range. Percent deletion was reported as 100% times 1 minus the ratio of copies per ul for HBG1-HBG2 and RNase P amplicons. Unedited control samples had calculated percent deletions up to 9%, which may reflect background in the assay.

Colony forming unit cell assay. Two days following RNP delivery, viable cells were enumerated by flow cytometry on an LSRFortessa (BD Biosciences) using TruCount tubes (BD Biosciences Cat #340334) according to the manufacturer's recommendations. Inviable cells were discriminated using DAPI (4',6-Diamidino-2-Phenylindole). Analysis was performed using FlowJo software (Tree Star). For the colony forming unit (CFU) assay, cells and 1× antibiotic/antimycotic (Gibco, Cat. #10378-016) were added to MethoCult H4034 Optimum (Stemcell Technologies) methylcellulose medium (StemCell Technologies) and 1 mL was plated in triplicate in SmartDish plates (StemCell Technologies). The culture dishes were incubated in a humidified incubator at 37° C. Cultures were imaged on day 14 post-plating using a StemVision (Stemcell Technologies). Colonies were manually scored using Colony Marker software (Stemcell Technologies). Colony number per well (average of three wells) was divided by the number of cells plated per ml of Methocult (ranged from 226 to 318) and multiplied by 1000 to obtain the CFU frequency per 1000 cells.

Results:

We have shown here that HSPCs function in colony formation assay following the targeted disruption of specific sequences within the HBG1 and HBG2 promoter regions associated with the production of F-cells. The genome edited and unedited HSPC were evaluated for progenitor cell composition and differentiation potential using a colony forming unit assay. Colonies were counted and classified as deriving from erythroid progenitor cells (CFU-erythroid [CFU-E] and burst-forming unit-erythroid [BFU-E]), granulocyte and/or macrophage progenitor cells (CFU-granulocyte, macrophage [CFU-GM]; CFU-granulocyte [CFU-G]; and CFU-macrophage [CFU-M]), or multi-potential progenitor cells (CFU-granulocyte, erythrocyte, macrophage, megakaryocyte [CFU-GEMM]).

TABLE 8

List of select gRNAs targeting the HBG1 and HBG2 promoter region used in the current study to edit cells from the first independent donor.

| Guide RNA targeting domain ID | % edited HBG1 | % edited HBG2 | % HBG1-HBG2 deletion | % approx. min. editing | BFU-E/CFU-E per 1000 cells | CFU-G/M/GM per 1000 cells | CFU-GEMM per 1000 cells | total colonies per 1000 cells |
|---|---|---|---|---|---|---|---|---|
| None/control | n/a | n/a | 8.6 | n/a | 48 | 162 | 3 | 213 |
| GCR-0008 | 80.7 | 78.9 | 42.6 | 88.9 | 18 | 134 | 2 | 154 |
| GCR-0010 | 34.9 | 18.0 | 29.5 | 54.1 | 25 | 118 | 4 | 148 |
| GCR-0048 | 81.4 | 84.0 | 40.6 | 90.5 | 28 | 130 | 0 | 158 |
| GCR-0051 | 51.0 | 74.9 | 41.2 | 85.2 | 28 | 133 | 2 | 164 |
| GCR-0067 | 82.9 | 88.6 | 51.3 | 94.4 | 25 | 123 | 5 | 153 |

TABLE 9

List of select gRNAs targeting the HBG1 and HBG2 promoter region used in the current study to edit cells from the second independent donor.

| Guide RNA targeting domain ID | % edited HBG1 | % edited HBG2 | % HBG1-HBG2 deletion | % approx. min. editing | BFU-E/CFU-E per 1000 cells | CFU-G/M/GM per 1000 cells | CFU-GEMM per 1000 cells | total colonies per 1000 cells |
|---|---|---|---|---|---|---|---|---|
| None/control | n/a | n/a | 8.9 | n/a | 90 | 241 | 12 | 343 |
| GCR-0008 | 82.3 | 85.2 | 47.0 | 92.1 | 51 | 151 | 4 | 206 |
| GCR-0010 | 42.3 | 35.1 | 43.0 | 67.1 | 56 | 162 | 5 | 223 |

TABLE 9-continued

List of select gRNAs targeting the HBG1 and HBG2 promoter region used in the current study to edit cells from the second independent donor.

| Guide RNA targeting domain ID | % edited HBG1 | % edited HBG2 | % HBG1-HBG2 deletion | % approx. min. editing | BFU-E/CFU-E per 1000 cells | CFU-G/M/GM per 1000 cells | CFU-GEMM per 1000 cells | total colonies per 1000 cells |
|---|---|---|---|---|---|---|---|---|
| GCR-0048 | 68.7 | 76.1 | 41.7 | 86.0 | 49 | 129 | 7 | 186 |
| GCR-0051 | 55.2 | 82.7 | 41.3 | 89.9 | 32 | 157 | 6 | 196 |
| GCR-0067 | 81.2 | 88.9 | 47.1 | 94.1 | 39 | 169 | 9 | 217 |

Figure 14:
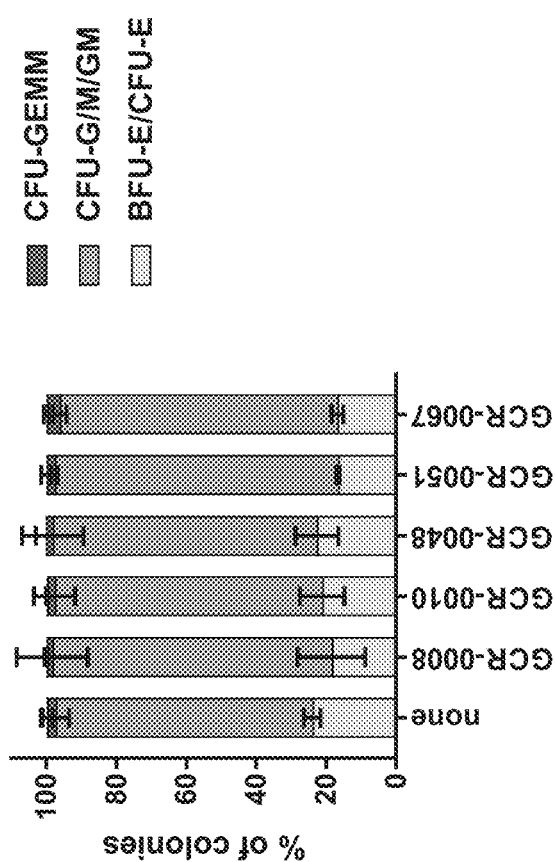
FIG. 14: Percentage of colonies corresponding to the indicated subtype, CFU-GEMM (dark gray bars), CFU-G/ M/GM (medium gray bars) or BFU-E/CFU-E (light gray bars), following electroporation with RNPs containing sgRNA of the indicated targeting domain or control cultures not treated with sgRNA. Mean+/−standard deviation is indicated (n=2 independent donors).

Both donors electroporated with RNPs with the indicated gRNAs had efficient editing, both indels localized to the HBG1 and HBG2 promotor target/off-target sites, as well as deletions of the intervening region (Tables 8 and 9). Edited cultures were associated with a drop in overall colony forming capacity (Tables 8 and 9), possibly indicating decreased fitness of cells undergoing editing. Despite this reduction in total colony number, erythroid, granulocyte/macrophage, and multi-potential colonies were all observed in at least one donor (Tables 8 and 9). Furthermore, there were minimal differences in the proportion of colony types between unedited and edited samples (FIG. 14), indicating that cell cultures edited at these target sites did not have skewed differentiation capacity.

Example 2.6: Cell Proliferation of Hspcs In Vitro after Gamma Globin Promoter Region Editing Methods:
Methods are as in Example 2.1, with the following modifications.

Human CD34$^+$ cell culture. Human CD34+ cells were derived from bone marrow from adult healthy donors (Lonza catalog #2M-101D and Hemacare catalog #BM34-C). Cells were thawed then expanded for 2 days prior to electroporation with RNP complexes.

Assembly of Cas9 and guide RNA ribonucleoprotein (RNP) complexes, preparation of HSPC, and electroporation of RNP into HSPC. For formation of RNP using single guide RNAs (sgRNAs), 12 μg of each of sgRNA, 12 μg of CAS9 protein and 1 μL of 10×CCE buffer (20 mM HEPES, 100 mM KCL, 5 mM MgCL2, 5% Glycerol and freshly added 1 mM DTT) were combined in a total volume of 10 ul, then incubated at 37° C. for 5 min. Cell density in P3 buffer + supplement was $1\times10^7$ to $2.5\times10^7$/mL. One electroporation replicate was performed with cells from each of three independent donors. For the None/control condition, vehicle rather than sgRNA was added. Following electroporation with RNP complexes, cells were returned to expansion medium.

Genomic DNA preparation and next generation sequencing (NGS). Genomic DNA was prepared from unedited and edited HSPC at 3 days post-electroporation using Quick Extract DNA Extraction Solution (Epicentre Cat #QE09050) or the DNeasy Blood & Tissue Kit (Qiagen Cat #69504) NGS analysis described below showed no significant editing in control samples electroporated with Cas9 alone.

NGS library preparation and sequencing of amplicons was carried out as described in Example 2.1. NGS sequencing data QC and variant analysis was performed as described in Example 2.1.

Cell proliferation and phenotyping. Two days following RNP delivery, viable cells were enumerated by flow cytometry on an LSRFortessa (BD Biosciences) using TruCount tubes (BD Biosciences Cat #340334) according to the manufacturer's recommendations. Inviable cells were discriminated using DAPI (4',6-Diamidino-2-Phenylindole), and CD34+ and CD34+CD90+ cell content was determined by inclusion of anti-CD34 (BD Biosciences Cat #348057, BD Biosciences Cat #340666 or eBioscience Cat #25-0349-425) and anti-CD90 (BD Biosciences Cat #559869) in FACS staining buffer consisting of HBSS (GE Life Sciences Cat. #SH30588.01) supplemented with 2% FBS (Omega Scientific Cat. #FB-11) and 2 mM EDTA (Corning Cat. #46-034-CL). Analysis was performed using FlowJo software (Tree Star). Cells were then seeded into expansion medium at either $2.0\times10^4$ or $1.0\times10^5$ viable cells/ml and cultured for 7 days. For cultures seeded at $1.0\times10^5$/ml, fresh medium was added during the culture period for a 3 or 4-fold dilution. After 7 days culture, the cells were once again enumerated as above. After 7 days culture, cells were additionally analyzed for surface marker expression after staining with the following antibody panels. Panel 1: Antibodies specific for CD38 (FITC-conjugate, BD Biosciences #340926, clone HB7), CD133 epitope 1 (PE-conjugate, Miltenyi #130-080-801, clone AC133), CD34 (PerCP-conjugate, BD Biosciences #340666, clone 8G12), CD90 (APC-conjugate, BD Biosciences #559869, clone 5E10), CD45RA (Pe-Cy7-conjugate, eBioscience #25-0458-42, clone HI100). Panel 2: CD34 (PerCP-conjugate, BD Biosciences #340666, clone 8G12), CD33 (PE-Cy7-conjugate, BD Biosciences #333946, clone P67.6), CD14 (APC-H7-conjugate, BD Biosciences #560270, clone MφP9), CD15 (PE-conjugate, Biolegend #301905, clone HI98). Panel 3: CD34 (PerCP-conjugate, BD Biosciences #340666, clone 8G12), CD41a (APC-H7-conjugate, BD Biosciences #561422, clone HIP8), CD71 (FITC-conjugate, BD Biosciences #555536, clone M-A712), CD19 (PE-conjugate, BD Biosciences #340720, clone SJ25C1), CD56 (APC-conjugate, Biolegend #318310, clone HCD56). Corresponding isotype control antibody panels were used to stain cultures in parallel. Inviable cells were discriminated by DAPI (4',6-Diamidino-2-Phenylindole) staining Stained samples were analyzed on an LSRFortessa flow cytometer (BD Biosciences) for cell surface protein expression. The results were analyzed using Flowjo, and data were presented as % of the DAPI negative viable cell population.

Results:
We have shown here that HSPCs can expand with typical cellular composition in vitro following the targeted disruption of specific sequences within the HBG1 and HBG2 promoter regions associated with the production of F-cells. The genome edited and unedited HSPC were evaluated for proliferation capacity and cell composition in culture conditions that promote expansion of HSPC. Replicate independent donors electroporated with RNPs containing GCR-0067 had efficient editing (Table 9-2).

TABLE 9-2

Percent edited amplicons of HBG1 or HBG2 promotor region in cells from three independent donors using indicated gRNA.

| Guide RNA targeting domain ID | % edited HBG1, donor A | % edited HBG2, donor A | % edited HBG1, donor B | % edited HBG2, donor B | % edited HBG1, donor C | % edited HBG2, donor C |
|---|---|---|---|---|---|---|
| GCR-0067 | 62.7 | 64.5 | 57.0 | 73.4 | 53.1 | 56.9 |

Figure 15:
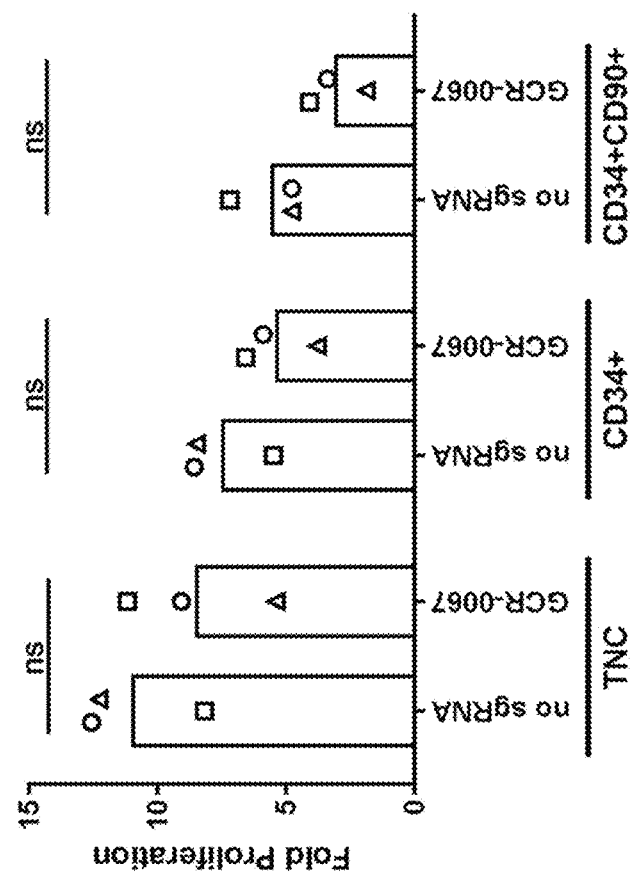
FIG. 15: Fold proliferation of total nucleated cells (TNC), CD34 positive cells (CD34+) and CD34 and CD90 dual positive cells (CD34+CD90+), as indicated, in medium comprising compound 4, following electroporation with RNPs containing sgRNA of the GCR-0067 targeting domain or control cultures not treated with sgRNA. Mean+/−standard deviation is indicated (n=2 independent donors). Mean (bar) of three independent cell donors is shown, along with value for each donor (square=donor A, triangle=donor B, circle=donor C). Differences between edited and control cultures were not significant (ns) by unpaired t-test (Graph-Pad Prism).
Figure 16A:
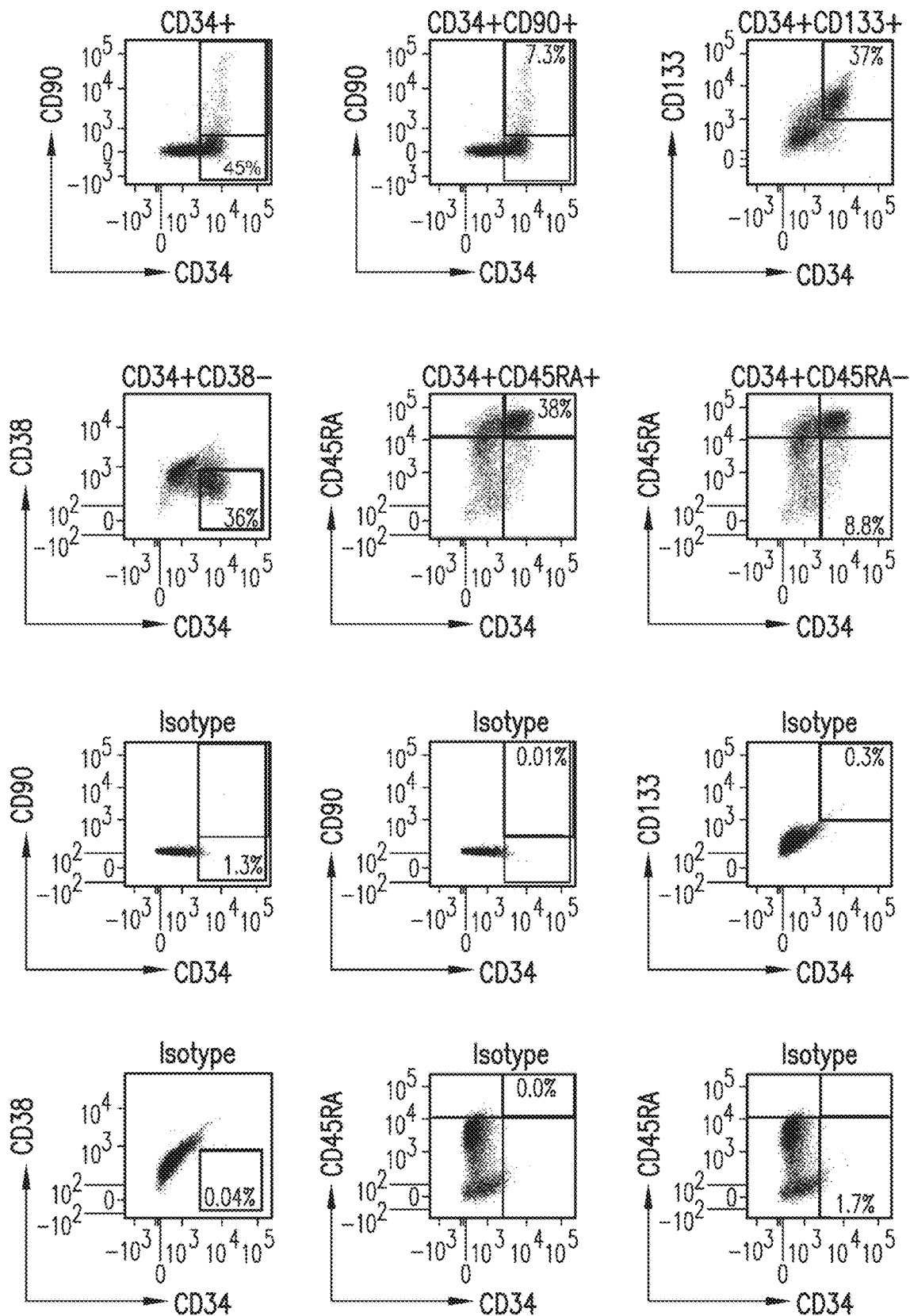
FIG. 16: Representative gating of cellular populations by flow cytometry. Dot plots of cellular fluorescence following immunostaining targeted to the indicated cell surface markers, or isotype control (isotype), are shown in FIGS. 16A and 16B. Gates indicated with the bold boxes were used to quantify the percentage of the indicated population and were set to exclude isotype control labeled cells. Only viable cells pre-gated as DAPI negative and within the cellular forward scatter and side scatter gates are shown and are derived from donor C electroporated with Cas9 alone.
Figure 16B:
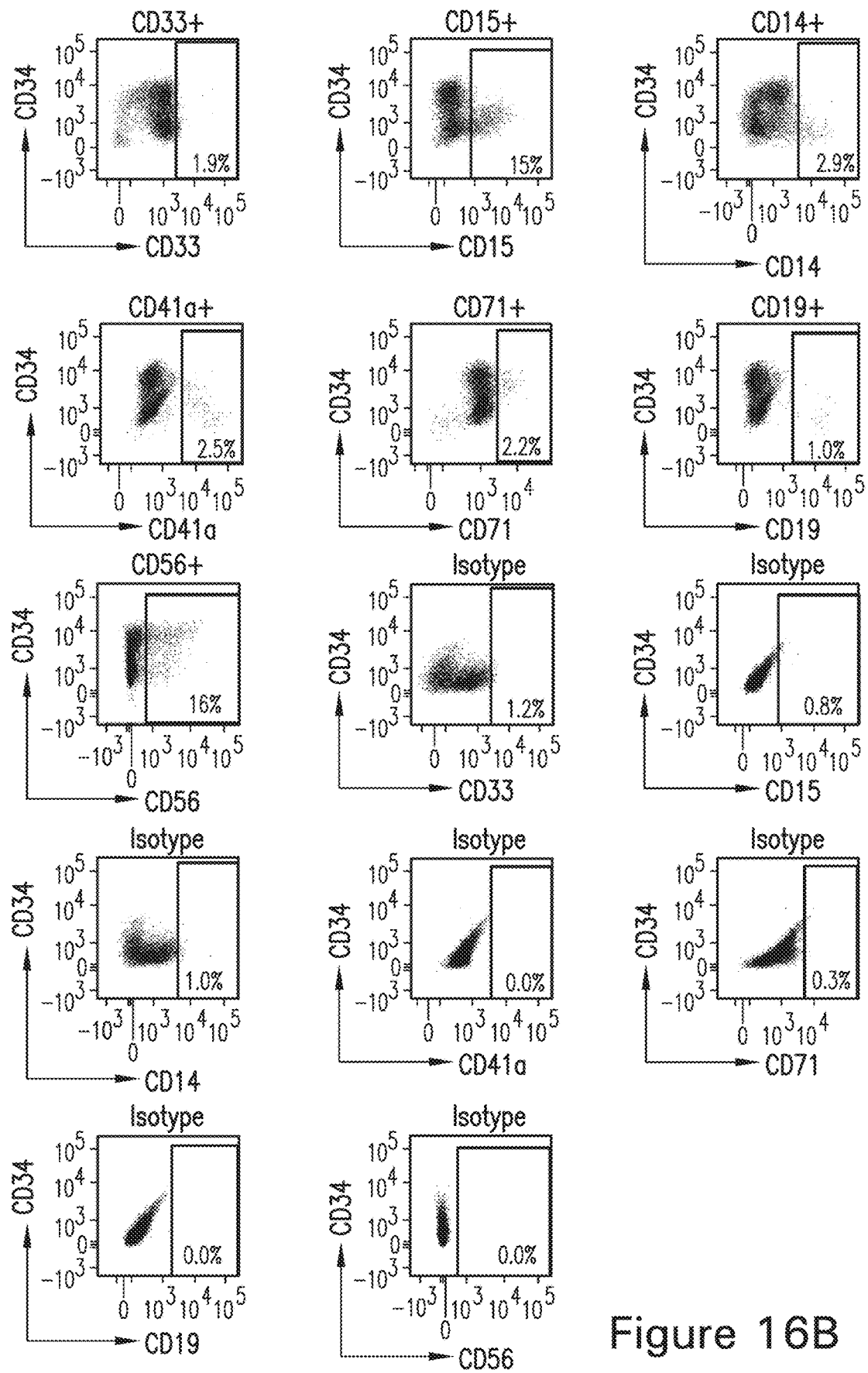
Figure 17:
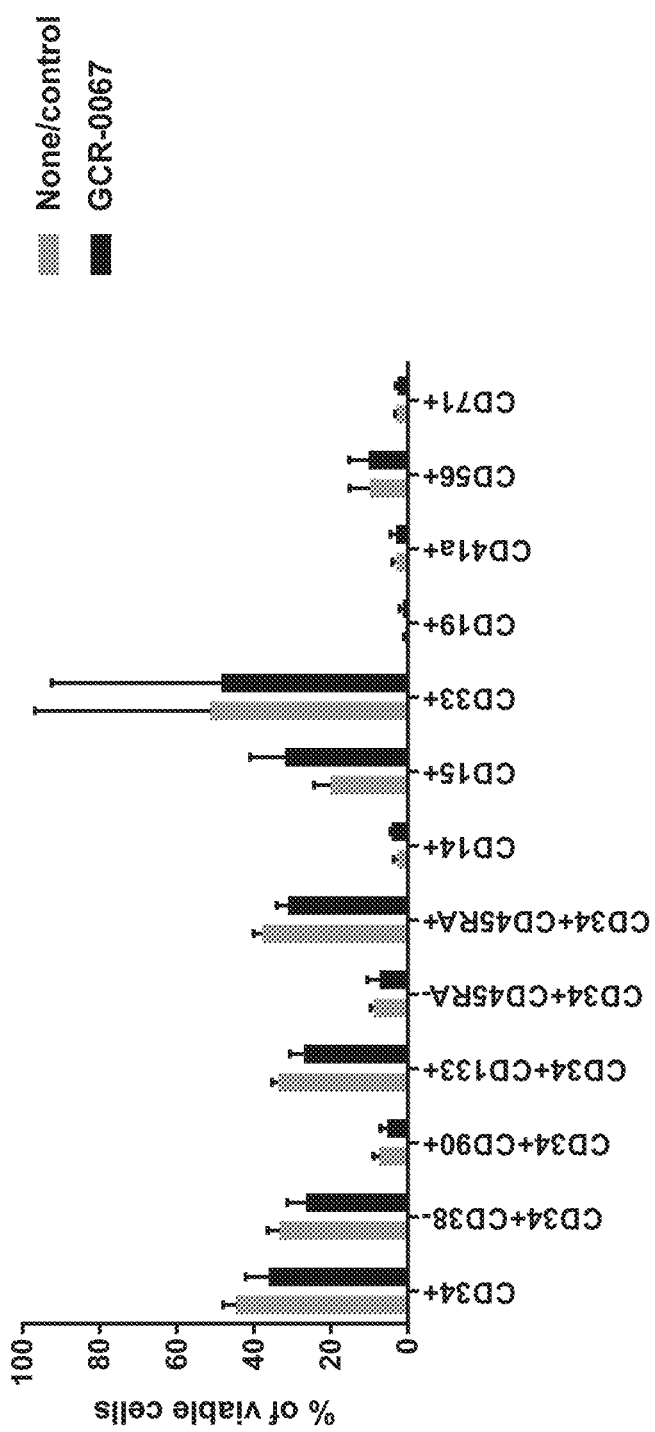
FIG. 17: Percentage of cells with the indicated cellular cell surface phenotype, as assessed by flow cytometry, following electroporation with RNPs containing sgRNA of the GCR-0067 targeting domain (black bars) or control cultures not treated with sgRNA (gray bars). Cells were expanded 2 days post electroporation of RNP in medium comprising Compound 4, and assessed by flow cytometry as described in FIGS. 16A and 16B. Mean+standard deviation is indicated (n=3 independent donors). There were no significant differences between edited and unedited cells for a given population by unpaired t-test (GraphPad Prism).

Edited cultures were associated with a drop in overall proliferation capacity, possibly indicating mildly decreased fitness of cells undergoing editing, although this did not reach significance over three independent cell donors (FIG. 15) Similar reductions were observed within the hematopoietic stem cell enriched CD34+CD90+ population as in the total CD34+ population, indicating that this population is not differentially effected (FIG. 15). Under these culture conditions, both the HSPC and differentiated progeny are expected to be present, thus, cellular composition was further analyzed for expression of a more comprehensive panel of cell surface markers. Discrimination of these cell populations is exemplified in FIGS. 16A-16B. Cellular composition was similar between genome edited and unedited cultures across three independent cell donors, with no significant difference in a given population by unpaired t-test (FIG. 17). The large error bars for the CD33+ population result from a single donor with negligible CD33+ cells in both the genome edited and unedited cultures (FIG. 17).

Example 3: Evaluation of Cas9 Variants

Evaluation in CD34+ Hematopoietic Stem Cells

Figure 6:
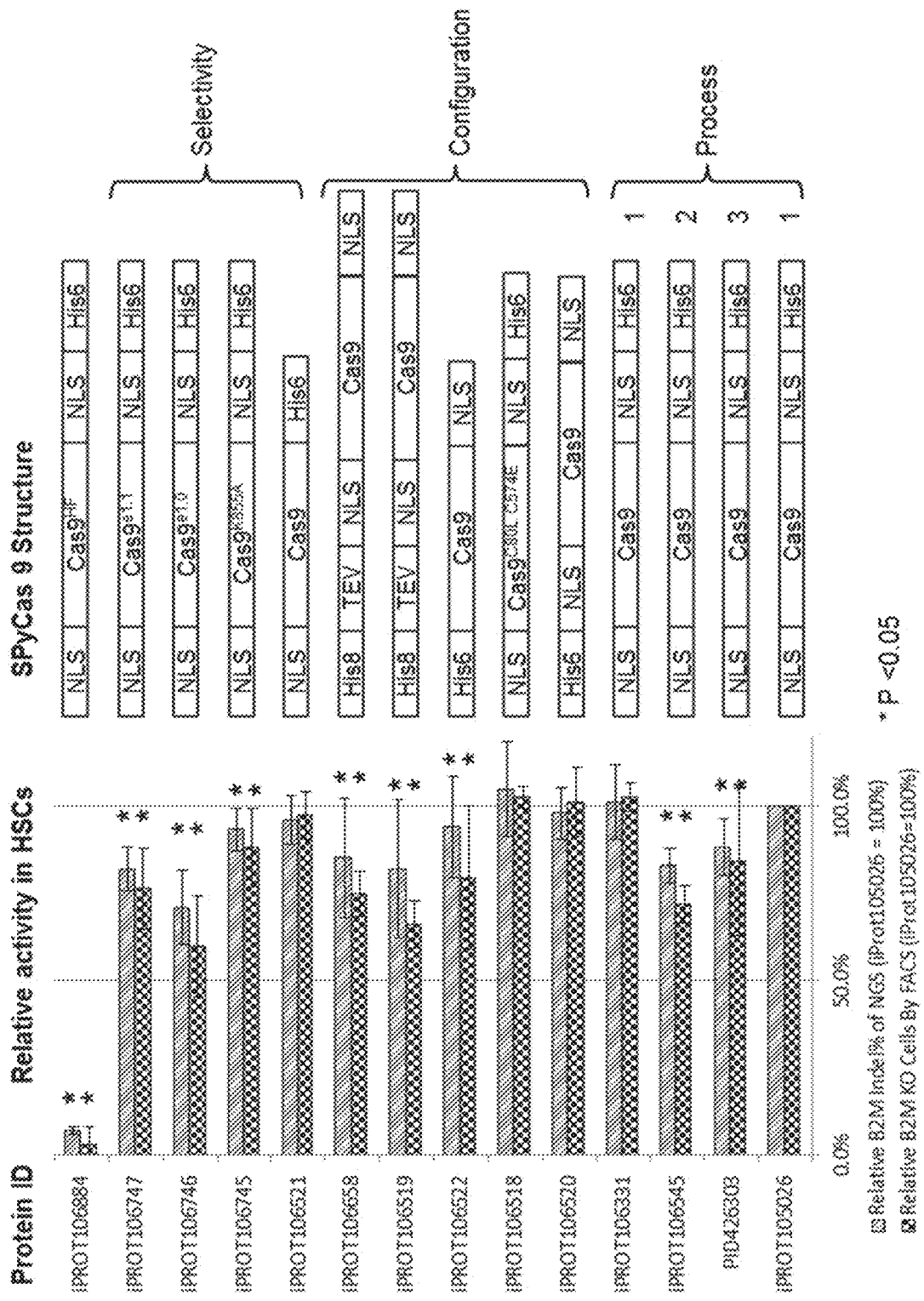
FIG. 6: Editing efficiency at targeted B2M locus in CD34+ HSPCs by different Cas9 variants, as evaluated by NGS and Flow cytometry. NLS=SV40 NLS; His6 (SEQ ID NO: 247) or His8 (SEQ ID NO: 248) refers to 6 (SEQ ID NO: 247) or 8 (SEQ ID NO: 248) histidine residues, respectively; TEV=tobacco etch virus cleavage site; Cas9=wild type *S. pyogenes* Cas9—mutations or variants are as indicated).

We evaluated 14 purified *Streptococcus pyogenes* Cas9 (SPyCas9) proteins by measuring their efficiency of knocking out the beta-2-microglobulin (B2M) gene in primary human hematopoietic stem cells (HSCs). These proteins were divided into 3 groups: the first group consisted of SPyCas9 variants with improved selectivity (Slaymaker et al. 2015, Science 351: 84 (e1.0, e1.1 and K855A); Kleinstiver et al. 2016, Nature 529: 490 (HF)). The second group consisted of wild type SPyCas9 with different numbers and/or positions of the SV40 nuclear localization signal (NLS) and the 6× Histidine (His6) (SEQ ID NO: 247) or 8× Histidine (His8) tag (SEQ ID NO: 248) with or without a cleavable TEV site, and a SPyCas9 protein with two cysteine substitutions (C80L, C574E), which have been reported to stabilize Cas9 for structural studies (Nishimasu et al. 2014, Cell 156:935). The third group consisted of the same recombinant SPyCas9 produced by different processes (FIG. 6). B2M knockout was determined by FACS and next generation sequencing (NGS).

Methods
Materials
1. Neon electroporation instrument (Invitrogen, MPK5000)
2. Neon electroporation kit (Invitrogen, MPK1025)
3. crRNA (targeting domain sequence of GGCCACG-GAGCGAGACAUCU (SEQ ID NO: 276), complementary to a sequence in the B2M gene, fused to SEQ ID NO: 201)
4. tracrRNA (SEQ ID NO: 224)
5. Cas9 storage buffer: 20 mM Tris-Cl, pH 8.0, 200 mM KCl, 10 mM $MgCl_2$
6. Bone marrow derived CD34+ HSCs (Lonza, 2M-101C)
7. Cell culture media (Stemcell Technologies, StemSpam SFEM II with StemSpam CC-100)
8. FACS wash buffer: 2% FCS in PBS
9. FACS block buffer: per mL PBS, add 0.5 ug mouse IgG, 150 ug Fc block, 20 uL FCS
10. Chelex suspension: 10% Chelex 100 (bioRad, Cat #142-1253) in $H_2O$
11. Anti-B2M antibody: Biolegend, cat #316304

Process

Thaw and grow the cells following Lonza's recommendations, add media every 2-3 days. On day 5, pellet the cells at 200×g for 15 min, wash once with PBS, resuspend the cells with T-buffer from NEON kit at $2 \times 10^4$/uL, put on ice. Dilute Cas 9 protein with Cas9 storage buffer to 5 mg/ml. Reconstitute crRNA and tracrRNA to 100 uM with $H_2O$. The ribonucleoprotein (RNP) complex is made by mixing 0.8 uL each of CAS 9 protein, crRNA and tracrRNA with 0.6 uL of Cas9 storage buffer, incubate at room temperature for 10 min. Mix 7 uL of HSCs with RNP complex for two minutes and transfer the entire 10 uL into a Neon pipette tip, electroporate at 1700 v, 20 ms and 1 pulse. After electroporation, immediately transfer cells into a well of 24-well plate containing 1 ml media pre-calibrated at 37° C., 5% $CO_2$. Harvest cells 72 hrs post-electroproation for FACS and NGS analysis.

FACS: take 250 uL of the cells from each well of 24-well plate, to wells of 96-well U-bottom plate and pellet the cells. Wash once with 2% FCS (fetal calf serum)-PBS. Add 50 uL FACS block buffer to the cells and incubate on ice for 10 minutes, add 1 uL FITC labeled B2M antibody and incubate for 30 minutes. Wash with 150 uL FACS wash buffer once followed by once more with 200 uL FACS wash buffer once. Cells were resuspended in 200 uL FACS buffer FACS analysis.

NGS sample prep: transfer 250 uL of cell suspension from each well of the 24-well plate to a 1.5 ml Eppendorf tube, add 1 mL PBS and pellet the cells. Add 100 uL of Chelex suspension, incubate at 99° C. for 8 minutes and vortex 10 seconds followed by incubating at 99° C. for 8 minutes, vortex 10 seconds. Pellet down the resin by centrifuging at 10,000×g for 3 minutes and the supernatant lysate is used for PCR. Take 4 uL lysate and do PCR reaction with the b2m primers (b2mg67F: CAGACAGCAAACTCACCCAGT (SEQ ID NO: 277), b2mg67R: CTGACGCT-TATCGACGCCCT (SEQ ID NO: 278)) using Titanium kit (Clonetech, cat #639208) and follow the manufacturer's instruction. The following PCR conditions are used: 5 minutes at 98° C. for 1 cycle; 15 seconds at 95° C., 15 seconds at 62° C., and 1 minute at 72° C. for 30 cycles; and finally 3 minutes at 72° C. for 1 cycle. The PCR product was used for NGS.

NGS library preparation and sequencing of amplicons was carried out as described in Example 2.1. NGS sequencing data QC and variant analysis was performed as described in Example 2.1.

Statistics: The percentage of B2M KO cells by FACS and the percentage of indels by NGS are used to evaluate the CAS 9 cleavage efficiency. The experiment was designed with Cas9 as fixed effect. Each experiment is nested within donors, as nested random effects. Therefore, the mixed linear model was applied for the analysis of FACS and NGS data.

Results

In order to normalize the experimental and donor variations, we graphed the relative activity of each protein to iProt105026, the original design with two SV40 NLS flanking the wild type SPyCas9 and the His6 tag (SEQ ID NO: 247) at the C-terminal of the protein (FIG. 6). The statistical analysis shows that compared with the reference Cas9 protein iProt105026, iProt106331, iProt106518, iProt106520 and iProt106521 are not significantly different in knocking out B2M in HSCs, while the other variants tested (PID426303, iProt106519, iProt106522, iProt106545, iProt106658, iProt106745, iProt106746, iProt106747, iProt106884) are highly significantly different from the reference iProt105026 in knocking out B2M in HSCs. We found that moving the His6 tag (SEQ ID NO: 247) from the C-terminal to N-terminal (iProt106520) did not affect the activity of the protein (FIG. 6). One NLS was sufficient to maintain activity only when it was placed at the C-terminal of the protein (iProt106521 vs. iProt106522, FIG. 6). Proteins purified from process 1 had consistent higher knockout efficiency than those from processes 2 and 3 (iProt106331 vs. iProt106545 & PID426303, FIG. 6). In general, the SPyCas9 variants with a reported improved selectivity were not as active as the wild type SPyCas9 (iProt106745, iProt106746 and iProt106747, FIG. 6). Interestingly iProt106884 did not cut the targeting site. This is consistent with the report by Kleinstiver et al that this variant failed to cut up to 20% of the legitimate targeting sites in mammalian cells (Kleinstiver et al. 2016, Nature 529: 490). Finally, the Cas9 variant with two cysteine substitutions (iProt106518) maintained high levels of enzymatic activity (FIG. 6).

Figure 18B:
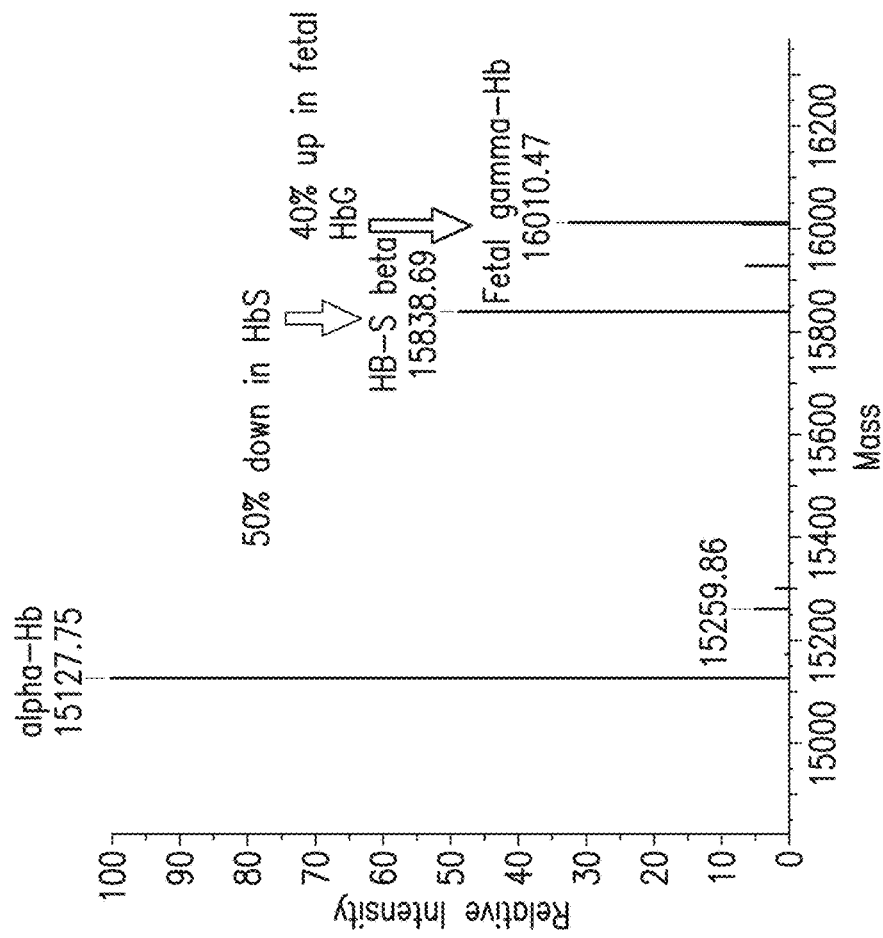
FIG. 18B. CE-MS quantification of globin subunits in genome-edited HSPCs derived from sickle cell patients (SCD1). After editing the HSCs, erythroid cells derived from the sample patient demonstrated 40% upregulation of fetal g-globin and a concurrent 50% downregulation of sickle b-globin subunit.
Figure 18A:
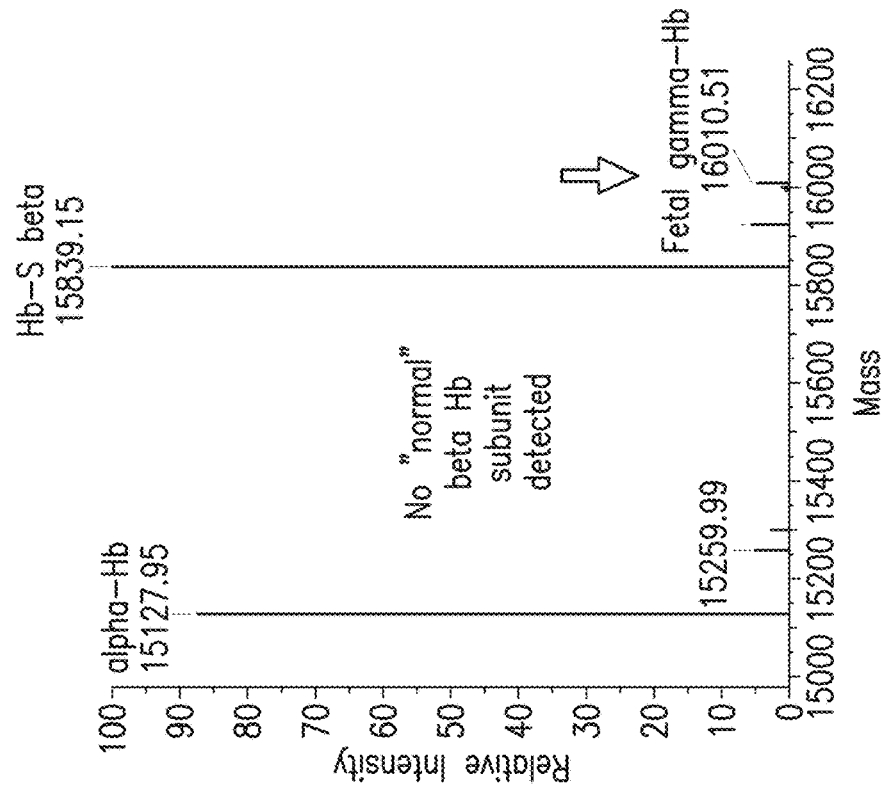
FIG. 18A. CE-MS quantification of globin subunits in mock edited HSCs derived from sickle cell disease patient (SCD1) mock edited with Cas9 and no sgRNA. After cells are differentiated into erythroid lineage, cells showed normal level of a-globin, no normal b-globin due to sickle homozygosity, high level of sickle b-globin subunit, and low level of fetal g-globin.

Example 4. Quantification of Hemoglobin Subunit Changes Upon Gene-Editing by Capillary Electrophoresis Mass Spectrometry Upon gene-editing of HSCs, in addition to capturing fetal hemoglobin production by flow cytometry, changes in individual hemoglobin subunits in erythroid cells were also measured by capillary electrophoresis mass spectrometry (CE-MS). CD34+ cells derived from the peripheral blood of sickle cell patients were either mock edited in the presence of Cas9 protein (with two NLS and one His Tag, iProt106331) and no guide RNA, or gene-edited in the presence of both Cas9 protein and guide RNA sg0067, and differentiated into erythroid lineage in culture as described previously. At day 14 of erythroid differentiation, same number of cells from each condition was stained with FITC-conjugated antibody recognizing fetal hemoglobin (HbF), and cells were subjected to flow cytometry to quantify HbF induction upon gene editing. Flow cytometry reported 30-50% upregulation of HbF+ cells (Table 10). In parallel, varying amounts of erythroid cells (6, 12, 66, and 99 million) per condition were harvested and subjected to CE-MS to quantify alpha-globin, normal beta-globin (HbB), sickle beta-globin (HbS), and fetal gamma-globin (HbF) subunits and data were normalized with the amount of input cells. CE-MS was able to detect all globin subunits in as few as 600 cells/ul concentration. Results showed that edited sickle cell patient samples had a ~40% increase in gamma-globin and a concurrent 50% decrease in sickle beta-globin (FIG. 18).

TABLE 10

Description of treatment and cell quantity of samples subjected to CE-MS quantification of globin subunits. Fetal hemoglobin expression of these samples was also measured by flow cytometry using anti-HbF antibody conjugated to a fluorophore.

| Donor ID | Sample ID | Sample Description | Number of Cells (1 × 10e6) | HbF + Cells Measured by Flow Cytometry (%) |
|---|---|---|---|---|
| Sickle cell patient 1 | 1 | Mock edited, no sgRNA, erythroid differentiated | 99.2 | 55.5 |
|  | 2 | Gene edited with sg0067, erythroid differentiated | 66.6 | 81.15 |
| Sickle cell patient 2 | 3 | Mock edited, no sgRNA, erythroid differentiated | 12.6 | 59.70 |
|  | 4 | Gene edited with sg0067, erythroid differentiated | 5.5 | 81.85 |

Figure 19:
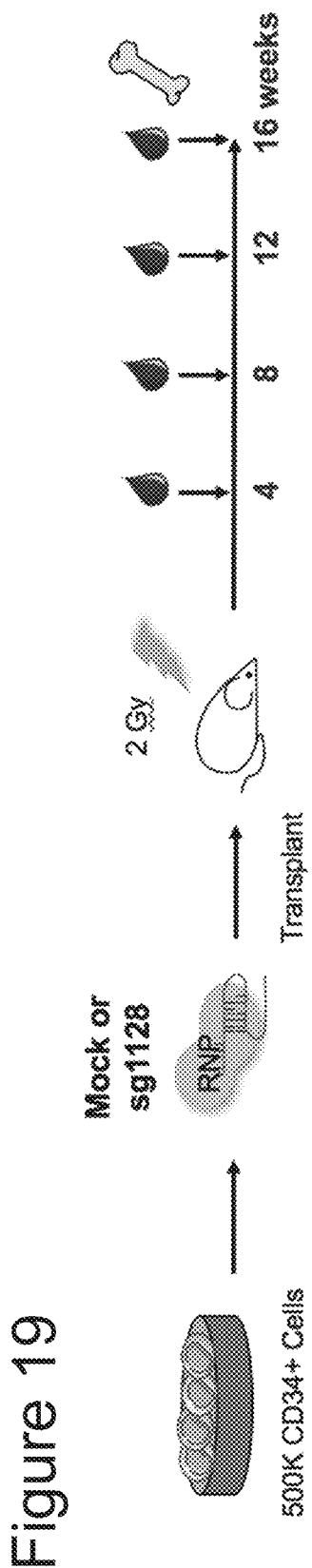
FIG. 19. Schematic protocol for studying engraftment of gene edited cells. Transplantation of HSCs gene-edited with Cas9 and sgRNA comprising the targeting domain of CR001128 (sg1128). Five hundred thousand human CD34+ cells were either mock edited with gRNA or gene edited with sg1128, followed by injection into 2 Gy irradiated NOD.Cg-Prkdc$^{scid}$Il2rg$^{tm1Wjl}$/SzJ (NSG) recipients. Mice were bled at 4, 8, 12, 16 weeks and bone marrow cells were harvested at 16 weeks post-transplant.
Figure 21:
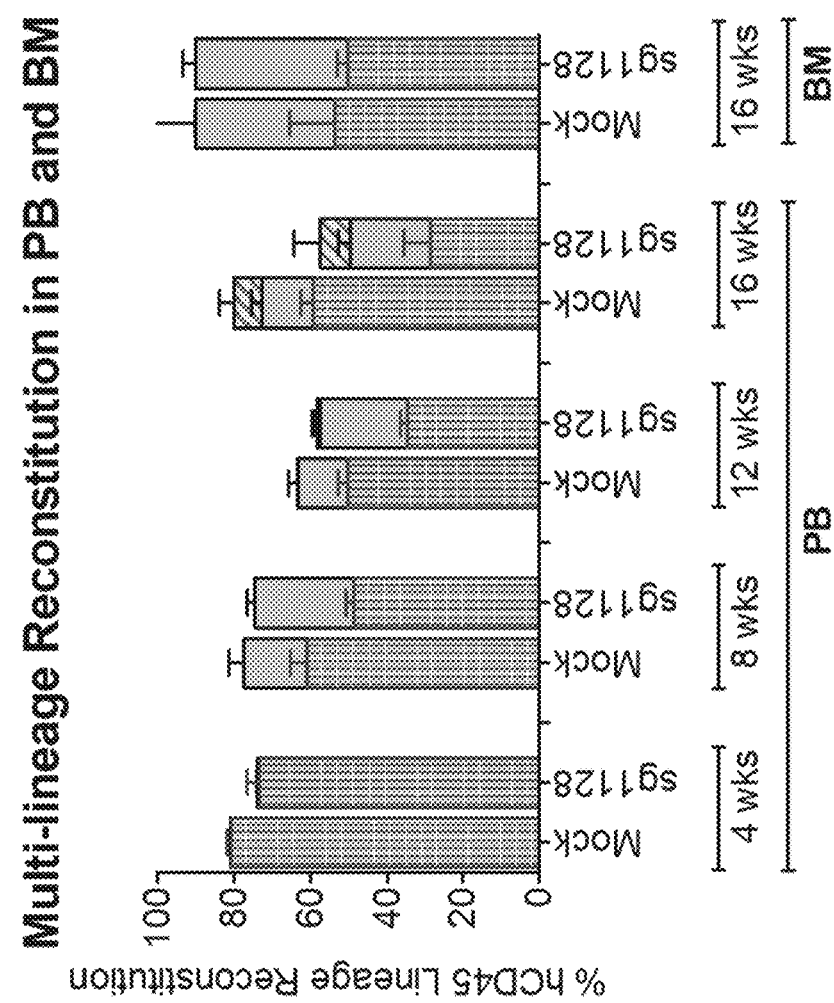
FIG. 21. Reconstitution of myeloid, B, and T lymphoid cells in the peripheral blood and bone marrow at multiple time points using the experimental protocol shown in FIG. 19. N=5/group, data show min to max, 4 independent experiments.
Figure 20:
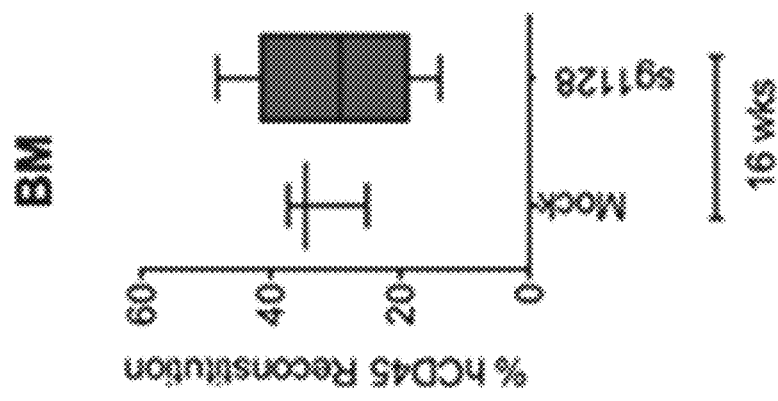
FIG. 20. Bone marrow reconstitution at 16 weeks post-transplant using the experimental protocol shown in FIG. 19.

Example 5. Gene-Edited Hematopoietic Stem Cells (HSCs) were Capable of Long-Term Engraftment and Support Multi-Lineage Reconstitution To evaluate the stem cell function of gene-edited HSCs, edited human HSCs were transplanted into immunocompromised mice to examine long-term hematopoietic regeneration. Five hundred thousand human bone marrow-derived CD34+ cells were thawed at day 0, electroporated at day 3 with either a mock RNP complex (Cas9 alone and no gRNA) or RNP complex formed with Cas9 and sgRNA comprising the targeting domain of CR001128 (sometimes referred to herein at sg1128) (AUCAGAGGCCAAACCCUUCCGUUUUAG AGCUAGAAAUAGCAAGUUAAAAUAAGGCUA GUCCGUUAUCAACUUGAAAAAGUGGCACCGAGU-CGGUGCUUUU (SEQ ID NO: 181), comprising the targeting domain sequence of AUCAGAGGCCAAACCC-UUCC (SEQ ID NO: 180)). Cell were subsequently maintained in the same concentration and medium described in Example 2.1, and at day 6 of culture, all cells from each treatment was transplanted into 2 Gray sublethally irradiated NOD.Cg-Prkdc$^{scid}$Il2$^{tm1 Wjl}$/SzJ (NSG) mice (FIG. 19). We observed approximately 30-40% human cell engraftment in the bone marrow of the recipients at 16 weeks post-transplant. Furthermore, this engraftment level was comparable to mock treatment control, suggesting that gene-editing does not impair the long-term engraftment ability of HSCs (FIG. 20). Gene-edited, transplanted HSCs sustained normal myeloid, B lymphoid, and T lymphoid cell regeneration at 4, 8, 12, 16 weeks post-transplant (FIG. 21). This data demonstrate that gene-edited HSCs were capable of long-term engraftment and support normal multi-lineage reconstitution including out to 16 weeks post transplantation.

Figure 22:
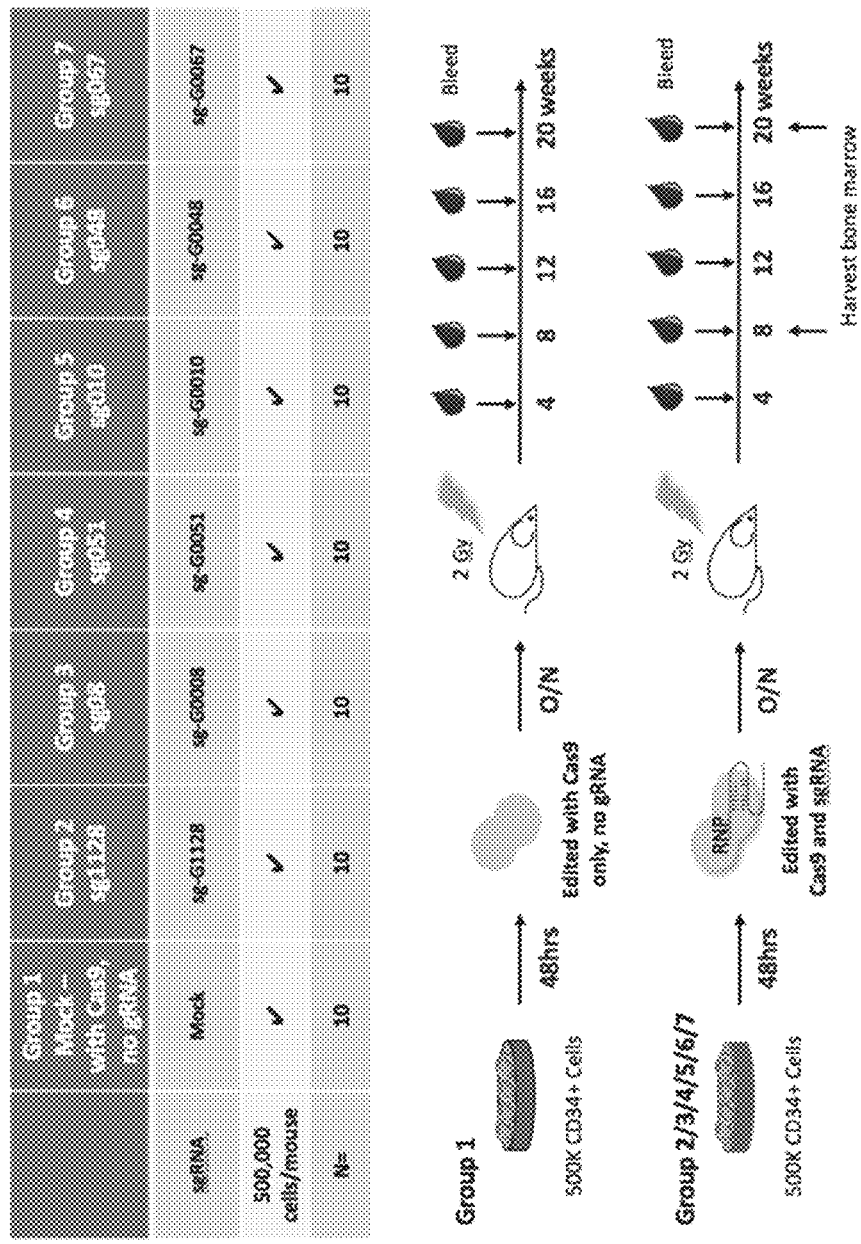
FIG. 22. Schematic diagram of transplant study to evaluate stem cell function of HSCs edited with sgRNAs from the gamma globin promoter region (sg-G0008, sg-G0051, sg-G0010, sg-G0048, sg-G0067) in comparison to gRNA from the erythroid-specific enhancer region of the BCL11A gene (sg-G1128; also referred to as sg1128). Cells were left in culture 24 hours post electroporation. Culture conditions both before and after electroporation were StemSpan SFEM+IL6, SCF, TPO, Flt3L; 750 nM Compound 4.
Figure 23:
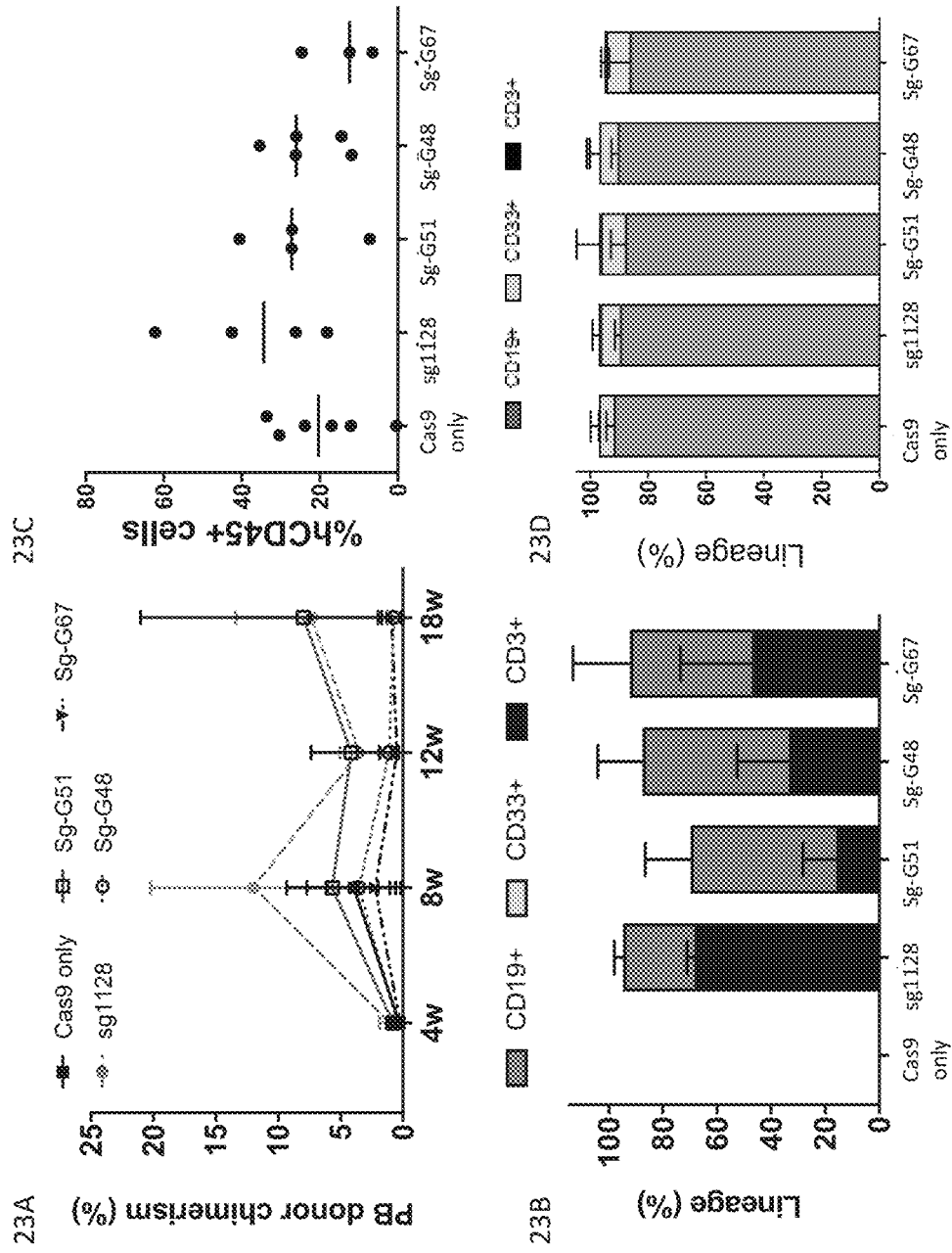
FIG. 23: Human engraftment and lineage analysis over 20 weeks in NSG mice.
Figure 23:
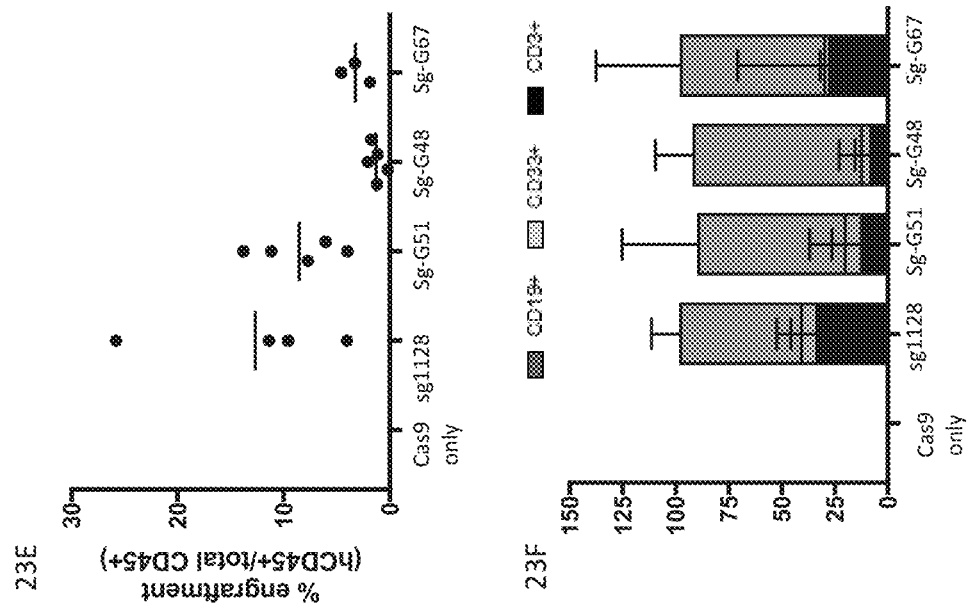
Figure 24A:
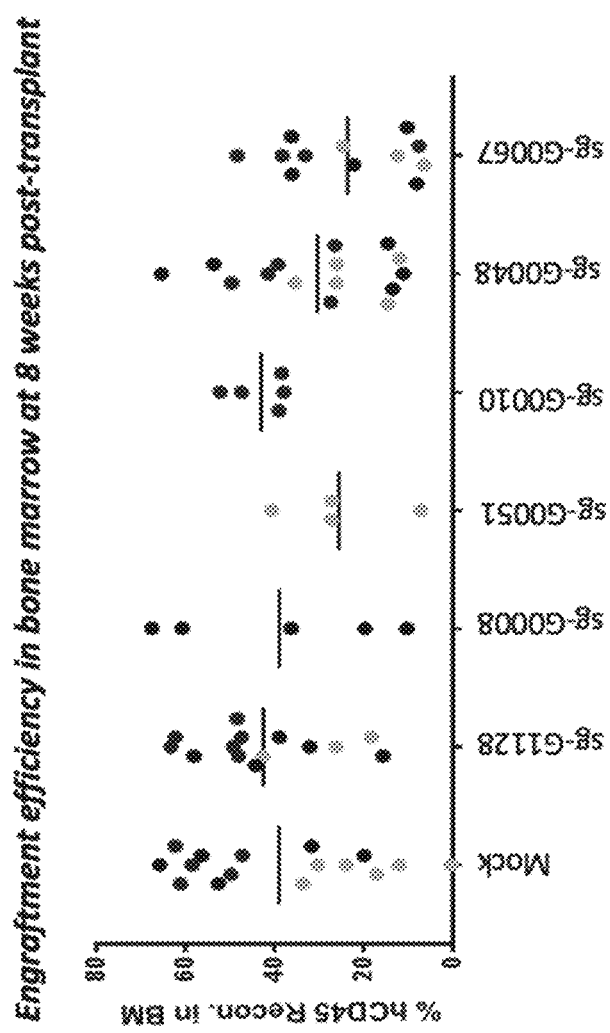
FIG. 24A. Engraftment efficiency of HSCs edited with sgRNAs with homology to the gamma globin promote region (sg-G0008, sg-G0051, sg-G0010, sg-G0048, sg-G0067) compared to sgRNA from the erythroid-specific enhancer region of the BCL11A gene (sg1128). Shows human cell engraftment in NSG mice at 8 weeks following transplantation N=10/group, 3 independent experiments. Graph shows pooled data.
Figure 24B:
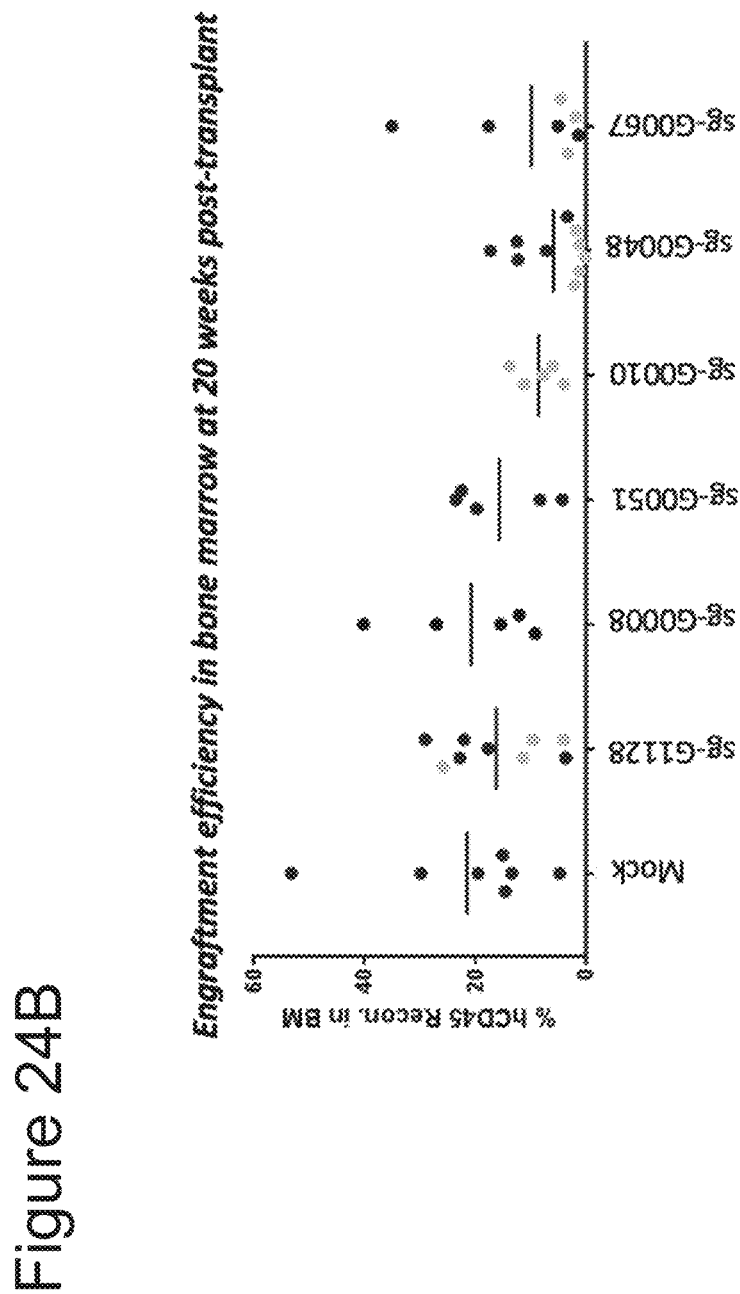
FIG. 24B. Engraftment efficiency of HSCs edited with sgRNAs with homology to the gamma globin promote region (sg-G0008, sg-G0051, sg-G0010, sg-G0048, sg-G0067) compared to sgRNA from the erythroid-specific enhancer region of the BCL11A gene (sg1128). Shows human cell engraftment in NSG mice at 20 weeks post-transplant. N=10/group, 3 independent experiments. Graph shows pooled data.
Figure 25:
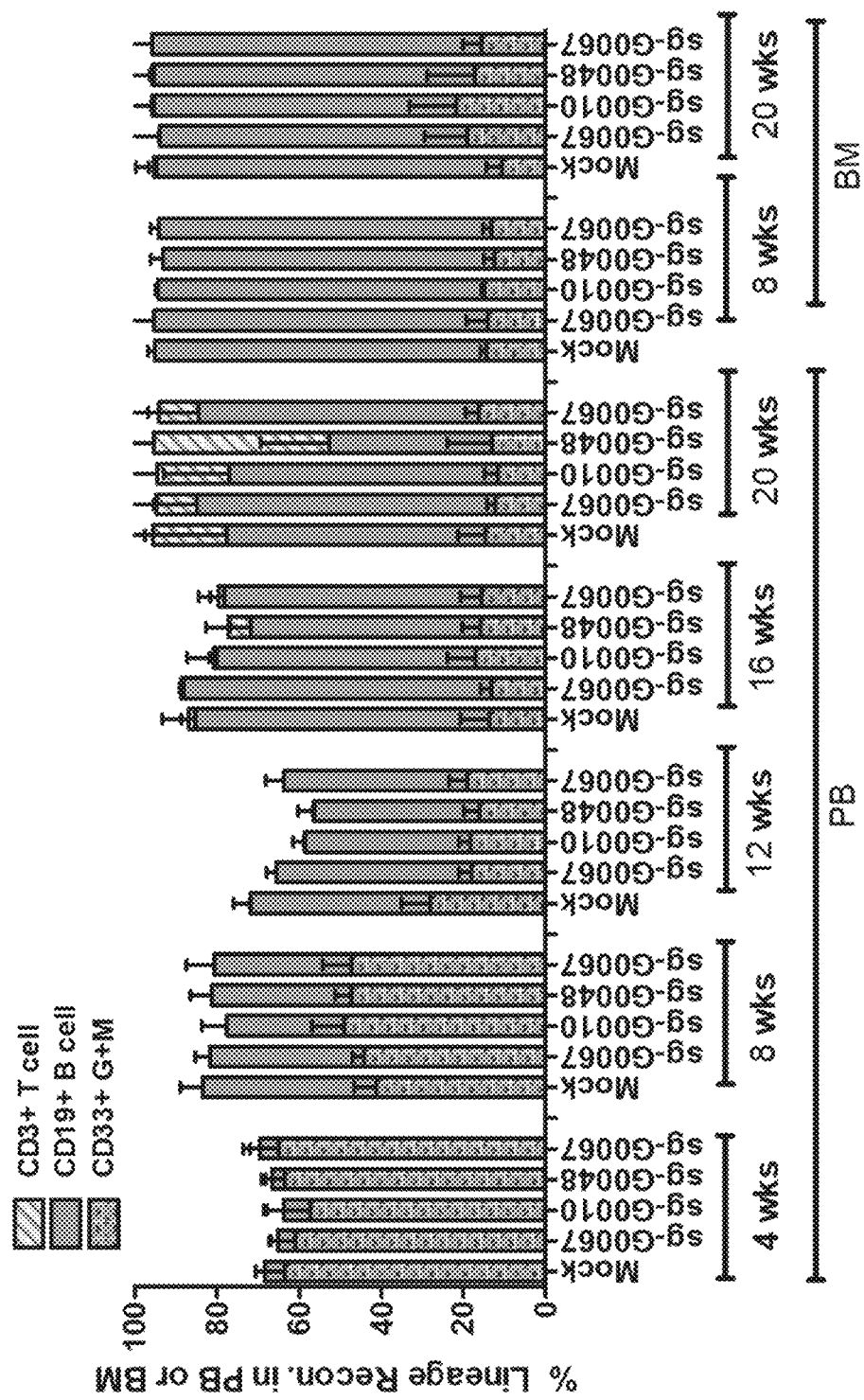
FIG. 25. Multi-lineage reconstitution of gene-edited CD34+ cell transplanted NSG mice. N=10/group, data from one representative experiment.

Example 6. Gene-Edited, Long-Term Engrafted HSCs were Capable of Sustained Fetal Hemoglobin (HbF) Production In a separate study, we evaluated the stem cell function of HSCs gene-edited with gRNAs from the gamma globin promoter region (sg-G0008, sg-G0051, sg-G0010, sg-G0048, sg-G0067 in Table 11) in comparison to gRNA from the erythroid-specific enhancer region of the BCL11A gene (sg-G1128). Human HSCs edited with these gRNAs were transplanted into immunocompromised NSG mice to examine hematopoietic regeneration (FIG. 22).

TABLE 11

Guide RNAs used in the transplant study, designed to target the gamma globin promoter region.

| sgRNA name | Target domain ID | crRNA ID | gRNA target domain sequence | sgRNA 100mer sequence |
|---|---|---|---|---|
| sg-G0008 | GCR-0008 | CR005821 | GGAGAAGGAA ACUAGCUAAA (SEQ ID NO: 8) | GGAGAAGGAAACUAGCUAAAGU UUUAGAGCUAGAAAUAGCAAGU UAAAAUAAGGCUAGUCCGUUAU CAACUUGAAAAAGUGGCACCGA GUCGGUGCUUUU (SEQ ID NO: 84) |
| sg-G0010 | GCR-0010 | CR005823 | GGGAGAAGGA AACUAGCUAA (SEQ ID NO: 10) | GGGAGAAGGAAACUAGCUAAGU UUUAGAGCUAGAAAUAGCAAGU UAAAAUAAGGCUAGUCCGUUAU CAACUUGAAAAAGUGGCACCGA GUCGGUGCUUUU (SEQ ID NO: 94) |
| sg-G0048 | GCR-0048 | CR005811 | ACGGCUGACA AAGAAGUCC (SEQ ID NO: 48) | ACGGCUGACAAAAGAAGUCCGU UUUAGAGCUAGAAAUAGCAAGU UAAAAUAAGGCUAGUCCGUUAU CAACUUGAAAAAGUGGCACCGA GUCGGUGCUUUU (SEQ ID NO: 134) |
| sg-G0051 | GCR-0051 | CR005813 | GGAGAAGAAA ACUAGCUAAA (SEQ ID NO: 51) | GGAGAAGAAAACUAGCUAAAGU UUUAGAGCUAGAAAUAGCAAGU UAAAAUAAGGCUAGUCCGUUAU CAACUUGAAAAAGUGGCACCGA GUCGGUGCUUUU (SEQ ID NO: 144) |
| sg-G0067 | GCR-0067 | CR005820 | ACUGAAUCGG AACAAGGCAA (SEQ ID NO: 67) | ACUGAAUCGGAACAAGGCAAGU UUUAGAGCUAGAAAUAGCAAGU UAAAAUAAGGCUAGUCCGUUAU CAACUUGAAAAAGUGGCACCGA GUCGGUGCUUUU (SEQ ID NO: 174) |

Experimental Procedure

CD34+ Thawing and Culture

Bone marrow CD34+ cells were thawed and cultured. Each vial of 1 million bone marrow CD34+ cells was removed from liquid nitrogen, sprayed with 70% ethanol and thawed rapidly in a 37° C. water bath until a small ice pellet remained. The vial was sprayed with 70% ethanol and wiped. Using a 5 ml pipet, the contents of the vial were transferred into a 50 ml falcon tube. The cryovial was rinsed once with 1 ml pre-warmed IMDM, 10% FBS and added dropwise to the 50 ml falcon tube; 25 ml of pre-warmed IMDM, 10% FBS was slowly added over 2 min to the cells, swirling gently to mix. Cells were spun at 300 g for 10 min. Twenty-eight million CD34+ cells were cultured in StemSpan SFEM+100 ng/ml SCF/IL6/Flt3L/TPO+500 nM Compound 4+1× Pen/Strep at 0.2-0.5×10e6 cells/ml.

RNP Electroporation

Forty-eight hours post-thaw, cells were electroporated with 1) Cas9 only; or 2) Cas9 RNP complex containing sg1128 (as described above), or one of the sgRNAs in Table 11. Briefly, the RNP was prepared using a 1:2 molar ratio of Cas9 protein to sgRNA resulting in a RNP mixture with 10 uM Cas9 and 20 uM sgRNA. 5 ul of 10 uM RNP was added to 1 million CD34+ cells in 20 ul P3 buffer (Lonza). 22 ul of the electroporation mix was transferred to one well of a 96 well electroporation plate and electroporated using the Lonza Amaxa 96-well Shuttle or Lonza Nucleofector System, program CA-137. Immediately after electroporation, 80 ul of culture media (StemSpan SFEM+100 ng/ml SCF/IL6/Flt3L/TPO+500 nM Compound 4+1× Pen/Strep) was added to the electroporated sample.

Twenty-four hours post-electroporation, 500K starting cell equivalents were transplanted per mouse. 30,000-100,000 cells were used for erythroid differentiation to assess HbF induction post-editing. The remaining cells were left in culture for an additional 24 h (48 h total post-electroporation) for NGS analysis of editing frequency.

Transplantation

Ten NSG mice/condition were irradiated 4-24 h prior to transplant with 200 Rad using the RadSource X-Ray irradiator, or 2 Gray using a Cesium[138] irradiator. Five hundred thousand starting cell equivalents were transplanted per mouse through tail vein injection. Following transplantation, the mice were placed on an antibiotic regiment for 4-8 weeks. The mice were treated in accordance with institutes' animal care procedures and following the approved IACUC protocol. At 4, 8, 12, 16 and 20 weeks peripheral blood was collected for engraftment and lineage analysis through tail vein nick. At 8-9 weeks and 20 weeks, bone marrow was collected for analysis (flow cytometry, Taqman qPCR and NGS as described in previous protocols, for example, Example 2.1) as well as for sorting of hCD45+CD34+ cells for erythroid differentiation as described in previous protocols. At week 20, the hCD45+CD34+ cell sort and erythroid differentiation were performed.

FIG. 22 shows the schematic diagram of the transplant study to evaluate stem cell function of HSCs edited with sgRNAs from the gamma globin promoter region (sg-G0008, sg-G0051, sg-G0010, sg-G0048, sg-G0067) in comparison to gRNA from the erythroid-specific enhancer region of the BCL11A gene (sg-G1128; also referred to as sg1128). Five hundred thousand human CD34+ cells were thawed at day 0, electroporated with either a mock RNP complex (Cas9 alone and no gRNA) or RNP complex formed with Cas9 (NLS-Cas9-NLS-His6 ("His6") disclosed as SEQ ID NO: 247)) and various gRNAs at day 3. At day 6, all cells from each condition were harvested and transplanted into 2 Gy sublethally irradiated NOD.Cg-Prkdc$^{scid}$Il2rg$^{tm1Wjl}$/SzJ (NSG) mice (FIG. 22). Mice were bled at 4, 8, 12, 16, and 20 weeks post-transplant. At 8 and 20 weeks post-transplant, bone marrow cells from animals were also harvested to examine human cell engraftment in the bone marrow.

Results

Editing HSCs were Capable of Long-Term Engraftment and Support Multi-Lineage Differentiation in NSG Mice Results showed that sgRNAs from the gamma globin promoter region achieved on average 20-40% bone marrow engraftment at 8 weeks following transplantation, comparable to sg-G1128. While engraftment from early time points can be contributed by short-lived hematopoietic progenitor cells, engraftment at longer time points (20 weeks) is proof of reconstitution by long-term HSCs. Tested sgRNAs showed 5-22% bone marrow engraftment at 20 weeks post-transplant (FIGS. 23A-F and 24A and 24B). It is important to note that we injected only 500,000 mock or genome-edited CD34+ cells into each mouse to achieve such level of engraftment. This engraftment level was comparable to other studies transplanting 1 million genome-edited CD34+ cells, indicating a highly efficient engraftment of the instant cells. In addition, we observed normal recovery of myeloid, B lymphoid, and T lymphoid cells at 4, 8, 12, 16, 20 weeks following transplantation (FIGS. 23A-F and 25) when comparing all gene-edited groups to the mock edited control. These data demonstrate that by targeting the gamma globin promoter region with a gRNA which does not map to any known HPFH, the genome editing strategy does not impact the engraftment capacity of long-term HSCs, nor does it alter their multi-lineage reconstitution function when transplanted into a new host. In contrast, we can achieve robust engraftment by injecting 50% less cells compared to other reported strategies. In summary, HSCs edited by these sgRNAs are capable of long-term engraftment with robust multi-lineage reconstitution in the hematopoietic stem cell niche to sustain long-term hematopoiesis.

High Editing Efficiency was Maintained Pre- and Post-Transplantation

Figure 26:
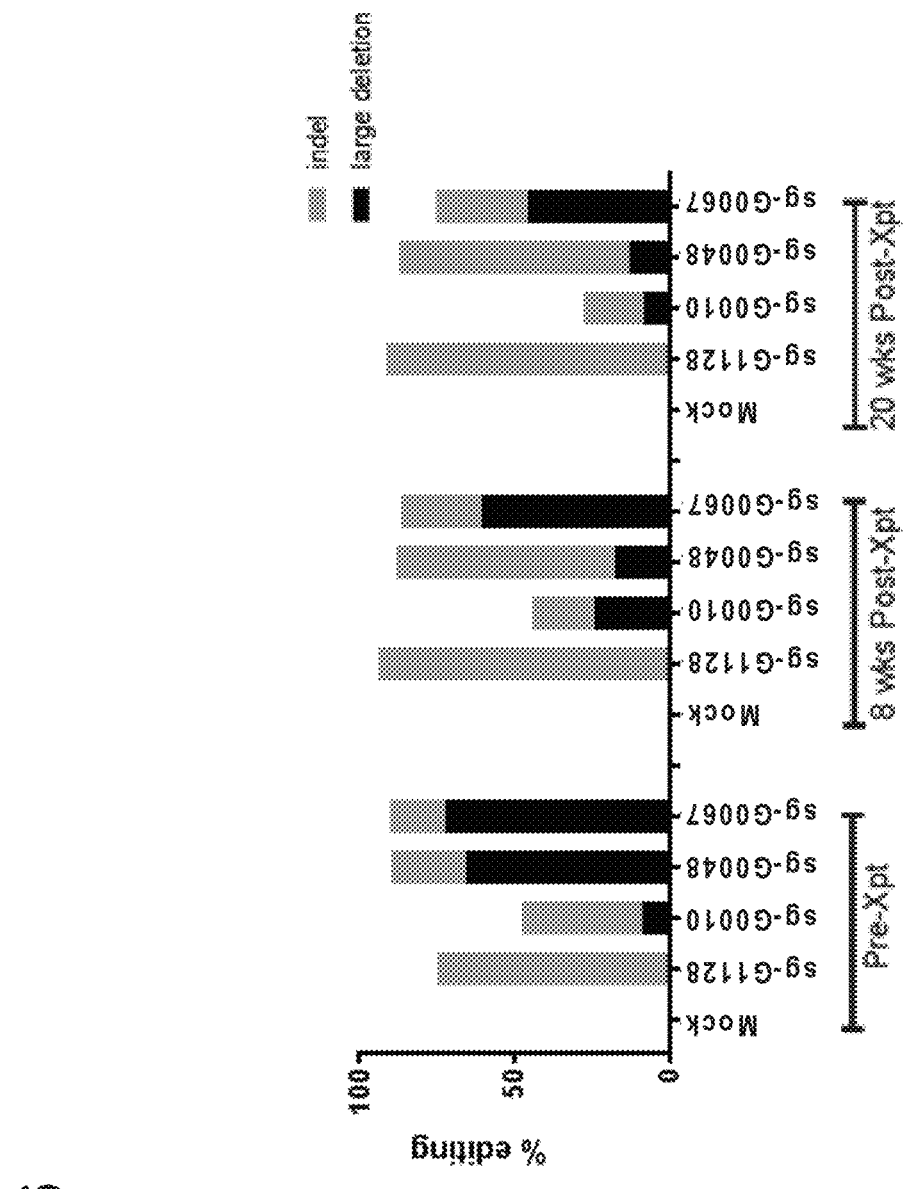
FIG. 26. High editing efficiency was maintained pre- and post-transplantation "Pre-Xpt": editing efficiency and indel pattern of individual sgRNA in human CD34+ cells as measured by NGS upon editing but prior to transplantation. "8 wks Post-Xpt": editing efficiency and indel pattern in human CD34+ cells 8 weeks after bone marrow transplantation in mice as measured by NGS. "20 wks Post-Xpt": editing efficiency and indel pattern in human CD34+ cells 20 weeks after bone marrow transplantation in mice as measured by NGS. Electroporation performed in triplicate per group, data from one representative experiment. As used in relation to this Figure, "indel" refers to sum of all indels of less than 200 nt; "large deletion" refers to the deletion of sequence between the predicted HBG1 and HBG2 binding sites for each gRNA.

We examined the editing efficiency of the tested sgRNAs by NGS as described in experimental procedure. Three days after gene-editing, 100,000 of the gene-edited human CD34+ cells, along with mock edited CD34+ cells were subjected to NGS analysis. The remaining cells were transplanted into NSG recipients as previously described. At 8 weeks and 20 weeks post-transplant, bone marrow cells from transplanted NSG mice were harvested, and 100,000 sorted human CD45+ cells were subjected to NGS to measure editing efficiency. Results show that sgRNA sg-G1128, sg-G0048, and sg-G0067 achieved 80-90% editing, while sg-G0010 demonstrated ~45% editing (FIG. 26). When comparing editing efficiency pre-transplant to after 8 or 20 weeks of transplantation, results showed that the edited events in the hematopoietic stem and progenitor populations were maintained long-term throughout the transplant period. This data demonstrate the durability of edited cells in transplanted individual. We even observe slightly increased editing efficiency for sg-G1128 at 20 weeks post-transplant, implying that edited cells were selected by the bone marrow microenvironment or have a survival advantage upon transplantation.

Figure 27:
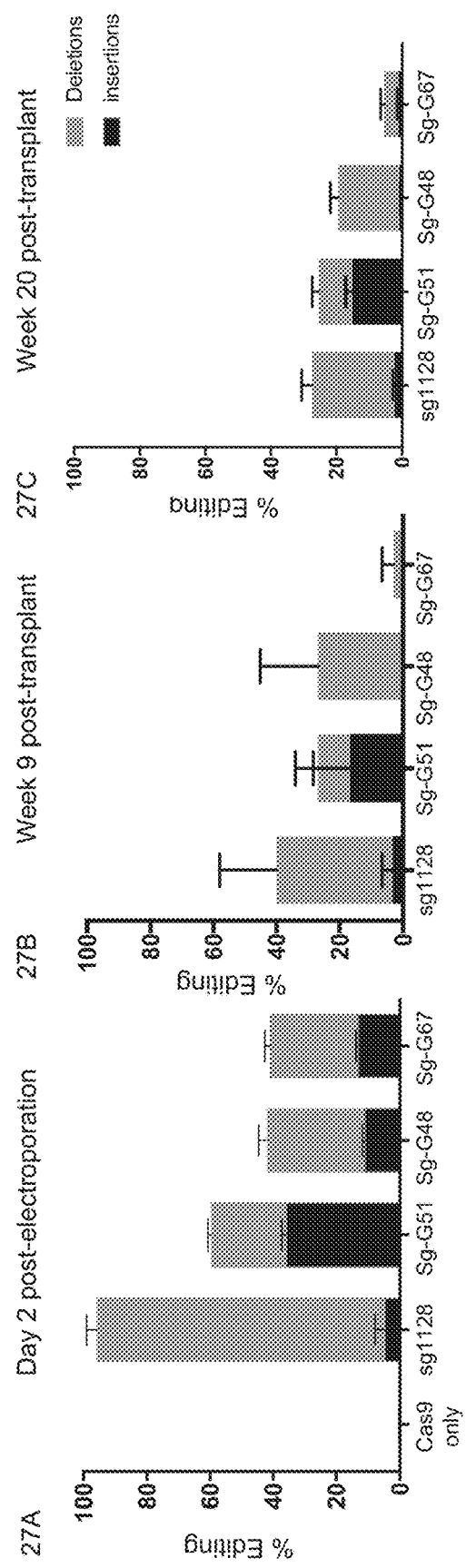
FIG. 27. NGS analysis of CD34+ cells post-editing with RNPs. sgRNA targeting specific regions are indicated on the x-axis.

In another independent transplant repeat, NGS analysis revealed a range of editing achieved with the gRNAs tested, with sg-G1128 resulting in greater than 90% editing two days post-electroporation (FIG. 8A). Editing was also detected in human CD34+ cells isolated at 9 and 20 weeks post-transplantation (FIGS. 27B and 27C).

Figure 28:
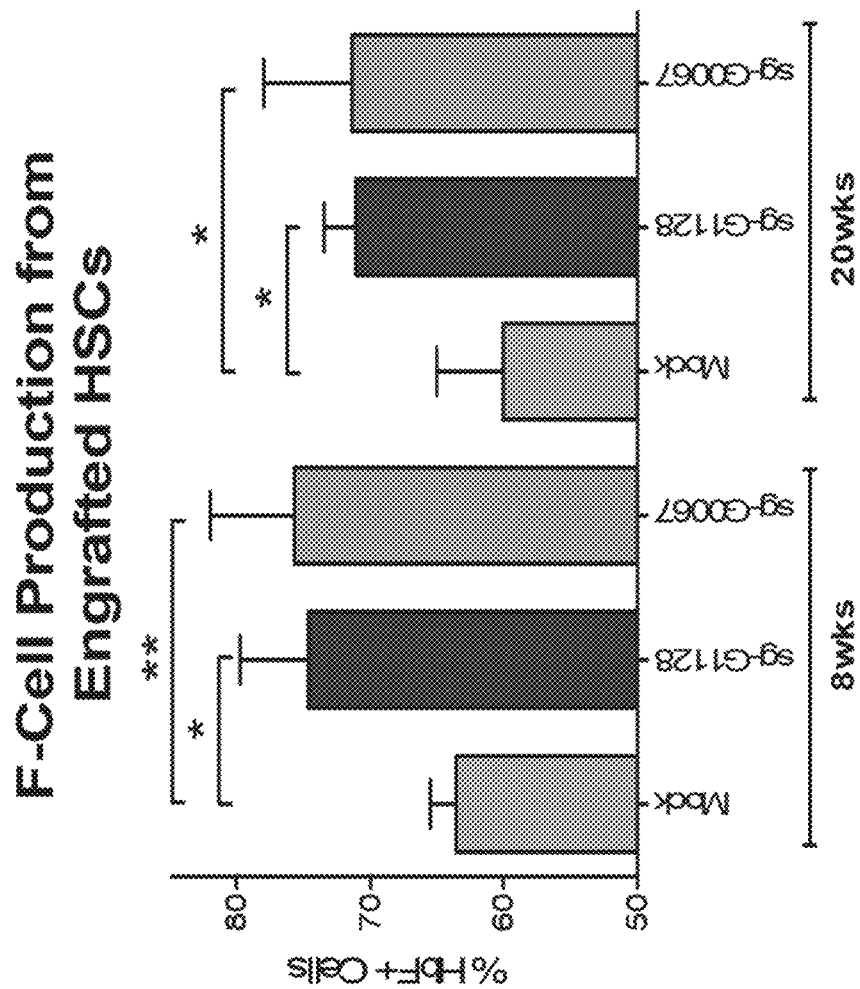
FIG. 28. Gene-edited, long-term engrafted human HSCs were capable to producing increased level of HbF upon erythroid cell differentiation Fifty thousand human CD34+ cells were sorted from the bone marrow of 8-week or 20-week transplanted NSG mice. Sorted cells were seeded into erythroid differentiation medium for 14-21 days. Mature red blood cells in culture were assayed for HbF expression and to enumerate the number of HbF+ cell by flow cytometry. Mock control represents CD34+ cells edited with Cas9 without gRNA, and transplanted into NSG mice in equal manner as gene-edited control group. N=10/group, 3 independent experiments.

Gene-Editing, Long-Term Engrafted HSCs Sustained Increased Production of Fetal Hemoglobin NSG mice do not support erythroid development since the mouse lack the right human cytokine to enable erythroid maturation. However, engrafted human HSCs can be harvested from the mouse bone marrow, placed in erythroid differentiation medium (as described elsewhere in these examples) to induce erythroid differentiation. Data show that gene-edited, 20 weeks engrafted HSCs were capable of producing higher level of HbF compare to mock edited and transplanted HSCs (FIG. 28).

Example 7. Off Target Indel Pattern Analysis

In Silico Identification of Potential gRNA Off-Target Loci

Potential off-target loci for the subset of HGB1/HBG2 region gRNAs GCR-0001, GCR-0008, GCR-0010, GCR-0048, GCR-0051 and GCR-0067 were identified as follows. For each gRNA, the 20 nucleotide gRNA targeting domain sequence was aligned to the human genome reference sequence (build GRCh38) using the BFAST sequence aligner (version 0.6.4f, Homer et al, PLoS One, 2009, 4(11), e7767, PMID: 19907642) using standard parameters allowing up to 5 nucleotide mismatches. Loci identified were filtered to only contain sites that are 5' adjacent to the Cas9 canonical 5'-NGG-3' PAM sequence (i.e. 5'-off-target locus-PAM-3'). Using the BEDTools script (version 2.11.2, Quinlan and Hall, Bioinformatics, 2010 26(6):841-2, PMID: 20110278) sites with 5 nucleotide mismatches were further filtered against RefSeq gene annotations (Pruitt et al, Nucleic Acids Res., 2014 42 (Database issue):D756-63, PMID: 24259432) to only contain loci annotated as exons. Counts of the potential off-target loci identified for the HGB1/HBG2 region gRNAs are shown in Table 12.

TABLE 12

Counts of in silico off-target loci identified for the HBG1/HBG2 region gRNAs GCR-0001, GCR-0008, GCR-0010, GCR-0048, GCR-0051 and GCR-0067 with 0, 1, 2, 3 and 4 nucleotide mismatches and 5 nucleotide mismatches within RefSeq exons are shown.

| gRNA name | Number of off-targets with N mismatches | | | | | 5 RefSeq exons | Total sites |
|---|---|---|---|---|---|---|---|
| | 0 | 1 | 2 | 3 | 4 | | |
| GCR-0001 | 0 | 0 | 4+ | 17 | 323 | 28 | 372 |
| GCR-0008 | 0 | 1+ | 0 | 27 | 267 | 60 | 355 |
| GCR-0010 | 0 | 1+ | 0 | 17 | 216 | 64 | 298 |
| GCR-0048* | 0 | 0 | 0 | 7 | 89 | 38 | 134 |
| GCR-0051 | 0 | 1+ | 3 | 25 | 369 | 66 | 464 |
| GCR-0067* | 0 | 0 | 0 | 11 | 95 | 38 | 144 |

*gRNAs GCR-0048 and GCR-0067 have two perfect match on-target sites one per HBG locus.
+includes one or two mismatch homologous HBG1 or HBG2 target sites.

Off-Target Analysis in CD34+ HSPCs

Genomic DNA Extraction

Genomic DNA was isolated from 3 day RNP edited and unedited bone marrow derived CD34+ HSPC using the Quick-DNA Miniprep kit (Zymo Research) following the manufacturer's recommendations.

PCR Primer Design for Targeted Amplification of Potential Off-Target Sites

PCR amplicons targeting potential off-target loci with 0-3 mismatches (and the on-target locus) identified for the HBG1/HBG2 region gRNAs (GCR-0001, GCR-0008, GCR-0010, GCR-0048, GCR-0051 and GCR-0067) were design using Primer3 (version 2.3.6, Untergasser et al, Nucleic Acids Res., 2012 40(15):e115, PMID: 22730293) using default parameters aiming for an amplicon size range of approximately 160-300 base pairs in length with the gRNA targeting domain sequence located in the center of the amplicon. Resulting PCR primer pairs and amplicon sequences were checked for uniqueness by BLAST searching (version 2.2.19, Altschul et al, J Mol Biol., 1990, 215(3):403-10, PMID: 2231712) sequences against the human genome reference sequence (build GRCh38). Primer pairs resulting in more than one amplicon sequence were discarded and redesigned. Table 3 shows counts of successful PCR primer pairs designed.

Illumina Sequencing Library Preparation, Quantification and Sequencing

Genomic DNA from RNP edited (2 replicates per gRNA) and unedited (2 replicate per gRNA) HSPC was quantified using the Quant-iT PicoGreen dsDNA kit (Thermo Fisher, Cat #P7581) using manufacture's recommendations. Illumina sequencing libraries targeting individual off-target loci (and the on-target locus) were generated for each sample using two sequential PCR reactions. The first PCR amplified the target locus using target specific PCR primers (designed above) that were tailed with universal Illumina sequencing compatible sequences. The second PCR added additional Illumina sequencing compatible sequences to the first PCR amplicon, including sample barcodes to enable multiplexing during sequencing. PCR 1 was performed in a final volume of 10 µL with each reaction containing approximately 6.5 ng of gDNA (equivalent to approximately 1000 cells), PCR 1 primer pairs (Integrated DNA Technologies) at a final concentration of 0.25 µM and 1× final concentration of Q5 Hot Start Master Mix (New England BioLabs, Cat #102500-140). PCR 1 left primers were 5' tailed (i.e. 5'-tail-target specific left primer-3') with sequence 5'-TCGTCGGCAGCGTCAGATGTGTATAAGAGACAG-3' (SEQ ID NO: 279) and right primers were 5' tailed (i.e. 5'-tail-target specific right primer-3') with sequence 5'-GTCTCGTGGGCTCGGAGATGTGTATAAGA-GACAG-3' (SEQ ID NO: 280). PCR 1 was performed on a thermocycler using the following cycling conditions: 1 cycle of 98° C. for 1 min; 25 cycles of 98° C. for 10 sec, 63° C. for 20 sec, and 72° C. for 30 sec; 1 cycle at 72° C. for 2 min. PCR 1 was then diluted 1 in 100 using nuclease free water (Ambion, Cat #AM9932) and used as input into PCR 2. PCR 2 was performed in a final volume of 10 µL with each reaction containing 2 µL of diluted PCR 1 product, PCR 2 primer pairs (Integrated DNA Technologies) at a final concentration of 0.5 µM and 1× final concentration of Q5 Hot Start Master Mix (New England BioLabs, Cat #102500-140). PCR 2 left primer sequence used was 5'-AATGA-TACGGCGACCACCGAGATCTA-CACNNNNNNNNTCGTCGGCAGCGTC-3' (SEQ ID NO: 281) and PCR 2 right primer sequence used was 5'-CAAGCAGAAGACGGCAT-ACGAGATNNNNNNNNGTCTCGTGGGCTCGG-3' (SEQ ID NO: 282) where the NNNNNNNN denote an 8 nucleotide barcode sequence used for sample multiplexing as part of the standard Illumina sequencing process. PCR 2 was performed on a thermocycler using the following cycling conditions: 1 cycle of 72° C. for 3 min; 1 cycle of 98° C. for 2 min; 15 cycles of 98° C. for 10 sec, 63° C. for 30 sec, and 72° C. for 2 min. PCR 2 amplicons, now viable Illumina sequencing libraries, were cleaned up using Agencourt AMPure XP beads (Beckman Coulter, Cat #A63882) following the manufacture's recommendations. The cleaned Illumina sequencing libraries were then quantified using standard qPCR quantification methods using Power SYBR Green PCR master mix (Life Technologies, Cat #4367660) and primers specific to the Illumina sequencing library ends (forward primer sequence 5'-CAAGCAGAAGACGGCAT-ACGA-3' (SEQ ID NO: 283) and reverse primer sequence 5'-AATGATACGGCGACCACCGAGA-3' (SEQ ID NO: 284)). Illumina sequencing libraries were then pooled equimolar and subjected to Illumina sequencing on a MiSeq instrument (Illumina, Cat #SY-410-1003) with 300 base paired-end reads using a MiSeq Reagent Kit v3 (Illumina, Cat #MS-102-3003) following the manufacture's recommendations. A minimum of 1000-fold sequence coverage was generated for each locus in each replicate. PCR, cleanup, pooling and sequencing of edited and unedited samples were performed separately to avoid any possibility of cross contamination between samples or PCR amplicons generated therefrom.

NGS Sequencing Data QC and Variant Analysis

Methods are as in Example 2.1 with the following modifications. For Stage 5 of analysis, sites with a combined indel frequency of >2% (editing in more than approximately 10-20 cell) were considered and potential active editing sites were further examined at the read alignment level using the Integrative Genome Viewer (IGV version 2.3, Robinson et al, Nat Biotechnol. 2011, 9(1):24-6, PMID: 21221095) that allows for visual inspection of read alignments to the genome reference sequence.

Quantification of Large Deletions.

Large deletions between targeting sites at the HBG1 and HBG2 promotors were quantified by digital droplet PCR (ddPCR) in non-competitive assay format for copy number determination according to manufacturer's recommendations. Briefly, gDNA was combined with ddPCR SuperMix for Probes (no dUTPs) (BioRad Cat #1863024), HindIII-HF restriction enzyme (NEB Cat #R3104S) and each primer probe mix, transferred to a DG8 cartridge along with Droplet Generation Oil for Probes (BioRad Cat #1863005) and droplets generated with a QX200 droplet generator (Bio-Rad). Droplets were subject to PCR on a C1000 Touch Thermal Cycler with 96-Deep Well Reaction Module (Bio-Rad), followed by detection with QX200 droplet reader (BioRad). Copies per ul was determined by analysis with QuantaSoft software (BioRad). A custom primer probe set (Life Technologies Cat #APZW76R, PN4331348, Forward primer: ACGGATAAGTAGATATTGAGGTAAGC (SEQ ID NO: 285), Reverse primer: GTCTCTTTCAGT-TAGCAGTGG (SEQ ID NO: 286), FAM TaqMan Probe: ACTGCGCTGAAACTGTGGCTTTATAG (SEQ ID NO: 287)) used to amplify gDNA within the HBG1-HBG2 intergenic region. A TaqMan Copy Number Reference Assay, human, RNase P (Thermo Fisher cat #4403326) was used as a reference amplicon. Copies per ul for HBG1-HBG2 and RNase P amplicons were within the manufacturer's reported linear range. Percent deletion was reported as 100% times 1 minus the ratio of copies per ul for HBG1-HBG2 and RNase P amplicons. Unedited control samples had calculated percent deletions up to 2%, which may reflect background in the assay.

HBG1/HBG2 Region in Silico Off-Target Analysis Results

Table 13 shows the number of off-target sites successfully characterized. Uncharacterized sites failed in PCR primer design or PCR amplification and remain to be evaluated.

gRNA GCR-0001: The HBG1 on-target site showed robust localized editing with an average INDEL frequency of approximately 58%, whereas the homologous HBG2 target site with two mismatches (here and below, shown in lowercase letters) relative to gRNA targeting domain sequence (5'-AGTCCTGGTATCtTCTATGg-PAM-3', PAM=TGG (SEQ ID NO: 288)) showed minimal localized editing. However, ddPCR analysis of the 4.9 kb deletion showed it occurring at a frequency of approximately 34%. Further analysis identified one positive off-target site with an average INDEL frequency of approximately 26% in both replicates. The site has 3 mismatches relative to the gRNA targeting domain sequence (5'-AtTCC caGTATCCTCTATGA-PAM-3', PAM=TGG (SEQ ID NO: 289)) and is located in an intergenic on the Y chromosome at base pair position 21,470,475-21,470,497. It is unclear whether editing at this off-target site has any detrimental effect on gene expression or cell viability, further analysis is required.

gRNA GCR-0008: The HBG1 on-target site showed robust localized editing with an average INDEL frequency of approximately 88%. The homologous HBG2 target site with one mismatch relative to the gRNA targeting domain sequence (5'-GGAGAAGaAAACTAGCTAAA-PAM-3', PAM=GGG (SEQ ID NO: 290)) showed robust localized editing with an average INDEL frequency of approximately 85%. ddPCR analysis of the 4.9 kb deletion showed it occurring at a frequency of approximately 50%. No other sites showed editing.

gRNA GCR-0010: The HBG1 on-target site showed robust localized editing with an average INDEL frequency of approximately 32%. The homologous HBG2 target site with one mismatch relative to the gRNA targeting domain sequence (5'-GGGAGAAGaAAACTAGCTAA-PAM-3', PAM=AGG (SEQ ID NO: 291)) showed robust localized editing with an average INDEL frequency of approximately 27%. ddPCR analysis of the 4.9 kb deletion showed it occurring at a frequency of approximately 33%. No other sites showed editing.

gRNA GCR-0048: The HBG1 and HBG2 on-target sites showed robust localized editing with an average INDEL frequency of approximately 86% for both sites. ddPCR analysis of the 4.9 kb deletion showed it occurring at a frequency of approximately 45%. No other sites showed editing.

gRNA GCR-0051: The HBG2 on-target site showed robust localized editing with an average INDEL frequency of approximately 88%. The homologous HBG1 target site with one mismatch relative to the gRNA targeting domain sequence (5'-GGAGAAGgAAACTAGCTAAA-PAM-3', PAM=GGG (SEQ ID NO: 292)) showed robust localized editing with an average INDEL frequency of approximately 59%. ddPCR analysis of the 4.9 kb deletion showed it occurring at a frequency of approximately 40%. No other sites showed editing.

gRNA GCR-0067: The HBG1 and HBG2 on-target sites showed robust localized editing with an average INDEL frequency of approximately 74% and 78% respectively. ddPCR analysis of the 4.9 kb deletion showed it occurring at a frequency of approximately 62%. No other sites showed editing.

The localized INDEL frequencies described above are not relative to the total indel frequency and do not take into account the frequency of the large 4.9 kb deletion.

TABLE 13

Counts of in silico 0-3 mismatch off-target sites identified for the HBG1/HBG2 region gRNAs GCR-0001, GCR-0008, GCR-0010, GCR-0048, GCR-0051 and GCR-0067, counts of sites successfully characterized in genome-edited HSPC and counts of sites that show editing are shown.

| gRNA name | Number of 0-3 mismatch in silico off-target sites | Number of in silico sites successfully characterized | Number of active in silico off-target sites identified |
| --- | --- | --- | --- |
| GCR-0001 | 21 | 19 | 1 |
| GCR-0008 | 28 | 28 | 1 (HBG2) |
| GCR-0010 | 18 | 18 | 1 (HBG2) |
| GCR-0048 | 7 | 7 | 0 |
| GCR-0051 | 29 | 29 | 1 (HBG1) |
| GCR-0067 | 11 | 11 | 0 |

Unbiased Off-Target Analysis

An oligo insertion based assay (See, e.g., Tsai et al., Nature Biotechnology. 33, 187-197; 2015) was used to determine potential off-target genomic sites cleaved by Cas9 targeting HBG1 and/or HBG2. In these experiments, Cas9GFP-expressing HEK293 cells (HEK-293_Cas9GFP) were transfected with gRNAs (15 nM crRNA:tracr) and insertion oligo (10 nM) using Lipofectamine® RNAiMAX. The assay relies on the identification of the oligo incorporated into double stranded breaks in the genome, which may or may not result from cleavage by Cas9.

Figure 29:
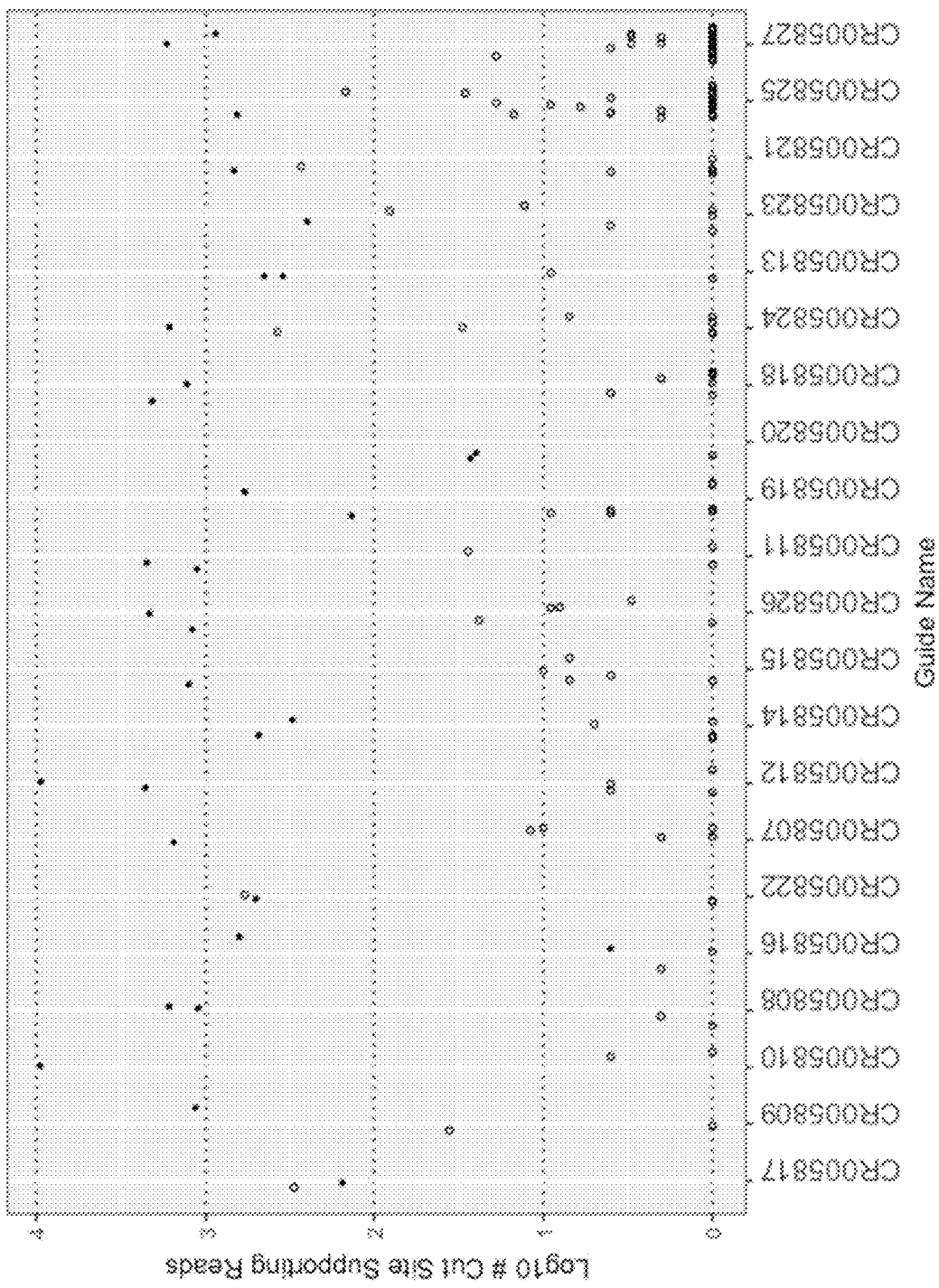
FIG. 29. Off-target activity for HBG1 and/or HBG2 guide RNAs was assessed using an dsDNA oligo-insertion method in Cas9-overexpressing HEK-293 cells. The on-target site (open circle) and the potential off-target sites (closed circles) detected are indicated; y-axis indicates frequency of detection. All gRNAs were tested in dgRNA format with the targeting domain indicated by the CRxxxxxx identifier.
Figure 30:
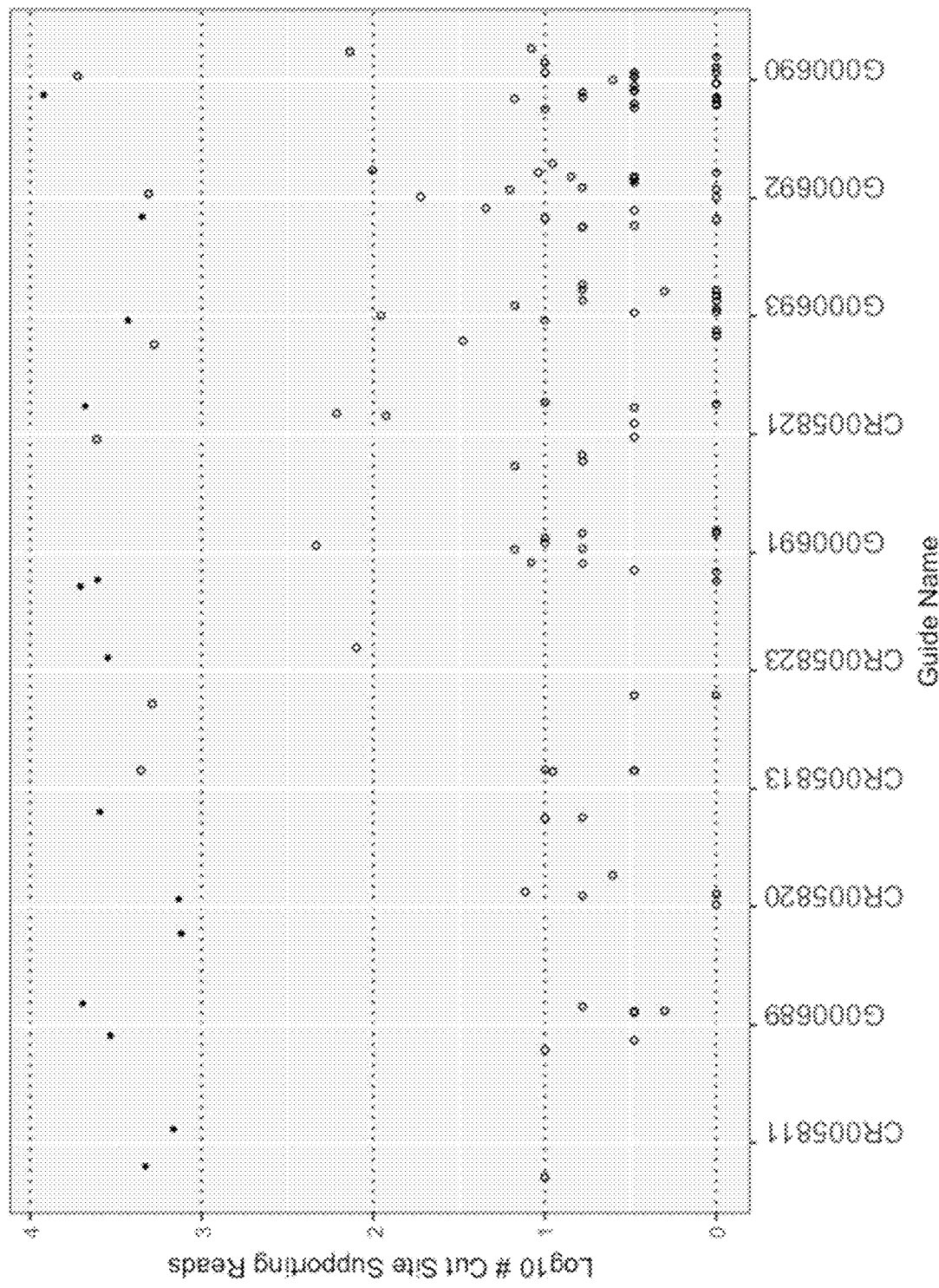
FIG. 30. Off-target activity for HBG1 and/or HBG2 guide RNAs was assessed using an dsDNA oligo-insertion method in Cas9-overexpressing HEK-293 cells. The on-target site (open circle) and the potential off-target sites (closed circles) detected are indicated; y-axis indicates frequency of detection. gRNAs were tested in either dgRNA format with the targeting domain indicated by the CRxxxxx identifier, or in sgRNA format with the targeting domain indicated by the Gxxxxxx identifier.

In one experiment, gRNAs (dual guide RNAs comprising the indicated targeting domain in FIG. 29) targeting HBG1 and/or HBG2 were screened in the HEK-293_Cas9GFP cells, and the results are plotted in FIG. 29. In a separate experiment, the same methodology was used to screen some of the same as well as additional gRNAs (including dual guide and single guide RNAs comprising the indicated targeting domain in FIG. 30) targeting HBG1 and/or HBG2 in the HEK-293_Cas9GFP cells, and the results are plotted in FIG. 30. The experiment with data depicted in FIG. 30 used an alternative insertion oligo with a balanced G/C content and minimized complementarity with the human genome, as well as other modifications to the PCR steps as compared to the published Tsai et al. methods, which improved sensitivity and diminished false positives. In both experiments, the assay detected high-efficiency editing at the expected target sequences and one or more potential off-target sites.

While the detection of the insertion oligo at sites in the genome other than the on-target site identifies potential off-target effects of Cas9, targeted deep sequencing of the potential off-target sites may be used to determine whether the potential sites are bona fide off-target sites cleaved by Cas9. To this end, an experiment was performed in which the HEK-293_Cas9GFP cells were similarly transfected with the gRNAs (at 25 nM crRNA:tracr) used in the previous two experiments, but without the insertion oligo. Amplicon deep sequencing of each of the identified potential off-target sites depicted in FIGS. 29 and 30 was used to identify whether indels (indicative of Cas9 cleavage events) were present at the potential off-target sites in the HEK-293_Cas9GFP cell line. The results of this experiment demonstrated that most of the potential off-target sites identified by the oligo insertion assay did not have detectable indels following transfection of the gRNAs, with a few exceptions as provided in Table 14 below. Of note, the HEK-293_Cas9GFP cells used in these experiments for detecting potential off-targets constitutively overexpress Cas9, likely leading to a higher number of potential off-target "hits" as compared to a transient delivery modality (e.g., RNP delivery) in various cell types of interest (e.g., CD34+ HSCs).

TABLE 14

Off-target sites validated in the HEK-293_Cas9GFP cell line.

| Guide ID | Off-target Coordinate | Average Indel Frequency |
|---|---|---|
| CR005813 (dgRNA; GCR-0051) | chr13: 95591406-95591426 | 2% |
| G000690 (sgRNA GCR-0051) | chr13: 95591406-95591426 | 2% |
| CR005821 (dgRNA GCR008) | chr20: 10409602-10409622 | 27.60% |
| G000692 (sgRNA GCR008) | chr20: 10409602-10409622 | 20.10% |

Using the methods described herein, potential off-target sites were examined in sgRNA/Cas9 edited CD34+ HSPCs and showed no editing in the CD34+ cell type.

Example 8

Experimental Procedure

CD34+ cells harvested from the mobilized peripheral blood (mPB) of healthy donors were cultured and gene edited in the same condition as described previously in Example 6. Cells were characterized for their biological function using the same methods described in previous paragraphs.

CD34+ Cells Derived from Mobilized Peripheral Blood Maintain their CD34+ Cell Count, Expansion Capacity, and Viability Upon Editing The number of CD34+ cells transplanted into patient is directly correlated with the success of a bone marrow transplant. Therefore, we enumerated the percentage of CD34+ cells over a 10-day period upon gene-editing using a clinically acceptable method, ISHAGE. Results show that neither editing with sg1128 nor sg0067 impacted CD34+ cell count (FIG. 31) when compared to mock edited control. For the total duration of our cell process, in which cells were only maintained in culture for 3 days after electroporation, the percentage of CD34+ cells was maintained at approximately 90%. (FIG. 31A). Gene editing also did not impact the capacity of CD34+ cells to expand (FIG. 31B) and their viability post-electroporation ranged between 70-90% (FIG. 31C). We observed a ~2 fold cell expansion at day 3 post-electroporation, ~10 fold expansion at day 7 post-electroporation, and 15-25 fold expansion at day 10 after electroporation (FIG. 31B).

Figure 32A:
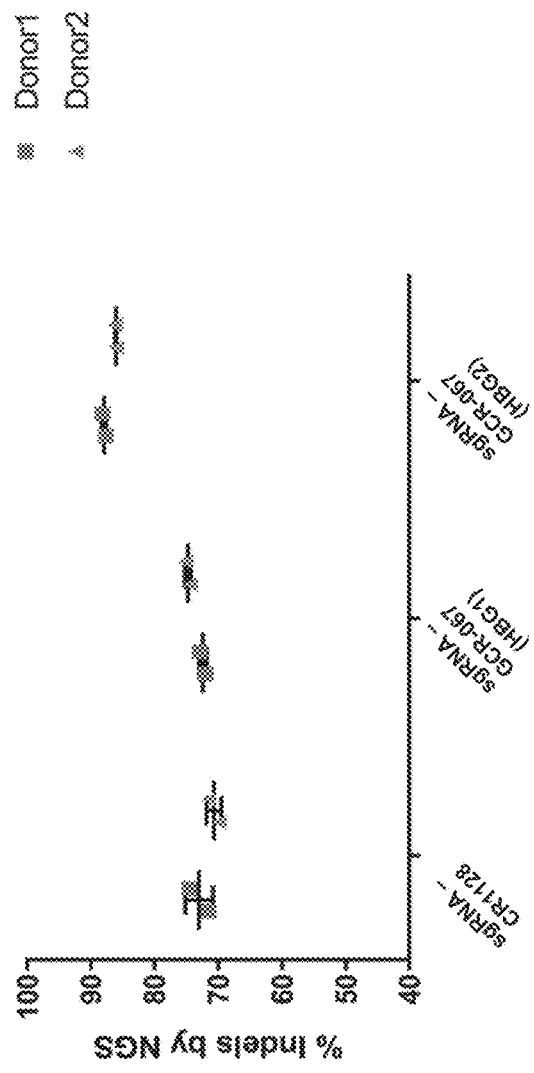
FIG. 32A. Editing efficiency of sg1128 and sg0067 in CD34+ cells mobilized from the peripheral blood of healthy individuals. Shown is the percentage of INDELs captured by NGS upon editing using sg1128 (targeting the BCL11A+58 region of ESH) and sg0067 (targeting the HbG-1 and HbG-2 gene cluster). This graph also indicates the total editing efficiency for sg1128 as only small INDELs were generated by this sgRNA. More than five independent experiments were performed in duplicate or triplicate, n=2-3/experiment.
Figure 32B:
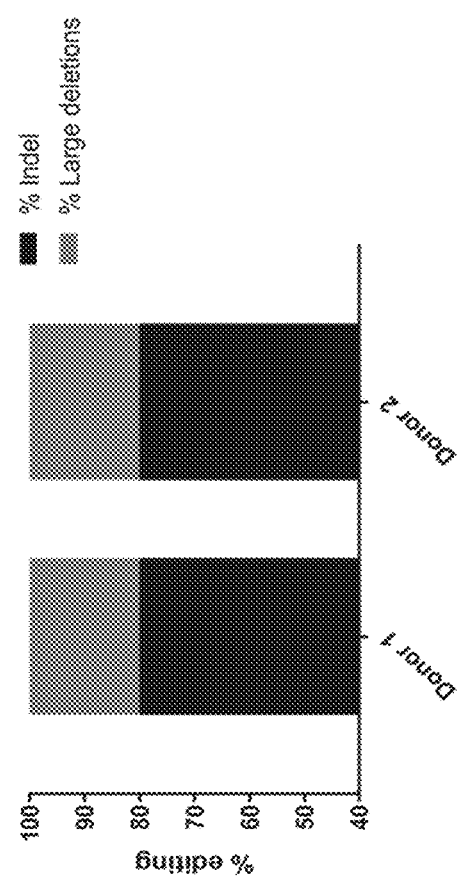
FIG. 32B. Editing efficiency of sg1128 and sg0067 in CD34+ cells mobilized from the peripheral blood of healthy individuals. A. The percentage of INDELs captured by NGS upon editing using sg0067 (targeting the HbG-1 and HbG-2 gene cluster). Shown is the total editing efficiency and editing pattern of sg0067. The editing pattern of sg0067 consists of a 5 kb large deletion (denoted by black bars) and smaller INDELs (denoted by grey bars). More than five independent experiments were performed in duplicate or triplicate, n=2-3/experiment.

CD34+ Cells Derived from Mobilized Peripheral Blood of Healthy Individuals Demonstrate Similar Editing Efficiencies Compared to Bone Marrow Cell Source or CD34+ Cells from Sickle Cell Disease Patients Sg1128 demonstrated about 70-75% editing efficiency in CD34+ cells derived from mPB of healthy donors, whereas sg0067 showed >95% total editing efficiency (including large 5 kb deletion and small indels) (FIG. 32). Editing efficiencies from these sgRNA were similar in cells from different sources, including bone marrow derived CD34+ cells from healthy donors or peripheral blood derived CD34+ cells from sickle cell disease patients (see other examples). It is important to note that both the editing efficiency and the editing pattern of each sgRNA were highly consistent across all donors tested.

Figure 33:
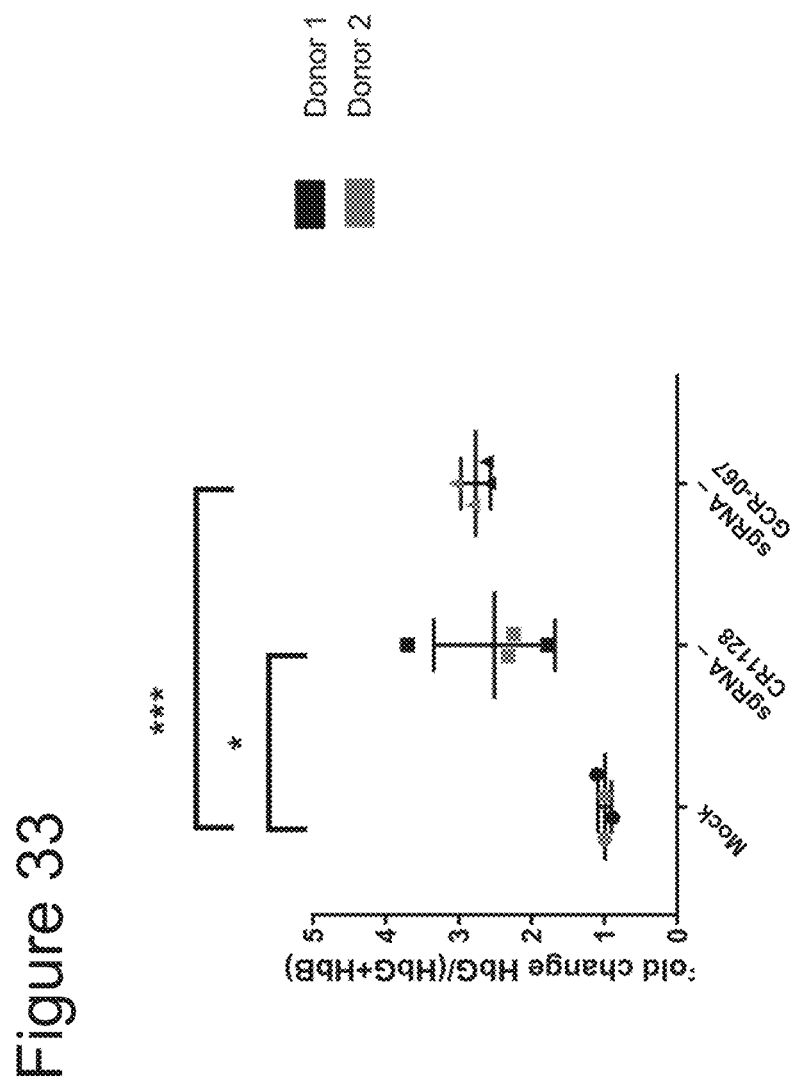
FIG. 33. Fold change of g-globin transcript in erythroid cells from patient samples upon CRISPR knockdown of BCL11A or indel/deletion formation in the HBG1/2 region. CD34+ cells derived from the mobilized peripheral blood of healthy donors were edited by CRISPR and differentiated into the erythroid lineage in vitro as described in previous procedures. At day 11 of erythroid differentiation, cells were harvested from culture and subjected to qPCR to measure g-globin and b-globin transcripts, normalizing to GAPDH. Experiment was performed independently twice, each in duplicate, n=2-3/experiment. Data show mean±SEM of pooled donors from one study.
Figure 34:
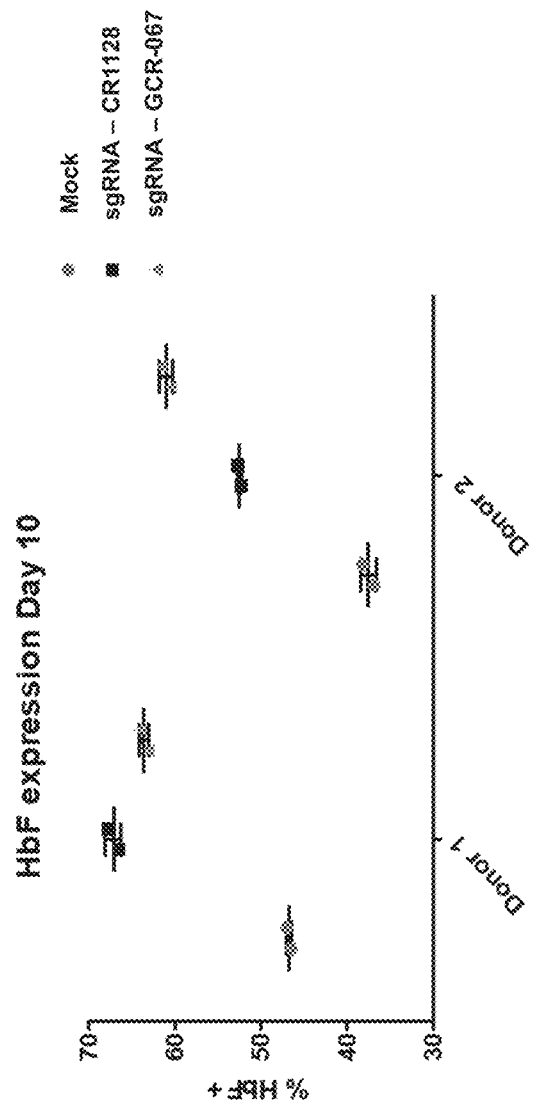
FIG. 34. Enumeration of HbF+ cells from healthy individuals upon gene editing. CD34+ cells derived from the mobilized peripheral blood of healthy donors were edited by CRISPR and differentiated into the erythroid lineage in vitro as described in previous procedures. At day 10, of erythroid differentiation, cells were stained with anti-HbF-FITC antibody to enumerate HbF+ cells by flow cytometry. Experiment was performed independently twice, each in duplicate, n=2-3/experiment. Data show average±SD from one study.

CRISPR knockdown of BCL11A or mutation of the g-globin gene cluster increases g-globin transcript and F-cell production Knockdown of BCL11A by sg1128, or mutating the potential BCL11A binding site at the g-globin gene cluster by sg0067, both significantly augmented g-globin transcripts (FIG. 33) leading to 15-20% upregulation of F-cell production compared to mock edited control (FIG. 34). In summary, sg1128 and sg0067 can edit CD34+ cells with high efficiency and generate highly consistent editing patterns. Edited cells maintain approximately 90% CD34+ cell count by the end of our 6 days cell processing procedure. The expansion capacity and viability of cells were not impaired by the gene editing procedure. Edited CD34+ cells, when differentiated into erythrocytes, expressed significantly higher level of g-globin transcripts, translating to an increased number of F-cell production. This improved hemoglobin expression and F-cell number may rescue the hematological features of sickle cell disease.

Example 9: In Vivo Engraftment and Characterization of Gene Edited Hspcs Derived from Sickle Cell Disease Patients Experimental Procedure CD34+ cells from sickle cell disease patients were cultured and gene edited in the same condition as described previously in Example 8. Cells were characterized for their biological function using the same methods described in previous Examples.

CD34+ Cells Derived from Sickle Cell Disease Individuals Maintain their CD34+ Immunophenotype and Viability Upon Editing.

Figure 35:
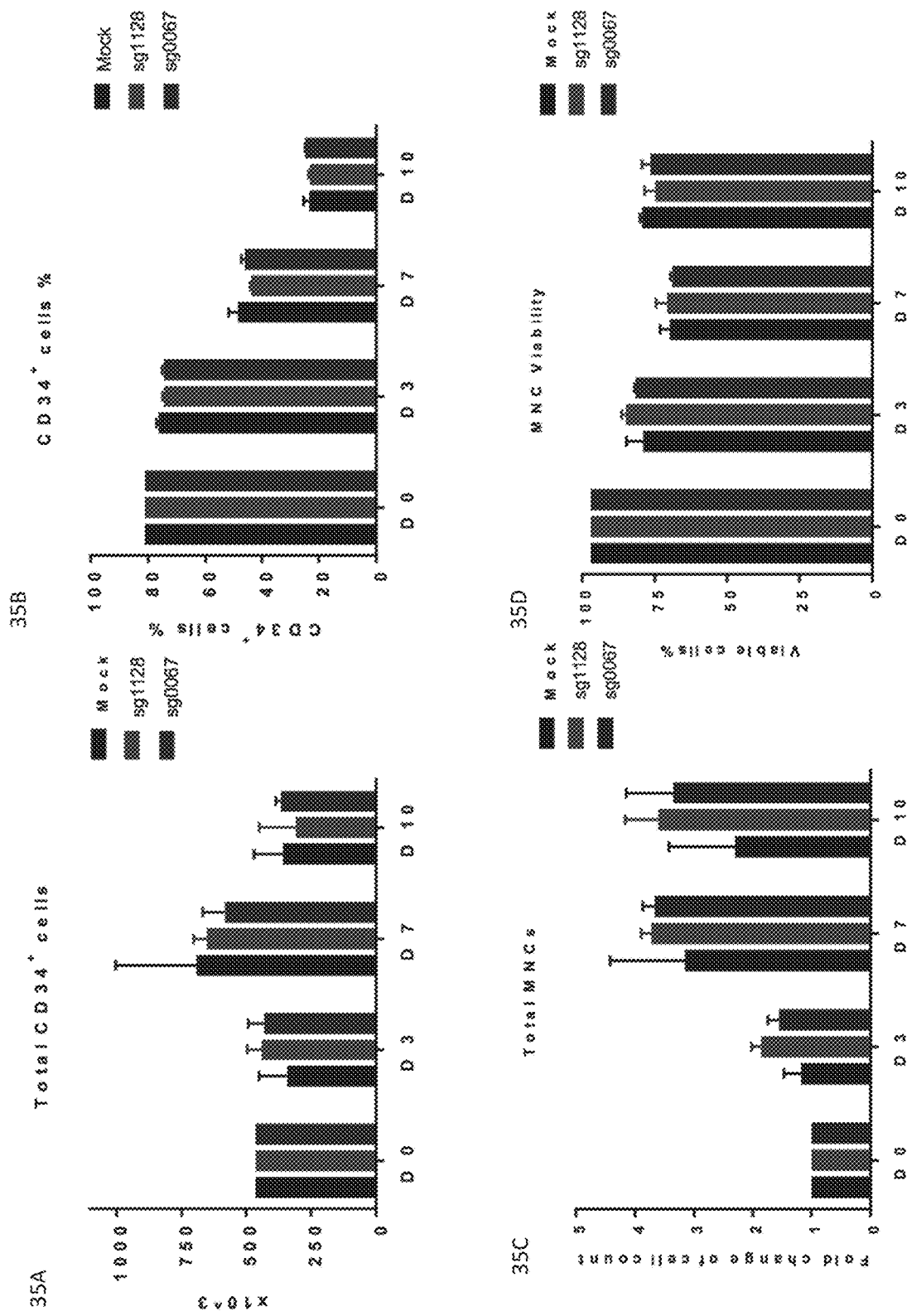
FIG. 35A. Expansion and viability of CD34+ cells derived from the peripheral blood of sickle cell disease individuals upon gene-editing. Cells were cultured for 6-10 days prior to electroporation. D0 refers to the day of electroporation. Shown is the absolute count of CD34+ cells by ISHAGE over 10 days following electroporation. N=4, data show mean±SEM. 4 independent experiments performed in duplicates. Bars are, from left to right at each time point, mock, sg1128, sg0067.
FIG. 35B. Expansion and viability of CD34+ cells derived from the peripheral blood of sickle cell disease individuals upon gene-editing. Cells were cultured for 6-10 days prior to electroporation. D0 refers to the day of electroporation. Shown is the percentage of CD34+ cells by ISHAGE over 10 days following electroporation. N=4, data show mean±SEM. 4 independent experiments performed in duplicates. Bars are, from left to right at each time point, mock, sg1128, sg0067.
FIG. 35C. Expansion and viability of CD34+ cells derived from the peripheral blood of sickle cell disease individuals upon gene-editing. Cells were cultured for 6-10 days prior to electroporation. D0 refers to the day of electroporation. Shown is expansion of total mononuclear cells at day 3, 7, and 10 upon editing. N=4, data show mean±SEM. 4 independent experiments performed in duplicates. Bars are, from left to right at each time point, mock, sg1128, sg0067.
FIG. 35D. Expansion and viability of CD34+ cells derived from the peripheral blood of sickle cell disease individuals upon gene-editing. Cells were cultured for 6-10 days prior to electroporation. D0 refers to the day of electroporation. Shown is viability of mononuclear cells at day 3, 7 and 10 post-editing. N=4, data show mean±SEM. 4 independent experiments performed in duplicates. Bars are, from left to right at each time point, mock, sg1128, sg0067.

Hematopoietic stem and progenitor cells (HSPCs) maintaining their primitive cell state should express CD34. This is one of the most important clinical markers that associates with engraftable hematopoietic stem cell upon transplantation, and the success of a transplant is directly correlated with the number of CD34+ cells transplanted. Therefore, we enumerated the number of CD34+ cells obtained from the peripheral blood of sickle individuals upon editing using a clinically acceptable method, ISHAGE. Results show that neither editing with sg1128 nor sg0067 impacted CD34+ cell count (FIG. 35A and FIG. 35B) when compared to mock edited control. The percentage of CD34+ cells were maintained at ~80% at day 3 upon editing (FIG. 35B). Gene editing also did not impact the capacity of patient derived CD34+ cells to expand (FIG. 35C) and their viability post-electroporation (electroporation at D0) was over 75% at all time points measured over a 10-day period (FIG. 35D).

Figure 36:
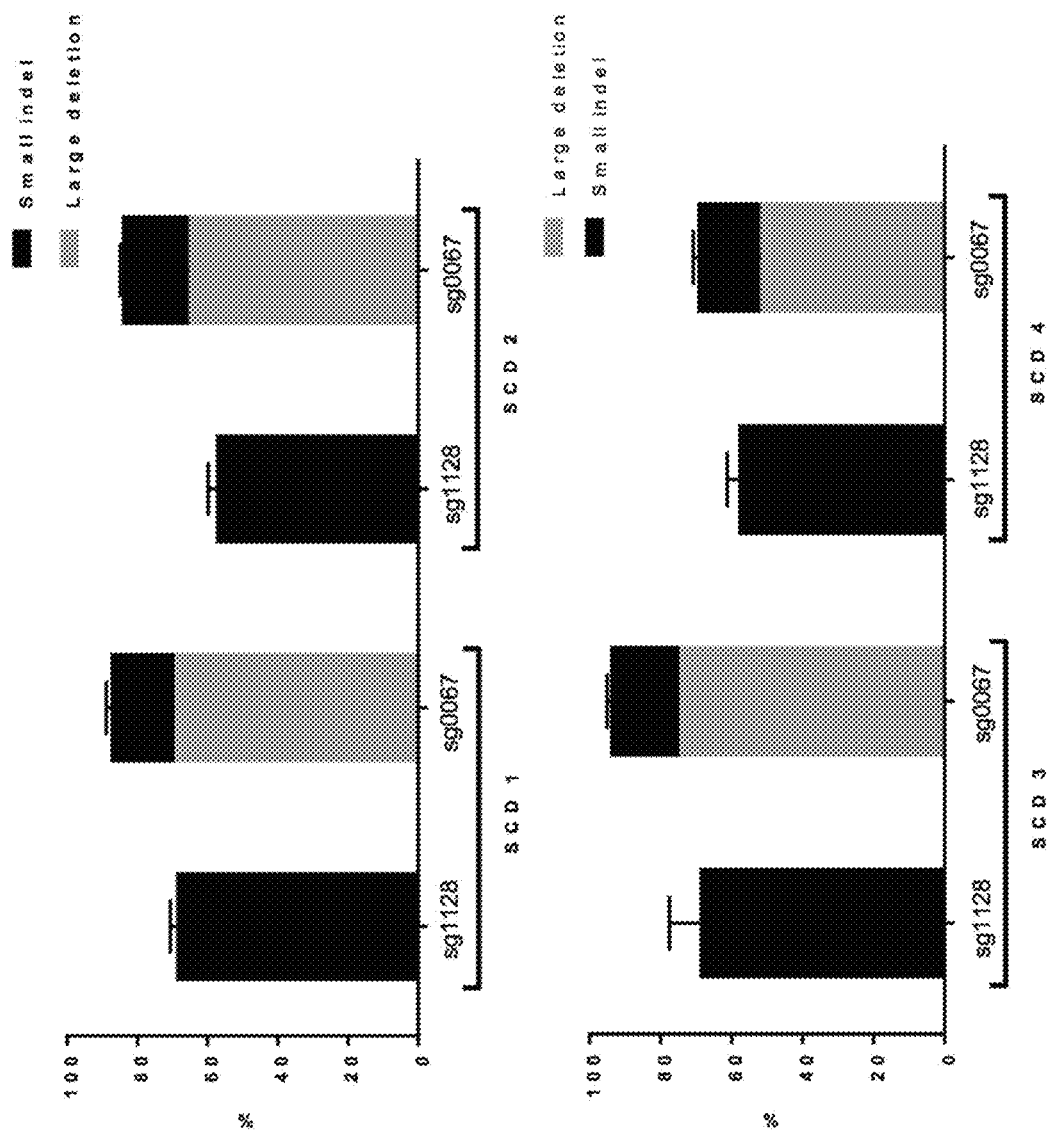
FIG. 36. Editing efficiency of sg1128 and sg0067 in CD34+ cells from sickle cell disease patient samples. Editing pattern of sg0067 was denoted by large deletion (grey) and sum of small indels (black). Data show mean±SEM of four independent editing experiments performed in duplicates with CD34+ cells from four different sickle cell disease patients (SCD1-4).

CD34+ Cells Derived from Sickle Cell Disease Individuals Demonstrate Similar Editing Efficiencies Compared to CD34+ Cells from Healthy Donors Sg1128 demonstrated about 65% editing efficiency in CD34+ cells derived from sickle cell patients, whereas sg0067 showed 80-95% editing efficiency in patient samples (FIG. 36). The level of editing efficiency is similar to those obtained using either bone marrow or mobilized peripheral blood derived CD34+ cells from healthy donors. Editing pattern of each guide RNA as measured by NGS (as described in Example 2.1) were also highly consistent across different patients.

Figure 37:
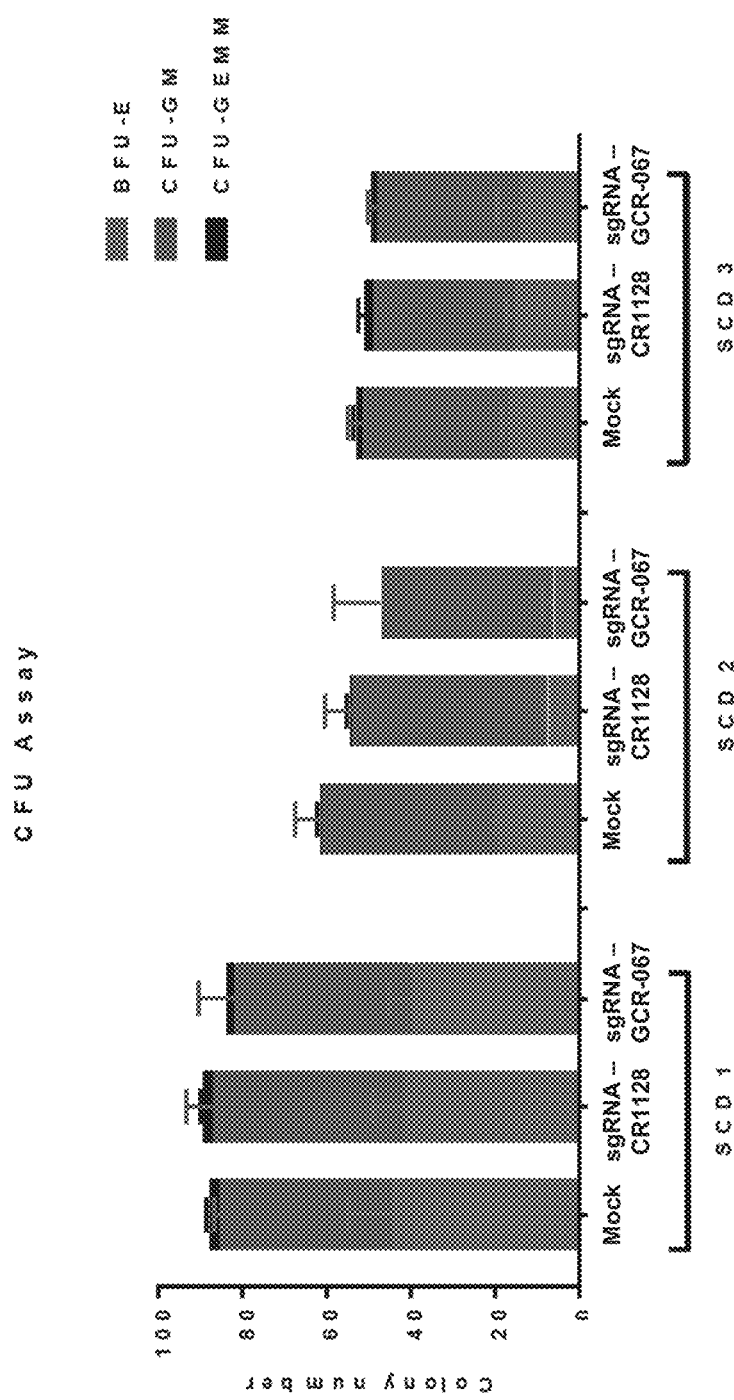
FIG. 37. In vitro multi-lineage differentiation capacity of HSPCs as measured by colony-forming unit assay. BFU-E=blast-forming unit, erythroid; CFU-GM=colony-forming unit, granulocyte, monocyte; CFU-GEMM=colony-forming unit, granulocyte, erythroid, monocyte, megakaryocyte. Graph shows three independent experiments from CD34+ cells from three different sickle cell disease patients (SCD1-3). Experiments were performed in triplicates. Data represent mean±SEM.

Gene Editing does not Compromise the In Vitro Multi-Lineage Differentiation Capacity of CD34+ Cells Derived from Sickle Cell Disease Individuals Gene edited hematopoietic stem and progenitor cells were fully capable of differentiating into erythroid, granulocytic, monocytic, and megakaryocytic lineages as measured by colony-forming unit assays (FIG. 37).

Figure 38:
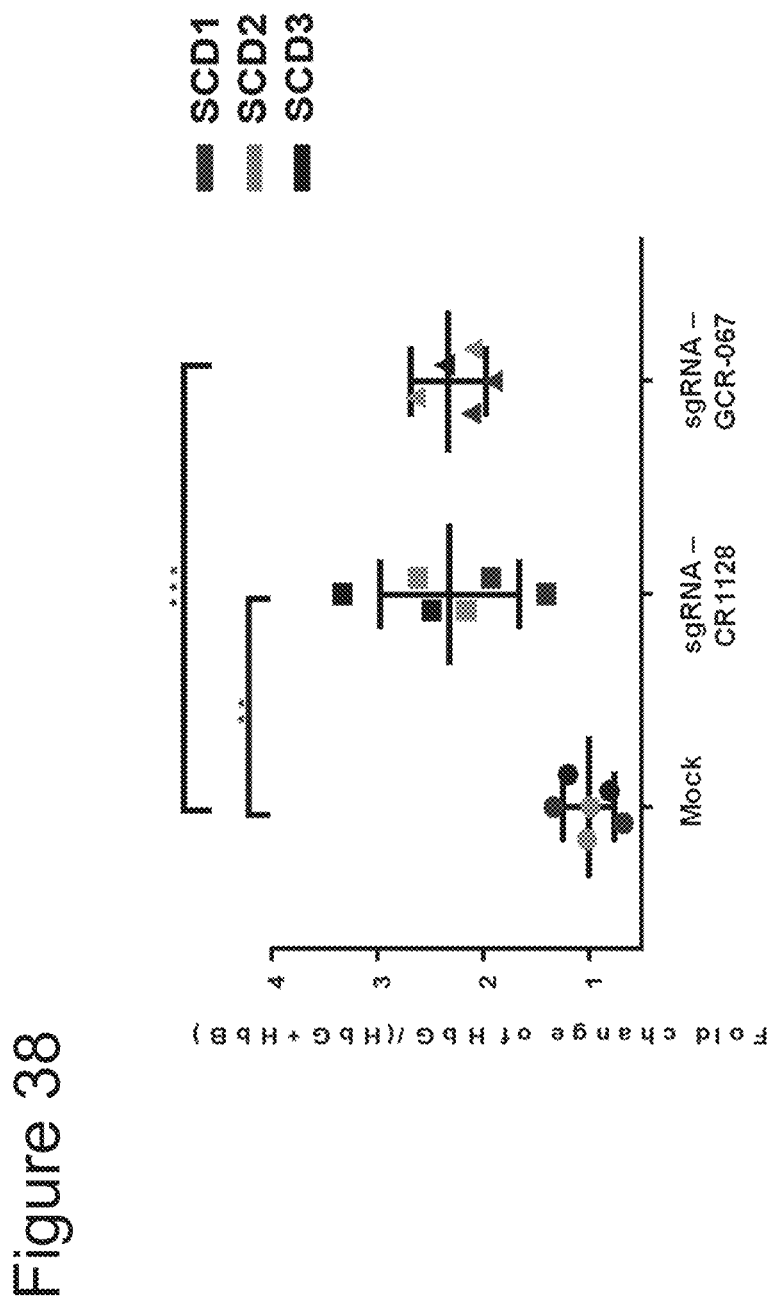
FIG. 38. Fold change of g-globin transcript in erythroid cells from patient samples upon CRISPR knockdown of BCL11A or indel/deletion formation at g-globin gene cluster. CD34+ cells derived from 3 sickle cell disease patients (SCD1-3) were edited by CRISPR and differentiated into the erythroid lineage in vitro as described in the Examples. At day 11 of erythroid differentiation, cells were harvested from culture and subjected to qPCR to measure g-globin and b-globin transcripts, normalizing to GAPDH. Experiment was performed in duplicate. Data show mean±SEM of pooled donors.
Figure 39:
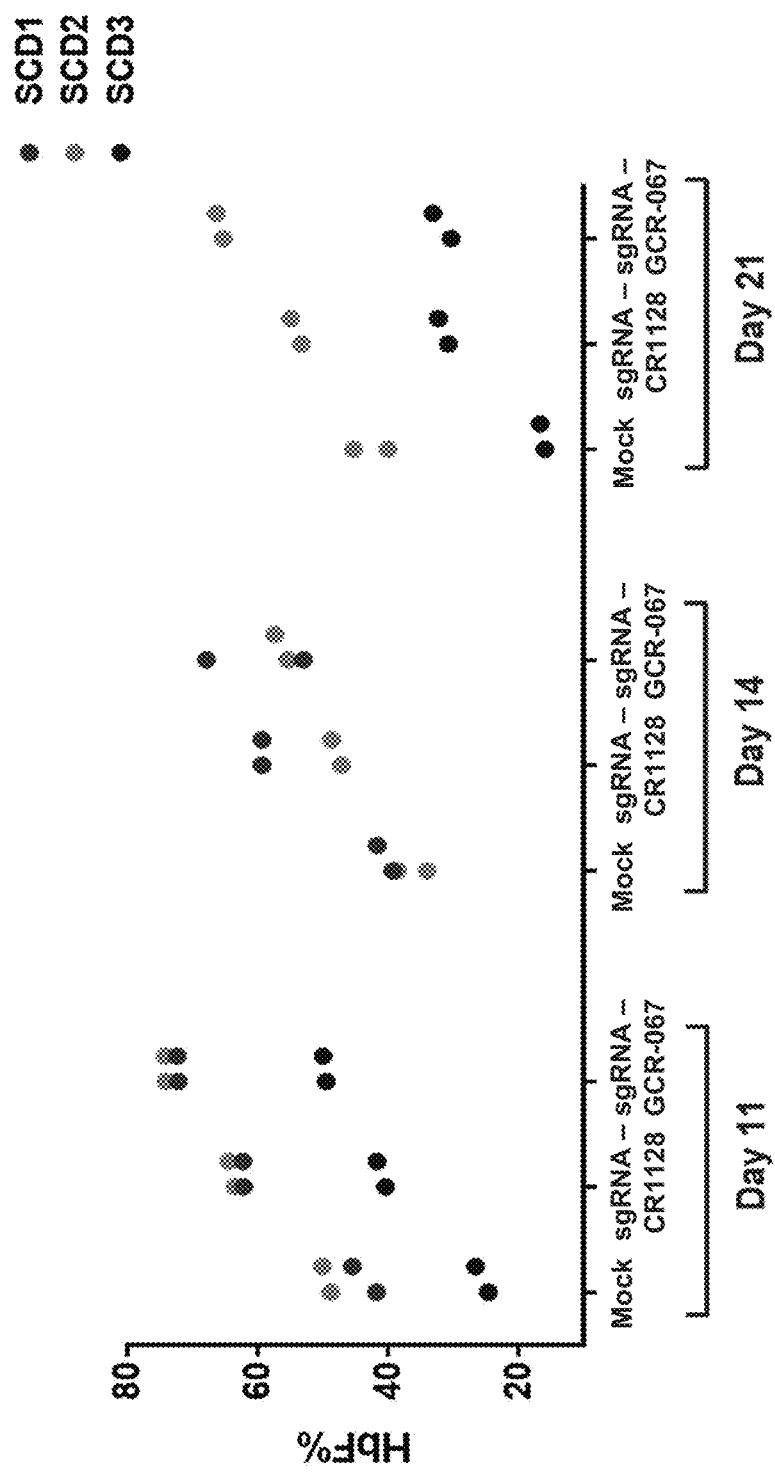
FIG. 39. Enumeration of HbF+ cells in sickle cell disease patient samples upon gene editing. CD34+ cells derived from 3 sickle cell disease patients (SCD1-3) were edited by CRISPR and differentiated into the erythroid lineage in vitro as described in the Examples. At day 11, 14, and 21 of erythroid differentiation, cells were stained with anti-HbF-FITC antibody to enumerate HbF+ cells by flow cytometry. Experiment was performed in duplicate. Data show mean±SEM. Shown at day 11 are results from SCD1-3; shown at day 14 are results from SCD-1 and SCD-2; shown at day 21 are results from SCD-2 and SCD-3.
Figure 40:
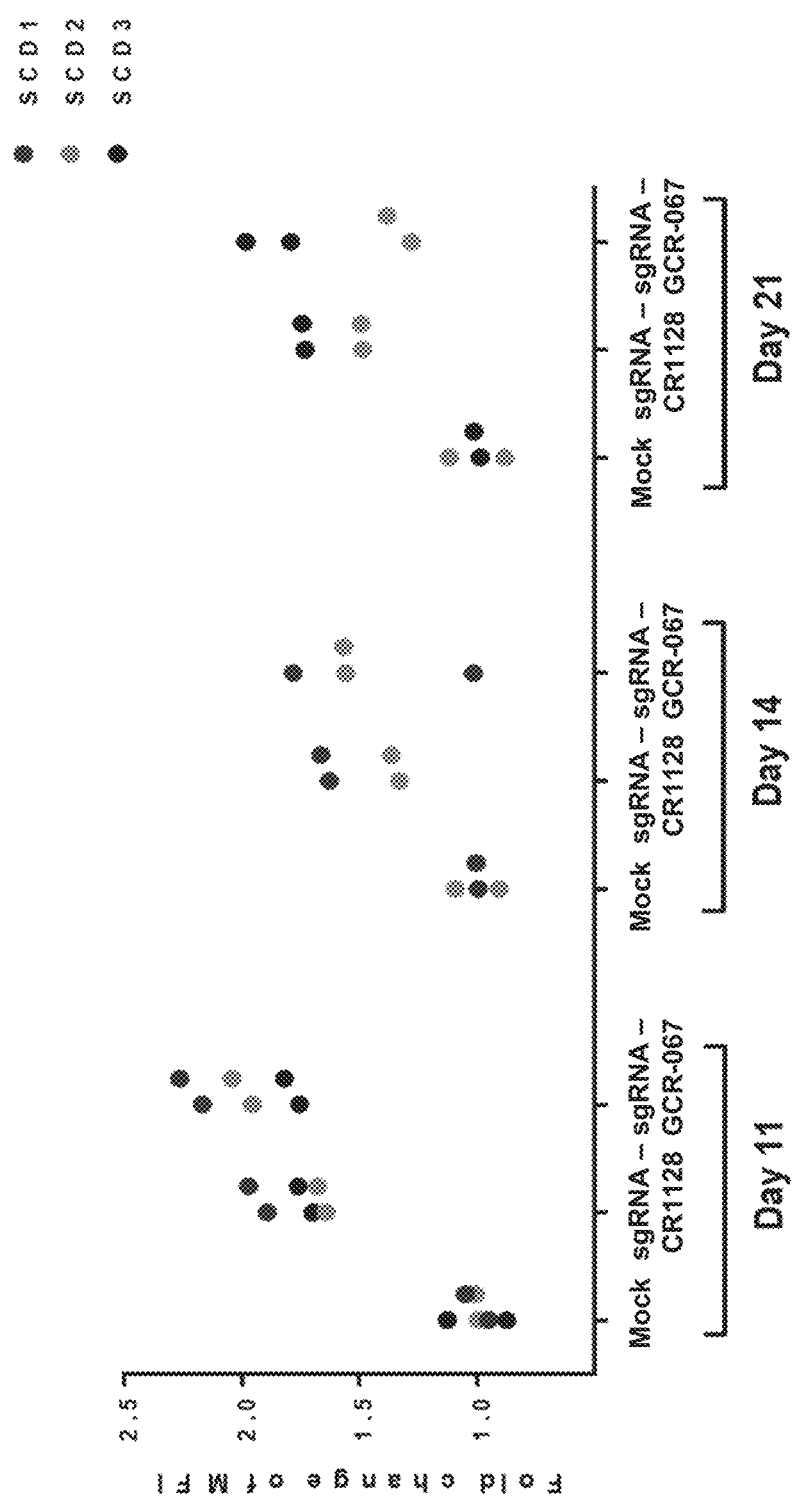
FIG. 40. Measurement of fetal hemoglobin expression in gene-edited sickle cell disease patient samples by flow cytometry. CD34+ cells derived from 3 sickle cell disease patients (SCD1-3) were edited by CRISPR and differentiated into the erythroid lineage in vitro as described in the Examples. At day 11, 14, and 21 of erythroid differentiation, cells were stained with anti-HbF-FITC antibody to measure the HbF expression intensity of each cell by flow cytometry. Experiment was performed in duplicate. Data show mean±SEM. MFI=mean fluorescent intensity. Shown at day 11 are results from SCD1-3; shown at day 14 are results from SCD-1 and SCD-2; shown at day 21 are results from SCD-2 and SCD-3.

CRISPR Knockdown of BCL11A or Mutation of the g-Globin Gene Cluster Increases g-Globin Transcript, F-Cell Production, and Fetal Hemoglobin Expression Either knockdown of BCL11A by sg1128, or creating indels/deletions at the g-globin cluster by sg0067, significantly augmented g-globin transcripts (FIG. 38) and increased the number of F-cells as measured by flow cytometry (FIG. 39). In addition, the fetal hemoglobin expression intensity of the F-cells was also improved on a per cell basis as measured by flow cytometry (FIG. 40).

Figure 41:
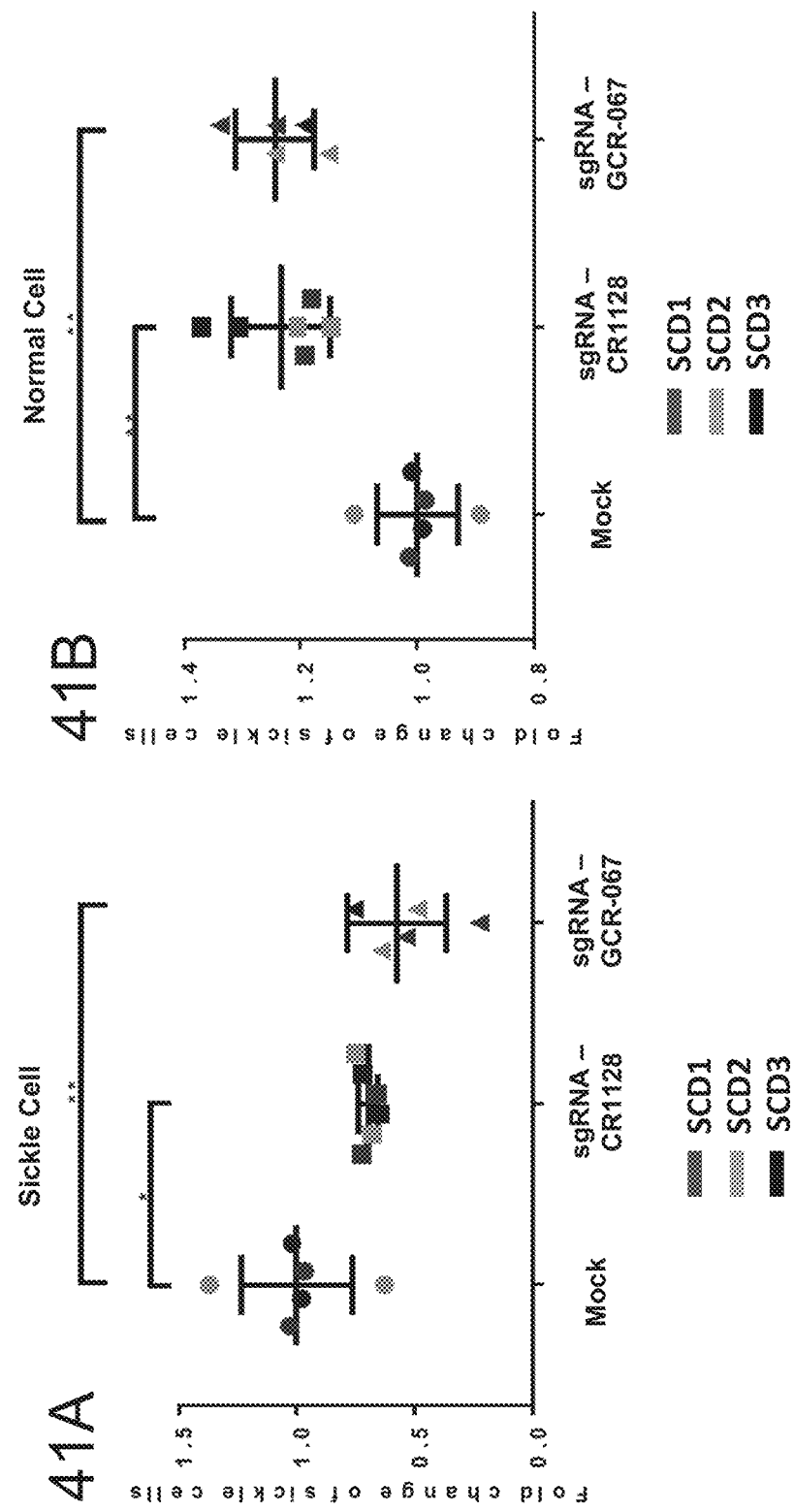
FIG. 41. Enumeration of the number of sickle cells versus normal cells upon CRISPR editing of patient samples. CD34+ cells derived from 3 sickle cell disease patients (SCD1-3) were edited by CRISPR and differentiated into the erythroid lineage in vitro as described in previous procedures. At day 21 of erythroid differentiation, cells were subjected to a % hypoxia chamber for 4 days, fixed, and followed by single cell imaging flow cytometry.

Gene Editing of Patient Derived CD34+ Cells LED to Significant Decrease in Sickle Cell Count and Increase in Normal Cell Number Finally, to understand whether gene editing can rescue the sickle cell morphology, we CRISPR-edited sickle cell disease patient derived CD34+ cells, differentiated these cells into red blood cells, and subjected these cells into a hypoxia chamber for 4 days to induce the sickle cell morphology. Cells were co-stained with anti-HbF-FITC antibody, fixed within the chamber, and subjected to imaging flow cytometry to capture one single image per cell. Single cell imaging flow cytometry can distinguish sickle cell versus normal cell based on cell length and expression of HbF in a high throughput manner (40,000 single cell images from each patient were used for data analysis). Results show that gene editing with either sg1128 or sg0067 were able to decrease sickle cell count by approximately 40% (FIG. 41A) and concomitantly increase normal cell count by 1.2 fold (FIG. 41B). The compound effect of decreasing sickle cell count and concurrently increasing normal red blood cell count will greatly benefit patients when translated to the clinic.

In summary, sg1128 and sg0067 can edit CD34+ cells from sickle cell disease patients with high efficiency and generate highly consistent editing patterns. The percentage of CD34+ cells, cell expansion capacity, and viability of cells were not impaired by the gene editing procedure when comparing edited cells to mock edited control group. Edited CD34+ cells, when differentiated into erythrocytes, expressed significantly higher level of g-globin transcripts. This translates to an increased number of F-cell and also augmented HbF expression per cell. The increase in the number of high HbF-expressing F-cell and reduction in the number of sickle red blood cell was reflected in our single cell imaging flow cytometry analysis. We observed a 50% decrease of sickle cells in gene edited group and simultaneously a 1.2 fold increase of high HbF-expressing normal red blood cells in edited groups when compared to mock edited control. This compound effect of reducing sickle cell number with a concomitant increase in high HbF-expressing normal red blood cell upon gene editing should significantly benefit patients when translated to the clinic. Together, these data support the development of CRISPR/Cas-mediated genome editing as a means of cell therapy to treat b-globinopathies.

To the extent there are any discrepancies between any sequence listing and any sequence recited in the specification, the sequence recited in the specification should be considered the correct sequence. Unless otherwise indicated, all genomic locations are according to hg38.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

The invention claimed is:

1. A guide RNA (gRNA) molecule comprising, from 5' to 3', [targeting domain]-SEQ ID NO: 195, wherein the targeting domain comprises SEQ ID NO: 67.

2. The gRNA molecule of claim 1, wherein said SEQ ID NO: 195 is disposed immediately 3' to said targeting domain.

3. The gRNA molecule of claim 1, further comprising, at the 3' end, 1, 2, 3, 4, 5, 6 or 7 uracil (U) nucleotides.

4. A guide RNA (gRNA) molecule comprising, from 5' to 3', [targeting domain]-SEQ ID NO: 231, wherein the targeting domain comprises SEQ ID NO: 67.

5. The gRNA molecule of claim 4, wherein said SEQ ID NO: 231 is disposed immediately 3' to said targeting domain.

6. The gRNA molecule of claim 1, comprising the sequence of:
   (a) SEQ ID NO: 174;
   (b) SEQ ID NO: 175; or
   (c) SEQ ID NO: 176.

7. The gRNA molecule of claim 1, wherein
   a) when a CRISPR system comprising the gRNA molecule is introduced into a cell, an indel is formed at or near a target sequence complementary to the targeting domain of the gRNA molecule; and/or
   b) when a CRISPR system comprising the gRNA molecule is introduced into a cell, a deletion is created comprising a sequence between a sequence complementary to the gRNA targeting domain in the HBG1 promoter region and a sequence complementary to the gRNA targeting domain in the HBG2 promoter region.

8. A composition comprising:
   1) the gRNA molecule of claim 1 and a Cas9 molecule;
   2) the gRNA molecule of claim 1 and a polynucleotide comprising a nucleic acid sequence encoding a Cas9 molecule;
   3) a polynucleotide comprising a nucleic acid sequence encoding the gRNA molecule of claim 1 and a Cas9 molecule;
   4) a polynucleotide comprising a nucleic acid sequence encoding the gRNA molecule of claim 1 and a polynucleotide comprising a nucleic acid sequence encoding a Cas9 molecule;
   5) a polynucleotide comprising a nucleic acid sequence encoding the gRNA molecule of claim 1;
   6) any of 1) to 5), above, and a template nucleic acid; or
   7) any of 1) to 5) above, and a polynucleotide comprising a nucleic acid sequence encoding a template nucleic acid.

9. A composition comprising the gRNA molecule of claim 1, further comprising a Cas9 molecule, wherein the Cas9 molecule comprises the sequence of SEQ ID NO: 205 or a sequence with at least 95% sequence homology thereto.

10. A nucleic acid sequence that encodes the gRNA molecule of claim 1.

11. A vector comprising the nucleic acid sequence of claim 10, wherein said vector is selected from the group consisting of a lentiviral vector, an adenoviral vector, an adeno-associated viral (AAV) vector, a herpes simplex virus (HSV) vector, a plasmid, a minicircle, a nanoplasmid, and an RNA vector.

12. A cell, comprising the gRNA molecule of claim 1 and a Cas9 molecule.

13. The gRNA molecule of claim 1, consisting of the sequence of:
(a) SEQ ID NO: 174;
(b) SEQ ID NO: 175; or
(c) SEQ ID NO: 176.

14. The gRNA molecule of claim 1, consisting of the sequence of SEQ ID NO: 174.

15. The composition of claim 9, wherein the Cas9 molecule comprises the sequence of:
(a) SEQ ID NO: 233;
(b) SEQ ID NO: 234;
(c) SEQ ID NO: 235;
(d) SEQ ID NO: 236;
(e) SEQ ID NO: 237;
(f) SEQ ID NO: 238;
(g) SEQ ID NO: 239;
(h) SEQ ID NO: 240;
(i) SEQ ID NO: 241;
(j) SEQ ID NO: 242;
(k) SEQ ID NO: 243; or
(l) SEQ ID NO: 244.

16. The composition of claim 9, wherein the Cas9 molecule comprises the sequence of SEQ ID NO: 244.

17. The composition of claim 9, formulated in a medium suitable for electroporation.

\* \* \* \* \*

SEQUENCE LISTING

```
<160> NUMBER OF SEQ ID NOS: 332

<210> SEQ ID NO 1
<211> LENGTH: 20
<212> TYPE: RNA
<213> ORGANISM: Homo sapiens

<400> SEQUENCE: 1
aguccuggua uccucuauga                                              20

<210> SEQ ID NO 2
<211> LENGTH: 20
<212> TYPE: RNA
<213> ORGANISM: Homo sapiens

<400> SEQUENCE: 2
aauuagcagu auccucuugg                                              20
```

```
<210> SEQ ID NO 3
<211> LENGTH: 20
<212> TYPE: RNA
<213> ORGANISM: Homo sapiens

<400> SEQUENCE: 3
agaauaaauu agagaaaaac                                                    20

<210> SEQ ID NO 4
<211> LENGTH: 20
<212> TYPE: RNA
<213> ORGANISM: Homo sapiens

<400> SEQUENCE: 4
aaaaauuagc aguauccucu                                                    20

<210> SEQ ID NO 5
<211> LENGTH: 20
<212> TYPE: RNA
<213> ORGANISM: Homo sapiens

<400> SEQUENCE: 5
aaaauuagca guauccucuu                                                    20

<210> SEQ ID NO 6
<211> LENGTH: 20
<212> TYPE: RNA
<213> ORGANISM: Homo sapiens

<400> SEQUENCE: 6
aaaaacugga augacugaau                                                    20

<210> SEQ ID NO 7
<211> LENGTH: 20
<212> TYPE: RNA
<213> ORGANISM: Homo sapiens

<400> SEQUENCE: 7
cucccaucau agaggauacc                                                    20

<210> SEQ ID NO 8
<211> LENGTH: 20
<212> TYPE: RNA
<213> ORGANISM: Homo sapiens

<400> SEQUENCE: 8
ggagaaggaa acuagcuaaa                                                    20

<210> SEQ ID NO 9
<211> LENGTH: 20
<212> TYPE: RNA
<213> ORGANISM: Homo sapiens

<400> SEQUENCE: 9
guuuccuucu cccaucauag                                                    20

<210> SEQ ID NO 10
<211> LENGTH: 20
<212> TYPE: RNA
<213> ORGANISM: Homo sapiens

<400> SEQUENCE: 10
gggagaagga aacuagcuaa                                                    20
```

```
<210> SEQ ID NO 11
<211> LENGTH: 20
<212> TYPE: RNA
<213> ORGANISM: Homo sapiens

<400> SEQUENCE: 11
cacuggagcu agagacaaga                                               20

<210> SEQ ID NO 12
<211> LENGTH: 20
<212> TYPE: RNA
<213> ORGANISM: Homo sapiens

<400> SEQUENCE: 12
agagacaaga agguaaaaaa                                               20

<210> SEQ ID NO 13
<211> LENGTH: 20
<212> TYPE: RNA
<213> ORGANISM: Homo sapiens

<400> SEQUENCE: 13
aaauuagcag uauccucuug                                               20

<210> SEQ ID NO 14
<211> LENGTH: 20
<212> TYPE: RNA
<213> ORGANISM: Homo sapiens

<400> SEQUENCE: 14
guccugguau ccucuaugau                                               20

<210> SEQ ID NO 15
<211> LENGTH: 20
<212> TYPE: RNA
<213> ORGANISM: Homo sapiens

<400> SEQUENCE: 15
guauccucua ugaugggaga                                               20

<210> SEQ ID NO 16
<211> LENGTH: 20
<212> TYPE: RNA
<213> ORGANISM: Homo sapiens

<400> SEQUENCE: 16
ccuagccagc cgccggcccc                                               20

<210> SEQ ID NO 17
<211> LENGTH: 20
<212> TYPE: RNA
<213> ORGANISM: Homo sapiens

<400> SEQUENCE: 17
auuaagcagc aguauccucu                                               20

<210> SEQ ID NO 18
<211> LENGTH: 20
<212> TYPE: RNA
<213> ORGANISM: Homo sapiens

<400> SEQUENCE: 18
uauccaguga ggccaggggc                                               20
```

```
<210> SEQ ID NO 19
<211> LENGTH: 20
<212> TYPE: RNA
<213> ORGANISM: Homo sapiens

<400> SEQUENCE: 19
cauugagaua gugugggaa                                                   20

<210> SEQ ID NO 20
<211> LENGTH: 20
<212> TYPE: RNA
<213> ORGANISM: Homo sapiens

<400> SEQUENCE: 20
ccagugaggc caggggccgg                                                  20

<210> SEQ ID NO 21
<211> LENGTH: 20
<212> TYPE: RNA
<213> ORGANISM: Homo sapiens

<400> SEQUENCE: 21 gugggaagg ggcccccaag                                                   20

<210> SEQ ID NO 22
<211> LENGTH: 20
<212> TYPE: RNA
<213> ORGANISM: Homo sapiens

<400> SEQUENCE: 22
agaauaaauu agagaaaaau                                                  20

<210> SEQ ID NO 23
<211> LENGTH: 20
<212> TYPE: RNA
<213> ORGANISM: Homo sapiens

<400> SEQUENCE: 23
ccaggggccg gcggcuggcu                                                  20

<210> SEQ ID NO 24
<211> LENGTH: 20
<212> TYPE: RNA
<213> ORGANISM: Homo sapiens

<400> SEQUENCE: 24
ugaggccagg ggccggcggc                                                  20

<210> SEQ ID NO 25
<211> LENGTH: 20
<212> TYPE: RNA
<213> ORGANISM: Homo sapiens

<400> SEQUENCE: 25
caguuccaca cacucgcuuc                                                  20

<210> SEQ ID NO 26
<211> LENGTH: 20
<212> TYPE: RNA
<213> ORGANISM: Homo sapiens

<400> SEQUENCE: 26
```

```
ccgccggccc cuggccucac                                              20

<210> SEQ ID NO 27
<211> LENGTH: 20
<212> TYPE: RNA
<213> ORGANISM: Homo sapiens

<400> SEQUENCE: 27
guuugccuug ucaaggcuau                                              20

<210> SEQ ID NO 28
<211> LENGTH: 20
<212> TYPE: RNA
<213> ORGANISM: Homo sapiens

<400> SEQUENCE: 28
ggcuagggau gaagaauaaa                                              20

<210> SEQ ID NO 29
<211> LENGTH: 20
<212> TYPE: RNA
<213> ORGANISM: Homo sapiens

<400> SEQUENCE: 29
agaaguccug guaucuucua                                              20

<210> SEQ ID NO 30
<211> LENGTH: 20
<212> TYPE: RNA
<213> ORGANISM: Homo sapiens

<400> SEQUENCE: 30
caggggccgg cggcuggcua                                              20

<210> SEQ ID NO 31
<211> LENGTH: 20
<212> TYPE: RNA
<213> ORGANISM: Homo sapiens

<400> SEQUENCE: 31
acuggauacu cuaagacuau                                              20

<210> SEQ ID NO 32
<211> LENGTH: 20
<212> TYPE: RNA
<213> ORGANISM: Homo sapiens

<400> SEQUENCE: 32
uuaagcagca guauccucuu                                              20

<210> SEQ ID NO 33
<211> LENGTH: 20
<212> TYPE: RNA
<213> ORGANISM: Homo sapiens

<400> SEQUENCE: 33
cccuggcuaa acuccaccca                                              20

<210> SEQ ID NO 34
<211> LENGTH: 20
<212> TYPE: RNA
<213> ORGANISM: Homo sapiens

<400> SEQUENCE: 34
```
aaaaauugga augacugaau                                                  20

<210> SEQ ID NO 35
<211> LENGTH: 20
<212> TYPE: RNA
<213> ORGANISM: Homo sapiens

<400> SEQUENCE: 35
uuagaguauc cagugaggcc                                                  20

<210> SEQ ID NO 36
<211> LENGTH: 20
<212> TYPE: RNA
<213> ORGANISM: Homo sapiens

<400> SEQUENCE: 36
cccaugggug gaguuuagcc                                                  20

<210> SEQ ID NO 37
<211> LENGTH: 20
<212> TYPE: RNA
<213> ORGANISM: Homo sapiens

<400> SEQUENCE: 37
aggcaaggcu ggccaaccca                                                  20

<210> SEQ ID NO 38
<211> LENGTH: 20
<212> TYPE: RNA
<213> ORGANISM: Homo sapiens

<400> SEQUENCE: 38
uagaguaucc agugaggcca                                                  20

<210> SEQ ID NO 39
<211> LENGTH: 20
<212> TYPE: RNA
<213> ORGANISM: Homo sapiens

<400> SEQUENCE: 39
uaucugucug aaacgguccc                                                  20

<210> SEQ ID NO 40
<211> LENGTH: 20
<212> TYPE: RNA
<213> ORGANISM: Homo sapiens

<400> SEQUENCE: 40
auugagauag ugugggggaag                                                 20

<210> SEQ ID NO 41
<211> LENGTH: 20
<212> TYPE: RNA
<213> ORGANISM: Homo sapiens

<400> SEQUENCE: 41
cuucaucccu agccagccgc                                                  20

<210> SEQ ID NO 42
<211> LENGTH: 20
<212> TYPE: RNA
<213> ORGANISM: Homo sapiens

```
<400> SEQUENCE: 42
gcuauugguc aaggcaaggc                                           20

<210> SEQ ID NO 43
<211> LENGTH: 20
<212> TYPE: RNA
<213> ORGANISM: Homo sapiens

<400> SEQUENCE: 43
augcaaauau cugucugaaa                                           20

<210> SEQ ID NO 44
<211> LENGTH: 20
<212> TYPE: RNA
<213> ORGANISM: Homo sapiens

<400> SEQUENCE: 44
gcauugagau agugugggga                                           20

<210> SEQ ID NO 45
<211> LENGTH: 20
<212> TYPE: RNA
<213> ORGANISM: Homo sapiens

<400> SEQUENCE: 45
uggucaaguu ugccuuguca                                           20

<210> SEQ ID NO 46
<211> LENGTH: 20
<212> TYPE: RNA
<213> ORGANISM: Homo sapiens

<400> SEQUENCE: 46
gggagaagaa aacuagcuaa                                           20

<210> SEQ ID NO 47
<211> LENGTH: 20
<212> TYPE: RNA
<213> ORGANISM: Homo sapiens

<400> SEQUENCE: 47
ggcaaggcug gccaacccau                                           20

<210> SEQ ID NO 48
<211> LENGTH: 20
<212> TYPE: RNA
<213> ORGANISM: Homo sapiens

<400> SEQUENCE: 48
acggcugaca aaagaagucc                                           20

<210> SEQ ID NO 49
<211> LENGTH: 20
<212> TYPE: RNA
<213> ORGANISM: Homo sapiens

<400> SEQUENCE: 49
cgagugugug gaacugcuga                                           20

<210> SEQ ID NO 50
<211> LENGTH: 20
<212> TYPE: RNA
<213> ORGANISM: Homo sapiens
```

```
<400> SEQUENCE: 50
ccuggcuaaa cuccacccau                                                 20

<210> SEQ ID NO 51
<211> LENGTH: 20
<212> TYPE: RNA
<213> ORGANISM: Homo sapiens

<400> SEQUENCE: 51
ggagaagaaa acuagcuaaa                                                 20

<210> SEQ ID NO 52
<211> LENGTH: 20
<212> TYPE: RNA
<213> ORGANISM: Homo sapiens

<400> SEQUENCE: 52
cucccaccau agaagauacc                                                 20

<210> SEQ ID NO 53
<211> LENGTH: 20
<212> TYPE: RNA
<213> ORGANISM: Homo sapiens

<400> SEQUENCE: 53
cuugucaagg cuauugguca                                                 20

<210> SEQ ID NO 54
<211> LENGTH: 20
<212> TYPE: RNA
<213> ORGANISM: Homo sapiens

<400> SEQUENCE: 54
aguccuggua ucuucuaugg                                                 20

<210> SEQ ID NO 55
<211> LENGTH: 20
<212> TYPE: RNA
<213> ORGANISM: Homo sapiens

<400> SEQUENCE: 55
auauuugcau ugagauagug                                                 20

<210> SEQ ID NO 56
<211> LENGTH: 20
<212> TYPE: RNA
<213> ORGANISM: Homo sapiens

<400> SEQUENCE: 56
gcuaaacucc acccaugggu                                                 20

<210> SEQ ID NO 57
<211> LENGTH: 20
<212> TYPE: RNA
<213> ORGANISM: Homo sapiens

<400> SEQUENCE: 57
acguuccaga agcgagugug                                                 20

<210> SEQ ID NO 58
<211> LENGTH: 20
<212> TYPE: RNA
```

```
<213> ORGANISM: Homo sapiens

<400> SEQUENCE: 58
guccugguau cuucuauggu                                      20

<210> SEQ ID NO 59
<211> LENGTH: 20
<212> TYPE: RNA
<213> ORGANISM: Homo sapiens

<400> SEQUENCE: 59
uauuugcauu gagauagugu                                      20

<210> SEQ ID NO 60
<211> LENGTH: 20
<212> TYPE: RNA
<213> ORGANISM: Homo sapiens

<400> SEQUENCE: 60
uaagcagcag uauccucuug                                      20

<210> SEQ ID NO 61
<211> LENGTH: 20
<212> TYPE: RNA
<213> ORGANISM: Homo sapiens

<400> SEQUENCE: 61
ggaaugacug aaucggaaca                                      20

<210> SEQ ID NO 62
<211> LENGTH: 20
<212> TYPE: RNA
<213> ORGANISM: Homo sapiens

<400> SEQUENCE: 62
cuugaccaau agccuugaca                                      20

<210> SEQ ID NO 63
<211> LENGTH: 20
<212> TYPE: RNA
<213> ORGANISM: Homo sapiens

<400> SEQUENCE: 63
caaggcuauu ggucaaggca                                      20

<210> SEQ ID NO 64
<211> LENGTH: 20
<212> TYPE: RNA
<213> ORGANISM: Homo sapiens

<400> SEQUENCE: 64
aaggcuggcc aacccauggg                                      20

<210> SEQ ID NO 65
<211> LENGTH: 20
<212> TYPE: RNA
<213> ORGANISM: Homo sapiens

<400> SEQUENCE: 65
acucgcuucu ggaacgucug                                      20

<210> SEQ ID NO 66
<211> LENGTH: 20
```

<212> TYPE: RNA
<213> ORGANISM: Homo sapiens

<400> SEQUENCE: 66
auuugcauug agauagugug                                                    20

<210> SEQ ID NO 67
<211> LENGTH: 20
<212> TYPE: RNA
<213> ORGANISM: Homo sapiens

<400> SEQUENCE: 67
acugaaucgg aacaaggcaa                                                    20

<210> SEQ ID NO 68
<211> LENGTH: 20
<212> TYPE: RNA
<213> ORGANISM: Homo sapiens

<400> SEQUENCE: 68
ccaugggugg aguuuagcca                                                    20

<210> SEQ ID NO 69
<211> LENGTH: 20
<212> TYPE: RNA
<213> ORGANISM: Homo sapiens

<400> SEQUENCE: 69
aagcagcagu auccucuugg                                                    20

<210> SEQ ID NO 70
<211> LENGTH: 20
<212> TYPE: RNA
<213> ORGANISM: Homo sapiens

<400> SEQUENCE: 70
agaguaucca gugaggccag                                                    20

<210> SEQ ID NO 71
<211> LENGTH: 20
<212> TYPE: RNA
<213> ORGANISM: Homo sapiens

<400> SEQUENCE: 71
gagugugugg aacugcugaa                                                    20

<210> SEQ ID NO 72
<211> LENGTH: 20
<212> TYPE: RNA
<213> ORGANISM: Homo sapiens

<400> SEQUENCE: 72
uagucuuaga guauccagug                                                    20

<210> SEQ ID NO 73
<211> LENGTH: 74
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73

```
aacagcauag caaguuaaaa uaaggcuagu ccguuaucaa cuugaaaaag uggcaccgag    60
ucggugcuuu uuuu                                                     74
```

<210> SEQ ID NO 74
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74

```
aguccuggua uccucuauga guuuuagagc uagaaauagc aaguuaaaau aaggcuaguc    60
cguuaucaac uugaaaaagu ggcaccgagu cggugcuuuu                        100
```

<210> SEQ ID NO 75
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75

```
aguccuggua uccucuauga guuuuagagc uagaaauagc aaguuaaaau aaggcuaguc    60
cguuaucaac uugaaaaagu ggcaccgagu cggugcuuuu                        100
```

<210> SEQ ID NO 76
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76

```
aguccuggua uccucuauga guuuuagagc uagaaauagc aaguuaaaau aaggcuaguc    60
cguuaucaac uugaaaaagu ggcaccgagu cggugcuuuu                        100
```

<210> SEQ ID NO 77
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77

```
aguccuggua uccucuauga guuuuagagc uaugcuguuu ug                      42
```

<210> SEQ ID NO 78
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78

```
aguccuggua uccucuauga guuuuagagc uaugcuguuu ug                      42
```

```
<210> SEQ ID NO 79
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
aaaaacugga augacugaau guuuuagagc uagaaauagc aaguuaaaau aaggcuaguc      60
cguuaucaac uugaaaaagu ggcaccgagu cggugcuuuu                          100

<210> SEQ ID NO 80
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
aaaaacugga augacugaau guuuuagagc uagaaauagc aaguuaaaau aaggcuaguc      60
cguuaucaac uugaaaaagu ggcaccgagu cggugcuuuu                          100

<210> SEQ ID NO 81
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81
aaaaacugga augacugaau guuuuagagc uagaaauagc aaguuaaaau aaggcuaguc      60
cguuaucaac uugaaaaagu ggcaccgagu cggugcuuuu                          100

<210> SEQ ID NO 82
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
aaaaacugga augacugaau guuuuagagc uaugcuguuu ug                        42

<210> SEQ ID NO 83
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
aaaaacugga augacugaau guuuuagagc uaugcuguuu ug                        42

<210> SEQ ID NO 84
```

```
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
ggagaaggaa acuagcuaaa guuuuagagc uagaaauagc aaguuaaaau aaggcuaguc      60
cguuaucaac uugaaaaagu ggcaccgagu cggugcuuuu                          100

<210> SEQ ID NO 85
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
ggagaaggaa acuagcuaaa guuuuagagc uagaaauagc aaguuaaaau aaggcuaguc      60
cguuaucaac uugaaaaagu ggcaccgagu cggugcuuuu                          100

<210> SEQ ID NO 86
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
ggagaaggaa acuagcuaaa guuuuagagc uagaaauagc aaguuaaaau aaggcuaguc      60
cguuaucaac uugaaaaagu ggcaccgagu cggugcuuuu                          100

<210> SEQ ID NO 87
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
ggagaaggaa acuagcuaaa guuuuagagc uaugcuguuu ug                        42

<210> SEQ ID NO 88
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
ggagaaggaa acuagcuaaa guuuuagagc uaugcuguuu ug                        42

<210> SEQ ID NO 89
<211> LENGTH: 100
<212> TYPE: RNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 89
guuuccuucu cccaucauag guuuuagagc uagaaauagc aaguuaaaau aaggcuaguc    60
cguuaucaac uugaaaaagu ggcaccgagu cggugcuuuu                        100

<210> SEQ ID NO 90
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
guuuccuucu cccaucauag guuuuagagc uagaaauagc aaguuaaaau aaggcuaguc    60
cguuaucaac uugaaaaagu ggcaccgagu cggugcuuuu                        100

<210> SEQ ID NO 91
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
guuuccuucu cccaucauag guuuuagagc uagaaauagc aaguuaaaau aaggcuaguc    60
cguuaucaac uugaaaaagu ggcaccgagu cggugcuuuu                        100

<210> SEQ ID NO 92
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
guuuccuucu cccaucauag guuuuagagc uaugcuguuu ug                      42

<210> SEQ ID NO 93
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
guuuccuucu cccaucauag guuuuagagc uaugcuguuu ug                      42

<210> SEQ ID NO 94
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 94
gggagaagga aacuagcuaa guuuuagagc uagaaauagc aaguuaaaau aaggcuaguc    60
cguuaucaac uugaaaaagu ggcaccgagu cggugcuuuu                         100

<210> SEQ ID NO 95
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
gggagaagga aacuagcuaa guuuuagagc uagaaauagc aaguuaaaau aaggcuaguc    60
cguuaucaac uugaaaaagu ggcaccgagu cggugcuuuu                         100

<210> SEQ ID NO 96
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
gggagaagga aacuagcuaa guuuuagagc uagaaauagc aaguuaaaau aaggcuaguc    60
cguuaucaac uugaaaaagu ggcaccgagu cggugcuuuu                         100

<210> SEQ ID NO 97
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gggagaagga aacuagcuaa guuuuagagc uaugcuguuu ug                      42

<210> SEQ ID NO 98
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gggagaagga aacuagcuaa guuuuagagc uaugcuguuu ug                      42

<210> SEQ ID NO 99
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99

```
cacuggagcu agagacaaga guuuuagagc uagaaauagc aaguuaaaau aaggcuaguc    60
cguuaucaac uugaaaaagu ggcaccgagu cggugcuuuu                        100
```

<210> SEQ ID NO 100
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100

```
cacuggagcu agagacaaga guuuuagagc uagaaauagc aaguuaaaau aaggcuaguc    60
cguuaucaac uugaaaaagu ggcaccgagu cggugcuuuu                        100
```

<210> SEQ ID NO 101
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

```
cacuggagcu agagacaaga guuuuagagc uagaaauagc aaguuaaaau aaggcuaguc    60
cguuaucaac uugaaaaagu ggcaccgagu cggugcuuuu                        100
```

<210> SEQ ID NO 102
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102

```
cacuggagcu agagacaaga guuuuagagc uaugcuguuu ug                      42
```

<210> SEQ ID NO 103
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103

```
cacuggagcu agagacaaga guuuuagagc uaugcuguuu ug                      42
```

<210> SEQ ID NO 104
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

```
agagacaaga agguaaaaaa guuuuagagc uagaaauagc aaguuaaaau aaggcuaguc    60
```
cguuaucaac uugaaaaagu ggcaccgagu cggugcuuuu                              100

<210> SEQ ID NO 105
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
agagacaaga agguaaaaaa guuuuagagc uagaaauagc aaguuaaaau aaggcuaguc        60
cguuaucaac uugaaaaagu ggcaccgagu cggugcuuuu                              100

<210> SEQ ID NO 106
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
agagacaaga agguaaaaaa guuuuagagc uagaaauagc aaguuaaaau aaggcuaguc        60
cguuaucaac uugaaaaagu ggcaccgagu cggugcuuuu                              100

<210> SEQ ID NO 107
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
agagacaaga agguaaaaaa guuuuagagc uaugcuguuu ug                           42

<210> SEQ ID NO 108
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
agagacaaga agguaaaaaa guuuuagagc uaugcuguuu ug                           42

<210> SEQ ID NO 109
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
ggcuagggau gaagaauaaa guuuuagagc uagaaauagc aaguuaaaau aaggcuaguc        60
cguuaucaac uugaaaaagu ggcaccgagu cggugcuuuu                              100

<210> SEQ ID NO 110
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110
ggcuagggau gaagaauaaa guuuuagagc uagaaauagc aaguuaaaau aaggcuaguc    60
cguuaucaac uugaaaaagu ggcaccgagu cggugcuuuu    100

<210> SEQ ID NO 111
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111
ggcuagggau gaagaauaaa guuuuagagc uagaaauagc aaguuaaaau aaggcuaguc    60
cguuaucaac uugaaaaagu ggcaccgagu cggugcuuuu    100

<210> SEQ ID NO 112
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 112
ggcuagggau gaagaauaaa guuuuagagc uaugcuguuu ug    42

<210> SEQ ID NO 113
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 113
ggcuagggau gaagaauaaa guuuuagagc uaugcuguuu ug    42

<210> SEQ ID NO 114
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114
aaaaauugga augacugaau guuuuagagc uagaaauagc aaguuaaaau aaggcuaguc    60
cguuaucaac uugaaaaagu ggcaccgagu cggugcuuuu    100

<210> SEQ ID NO 115
<211> LENGTH: 100
<212> TYPE: RNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115
aaaaauugga augacugaau guuuuagagc uagaaauagc aaguuaaaau aaggcuaguc    60
cguuaucaac uugaaaaagu ggcaccgagu cggugcuuuu                        100

<210> SEQ ID NO 116
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116
aaaaauugga augacugaau guuuuagagc uagaaauagc aaguuaaaau aaggcuaguc    60
cguuaucaac uugaaaaagu ggcaccgagu cggugcuuuu                        100

<210> SEQ ID NO 117
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
aaaaauugga augacugaau guuuuagagc uaugcuguuu ug                      42

<210> SEQ ID NO 118
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 118
aaaaauugga augacugaau guuuuagagc uaugcuguuu ug                      42

<210> SEQ ID NO 119
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 119
uggucaaguu ugccuuguca guuuuagagc uagaaauagc aaguuaaaau aaggcuaguc    60
cguuaucaac uugaaaaagu ggcaccgagu cggugcuuuu                        100

<210> SEQ ID NO 120
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
uggucaaguu ugccuuguca guuuuagagc uagaaauagc aaguuaaaau aaggcuaguc    60
cguuaucaac uugaaaaagu ggcaccgagu cggugcuuuu                        100

<210> SEQ ID NO 121
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
uggucaaguu ugccuuguca guuuuagagc uagaaauagc aaguuaaaau aaggcuaguc    60
cguuaucaac uugaaaaagu ggcaccgagu cggugcuuuu                        100

<210> SEQ ID NO 122
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
uggucaaguu ugccuuguca guuuuagagc uaugcuguuu ug                      42

<210> SEQ ID NO 123
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
uggucaaguu ugccuuguca guuuuagagc uaugcuguuu ug                      42

<210> SEQ ID NO 124
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124
gggagaagaa aacuagcuaa guuuuagagc uagaaauagc aaguuaaaau aaggcuaguc    60
cguuaucaac uugaaaaagu ggcaccgagu cggugcuuuu                        100

<210> SEQ ID NO 125
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 125
gggagaagaa aacuagcuaa guuuuagagc uagaaauagc aaguuaaaau aaggcuaguc      60
cguuaucaac uugaaaaagu ggcaccgagu cggugcuuuu                          100

<210> SEQ ID NO 126
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126
gggagaagaa aacuagcuaa guuuuagagc uagaaauagc aaguuaaaau aaggcuaguc      60
cguuaucaac uugaaaaagu ggcaccgagu cggugcuuuu                          100

<210> SEQ ID NO 127
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gggagaagaa aacuagcuaa guuuuagagc uaugcuguuu ug                        42

<210> SEQ ID NO 128
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
gggagaagaa aacuagcuaa guuuuagagc uaugcuguuu ug                        42

<210> SEQ ID NO 129
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
ggcaaggcug gccaacccau guuuuagagc uagaaauagc aaguuaaaau aaggcuaguc      60
cguuaucaac uugaaaaagu ggcaccgagu cggugcuuuu                          100

<210> SEQ ID NO 130
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
ggcaaggcug gccaacccau guuuuagagc uagaaauagc aaguuaaaau aaggcuaguc      60
```
cguuaucaac uugaaaaagu ggcaccgagu cggugcuuuu                     100

<210> SEQ ID NO 131
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
ggcaaggcug gccaacccau guuuuagagc uagaaauagc aaguuaaaau aaggcuaguc    60
cguuaucaac uugaaaaagu ggcaccgagu cggugcuuuu                        100

<210> SEQ ID NO 132
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
ggcaaggcug gccaacccau guuuuagagc uaugcuguuu ug                      42

<210> SEQ ID NO 133
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
ggcaaggcug gccaacccau guuuuagagc uaugcuguuu ug                      42

<210> SEQ ID NO 134
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
acggcugaca aaagaagucc guuuuagagc uagaaauagc aaguuaaaau aaggcuaguc    60
cguuaucaac uugaaaaagu ggcaccgagu cggugcuuuu                        100

<210> SEQ ID NO 135
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135
acggcugaca aaagaagucc guuuuagagc uagaaauagc aaguuaaaau aaggcuaguc    60
cguuaucaac uugaaaaagu ggcaccgagu cggugcuuuu                        100

<210> SEQ ID NO 136
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136
acggcugaca aaagaagucc guuuuagagc uagaaauagc aaguuaaaau aaggcuaguc    60
cguuaucaac uugaaaaagu ggcaccgagu cggugcuuuu                         100

<210> SEQ ID NO 137
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
acggcugaca aaagaagucc guuuuagagc uaugcuguuu ug                       42

<210> SEQ ID NO 138
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
acggcugaca aaagaagucc guuuuagagc uaugcuguuu ug                       42

<210> SEQ ID NO 139
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 139
ccuggcuaaa cuccacccau guuuuagagc uagaaauagc aaguuaaaau aaggcuaguc    60
cguuaucaac uugaaaaagu ggcaccgagu cggugcuuuu                         100

<210> SEQ ID NO 140
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140
ccuggcuaaa cuccacccau guuuuagagc uagaaauagc aaguuaaaau aaggcuaguc    60
cguuaucaac uugaaaaagu ggcaccgagu cggugcuuuu                         100

<210> SEQ ID NO 141
<211> LENGTH: 100

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 141
ccuggcuaaa cuccacccau guuuuagagc uagaaauagc aaguuaaaau aaggcuaguc    60
cguuaucaac uugaaaaagu ggcaccgagu cggugcuuuu                        100

<210> SEQ ID NO 142
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
ccuggcuaaa cuccacccau guuuuagagc uaugcuguuu ug                      42

<210> SEQ ID NO 143
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ccuggcuaaa cuccacccau guuuuagagc uaugcuguuu ug                      42

<210> SEQ ID NO 144
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 144
ggagaagaaa acuagcuaaa guuuuagagc uagaaauagc aaguuaaaau aaggcuaguc    60
cguuaucaac uugaaaaagu ggcaccgagu cggugcuuuu                        100

<210> SEQ ID NO 145
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 145
ggagaagaaa acuagcuaaa guuuuagagc uagaaauagc aaguuaaaau aaggcuaguc    60
cguuaucaac uugaaaaagu ggcaccgagu cggugcuuuu                        100

<210> SEQ ID NO 146
<211> LENGTH: 100
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic polynucleotide"

<400> SEQUENCE: 146
ggagaagaaa acuagcuaaa guuuuagagc uagaaauagc aaguuaaaau aaggcuaguc    60
cguuaucaac uugaaaaagu ggcaccgagu cggugcuuuu                         100

<210> SEQ ID NO 147
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
ggagaagaaa acuagcuaaa guuuuagagc uaugcuguuu ug                      42

<210> SEQ ID NO 148
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
ggagaagaaa acuagcuaaa guuuuagagc uaugcuguuu ug                      42

<210> SEQ ID NO 149
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 149
cuugucaagg cuauugguca guuuuagagc uagaaauagc aaguuaaaau aaggcuaguc    60
cguuaucaac uugaaaaagu ggcaccgagu cggugcuuuu                         100

<210> SEQ ID NO 150
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150
cuugucaagg cuauugguca guuuuagagc uagaaauagc aaguuaaaau aaggcuaguc    60
cguuaucaac uugaaaaagu ggcaccgagu cggugcuuuu                         100

<210> SEQ ID NO 151
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 151 cugucaagg cuauugguca guuuuagagc uagaaauagc aaguuaaaau aaggcuaguc    60
cguuaucaac uugaaaaagu ggcaccgagu cggugcuuuu    100

<210> SEQ ID NO 152
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
cuugucaagg cuauugguca guuuuagagc uaugcuguuu ug    42

<210> SEQ ID NO 153
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
cuugucaagg cuauugguca guuuuagagc uaugcuguuu ug    42

<210> SEQ ID NO 154
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 154
aguccuggua ucuucuaugg guuuuagagc uagaaauagc aaguuaaaau aaggcuaguc    60
cguuaucaac uugaaaaagu ggcaccgagu cggugcuuuu    100

<210> SEQ ID NO 155
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
aguccuggua ucuucuaugg guuuuagagc uagaaauagc aaguuaaaau aaggcuaguc    60
cguuaucaac uugaaaaagu ggcaccgagu cggugcuuuu    100

<210> SEQ ID NO 156
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
aguccuggua ucuucuaugg guuuuagagc uagaaauagc aaguuaaaau aaggcuaguc    60
cguuaucaac uugaaaaagu ggcaccgagu cggugcuuuu    100

<210> SEQ ID NO 157
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
aguccuggua ucuucuaugg guuuuagagc uaugcuguuu ug    42

<210> SEQ ID NO 158
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
aguccuggua ucuucuaugg guuuuagagc uaugcuguuu ug    42

<210> SEQ ID NO 159
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 159
guccugguau cuucuauggu guuuuagagc uagaaauagc aaguuaaaau aaggcuaguc    60
cguuaucaac uugaaaaagu ggcaccgagu cggugcuuuu    100

<210> SEQ ID NO 160
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160
guccugguau cuucuauggu guuuuagagc uagaaauagc aaguuaaaau aaggcuaguc    60
cguuaucaac uugaaaaagu ggcaccgagu cggugcuuuu    100

<210> SEQ ID NO 161
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161
guccugguau cuucuauggu guuuuagagc uagaaauagc aaguuaaaau aaggcuaguc    60
cguuaucaac uugaaaaagu ggcaccgagu cggugcuuuu    100

<210> SEQ ID NO 162
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
guccugguau cuucuauggu guuuuagagc uaugcuguuu ug                    42

<210> SEQ ID NO 163
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
guccugguau cuucuauggu guuuuagagc uaugcuguuu ug                    42

<210> SEQ ID NO 164
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
cuugaccaau agccuugaca guuuuagagc uagaaauagc aaguuaaaau aaggcuaguc    60
cguuaucaac uugaaaaagu ggcaccgagu cggugcuuuu                        100

<210> SEQ ID NO 165
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 165
cuugaccaau agccuugaca guuuuagagc uagaaauagc aaguuaaaau aaggcuaguc    60
cguuaucaac uugaaaaagu ggcaccgagu cggugcuuuu                        100

<210> SEQ ID NO 166
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166
cuugaccaau agccuugaca guuuuagagc uagaaauagc aaguuaaaau aaggcuaguc    60
cguuaucaac uugaaaaagu ggcaccgagu cggugcuuuu                        100

<210> SEQ ID NO 167

```
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
cuugaccaau agccuugaca guuuuagagc uaugcuguuu ug                        42

<210> SEQ ID NO 168
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
cuugaccaau agccuugaca guuuuagagc uaugcuguuu ug                        42

<210> SEQ ID NO 169
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 169
caaggcuauu ggucaaggca guuuuagagc uagaaauagc aaguuaaaau aaggcuaguc     60
cguuaucaac uugaaaaagu ggcaccgagu cggugcuuuu                          100

<210> SEQ ID NO 170
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 170
caaggcuauu ggucaaggca guuuuagagc uagaaauagc aaguuaaaau aaggcuaguc     60
cguuaucaac uugaaaaagu ggcaccgagu cggugcuuuu                          100

<210> SEQ ID NO 171
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 171
caaggcuauu ggucaaggca guuuuagagc uagaaauagc aaguuaaaau aaggcuaguc     60
cguuaucaac uugaaaaagu ggcaccgagu cggugcuuuu                          100

<210> SEQ ID NO 172
<211> LENGTH: 42
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 172
caaggcuauu ggucaaggca guuuuagagc uaugcuguuu ug                    42

<210> SEQ ID NO 173
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
caaggcuauu ggucaaggca guuuuagagc uaugcuguuu ug                    42

<210> SEQ ID NO 174
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174
acugaaucgg aacaaggcaa guuuuagagc uagaaauagc aaguuaaaau aaggcuaguc    60
cguuaucaac uugaaaaagu ggcaccgagu cggugcuuuu                        100

<210> SEQ ID NO 175
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175
acugaaucgg aacaaggcaa guuuuagagc uagaaauagc aaguuaaaau aaggcuaguc    60
cguuaucaac uugaaaaagu ggcaccgagu cggugcuuuu                        100

<210> SEQ ID NO 176
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 176
acugaaucgg aacaaggcaa guuuuagagc uagaaauagc aaguuaaaau aaggcuaguc    60
cguuaucaac uugaaaaagu ggcaccgagu cggugcuuuu                        100

<210> SEQ ID NO 177
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 177
acugaaucgg aacaaggcaa guuuuagagc uaugcuguuu ug             42

<210> SEQ ID NO 178
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
acugaaucgg aacaaggcaa guuuuagagc uaugcuguuu ug             42

<210> SEQ ID NO 179

<400> SEQUENCE: 179

000

<210> SEQ ID NO 180
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
aucagaggcc aaacccuucc                                      20

<210> SEQ ID NO 181
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181
aucagaggcc aaacccuucc guuuuagagc uagaaauagc aaguuaaaau aaggcuaguc    60
cguuaucaac uugaaaaagu ggcaccgagu cggugcuuuu                         100

<210> SEQ ID NO 182
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
guuuuagagc ua                                              12

<210> SEQ ID NO 183
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 183
guuuaagagc ua                                               12

<210> SEQ ID NO 184
<211> LENGTH: 5
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184 ugcug                                                       5

<210> SEQ ID NO 185
<211> LENGTH: 5
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185 uuuug                                                       5

<210> SEQ ID NO 186
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186 gaaa                                                        4

<210> SEQ ID NO 187
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
uagcaaguua aauaaggcu aguccguuau caacuugaaa aaguggcacc gagucggugc   60

<210> SEQ ID NO 188
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
uagcaaguuu aauaaggcu aguccguuau caacuugaaa aaguggcacc gagucggugc   60

<210> SEQ ID NO 189
<211> LENGTH: 5

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189 cagca                                                                        5

<210> SEQ ID NO 190
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: MISC_FEATURE
<222> LOCATION: (1)..(5000)
<223> OTHER INFORMATION: /note="This sequence may encompass 50-5000
      nucleotides"
<220> FEATURE:
<221> NAME/KEY: source
<223> OTHER INFORMATION: /note="See specification as filed for detailed
      description of substitutions and preferred embodiments"

<400> SEQUENCE: 190
aaaaaaaaaa aaaaaaaaaa aaaaaaaaaa aaaaaaaaaa aaaaaaaaaa aaaaaaaaaa            60
aaaaaaaaaa aaaaaaaaaa aaaaaaaaaa aaaaaaaaaa aaaaaaaaaa aaaaaaaaaa           120
aaaaaaaaaa aaaaaaaaaa aaaaaaaaaa aaaaaaaaaa aaaaaaaaaa aaaaaaaaaa           180
aaaaaaaaaa aaaaaaaaaa aaaaaaaaaa aaaaaaaaaa aaaaaaaaaa aaaaaaaaaa           240
aaaaaaaaaa aaaaaaaaaa aaaaaaaaaa aaaaaaaaaa aaaaaaaaaa aaaaaaaaaa           300
aaaaaaaaaa aaaaaaaaaa aaaaaaaaaa aaaaaaaaaa aaaaaaaaaa aaaaaaaaaa           360
aaaaaaaaaa aaaaaaaaaa aaaaaaaaaa aaaaaaaaaa aaaaaaaaaa aaaaaaaaaa           420
aaaaaaaaaa aaaaaaaaaa aaaaaaaaaa aaaaaaaaaa aaaaaaaaaa aaaaaaaaaa           480
aaaaaaaaaa aaaaaaaaaa aaaaaaaaaa aaaaaaaaaa aaaaaaaaaa aaaaaaaaaa           540
aaaaaaaaaa aaaaaaaaaa aaaaaaaaaa aaaaaaaaaa aaaaaaaaaa aaaaaaaaaa           600
aaaaaaaaaa aaaaaaaaaa aaaaaaaaaa aaaaaaaaaa aaaaaaaaaa aaaaaaaaaa           660
aaaaaaaaaa aaaaaaaaaa aaaaaaaaaa aaaaaaaaaa aaaaaaaaaa aaaaaaaaaa           720
aaaaaaaaaa aaaaaaaaaa aaaaaaaaaa aaaaaaaaaa aaaaaaaaaa aaaaaaaaaa           780
aaaaaaaaaa aaaaaaaaaa aaaaaaaaaa aaaaaaaaaa aaaaaaaaaa aaaaaaaaaa           840
aaaaaaaaaa aaaaaaaaaa aaaaaaaaaa aaaaaaaaaa aaaaaaaaaa aaaaaaaaaa           900
aaaaaaaaaa aaaaaaaaaa aaaaaaaaaa aaaaaaaaaa aaaaaaaaaa aaaaaaaaaa           960
aaaaaaaaaa aaaaaaaaaa aaaaaaaaaa aaaaaaaaaa aaaaaaaaaa aaaaaaaaaa          1020
aaaaaaaaaa aaaaaaaaaa aaaaaaaaaa aaaaaaaaaa aaaaaaaaaa aaaaaaaaaa          1080
aaaaaaaaaa aaaaaaaaaa aaaaaaaaaa aaaaaaaaaa aaaaaaaaaa aaaaaaaaaa          1140
aaaaaaaaaa aaaaaaaaaa aaaaaaaaaa aaaaaaaaaa aaaaaaaaaa aaaaaaaaaa          1200
aaaaaaaaaa aaaaaaaaaa aaaaaaaaaa aaaaaaaaaa aaaaaaaaaa aaaaaaaaaa          1260
aaaaaaaaaa aaaaaaaaaa aaaaaaaaaa aaaaaaaaaa aaaaaaaaaa aaaaaaaaaa          1320
aaaaaaaaaa aaaaaaaaaa aaaaaaaaaa aaaaaaaaaa aaaaaaaaaa aaaaaaaaaa          1380
aaaaaaaaaa aaaaaaaaaa aaaaaaaaaa aaaaaaaaaa aaaaaaaaaa aaaaaaaaaa          1440
```

```
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
```

| | |
|---|---|
| aaaaaaaaaa aaaaaaaaaa aaaaaaaaaa aaaaaaaaaa aaaaaaaaaa aaaaaaaaaa | 3840 |
| aaaaaaaaaa aaaaaaaaaa aaaaaaaaaa aaaaaaaaaa aaaaaaaaaa aaaaaaaaaa | 3900 |
| aaaaaaaaaa aaaaaaaaaa aaaaaaaaaa aaaaaaaaaa aaaaaaaaaa aaaaaaaaaa | 3960 |
| aaaaaaaaaa aaaaaaaaaa aaaaaaaaaa aaaaaaaaaa aaaaaaaaaa aaaaaaaaaa | 4020 |
| aaaaaaaaaa aaaaaaaaaa aaaaaaaaaa aaaaaaaaaa aaaaaaaaaa aaaaaaaaaa | 4080 |
| aaaaaaaaaa aaaaaaaaaa aaaaaaaaaa aaaaaaaaaa aaaaaaaaaa aaaaaaaaaa | 4140 |
| aaaaaaaaaa aaaaaaaaaa aaaaaaaaaa aaaaaaaaaa aaaaaaaaaa aaaaaaaaaa | 4200 |
| aaaaaaaaaa aaaaaaaaaa aaaaaaaaaa aaaaaaaaaa aaaaaaaaaa aaaaaaaaaa | 4260 |
| aaaaaaaaaa aaaaaaaaaa aaaaaaaaaa aaaaaaaaaa aaaaaaaaaa aaaaaaaaaa | 4320 |
| aaaaaaaaaa aaaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa aaaaaaaaaa aaaaaaaaaa aaaaaaaaaa | 4740 |
| aaaaaaaaaa aaaaaaaaaa aaaaaaaaaa aaaaaaaaaa aaaaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| aaaaaaaaaa aaaaaaaaaa aaaaaaaaaa aaaaaaaaaa aaaaaaaaaa aaaaaaaaaa | 4920 |
| aaaaaaaaaa aaaaaaaaaa aaaaaaaaaa aaaaaaaaaa aaaaaaaaaa aaaaaaaaaa | 4980 |
| aaaaaaaaaa aaaaaaaaaa | 5000 |

```
<210> SEQ ID NO 191
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
```

| | |
|---|---|
| uagcaaguua aaa | 13 |

```
<210> SEQ ID NO 192
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
```

| | |
|---|---|
| uagcaaguuu aaa | 13 |

```
<210> SEQ ID NO 193
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 193
uaaggcuagu ccguuaucaa cuugaaaaag uggcaccgag ucggugc  47

<210> SEQ ID NO 194
<211> LENGTH: 51
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 194
uaaggcuagu ccguuaucaa cuugaaaaag uggcaccgag ucggugcuuu u  51

<210> SEQ ID NO 195
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 195
guuuuagagc uagaaauagc aaguuaaaau aaggcuaguc cguuaucaac uugaaaagu  60 ggcaccgagu cggugc  76

<210> SEQ ID NO 196
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 196
guuuaagagc uagaaauagc aaguuuaaau aaggcuaguc cguuaucaac uugaaaagu  60 ggcaccgagu cggugc  76

<210> SEQ ID NO 197
<211> LENGTH: 86
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 197
guuuuagagc uaugcuggaa acagcauagc aaguuaaaau aaggcuaguc cguuaucaac  60 uugaaaagu ggcaccgagu cggugc  86

<210> SEQ ID NO 198
<211> LENGTH: 86
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 198

```
guuuaagagc uaugcuggaa acagcauagc aaguuuaaau aaggcuaguc cguuaucaac    60
uugaaaaagu ggcaccgagu cggugc                                        86

<210> SEQ ID NO 199
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
guuuuagagc uaugcug                                                  17

<210> SEQ ID NO 200
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
guuuaagagc uaugcug                                                  17

<210> SEQ ID NO 201
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
guuuuagagc uaugcuguuu ug                                            22

<210> SEQ ID NO 202
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
guuuaagagc uaugcuguuu ug                                            22

<210> SEQ ID NO 203
<211> LENGTH: 65
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
cagcauagca aguuaaaaua aggcuagucc guuaucaacu ugaaaaagug gcaccgaguc    60
ggugc                                                               65

<210> SEQ ID NO 204
<211> LENGTH: 65
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
cagcauagca aguuuaaaua aggcuagucc guuaucaacu ugaaaaagug gcaccgaguc    60
ggugc                                                                65

<210> SEQ ID NO 205
<211> LENGTH: 1368
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205
```

| | | | | | | | | | | | | | | | |
|---|---|---|---|---|---|---|---|---|---|---|---|---|---|---|---|
| Met | Asp | Lys | Lys | Tyr | Ser | Ile | Gly | Leu | Asp | Ile | Gly | Thr | Asn | Ser | Val |
| 1 | | | | 5 | | | | | 10 | | | | | 15 | |
| Gly | Trp | Ala | Val | Ile | Thr | Asp | Glu | Tyr | Lys | Val | Pro | Ser | Lys | Lys | Phe |
| | | | 20 | | | | | 25 | | | | | 30 | | |
| Lys | Val | Leu | Gly | Asn | Thr | Asp | Arg | His | Ser | Ile | Lys | Lys | Asn | Leu | Ile |
| | | 35 | | | | | 40 | | | | | 45 | | | |
| Gly | Ala | Leu | Leu | Phe | Asp | Ser | Gly | Glu | Thr | Ala | Glu | Ala | Thr | Arg | Leu |
| | 50 | | | | | 55 | | | | | 60 | | | | |
| Lys | Arg | Thr | Ala | Arg | Arg | Arg | Tyr | Thr | Arg | Arg | Lys | Asn | Arg | Ile | Cys |
| 65 | | | | | 70 | | | | | 75 | | | | | 80 |
| Tyr | Leu | Gln | Glu | Ile | Phe | Ser | Asn | Glu | Met | Ala | Lys | Val | Asp | Asp | Ser |
| | | | | 85 | | | | | 90 | | | | | 95 | |
| Phe | Phe | His | Arg | Leu | Glu | Glu | Ser | Phe | Leu | Val | Glu | Glu | Asp | Lys | Lys |
| | | | 100 | | | | | 105 | | | | | 110 | | |
| His | Glu | Arg | His | Pro | Ile | Phe | Gly | Asn | Ile | Val | Asp | Glu | Val | Ala | Tyr |
| | | 115 | | | | | 120 | | | | | 125 | | | |
| His | Glu | Lys | Tyr | Pro | Thr | Ile | Tyr | His | Leu | Arg | Lys | Lys | Leu | Val | Asp |
| | 130 | | | | | 135 | | | | | 140 | | | | |
| Ser | Thr | Asp | Lys | Ala | Asp | Leu | Arg | Leu | Ile | Tyr | Leu | Ala | Leu | Ala | His |
| 145 | | | | | 150 | | | | | 155 | | | | | 160 |
| Met | Ile | Lys | Phe | Arg | Gly | His | Phe | Leu | Ile | Glu | Gly | Asp | Leu | Asn | Pro |
| | | | | 165 | | | | | 170 | | | | | 175 | |
| Asp | Asn | Ser | Asp | Val | Asp | Lys | Leu | Phe | Ile | Gln | Leu | Val | Gln | Thr | Tyr |
| | | | 180 | | | | | 185 | | | | | 190 | | |
| Asn | Gln | Leu | Phe | Glu | Glu | Asn | Pro | Ile | Asn | Ala | Ser | Gly | Val | Asp | Ala |
| | | 195 | | | | | 200 | | | | | 205 | | | |
| Lys | Ala | Ile | Leu | Ser | Ala | Arg | Leu | Ser | Lys | Ser | Arg | Arg | Leu | Glu | Asn |
| | 210 | | | | | 215 | | | | | 220 | | | | |
| Leu | Ile | Ala | Gln | Leu | Pro | Gly | Glu | Lys | Lys | Asn | Gly | Leu | Phe | Gly | Asn |
| 225 | | | | | 230 | | | | | 235 | | | | | 240 |
| Leu | Ile | Ala | Leu | Ser | Leu | Gly | Leu | Thr | Pro | Asn | Phe | Lys | Ser | Asn | Phe |
| | | | | 245 | | | | | 250 | | | | | 255 | |
| Asp | Leu | Ala | Glu | Asp | Ala | Lys | Leu | Gln | Leu | Ser | Lys | Asp | Thr | Tyr | Asp |
| | | | 260 | | | | | 265 | | | | | 270 | | |
| Asp | Asp | Leu | Asp | Asn | Leu | Leu | Ala | Gln | Ile | Gly | Asp | Gln | Tyr | Ala | Asp |
| | | 275 | | | | | 280 | | | | | 285 | | | |

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu

```
                705                 710                 715                 720
            His Glu His Ile Ala Asn Leu Ala Gly Ser Pro Ala Ile Lys Lys Gly
                            725                 730                 735

Ile Leu Gln Thr Val Lys Val Val Asp Glu Leu Val Lys Val Met Gly
                            740                 745                 750

Arg His Lys Pro Glu Asn Ile Val Ile Glu Met Ala Arg Glu Asn Gln
                            755                 760                 765

Thr Thr Gln Lys Gly Lys Asn Ser Arg Glu Arg Met Lys Arg Ile
                770                 775                 780

Glu Glu Gly Ile Lys Glu Leu Gly Ser Gln Ile Leu Lys Glu His Pro
            785                 790                 795                 800

Val Glu Asn Thr Gln Leu Gln Asn Glu Lys Leu Tyr Leu Tyr Tyr Leu
                            805                 810                 815

Gln Asn Gly Arg Asp Met Tyr Val Asp Gln Glu Leu Asp Ile Asn Arg
                            820                 825                 830

Leu Ser Asp Tyr Asp Val Asp His Ile Val Pro Gln Ser Phe Leu Lys
                            835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
            865                 870                 875                 880

Asn Tyr Trp Arg Gln Leu Leu Asn Ala Lys Leu Ile Thr Gln Arg Lys
                            885                 890                 895

Phe Asp Asn Leu Thr Lys Ala Glu Arg Gly Gly Leu Ser Glu Leu Asp
                            900                 905                 910

Lys Ala Gly Phe Ile Lys Arg Gln Leu Val Glu Thr Arg Gln Ile Thr
                            915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
            945                 950                 955                 960

Lys Leu Val Ser Asp Phe Arg Lys Asp Phe Gln Phe Tyr Lys Val Arg
                            965                 970                 975

Glu Ile Asn Asn Tyr His His Ala His Asp Ala Tyr Leu Asn Ala Val
                            980                 985                 990

Val Gly Thr Ala Leu Ile Lys Lys Tyr Pro Lys Leu Glu Ser Glu Phe
                            995                 1000                1005

Val Tyr Gly Asp Tyr Lys Val Tyr Asp Val Arg Lys Met Ile Ala
                1010                1015                1020

Lys Ser Glu Gln Glu Ile Gly Lys Ala Thr Ala Lys Tyr Phe Phe
                1025                1030                1035

Tyr Ser Asn Ile Met Asn Phe Phe Lys Thr Glu Ile Thr Leu Ala
                1040                1045                1050

Asn Gly Glu Ile Arg Lys Arg Pro Leu Ile Glu Thr Asn Gly Glu
                1055                1060                1065

Thr Gly Glu Ile Val Trp Asp Lys Gly Arg Asp Phe Ala Thr Val
                1070                1075                1080

Arg Lys Val Leu Ser Met Pro Gln Val Asn Ile Val Lys Lys Thr
                1085                1090                1095

Glu Val Gln Thr Gly Gly Phe Ser Lys Glu Ser Ile Leu Pro Lys
                1100                1105                1110

Arg Asn Ser Asp Lys Leu Ile Ala Arg Lys Lys Asp Trp Asp Pro
                1115                1120                1125
```

-continued

```
Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 206
<211> LENGTH: 7
<212> TYPE: PRT
<213> ORGANISM: Simian virus 40

<400> SEQUENCE: 206

```
Pro Lys Lys Lys Arg Lys Val
1               5
```

<210> SEQ ID NO 207
<211> LENGTH: 16
<212> TYPE: PRT
<213> ORGANISM: Unknown
<220> FEATURE:
<221> NAME/KEY: source
<223> OTHER INFORMATION: /note="Description of Unknown: Nucleoplasmin bipartite NLS sequence"

<400> SEQUENCE: 207

```
Lys Arg Pro Ala Ala Thr Lys Lys Ala Gly Gln Ala Lys Lys Lys Lys
1               5                   10                  15
```

<210> SEQ ID NO 208
<211> LENGTH: 9
<212> TYPE: PRT

```
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 208

Pro Ala Ala Lys Arg Val Lys Leu Asp
1               5

<210> SEQ ID NO 209
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 209

Arg Gln Arg Arg Asn Glu Leu Lys Arg Ser Pro
1               5                   10

<210> SEQ ID NO 210
<211> LENGTH: 38
<212> TYPE: PRT
<213> ORGANISM: Homo sapiens

<400> SEQUENCE: 210

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 211
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 211

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 212
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 212

Val Ser Arg Lys Arg Pro Arg Pro
1               5
```

<210> SEQ ID NO 213
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 213

Pro Pro Lys Lys Ala Arg Glu Asp
1               5

<210> SEQ ID NO 214
<211> LENGTH: 8
<212> TYPE: PRT
<213> ORGANISM: Homo sapiens

<400> SEQUENCE: 214

Pro Gln Pro Lys Lys Lys Pro Leu
1               5

<210> SEQ ID NO 215
<211> LENGTH: 12
<212> TYPE: PRT
<213> ORGANISM: Mus musculus

<400> SEQUENCE: 215

Ser Ala Leu Ile Lys Lys Lys Lys Lys Met Ala Pro
1               5                   10

<210> SEQ ID NO 216
<211> LENGTH: 5
<212> TYPE: PRT
<213> ORGANISM: Influenza virus

<400> SEQUENCE: 216

Asp Arg Leu Arg Arg
1               5

<210> SEQ ID NO 217
<211> LENGTH: 7
<212> TYPE: PRT
<213> ORGANISM: Influenza virus

<400> SEQUENCE: 217

Pro Lys Gln Lys Lys Arg Lys
1               5

<210> SEQ ID NO 218
<211> LENGTH: 10
<212> TYPE: PRT
<213> ORGANISM: Hepatitis delta virus

<400> SEQUENCE: 218

Arg Lys Leu Lys Lys Lys Ile Lys Lys Leu
1               5                   10

<210> SEQ ID NO 219
<211> LENGTH: 10
<212> TYPE: PRT
<213> ORGANISM: Mus musculus

<400> SEQUENCE: 219

Arg Glu Lys Lys Lys Phe Leu Lys Arg Arg

<210> SEQ ID NO 220
<211> LENGTH: 20
<212> TYPE: PRT
<213> ORGANISM: Homo sapiens

<400> SEQUENCE: 220

Lys Arg Lys Gly Asp Glu Val Asp Gly Val Asp Glu Val Ala Lys Lys
1               5                   10                  15

Lys Ser Lys Lys
            20

<210> SEQ ID NO 221
<211> LENGTH: 17
<212> TYPE: PRT
<213> ORGANISM: Homo sapiens

<400> SEQUENCE: 221

Arg Lys Cys Leu Gln Ala Gly Met Asn Leu Glu Ala Arg Lys Thr Lys
1               5                   10                  15

Lys

<210> SEQ ID NO 222
<211> LENGTH: 4107
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222

| | | | | | |
|---|---|---|---|---|---|
| atggataaaa | agtacagcat | cgggctggac | atcggtacaa | actcagtggg | gtgggccgtg | 60 |
| attacgacg | agtacaaggt | accctccaaa | aaatttaaag | tgctgggtaa | cacggacaga | 120 |
| cactctataa | agaaaaatct | tattggagcc | ttgctgttcg | actcaggcga | gacagccgaa | 180 |
| gccacaaggt | tgaagcggac | cgccaggagg | cggtatacca | ggagaaagaa | ccgcatatgc | 240 |
| tacctgcaag | aaatcttcag | taacgagatg | gcaaaggttg | acgatagctt | tttccatcgc | 300 |
| ctggaagaat | cctttcttgt | tgaggaagac | aagaagcacg | aacggcaccc | catctttggc | 360 |
| aatattgtcg | acgaagtggc | atatcacgaa | agtacccga | ctatctacca | cctcaggaag | 420 |
| aagctggtgg | actctaccga | taaggcggac | ctcagactta | tttatttggc | actcgcccac | 480 |
| atgattaaat | ttagaggaca | tttcttgatc | gagggcgacc | tgaacccgga | caacagtgac | 540 |
| gtcgataagc | tgttcatcca | acttgtgcag | acctacaatc | aactgttcga | agaaaaccct | 600 |
| ataaatgctt | caggagtcga | cgctaaagca | atcctgtccg | cgcgcctctc | aaaatctaga | 660 |
| agacttgaga | atctgattgc | tcagttgccc | ggggaaaaga | aaaatggatt | gtttggcaac | 720 |
| ctgatcgccc | tcagtctcgg | actgacccca | aatttcaaaa | gtaacttcga | cctggccgaa | 780 |
| gacgctaagc | tccagctgtc | caaggacaca | tacgatgacg | acctcgacaa | tctgctggcc | 840 |
| cagattgggg | atcagtacgc | cgatctcttt | ttggcagcaa | agaacctgtc | cgacgccatc | 900 |
| ctgttgagcg | atatcttgag | agtgaacacc | gaaattacta | agcacccct | agcgcatct | 960 |
| atgatcaagc | ggtacgacga | gcatcatcag | gatctgaccc | tgctgaaggc | tcttgtgagg | 1020 |
| caacagctcc | ccgaaaaata | caaggaaatc | ttctttgacc | agagcaaaaa | cggctacgct | 1080 |
| ggctatatag | atggtggggc | cagtcaggag | gaattctata | aattcatcaa | gcccattctc | 1140 |

-continued

```
gagaaaatgg acggcacaga ggagttgctg gtcaaactta acaggagga cctgctgcgg   1200 aagcagcgga cctttgacaa cgggtctatc ccccaccaga ttcatctggg cgaactgcac   1260
gcaatcctga ggaggcagga ggattttat ccttttctta aagataaccg cgagaaaata   1320
gaaaagattc ttacattcag gatcccgtac tacgtgggac ctctcgcccg ggcaattca   1380 cggtttgcct ggatgacaag gaagtcagag gagactatta caccttggaa cttcgaagaa   1440
gtggtggaca agggtgcatc tgcccagtct ttcatcgagc ggatgacaaa ttttgacaag   1500
aacctcccta atgagaaggt gctgcccaaa cattctctgc tctacgagta ctttaccgtc   1560
tacaatgaac tgactaaagt caagtacgtc accgagggaa tgaggaagcc ggcattcctt   1620
agtggagaac agaagaaggc gattgtagac ctgttgttca agaccaacag gaaggtgact   1680
gtgaagcaac ttaaagaaga ctactttaag aagatcgaat gttttgacag tgtggaaatt   1740
tcaggggttg aagaccgctt caatgcgtca ttggggactt accatgatct tctcaagatc   1800
ataaaggaca aagacttcct ggacaacgaa gaaaatgagg atattctcga agacatcgtc   1860 ctcacccctga ccctgttcga agacaggaa atgatagaag agcgcttgaa aacctatgcc   1920
cacctcttcg acgataaagt tatgaagcag ctgaagcgca ggagatacac aggatgggga   1980
agattgtcaa ggaagctgat caatggaatt agggataaac agagtggcaa gaccatactg   2040
gatttcctca atctgatgg cttcgccaat aggaacttca tgcaactgat tcacgatgac   2100
tctcttacct tcaaggagga cattcaaaag gctcaggtga gcgggcaggg agactccctt   2160
catgaacaca tcgcgaattt ggcaggttcc cccgctatta aaagggcat ccttcaaact   2220 gtcaaggtgg tggatgaatt ggtcaaggta atgggcagac ataagccaga aaatattgtg   2280
atcgagatgg cccgcgaaaa ccagaccaca cagaagggcc agaaaaatag tagagagcgg   2340
atgaagagga tcgaggaggg catcaaagag ctgggatctc agattctcaa agaacacccc   2400
gtagaaaaca cacagctgca gaacgaaaaa ttgtacttgt actatctgca gaacggcaga   2460
gacatgtacg tcgaccaaga acttgatatt aatagactgt ccgactatga cgtagaccat   2520
atcgtgcccc agtccttcct gaaggacgac tccattgata caaagtctt gacaagaagc   2580 gacaagaaca ggggtaaaag tgataatgtg cctagcgagg aggtggtgaa aaaaatgaag   2640
aactactggc gacagctgct taatgcaaag ctcattacac aacggaagtt cgataatctg   2700
acgaaagcag agagaggtgg cttgtctgag ttggacaagg cagggtttat taagcggcag   2760
ctggtggaaa ctaggcagat cacaaagcac gtggcgcaga ttttggacag ccggatgaac   2820
acaaaatacg acgaaaatga taaactgata cgagaggtca agttatcac gctgaaaagc   2880 aagctggtgt ccgatttcg gaaagacttc cagttctaca agttcgcga gattaataac   2940 taccatcatg ctcacgatgc gtacctgaac gctgttgtcg ggaccgcctt gataaagaag   3000
tacccaaagc tggaatccga gttcgtatac ggggattaca agtgtacga tgtgaggaaa   3060 atgatagcca agtccgagca ggagattgga aaggccacag ctaagtactt cttttatct   3120 aacatcatga ttttttaa gacggaaatt acctggcca acggagagat cagaaagcgg   3180 cccttatag agacaaatgg tgaaacaggt gaaatcgtct gggataaggg cagggatttc   3240
gctactgtga ggaaggtgct gagtatgcca caggtaaata tcgtgaaaaa accgaagta   3300 cagaccggag gattttccaa ggaaagcatt ttgcctaaaa gaaactcaga caagctcatc   3360
gcccgcaaga aagattggga ccctaagaaa tacgggggat tgactcacc caccgtagcc   3420 tattctgtgc tggtggtagc taaggtgaa aaaggaaagt ctaagaagct gaagtccgtg   3480
aaggaactct ggggaatcac tatcatggaa agatcatcct ttgaaaagaa ccctatcgat   3540
```

```
ttcctggagg ctaagggtta caaggaggtc aagaaagacc tcatcattaa actgccaaaa    3600
tactctctct tcgagctgga aaatggcagg aagagaatgt tggccagcgc cggagagctg    3660
caaaagggaa acgagcttgc tctgccctcc aaatatgtta attttctcta tctcgcttcc    3720
cactatgaaa agctgaaagg gtctcccgaa gataacgagc agaagcagct gttcgtcgaa    3780
cagcacaagc actatctgga tgaaataatc gaacaaataa gcgagttcag caaaagggtt    3840
atcctggcgg atgctaattt ggacaaagta ctgtctgctt ataacaagca ccgggataag    3900
cctattaggg aacaagccga gaatataatt cacctcttta cactcacgaa tctcggagcc    3960
cccgccgcct tcaaatactt tgatacgact atcgaccgga acggtatac cagtaccaaa     4020 gaggtcctcg atgccaccct catccaccag tcaattactg gcctgtacga aacacggatc    4080
gacctctctc aactgggcgg cgactag                                        4107
```

<210> SEQ ID NO 223
<211> LENGTH: 4164
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 223

```
atggctccga agaaaaagcg taaagtggat aaaaaatca gcattggtct ggacattggc       60
acgaactcag tgggttgggc ggtcatcacg gatgaatata aggtcccgtc aaaaaagttc     120
aaagtgctgg gcaacaccga tcgccattcg attaaaaaga tctgatcgg cgcgctgctg     180 tttgatagcg gtgaaaccgc ggaagcaacg cgtctgaaac gtaccgcacg tcgccgttac    240
acgcgccgta aaaatcgtat tctgtatctg caggaaatct ttagcaacga aatggcgaaa    300
gttgatgact cattttttcca ccgcctggaa gaatcgtttc tggtcgaaga agacaaaaag    360
catgaacgtc acccgatttt cggtaatatc gttgatgaag tcgcgtacca tgaaaaatat    420
ccgacgattt accatctgcg taaaaaactg gtggattcaa ccgacaaagc cgatctgcgc    480
ctgatttacc tggcactggc tcatatgatc aaatttcgtg gccacttcct gattgaaggt    540
gacctgaacc cggataactc tgacgttgat aagctgttca tccagctggt ccaaacctat    600
aatcagctgt tcgaagaaaa cccgatcaat gcaagtggcg ttgatgcgaa ggccattctg    660
tccgctcgcc tgagtaaaat ccgccgtctg gaaaacctga ttgcacaact gccgggcgaa    720
aagaaaaacg gcctgtttgg taatctgatc gctctgtcac tgggtctgac gccgaacttt    780
aaatcgaatt tcgacctggc agaagatgct aagctgcagc tgagcaaaga tacctacgat    840
gacgatctga caacctgctg ggcgcaaatt ggtgaccagt atgccgacct gtttctggcg    900
gccaaaaatc tgtcagatgc cattctgctg tcggacatcc tgcgcgtgaa caccgaaatc    960
acgaaagcgc cgctgtcagc ctcgatgatt aaacgctacg atgaacatca ccaggacctg   1020
accctgctga agcactggt tcgtcagcaa ctgccggaaa agtacaagga atttttcttt    1080
gaccaatcta gaacggcta tgcaggttac atcgatggcg gtgctagtca ggaagaattc    1140
tacaagttca tcaagccgat cctggaaaaa atggatggca cggaagaact gctggtgaaa    1200
ctgaatcgtg aagatctgct gcgtaaacaa cgcacctttg acaacggcag cattccgcat    1260
cagatccacc tgggtgaact gcatgcgatt ctgcgccgtc aggaagattt ttatccgttc    1320
ctgaaagaca accgtgaaaa aattgaaaag atcctgacgt ttcgcatccc gtattacgtt    1380
```

-continued

```
ggcccgctgg cgcgtggtaa tagccgcttc gcctggatga cccgcaaatc tgaagaaacc   1440
attacgccgt ggaactttga agaagtggtt gataaaggtg caagcgctca gtcttttatc   1500
gaacgtatga ccaatttcga taaaaacctg ccgaatgaaa aggtcctgcc gaaacatagc   1560
ctgctgtatg aatactttac cgtgtacaac gaactgacga agtgaagta tgttaccgaa    1620 ggcatgcgca accggcgtt tctgtctggt gaacagaaaa aagccattgt ggatctgctg    1680
ttcaagacca atcgtaaagt tacggtcaaa cagctgaagg aagattactt caaaaagatc   1740
gaagaattcg acagcgtgga aatttctggc gttgaagatc gtttcaacgc cagtctgggt   1800
acctatcatg acctgctgaa gatcatcaag gacaaggatt ttctggataa cgaagaaaat   1860
gaagacattc tggaagatat cgtgctgacc ctgacgctgt tcgaagatcg tgaaatgatt   1920
gaagaacgcc tgaaaacgta cgcacacctg tttgacgata agttatgaa gcagctgaaa    1980 cgccgtcgct ataccggctg gggtcgtctg tctcgcaaac tgattaatgg catccgcgat   2040
aagcaaagtg gtaaaacgat tctggatttc ctgaaatccg acggctttgc caaccgtaat   2100
ttcatgcagc tgatccatga cgatagtctg accttaagg aagacattca gaaagcacaa    2160
gtgtcaggcc agggtgattc gctgcatgaa cacattgcga acctggccgg ctccccggct   2220
attaaaaagg gtatcctgca gaccgtcaaa gtcgtggatg aactggtgaa ggttatgggc   2280
cgtcacaaac cggaaaacat tgtgatcgaa atggcgcgcg aaaatcagac cacgcaaaag   2340
ggtcagaaaa actcacgtga acgcatgaag cgcattgaag aaggcatcaa gaactgggt    2400 tcgcagattc tgaaagaaca tccggttgaa aacacccagc tgcaaaatga aaaactgtac   2460
ctgtattacc tgcaaaatgg ccgtgacatg tatgtcgatc aggaactgga catcaaccgc   2520
ctgagcgact atgatgtcga ccacattgtg ccgcagagct ttctgaagga cgattctatc   2580
gataataaag tgctgacccg ttctgataag aaccgcggta aaagcgacaa tgttccgtct   2640
gaagaagttg tcaaaaagat gaagaactac tggcgtcaac tgctgaatgc gaagctgatt   2700
acgcagcgta aattcgataa cctgaccaag gcggaacgcg gcggtctgag tgaactggat   2760
aaggccggct ttatcaaacg tcaactggtg gaaacccgcc agattacgaa acatgttgcc   2820
cagatcctgg attcccgcat gaacacgaaa tatgacgaaa atgataagct gattcgtgaa   2880
gtcaaagtga tcaccctgaa gagtaagctg gtgtccgatt ccgtaagga ctttcagttc    2940 tacaaagttc gcgaaattaa caattaccat cacgcacacg atgcttatct gaatgcagtg   3000
gttggcaccg ctctgatcaa aaagtatccg aaactggaaa gcgaatttgt gtatggtgat   3060
tacaaagtct atgacgtgcg caagatgatt gcgaaaagtg aacaggaaat cggcaaggcg   3120
accgccaagt acttttcta ttccaacatc atgaactttt tcaagaccga atcacgctg     3180 gcaaatggcg aaattcgtaa acgcccgctg atcgaaacca acggcgaaac gggtgaaatt   3240
gtgtgggata aggtcgtga cttcgcgacc gttcgcaaag tcctgtcaat gccgcaagtg   3300
aatatcgtta aaaagaccga agttcagacg ggcggtttta gtaaagaatc catcctgccg   3360
aagcgtaact cggataaact gattgcgcgc aaaaaggatt gggacccgaa aaagtacggc   3420
ggttttgata gtccgaccgt tgcatattcc gtcctggtcg tggctaaagt tgaaaaaggc   3480
aagagtaaaa agctgaagtc cgtcaaagaa ctgctgggta ttaccatcat ggaacgtagc   3540
tcttttgaaa agaacccgat tgacttcctg gaagccaagg gctacaaaga agtgaaaaag   3600
gatctgatta tcaagctgcc gaaatattcg ctgttcgaac tggaaaacgg tcgtaaacgc   3660
atgctggcaa cgctggcga actgcagaag ggtaatgaac tggcactgcc gtctaaatat   3720
gtgaactttc tgtacctggc tagccattat gaaaaactga agggttctcc ggaagataac   3780
```

-continued

```
gaacagaagc aactgttcgt tgaacaacat aaacactacc tggatgaaat catcgaacag    3840
atctcagaat tctcgaaacg cgtcattctg gcggatgcca atctggacaa agtgctgagc    3900
gcgtataaca agcatcgtga taaaccgatt cgcgaacagg ccgaaaatat tatccacctg    3960
tttaccctga cgaacctggg cgcaccggca gcttttaaat acttcgatac cacgatcgac    4020
cgtaagcgct ataccagcac gaaagaagtt ctggatgcta ccctgattca tcagtcaatc    4080
accggtctgt atgaaacgcg tattgacctg agccaactgg gcggtgatag ccgtgccgac    4140
catcaccatc accatcacta atag                                          4164
```

<210> SEQ ID NO 224
<211> LENGTH: 74
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224

```
aacagcauag caaguuaaaa uaaggcuagu ccguuaucaa cuugaaaaag uggcaccgag    60
ucggugcuuu uuuu                                                      74
```

<210> SEQ ID NO 225
<211> LENGTH: 74
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225

```
aacagcauag caaguuuaaa uaaggcuagu ccguuaucaa cuugaaaaag uggcaccgag    60
ucggugcuuu uuuu                                                      74
```

<210> SEQ ID NO 226
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226

```
guuuuagagc uaugcu                                                    16
```

<210> SEQ ID NO 227
<211> LENGTH: 90
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227

```
guuuaagagc uaugcuggaa acagcauagc aaguuuaaau aaggcuaguc cguuaucaac    60
uugaaaaagu ggcaccgagu cggugcuuuu                                     90
```

<210> SEQ ID NO 228

```
<211> LENGTH: 67
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
agcauagcaa guuaaaauaa ggcuaguccg uuaucaacuu gaaaagugg caccgagucg    60 gugcuuu                                                             67

<210> SEQ ID NO 229
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
guuggaacca uucaaaacag cauagcaagu uaaaauaagg cuaguccguu aucaacuuga    60
aaaaguggca ccgagucggu gcuuu                                         85

<210> SEQ ID NO 230
<211> LENGTH: 7
<212> TYPE: PRT
<213> ORGANISM: Tobacco etch virus

<400> SEQUENCE: 230

Glu Asn Leu Tyr Phe Gln Gly
 1               5

<210> SEQ ID NO 231
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
guuuuagagc uagaaauagc aaguuaaaau aaggcuaguc cguuaucaac uugaaaaagu    60
ggcaccgagu cggugcuuuu                                               80

<210> SEQ ID NO 232
<211> LENGTH: 67
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
aacagcauag caaguuaaaa uaaggcuagu ccguuaucaa cuugaaaaag uggcaccgag    60
ucggugc                                                             67

<210> SEQ ID NO 233
<211> LENGTH: 1393
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 233
```

Met Ala Pro Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
            20                  25                  30

Tyr Lys Val Pro Ser Lys Lys Phe Lys Val Leu Gly Asn Thr Asp Arg
        35                  40                  45

His Ser Ile Lys Lys Asn Leu Ile Gly Ala Leu Leu Phe Asp Ser Gly
    50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Cys Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
    130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
    210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Leu Asp Asn Leu Leu Ala
        275                 280                 285

Gln Ile Gly Asp Gln Tyr Ala Asp Leu Phe Leu Ala Ala Lys Asn Leu
    290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
            340                 345                 350

Glu Lys Tyr Lys Glu Ile Phe Phe Asp Gln Ser Lys Asn Gly Tyr Ala
        355                 360                 365

Gly Tyr Ile Asp Gly Gly Ala Ser Gln Glu Glu Phe Tyr Lys Phe Ile
    370                 375                 380

Lys Pro Ile Leu Glu Lys Met Asp Gly Thr Glu Glu Leu Leu Val Lys

-continued

```
            385                 390                 395                 400
Leu Asn Arg Glu Asp Leu Leu Arg Lys Gln Arg Thr Phe Asp Asn Gly
                    405                 410                 415

Ser Ile Pro His Gln Ile His Leu Gly Glu Leu His Ala Ile Leu Arg
                    420                 425                 430

Arg Gln Glu Asp Phe Tyr Pro Phe Leu Asp Asn Arg Glu Lys Ile
                    435                 440                 445

Glu Lys Ile Leu Thr Phe Arg Ile Pro Tyr Tyr Val Gly Pro Leu Ala
            450                 455                 460

Arg Gly Asn Ser Arg Phe Ala Trp Met Thr Arg Lys Ser Glu Glu Thr
465                 470                 475                 480

Ile Thr Pro Trp Asn Phe Glu Val Val Asp Lys Gly Ala Ser Ala
                    485                 490                 495

Gln Ser Phe Ile Glu Arg Met Thr Asn Phe Asp Lys Asn Leu Pro Asn
                    500                 505                 510

Glu Lys Val Leu Pro Lys His Ser Leu Leu Tyr Glu Tyr Phe Thr Val
            515                 520                 525

Tyr Asn Glu Leu Thr Lys Val Lys Tyr Val Thr Glu Gly Met Arg Lys
            530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                    565                 570                 575

Phe Lys Lys Ile Glu Cys Phe Asp Ser Val Glu Ile Ser Gly Val Glu
                    580                 585                 590

Asp Arg Phe Asn Ala Ser Leu Gly Thr Tyr His Asp Leu Leu Lys Ile
            595                 600                 605

Ile Lys Asp Lys Asp Phe Leu Asp Asn Glu Glu Asn Glu Asp Ile Leu
            610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                    645                 650                 655

Lys Gln Leu Lys Arg Arg Arg Tyr Thr Gly Trp Gly Arg Leu Ser Arg
                    660                 665                 670

Lys Leu Ile Asn Gly Ile Arg Asp Lys Gln Ser Gly Lys Thr Ile Leu
            675                 680                 685

Asp Phe Leu Lys Ser Asp Gly Phe Ala Asn Arg Asn Phe Met Gln Leu
            690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                    725                 730                 735

Gly Ser Pro Ala Ile Lys Lys Gly Ile Leu Gln Thr Val Lys Val Val
                    740                 745                 750

Asp Glu Leu Val Lys Val Met Gly Arg His Lys Pro Glu Asn Ile Val
            755                 760                 765

Ile Glu Met Ala Arg Glu Asn Gln Thr Thr Gln Lys Gly Gln Lys Asn
            770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                    805                 810                 815
```

```
Glu Lys Leu Tyr Leu Tyr Tyr Leu Gln Asn Gly Arg Asp Met Tyr Val
            820                 825                 830

Asp Gln Glu Leu Asp Ile Asn Arg Leu Ser Asp Tyr Asp Val Asp His
        835                 840                 845

Ile Val Pro Gln Ser Phe Leu Lys Asp Ser Ile Asp Asn Lys Val
850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
                885                 890                 895

Ala Lys Leu Ile Thr Gln Arg Lys Phe Asp Asn Leu Thr Lys Ala Glu
                900                 905                 910

Arg Gly Gly Leu Ser Glu Leu Asp Lys Ala Gly Phe Ile Lys Arg Gln
                915                 920                 925

Leu Val Glu Thr Arg Gln Ile Thr Lys His Val Ala Gln Ile Leu Asp
            930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
                965                 970                 975

Asp Phe Gln Phe Tyr Lys Val Arg Glu Ile Asn Asn Tyr His His Ala
            980                 985                 990

His Asp Ala Tyr Leu Asn Ala Val  Val Gly Thr Ala Leu  Ile Lys Lys
        995                 1000                1005

Tyr Pro  Lys Leu Glu Ser Glu  Phe Val Tyr Gly Asp  Tyr Lys Val
    1010                1015                1020

Tyr Asp  Val Arg Lys Met Ile  Ala Lys Ser Glu Gln  Glu Ile Gly
    1025                1030                1035

Lys Ala  Thr Ala Lys Tyr Phe  Phe Tyr Ser Asn Ile  Met Asn Phe
    1040                1045                1050

Phe Lys  Thr Glu Ile Thr Leu  Ala Asn Gly Glu Ile  Arg Lys Arg
    1055                1060                1065

Pro Leu  Ile Glu Thr Asn Gly  Glu Thr Gly Glu Ile  Val Trp Asp
    1070                1075                1080

Lys Gly  Arg Asp Phe Ala Thr  Val Arg Lys Val Leu  Ser Met Pro
    1085                1090                1095

Gln Val  Asn Ile Val Lys Lys  Thr Glu Val Gln Thr  Gly Gly Phe
    1100                1105                1110

Ser Lys  Glu Ser Ile Leu Pro  Lys Arg Asn Ser Asp  Lys Leu Ile
    1115                1120                1125

Ala Arg  Lys Lys Asp Trp Asp  Pro Lys Lys Tyr Gly  Gly Phe Asp
    1130                1135                1140

Ser Pro  Thr Val Ala Tyr Ser  Val Leu Val Val Ala  Lys Val Glu
    1145                1150                1155

Lys Gly  Lys Ser Lys Lys Leu  Lys Ser Val Lys Glu  Leu Leu Gly
    1160                1165                1170

Ile Thr  Ile Met Glu Arg Ser  Ser Phe Glu Lys Asn  Pro Ile Asp
    1175                1180                1185

Phe Leu  Glu Ala Lys Gly Tyr  Lys Glu Val Lys Lys  Asp Leu Ile
    1190                1195                1200

Ile Lys  Leu Pro Lys Tyr Ser  Leu Phe Glu Leu Glu  Asn Gly Arg
    1205                1210                1215
```

Lys Arg Met Leu Ala Ser Ala Gly Glu Leu Gln Lys Gly Asn Glu
    1220                1225                1230

Leu Ala Leu Pro Ser Lys Tyr Val Asn Phe Leu Tyr Leu Ala Ser
    1235                1240                1245

His Tyr Glu Lys Leu Lys Gly Ser Pro Glu Asp Asn Glu Gln Lys
    1250                1255                1260

Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305

Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp Ser Arg Ala Asp Pro Lys Lys
    1370                1375                1380

Lys Arg Lys Val His His His His His His
    1385                1390

<210> SEQ ID NO 234
<211> LENGTH: 1393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 234

Met Ala Pro Lys Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
                20                  25                  30

Tyr Lys Val Pro Ser Lys Lys Phe Lys Val Leu Gly Asn Thr Asp Arg
            35                  40                  45

His Ser Ile Lys Lys Asn Leu Ile Gly Ala Leu Leu Phe Asp Ser Gly
        50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Leu Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
    130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe

-continued

```
                165                 170                 175
Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
            195                 200                 205

Ile Asn Ala Ser Gly Val Asp Ala Lys Ala Ile Leu Ser Ala Arg Leu
            210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Asp Leu Asp Asn Leu Leu Ala
            275                 280                 285

Gln Ile Gly Asp Gln Tyr Ala Asp Leu Phe Leu Ala Ala Lys Asn Leu
            290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
            340                 345                 350

Glu Lys Tyr Lys Glu Ile Phe Phe Asp Gln Ser Lys Asn Gly Tyr Ala
            355                 360                 365

Gly Tyr Ile Asp Gly Gly Ala Ser Gln Glu Glu Phe Tyr Lys Phe Ile
            370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
            420                 425                 430

Arg Gln Glu Asp Phe Tyr Pro Phe Leu Lys Asp Asn Arg Glu Lys Ile
            435                 440                 445

Glu Lys Ile Leu Thr Phe Arg Ile Pro Tyr Tyr Val Gly Pro Leu Ala
            450                 455                 460

Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala
                485                 490                 495

Gln Ser Phe Ile Glu Arg Met Thr Asn Phe Asp Lys Asn Leu Pro Asn
            500                 505                 510

Glu Lys Val Leu Pro Lys His Ser Leu Leu Tyr Glu Tyr Phe Thr Val
            515                 520                 525

Tyr Asn Glu Leu Thr Lys Val Lys Tyr Val Thr Glu Gly Met Arg Lys
            530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                565                 570                 575

Phe Lys Lys Ile Glu Glu Phe Asp Ser Val Glu Ile Ser Gly Val Glu
            580                 585                 590
```

```
Asp Arg Phe Asn Ala Ser Leu Gly Thr Tyr His Asp Leu Leu Lys Ile
        595                 600                 605

Ile Lys Asp Lys Asp Phe Leu Asp Asn Glu Glu Asn Glu Asp Ile Leu
    610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                645                 650                 655

Lys Gln Leu Lys Arg Arg Tyr Thr Gly Trp Gly Arg Leu Ser Arg
                660                 665                 670

Lys Leu Ile Asn Gly Ile Arg Asp Lys Gln Ser Gly Lys Thr Ile Leu
                675                 680                 685

Asp Phe Leu Lys Ser Asp Gly Phe Ala Asn Arg Asn Phe Met Gln Leu
        690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                    725                 730                 735

Gly Ser Pro Ala Ile Lys Lys Gly Ile Leu Gln Thr Val Lys Val Val
                740                 745                 750

Asp Glu Leu Val Lys Val Met Gly Arg His Lys Pro Glu Asn Ile Val
                755                 760                 765

Ile Glu Met Ala Arg Glu Asn Gln Thr Thr Gln Lys Gly Gln Lys Asn
    770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                805                 810                 815

Glu Lys Leu Tyr Leu Tyr Tyr Leu Gln Asn Gly Arg Asp Met Tyr Val
                820                 825                 830

Asp Gln Glu Leu Asp Ile Asn Arg Leu Ser Asp Tyr Asp Val Asp His
            835                 840                 845

Ile Val Pro Gln Ser Phe Leu Lys Asp Asp Ser Ile Asp Asn Lys Val
    850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
                885                 890                 895

Ala Lys Leu Ile Thr Gln Arg Lys Phe Asp Asn Leu Thr Lys Ala Glu
            900                 905                 910

Arg Gly Gly Leu Ser Glu Leu Asp Lys Ala Gly Phe Ile Lys Arg Gln
            915                 920                 925

Leu Val Glu Thr Arg Gln Ile Thr Lys His Val Ala Gln Ile Leu Asp
    930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
                965                 970                 975

Asp Phe Gln Phe Tyr Lys Val Arg Glu Ile Asn Asn Tyr His His Ala
            980                 985                 990

His Asp Ala Tyr Leu Asn Ala Val Val Gly Thr Ala Leu Ile Lys Lys
        995                 1000                1005
```

-continued

Tyr Pro Lys Leu Glu Ser Glu Phe Val Tyr Gly Asp Tyr Lys Val
1010                 1015                1020

Tyr Asp Val Arg Lys Met Ile Ala Lys Ser Glu Gln Glu Ile Gly
1025                 1030                1035

Lys Ala Thr Ala Lys Tyr Phe Phe Tyr Ser Asn Ile Met Asn Phe
1040                 1045                1050

Phe Lys Thr Glu Ile Thr Leu Ala Asn Gly Glu Ile Arg Lys Arg
1055                 1060                1065

Pro Leu Ile Glu Thr Asn Gly Glu Thr Gly Glu Ile Val Trp Asp
1070                 1075                1080

Lys Gly Arg Asp Phe Ala Thr Val Arg Lys Val Leu Ser Met Pro
1085                 1090                1095

Gln Val Asn Ile Val Lys Lys Thr Glu Val Gln Thr Gly Gly Phe
1100                 1105                1110

Ser Lys Glu Ser Ile Leu Pro Lys Arg Asn Ser Asp Lys Leu Ile
1115                 1120                1125

Ala Arg Lys Lys Asp Trp Asp Pro Lys Lys Tyr Gly Gly Phe Asp
1130                 1135                1140

Ser Pro Thr Val Ala Tyr Ser Val Leu Val Val Ala Lys Val Glu
1145                 1150                1155

Lys Gly Lys Ser Lys Lys Leu Lys Ser Val Lys Glu Leu Leu Gly
1160                 1165                1170

Ile Thr Ile Met Glu Arg Ser Ser Phe Glu Lys Asn Pro Ile Asp
1175                 1180                1185

Phe Leu Glu Ala Lys Gly Tyr Lys Glu Val Lys Lys Asp Leu Ile
1190                 1195                1200

Ile Lys Leu Pro Lys Tyr Ser Leu Phe Glu Leu Glu Asn Gly Arg
1205                 1210                1215

Lys Arg Met Leu Ala Ser Ala Gly Glu Leu Gln Lys Gly Asn Glu
1220                 1225                1230

Leu Ala Leu Pro Ser Lys Tyr Val Asn Phe Leu Tyr Leu Ala Ser
1235                 1240                1245

His Tyr Glu Lys Leu Lys Gly Ser Pro Glu Asp Asn Glu Gln Lys
1250                 1255                1260

Gln Leu Phe Val Glu Gln His Lys His Tyr Leu Asp Glu Ile Ile
1265                 1270                1275

Glu Gln Ile Ser Glu Phe Ser Lys Arg Val Ile Leu Ala Asp Ala
1280                 1285                1290

Asn Leu Asp Lys Val Leu Ser Ala Tyr Asn Lys His Arg Asp Lys
1295                 1300                1305

Pro Ile Arg Glu Gln Ala Glu Asn Ile Ile His Leu Phe Thr Leu
1310                 1315                1320

Thr Asn Leu Gly Ala Pro Ala Ala Phe Lys Tyr Phe Asp Thr Thr
1325                 1330                1335

Ile Asp Arg Lys Arg Tyr Thr Ser Thr Lys Glu Val Leu Asp Ala
1340                 1345                1350

Thr Leu Ile His Gln Ser Ile Thr Gly Leu Tyr Glu Thr Arg Ile
1355                 1360                1365

Asp Leu Ser Gln Leu Gly Gly Asp Ser Arg Ala Asp Pro Lys Lys
1370                 1375                1380

Lys Arg Lys Val His His His His His His
1385                 1390

```
<210> SEQ ID NO 235
<211> LENGTH: 1399
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235
```

Met Gly Ser Ser His His His His His His Glu Asn Leu Tyr
1               5                   10                  15

Phe Gln Gly Ser Met Asp Lys Lys Tyr Ser Ile Gly Leu Asp Ile Gly
                20                  25                  30

Thr Asn Ser Val Gly Trp Ala Val Ile Thr Asp Glu Tyr Lys Val Pro
            35                  40                  45

Ser Lys Lys Phe Lys Val Leu Gly Asn Thr Asp Arg His Ser Ile Lys
50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Tyr Thr Arg Arg Lys
                85                  90                  95

Asn Arg Ile Cys Tyr Leu Gln Glu Ile Phe Ser Asn Glu Met Ala Lys
                100                 105                 110

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
        195                 200                 205

Val Gln Thr Tyr Asn Gln Leu Phe Glu Glu Asn Pro Ile Asn Ala Ser
210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
        275                 280                 285

Asp Thr Tyr Asp Asp Asp Leu Asp Asn Leu Leu Ala Gln Ile Gly Asp
        290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
        355                 360                 365

-continued

Glu Ile Phe Phe Asp Gln Ser Lys Asn Gly Tyr Ala Gly Tyr Ile Asp
    370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
            405                 410                 415

Asp Leu Leu Arg Lys Gln Arg Thr Phe Asp Asn Gly Ser Ile Pro His
        420                 425                 430

Gln Ile His Leu Gly Glu Leu His Ala Ile Leu Arg Arg Gln Glu Asp
            435                 440                 445

Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
            485                 490                 495

Asn Phe Glu Glu Val Val Asp Lys Gly Ala Ser Ala Gln Ser Phe Ile
        500                 505                 510

Glu Arg Met Thr Asn Phe Asp Lys Asn Leu Pro Asn Glu Lys Val Leu
            515                 520                 525

Pro Lys His Ser Leu Leu Tyr Glu Tyr Phe Thr Val Tyr Asn Glu Leu
    530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
            565                 570                 575

Arg Lys Val Thr Val Lys Gln Leu Lys Glu Asp Tyr Phe Lys Lys Ile
        580                 585                 590

Glu Cys Phe Asp Ser Val Glu Ile Ser Gly Val Glu Asp Arg Phe Asn
            595                 600                 605

Ala Ser Leu Gly Thr Tyr His Asp Leu Leu Lys Ile Ile Lys Asp Lys
    610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
            645                 650                 655

Lys Thr Tyr Ala His Leu Phe Asp Asp Lys Val Met Lys Gln Leu Lys
        660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
    690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
            725                 730                 735

Gly Asp Ser Leu His Glu His Ile Ala Asn Leu Ala Gly Ser Pro Ala
        740                 745                 750

Ile Lys Lys Gly Ile Leu Gln Thr Val Lys Val Val Asp Glu Leu Val
    755                 760                 765

Lys Val Met Gly Arg His Lys Pro Glu Asn Ile Val Ile Glu Met Ala
770                 775                 780

-continued

```
Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
            805                 810                 815

Lys Glu His Pro Val Glu Asn Thr Gln Leu Gln Asn Glu Lys Leu Tyr
        820                 825                 830

Leu Tyr Tyr Leu Gln Asn Gly Arg Asp Met Tyr Val Asp Gln Glu Leu
    835                 840                 845

Asp Ile Asn Arg Leu Ser Tyr Asp Val Asp His Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
            885                 890                 895

Lys Lys Met Lys Asn Tyr Trp Arg Gln Leu Leu Asn Ala Lys Leu Ile
        900                 905                 910

Thr Gln Arg Lys Phe Asp Asn Leu Thr Lys Ala Glu Arg Gly Gly Leu
    915                 920                 925

Ser Glu Leu Asp Lys Ala Gly Phe Ile Lys Arg Gln Leu Val Glu Thr
930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
        980                 985                 990

Tyr Lys Val Arg Glu Ile Asn Asn Tyr His His Ala His Asp Ala Tyr
    995                 1000                1005

Leu Asn Ala Val Val Gly Thr Ala Leu Ile Lys Lys Tyr Pro Lys
    1010                1015                1020

Leu Glu Ser Glu Phe Val Tyr Gly Asp Tyr Lys Val Tyr Asp Val
    1025                1030                1035

Arg Lys Met Ile Ala Lys Ser Glu Gln Glu Ile Gly Lys Ala Thr
    1040                1045                1050

Ala Lys Tyr Phe Phe Tyr Ser Asn Ile Met Asn Phe Phe Lys Thr
    1055                1060                1065

Glu Ile Thr Leu Ala Asn Gly Glu Ile Arg Lys Arg Pro Leu Ile
    1070                1075                1080

Glu Thr Asn Gly Glu Thr Gly Glu Ile Val Trp Asp Lys Gly Arg
    1085                1090                1095

Asp Phe Ala Thr Val Arg Lys Val Leu Ser Met Pro Gln Val Asn
    1100                1105                1110

Ile Val Lys Lys Thr Glu Val Gln Thr Gly Gly Phe Ser Lys Glu
    1115                1120                1125

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
```

1190                1195                1200

Ala Lys Gly Tyr Lys Glu Val Lys Lys Asp Leu Ile Ile Lys Leu
        1205                1210                1215

Pro Lys Tyr Ser Leu Phe Glu Leu Glu Asn Gly Arg Lys Arg Met
        1220                1225                1230

Leu Ala Ser Ala Gly Glu Leu Gln Lys Gly Asn Glu Leu Ala Leu
        1235                1240                1245

Pro Ser Lys Tyr Val Asn Phe Leu Tyr Leu Ala Ser His Tyr Glu
        1250                1255                1260

Lys Leu Lys Gly Ser Pro Glu Asp Asn Glu Gln Lys Gln Leu Phe
        1265                1270                1275

Val Glu Gln His Lys His Tyr Leu Asp Glu Ile Ile Glu Gln Ile
        1280                1285                1290

Ser Glu Phe Ser Lys Arg Val Ile Leu Ala Asp Ala Asn Leu Asp
        1295                1300                1305

Lys Val Leu Ser Ala Tyr Asn Lys His Arg Asp Lys Pro Ile Arg
        1310                1315                1320

Glu Gln Ala Glu Asn Ile Ile His Leu Phe Thr Leu Thr Asn Leu
        1325                1330                1335

Gly Ala Pro Ala Ala Phe Lys Tyr Phe Asp Thr Thr Ile Asp Arg
        1340                1345                1350

Lys Arg Tyr Thr Ser Thr Lys Glu Val Leu Asp Ala Thr Leu Ile
        1355                1360                1365

His Gln Ser Ile Thr Gly Leu Tyr Glu Thr Arg Ile Asp Leu Ser
        1370                1375                1380

Gln Leu Gly Gly Asp Gly Gly Gly Ser Pro Lys Lys Lys Arg Lys
        1385                1390                1395

Val

<210> SEQ ID NO 236
<211> LENGTH: 1396
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 236

Met Ala His His His His His His Gly Gly Ser Pro Lys Lys Lys Arg
1               5                   10                  15

Lys Val Asp Lys Lys Tyr Ser Ile Gly Leu Asp Ile Gly Thr Asn Ser
            20                  25                  30

Val Gly Trp Ala Val Ile Thr Asp Glu Tyr Lys Val Pro Ser Lys Lys
        35                  40                  45

Phe Lys Val Leu Gly Asn Thr Asp Arg His Ser Ile Lys Lys Asn Leu
    50                  55                  60

Ile Gly Ala Leu Leu Phe Asp Ser Gly Glu Thr Ala Glu Ala Thr Arg
65                  70                  75                  80

Leu Lys Arg Thr Ala Arg Arg Arg Tyr Thr Arg Arg Lys Asn Arg Ile
                85                  90                  95

Cys Tyr Leu Gln Glu Ile Phe Ser Asn Glu Met Ala Lys Val Asp Asp
            100                 105                 110

Ser Phe Phe His Arg Leu Glu Glu Ser Phe Leu Val Glu Glu Asp Lys
        115                 120                 125

```
Lys His Glu Arg His Pro Ile Phe Gly Asn Ile Val Asp Glu Val Ala
    130                 135                 140

Tyr His Glu Lys Tyr Pro Thr Ile Tyr His Leu Arg Lys Lys Leu Val
145                 150                 155                 160

Asp Ser Thr Asp Lys Ala Asp Leu Arg Leu Ile Tyr Leu Ala Leu Ala
                165                 170                 175

His Met Ile Lys Phe Arg Gly His Phe Leu Ile Glu Gly Asp Leu Asn
            180                 185                 190

Pro Asp Asn Ser Asp Val Asp Lys Leu Phe Ile Gln Leu Val Gln Thr
        195                 200                 205

Tyr Asn Gln Leu Phe Glu Glu Asn Pro Ile Asn Ala Ser Gly Val Asp
210                 215                 220

Ala Lys Ala Ile Leu Ser Ala Arg Leu Ser Lys Ser Arg Arg Leu Glu
225                 230                 235                 240

Asn Leu Ile Ala Gln Leu Pro Gly Glu Lys Lys Asn Gly Leu Phe Gly
                245                 250                 255

Asn Leu Ile Ala Leu Ser Leu Gly Leu Thr Pro Asn Phe Lys Ser Asn
            260                 265                 270

Phe Asp Leu Ala Glu Asp Ala Lys Leu Gln Leu Ser Lys Asp Thr Tyr
        275                 280                 285

Asp Asp Asp Leu Asp Asn Leu Leu Ala Gln Ile Gly Asp Gln Tyr Ala
290                 295                 300

Asp Leu Phe Leu Ala Ala Lys Asn Leu Ser Asp Ala Ile Leu Leu Ser
305                 310                 315                 320

Asp Ile Leu Arg Val Asn Thr Glu Ile Thr Lys Ala Pro Leu Ser Ala
                325                 330                 335

Ser Met Ile Lys Arg Tyr Asp Glu His His Gln Asp Leu Thr Leu Leu
            340                 345                 350

Lys Ala Leu Val Arg Gln Gln Leu Pro Glu Lys Tyr Lys Glu Ile Phe
        355                 360                 365

Phe Asp Gln Ser Lys Asn Gly Tyr Ala Gly Tyr Ile Asp Gly Gly Ala
370                 375                 380

Ser Gln Glu Glu Phe Tyr Lys Phe Ile Lys Pro Ile Leu Glu Lys Met
385                 390                 395                 400

Asp Gly Thr Glu Glu Leu Leu Val Lys Leu Asn Arg Glu Asp Leu Leu
                405                 410                 415

Arg Lys Gln Arg Thr Phe Asp Asn Gly Ser Ile Pro His Gln Ile His
            420                 425                 430

Leu Gly Glu Leu His Ala Ile Leu Arg Arg Gln Glu Asp Phe Tyr Pro
        435                 440                 445

Phe Leu Lys Asp Asn Arg Glu Lys Ile Glu Lys Ile Leu Thr Phe Arg
450                 455                 460

Ile Pro Tyr Tyr Val Gly Pro Leu Ala Arg Gly Asn Ser Arg Phe Ala
465                 470                 475                 480

Trp Met Thr Arg Lys Ser Glu Glu Thr Ile Thr Pro Trp Asn Phe Glu
                485                 490                 495

Glu Val Val Asp Lys Gly Ala Ser Ala Gln Ser Phe Ile Glu Arg Met
            500                 505                 510

Thr Asn Phe Asp Lys Asn Leu Pro Asn Glu Lys Val Leu Pro Lys His
        515                 520                 525

Ser Leu Leu Tyr Glu Tyr Phe Thr Val Tyr Asn Glu Leu Thr Lys Val
530                 535                 540

Lys Tyr Val Thr Glu Gly Met Arg Lys Pro Ala Phe Leu Ser Gly Glu
```

```
            545                 550                 555                 560
        Gln Lys Lys Ala Ile Val Asp Leu Leu Phe Lys Thr Asn Arg Lys Val
                        565                 570                 575
        Thr Val Lys Gln Leu Lys Glu Asp Tyr Phe Lys Lys Ile Glu Cys Phe
                        580                 585                 590
        Asp Ser Val Glu Ile Ser Gly Val Glu Asp Arg Phe Asn Ala Ser Leu
                        595                 600                 605
        Gly Thr Tyr His Asp Leu Leu Lys Ile Ile Lys Asp Lys Asp Phe Leu
                        610                 615                 620
        Asp Asn Glu Glu Asn Glu Asp Ile Leu Glu Asp Ile Val Leu Thr Leu
        625                 630                 635                 640
        Thr Leu Phe Glu Asp Arg Glu Met Ile Glu Glu Arg Leu Lys Thr Tyr
                        645                 650                 655
        Ala His Leu Phe Asp Asp Lys Val Met Lys Gln Leu Lys Arg Arg Arg
                        660                 665                 670
        Tyr Thr Gly Trp Gly Arg Leu Ser Arg Lys Leu Ile Asn Gly Ile Arg
                        675                 680                 685
        Asp Lys Gln Ser Gly Lys Thr Ile Leu Asp Phe Leu Lys Ser Asp Gly
                        690                 695                 700
        Phe Ala Asn Arg Asn Phe Met Gln Leu Ile His Asp Asp Ser Leu Thr
        705                 710                 715                 720
        Phe Lys Glu Asp Ile Gln Lys Ala Gln Val Ser Gly Gln Gly Asp Ser
                        725                 730                 735
        Leu His Glu His Ile Ala Asn Leu Ala Gly Ser Pro Ala Ile Lys Lys
                        740                 745                 750
        Gly Ile Leu Gln Thr Val Lys Val Val Asp Glu Leu Val Lys Val Met
                        755                 760                 765
        Gly Arg His Lys Pro Glu Asn Ile Val Ile Glu Met Ala Arg Glu Asn
                        770                 775                 780
        Gln Thr Thr Gln Lys Gly Gln Lys Asn Ser Arg Glu Arg Met Lys Arg
        785                 790                 795                 800
        Ile Glu Glu Gly Ile Lys Glu Leu Gly Ser Gln Ile Leu Lys Glu His
                        805                 810                 815
        Pro Val Glu Asn Thr Gln Leu Gln Asn Glu Lys Leu Tyr Leu Tyr Tyr
                        820                 825                 830
        Leu Gln Asn Gly Arg Asp Met Tyr Val Asp Gln Glu Leu Asp Ile Asn
                        835                 840                 845
        Arg Leu Ser Asp Tyr Asp Val Asp His Ile Val Pro Gln Ser Phe Leu
                        850                 855                 860
        Lys Asp Asp Ser Ile Asp Asn Lys Val Leu Thr Arg Ser Asp Lys Asn
        865                 870                 875                 880
        Arg Gly Lys Ser Asp Asn Val Pro Ser Glu Glu Val Val Lys Lys Met
                        885                 890                 895
        Lys Asn Tyr Trp Arg Gln Leu Leu Asn Ala Lys Leu Ile Thr Gln Arg
                        900                 905                 910
        Lys Phe Asp Asn Leu Thr Lys Ala Glu Arg Gly Gly Leu Ser Glu Leu
                        915                 920                 925
        Asp Lys Ala Gly Phe Ile Lys Arg Gln Leu Val Glu Thr Arg Gln Ile
                        930                 935                 940
        Thr Lys His Val Ala Gln Ile Leu Asp Ser Arg Met Asn Thr Lys Tyr
        945                 950                 955                 960
        Asp Glu Asn Asp Lys Leu Ile Arg Glu Val Lys Val Ile Thr Leu Lys
                        965                 970                 975
```

-continued

```
Ser Lys Leu Val Ser Asp Phe Arg Lys Asp Phe Gln Phe Tyr Lys Val
            980                 985                 990

Arg Glu Ile Asn Asn Tyr His His Ala His Asp Ala Tyr Leu Asn Ala
            995                1000                1005

Val Val Gly Thr Ala Leu Ile Lys Lys Tyr Pro Lys Leu Glu Ser
    1010                1015                1020

Glu Phe Val Tyr Gly Asp Tyr Lys Val Tyr Asp Val Arg Lys Met
    1025                1030                1035

Ile Ala Lys Ser Glu Gln Glu Ile Gly Lys Ala Thr Ala Lys Tyr
    1040                1045                1050

Phe Phe Tyr Ser Asn Ile Met Asn Phe Phe Lys Thr Glu Ile Thr
    1055                1060                1065

Leu Ala Asn Gly Glu Ile Arg Lys Arg Pro Leu Ile Glu Thr Asn
    1070                1075                1080

Gly Glu Thr Gly Glu Ile Val Trp Asp Lys Gly Arg Asp Phe Ala
    1085                1090                1095

Thr Val Arg Lys Val Leu Ser Met Pro Gln Val Asn Ile Val Lys
    1100                1105                1110

Lys Thr Glu Val Gln Thr Gly Gly Phe Ser Lys Glu Ser Ile Leu
    1115                1120                1125

Pro Lys Arg Asn Ser Asp Lys Leu Ile Ala Arg Lys Lys Asp Trp
    1130                1135                1140

Asp Pro Lys Lys Tyr Gly Gly Phe Asp Ser Pro Thr Val Ala Tyr
    1145                1150                1155

Ser Val Leu Val Val Ala Lys Val Glu Lys Gly Lys Ser Lys Lys
    1160                1165                1170

Leu Lys Ser Val Lys Glu Leu Leu Gly Ile Thr Ile Met Glu Arg
    1175                1180                1185

Ser Ser Phe Glu Lys Asn Pro Ile Asp Phe Leu Glu Ala Lys Gly
    1190                1195                1200

Tyr Lys Glu Val Lys Lys Asp Leu Ile Ile Lys Leu Pro Lys Tyr
    1205                1210                1215

Ser Leu Phe Glu Leu Glu Asn Gly Arg Lys Arg Met Leu Ala Ser
    1220                1225                1230

Ala Gly Glu Leu Gln Lys Gly Asn Glu Leu Ala Leu Pro Ser Lys
    1235                1240                1245

Tyr Val Asn Phe Leu Tyr Leu Ala Ser His Tyr Glu Lys Leu Lys
    1250                1255                1260

Gly Ser Pro Glu Asp Asn Glu Gln Lys Gln Leu Phe Val Glu Gln
    1265                1270                1275

His Lys His Tyr Leu Asp Glu Ile Ile Glu Gln Ile Ser Glu Phe
    1280                1285                1290

Ser Lys Arg Val Ile Leu Ala Asp Ala Asn Leu Asp Lys Val Leu
    1295                1300                1305

Ser Ala Tyr Asn Lys His Arg Asp Lys Pro Ile Arg Glu Gln Ala
    1310                1315                1320

Glu Asn Ile Ile His Leu Phe Thr Leu Thr Asn Leu Gly Ala Pro
    1325                1330                1335

Ala Ala Phe Lys Tyr Phe Asp Thr Thr Ile Asp Arg Lys Arg Tyr
    1340                1345                1350

Thr Ser Thr Lys Glu Val Leu Asp Ala Thr Leu Ile His Gln Ser
    1355                1360                1365
```

Ile Thr Gly Leu Tyr Glu Thr Arg Ile Asp Leu Ser Gln Leu Gly
1370                1375                1380

Gly Asp Ser Arg Ala Asp Pro Lys Lys Lys Arg Lys Val
1385                1390                1395

<210> SEQ ID NO 237
<211> LENGTH: 1386
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Met Ala Pro Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
                20                  25                  30

Tyr Lys Val Pro Ser Lys Lys Phe Lys Val Leu Gly Asn Thr Asp Arg
                35                  40                  45

His Ser Ile Lys Lys Asn Leu Ile Gly Ala Leu Leu Phe Asp Ser Gly
            50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Cys Tyr Leu Gln Glu Ile Phe Ser Asn
                    85                  90                  95

Glu Met Ala Lys Val Asp Asp Ser Phe Phe His Arg Leu Glu Glu Ser
                100                 105                 110

Phe Leu Val Glu Glu Asp Lys Lys His Glu Arg His Pro Ile Phe Gly
            115                 120                 125

Asn Ile Val Asp Glu Val Ala Tyr His Glu Lys Tyr Pro Thr Ile Tyr
            130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                    165                 170                 175

Leu Ile Glu Gly Asp Leu Asn Pro Asp Asn Ser Asp Val Asp Lys Leu
                180                 185                 190

Phe Ile Gln Leu Val Gln Thr Tyr Asn Gln Leu Phe Glu Glu Asn Pro
            195                 200                 205

Ile Asn Ala Ser Gly Val Asp Ala Lys Ala Ile Leu Ser Ala Arg Leu
            210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                    245                 250                 255

Thr Pro Asn Phe Lys Ser Asn Phe Asp Leu Ala Glu Asp Ala Lys Leu
                260                 265                 270

Gln Leu Ser Lys Asp Thr Tyr Asp Asp Asp Leu Asp Asn Leu Leu Ala
            275                 280                 285

Gln Ile Gly Asp Gln Tyr Ala Asp Leu Phe Leu Ala Ala Lys Asn Leu
            290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His

```
                325                 330                 335
His Gln Asp Leu Thr Leu Leu Lys Ala Leu Val Arg Gln Gln Leu Pro
            340                 345                 350
Glu Lys Tyr Lys Glu Ile Phe Phe Asp Gln Ser Lys Asn Gly Tyr Ala
            355                 360                 365
Gly Tyr Ile Asp Gly Gly Ala Ser Gln Glu Glu Phe Tyr Lys Phe Ile
            370                 375                 380
Lys Pro Ile Leu Glu Lys Met Asp Gly Thr Glu Glu Leu Leu Val Lys
385                 390                 395                 400
Leu Asn Arg Glu Asp Leu Leu Arg Lys Gln Arg Thr Phe Asp Asn Gly
                405                 410                 415
Ser Ile Pro His Gln Ile His Leu Gly Glu Leu His Ala Ile Leu Arg
            420                 425                 430
Arg Gln Glu Asp Phe Tyr Pro Phe Leu Lys Asp Asn Arg Glu Lys Ile
            435                 440                 445
Glu Lys Ile Leu Thr Phe Arg Ile Pro Tyr Tyr Val Gly Pro Leu Ala
            450                 455                 460
Arg Gly Asn Ser Arg Phe Ala Trp Met Thr Arg Lys Ser Glu Glu Thr
465                 470                 475                 480
Ile Thr Pro Trp Asn Phe Glu Glu Val Val Asp Lys Gly Ala Ser Ala
                485                 490                 495
Gln Ser Phe Ile Glu Arg Met Thr Asn Phe Asp Lys Asn Leu Pro Asn
            500                 505                 510
Glu Lys Val Leu Pro Lys His Ser Leu Leu Tyr Glu Tyr Phe Thr Val
            515                 520                 525
Tyr Asn Glu Leu Thr Lys Val Lys Tyr Val Thr Glu Gly Met Arg Lys
            530                 535                 540
Pro Ala Phe Leu Ser Gly Glu Gln Lys Lys Ala Ile Val Asp Leu Leu
545                 550                 555                 560
Phe Lys Thr Asn Arg Lys Val Thr Val Lys Gln Leu Lys Glu Asp Tyr
                565                 570                 575
Phe Lys Lys Ile Glu Cys Phe Asp Ser Val Glu Ile Ser Gly Val Glu
            580                 585                 590
Asp Arg Phe Asn Ala Ser Leu Gly Thr Tyr His Asp Leu Leu Lys Ile
            595                 600                 605
Ile Lys Asp Lys Asp Phe Leu Asp Asn Glu Glu Asn Glu Asp Ile Leu
            610                 615                 620
Glu Asp Ile Val Leu Thr Leu Thr Leu Phe Glu Asp Arg Glu Met Ile
625                 630                 635                 640
Glu Glu Arg Leu Lys Thr Tyr Ala His Leu Phe Asp Asp Lys Val Met
                645                 650                 655
Lys Gln Leu Lys Arg Arg Arg Tyr Thr Gly Trp Gly Arg Leu Ser Arg
            660                 665                 670
Lys Leu Ile Asn Gly Ile Arg Asp Lys Gln Ser Gly Lys Thr Ile Leu
            675                 680                 685
Asp Phe Leu Lys Ser Asp Gly Phe Ala Asn Arg Asn Phe Met Gln Leu
            690                 695                 700
Ile His Asp Asp Ser Leu Thr Phe Lys Glu Asp Ile Gln Lys Ala Gln
705                 710                 715                 720
Val Ser Gly Gln Gly Asp Ser Leu His Glu His Ile Ala Asn Leu Ala
                725                 730                 735
Gly Ser Pro Ala Ile Lys Lys Gly Ile Leu Gln Thr Val Lys Val Val
            740                 745                 750
```

-continued

```
Asp Glu Leu Val Lys Val Met Gly Arg His Lys Pro Glu Asn Ile Val
        755                 760                 765

Ile Glu Met Ala Arg Glu Asn Gln Thr Thr Gln Lys Gly Gln Lys Asn
    770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
            805                 810                 815

Glu Lys Leu Tyr Leu Tyr Tyr Leu Gln Asn Gly Arg Asp Met Tyr Val
        820                 825                 830

Asp Gln Glu Leu Asp Ile Asn Arg Leu Ser Asp Tyr Asp Val Asp His
        835                 840                 845

Ile Val Pro Gln Ser Phe Leu Lys Asp Asp Ser Ile Asp Asn Lys Val
    850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
            885                 890                 895

Ala Lys Leu Ile Thr Gln Arg Lys Phe Asp Asn Leu Thr Lys Ala Glu
        900                 905                 910

Arg Gly Gly Leu Ser Glu Leu Asp Lys Ala Gly Phe Ile Lys Arg Gln
        915                 920                 925

Leu Val Glu Thr Arg Gln Ile Thr Lys His Val Ala Gln Ile Leu Asp
    930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
            965                 970                 975

Asp Phe Gln Phe Tyr Lys Val Arg Glu Ile Asn Asn Tyr His His Ala
        980                 985                 990

His Asp Ala Tyr Leu Asn Ala Val Val Gly Thr Ala Leu Ile Lys Lys
        995                 1000                1005

Tyr Pro Lys Leu Glu Ser Glu Phe Val Tyr Gly Asp Tyr Lys Val
    1010                1015                1020

Tyr Asp Val Arg Lys Met Ile Ala Lys Ser Glu Gln Glu Ile Gly
    1025                1030                1035

Lys Ala Thr Ala Lys Tyr Phe Phe Tyr Ser Asn Ile Met Asn Phe
    1040                1045                1050

Phe Lys Thr Glu Ile Thr Leu Ala Asn Gly Glu Ile Arg Lys Arg
    1055                1060                1065

Pro Leu Ile Glu Thr Asn Gly Glu Thr Gly Glu Ile Val Trp Asp
    1070                1075                1080

Lys Gly Arg Asp Phe Ala Thr Val Arg Lys Val Leu Ser Met Pro
    1085                1090                1095

Gln Val Asn Ile Val Lys Lys Thr Glu Val Gln Thr Gly Gly Phe
    1100                1105                1110

Ser Lys Glu Ser Ile Leu Pro Lys Arg Asn Ser Asp Lys Leu Ile
    1115                1120                1125

Ala Arg Lys Lys Asp Trp Asp Pro Lys Lys Tyr Gly Gly Phe Asp
    1130                1135                1140

Ser Pro Thr Val Ala Tyr Ser Val Leu Val Val Ala Lys Val Glu
    1145                1150                1155
```

```
Lys Gly Lys Ser Lys Lys Leu Lys Ser Val Lys Glu Leu Leu Gly
    1160                1165                1170

Ile Thr Ile Met Glu Arg Ser Ser Phe Glu Lys Asn Pro Ile Asp
    1175                1180                1185

Phe Leu Glu Ala Lys Gly Tyr Lys Glu Val Lys Lys Asp Leu Ile
    1190                1195                1200

Ile Lys Leu Pro Lys Tyr Ser Leu Phe Glu Leu Glu Asn Gly Arg
    1205                1210                1215

Lys Arg Met Leu Ala Ser Ala Gly Glu Leu Gln Lys Gly Asn Glu
    1220                1225                1230

Leu Ala Leu Pro Ser Lys Tyr Val Asn Phe Leu Tyr Leu Ala Ser
    1235                1240                1245

His Tyr Glu Lys Leu Lys Gly Ser Pro Glu Asp Asn Glu Gln Lys
    1250                1255                1260

Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305

Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp Ser Arg Ala Asp His His His
    1370                1375                1380

His His His
    1385

<210> SEQ ID NO 238
<211> LENGTH: 1389
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Met Ala His His His His His His Gly Gly Ser Asp Lys Lys Tyr Ser
1               5                   10                  15

Ile Gly Leu Asp Ile Gly Thr Asn Ser Val Gly Trp Ala Val Ile Thr
                20                  25                  30

Asp Glu Tyr Lys Val Pro Ser Lys Phe Lys Val Leu Gly Asn Thr
            35                  40                  45

Asp Arg His Ser Ile Lys Lys Asn Leu Ile Gly Ala Leu Leu Phe Asp
        50                  55                  60

Ser Gly Glu Thr Ala Glu Ala Thr Arg Leu Lys Arg Thr Ala Arg Arg
65                  70                  75                  80

Arg Tyr Thr Arg Arg Lys Asn Arg Ile Cys Tyr Leu Gln Glu Ile Phe
                85                  90                  95

Ser Asn Glu Met Ala Lys Val Asp Asp Ser Phe Phe His Arg Leu Glu
```

```
            100                 105                 110
Glu Ser Phe Leu Val Glu Glu Asp Lys Lys His Glu Arg His Pro Ile
            115                 120                 125
Phe Gly Asn Ile Val Asp Glu Val Ala Tyr His Glu Lys Tyr Pro Thr
            130                 135                 140
Ile Tyr His Leu Arg Lys Lys Leu Val Asp Ser Thr Asp Lys Ala Asp
145                 150                 155                 160
Leu Arg Leu Ile Tyr Leu Ala Leu Ala His Met Ile Lys Phe Arg Gly
                    165                 170                 175
His Phe Leu Ile Glu Gly Asp Leu Asn Pro Asp Asn Ser Asp Val Asp
                            180                 185                 190
Lys Leu Phe Ile Gln Leu Val Gln Thr Tyr Asn Gln Leu Phe Glu Glu
                    195                 200                 205
Asn Pro Ile Asn Ala Ser Gly Val Asp Ala Lys Ala Ile Leu Ser Ala
            210                 215                 220
Arg Leu Ser Lys Ser Arg Arg Leu Glu Asn Leu Ile Ala Gln Leu Pro
225                 230                 235                 240
Gly Glu Lys Lys Asn Gly Leu Phe Gly Asn Leu Ile Ala Leu Ser Leu
                    245                 250                 255
Gly Leu Thr Pro Asn Phe Lys Ser Asn Phe Asp Leu Ala Glu Asp Ala
                    260                 265                 270
Lys Leu Gln Leu Ser Lys Asp Thr Tyr Asp Asp Leu Asp Asn Leu
                    275                 280                 285
Leu Ala Gln Ile Gly Asp Gln Tyr Ala Asp Leu Phe Leu Ala Ala Lys
            290                 295                 300
Asn Leu Ser Asp Ala Ile Leu Leu Ser Asp Ile Leu Arg Val Asn Thr
305                 310                 315                 320
Glu Ile Thr Lys Ala Pro Leu Ser Ala Ser Met Ile Lys Arg Tyr Asp
                    325                 330                 335
Glu His His Gln Asp Leu Thr Leu Leu Lys Ala Leu Val Arg Gln Gln
                    340                 345                 350
Leu Pro Glu Lys Tyr Lys Glu Ile Phe Phe Asp Gln Ser Lys Asn Gly
                    355                 360                 365
Tyr Ala Gly Tyr Ile Asp Gly Gly Ala Ser Gln Glu Glu Phe Tyr Lys
            370                 375                 380
Phe Ile Lys Pro Ile Leu Glu Lys Met Asp Gly Thr Glu Glu Leu Leu
385                 390                 395                 400
Val Lys Leu Asn Arg Glu Asp Leu Leu Arg Lys Gln Arg Thr Phe Asp
                    405                 410                 415
Asn Gly Ser Ile Pro His Gln Ile His Leu Gly Glu Leu His Ala Ile
                    420                 425                 430
Leu Arg Arg Gln Glu Asp Phe Tyr Pro Phe Leu Lys Asp Asn Arg Glu
                    435                 440                 445
Lys Ile Glu Lys Ile Leu Thr Phe Arg Ile Pro Tyr Tyr Val Gly Pro
            450                 455                 460
Leu Ala Arg Gly Asn Ser Arg Phe Ala Trp Met Thr Arg Lys Ser Glu
465                 470                 475                 480
Glu Thr Ile Thr Pro Trp Asn Phe Glu Glu Val Val Asp Lys Gly Ala
                    485                 490                 495
Ser Ala Gln Ser Phe Ile Glu Arg Met Thr Asn Phe Asp Lys Asn Leu
                    500                 505                 510
Pro Asn Glu Lys Val Leu Pro Lys His Ser Leu Leu Tyr Glu Tyr Phe
            515                 520                 525
```

```
Thr Val Tyr Asn Glu Leu Thr Lys Val Lys Tyr Val Thr Glu Gly Met
        530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ser Gly
            580                 585                 590

Val Glu Asp Arg Phe Asn Ala Ser Leu Gly Thr Tyr His Asp Leu Leu
        595                 600                 605

Lys Ile Ile Lys Asp Lys Asp Phe Leu Asp Asn Glu Glu Asn Glu Asp
    610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
                645                 650                 655

Val Met Lys Gln Leu Lys Arg Arg Arg Tyr Thr Gly Trp Gly Arg Leu
            660                 665                 670

Ser Arg Lys Leu Ile Asn Gly Ile Arg Asp Lys Gln Ser Gly Lys Thr
        675                 680                 685

Ile Leu Asp Phe Leu Lys Ser Asp Gly Phe Ala Asn Arg Asn Phe Met
    690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
                725                 730                 735

Leu Ala Gly Ser Pro Ala Ile Lys Lys Gly Ile Leu Gln Thr Val Lys
            740                 745                 750

Val Val Asp Glu Leu Val Lys Val Met Gly Arg His Lys Pro Glu Asn
        755                 760                 765

Ile Val Ile Glu Met Ala Arg Glu Asn Gln Thr Thr Gln Lys Gly Gln
    770                 775                 780

Lys Asn Ser Arg Glu Arg Met Lys Arg Ile Glu Glu Gly Ile Lys Glu
785                 790                 795                 800

Leu Gly Ser Gln Ile Leu Lys Glu His Pro Val Glu Asn Thr Gln Leu
                805                 810                 815

Gln Asn Glu Lys Leu Tyr Leu Tyr Tyr Leu Gln Asn Gly Arg Asp Met
            820                 825                 830

Tyr Val Asp Gln Glu Leu Asp Ile Asn Arg Leu Ser Asp Tyr Asp Val
        835                 840                 845

Asp His Ile Val Pro Gln Ser Phe Leu Lys Asp Ser Ile Asp Asn
    850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
                885                 890                 895

Leu Asn Ala Lys Leu Ile Thr Gln Arg Lys Phe Asp Asn Leu Thr Lys
            900                 905                 910

Ala Glu Arg Gly Gly Leu Ser Glu Leu Asp Lys Ala Gly Phe Ile Lys
        915                 920                 925

Arg Gln Leu Val Glu Thr Arg Gln Ile Thr Lys His Val Ala Gln Ile
    930                 935                 940
```

```
Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
                965                 970                 975

Arg Lys Asp Phe Gln Phe Tyr Lys Val Arg Glu Ile Asn Asn Tyr His
            980                 985                 990

His Ala His Asp Ala Tyr Leu Asn Ala Val Val Gly Thr Ala Leu Ile
        995                1000                1005

Lys Lys Tyr Pro Lys Leu Glu Ser Glu Phe Val Tyr Gly Asp Tyr
    1010                1015                1020

Lys Val Tyr Asp Val Arg Lys Met Ile Ala Lys Ser Glu Gln Glu
    1025                1030                1035

Ile Gly Lys Ala Thr Ala Lys Tyr Phe Phe Tyr Ser Asn Ile Met
    1040                1045                1050

Asn Phe Phe Lys Thr Glu Ile Thr Leu Ala Asn Gly Glu Ile Arg
    1055                1060                1065

Lys Arg Pro Leu Ile Glu Thr Asn Gly Glu Thr Gly Glu Ile Val
    1070                1075                1080

Trp Asp Lys Gly Arg Asp Phe Ala Thr Val Arg Lys Val Leu Ser
    1085                1090                1095

Met Pro Gln Val Asn Ile Val Lys Lys Thr Glu Val Gln Thr Gly
    1100                1105                1110

Gly Phe Ser Lys Glu Ser Ile Leu Pro Lys Arg Asn Ser Asp Lys
    1115                1120                1125

Leu Ile Ala Arg Lys Lys Asp Trp Asp Pro Lys Lys Tyr Gly Gly
    1130                1135                1140

Phe Asp Ser Pro Thr Val Ala Tyr Ser Val Leu Val Val Ala Lys
    1145                1150                1155

Val Glu Lys Gly Lys Ser Lys Lys Leu Lys Ser Val Lys Glu Leu
    1160                1165                1170

Leu Gly Ile Thr Ile Met Glu Arg Ser Ser Phe Glu Lys Asn Pro
    1175                1180                1185

Ile Asp Phe Leu Glu Ala Lys Gly Tyr Lys Glu Val Lys Lys Asp
    1190                1195                1200

Leu Ile Ile Lys Leu Pro Lys Tyr Ser Leu Phe Glu Leu Glu Asn
    1205                1210                1215

Gly Arg Lys Arg Met Leu Ala Ser Ala Gly Glu Leu Gln Lys Gly
    1220                1225                1230

Asn Glu Leu Ala Leu Pro Ser Lys Tyr Val Asn Phe Leu Tyr Leu
    1235                1240                1245

Ala Ser His Tyr Glu Lys Leu Lys Gly Ser Pro Glu Asp Asn Glu
    1250                1255                1260

Gln Lys Gln Leu Phe Val Glu Gln His Lys His Tyr Leu Asp Glu
    1265                1270                1275

Ile Ile Glu Gln Ile Ser Glu Phe Ser Lys Arg Val Ile Leu Ala
    1280                1285                1290

Asp Ala Asn Leu Asp Lys Val Leu Ser Ala Tyr Asn Lys His Arg
    1295                1300                1305

Asp Lys Pro Ile Arg Glu Gln Ala Glu Asn Ile Ile His Leu Phe
    1310                1315                1320

Thr Leu Thr Asn Leu Gly Ala Pro Ala Ala Phe Lys Tyr Phe Asp
    1325                1330                1335

Thr Thr Ile Asp Arg Lys Arg Tyr Thr Ser Thr Lys Glu Val Leu
```

1340                1345                1350

Asp Ala Thr Leu Ile His Gln Ser Ile Thr Gly Leu Tyr Glu Thr
    1355                1360                1365

Arg Ile Asp Leu Ser Gln Leu Gly Gly Asp Ser Arg Ala Asp Pro
    1370                1375                1380

Lys Lys Lys Arg Lys Val
    1385

<210> SEQ ID NO 239
<211> LENGTH: 1399
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Met Gly Ser Ser His His His His His His Glu Asn Leu Tyr
1               5                   10                  15

Phe Gln Gly Ser Met Asp Lys Lys Tyr Ser Ile Gly Leu Asp Ile Gly
                20                  25                  30

Thr Asn Ser Val Gly Trp Ala Val Ile Thr Asp Glu Tyr Lys Val Pro
            35                  40                  45

Ser Lys Lys Phe Lys Val Leu Gly Asn Thr Asp Arg His Ser Ile Lys
50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Arg Tyr Thr Arg Arg Lys
                85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
        195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
        275                 280                 285

Asp Thr Tyr Asp Asp Asp Leu Asp Asn Leu Leu Ala Gln Ile Gly Asp
    290                 295                 300

-continued

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
            325                 330                 335

Leu Ser Ala Ser Met Ile Lys Arg Tyr Asp Glu His His Gln Asp Leu
        340                 345                 350

Thr Leu Leu Lys Ala Leu Val Arg Gln Gln Leu Pro Glu Lys Tyr Lys
    355                 360                 365

Glu Ile Phe Phe Asp Gln Ser Lys Asn Gly Tyr Ala Gly Tyr Ile Asp
370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
            405                 410                 415

Asp Leu Leu Arg Lys Gln Arg Thr Phe Asp Asn Gly Ser Ile Pro His
        420                 425                 430

Gln Ile His Leu Gly Glu Leu His Ala Ile Leu Arg Arg Gln Glu Asp
    435                 440                 445

Phe Tyr Pro Phe Leu Lys Asp Asn Arg Glu Lys Ile Glu Lys Ile Leu
450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
            485                 490                 495

Asn Phe Glu Glu Val Val Asp Lys Gly Ala Ser Ala Gln Ser Phe Ile
        500                 505                 510

Glu Arg Met Thr Asn Phe Asp Lys Asn Leu Pro Asn Glu Lys Val Leu
    515                 520                 525

Pro Lys His Ser Leu Leu Tyr Glu Tyr Phe Thr Val Tyr Asn Glu Leu
530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
            565                 570                 575

Arg Lys Val Thr Val Lys Gln Leu Lys Glu Asp Tyr Phe Lys Lys Ile
        580                 585                 590

Glu Cys Phe Asp Ser Val Glu Ile Ser Gly Val Glu Asp Arg Phe Asn
    595                 600                 605

Ala Ser Leu Gly Thr Tyr His Asp Leu Leu Lys Ile Ile Lys Asp Lys
610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
            645                 650                 655

Lys Thr Tyr Ala His Leu Phe Asp Asp Lys Val Met Lys Gln Leu Lys
        660                 665                 670

Arg Arg Arg Tyr Thr Gly Trp Gly Arg Leu Ser Arg Lys Leu Ile Asn
    675                 680                 685

Gly Ile Arg Asp Lys Gln Ser Gly Lys Thr Ile Leu Asp Phe Leu Lys
690                 695                 700

Ser Asp Gly Phe Ala Asn Arg Asn Phe Met Gln Leu Ile His Asp Asp
705                 710                 715                 720

```
Ser Leu Thr Phe Lys Glu Asp Ile Gln Lys Ala Gln Val Ser Gly Gln
            725                 730                 735

Gly Asp Ser Leu His Glu His Ile Ala Asn Leu Ala Gly Ser Pro Ala
            740                 745                 750

Ile Lys Lys Gly Ile Leu Gln Thr Val Lys Val Val Asp Glu Leu Val
            755                 760                 765

Lys Val Met Gly Arg His Lys Pro Glu Asn Ile Val Ile Glu Met Ala
            770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                805                 810                 815

Lys Glu His Pro Val Glu Asn Thr Gln Leu Gln Asn Glu Lys Leu Tyr
            820                 825                 830

Leu Tyr Tyr Leu Gln Asn Gly Arg Asp Met Tyr Val Asp Gln Glu Leu
            835                 840                 845

Asp Ile Asn Arg Leu Ser Asp Tyr Asp Val Asp His Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
            885                 890                 895

Lys Lys Met Lys Asn Tyr Trp Arg Gln Leu Leu Asn Ala Lys Leu Ile
            900                 905                 910

Thr Gln Arg Lys Phe Asp Asn Leu Thr Lys Ala Glu Arg Gly Gly Leu
            915                 920                 925

Ser Glu Leu Asp Lys Ala Gly Phe Ile Lys Arg Gln Leu Val Glu Thr
            930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
            980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
            1010                1015                1020

Leu Glu Ser Glu Phe Val Tyr Gly Asp Tyr Lys Val Tyr Asp Val
            1025                1030                1035

Arg Lys Met Ile Ala Lys Ser Glu Gln Glu Ile Gly Lys Ala Thr
            1040                1045                1050

Ala Lys Tyr Phe Phe Tyr Ser Asn Ile Met Asn Phe Phe Lys Thr
            1055                1060                1065

Glu Ile Thr Leu Ala Asn Gly Glu Ile Arg Lys Arg Pro Leu Ile
            1070                1075                1080

Glu Thr Asn Gly Glu Thr Gly Glu Ile Val Trp Asp Lys Gly Arg
            1085                1090                1095

Asp Phe Ala Thr Val Arg Lys Val Leu Ser Met Pro Gln Val Asn
            1100                1105                1110

Ile Val Lys Lys Thr Glu Val Gln Thr Gly Gly Phe Ser Lys Glu
            1115                1120                1125

Ser Ile Leu Pro Lys Arg Asn Ser Asp Lys Leu Ile Ala Arg Lys
```

```
                      1130                1135                1140

Lys Asp Trp Asp Pro Lys Lys Tyr Gly Gly Phe Asp Ser Pro Thr
                      1145                1150                1155

Val Ala Tyr Ser Val Leu Val Ala Lys Val Glu Lys Gly Lys
                      1160                1165                1170

Ser Lys Lys Leu Lys Ser Val Lys Glu Leu Leu Gly Ile Thr Ile
                      1175                1180                1185

Met Glu Arg Ser Ser Phe Glu Lys Asn Pro Ile Asp Phe Leu Glu
                      1190                1195                1200

Ala Lys Gly Tyr Lys Glu Val Lys Lys Asp Leu Ile Ile Lys Leu
                      1205                1210                1215

Pro Lys Tyr Ser Leu Phe Glu Leu Glu Asn Gly Arg Lys Arg Met
                      1220                1225                1230

Leu Ala Ser Ala Gly Glu Leu Gln Lys Gly Asn Glu Leu Ala Leu
                      1235                1240                1245

Pro Ser Lys Tyr Val Asn Phe Leu Tyr Leu Ala Ser His Tyr Glu
                      1250                1255                1260

Lys Leu Lys Gly Ser Pro Glu Asp Asn Glu Gln Lys Gln Leu Phe
                      1265                1270                1275

Val Glu Gln His Lys His Tyr Leu Asp Glu Ile Ile Glu Gln Ile
                      1280                1285                1290

Ser Glu Phe Ser Lys Arg Val Ile Leu Ala Asp Ala Asn Leu Asp
                      1295                1300                1305

Lys Val Leu Ser Ala Tyr Asn Lys His Arg Asp Lys Pro Ile Arg
                      1310                1315                1320

Glu Gln Ala Glu Asn Ile Ile His Leu Phe Thr Leu Thr Asn Leu
                      1325                1330                1335

Gly Ala Pro Ala Ala Phe Lys Tyr Phe Asp Thr Thr Ile Asp Arg
                      1340                1345                1350

Lys Arg Tyr Thr Ser Thr Lys Glu Val Leu Asp Ala Thr Leu Ile
                      1355                1360                1365

His Gln Ser Ile Thr Gly Leu Tyr Glu Thr Arg Ile Asp Leu Ser
                      1370                1375                1380

Gln Leu Gly Gly Asp Gly Gly Gly Ser Pro Lys Lys Lys Arg Lys
                      1385                1390                1395

Val

<210> SEQ ID NO 240
<211> LENGTH: 1393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Met Ala Pro Lys Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
                20                  25                  30

Tyr Lys Val Pro Ser Lys Lys Phe Lys Val Leu Gly Asn Thr Asp Arg
            35                  40                  45

His Ser Ile Lys Lys Asn Leu Ile Gly Ala Leu Leu Phe Asp Ser Gly
        50                  55                  60
```

-continued

Glu Thr Ala Glu Ala Thr Arg Leu Lys Arg Thr Ala Arg Arg Arg Tyr
65                  70                  75                  80

Thr Arg Arg Lys Asn Arg Ile Cys Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
    130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
    210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Leu Asp Asn Leu Leu Ala
        275                 280                 285

Gln Ile Gly Asp Gln Tyr Ala Asp Leu Phe Leu Ala Ala Lys Asn Leu
    290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
            340                 345                 350

Glu Lys Tyr Lys Glu Ile Phe Phe Asp Gln Ser Lys Asn Gly Tyr Ala
        355                 360                 365

Gly Tyr Ile Asp Gly Gly Ala Ser Gln Glu Glu Phe Tyr Lys Phe Ile
    370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
            420                 425                 430

Arg Gln Glu Asp Phe Tyr Pro Phe Leu Lys Asp Asn Arg Glu Lys Ile
        435                 440                 445

Glu Lys Ile Leu Thr Phe Arg Ile Pro Tyr Tyr Val Gly Pro Leu Ala
    450                 455                 460

Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala

```
                485                 490                 495
Gln Ser Phe Ile Glu Arg Met Thr Asn Phe Asp Lys Asn Leu Pro Asn
                500                 505                 510

Glu Lys Val Leu Pro Lys His Ser Leu Leu Tyr Glu Tyr Phe Thr Val
            515                 520                 525

Tyr Asn Glu Leu Thr Lys Val Lys Tyr Val Thr Glu Gly Met Arg Lys
        530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                565                 570                 575

Phe Lys Lys Ile Glu Cys Phe Asp Ser Val Glu Ile Ser Gly Val Glu
                580                 585                 590

Asp Arg Phe Asn Ala Ser Leu Gly Thr Tyr His Asp Leu Leu Lys Ile
            595                 600                 605

Ile Lys Asp Lys Asp Phe Leu Asp Asn Glu Glu Asn Glu Asp Ile Leu
        610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                645                 650                 655

Lys Gln Leu Lys Arg Arg Arg Tyr Thr Gly Trp Gly Arg Leu Ser Arg
                660                 665                 670

Lys Leu Ile Asn Gly Ile Arg Asp Lys Gln Ser Gly Lys Thr Ile Leu
            675                 680                 685

Asp Phe Leu Lys Ser Asp Gly Phe Ala Asn Arg Asn Phe Met Gln Leu
        690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                725                 730                 735

Gly Ser Pro Ala Ile Lys Lys Gly Ile Leu Gln Thr Val Lys Val Val
                740                 745                 750

Asp Glu Leu Val Lys Val Met Gly Arg His Lys Pro Glu Asn Ile Val
            755                 760                 765

Ile Glu Met Ala Arg Glu Asn Gln Thr Thr Gln Lys Gly Gln Lys Asn
        770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                805                 810                 815

Glu Lys Leu Tyr Leu Tyr Tyr Leu Gln Asn Gly Arg Asp Met Tyr Val
                820                 825                 830

Asp Gln Glu Leu Asp Ile Asn Arg Leu Ser Asp Tyr Asp Val Asp His
            835                 840                 845

Ile Val Pro Gln Ser Phe Leu Lys Asp Asp Ser Ile Asp Asn Ala Val
        850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
                885                 890                 895

Ala Lys Leu Ile Thr Gln Arg Lys Phe Asp Asn Leu Thr Lys Ala Glu
                900                 905                 910
```

```
Arg Gly Gly Leu Ser Glu Leu Asp Lys Ala Gly Phe Ile Lys Arg Gln
        915                 920                 925

Leu Val Glu Thr Arg Gln Ile Thr Lys His Val Ala Gln Ile Leu Asp
    930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
                965                 970                 975

Asp Phe Gln Phe Tyr Lys Val Arg Glu Ile Asn Asn Tyr His His Ala
            980                 985                 990

His Asp Ala Tyr Leu Asn Ala Val Val Gly Thr Ala Leu Ile Lys Lys
        995                 1000                1005

Tyr Pro Lys Leu Glu Ser Glu Phe Val Tyr Gly Asp Tyr Lys Val
    1010                1015                1020

Tyr Asp Val Arg Lys Met Ile Ala Lys Ser Glu Gln Glu Ile Gly
    1025                1030                1035

Lys Ala Thr Ala Lys Tyr Phe Phe Tyr Ser Asn Ile Met Asn Phe
    1040                1045                1050

Phe Lys Thr Glu Ile Thr Leu Ala Asn Gly Glu Ile Arg Lys Arg
    1055                1060                1065

Pro Leu Ile Glu Thr Asn Gly Glu Thr Gly Glu Ile Val Trp Asp
    1070                1075                1080

Lys Gly Arg Asp Phe Ala Thr Val Arg Lys Val Leu Ser Met Pro
    1085                1090                1095

Gln Val Asn Ile Val Lys Lys Thr Glu Val Gln Thr Gly Gly Phe
    1100                1105                1110

Ser Lys Glu Ser Ile Leu Pro Lys Arg Asn Ser Asp Lys Leu Ile
    1115                1120                1125

Ala Arg Lys Lys Asp Trp Asp Pro Lys Lys Tyr Gly Gly Phe Asp
    1130                1135                1140

Ser Pro Thr Val Ala Tyr Ser Val Leu Val Val Ala Lys Val Glu
    1145                1150                1155

Lys Gly Lys Ser Lys Lys Leu Lys Ser Val Lys Glu Leu Leu Gly
    1160                1165                1170

Ile Thr Ile Met Glu Arg Ser Ser Phe Glu Lys Asn Pro Ile Asp
    1175                1180                1185

Phe Leu Glu Ala Lys Gly Tyr Lys Glu Val Lys Lys Asp Leu Ile
    1190                1195                1200

Ile Lys Leu Pro Lys Tyr Ser Leu Phe Glu Leu Glu Asn Gly Arg
    1205                1210                1215

Lys Arg Met Leu Ala Ser Ala Gly Glu Leu Gln Lys Gly Asn Glu
    1220                1225                1230

Leu Ala Leu Pro Ser Lys Tyr Val Asn Phe Leu Tyr Leu Ala Ser
    1235                1240                1245

His Tyr Glu Lys Leu Lys Gly Ser Pro Glu Asp Asn Glu Gln Lys
    1250                1255                1260

Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305
```

```
Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp Ser Arg Ala Asp Pro Lys Lys
    1370                1375                1380

Lys Arg Lys Val His His His His His His
    1385                1390
```

<210> SEQ ID NO 241
<211> LENGTH: 1393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

```
Met Ala Pro Lys Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
                20                  25                  30

Tyr Lys Val Pro Ser Lys Lys Phe Lys Val Leu Gly Asn Thr Asp Arg
            35                  40                  45

His Ser Ile Lys Lys Asn Leu Ile Gly Ala Leu Leu Phe Asp Ser Gly
        50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Cys Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
    130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
    210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
```

```
                    260                 265                 270
Gln Leu Ser Lys Asp Thr Tyr Asp Asp Leu Asp Asn Leu Leu Ala
                275                 280                 285
Gln Ile Gly Asp Gln Tyr Ala Asp Leu Phe Leu Ala Ala Lys Asn Leu
            290                 295                 300
Ser Asp Ala Ile Leu Leu Ser Asp Ile Leu Arg Val Asn Thr Glu Ile
305                 310                 315                 320
Thr Lys Ala Pro Leu Ser Ala Ser Met Ile Lys Arg Tyr Asp Glu His
                325                 330                 335
His Gln Asp Leu Thr Leu Leu Lys Ala Leu Val Arg Gln Gln Leu Pro
                340                 345                 350
Glu Lys Tyr Lys Glu Ile Phe Phe Asp Gln Ser Lys Asn Gly Tyr Ala
                355                 360                 365
Gly Tyr Ile Asp Gly Gly Ala Ser Gln Glu Glu Phe Tyr Lys Phe Ile
            370                 375                 380
Lys Pro Ile Leu Glu Lys Met Asp Gly Thr Glu Glu Leu Leu Val Lys
385                 390                 395                 400
Leu Asn Arg Glu Asp Leu Leu Arg Lys Gln Arg Thr Phe Asp Asn Gly
                405                 410                 415
Ser Ile Pro His Gln Ile His Leu Gly Glu Leu His Ala Ile Leu Arg
                420                 425                 430
Arg Gln Glu Asp Phe Tyr Pro Phe Leu Lys Asp Asn Arg Glu Lys Ile
            435                 440                 445
Glu Lys Ile Leu Thr Phe Arg Ile Pro Tyr Tyr Val Gly Pro Leu Ala
            450                 455                 460
Arg Gly Asn Ser Arg Phe Ala Trp Met Thr Arg Lys Ser Glu Glu Thr
465                 470                 475                 480
Ile Thr Pro Trp Asn Phe Glu Glu Val Val Asp Lys Gly Ala Ser Ala
                485                 490                 495
Gln Ser Phe Ile Glu Arg Met Thr Asn Phe Asp Lys Asn Leu Pro Asn
            500                 505                 510
Glu Lys Val Leu Pro Lys His Ser Leu Leu Tyr Glu Tyr Phe Thr Val
            515                 520                 525
Tyr Asn Glu Leu Thr Lys Val Lys Tyr Val Thr Glu Gly Met Arg Lys
            530                 535                 540
Pro Ala Phe Leu Ser Gly Glu Gln Lys Lys Ala Ile Val Asp Leu Leu
545                 550                 555                 560
Phe Lys Thr Asn Arg Lys Val Thr Val Lys Gln Leu Lys Glu Asp Tyr
                565                 570                 575
Phe Lys Lys Ile Glu Cys Phe Asp Ser Val Glu Ile Ser Gly Val Glu
            580                 585                 590
Asp Arg Phe Asn Ala Ser Leu Gly Thr Tyr His Asp Leu Leu Lys Ile
                595                 600                 605
Ile Lys Asp Lys Asp Phe Leu Asp Asn Glu Glu Asn Glu Asp Ile Leu
            610                 615                 620
Glu Asp Ile Val Leu Thr Leu Thr Leu Phe Glu Asp Arg Glu Met Ile
625                 630                 635                 640
Glu Glu Arg Leu Lys Thr Tyr Ala His Leu Phe Asp Asp Lys Val Met
                645                 650                 655
Lys Gln Leu Lys Arg Arg Arg Tyr Thr Gly Trp Gly Arg Leu Ser Arg
                660                 665                 670
Lys Leu Ile Asn Gly Ile Arg Asp Lys Gln Ser Gly Lys Thr Ile Leu
            675                 680                 685
```

```
Asp Phe Leu Lys Ser Asp Gly Phe Ala Asn Arg Asn Phe Met Gln Leu
        690             695                 700

Ile His Asp Asp Ser Leu Thr Phe Lys Glu Asp Ile Gln Lys Ala Gln
    705                 710                 715                 720

Val Ser Gly Gln Gly Asp Ser Leu His Glu His Ile Ala Asn Leu Ala
            725                 730                 735

Gly Ser Pro Ala Ile Lys Lys Gly Ile Leu Gln Thr Val Lys Val Val
            740                 745                 750

Asp Glu Leu Val Lys Val Met Gly Arg His Lys Pro Glu Asn Ile Val
            755                 760                 765

Ile Glu Met Ala Arg Glu Asn Gln Thr Thr Gln Lys Gly Gln Lys Asn
    770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                805                 810                 815

Glu Ala Leu Tyr Leu Tyr Tyr Leu Gln Asn Gly Arg Asp Met Tyr Val
                820                 825                 830

Asp Gln Glu Leu Asp Ile Asn Arg Leu Ser Asp Tyr Asp Val Asp His
            835                 840                 845

Ile Val Pro Gln Ser Phe Leu Lys Asp Asp Ser Ile Asp Asn Lys Val
    850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
                885                 890                 895

Ala Lys Leu Ile Thr Gln Arg Lys Phe Asp Asn Leu Thr Lys Ala Glu
            900                 905                 910

Arg Gly Gly Leu Ser Glu Leu Asp Lys Ala Gly Phe Ile Lys Arg Gln
            915                 920                 925

Leu Val Glu Thr Arg Gln Ile Thr Lys His Val Ala Gln Ile Leu Asp
    930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
                965                 970                 975

Asp Phe Gln Phe Tyr Lys Val Arg Glu Ile Asn Asn Tyr His His Ala
            980                 985                 990

His Asp Ala Tyr Leu Asn Ala Val Val Gly Thr Ala Leu Ile Lys Lys
        995                 1000                1005

Tyr Pro Ala Leu Glu Ser Glu Phe Val Tyr Gly Asp Tyr Lys Val
    1010                1015                1020

Tyr Asp Val Arg Lys Met Ile Ala Lys Ser Glu Gln Glu Ile Gly
    1025                1030                1035

Lys Ala Thr Ala Lys Tyr Phe Phe Tyr Ser Asn Ile Met Asn Phe
    1040                1045                1050

Phe Lys Thr Glu Ile Thr Leu Ala Asn Gly Glu Ile Arg Lys Ala
    1055                1060                1065

Pro Leu Ile Glu Thr Asn Gly Glu Thr Gly Glu Ile Val Trp Asp
    1070                1075                1080

Lys Gly Arg Asp Phe Ala Thr Val Arg Lys Val Leu Ser Met Pro
    1085                1090                1095
```

```
Gln Val Asn Ile Val Lys Lys Thr Glu Val Gln Thr Gly Gly Phe
    1100                1105                1110

Ser Lys Glu Ser Ile Leu Pro Lys Arg Asn Ser Asp Lys Leu Ile
    1115                1120                1125

Ala Arg Lys Lys Asp Trp Asp Pro Lys Lys Tyr Gly Gly Phe Asp
    1130                1135                1140

Ser Pro Thr Val Ala Tyr Ser Val Leu Val Val Ala Lys Val Glu
    1145                1150                1155

Lys Gly Lys Ser Lys Lys Leu Lys Ser Val Lys Glu Leu Leu Gly
    1160                1165                1170

Ile Thr Ile Met Glu Arg Ser Ser Phe Glu Lys Asn Pro Ile Asp
    1175                1180                1185

Phe Leu Glu Ala Lys Gly Tyr Lys Glu Val Lys Lys Asp Leu Ile
    1190                1195                1200

Ile Lys Leu Pro Lys Tyr Ser Leu Phe Glu Leu Glu Asn Gly Arg
    1205                1210                1215

Lys Arg Met Leu Ala Ser Ala Gly Glu Leu Gln Lys Gly Asn Glu
    1220                1225                1230

Leu Ala Leu Pro Ser Lys Tyr Val Asn Phe Leu Tyr Leu Ala Ser
    1235                1240                1245

His Tyr Glu Lys Leu Lys Gly Ser Pro Glu Asp Asn Glu Gln Lys
    1250                1255                1260

Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305

Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp Ser Arg Ala Asp Pro Lys Lys
    1370                1375                1380

Lys Arg Lys Val His His His His His His
    1385                1390

<210> SEQ ID NO 242
<211> LENGTH: 1393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Met Ala Pro Lys Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
                20                  25                  30

Tyr Lys Val Pro Ser Lys Lys Phe Lys Val Leu Gly Asn Thr Asp Arg
```

```
                35                  40                  45
His Ser Ile Lys Lys Asn Leu Ile Gly Ala Leu Leu Phe Asp Ser Gly
 50                  55                  60

Glu Thr Ala Glu Ala Thr Arg Leu Lys Arg Thr Ala Arg Arg Tyr
 65                  70                  75                  80

Thr Arg Arg Lys Asn Arg Ile Cys Tyr Leu Gln Glu Ile Phe Ser Asn
                     85                  90                  95

Glu Met Ala Lys Val Asp Asp Ser Phe Phe His Arg Leu Glu Glu Ser
                100                 105                 110

Phe Leu Val Glu Glu Asp Lys Lys His Glu Arg His Pro Ile Phe Gly
            115                 120                 125

Asn Ile Val Asp Glu Val Ala Tyr His Glu Lys Tyr Pro Thr Ile Tyr
        130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
    210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Leu Asp Asn Leu Leu Ala
        275                 280                 285

Gln Ile Gly Asp Gln Tyr Ala Asp Leu Phe Leu Ala Ala Lys Asn Leu
    290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
            340                 345                 350

Glu Lys Tyr Lys Glu Ile Phe Phe Asp Gln Ser Lys Asn Gly Tyr Ala
        355                 360                 365

Gly Tyr Ile Asp Gly Gly Ala Ser Gln Glu Glu Phe Tyr Lys Phe Ile
    370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
            420                 425                 430

Arg Gln Glu Asp Phe Tyr Pro Phe Leu Lys Asp Asn Arg Glu Lys Ile
        435                 440                 445

Glu Lys Ile Leu Thr Phe Arg Ile Pro Tyr Tyr Val Gly Pro Leu Ala
    450                 455                 460
```

```
Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala
                485                 490                 495

Gln Ser Phe Ile Glu Arg Met Thr Asn Phe Asp Lys Asn Leu Pro Asn
            500                 505                 510

Glu Lys Val Leu Pro Lys His Ser Leu Leu Tyr Glu Tyr Phe Thr Val
        515                 520                 525

Tyr Asn Glu Leu Thr Lys Val Lys Tyr Val Thr Glu Gly Met Arg Lys
    530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                565                 570                 575

Phe Lys Lys Ile Glu Cys Phe Asp Ser Val Glu Ile Ser Gly Val Glu
            580                 585                 590

Asp Arg Phe Asn Ala Ser Leu Gly Thr Tyr His Asp Leu Leu Lys Ile
        595                 600                 605

Ile Lys Asp Lys Asp Phe Leu Asp Asn Glu Glu Asn Glu Asp Ile Leu
    610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                645                 650                 655

Lys Gln Leu Lys Arg Arg Arg Tyr Thr Gly Trp Gly Arg Leu Ser Arg
            660                 665                 670

Lys Leu Ile Asn Gly Ile Arg Asp Lys Gln Ser Gly Lys Thr Ile Leu
        675                 680                 685

Asp Phe Leu Lys Ser Asp Gly Phe Ala Asn Arg Asn Phe Met Gln Leu
    690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                725                 730                 735

Gly Ser Pro Ala Ile Lys Lys Gly Ile Leu Gln Thr Val Lys Val Val
            740                 745                 750

Asp Glu Leu Val Lys Val Met Gly Arg His Lys Pro Glu Asn Ile Val
        755                 760                 765

Ile Glu Met Ala Arg Glu Asn Gln Thr Thr Gln Lys Gly Gln Lys Asn
    770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                805                 810                 815

Glu Lys Leu Tyr Leu Tyr Tyr Leu Gln Asn Gly Arg Asp Met Tyr Val
            820                 825                 830

Asp Gln Glu Leu Asp Ile Asn Arg Leu Ser Asp Tyr Asp Val Asp His
        835                 840                 845

Ile Val Pro Gln Ser Phe Leu Ala Asp Asp Ser Ile Asp Asn Lys Val
    850                 855                 860

Leu Thr Arg Ser Asp Lys Asn Arg Gly Lys Ser Asp Asn Val Pro Ser
865                 870                 875                 880
```

```
Glu Glu Val Val Lys Lys Met Lys Asn Tyr Trp Arg Gln Leu Leu Asn
                885                 890                 895
Ala Lys Leu Ile Thr Gln Arg Lys Phe Asp Asn Leu Thr Lys Ala Glu
            900                 905                 910
Arg Gly Gly Leu Ser Glu Leu Asp Lys Ala Gly Phe Ile Lys Arg Gln
            915                 920                 925
Leu Val Glu Thr Arg Gln Ile Thr Lys His Val Ala Gln Ile Leu Asp
            930                 935                 940
Ser Arg Met Asn Thr Lys Tyr Asp Glu Asn Asp Lys Leu Ile Arg Glu
945                 950                 955                 960
Val Lys Val Ile Thr Leu Lys Ser Lys Leu Val Ser Asp Phe Arg Lys
                965                 970                 975
Asp Phe Gln Phe Tyr Lys Val Arg Glu Ile Asn Asn Tyr His His Ala
            980                 985                 990
His Asp Ala Tyr Leu Asn Ala Val  Val Gly Thr Ala Leu  Ile Lys Lys
            995                 1000                1005
Tyr Pro  Ala Leu Glu Ser Glu  Phe Val Tyr Gly Asp  Tyr Lys Val
            1010                1015                1020
Tyr Asp  Val Arg Lys Met Ile  Ala Lys Ser Glu Gln  Glu Ile Gly
            1025                1030                1035
Lys Ala  Thr Ala Lys Tyr Phe  Phe Tyr Ser Asn Ile  Met Asn Phe
            1040                1045                1050
Phe Lys  Thr Glu Ile Thr Leu  Ala Asn Gly Glu Ile  Arg Lys Ala
            1055                1060                1065
Pro Leu  Ile Glu Thr Asn Gly  Glu Thr Gly Glu Ile  Val Trp Asp
            1070                1075                1080
Lys Gly  Arg Asp Phe Ala Thr  Val Arg Lys Val Leu  Ser Met Pro
            1085                1090                1095
Gln Val  Asn Ile Val Lys Lys  Thr Glu Val Gln Thr  Gly Gly Phe
            1100                1105                1110
Ser Lys  Glu Ser Ile Leu Pro  Lys Arg Asn Ser Asp  Lys Leu Ile
            1115                1120                1125
Ala Arg  Lys Lys Asp Trp Asp  Pro Lys Lys Tyr Gly  Gly Phe Asp
            1130                1135                1140
Ser Pro  Thr Val Ala Tyr Ser  Val Leu Val Val Ala  Lys Val Glu
            1145                1150                1155
Lys Gly  Lys Ser Lys Lys Leu  Lys Ser Val Lys Glu  Leu Leu Gly
            1160                1165                1170
Ile Thr  Ile Met Glu Arg Ser  Ser Phe Glu Lys Asn  Pro Ile Asp
            1175                1180                1185
Phe Leu  Glu Ala Lys Gly Tyr  Lys Glu Val Lys Lys  Asp Leu Ile
            1190                1195                1200
Ile Lys  Leu Pro Lys Tyr Ser  Leu Phe Glu Leu Glu  Asn Gly Arg
            1205                1210                1215
Lys Arg  Met Leu Ala Ser Ala  Gly Glu Leu Gln Lys  Gly Asn Glu
            1220                1225                1230
Leu Ala  Leu Pro Ser Lys Tyr  Val Asn Phe Leu Tyr  Leu Ala Ser
            1235                1240                1245
His Tyr  Glu Lys Leu Lys Gly  Ser Pro Glu Asp Asn  Glu Gln Lys
            1250                1255                1260
Gln Leu  Phe Val Glu Gln His  Lys His Tyr Leu Asp  Glu Ile Ile
            1265                1270                1275
Glu Gln  Ile Ser Glu Phe Ser  Lys Arg Val Ile Leu  Ala Asp Ala
```

```
                1280                1285                1290

Asn Leu Asp Lys Val Leu Ser Ala Tyr Asn Lys His Arg Asp Lys
        1295                1300                1305

Pro Ile Arg Glu Gln Ala Glu Asn Ile Ile His Leu Phe Thr Leu
        1310                1315                1320

Thr Asn Leu Gly Ala Pro Ala Ala Phe Lys Tyr Phe Asp Thr Thr
        1325                1330                1335

Ile Asp Arg Lys Arg Tyr Thr Ser Thr Lys Glu Val Leu Asp Ala
        1340                1345                1350

Thr Leu Ile His Gln Ser Ile Thr Gly Leu Tyr Glu Thr Arg Ile
        1355                1360                1365

Asp Leu Ser Gln Leu Gly Gly Asp Ser Arg Ala Asp Pro Lys Lys
        1370                1375                1380

Lys Arg Lys Val His His His His His His
        1385                1390

<210> SEQ ID NO 243
<211> LENGTH: 1393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

Met Ala Pro Lys Lys Lys Arg Lys Val Asp Lys Lys Tyr Ser Ile Gly
1               5                   10                  15

Leu Asp Ile Gly Thr Asn Ser Val Gly Trp Ala Val Ile Thr Asp Glu
                20                  25                  30

Tyr Lys Val Pro Ser Lys Lys Phe Lys Val Leu Gly Asn Thr Asp Arg
            35                  40                  45

His Ser Ile Lys Lys Asn Leu Ile Gly Ala Leu Leu Phe Asp Ser Gly
        50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Cys Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
    130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
    210                 215                 220

Ser Lys Ser Arg Arg Leu Glu Asn Leu Ile Ala Gln Leu Pro Gly Glu
225                 230                 235                 240
```

-continued

```
Lys Lys Asn Gly Leu Phe Gly Asn Leu Ile Ala Leu Ser Leu Gly Leu
            245                 250                 255

Thr Pro Asn Phe Lys Ser Asn Phe Asp Leu Ala Glu Asp Ala Lys Leu
        260                 265                 270

Gln Leu Ser Lys Asp Thr Tyr Asp Asp Leu Asp Asn Leu Leu Ala
        275                 280                 285

Gln Ile Gly Asp Gln Tyr Ala Asp Leu Phe Leu Ala Ala Lys Asn Leu
    290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
            325                 330                 335

His Gln Asp Leu Thr Leu Leu Lys Ala Leu Val Arg Gln Gln Leu Pro
        340                 345                 350

Glu Lys Tyr Lys Glu Ile Phe Phe Asp Gln Ser Lys Asn Gly Tyr Ala
        355                 360                 365

Gly Tyr Ile Asp Gly Gly Ala Ser Gln Glu Glu Phe Tyr Lys Phe Ile
    370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
            405                 410                 415

Ser Ile Pro His Gln Ile His Leu Gly Glu Leu His Ala Ile Leu Arg
        420                 425                 430

Arg Gln Glu Asp Phe Tyr Pro Phe Leu Lys Asp Asn Arg Glu Lys Ile
        435                 440                 445

Glu Lys Ile Leu Thr Phe Arg Ile Pro Tyr Tyr Val Gly Pro Leu Ala
    450                 455                 460

Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala
            485                 490                 495

Gln Ser Phe Ile Glu Arg Met Thr Ala Phe Asp Lys Asn Leu Pro Asn
        500                 505                 510

Glu Lys Val Leu Pro Lys His Ser Leu Leu Tyr Glu Tyr Phe Thr Val
        515                 520                 525

Tyr Asn Glu Leu Thr Lys Val Lys Tyr Val Thr Glu Gly Met Arg Lys
    530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
            565                 570                 575

Phe Lys Lys Ile Glu Cys Phe Asp Ser Val Glu Ile Ser Gly Val Glu
        580                 585                 590

Asp Arg Phe Asn Ala Ser Leu Gly Thr Tyr His Asp Leu Leu Lys Ile
        595                 600                 605

Ile Lys Asp Lys Asp Phe Leu Asp Asn Glu Glu Asn Glu Asp Ile Leu
    610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
            645                 650                 655
```

```
Lys Gln Leu Lys Arg Arg Arg Tyr Thr Gly Trp Gly Ala Leu Ser Arg
                660                 665                 670

Lys Leu Ile Asn Gly Ile Arg Asp Lys Gln Ser Gly Lys Thr Ile Leu
                675                 680                 685

Asp Phe Leu Lys Ser Asp Gly Phe Ala Asn Arg Asn Phe Met Ala Leu
                690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                725                 730                 735

Gly Ser Pro Ala Ile Lys Lys Gly Ile Leu Gln Thr Val Lys Val Val
                740                 745                 750

Asp Glu Leu Val Lys Val Met Gly Arg His Lys Pro Glu Asn Ile Val
                755                 760                 765

Ile Glu Met Ala Arg Glu Asn Gln Thr Thr Gln Lys Gly Gln Lys Asn
                770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
                805                 810                 815

Glu Lys Leu Tyr Leu Tyr Tyr Leu Gln Asn Gly Arg Asp Met Tyr Val
                820                 825                 830

Asp Gln Glu Leu Asp Ile Asn Arg Leu Ser Asp Tyr Asp Val Asp His
                835                 840                 845

Ile Val Pro Gln Ser Phe Leu Lys Asp Asp Ser Ile Asp Asn Lys Val
850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
                885                 890                 895

Ala Lys Leu Ile Thr Gln Arg Lys Phe Asp Asn Leu Thr Lys Ala Glu
                900                 905                 910

Arg Gly Gly Leu Ser Glu Leu Asp Lys Ala Gly Phe Ile Lys Arg Gln
                915                 920                 925

Leu Val Glu Thr Arg Ala Ile Thr Lys His Val Ala Gln Ile Leu Asp
                930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
                965                 970                 975

Asp Phe Gln Phe Tyr Lys Val Arg Glu Ile Asn Asn Tyr His His Ala
                980                 985                 990

His Asp Ala Tyr Leu Asn Ala Val  Val Gly Thr Ala Leu  Ile Lys Lys
                995                 1000                1005

Tyr Pro Lys Leu Glu Ser Glu  Phe Val Tyr Gly Asp  Tyr Lys Val
    1010                1015                1020

Tyr Asp Val Arg Lys Met Ile  Ala Lys Ser Glu Gln  Glu Ile Gly
    1025                1030                1035

Lys Ala  Thr Ala Lys Tyr Phe  Phe Tyr Ser Asn Ile  Met Asn Phe
    1040                1045                1050

Phe Lys  Thr Glu Ile Thr Leu  Ala Asn Gly Glu Ile  Arg Lys Arg
    1055                1060                1065

Pro Leu  Ile Glu Thr Asn Gly  Glu Thr Gly Glu Ile  Val Trp Asp
```

|      |      |      |      |      | 1070 |      |      |      | 1075 |      |      |      | 1080 |      |
| ---- | ---- | ---- | ---- | ---- | ---- | ---- | ---- | ---- | ---- | ---- | ---- | ---- | ---- | ---- |

Lys Gly Arg Asp Phe Ala Thr Val Arg Lys Val Leu Ser Met Pro
        1085                    1090                    1095

Gln Val Asn Ile Val Lys Lys Thr Glu Val Gln Thr Gly Gly Phe
        1100                    1105                    1110

Ser Lys Glu Ser Ile Leu Pro Lys Arg Asn Ser Asp Lys Leu Ile
        1115                    1120                    1125

Ala Arg Lys Lys Asp Trp Asp Pro Lys Lys Tyr Gly Gly Phe Asp
        1130                    1135                    1140

Ser Pro Thr Val Ala Tyr Ser Val Leu Val Val Ala Lys Val Glu
        1145                    1150                    1155

Lys Gly Lys Ser Lys Lys Leu Lys Ser Val Lys Glu Leu Leu Gly
        1160                    1165                    1170

Ile Thr Ile Met Glu Arg Ser Ser Phe Glu Lys Asn Pro Ile Asp
        1175                    1180                    1185

Phe Leu Glu Ala Lys Gly Tyr Lys Glu Val Lys Lys Asp Leu Ile
        1190                    1195                    1200

Ile Lys Leu Pro Lys Tyr Ser Leu Phe Glu Leu Glu Asn Gly Arg
        1205                    1210                    1215

Lys Arg Met Leu Ala Ser Ala Gly Glu Leu Gln Lys Gly Asn Glu
        1220                    1225                    1230

Leu Ala Leu Pro Ser Lys Tyr Val Asn Phe Leu Tyr Leu Ala Ser
        1235                    1240                    1245

His Tyr Glu Lys Leu Lys Gly Ser Pro Glu Asp Asn Glu Gln Lys
        1250                    1255                    1260

Gln Leu Phe Val Glu Gln His Lys His Tyr Leu Asp Glu Ile Ile
        1265                    1270                    1275

Glu Gln Ile Ser Glu Phe Ser Lys Arg Val Ile Leu Ala Asp Ala
        1280                    1285                    1290

Asn Leu Asp Lys Val Leu Ser Ala Tyr Asn Lys His Arg Asp Lys
        1295                    1300                    1305

Pro Ile Arg Glu Gln Ala Glu Asn Ile Ile His Leu Phe Thr Leu
        1310                    1315                    1320

Thr Asn Leu Gly Ala Pro Ala Ala Phe Lys Tyr Phe Asp Thr Thr
        1325                    1330                    1335

Ile Asp Arg Lys Arg Tyr Thr Ser Thr Lys Glu Val Leu Asp Ala
        1340                    1345                    1350

Thr Leu Ile His Gln Ser Ile Thr Gly Leu Tyr Glu Thr Arg Ile
        1355                    1360                    1365

Asp Leu Ser Gln Leu Gly Gly Asp Ser Arg Ala Asp Pro Lys Lys
        1370                    1375                    1380

Lys Arg Lys Val His His His His His His
        1385                    1390

<210> SEQ ID NO 244
<211> LENGTH: 1386
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 244

Met Ala Pro Lys Lys Lys Arg Lys Val Asp Lys Lys Tyr Ser Ile Gly
1              5                  10                15

```
Leu Asp Ile Gly Thr Asn Ser Val Gly Trp Ala Val Ile Thr Asp Glu
            20                  25                  30

Tyr Lys Val Pro Ser Lys Lys Phe Lys Val Leu Gly Asn Thr Asp Arg
        35                  40                  45

His Ser Ile Lys Lys Asn Leu Ile Gly Ala Leu Leu Phe Asp Ser Gly
50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Leu Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Leu Asp Asn Leu Leu Ala
        275                 280                 285

Gln Ile Gly Asp Gln Tyr Ala Asp Leu Phe Leu Ala Ala Lys Asn Leu
290                 295                 300

Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
            340                 345                 350

Glu Lys Tyr Lys Glu Ile Phe Phe Asp Gln Ser Lys Asn Gly Tyr Ala
        355                 360                 365

Gly Tyr Ile Asp Gly Gly Ala Ser Gln Glu Glu Phe Tyr Lys Phe Ile
370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
            420                 425                 430
```

```
Arg Gln Glu Asp Phe Tyr Pro Phe Leu Lys Asp Asn Arg Glu Lys Ile
            435                 440                 445
Glu Lys Ile Leu Thr Phe Arg Ile Pro Tyr Tyr Val Gly Pro Leu Ala
    450                 455                 460
Arg Gly Asn Ser Arg Phe Ala Trp Met Thr Arg Lys Ser Glu Glu Thr
465                 470                 475                 480
Ile Thr Pro Trp Asn Phe Glu Glu Val Val Asp Lys Gly Ala Ser Ala
                485                 490                 495
Gln Ser Phe Ile Glu Arg Met Thr Asn Phe Asp Lys Asn Leu Pro Asn
                500                 505                 510
Glu Lys Val Leu Pro Lys His Ser Leu Leu Tyr Glu Tyr Phe Thr Val
            515                 520                 525
Tyr Asn Glu Leu Thr Lys Val Lys Tyr Val Thr Glu Gly Met Arg Lys
        530                 535                 540
Pro Ala Phe Leu Ser Gly Glu Gln Lys Lys Ala Ile Val Asp Leu Leu
545                 550                 555                 560
Phe Lys Thr Asn Arg Lys Val Thr Val Lys Gln Leu Lys Glu Asp Tyr
                565                 570                 575
Phe Lys Lys Ile Glu Glu Phe Asp Ser Val Glu Ile Ser Gly Val Glu
            580                 585                 590
Asp Arg Phe Asn Ala Ser Leu Gly Thr Tyr His Asp Leu Leu Lys Ile
        595                 600                 605
Ile Lys Asp Lys Asp Phe Leu Asp Asn Glu Glu Asn Glu Asp Ile Leu
    610                 615                 620
Glu Asp Ile Val Leu Thr Leu Thr Leu Phe Glu Asp Arg Glu Met Ile
625                 630                 635                 640
Glu Glu Arg Leu Lys Thr Tyr Ala His Leu Phe Asp Asp Lys Val Met
                645                 650                 655
Lys Gln Leu Lys Arg Arg Arg Tyr Thr Gly Trp Gly Arg Leu Ser Arg
            660                 665                 670
Lys Leu Ile Asn Gly Ile Arg Asp Lys Gln Ser Gly Lys Thr Ile Leu
        675                 680                 685
Asp Phe Leu Lys Ser Asp Gly Phe Ala Asn Arg Asn Phe Met Gln Leu
    690                 695                 700
Ile His Asp Asp Ser Leu Thr Phe Lys Glu Asp Ile Gln Lys Ala Gln
705                 710                 715                 720
Val Ser Gly Gln Gly Asp Ser Leu His Glu His Ile Ala Asn Leu Ala
                725                 730                 735
Gly Ser Pro Ala Ile Lys Lys Gly Ile Leu Gln Thr Val Lys Val Val
            740                 745                 750
Asp Glu Leu Val Lys Val Met Gly Arg His Lys Pro Glu Asn Ile Val
        755                 760                 765
Ile Glu Met Ala Arg Glu Asn Gln Thr Thr Gln Lys Gly Gln Lys Asn
    770                 775                 780
Ser Arg Glu Arg Met Lys Arg Ile Glu Glu Gly Ile Lys Glu Leu Gly
785                 790                 795                 800
Ser Gln Ile Leu Lys Glu His Pro Val Glu Asn Thr Gln Leu Gln Asn
                805                 810                 815
Glu Lys Leu Tyr Leu Tyr Tyr Leu Gln Asn Gly Arg Asp Met Tyr Val
            820                 825                 830
Asp Gln Glu Leu Asp Ile Asn Arg Leu Ser Asp Tyr Asp Val Asp His
        835                 840                 845
Ile Val Pro Gln Ser Phe Leu Lys Asp Asp Ser Ile Asp Asn Lys Val
```

-continued

```
            850                 855                 860
Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
                    885                 890                 895

Ala Lys Leu Ile Thr Gln Arg Lys Phe Asp Asn Leu Thr Lys Ala Glu
                900                 905                 910

Arg Gly Gly Leu Ser Glu Leu Asp Lys Ala Gly Phe Ile Lys Arg Gln
            915                 920                 925

Leu Val Glu Thr Arg Gln Ile Thr Lys His Val Ala Gln Ile Leu Asp
        930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
                    965                 970                 975

Asp Phe Gln Phe Tyr Lys Val Arg Glu Ile Asn Asn Tyr His His Ala
                980                 985                 990

His Asp Ala Tyr Leu Asn Ala Val Val Gly Thr Ala Leu Ile Lys Lys
            995                 1000                1005

Tyr Pro Lys Leu Glu Ser Glu Phe Val Tyr Gly Asp Tyr Lys Val
        1010                1015                1020

Tyr Asp Val Arg Lys Met Ile Ala Lys Ser Glu Gln Glu Ile Gly
        1025                1030                1035

Lys Ala Thr Ala Lys Tyr Phe Phe Tyr Ser Asn Ile Met Asn Phe
        1040                1045                1050

Phe Lys Thr Glu Ile Thr Leu Ala Asn Gly Glu Ile Arg Lys Arg
        1055                1060                1065

Pro Leu Ile Glu Thr Asn Gly Glu Thr Gly Glu Ile Val Trp Asp
        1070                1075                1080

Lys Gly Arg Asp Phe Ala Thr Val Arg Lys Val Leu Ser Met Pro
        1085                1090                1095

Gln Val Asn Ile Val Lys Lys Thr Glu Val Gln Thr Gly Gly Phe
        1100                1105                1110

Ser Lys Glu Ser Ile Leu Pro Lys Arg Asn Ser Asp Lys Leu Ile
        1115                1120                1125

Ala Arg Lys Lys Asp Trp Asp Pro Lys Lys Tyr Gly Gly Phe Asp
        1130                1135                1140

Ser Pro Thr Val Ala Tyr Ser Val Leu Val Val Ala Lys Val Glu
        1145                1150                1155

Lys Gly Lys Ser Lys Lys Leu Lys Ser Val Lys Glu Leu Leu Gly
        1160                1165                1170

Ile Thr Ile Met Glu Arg Ser Ser Phe Glu Lys Asn Pro Ile Asp
        1175                1180                1185

Phe Leu Glu Ala Lys Gly Tyr Lys Glu Val Lys Lys Asp Leu Ile
        1190                1195                1200

Ile Lys Leu Pro Lys Tyr Ser Leu Phe Glu Leu Glu Asn Gly Arg
        1205                1210                1215

Lys Arg Met Leu Ala Ser Ala Gly Glu Leu Gln Lys Gly Asn Glu
        1220                1225                1230

Leu Ala Leu Pro Ser Lys Tyr Val Asn Phe Leu Tyr Leu Ala Ser
        1235                1240                1245

His Tyr Glu Lys Leu Lys Gly Ser Pro Glu Asp Asn Glu Gln Lys
        1250                1255                1260
```

-continued

```
Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305

Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp Ser Arg Ala Asp His His His
    1370                1375                1380

His His His
    1385

<210> SEQ ID NO 245
<211> LENGTH: 835
<212> TYPE: PRT
<213> ORGANISM: Homo sapiens

<400> SEQUENCE: 245

Met Ser Arg Arg Lys Gln Gly Lys Pro Gln His Leu Ser Lys Arg Glu
1               5                   10                  15

Phe Ser Pro Glu Pro Leu Glu Ala Ile Leu Thr Asp Asp Glu Pro Asp
                20                  25                  30

His Gly Pro Leu Gly Ala Pro Glu Gly Asp His Asp Leu Leu Thr Cys
            35                  40                  45

Gly Gln Cys Gln Met Asn Phe Pro Leu Gly Asp Ile Leu Ile Phe Ile
        50                  55                  60

Glu His Lys Arg Lys Gln Cys Asn Gly Ser Leu Cys Leu Glu Lys Ala
65                  70                  75                  80

Val Asp Lys Pro Pro Ser Pro Ser Pro Ile Glu Met Lys Lys Ala Ser
                85                  90                  95

Asn Pro Val Glu Val Gly Ile Gln Val Thr Pro Glu Asp Asp Asp Cys
            100                 105                 110

Leu Ser Thr Ser Ser Arg Gly Ile Cys Pro Lys Gln Glu His Ile Ala
        115                 120                 125

Asp Lys Leu Leu His Trp Arg Gly Leu Ser Ser Pro Arg Ser Ala His
    130                 135                 140

Gly Ala Leu Ile Pro Thr Pro Gly Met Ser Ala Glu Tyr Ala Pro Gln
145                 150                 155                 160

Gly Ile Cys Lys Asp Glu Pro Ser Ser Tyr Thr Cys Thr Thr Cys Lys
                165                 170                 175

Gln Pro Phe Thr Ser Ala Trp Phe Leu Leu Gln His Ala Gln Asn Thr
            180                 185                 190

His Gly Leu Arg Ile Tyr Leu Glu Ser Glu His Gly Ser Pro Leu Thr
        195                 200                 205

Pro Arg Val Gly Ile Pro Ser Gly Leu Gly Ala Glu Cys Pro Ser Gln
    210                 215                 220

Pro Pro Leu His Gly Ile His Ile Ala Asp Asn Asn Pro Phe Asn Leu
```

```
              225                 230                 235                 240
Leu Arg Ile Pro Gly Ser Val Ser Arg Glu Ala Ser Gly Leu Ala Glu
                    245                 250                 255
Gly Arg Phe Pro Pro Thr Pro Pro Leu Phe Ser Pro Pro Arg His
                260                 265                 270
His Leu Asp Pro His Arg Ile Glu Arg Leu Gly Ala Glu Met Ala
                275                 280                 285
Leu Ala Thr His His Pro Ser Ala Phe Asp Arg Val Leu Arg Leu Asn
            290                 295                 300
Pro Met Ala Met Glu Pro Ala Met Asp Phe Ser Arg Arg Leu Arg
305                 310                 315                 320
Glu Leu Ala Gly Asn Thr Ser Ser Pro Pro Leu Ser Pro Gly Arg Pro
                    325                 330                 335
Ser Pro Met Gln Arg Leu Leu Gln Pro Phe Gln Pro Gly Ser Lys Pro
                340                 345                 350
Pro Phe Leu Ala Thr Pro Pro Leu Pro Pro Leu Gln Ser Ala Pro Pro
            355                 360                 365
Pro Ser Gln Pro Pro Val Lys Ser Lys Ser Cys Glu Phe Cys Gly Lys
        370                 375                 380
Thr Phe Lys Phe Gln Ser Asn Leu Val Val His Arg Arg Ser His Thr
385                 390                 395                 400
Gly Glu Lys Pro Tyr Lys Cys Asn Leu Cys Asp His Ala Cys Thr Gln
                    405                 410                 415
Ala Ser Lys Leu Lys Arg His Met Lys Thr His Met His Lys Ser Ser
                420                 425                 430
Pro Met Thr Val Lys Ser Asp Asp Gly Leu Ser Thr Ala Ser Ser Pro
            435                 440                 445
Glu Pro Gly Thr Ser Asp Leu Val Gly Ser Ala Ser Ser Ala Leu Lys
        450                 455                 460
Ser Val Val Ala Lys Phe Lys Ser Glu Asn Asp Pro Asn Leu Ile Pro
465                 470                 475                 480
Glu Asn Gly Asp Glu Glu Glu Glu Asp Asp Glu Glu Glu Glu
                    485                 490                 495
Glu Glu Glu Glu Glu Glu Glu Leu Thr Glu Ser Glu Arg Val Asp
                500                 505                 510
Tyr Gly Phe Gly Leu Ser Leu Glu Ala Ala Arg His His Glu Asn Ser
            515                 520                 525
Ser Arg Gly Ala Val Val Gly Val Gly Asp Glu Ser Arg Ala Leu Pro
        530                 535                 540
Asp Val Met Gln Gly Met Val Leu Ser Ser Met Gln His Phe Ser Glu
545                 550                 555                 560
Ala Phe His Gln Val Leu Gly Glu Lys His Lys Arg Gly His Leu Ala
                    565                 570                 575
Glu Ala Glu Gly His Arg Asp Thr Cys Asp Glu Asp Ser Val Ala Gly
                580                 585                 590
Glu Ser Asp Arg Ile Asp Asp Gly Thr Val Asn Gly Arg Gly Cys Ser
            595                 600                 605
Pro Gly Glu Ser Ala Ser Gly Leu Ser Lys Lys Leu Leu Leu Gly
        610                 615                 620
Ser Pro Ser Ser Leu Ser Pro Phe Ser Lys Arg Ile Lys Leu Glu Lys
625                 630                 635                 640
Glu Phe Asp Leu Pro Pro Ala Ala Met Pro Asn Thr Glu Asn Val Tyr
                    645                 650                 655
```

```
Ser Gln Trp Leu Ala Gly Tyr Ala Ala Ser Arg Gln Leu Lys Asp Pro
            660                 665                 670

Phe Leu Ser Phe Gly Asp Ser Arg Gln Ser Pro Phe Ala Ser Ser Ser
        675                 680                 685

Glu His Ser Ser Glu Asn Gly Ser Leu Arg Phe Ser Thr Pro Pro Gly
    690                 695                 700

Glu Leu Asp Gly Gly Ile Ser Gly Arg Ser Gly Thr Gly Ser Gly Gly
705                 710                 715                 720

Ser Thr Pro His Ile Ser Gly Pro Gly Pro Arg Pro Ser Ser Lys
                725                 730                 735

Glu Gly Arg Arg Ser Asp Thr Cys Glu Tyr Cys Gly Lys Val Phe Lys
                740                 745                 750

Asn Cys Ser Asn Leu Thr Val His Arg Arg Ser His Thr Gly Glu Arg
                755                 760                 765

Pro Tyr Lys Cys Glu Leu Cys Asn Tyr Ala Cys Ala Gln Ser Ser Lys
            770                 775                 780

Leu Thr Arg His His Met Lys Thr His Gly Gln Val Gly Lys Asp Val Tyr
785                 790                 795                 800

Lys Cys Glu Ile Cys Lys Met Pro Phe Ser Val Tyr Ser Thr Leu Glu
                805                 810                 815

Lys His Met Lys Lys Trp His Ser Asp Arg Val Leu Asn Asn Asp Ile
            820                 825                 830

Lys Thr Glu
        835

<210> SEQ ID NO 246
<211> LENGTH: 74
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
aacagcauag caaguuaaaa uaaggcuagu ccguuaucaa cuugaaaaag uggcaccgag    60
ucggugcuuu uuuu                                                     74

<210> SEQ ID NO 247
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 247

His His His His His His
1               5

<210> SEQ ID NO 248
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 248
```

His His His His His His His His
1               5

<210> SEQ ID NO 249
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: MISC_FEATURE
<222> LOCATION: (1)..(10)
<223> OTHER INFORMATION: /note="This sequence may encompass 1-10
      nucleotides"

<400> SEQUENCE: 249
uuuuuuuuuu                                                              10

<210> SEQ ID NO 250
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: MISC_FEATURE
<222> LOCATION: (1)..(10)
<223> OTHER INFORMATION: /note="This sequence may encompass 1-10
      nucleotides"

<400> SEQUENCE: 250
aaaaaaaaaa                                                              10

<210> SEQ ID NO 251
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 251
nnnnnnnnnn nnnnnnnnnn guuuuagagc uaugcu                                 36

<210> SEQ ID NO 252
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 252
nnnnnnnnnn nnnnnnnnnn guuuuagagc uaugcuguuu ug                          42

```
<210> SEQ ID NO 253
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 253
nnnnnnnnnn nnnnnnnnnn guuuuagagc uaugcuguuu ug                    42

<210> SEQ ID NO 254
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, u, g, unknown or other

<400> SEQUENCE: 254
nnnnnnnnnn nnnnnnnnnn guuuuagagc uagaaauagc aaguuaaaau aaggcuaguc    60
cguuaucaac uugaaaaagu ggcaccgagu cggugcuuuu                        100

<210> SEQ ID NO 255
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, u, g, unknown or other

<400> SEQUENCE: 255
nnnnnnnnnn nnnnnnnnnn guuuuagagc uagaaauagc aaguuaaaau aaggcuaguc    60
cguuaucaac uugaaaaagu ggcaccgagu cggugcuuuu                        100

<210> SEQ ID NO 256
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, u, g, unknown or other

<400> SEQUENCE: 256
nnnnnnnnnn nnnnnnnnnn guuuuagagc uagaaauagc aaguuaaaau aaggcuaguc    60
cguuaucaac uugaaaaagu ggcaccgagu cggugcuuuu                        100

<210> SEQ ID NO 257
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 257
tgctgagatg aaacaggcgt                                              20

<210> SEQ ID NO 258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 258
ttaggcatcc acaagggctg                                              20

<210> SEQ ID NO 259
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 259
gctctacaaa tggaacccaa cc                                           22

<210> SEQ ID NO 260
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 260
ctgctctgat ctctaacacc tca                                          23

<210> SEQ ID NO 261
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
gaagatacag cttgcctccg a                                            21

<210> SEQ ID NO 262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 262
```
ttgctgagat gaaacaggcg t                                    21

<210> SEQ ID NO 263
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
acggataagt agatattgag gtaagc                               26

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
gtctctttca gttagcagtg g                                    21

<210> SEQ ID NO 265
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 265
actgcgctga aactgtggct ttatag                               26

<210> SEQ ID NO 266
<211> LENGTH: 20
<212> TYPE: DNA
<213> ORGANISM: Homo sapiens

<400> SEQUENCE: 266
ccctttagct agttttcttc                                      20

<210> SEQ ID NO 267
<211> LENGTH: 16
<212> TYPE: DNA
<213> ORGANISM: Homo sapiens

<400> SEQUENCE: 267
ggacttcttt tgtcag                                          16

<210> SEQ ID NO 268
<211> LENGTH: 15
<212> TYPE: DNA
<213> ORGANISM: Homo sapiens

<400> SEQUENCE: 268
ttagctagtt tcctt                                           15

<210> SEQ ID NO 269
<211> LENGTH: 20
<212> TYPE: DNA

<213> ORGANISM: Homo sapiens

<400> SEQUENCE: 269 cccttagct agttttcttc                                         20

<210> SEQ ID NO 270
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 270
acggataagt agatattgag gtaagc                                 26

<210> SEQ ID NO 271
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 271
gtctctttca gttagcagtg g                                      21

<210> SEQ ID NO 272
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 272
actgcgctga aactgtggct ttatag                                 26

<210> SEQ ID NO 273
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 273
acggataagt agatattgag gtaagc                                 26

<210> SEQ ID NO 274
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 274
gtctctttca gttagcagtg g                                      21

<210> SEQ ID NO 275
<211> LENGTH: 26

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 275
actgcgctga aactgtggct ttatag                                          26

<210> SEQ ID NO 276
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
ggccacggag cgagacaucu                                                 20

<210> SEQ ID NO 277
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 277
cagacagcaa actcacccag t                                               21

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 278
ctgacgctta tcgacgccct                                                 20

<210> SEQ ID NO 279
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 279
tcgtcggcag cgtcagatgt gtataagaga cag                                  33

<210> SEQ ID NO 280
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 280
```

```
gtctcgtggg ctcggagatg tgtataagag acag                                    34
```

```
<210> SEQ ID NO 281
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (30)..(37)
<223> OTHER INFORMATION: a, c, t, g, unknown or other

<400> SEQUENCE: 281
```

```
aatgatacgg cgaccaccga gatctacacn nnnnnnntcg tcggcagcgt c                 51
```

```
<210> SEQ ID NO 282
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (25)..(32)
<223> OTHER INFORMATION: a, c, t, g, unknown or other

<400> SEQUENCE: 282
```

```
caagcagaag acggcatacg agatnnnnnn nngtctcgtg ggctcgg                     47
```

```
<210> SEQ ID NO 283
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 283
```

```
caagcagaag acggcatacg a                                                  21
```

```
<210> SEQ ID NO 284
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 284
```

```
aatgatacgg cgaccaccga ga                                                 22
```

```
<210> SEQ ID NO 285
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 285
```

```
acggataagt agatattgag gtaagc                                             26
```

-continued

<210> SEQ ID NO 286
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 286
gtctctttca gttagcagtg g                                               21

<210> SEQ ID NO 287
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 287
actgcgctga aactgtggct ttatag                                          26

<210> SEQ ID NO 288
<211> LENGTH: 23
<212> TYPE: DNA
<213> ORGANISM: Homo sapiens

<400> SEQUENCE: 288
agtcctggta tcttctatgg tgg                                             23

<210> SEQ ID NO 289
<211> LENGTH: 23
<212> TYPE: DNA
<213> ORGANISM: Homo sapiens

<400> SEQUENCE: 289
attcccagta tcctctatga tgg                                             23

<210> SEQ ID NO 290
<211> LENGTH: 23
<212> TYPE: DNA
<213> ORGANISM: Homo sapiens

<400> SEQUENCE: 290
ggagaagaaa actagctaaa ggg                                             23

<210> SEQ ID NO 291
<211> LENGTH: 23
<212> TYPE: DNA
<213> ORGANISM: Homo sapiens

<400> SEQUENCE: 291
gggagaagaa aactagctaa agg                                             23

<210> SEQ ID NO 292
<211> LENGTH: 23
<212> TYPE: DNA
<213> ORGANISM: Homo sapiens

<400> SEQUENCE: 292
ggagaaggaa actagctaaa ggg                                             23

```
<210> SEQ ID NO 293
<211> LENGTH: 20
<212> TYPE: DNA
<213> ORGANISM: Homo sapiens

<400> SEQUENCE: 293
ggagaaggaa actagctaaa                                               20

<210> SEQ ID NO 294
<211> LENGTH: 20
<212> TYPE: DNA
<213> ORGANISM: Homo sapiens

<400> SEQUENCE: 294
actgaatcgg aacaaggcaa                                               20

<210> SEQ ID NO 295
<211> LENGTH: 20
<212> TYPE: DNA
<213> ORGANISM: Homo sapiens

<400> SEQUENCE: 295
gggagaagga aactagctaa                                               20

<210> SEQ ID NO 296
<211> LENGTH: 20
<212> TYPE: DNA
<213> ORGANISM: Homo sapiens

<400> SEQUENCE: 296
aaaaactgga atgactgaat                                               20

<210> SEQ ID NO 297
<211> LENGTH: 20
<212> TYPE: DNA
<213> ORGANISM: Homo sapiens

<400> SEQUENCE: 297
agagacaaga aggtaaaaaa                                               20

<210> SEQ ID NO 298
<211> LENGTH: 20
<212> TYPE: DNA
<213> ORGANISM: Homo sapiens

<400> SEQUENCE: 298
agtcctggta tcctctatga                                               20

<210> SEQ ID NO 299
<211> LENGTH: 20
<212> TYPE: DNA
<213> ORGANISM: Homo sapiens

<400> SEQUENCE: 299
cactggagct agagacaaga                                               20

<210> SEQ ID NO 300
<211> LENGTH: 20
<212> TYPE: DNA
<213> ORGANISM: Homo sapiens

<400> SEQUENCE: 300
acggctgaca aaagaagtcc                                               20
```

<210> SEQ ID NO 301
<211> LENGTH: 20
<212> TYPE: DNA
<213> ORGANISM: Homo sapiens

<400> SEQUENCE: 301
gggagaagaa aactagctaa                                               20

<210> SEQ ID NO 302
<211> LENGTH: 20
<212> TYPE: DNA
<213> ORGANISM: Homo sapiens

<400> SEQUENCE: 302
aaaaattgga atgactgaat                                               20

<210> SEQ ID NO 303
<211> LENGTH: 492
<212> TYPE: DNA
<213> ORGANISM: Homo sapiens

<400> SEQUENCE: 303
tggtacatgc tttagcttta aactacaggc ctcactggag ctagagacaa gaaggtaaaa    60
aacggctgac aaaagaagtc ctggtatcct ctatgatggg agaaggaaac tagctaaagg   120
gaagaataaa ttagagaaaa actggaatga ctgaatcgga acaaggcaaa ggctataaaa   180
aaaattagca gtatcctctt gggggcccct tccccacact atctcaatgc aaatatctgt   240
ctgaaacggt ccctggctaa actccaccca tgggttggcc agccttgcct tgaccaatag   300
ccttgacaag gcaaacttga ccaatagtct tagagtatcc agtgaggcca ggggccggcg   360
gctggctagg gatgaagaat aaaaggaagc acccttcagc agttccacac actcgcttct   420
ggaacgtctg aggttatcaa taagctccta gtccagacgc catgggtcat ttcacagagg   480
aggacaaggc ta                                                      492

<210> SEQ ID NO 304
<211> LENGTH: 20
<212> TYPE: DNA
<213> ORGANISM: Homo sapiens

<400> SEQUENCE: 304
gtttccttct cccatcatag                                               20

<210> SEQ ID NO 305
<211> LENGTH: 20
<212> TYPE: DNA
<213> ORGANISM: Homo sapiens

<400> SEQUENCE: 305
cctggctaaa ctccacccat                                               20

<210> SEQ ID NO 306
<211> LENGTH: 20
<212> TYPE: DNA
<213> ORGANISM: Homo sapiens

<400> SEQUENCE: 306
cttgaccaat agccttgaca                                               20

<210> SEQ ID NO 307

```
<211> LENGTH: 20
<212> TYPE: DNA
<213> ORGANISM: Homo sapiens

<400> SEQUENCE: 307
ggctagggat gaagaataaa                                               20

<210> SEQ ID NO 308
<211> LENGTH: 10
<212> TYPE: PRT
<213> ORGANISM: Homo sapiens

<400> SEQUENCE: 308

Met Gly His Phe Thr Glu Glu Asp Lys Ala
1               5                   10

<210> SEQ ID NO 309
<211> LENGTH: 20
<212> TYPE: DNA
<213> ORGANISM: Homo sapiens

<400> SEQUENCE: 309
ggcaaggctg gccaacccat                                               20

<210> SEQ ID NO 310
<211> LENGTH: 20
<212> TYPE: DNA
<213> ORGANISM: Homo sapiens

<400> SEQUENCE: 310
cttgtcaagg ctattggtca                                               20

<210> SEQ ID NO 311
<211> LENGTH: 20
<212> TYPE: DNA
<213> ORGANISM: Homo sapiens

<400> SEQUENCE: 311
caaggctatt ggtcaaggca                                               20

<210> SEQ ID NO 312
<211> LENGTH: 20
<212> TYPE: DNA
<213> ORGANISM: Homo sapiens

<400> SEQUENCE: 312
tggtcaagtt tgccttgtca                                               20

<210> SEQ ID NO 313
<211> LENGTH: 20
<212> TYPE: DNA
<213> ORGANISM: Homo sapiens

<400> SEQUENCE: 313
ggagaaggaa actagctaaa                                               20

<210> SEQ ID NO 314
<211> LENGTH: 20
<212> TYPE: DNA
<213> ORGANISM: Homo sapiens

<400> SEQUENCE: 314
gggagaagga aactagctaa                                               20
```

<210> SEQ ID NO 315
<211> LENGTH: 20
<212> TYPE: DNA
<213> ORGANISM: Homo sapiens

<400> SEQUENCE: 315
actgaatcgg aacaaggcaa 20

<210> SEQ ID NO 316
<211> LENGTH: 20
<212> TYPE: DNA
<213> ORGANISM: Homo sapiens

<400> SEQUENCE: 316
gtcctggtat cttctatggt 20

<210> SEQ ID NO 317
<211> LENGTH: 20
<212> TYPE: DNA
<213> ORGANISM: Homo sapiens

<400> SEQUENCE: 317
agtcctggta tcttctatgg 20

<210> SEQ ID NO 318
<211> LENGTH: 20
<212> TYPE: DNA
<213> ORGANISM: Homo sapiens

<400> SEQUENCE: 318
ggagaagaaa actagctaaa 20

<210> SEQ ID NO 319
<211> LENGTH: 20
<212> TYPE: DNA
<213> ORGANISM: Homo sapiens

<400> SEQUENCE: 319
aaaaactgga atgactgaat 20

<210> SEQ ID NO 320
<211> LENGTH: 20
<212> TYPE: DNA
<213> ORGANISM: Homo sapiens

<400> SEQUENCE: 320
cactggagct agagacaaga 20

<210> SEQ ID NO 321
<211> LENGTH: 20
<212> TYPE: DNA
<213> ORGANISM: Homo sapiens

<400> SEQUENCE: 321
acggctgaca aaagaagtcc 20

<210> SEQ ID NO 322
<211> LENGTH: 20
<212> TYPE: DNA
<213> ORGANISM: Homo sapiens

<400> SEQUENCE: 322
gggagaagaa aactagctaa 20

<210> SEQ ID NO 323
<211> LENGTH: 20
<212> TYPE: DNA
<213> ORGANISM: Homo sapiens

<400> SEQUENCE: 323
aaaaattgga atgactgaat                                                  20

<210> SEQ ID NO 324
<211> LENGTH: 500
<212> TYPE: DNA
<213> ORGANISM: Homo sapiens

<400> SEQUENCE: 324
acaatccctg aacttttcaa aaattggtac atgctttaac tttaaactac aggcctcact      60
ggagctacag acaagaaggt gaaaaacggc tgacaaaaga agtcctggta tcttctatgg    120
tgggagaaga aaactagcta aagggaagaa taaattagag aaaaattgga atgactgaat    180
cggaacaagg caaaggctat aaaaaaaatt aagcagcagt atcctcttgg gggccccttc    240
cccacactat ctcaatgcaa atatctgtct gaaacggtcc ctggctaaac tccacccatg    300
ggttggccag ccttgccttg accaatagcc ttgacaaggc aaacttgacc aatagtctta    360
gagtatccag tgaggccagg ggccggcggc tggctaggga tgaagaataa aaggaagcac    420
ccttcagcag ttccacacac tcgcttctgg aacgtctgag gttatcaata agctcctagt    480
ccagacgcca tgggtcattt                                                500

<210> SEQ ID NO 325
<211> LENGTH: 20
<212> TYPE: DNA
<213> ORGANISM: Homo sapiens

<400> SEQUENCE: 325
cctggctaaa ctccacccat                                                  20

<210> SEQ ID NO 326
<211> LENGTH: 20
<212> TYPE: DNA
<213> ORGANISM: Homo sapiens

<400> SEQUENCE: 326
cttgaccaat agccttgaca                                                  20

<210> SEQ ID NO 327
<211> LENGTH: 20
<212> TYPE: DNA
<213> ORGANISM: Homo sapiens

<400> SEQUENCE: 327
ggctagggat gaagaataaa                                                  20

<210> SEQ ID NO 328
<211> LENGTH: 4
<212> TYPE: PRT
<213> ORGANISM: Homo sapiens

<400> SEQUENCE: 328

Met Gly His Phe
1

```
<210> SEQ ID NO 329
<211> LENGTH: 20
<212> TYPE: DNA
<213> ORGANISM: Homo sapiens

<400> SEQUENCE: 329
ggcaaggctg gccaacccat                                                   20

<210> SEQ ID NO 330
<211> LENGTH: 20
<212> TYPE: DNA
<213> ORGANISM: Homo sapiens

<400> SEQUENCE: 330
cttgtcaagg ctattggtca                                                   20

<210> SEQ ID NO 331
<211> LENGTH: 20
<212> TYPE: DNA
<213> ORGANISM: Homo sapiens

<400> SEQUENCE: 331
caaggctatt ggtcaaggca                                                   20

<210> SEQ ID NO 332
<211> LENGTH: 20
<212> TYPE: DNA
<213> ORGANISM: Homo sapiens

<400> SEQUENCE: 332
tggtcaagtt tgccttgtca                                                   20
```